US008318702B2

(12) United States Patent
Kondoh et al.

(10) Patent No.: US 8,318,702 B2
(45) Date of Patent: Nov. 27, 2012

(54) DI(ARYLAMINO)ARYL COMPOUNDS

(75) Inventors: Yutaka Kondoh, Tokyo (JP); Kazuhiko Iikubo, Tokyo (JP); Sadao Kuromitsu, Tokyo (JP); Nobuaki Shindo, Tokyo (JP); Takatoshi Soga, Tokyo (JP); Takashi Furutani, Tokyo (JP); Itsuro Shimada, Tokyo (JP); Takahiro Matsuya, Tokyo (JP); Kazuo Kurosawa, Tokyo (JP); Akio Kamikawa, Tokyo (JP); Hiroyuki Mano, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 177 days.

(21) Appl. No.: 12/448,759

(22) PCT Filed: Jul. 4, 2008

(86) PCT No.: PCT/JP2008/062188
§ 371 (c)(1),
(2), (4) Date: Aug. 6, 2009

(87) PCT Pub. No.: WO2009/008371
PCT Pub. Date: Jan. 15, 2009

(65) Prior Publication Data
US 2010/0099658 A1    Apr. 22, 2010

(30) Foreign Application Priority Data
Jul. 6, 2007    (JP) ................................. 2007-178795

(51) Int. Cl.
A01N 57/00    (2006.01)
A01N 43/00    (2006.01)
A01N 43/66    (2006.01)
A61K 31/675    (2006.01)
A61K 31/00    (2006.01)
A61K 31/53    (2006.01)
C07D 251/00    (2006.01)
C07D 253/00    (2006.01)
C07D 251/40    (2006.01)
C07D 251/18    (2006.01)
C07D 251/48    (2006.01)

(52) U.S. Cl. ..................... 514/84; 514/210.21; 514/241; 544/180; 544/194; 544/204; 544/205

(58) Field of Classification Search ................... 514/84, 514/210.21, 241; 544/180, 194, 204, 205
See application file for complete search history.

(56) References Cited

U.S. PATENT DOCUMENTS

| 2004/0116388 A1 | 6/2004 | Armistead et al. |
| 2005/0085637 A1 | 4/2005 | Cheung et al. |
| 2006/0100227 A1 | 5/2006 | Baenteli et al. |
| 2006/0247241 A1 | 11/2006 | Garcia-Echeverria et al. |
| 2006/0247262 A1 | 11/2006 | Baenteli et al. |
| 2007/0105839 A1 | 5/2007 | Imbach et al. |
| 2008/0090776 A1 | 4/2008 | Mano et al. |
| 2008/0132504 A1 | 6/2008 | Garcia-Echeverria et al. |
| 2008/0279870 A1 | 11/2008 | Inghirami et al. |
| 2008/0293708 A1 | 11/2008 | Kawahara et al. |
| 2009/0099193 A1 | 4/2009 | Mano et al. |
| 2009/0131436 A1 | 5/2009 | Imbach et al. |
| 2009/0156475 A1 | 6/2009 | Rikova et al. |
| 2010/0240673 A1 | 9/2010 | Mano et al. |

FOREIGN PATENT DOCUMENTS

| EP | 1 479 397 | | 11/2004 |
| EP | 1 914 240 | A1 | 4/2008 |
| JP | 2005-522438 | | 7/2005 |
| JP | 2006-520354 | | 9/2006 |
| WO | WO 97/20822 | | 6/1997 |
| WO | WO 01/25220 | A1 | 4/2001 |
| WO | WO 03/055866 | | 7/2003 |
| WO | WO 03/055866 | A1 | 7/2003 |
| WO | WO 03/066601 | A1 | 8/2003 |
| WO | WO 03/078404 | A1 | 9/2003 |
| WO | WO 2004/080980 | | 9/2004 |
| WO | WO 2005/016894 | A1 | 2/2005 |
| WO | WO 2005/026130 | A1 | 3/2005 |
| WO | WO 2005/026158 | A1 | 3/2005 |
| WO | WO 2006/021454 | A2 | 3/2006 |
| WO | WO 2006/021457 | A2 | 3/2006 |
| WO | WO 2007/059300 | A2 | 5/2007 |
| WO | WO 2007/095812 | | 8/2007 |
| WO | WO 2007/095812 | A1 | 8/2007 |
| WO | WO 2008/051547 | A1 | 5/2008 |
| WO | WO 2008/073687 | A2 | 6/2008 |
| WO | WO 2008/127248 | A1 | 10/2008 |

(Continued)

OTHER PUBLICATIONS

Supplementary European Search Report dated May 6, 2011 for European Application No. 0877903.9.

(Continued)

Primary Examiner — Samira Jean-Louis
(74) Attorney, Agent, or Firm — Oblon, Spivak, McClelland, Maier & Neustadt, L.L.P.

(57) ABSTRACT

The present invention provides a compound which is useful as an inhibitor against the kinase activity of EML4-ALK fusion proteins and mutant EGFR proteins.
As a result of extensive and intensive studies on compounds having an inhibitory effect against the kinase activity of EML4-ALK fusion proteins and mutant EGFR proteins, the inventors of the present invention have found that the di(arylamino)aryl compound of the present invention has inhibitory activity against the kinase activity of EML4-ALK fusion proteins and mutant EGFR proteins. This finding led to the completion of the present invention. The compound of the present invention can be used as a pharmaceutical composition for preventing and/or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer, etc.

7 Claims, 2 Drawing Sheets

FOREIGN PATENT DOCUMENTS

| | | |
|---|---|---|
| WO | WO 2009/020990 A1 | 2/2009 |
| WO | WO 2009/032694 | 3/2009 |
| WO | WO 2009/032703 A1 | 3/2009 |
| WO | WO 2009/054939 A1 | 4/2009 |
| WO | WO 2009/143389 | 9/2009 |
| WO | WO 2009/126514 | 10/2009 |
| WO | WO 2009/126515 | 10/2009 |

OTHER PUBLICATIONS

International Search Report for PCT/JP2008/062188, mailed Jul. 29, 2008.

Whitten, J.P. et al., "Rapid Microscale Synthesis, a New Method for Lead Optimization Using Robotics and Solution Phase Chemistry: Application to the Synthesis and Optimization of Corticotropin-Releasing Factor Receptor Antagonists", Journal of Medicinal Chemistry, vol. 39, No. 22, (1996), pp. 4354-4357.

Office Action dated Jul. 12, 2011 issued in connection with corresponding Chinese Appln. No. 200880023605.5 (2011070700484100) with English Translation.

Dirks et al, "Expression and Functional Analysis of the Anaplastic Lymphoma Kinase (*ALK*) Gene in Tumor Cell Lines", Int. J. Cancer 100:49-56 (2002).

Soda et al, "Identification of the transforming EML4-ALK fusion gene in non0small-cell lung cancer", Nature 448:561-566 (2007).

Marzec et al, "Inhibition of ALK enzymatic activity in T-cell lymphoma cells induces apoptosis and suppresses proliferation and STAT3 phosphorylation independently of Jak3", Laboratory Investigation 85:1544-1554 (2005).

Galkin et al, "Identification of NVP-TAE684, a potent, selective, and efficacious inhibitor of NPM-ALK", PNAS 104(1):270-275 (2007).

Rikova et al, "Global Survey of Phsophotyrosine Signaling Identifies Oncogenic Kinases in Lung Cancer", Cell 131:1190-1203 (2007).

McDermott et al, "Identification of genotype-correlated sensitivity to selective kinase inhibitors by using high-throughput tumor cell line profiling", PNAS 104(50):19936-19941 (2007).

Koivunen et al, "EML4-ALK fusion gene and sensitivity to an ALK kinase inhibitor in lung cancer", Proceedings of the American Associateion for Cancer Research 49:560, No. 2373 (2008).

Whitten et al, "Rapid Microscale Synthesis, a New Method for Lead Optimization Using Robotics and Solution Phase Chemistry: Application to the Synthesis and Optimization of Corticotropin-Releasing Factor$_1$ Receptor Antagonists", J. Med. Chem. 39:4354-4357 (1996).

Piva et al, "Ablation of oncogenic ALK is a viable therapeutic approach for anaplastic large-cell lymphomas", Blood 107:689-697 (2006).

Turturro et al, "Model of Inhibition of the NPM-ALK Kinase Activity by Herbimycin A", Clinical Cancer Research 8:240-245 (2002).

Elenitoba-Johnson et al, "Proteomic identification of oncogenic chromosomal translocation partners encoding chimeric anaplastic lymphoma kinase fusion proteins", PNAS 103(19):7402-7407 (2006).

Takeuchi et al, "KIF5B-ALK, a Novel Fusion Oncokinase Identified by an Immunohistochemistry-based Diagnostic System for ALK-positive Lung Cancer", Clin. Cancer Res. 15(9):3143-3149 (2009).

Wan et al, "Anaplastic lymphoma kinase activity is essential for the proliferation and survival of anaplastic large-cell lymphoma cells", Blood 107:1617-1623 (2006).

Du et al, "Proteomic profiling of proteins dysregulted in Chinese esophageal squamous cell carcinoma", J. Mol. Med. 85:863-875 (2007).

Chiarle et al, "The anaplastic lymphoma kinase in the pathogenesis of cancer", Nature Reviews Cancer 8:11-23 (2008).

Corrections, PNAS 104(6):2024-2025 (2007).

Official Action dated Dec. 2, 2011 issued in connection with Russian Appln. No. 2010103969/4.

Official Action dated Dec. 2, 2011 issued in connection with Russian Appln. No. 2010103969/4—English Translation.

Office Action issued May 30, 2012, in European Application No. 08 777 903.9.

Office Action issued Jun. 28, 2012, in Australian Patent Application No. 2008273426, filed Jul. 4, 2008 (with English-language Translation).

Office Action issued Jul. 20, 2012, in Indonesian Patent Application No. W-00 2010 00004, (with English-language Translation).

```
                        SEQUENCE LISTING

<160> NUMBER OF SEQ ID NOS: 10

<210> SEQ ID NO 1
<211> LENGTH: 3900
<212> TYPE: DNA
<213> ORGANISM: Homo sapiens
<220> FEATURE:
<221> NAME/KEY: CDS
<222> LOCATION: (271)..(3447)

<400> SEQUENCE: 1
ggcggcgcgg cgcggcgctc gcggctgctg cctgggaggg aggccgggca ggcggctgag       60
cggcgcggct ctcaacgtga cggggaagtg gttcgggcgg ccgcggctta ctaccccagg      120
gcgaacggac ggacgacgga ggcgggagcc ggtagccgag ccgggcgacc tagagaacga      180
gcgggtcagg ctcagcgtcg gccactctgt cggtccgctg aatgaagtgc ccgcccctct      240
gagcccggag cccggcgctt tccccgcaag atg gac ggt ttc gcc ggc agt ctc       294
                                 Met Asp Gly Phe Ala Gly Ser Leu
                                  1               5
```

-continued

| | | |
|---|---|---|
| gat gat agt att tct gct gca agt act tct gat gtt caa gat cgc ctg<br>Asp Asp Ser Ile Ser Ala Ala Ser Thr Ser Asp Val Gln Asp Arg Leu<br>10                                 15                                20 | 342 |
| tca gct ctt gag tca cga gtt cag caa caa gaa gat gaa atc act gtg<br>Ser Ala Leu Glu Ser Arg Val Gln Gln Gln Glu Asp Glu Ile Thr Val<br>25                                 30                                35                                40 | 390 |
| cta aag gcg gct ttg gct gat gtt ttg agg cgt ctt gca atc tct gaa<br>Leu Lys Ala Ala Leu Ala Asp Val Leu Arg Arg Leu Ala Ile Ser Glu<br>                             45                                50                                55 | 438 |
| gat cat gtg gcc tca gtg aaa aaa tca gtc tca agt aaa ggc caa cca<br>Asp His Val Ala Ser Val Lys Lys Ser Val Ser Ser Lys Gly Gln Pro<br>                      60                                65                                70 | 486 |
| agc cct cga gca gtt att ccc atg tcc tgt ata acc aat gga agt ggt<br>Ser Pro Arg Ala Val Ile Pro Met Ser Cys Ile Thr Asn Gly Ser Gly<br>75                                 80                                85 | 534 |
| gca aac aga aaa cca agt cat acc agt gct gtc tca att gca gga aaa<br>Ala Asn Arg Lys Pro Ser His Thr Ser Ala Val Ser Ile Ala Gly Lys<br>90                                 95                               100 | 582 |
| gaa act ctt tca tct gct gct aaa agt ggt aca gaa aaa aag aaa gaa<br>Glu Thr Leu Ser Ser Ala Ala Lys Ser Gly Thr Glu Lys Lys Lys Glu<br>105                              110                          115                          120 | 630 |
| aaa cca caa gga cag aga gaa aaa aaa gag gaa tct cat tct aat gat<br>Lys Pro Gln Gly Gln Arg Glu Lys Lys Glu Glu Ser His Ser Asn Asp<br>                           125                                130                                135 | 678 |
| caa agt cca caa att cga gca tca cct tct ccc cag ccc tct tca caa<br>Gln Ser Pro Gln Ile Arg Ala Ser Pro Ser Pro Gln Pro Ser Ser Gln<br>140                              145                                150 | 726 |
| cct ctc caa ata cac aga caa act cca gaa agc aag aat gct act ccc<br>Pro Leu Gln Ile His Arg Gln Thr Pro Glu Ser Lys Asn Ala Thr Pro<br>          155                              160                          165 | 774 |
| acc aaa agc ata aaa cga cca tca cca gct gaa aag tca cat aat tct<br>Thr Lys Ser Ile Lys Arg Pro Ser Pro Ala Glu Lys Ser His Asn Ser<br>170                              175                          180 | 822 |
| tgg gaa aat tca gat gat agc cgt aat aaa ttg tcg aaa ata cct tca<br>Trp Glu Asn Ser Asp Asp Ser Arg Asn Lys Leu Ser Lys Ile Pro Ser<br>185                              190                          195                          200 | 870 |
| aca ccc aaa tta ata cca aaa gtt acc aaa act gca gac aag cat aaa<br>Thr Pro Lys Leu Ile Pro Lys Val Thr Lys Thr Ala Asp Lys His Lys<br>                           205                                210                                215 | 918 |
| gat gtc atc atc aac caa gaa gga gaa tat att aaa atg ttt atg cgc<br>Asp Val Ile Ile Asn Gln Glu Gly Glu Tyr Ile Lys Met Phe Met Arg<br>                      220                                225                          230 | 966 |
| ggt cgg cca att acc atg ttc att cct tcc gat gtt gac aac tat gat<br>Gly Arg Pro Ile Thr Met Phe Ile Pro Ser Asp Val Asp Asn Tyr Asp<br>235                              240                                245 | 1014 |
| gac atc aga acg gaa ctg cct cct gag aag ctc aaa ctg gag tgg gca<br>Asp Ile Arg Thr Glu Leu Pro Pro Glu Lys Leu Lys Leu Glu Trp Ala<br>250                              255                          260 | 1062 |
| tat ggt tat cga gga aag gac tgt aga gct aat gtt tac ctt ctt ccg<br>Tyr Gly Tyr Arg Gly Lys Asp Cys Arg Ala Asn Val Tyr Leu Leu Pro<br>265                              270                          275                          280 | 1110 |
| acc ggg gaa ata gtt tat ttc att gca tca gta gta gta cta ttt aat<br>Thr Gly Glu Ile Val Tyr Phe Ile Ala Ser Val Val Val Leu Phe Asn<br>                         285                                290                                295 | 1158 |
| tat gag gag aga act cag cga cac tac ctg ggc cat aca gac tgt gtg<br>Tyr Glu Glu Arg Thr Gln Arg His Tyr Leu Gly His Thr Asp Cys Val<br>                      300                                305                          310 | 1206 |
| aaa tgc ctt gct ata cat cct gac aaa att agg att gca act gga cag<br>Lys Cys Leu Ala Ile His Pro Asp Lys Ile Arg Ile Ala Thr Gly Gln<br>315                              320                          325 | 1254 |

```
ata gct ggc gtg gat aaa gat gga agg cct cta caa ccc cac gtc aga      1302
Ile Ala Gly Val Asp Lys Asp Gly Arg Pro Leu Gln Pro His Val Arg
        330                 335                 340 gtg tgg gat tct gtt act cta tcc aca ctg cag att att gga ctt ggc      1350
Val Trp Asp Ser Val Thr Leu Ser Thr Leu Gln Ile Ile Gly Leu Gly
345                 350                 355                 360 act ttt gag cgt gga gta gga tgc ctg gat ttt tca aaa gca gat tca      1398
Thr Phe Glu Arg Gly Val Gly Cys Leu Asp Phe Ser Lys Ala Asp Ser
                365                 370                 375 ggt gtt cat tta tgt gtt att gat gac tcc aat gag cat atg ctt act      1446
Gly Val His Leu Cys Val Ile Asp Asp Ser Asn Glu His Met Leu Thr
        380                 385                 390 gta tgg gac tgg cag aag aaa gca aaa gga gca gaa ata aag aca aca      1494
Val Trp Asp Trp Gln Lys Lys Ala Lys Gly Ala Glu Ile Lys Thr Thr
395                 400                 405 aat gaa gtt gtt ttg gct gtg gag ttt cac cca aca gat gca aat acc      1542
Asn Glu Val Val Leu Ala Val Glu Phe His Pro Thr Asp Ala Asn Thr
                410                 415                 420 ata att aca tgc ggt aaa tct cat att ttc ttc tgg acc tgg agc ggc      1590
Ile Ile Thr Cys Gly Lys Ser His Ile Phe Phe Trp Thr Trp Ser Gly
425                 430                 435                 440 aat tca cta aca aga aaa cag gga att ttt ggg aaa tat gaa aag cca      1638
Asn Ser Leu Thr Arg Lys Gln Gly Ile Phe Gly Lys Tyr Glu Lys Pro
                445                 450                 455 aaa ttt gtg cag tgt tta gca ttc ttg ggg aat gga gat gtt ctt act      1686
Lys Phe Val Gln Cys Leu Ala Phe Leu Gly Asn Gly Asp Val Leu Thr
        460                 465                 470 gga gac tca ggt gga gtc atg ctt ata tgg agc aaa act act gta gag      1734
Gly Asp Ser Gly Gly Val Met Leu Ile Trp Ser Lys Thr Thr Val Glu
                475                 480                 485 ccc aca cct ggg aaa gga cct aaa gtg tac cgc cgg aag cac cag gag      1782
Pro Thr Pro Gly Lys Gly Pro Lys Val Tyr Arg Arg Lys His Gln Glu
        490                 495                 500 ctg caa gcc atg cag atg gag ctg cag agc cct gag tac aag ctg agc      1830
Leu Gln Ala Met Gln Met Glu Leu Gln Ser Pro Glu Tyr Lys Leu Ser
505                 510                 515                 520 aag ctc cgc acc tcg acc atc atg acc gac tac aac ccc aac tac tgc      1878
Lys Leu Arg Thr Ser Thr Ile Met Thr Asp Tyr Asn Pro Asn Tyr Cys
                525                 530                 535 ttt gct ggc aag acc tcc tcc atc agt gac ctg aag gag gtg ccg cgg      1926
Phe Ala Gly Lys Thr Ser Ser Ile Ser Asp Leu Lys Glu Val Pro Arg
        540                 545                 550 aaa aac atc acc ctc att cgg ggt ctg ggc cat gga gcc ttt ggg gag      1974
Lys Asn Ile Thr Leu Ile Arg Gly Leu Gly His Gly Ala Phe Gly Glu
        555                 560                 565 gtg tat gaa ggc cag gtg tcc gga atg ccc aac gac cca agc ccc ctg      2022
Val Tyr Glu Gly Gln Val Ser Gly Met Pro Asn Asp Pro Ser Pro Leu
        570                 575                 580 caa gtg gct gtg aag acg ctg cct gaa gtg tgc tct gaa cag gac gaa      2070
Gln Val Ala Val Lys Thr Leu Pro Glu Val Cys Ser Glu Gln Asp Glu
585                 590                 595                 600 ctg gat ttc ctc atg gaa gcc ctg atc atc agc aaa ttc aac cac cag      2118
Leu Asp Phe Leu Met Glu Ala Leu Ile Ile Ser Lys Phe Asn His Gln
                605                 610                 615 aac att gtt cgc tgc att ggg gtg agc ctg caa tcc ctg ccc cgg ttc      2166
Asn Ile Val Arg Cys Ile Gly Val Ser Leu Gln Ser Leu Pro Arg Phe
        620                 625                 630 atc ctg ctg gag ctc atg gcg ggg gac ctc aag tcc ttc ctc cga           2214
Ile Leu Leu Glu Leu Met Ala Gly Gly Asp Leu Lys Ser Phe Leu Arg
                635                 640                 645
```

```
gag acc cgc cct cgc ccg agc cag ccc tcc tcc ctg gcc atg ctg gac      2262
Glu Thr Arg Pro Arg Pro Ser Gln Pro Ser Ser Leu Ala Met Leu Asp
650                 655                 660 ctt ctg cac gtg gct cgg gac att gcc tgt ggc tgt cag tat ttg gag      2310
Leu Leu His Val Ala Arg Asp Ile Ala Cys Gly Cys Gln Tyr Leu Glu
665                 670                 675                 680 gaa aac cac ttc atc cac cga gac att gct gcc aga aac tgc ctc ttg      2358
Glu Asn His Phe Ile His Arg Asp Ile Ala Ala Arg Asn Cys Leu Leu
                685                 690                 695 acc tgt cca ggc cct gga aga gtg gcc aag att gga gac ttc ggg atg      2406
Thr Cys Pro Gly Pro Gly Arg Val Ala Lys Ile Gly Asp Phe Gly Met
            700                 705                 710 gcc cga gac atc tac agg gcg agc tac tat aga aag gga ggc tgt gcc      2454
Ala Arg Asp Ile Tyr Arg Ala Ser Tyr Tyr Arg Lys Gly Gly Cys Ala
                715                 720                 725 atg ctg cca gtt aag tgg atg ccc cca gag gcc ttc atg gaa gga ata      2502
Met Leu Pro Val Lys Trp Met Pro Pro Glu Ala Phe Met Glu Gly Ile
730                 735                 740 ttc act tct aaa aca gac aca tgg tcc ttt gga gtg ctg cta tgg gaa      2550
Phe Thr Ser Lys Thr Asp Thr Trp Ser Phe Gly Val Leu Leu Trp Glu
745                 750                 755                 760 atc ttt tct ctt gga tat atg cca tac ccc agc aaa agc aac cag gaa      2598
Ile Phe Ser Leu Gly Tyr Met Pro Tyr Pro Ser Lys Ser Asn Gln Glu
                765                 770                 775 gtt ctg gag ttt gtc acc agt gga ggc cgg atg gac cca ccc aag aac      2646
Val Leu Glu Phe Val Thr Ser Gly Gly Arg Met Asp Pro Pro Lys Asn
            780                 785                 790 tgc cct ggg cct gta tac cgg ata atg act cag tgc tgg caa cat cag      2694
Cys Pro Gly Pro Val Tyr Arg Ile Met Thr Gln Cys Trp Gln His Gln
                795                 800                 805 cct gaa gac agg ccc aac ttt gcc atc att ttg gag agg att gaa tac      2742
Pro Glu Asp Arg Pro Asn Phe Ala Ile Ile Leu Glu Arg Ile Glu Tyr
810                 815                 820 tgc acc cag gac ccg gat gta atc aac acc gct ttg ccg ata gaa tat      2790
Cys Thr Gln Asp Pro Asp Val Ile Asn Thr Ala Leu Pro Ile Glu Tyr
825                 830                 835                 840 ggt cca ctt gtg gaa gag gaa gag aaa gtg cct gtg agg ccc aag gac      2838
Gly Pro Leu Val Glu Glu Glu Glu Lys Val Pro Val Arg Pro Lys Asp
                845                 850                 855 cct gag ggg gtt cct cct ctc ctg gtc tct caa cag gca aaa cgg gag      2886
Pro Glu Gly Val Pro Pro Leu Leu Val Ser Gln Gln Ala Lys Arg Glu
            860                 865                 870 gag gag cgc agc cca gct gcc cca cca cct ctg cct acc acc tcc tct      2934
Glu Glu Arg Ser Pro Ala Ala Pro Pro Pro Leu Pro Thr Thr Ser Ser
            875                 880                 885 ggc aag gct gca aag aaa ccc aca gct gca gag gtc tct gtt cga gtc      2982
Gly Lys Ala Ala Lys Lys Pro Thr Ala Ala Glu Val Ser Val Arg Val
890                 895                 900 cct aga ggg ccg gcc gtg gaa ggg gga cac gtg aat atg gca ttc tct      3030
Pro Arg Gly Pro Ala Val Glu Gly Gly His Val Asn Met Ala Phe Ser
905                 910                 915                 920 cag tcc aac cct cct tcg gag ttg cac agg gtc cac gga tcc aga aac      3078
Gln Ser Asn Pro Pro Ser Glu Leu His Arg Val His Gly Ser Arg Asn
                925                 930                 935 aag ccc acc agc ttg tgg aac cca acg tac ggc tcc tgg ttt aca gag      3126
Lys Pro Thr Ser Leu Trp Asn Pro Thr Tyr Gly Ser Trp Phe Thr Glu
            940                 945                 950 aaa ccc acc aaa aag aat aat cct ata gca aag aag gag cca cac gag      3174
Lys Pro Thr Lys Lys Asn Asn Pro Ile Ala Lys Lys Glu Pro His Glu
955                 960                 965
```

| | | |
|---|---|---|
| agg ggt aac ctg ggg ctg gag gga agc tgt act gtc cca cct aac gtt<br>Arg Gly Asn Leu Gly Leu Glu Gly Ser Cys Thr Val Pro Pro Asn Val<br>970                                        975                                       980 | | 3222 |
| gca act ggg aga ctt ccg ggg gcc tca ctg ctc cta gag ccc tct tcg<br>Ala Thr Gly Arg Leu Pro Gly Ala Ser Leu Leu Leu Glu Pro Ser Ser<br>985                                      990                                 995                        1000 | | 3270 |
| ctg act gcc aat atg aag gag gta cct ctg ttc agg cta cgt cac<br>Leu Thr Ala Asn Met Lys Glu Val Pro Leu Phe Arg Leu Arg His<br>                         1005                                1010                          1015 | | 3315 |
| ttc cct tgt ggg aat gtc aat tac ggc tac cag caa cag ggc ttg<br>Phe Pro Cys Gly Asn Val Asn Tyr Gly Tyr Gln Gln Gln Gly Leu<br>                    1020                                1025                          1030 | | 3360 |
| ccc tta gaa gcc gct act gcc cct gga gct ggt cat tac gag gat<br>Pro Leu Glu Ala Ala Thr Ala Pro Gly Ala Gly His Tyr Glu Asp<br>                    1035                                1040                          1045 | | 3405 |
| acc att ctg aaa agc aag aat agc atg aac cag cct ggg ccc<br>Thr Ile Leu Lys Ser Lys Asn Ser Met Asn Gln Pro Gly Pro<br>                 1050                                1055 | | 3447 |
| tgagctcggt cacacactca cttctcttcc ttgggatccc taagaccgtg gaggagagag | | 3507 |
| aggcaatcaa tggctccttc acaaaccaga gaccaaatgt cacgttttgt tttgtgccaa | | 3567 |
| cctattttga agtaccacca aaaaagctgt attttgaaaa tgctttagaa aggttttgag | | 3627 |
| catgggttca tcctattctt tcgaaagaag aaaatatcat aaaaatgagt gataaataca | | 3687 |
| aggcccagat gtggttgcat aaggttttta tgcatgtttg ttgtatactt ccttatgctt | | 3747 |
| cttttaaatt gtgtgtgctc tgcttcaatg tagtcagaat tagctgcttc tatgtttcat | | 3807 |
| agttggggtc atagatgttt ccttgccttg ttgatgtgga catgagccat ttgaggggag | | 3867 |
| agggaacgga aataaaggag ttatttgtaa tga | | 3900 |

<210> SEQ ID NO 2
<211> LENGTH: 1059
<212> TYPE: PRT
<213> ORGANISM: Homo sapiens

<400> SEQUENCE: 2

Met Asp Gly Phe Ala Gly Ser Leu Asp Asp Ser Ile Ser Ala Ala Ser
1                 5                   10                  15

Thr Ser Asp Val Gln Asp Arg Leu Ser Ala Leu Glu Ser Arg Val Gln
                 20                  25                 30

Gln Gln Glu Asp Glu Ile Thr Val Leu Lys Ala Ala Leu Ala Asp Val
                     35                  40                 45

Leu Arg Arg Leu Ala Ile Ser Glu Asp His Val Ala Ser Val Lys Lys
50                               55                           60

Ser Val Ser Ser Lys Gly Gln Pro Ser Pro Arg Ala Val Ile Pro Met
65                               70                           75                          80

Ser Cys Ile Thr Asn Gly Ser Gly Ala Asn Arg Lys Pro Ser His Thr
                     85                  90                 95

Ser Ala Val Ser Ile Ala Gly Lys Glu Thr Leu Ser Ser Ala Ala Lys
                100                 105                110

Ser Gly Thr Glu Lys Lys Lys Glu Lys Pro Gln Gly Gln Arg Glu Lys
               115                 120                125

Lys Glu Glu Ser His Ser Asn Asp Gln Ser Pro Gln Ile Arg Ala Ser
        130                  135                140

Pro Ser Pro Gln Pro Ser Ser Gln Pro Leu Gln Ile His Arg Gln Thr
145                             150                          155                         160

```
Pro Glu Ser Lys Asn Ala Thr Pro Thr Lys Ser Ile Lys Arg Pro Ser
            165                 170                 175
Pro Ala Glu Lys Ser His Asn Ser Trp Glu Asn Ser Asp Asp Ser Arg
        180                 185                 190
Asn Lys Leu Ser Lys Ile Pro Ser Thr Pro Lys Leu Ile Pro Lys Val
        195                 200                 205
Thr Lys Thr Ala Asp Lys His Lys Asp Val Ile Ile Asn Gln Glu Gly
        210                 215                 220
Glu Tyr Ile Lys Met Phe Met Arg Gly Arg Pro Ile Thr Met Phe Ile
225                 230                 235                 240
Pro Ser Asp Val Asp Asn Tyr Asp Asp Ile Arg Thr Glu Leu Pro Pro
                245                 250                 255
Glu Lys Leu Lys Leu Glu Trp Ala Tyr Gly Tyr Arg Gly Lys Asp Cys
            260                 265                 270
Arg Ala Asn Val Tyr Leu Leu Pro Thr Gly Glu Ile Val Tyr Phe Ile
        275                 280                 285
Ala Ser Val Val Leu Phe Asn Tyr Glu Glu Arg Thr Gln Arg His
        290                 295                 300
Tyr Leu Gly His Thr Asp Cys Val Lys Cys Leu Ala Ile His Pro Asp
305                 310                 315                 320
Lys Ile Arg Ile Ala Thr Gly Gln Ile Ala Gly Val Asp Lys Asp Gly
                325                 330                 335
Arg Pro Leu Gln Pro His Val Arg Val Trp Asp Ser Val Thr Leu Ser
            340                 345                 350
Thr Leu Gln Ile Ile Gly Leu Gly Thr Phe Glu Arg Gly Val Gly Cys
        355                 360                 365
Leu Asp Phe Ser Lys Ala Asp Ser Gly Val His Leu Cys Val Ile Asp
370                 375                 380
Asp Ser Asn Glu His Met Leu Thr Val Trp Asp Trp Gln Lys Lys Ala
385                 390                 395                 400
Lys Gly Ala Glu Ile Lys Thr Thr Asn Glu Val Val Leu Ala Val Glu
                405                 410                 415
Phe His Pro Thr Asp Ala Asn Thr Ile Ile Thr Cys Gly Lys Ser His
            420                 425                 430
Ile Phe Phe Trp Thr Trp Ser Gly Asn Ser Leu Thr Arg Lys Gln Gly
        435                 440                 445
Ile Phe Gly Lys Tyr Glu Lys Pro Lys Phe Val Gln Cys Leu Ala Phe
        450                 455                 460
Leu Gly Asn Gly Asp Val Leu Thr Gly Asp Ser Gly Gly Val Met Leu
465                 470                 475                 480
Ile Trp Ser Lys Thr Thr Val Glu Pro Thr Pro Gly Lys Gly Pro Lys
                485                 490                 495
Val Tyr Arg Arg Lys His Gln Glu Leu Gln Ala Met Gln Met Glu Leu
            500                 505                 510
Gln Ser Pro Glu Tyr Lys Leu Ser Lys Leu Arg Thr Ser Thr Ile Met
        515                 520                 525
Thr Asp Tyr Asn Pro Asn Tyr Cys Phe Ala Gly Lys Thr Ser Ser Ile
        530                 535                 540
Ser Asp Leu Lys Glu Val Pro Arg Lys Asn Ile Thr Leu Ile Arg Gly
545                 550                 555                 560
Leu Gly His Gly Ala Phe Gly Glu Val Tyr Glu Gly Gln Val Ser Gly
                565                 570                 575
Met Pro Asn Asp Pro Ser Pro Leu Gln Val Ala Val Lys Thr Leu Pro
            580                 585                 590
```

-continued

```
Glu Val Cys Ser Glu Gln Asp Glu Leu Asp Phe Leu Met Glu Ala Leu
        595                 600                 605
Ile Ile Ser Lys Phe Asn His Gln Asn Ile Val Arg Cys Ile Gly Val
610                 615                 620
Ser Leu Gln Ser Leu Pro Arg Phe Ile Leu Leu Glu Leu Met Ala Gly
625                 630                 635                 640
Gly Asp Leu Lys Ser Phe Leu Arg Glu Thr Arg Pro Arg Pro Ser Gln
                645                 650                 655
Pro Ser Ser Leu Ala Met Leu Asp Leu Leu His Val Ala Arg Asp Ile
                660                 665                 670
Ala Cys Gly Cys Gln Tyr Leu Glu Glu Asn His Phe Ile His Arg Asp
        675                 680                 685
Ile Ala Ala Arg Asn Cys Leu Leu Thr Cys Pro Gly Pro Gly Arg Val
        690                 695                 700
Ala Lys Ile Gly Asp Phe Gly Met Ala Arg Asp Ile Tyr Arg Ala Ser
705                 710                 715                 720
Tyr Tyr Arg Lys Gly Gly Cys Ala Met Leu Pro Val Lys Trp Met Pro
                725                 730                 735
Pro Glu Ala Phe Met Glu Gly Ile Phe Thr Ser Lys Thr Asp Thr Trp
                740                 745                 750
Ser Phe Gly Val Leu Leu Trp Glu Ile Phe Ser Leu Gly Tyr Met Pro
        755                 760                 765
Tyr Pro Ser Lys Ser Asn Gln Glu Val Leu Glu Phe Val Thr Ser Gly
        770                 775                 780
Gly Arg Met Asp Pro Pro Lys Asn Cys Pro Gly Pro Val Tyr Arg Ile
785                 790                 795                 800
Met Thr Gln Cys Trp Gln His Gln Pro Glu Asp Arg Pro Asn Phe Ala
                805                 810                 815
Ile Ile Leu Glu Arg Ile Glu Tyr Cys Thr Gln Asp Pro Asp Val Ile
                820                 825                 830
Asn Thr Ala Leu Pro Ile Glu Tyr Gly Pro Leu Val Glu Glu Glu Glu
        835                 840                 845
Lys Val Pro Val Arg Pro Lys Asp Pro Glu Gly Val Pro Pro Leu Leu
        850                 855                 860
Val Ser Gln Gln Ala Lys Arg Glu Glu Arg Ser Pro Ala Ala Pro
865                 870                 875                 880
Pro Pro Leu Pro Thr Thr Ser Ser Gly Lys Ala Ala Lys Lys Pro Thr
                885                 890                 895
Ala Ala Glu Val Ser Val Arg Val Pro Arg Gly Pro Ala Val Glu Gly
                900                 905                 910
Gly His Val Asn Met Ala Phe Ser Gln Ser Asn Pro Pro Ser Glu Leu
        915                 920                 925
His Arg Val His Gly Ser Arg Asn Lys Pro Thr Ser Leu Trp Asn Pro
        930                 935                 940
Thr Tyr Gly Ser Trp Phe Thr Glu Lys Pro Thr Lys Lys Asn Asn Pro
945                 950                 955                 960
Ile Ala Lys Lys Glu Pro His Glu Arg Gly Asn Leu Gly Leu Glu Gly
                965                 970                 975
Ser Cys Thr Val Pro Pro Asn Val Ala Thr Gly Arg Leu Pro Gly Ala
                980                 985                 990
Ser Leu Leu Leu Glu Pro Ser Ser  Leu Thr Ala Asn Met Lys Glu Val
        995                 1000                1005
```

```
Pro Leu Phe Arg Leu Arg His Phe Pro Cys Gly Asn Val Asn Tyr
    1010                1015            1020

Gly Tyr Gln Gln Gln Gly Leu Pro Leu Glu Ala Ala Thr Ala Pro
    1025            1030            1035

Gly Ala Gly His Tyr Glu Asp Thr Ile Leu Lys Ser Lys Asn Ser
    1040            1045            1050

Met Asn Gln Pro Gly Pro
    1055
```

<210> SEQ ID NO 3
<211> LENGTH: 23
<212> TYPE: DNA
<213> ORGANISM: Homo sapiens

<400> SEQUENCE: 3
aagcagtggt atcaacgcag agt                                          23

<210> SEQ ID NO 4
<211> LENGTH: 24
<212> TYPE: DNA
<213> ORGANISM: Homo sapiens

<400> SEQUENCE: 4
gtgcagtgtt tagcattctt gggg                                         24

<210> SEQ ID NO 5
<211> LENGTH: 24
<212> TYPE: DNA
<213> ORGANISM: Homo sapiens

<400> SEQUENCE: 5
tcttgccagc aaagcagtag ttgg                                         24

<210> SEQ ID NO 6
<211> LENGTH: 20
<212> TYPE: DNA
<213> ORGANISM: Homo sapiens

<400> SEQUENCE: 6
gtcagtggtg gacctgacct                                              20

<210> SEQ ID NO 7
<211> LENGTH: 20
<212> TYPE: DNA
<213> ORGANISM: Homo sapiens

<400> SEQUENCE: 7
tgagcttgac aaagtggtcg                                              20

<210> SEQ ID NO 8
<211> LENGTH: 247
<212> TYPE: DNA
<213> ORGANISM: Homo sapiens

<400> SEQUENCE: 8
gtgcagtgtt tagcattctt ggggaatgga gatgttctta ctggagactc aggtggagtc    60
atgcttatat ggagcaaaac tactgtagag cccacacctg ggaaggacc taaagtgtac    120 cgccggaagc accaggagct gcaagccatg cagatggagc tgcagagccc tgagtacaag    180
ctgagcaagc tccgcacctc gaccatcatg accgactaca ccccaacta ctgctttgct    240 ggcaaga                                                            247

```
<210> SEQ ID NO 9
<211> LENGTH: 35
<212> TYPE: DNA
<213> ORGANISM: Artificial
<220> FEATURE:
<223> OTHER INFORMATION: Description of Artificial Sequence: an
      artificially synthesized primer sequence

<400> SEQUENCE: 9
ccctgcaagt ggctgtgatg acgctgcctg aagtg                          35

<210> SEQ ID NO 10
<211> LENGTH: 35
<212> TYPE: DNA
<213> ORGANISM: Artificial
<220> FEATURE:
<223> OTHER INFORMATION: Description of Artificial Sequence: an
      artificially synthesized primer sequence

<400> SEQUENCE: 10
cacttcaggc agcgtcatca cagccacttg caggg                          35
```

DI(ARYLAMINO)ARYL COMPOUNDS

This application is the U.S. national phase of International Application No. PCT/JP2008/062188 filed 4 Jul. 2008, which designated the U.S. and claims priority to Japan Application No. 2007-178795 filed 6 Jul. 2007, the entire contents of each of which are hereby incorporated by reference.

TECHNICAL FIELD

The present invention relates to di(arylamino)aryl compounds useful as active ingredients in pharmaceutical compositions, particularly pharmaceutical compositions for cancer therapy.

BACKGROUND ART

Lung cancer is caused by disordered growth of tracheal, bronchial and/or alveolar cells as a result of losing their normal functions. The number of people who die of lung cancer is the largest of the total of cancer deaths (17%), and worldwide about 1.3 million people die of lung cancer each year.

Treatment for lung cancer is divided into three major categories: surgical operation (surgical therapy), anticancer agent (chemotherapy) and radioactive irradiation (radiation therapy), but the effectiveness of treatment will vary depending on the tissue type of lung cancer. For example, although a definite diagnosis of lung cancer is made by a pathologist based on his cytohistopathological diagnosis on a microscope specimen, small cell lung cancer, which constitutes about 20% of lung cancer cases, has often reached an advanced stage at the time of discovery because it generally has a high grade of malignancy and will rapidly grow and spread and will often metastasize to other organs. For this reason, chemotherapy and/or radiation therapy is often used for treatment of this cancer, but the prognosis is poor because small cell lung cancer will often recur although it is relatively sensitive to these therapies. On the other hand, in the case of non-small cell lung cancer, which constitutes the remainder of about 80%, surgical therapy is considered for use until a certain stage, but there is little opportunity to use surgical operation in the subsequent stages where chemotherapy and/or radiation therapy is mainly used for treatment.

Thus, in either type of lung cancer, chemotherapy is an important option for treatment.

EGFR is a receptor tyrosine kinase and, when activated upon ligand binding, causes phosphorylation of tyrosine residues in the receptor's intracellular region and subsequently induces successive activation of cytoplasmic proteins, thereby facilitating cell differentiation and growth (Clinical Cancer Research, 12(18), 2006, p. 5268-5272). EGFR is found to be overexpressed in various malignant tumors (Journal of Cellular Physiology, 194(1), 2003, p. 13-19), and EGFR overexpression is shown to be a factor responsible for bad prognosis in cancer (Annals of Oncology, 15(1), 2004, p. 28-32, Journal of Clinical Oncology, 21(20), 2003, p. 3798-3807). In recent years, EGFR inhibitors have been observed to produce a high clinical effect on a limited population of non-small cell lung cancer patients, and it has been reported that active mutation of EGFR existed in such a patient segment (N. Engl. J. Med. 350, 2004, p. 2129-2139, Science 304, 2004, p. 1497-1500, Proc. Natl. Acad. Sci. 101, 2004, p. 13306-13311). As a result of a conformational change in the ATP-binding site of EGFR, this mutant EGFR is constitutively activated even in the absence of ligand stimulation, and thereby causes canceration of cells. In cancer cells having this mutant EGFR, it is known that they develop apoptosis by the action of gefitinib or erlotinib known as an EGFR inhibitor, resulting in a reduction of the tumor size (Nat. Rev. Cancer 7, 2007, p. 169-181).

ALK (Anaplastic Lymphoma Kinase) is a receptor tyrosine kinase and is a protein having a transmembrane region in the middle part, flanked by a tyrosine kinase region on the carboxyl-terminal side and an extracellular region on the amino-terminal side. It has previously been reported that full-length ALK is expressed in several types of cancer cells of ectodermal origin (e.g., neuroblastoma, glioblastoma, breast cancer, melanoma) (Non-patent Document 1). In some cases of human malignant lymphoma, it has also been reported that the ALK gene is fused with another gene (e.g., NPM gene, CLTCL gene, TFG gene) as a result of chromosomal translocation, and thereby produces an oncogenic fusion tyrosine kinase (Science, vol. 263, p. 1281, 1994; Blood, vol. 86, p. 1954, 1995; Blood, vol. 95, p. 3204, 2000; Blood, vol. 94, p. 3265, 1999). Also in the case of inflammatory myofibroblastic tumor, it is known that the ALK gene is fused with another gene (e.g., CARS gene, SEC31L1 gene) as a result of chromosomal translocation, and thereby produces a fusion tyrosine kinase (Laboratory Investigation, a journal of technical methods and pathology, vol. 83, p. 1255, 2003; International Journal of Cancer, vol. 118, p. 1181, 2006). Most of partner molecules (including EML4 (echinoderm microtubule associated protein like-4)) to be fused with ALK have a complex-forming domain, and the generated fusion products per se also appear to form complexes. This complex formation would induce uncontrol of ALK tyrosine kinase activity and abnormal activation of intracellular signals, thereby causing canceration (Cellular and Molecular Life Science, vol. 61, p. 2939, 2004; Nature Reviews Cancer, vol. 8, p. 11, 2008).

Moreover, recent reports have indicated the presence of a TPM4-ALK fusion protein in esophageal cancer by proteomics analysis procedures (World Journal of Gastroenterology, vol. 12, p. 7104, 2006; Journal Molecular Medicine, vol. 85, p. 863, 2007). Further, after the priority date of the present application, a fusion gene between EML4 and ALK was confirmed in specimens from lung cancer patients, and it was also reported that this EML4-ALK fusion gene has tumorgenicity and is a causal gene of cancer, and that inhibitors against its kinase activity suppress the growth of various cells where the EML4-ALK fusion protein is expressed (Patent Document 1 and Non-patent Document 2). These documents further show that inhibitors of the EML4-ALK fusion protein are useful as therapeutic agents for lung cancer in EML4-ALK polynucleotide-positive lung cancer patients.

Gefitinib and erlotinib mentioned above, which are EGFR inhibitors and are known as useful therapeutic agents for non-small cell lung cancer, have the following chemical structures.

[Formula 1]

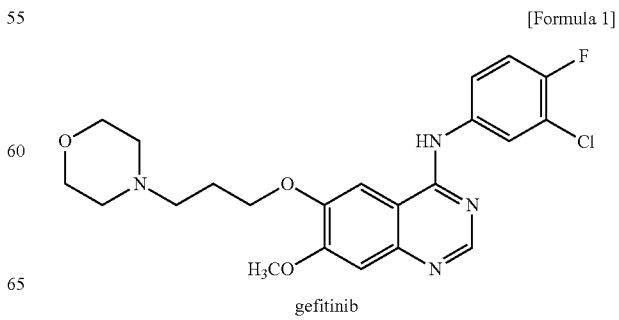

gefitinib

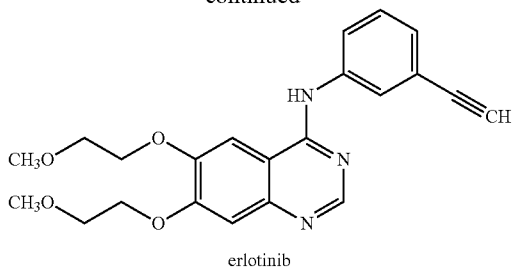

erlotinib

Moreover, Patent Document 1 published after the priority date of the present application shows the following compounds (each being known as an ALK inhibitor) as examples of compounds having inhibitory activity against the EML4-ALK fusion protein, and it also discloses the actual values of their inhibitory activity against the EML4-ALK fusion protein (Patent Document 1). It should be noted that abbreviations for the following compounds are those used in Patent Document 1.

[Formula 2]

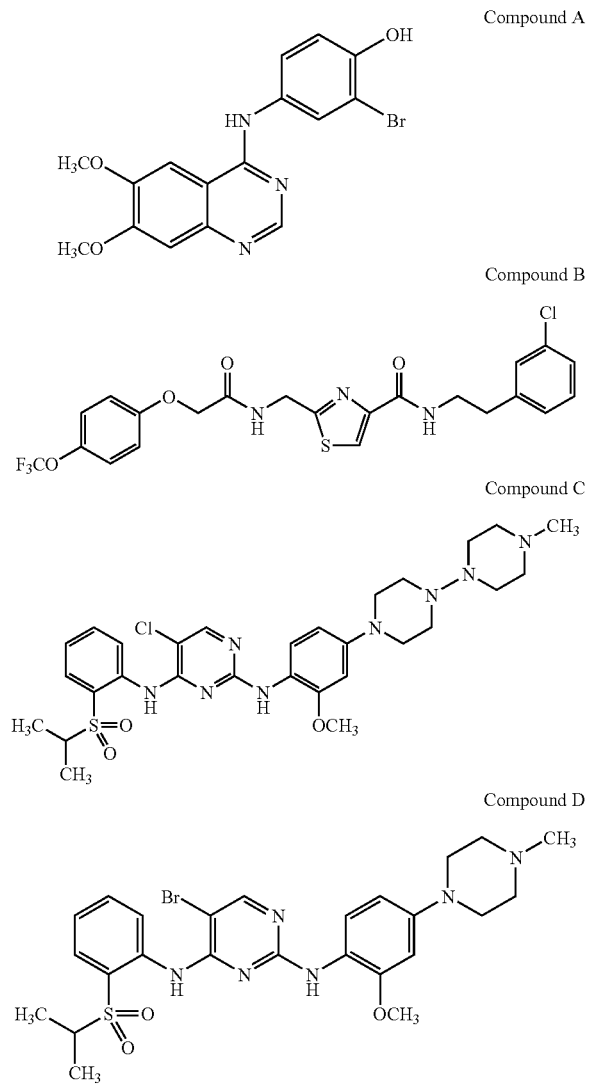

Their respective chemical names are: 4-[(3'-bromo-4'-hydroxyphenyl)amino]-6,7-dimethoxyquinazoline (also called WHI-P154) for compound A; N-[2-(3-chlorophenyl)ethyl]-2-[({[4-(trifluoromethoxy)phenoxy]acetyl}amino)methyl]-1,3-thiazole-4-carboxamide for compound B; 5-chloro-$N^4$-[2-(isopropylsulfonyl)phenyl]-$N^2$-{2-methoxy-4-[4-(4-methylpiperazin-1-yl)piperidin-1-yl]phenyl}pyrimidine-2,4-diamine for compound C; and 2-[(5-bromo-2-{[2-methoxy-4-(4-methylpiperazin-1-yl)phenyl]amino}pyrimidin-4-yl)amino]-N-methylbenzenesulfonamide for compound D.

Moreover, in ALK fusion protein-expressing lymphoma cells, a compound having ALK inhibitory activity, WHI-P154, has been reported to inhibit cell growth and induce apoptosis (Non-patent Document 3). It should be noted that WHI-P154 is the same as compound A shown above.

Likewise, TAE684 represented by the following formula is known as an inhibitor of a fusion protein from a fusion gene between NPM gene and ALK gene. It should be noted that this compound is the same as compound C shown above.

[Formula 3]

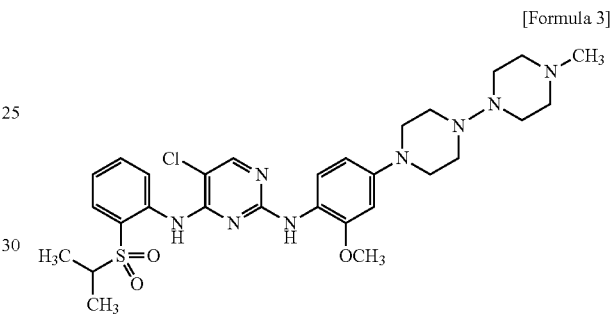

TAE684 structurally differs from the compounds of the present invention in that the center ring sandwiched between two —NH groups is a chloro-substituted pyrimidine ring.

Moreover, TAE684 has been reported to inhibit the spread of anaplastic large cell lymphoma (ALCL) by its inhibitory activity against the NPM-ALK fusion protein (Non-patent Document 4). On the other hand, although it is described that compounds including TAE684 have inhibitory activity against focal adhesion kinase (FAK) and are thereby useful for preventing and/or treating non-small cell lung cancer and small cell lung cancer, there is no information about actual therapeutic effects on these lung cancers (Patent Document 2).

After the priority date of the present application, further reports were issued showing that EML4-ALK is expressed in non-small cell lung cancer cells (NCI-H2228), that TFG-ALK is expressed in non-small cell lung cancer patients, and that TAE684 inhibits the growth of non-small cell lung cancer cells (NCI-H2228) (Patent Document 1 and Non-patent Documents 5 and 6).

The supplemental data of Non-patent Document 6 shows that TAE684 has little growth inhibitory activity (inhibition rate: 7.5%) on HCC-827 cells (mutant EGFR protein-expressing cells) under the conditions shown in the document.

Further, after the priority date of the present application, a more recent report has indicated that TAE684 shows growth inhibitory activity on EGFR (L858R mutation)/BaF cells (Non-patent Document 7).

Patent Document 1: European Patent Publication No. EP 1914240

Patent Document 2: International Publication No. WO 2004/080980

Non-patent Document 1: International Journal of Cancer, vol. 100, p. 49, 2002

Non-patent Document 2: Nature, vol. 448, no. 2, p. 561, 2007

Non-patent Document 3: Laboratory Investigation, vol. 85, p. 1544, 2005

Non-patent Document 4: Proceedings of the National Academy of Science, vol. 104, no. 1, p. 270, 2007

Non-patent Document 5: Cell, vol. 131, p. 1190, 2007

Non-patent Document 6: Proceedings of the National Academy of Science, vol. 104, no. 50, p. 19936, 2007

Non-patent Document 7: American Association for Cancer Research Annual Meeting 2008 Proceedings, vol. 49, April 2008, p. 560, #2373

DISCLOSURE OF THE INVENTION

Problems to be Solved by the Invention

The present invention provides a compound which is useful as an active ingredient in pharmaceutical compositions, particularly pharmaceutical compositions for cancer therapy, and which can be used more safely as an active ingredient in pharmaceutical compositions.

Means for Solving the Problem

As a result of extensive and intensive studies on compounds useful as active ingredients in pharmaceutical compositions for cancer therapy, the inventors of the present invention have found that the di(arylamino)aryl compound of the present invention has excellent inhibitory activity against the kinase activity of EML4-ALK fusion proteins and mutant EGFR proteins, and is useful as an active ingredient in pharmaceutical compositions for cancer therapy. This finding led to the completion of the present invention.

Namely, the present invention relates to a compound of formula (I) or a salt thereof, as well as a pharmaceutical composition comprising a compound of formula (I) or a salt thereof and an excipient.

[Formula 4]

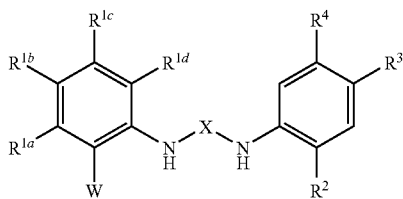
(I)

(wherein the symbols are as defined below:
—X— represents
(1) a group of formula (II), or
(2) a group of formula (III)

[Formula 5]

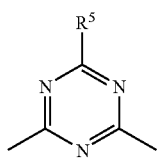
(II)

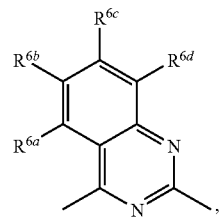
(III)

—$R^5$ represents
(1) —H,
(2) —OH,
(3) halogen,
(4) lower alkyl which may be substituted with one or more halogens,
(5) O-lower alkyl which may be substituted with one or more halogens,
(6) —S-lower alkyl,
(7) cyano,
(8) amino which may be substituted with one or two lower alkyls, or
(9) cyclic amino which may be substituted with one or more groups selected from the group consisting of lower alkyl, oxo, —OH, —O-lower alkyl, and amino which may be substituted with one or two lower alkyls (provided that the triazine ring to which —$R^5$ is attached is attached to the nitrogen atom in the cyclic amino),
—$R^{6a}$, —$R^{6b}$, —$R^{6c}$ and —$R^{6d}$, which may be the same or different, each represent
(1) —H,
(2) halogen,
(3) lower alkyl which may be substituted with one or more halogens,
(4) O-lower alkyl which may be substituted with one or more halogens,
(5) —S-lower alkyl, or
(6) cyano,
—W represents
(1) —H,
(2) halogen,
(3) lower alkyl which may be substituted with one or more halogens,
(4) O-lower alkyl which may be substituted with one or more halogens,
(5) —S-lower alkyl,
(6) cyano, or
(7) a group represented by -A-B,
-A- represents
(1) —S(=O)$_2$—, or
(2) —C(=O)—,
—B represents
(1) lower alkyl,
(2) amino which may be substituted with one or two $R^{ZA}$,
(3) cyclic amino (provided that -A- is attached to the nitrogen atom in the cyclic amino), or
(4) cycloalkyl,
$R^{ZA}$ represents
(1) lower alkyl, or
(2) cycloalkyl,
—$R^{1a}$, —$R^{1b}$, —$R^{1c}$ and —$R^{1d}$, which may be the same or different, each represent
(1) —H,
(2) halogen,
(3) lower alkyl which may be substituted with one or more halogens, (4) O-lower alkyl which may be substituted with one or more halogens,
(5) —S-lower alkyl, or
(6) cyano,
or alternatively
if —W is —H, one of —$R^{1a}$ or —$R^{1b}$ is a group represented by -A-B, and the other of —$R^{1a}$ or —$R^{1b}$, and —$R^{1c}$ and —$R^{1d}$, which may be the same or different, each represent any of (1) to (6) shown above,
—$R^2$ represents
(1) —H,
(2) —OH,
(3) halogen,
(4) lower alkyl which may be substituted with one or more halogens,
(5) O-lower alkyl which may be substituted with one or more halogens,
(6) —S-lower alkyl, or
(7) cyano,
—$R^3$ and —$R^4$ are as follows:
(1) one of them represents —H, and the other represents cyclic amino which may be substituted with one or more groups selected from the group consisting of $R^{ZB}$, oxo, —OH, —O-lower alkyl, and amino which may be substituted with one or two $R^{ZB}$ (provided that the benzene ring to which —$R^3$ or —$R^4$ is attached is attached to the nitrogen atom in the cyclic amino),
(2) one of them represents —H, and the other represents a group represented by formula (IV) (provided that -$L^1$ and -$L^2$ taken together with their adjacent carbon atom represent a non-aromatic heterocyclic ring, wherein if the non-aromatic heterocyclic ring has a nitrogen atom, this nitrogen atom may be substituted with $R^{ZC}$)

[Formula 6]

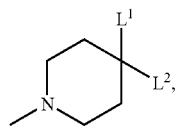

(IV)

(3) one of them represents —H, and the other represents a group represented by —Y—Z, or
(4) —$R^3$ and —$R^4$ taken together with their adjacent carbon atom represent a non-aromatic heterocyclic ring (provided that if the non-aromatic heterocyclic ring has a nitrogen atom, this nitrogen atom may be substituted with —$CO_2$-(lower alkyl which may be substituted with one or more halogens)),
$R^{ZB}$ represents
(1) lower alkyl which may be substituted with one or more groups selected from the group consisting of oxo, —OH, —O-lower alkyl, —S-lower alkyl, halogen and amino which may be substituted with one or two lower alkyls,
$R^{ZC}$ represents
(1) lower alkyl, or
(2) —$CO_2$-(lower alkyl which may be substituted with phenyl),
—Y— represents
(1) piperidine-1,4-diyl which may be substituted with one or more groups selected from the group consisting of lower alkyl and oxo (provided that the benzene ring to which —$R^3$ or —$R^4$ is attached is attached to the nitrogen atom at the 1-position of the piperidine, and —Z is attached to the carbon atom at the 4-position of the piperidine),
(2) piperazine-1,4-diyl which may be substituted with one or more groups selected from the group consisting of lower alkyl and oxo,
(3) pyrrolidine-1,3-diyl which may be substituted with one or more groups selected from the group consisting of lower alkyl and oxo (provided that the benzene ring to which —$R^3$ or —$R^4$ is attached is attached to the nitrogen atom at the 1-position of the pyrrolidine, and —Z is attached to the carbon atom at the 3-position of the pyrrolidine),
(4) azetidine-1,3-diyl which may be substituted with one or more groups selected from the group consisting of lower alkyl and oxo (provided that the benzene ring to which —$R^3$ or —$R^4$ is attached is attached to the nitrogen atom at the 1-position of the azetidine, and —Z is attached to the carbon atom at the 3-position of the azetidine),
(5) —O—, or
(6) —N($R^{ZD}$)—,
—$R^{ZD}$ represents
(1) —H, or
(2) lower alkyl,
—Z represents
(1) cyclic amino which may be substituted with one or more groups selected from the group consisting of —$R^{ZE}$, oxo, —OH, —O-lower alkyl, phenyl which may be substituted with halogen, piperidin-1-yl, pyrimidin-2-yl, and amino which may be substituted with one or two lower alkyls,
(2) aryl which may be substituted with one or more groups selected from the group consisting of halogen, lower alkyl which may be substituted with one or more halogens, —O-lower alkyl, and cyano,
(3) cycloalkyl which may be substituted with one or more groups selected from the group consisting of halogen, lower alkyl which may be substituted with one or more halogens, —O-lower alkyl, cyano, and oxo,
(4) an aromatic heterocyclic ring which may be substituted with one or more groups selected from the group consisting of halogen, lower alkyl which may be substituted with one or more halogens, —OH, —O-lower alkyl, and cyano, or
(5) a group of formula (V)

[Formula 7]

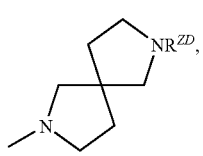

(V)

and
—$R^{ZE}$ represents
(1) lower alkyl which may be substituted with one or more groups selected from the group consisting of oxo, —OH, phenyl which may be substituted with halogen, and amino which may be substituted with one or two lower alkyls).

Unless otherwise specified, when symbols used in one chemical formula are also used in another chemical formula, the same symbols have the same meanings.

The present invention also relates to an inhibitor against the kinase activity of mutant EGFR proteins, which comprises a compound of formula (I) or a salt thereof. In a certain embodiment, the present invention relates to an inhibitor against the kinase activity of EML4-ALK fusion proteins and mutant EGFR proteins.

Moreover, the present invention also relates to a pharmaceutical composition for cancer therapy, which comprises a compound of formula (I) or a salt thereof, i.e., a therapeutic agent for cancer, which comprises a compound of formula (I) or a salt thereof.

Moreover, the present invention also relates to the use of a compound of formula (I) or a salt thereof for the manufacture of a pharmaceutical composition for cancer therapy, the use of a compound of formula (I) or a salt thereof for cancer therapy, as well as a method for cancer therapy, which comprises administering an effective amount of a compound of formula (I) or a salt thereof to a patient.

Advantages of the Invention

The compound of formula (I) or a salt thereof has inhibitory activity against the kinase activity of EML4-ALK fusion proteins and mutant EGFR proteins, as well as growth inhibitory activity against human non-small cell lung cancer cell lines NCI-H2228 and HCC827, and can be used as an active ingredient in pharmaceutical compositions for preventing and/or treating cancer, such as lung cancer in one embodiment, non-small cell lung cancer or small cell lung cancer in another embodiment, EML4-ALK fusion polynucleotide-positive and/or mutant EGFR polynucleotide-positive cancer in yet another embodiment, EML4-ALK fusion polynucleotide-positive and/or mutant EGFR polynucleotide-positive lung cancer in yet another embodiment, or EML4-ALK fusion polynucleotide-positive and/or mutant EGFR polynucleotide-positive non-small cell lung cancer in yet another embodiment.

BEST MODE FOR CARRYING OUT THE INVENTION

Figure 1:
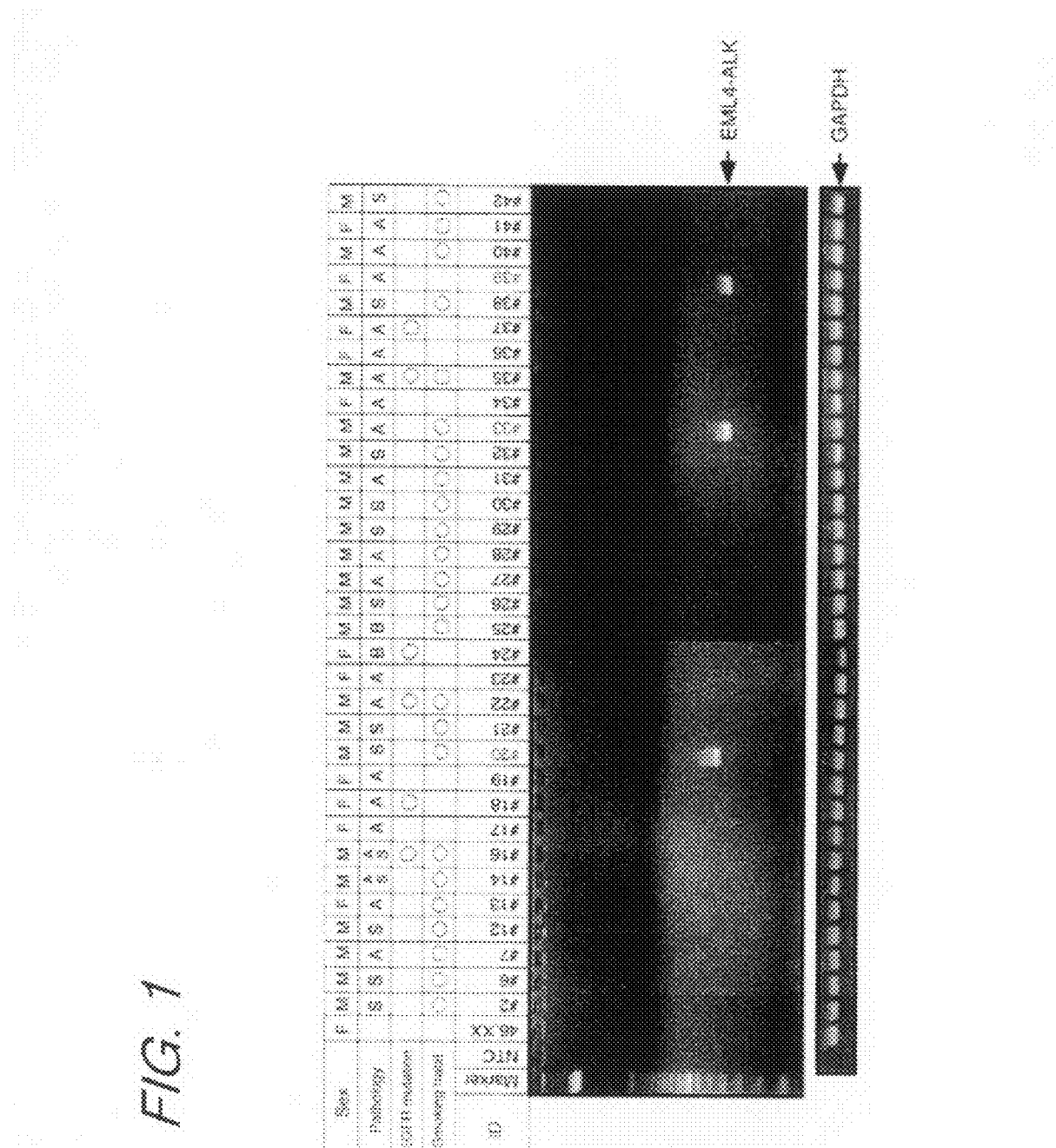
FIG. 1 shows the results of the screening for EML4-ALK fusion polynucleotide in specimens of lung cancer patients. Lane "46, XX" shows the result of using peripheral monocytes of a normal healthy female subject, and "ID #2" to "ID #42" show the result of using samples obtained from excised specimens from lung cancer patients. In addition, lane "NTC" shows the result without added substrate cDNA. Lane "marker" is the lane where the size marker DNA was electrophoresed (upper section). The results of amplification of GAPDH cDNA are shown in the lower section. Sex (M, male; F, female), pathology (S, squamous cell carcinoma; A, adenocarcinoma; AS, adenosquamous carcinoma; B, bronchioloalveolar carcinoma) and the presence or absence of EGFR mutation and the presence or absence of smoking history are shown in the upper part of the figure.

The present invention provides the following.
[1] A compound of formula (I) or a salt thereof:

[Formula 8]

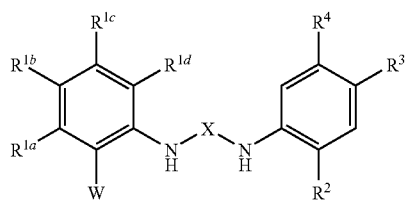

(wherein the symbols are as defined below:
—X— represents
(1) a group of formula (II), or
(2) a group of formula (III)

[Formula 9]

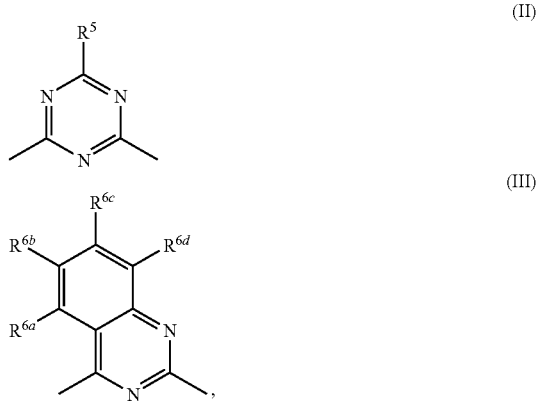

—$R^5$ represents
(1) —H,
(2) —OH,
(3) halogen,
(4) lower alkyl which may be substituted with one or more halogens,
(5) O-lower alkyl which may be substituted with one or more halogens,
(6) —S-lower alkyl,
(7) cyano,
(8) amino which may be substituted with one or two lower alkyls, or
(9) cyclic amino which may be substituted with one or more groups selected from the group consisting of lower alkyl, oxo, —OH, —O-lower alkyl, and amino which may be substituted with one or two lower alkyls (provided that the triazine ring to which —$R^5$ is attached is attached to the nitrogen atom in the cyclic amino),
—$R^{6a}$, —$R^{6b}$, —$R^{6c}$ and —$R^{6d}$, which may be the same or different, each represent
(1) —H,
(2) halogen,
(3) lower alkyl which may be substituted with one or more halogens,
(4) O-lower alkyl which may be substituted with one or more halogens,
(5) —S-lower alkyl, or
(6) cyano,
—W represents
(1) —H,
(2) halogen,
(3) lower alkyl which may be substituted with one or more halogens,
(4) O-lower alkyl which may be substituted with one or more halogens,
(5) —S-lower alkyl,
(6) cyano, or
(7) a group represented by -A-B,
-A- represents
(1) —S(=O)$_2$—, or
(2) —C(=O)—,
—B represents
(1) lower alkyl,
(2) amino which may be substituted with one or two $R^{ZA}$,
(3) cyclic amino (provided that -A- is attached to the nitrogen atom in the cyclic amino), or
(4) cycloalkyl, $R^{ZA}$ represents (1) lower alkyl, or (2) cycloalkyl, $—R^{1a}$, $—R^{1b}$, $—R^{1c}$ and $—R^{1d}$, which may be the same or different, each represent (1) —H, (2) halogen, (3) lower alkyl which may be substituted with one or more halogens, (4) O-lower alkyl which may be substituted with one or more halogens, (5) —S-lower alkyl, or (6) cyano, or alternatively if —W is —H, one of —$R^{1a}$ or —$R^{1b}$ is a group represented by -A-B, and the other of —$R^{1a}$ or —$R^{1b}$, and —$R^{1c}$ and —$R^{1d}$, which may be the same or different, each represent any of (1) to (6) shown above, —$R^2$ represents (1) —H, (2) —OH, (3) halogen, (4) lower alkyl which may be substituted with one or more halogens, (5) O-lower alkyl which may be substituted with one or more halogens, (6) —S-lower alkyl, or (7) cyano, —$R^3$ and —$R^4$ are as follows:

(1) one of them represents —H, and the other represents cyclic amino which may be substituted with one or more groups selected from the group consisting of $R^{ZB}$, oxo, —OH, —O-lower alkyl, and amino which may be substituted with one or two $R^{ZB}$ (provided that the benzene ring to which —$R^3$ or —$R^4$ is attached is attached to the nitrogen atom in the cyclic amino), (2) one of them represents —H, and the other represents a group represented by formula (IV) (provided that -$L^1$ and -$L^2$ taken together with their adjacent carbon atom represent a non-aromatic heterocyclic ring, wherein if the non-aromatic heterocyclic ring has a nitrogen atom, this nitrogen atom may be substituted with $R^{ZC}$)

[Formula 10]

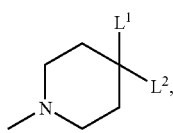

(IV)

(3) one of them represents —H, and the other represents a group represented by —Y—Z, or (4) —$R^3$ and —$R^4$ taken together with their adjacent carbon atom represent a non-aromatic heterocyclic ring (provided that if the non-aromatic heterocyclic ring has a nitrogen atom, this nitrogen atom may be substituted with —$CO_2$-(lower alkyl which may be substituted with one or more halogens)), $R^{ZB}$ represents (1) lower alkyl which may be substituted with one or more groups selected from the group consisting of oxo, —OH, —O-lower alkyl, —S-lower alkyl, halogen and amino which may be substituted with one or two lower alkyls, $R^{ZC}$ represents (1) lower alkyl, or (2) —$CO_2$-(lower alkyl which may be substituted with phenyl), —Y— represents (1) piperidine-1,4-diyl which may be substituted with one or more groups selected from the group consisting of lower alkyl and oxo (provided that the benzene ring to which —$R^3$ or —$R^4$ is attached is attached to the nitrogen atom at the 1-position of the piperidine, and —Z is attached to the carbon atom at the 4-position of the piperidine), (2) piperazine-1,4-diyl which may be substituted with one or more groups selected from the group consisting of lower alkyl and oxo, (3) pyrrolidine-1,3-diyl which may be substituted with one or more groups selected from the group consisting of lower alkyl and oxo (provided that the benzene ring to which —$R^3$ or —$R^4$ is attached is attached to the nitrogen atom at the 1-position of the pyrrolidine, and —Z is attached to the carbon atom at the 3-position of the pyrrolidine), (4) azetidine-1,3-diyl which may be substituted with one or more groups selected from the group consisting of lower alkyl and oxo (provided that the benzene ring to which —$R^3$ or —$R^4$ is attached is attached to the nitrogen atom at the 1-position of the azetidine, and —Z is attached to the carbon atom at the 3-position of the azetidine), (5) —O—, or (6) —N(—$R^{ZD}$)—, —$R^{ZD}$ represents (1) —H, or (2) lower alkyl, —Z represents (1) cyclic amino which may be substituted with one or more groups selected from the group consisting of —$R^{ZE}$, oxo, —OH, —O-lower alkyl, phenyl which may be substituted with halogen, piperidin-1-yl, pyrimidin-2-yl, and amino which may be substituted with one or two lower alkyls, (2) aryl which may be substituted with one or more groups selected from the group consisting of halogen, lower alkyl which may be substituted with one or more halogens, —O-lower alkyl, and cyano, (3) cycloalkyl which may be substituted with one or more groups selected from the group consisting of halogen, lower alkyl which may be substituted with one or more halogens, —O-lower alkyl, cyano, and oxo, (4) an aromatic heterocyclic ring which may be substituted with one or more groups selected from the group consisting of halogen, lower alkyl which may be substituted with one or more halogens, —OH, —O-lower alkyl, and cyano, or (5) a group of formula (V)

[Formula 11]

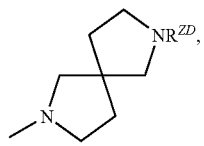

(V)

and

—$R^{ZE}$ represents (1) lower alkyl which may be substituted with one or more groups selected from the group consisting of oxo, —OH, phenyl which may be substituted with halogen, and amino which may be substituted with one or two lower alkyls).

[2] The compound according to [1] or a salt thereof, wherein
—$R^5$ represents
(1) —H,
(2) —OH,
(3) halogen,
(4) lower alkyl,
(5) amino which may be substituted with one or two lower alkyls, or
(6) cyclic amino (provided that the triazine ring to which —$R^5$ is attached is attached to the nitrogen atom in the cyclic amino),
—$R^{6a}$, —$R^{6b}$, —$R^{6c}$ and —$R^{6d}$, which may be the same or different, each represent
(1) —H, or
(2) halogen,
—W represents
(1) —H,
(2) halogen, or
(3) a group represented by -A-B,
—$R^{1a}$, —$R^{1b}$, —$R^{1c}$ and —$R^{1d}$, which may be the same or different, each represent
(1) —H,
(2) halogen, or
(3) —O-lower alkyl,
or alternatively
if —W is —H, one of —$R^{1a}$ or —$R^{1b}$ is a group represented by -A-B, and the other of —$R^{1a}$ or —$R^{1b}$, and —$R^{1c}$ and —$R^{1d}$, which may be the same or different, each represent any of (1) to (3) shown above,
—$R^2$ represents
(1) —H,
(2) —OH,
(3) halogen,
(4) lower alkyl, or
(5) —O-lower alkyl,
—$R^3$ and —$R^4$ are as follows:
(1) one of them represents —H, and the other represents cyclic amino which may be substituted with one or more groups selected from the group consisting of $R^{ZB}$, oxo, —OH, and amino which may be substituted with one or two $R^{ZB}$ (provided that the benzene ring to which —$R^3$ or —$R^4$ is attached is attached to the nitrogen atom in the cyclic amino),
(2) one of them represents —H, and the other represents a group represented by formula (IV) (provided that -$L^1$ and -$L^2$ taken together with their adjacent carbon atom represent a non-aromatic heterocyclic ring, wherein if the non-aromatic heterocyclic ring has a nitrogen atom, this nitrogen atom may be substituted with $R^{ZC}$),
(3) one of them represents —H, and the other represents a group represented by —Y—Z, or
(4) —$R^3$ and —$R^4$ taken together with their adjacent carbon atom represent a non-aromatic heterocyclic ring (provided that if the non-aromatic heterocyclic ring has a nitrogen atom, this nitrogen atom may be substituted with —$CO_2$-(lower alkyl which may be substituted with one or more halogens)),
—Y— represents
(1) piperidine-1,4-diyl (provided that the benzene ring to which —$R^3$ or —$R^4$ is attached is attached to the nitrogen atom at the 1-position of the piperidine, and —Z is attached to the carbon atom at the 4-position of the piperidine),
(2) piperazine-1,4-diyl,
(3) pyrrolidine-1,3-diyl (provided that the benzene ring to which —$R^3$ or —$R^4$ is attached is attached to the nitrogen atom at the 1-position of the pyrrolidine, and —Z is attached to the carbon atom at the 3-position of the pyrrolidine),
(4) azetidine-1,3-diyl (provided that the benzene ring to which —$R^3$ or —$R^4$ is attached is attached to the nitrogen atom at the 1-position of the azetidine, and —Z is attached to the carbon atom at the 3-position of the azetidine),
(5) —O—, or
(6) —N($R^{ZD}$)—,
—Z represents
(1) cyclic amino which may be substituted with one or more groups selected from the group consisting of —$R^{ZE}$, oxo, —OH, phenyl which may be substituted with halogen, piperidin-1-yl, pyrimidin-2-yl, and amino which may be substituted with one or two lower alkyls,
(2) aryl,
(3) cycloalkyl,
(4) an aromatic heterocyclic ring, or
(5) a group of formula (V), and
—$R^{ZE}$ represents
(1) lower alkyl which may be substituted with one or more groups selected from the group consisting of oxo, —OH, phenyl, and amino which may be substituted with one or two lower alkyls.

[3] A compound of formula (VI) or a salt thereof:

[Formula 12]

(wherein the symbols are as defined below:
—$X^1$—: a group of formula (VII) or (VIII)

[Formula 13]

—$R^{15}$: —H, halogen, lower alkyl which may be substituted with one or more halogens, O-lower alkyl which may be substituted with one or more halogens, —S-lower alkyl, cyano, amino which may be substituted with one or two lower alkyls, or cyclic amino which may be substituted with one or more groups selected from the group consisting of lower alkyl, oxo, —OH, —O-lower alkyl, and amino which may be substituted with one or two lower alkyls, —R$^{16a}$, —R$^{16b}$, —R$^{16c}$ and —R$^{16d}$, which may be the same or different: —H, halogen, lower alkyl which may be substituted with one or more halogens, O-lower alkyl which may be substituted with one or more halogens, —S-lower alkyl, or cyano, —W$^1$: halogen, lower alkyl Which may be substituted with one or more halogens, O-lower alkyl which may be substituted with one or more halogens, —S-lower alkyl, cyano, or a group represented by -A$^1$-B$^1$, -A$^1$-: —S(═O)$_2$—, or —C(═O)—, —B$^1$: lower alkyl, or amino which may be substituted with one or two lower alkyls, —R$^{11a}$, —R$^{11b}$, —R$^{11c}$ and —R$^{11d}$, which may be the same or different: —H, halogen, lower alkyl which may be substituted with one or more halogens, O-lower alkyl which may be substituted with one or more halogens, —S-lower alkyl, or cyano, —R$^{12}$: halogen, lower alkyl which may be substituted with one or more halogens, O-lower alkyl which may be substituted with one or more halogens, —S-lower alkyl, or cyano, —R$^{13}$ and —R$^{14}$: one of them represents —H, and the other represents cyclic amino which may be substituted with one or more groups selected from the group consisting of lower alkyl, oxo, —OH, —O-lower alkyl, and amino which may be substituted with one or two lower alkyls, or a group represented by —Y$^1$—Z$^1$, —Y$^1$—: piperidine-1,4-diyl or piperazine-1,4-diyl, each of which may be substituted with one or more groups selected from the group consisting of lower alkyl and oxo, or —O— or —N(—R$^Y$)—, provided that if —R$^{13}$ or and —R$^{14}$ is —Y$^1$—Z$^1$ is piperidine-1,4-diyl, the benzene ring to which —R$^{13}$ or —R$^{14}$ is attached is attached to the nitrogen atom at the 1-position of the piperidine, and —Z$^1$ is attached to the carbon atom at the 4-position of the piperidine, and wherein —R$^Y$ represents —H or lower alkyl, and —Z$^1$: cyclic amino which may be substituted with one or more groups selected from the group consisting of lower alkyl, oxo, —OH, —O-lower alkyl, and amino which may be substituted with one or two lower alkyls; aryl which may be substituted with one or more groups selected from the group consisting of halogen, lower alkyl which may be substituted with one or more halogens, —O-lower alkyl, and cyano; cycloalkyl which may be substituted with one or more groups selected from the group consisting of halogen, lower alkyl which may be substituted with one or more halogens, —O-lower alkyl, cyano, and oxo; or an aromatic heterocyclic ring which may be substituted with one or more groups selected from the group consisting of halogen, lower alkyl which may be substituted with one or more halogens, —OH, —O-lower alkyl, and cyano).

[4]
The compound according to [1] or a salt thereof, wherein —R$^{1a}$, —R$^{1b}$, —R$^{1c}$ and —R$^{1d}$ are each —H, —R$^2$ is —O-methyl, and —R$^4$ is —H.

[5]
The compound according to [4] or a salt thereof, wherein —R$^3$ is 4-(4-methylpiperazin-1-yl)piperidin-1-yl.

[6]
The compound according to [5] or a salt thereof, wherein —X— is a group represented by formula (II), and —R$^5$ is —H.

[7]
The compound according to [6] or a salt thereof, wherein —W is a group represented by -A-B, -A- is —S(═O)$_2$—, and —B is isopropyl.

[8]
The compound according to [6] or a salt thereof, wherein —W is a group represented by -A-B, -A- is —S(═O)$_2$—, —B is amino which may be substituted with one or two R$^{ZA}$, and R$^{ZA}$ is methyl, ethyl, isopropyl or cyclopropyl.

[9]
The compound according to [1] or a salt thereof, wherein said compound is:
N-ethyl-2-{[4-({2-methoxy-4-[4-(4-methylpiperazin-1-yl)piperidin-1-yl]phenyl}amino)-1,3,5-triazin-2-yl]amino}benzenesulfonamide,
2-{[4-({2-methoxy-4-[4-(4-methylpiperazin-1-yl)piperidin-1-yl]phenyl}amino)-1,3,5-triazin-2-yl]amino}-N,N-dimethylbenzenesulfonamide,
N-isopropyl-2-{[4-({2-methoxy-4-[4-(4-methylpiperazin-1-yl)piperidin-1-yl]phenyl}amino)-1,3,5-triazin-2-yl]amino}benzenesulfonamide,
N-isopropyl-2-{[4-({2-methoxy-4-[4-(4-methylpiperazin-1-yl)piperidin-1-yl]phenyl}amino)-1,3,5-triazin-2-yl]amino}-N-methylbenzenesulfonamide,
2-{[4-({2-methoxy-4-[4-(4-methylpiperazin-1-yl)piperidin-1-yl]phenyl}amino)-1,3,5-triazin-2-yl]amino}-N-methylbenzenesulfonamide,
N-[2-(isopropylsulfonyl)phenyl]-N'-{2-methoxy-4-[3-(4-methylpiperazin-1-yl)azetidin-1-yl]phenyl}-1,3,5-triazine-2,4-diamine,
N$^4$-[2-(isopropylsulfonyl)phenyl]-N$^2$-{2-methoxy-4-[4-(4-methylpiperazin-1-yl)piperidin-1-yl]phenyl}quinazoline-2,4-diamine,
N-[2-(isopropylsulfonyl)phenyl]-N'-{2-methoxy-4-[4-(4-methylpiperazin-1-yl)piperidin-1-yl]phenyl}-1,3,5-triazine-2,4-diamine,
N-[2-(isopropylsulfonyl)phenyl]-N'-(2-methoxy-4-piperazin-1-ylphenyl)-1,3,5-triazine-2,4-diamine,
N-[2-(isopropylsulfonyl)phenyl]-N'-[2-methoxy-4-(1-methyl-1,8-diazaspiro[4.5]decan-8-yl)phenyl]-1,3,5-triazine-2,4-diamine,
N-[2-(isopropylsulfonyl)phenyl]-N'-[2-methoxy-4-(1-methyl-1,9-diazaspiro[5.5]undecan-9-yl)phenyl]-1,3,5-triazine-2,4-diamine,
N-cyclopropyl-2-{[4-({2-methoxy-4-[4-(4-methylpiperazin-1-yl)piperidin-1-yl]phenyl}amino)-1,3,5-triazin-2-yl]amino}benzenesulfonamide,
N-[2-(isopropylsulfonyl)phenyl]-N'-{2-methoxy-4-[methyl(1-methylpiperidin-4-yl)amino]phenyl}-1,3,5-triazine-2,4-diamine,
N-[2-(isopropylsulfonyl)phenyl]-N'-[2-methoxy-4-(4-pyrrolidin-1-ylpiperidin-1-yl)phenyl]-1,3,5-triazine-2,4-diamine,
1-(1-{4-[(4-{[2-(isopropylsulfonyl)phenyl]amino}-1,3,5-triazin-2-yl)amino]-3-methoxyphenyl}piperidin-4-yl)pyrrolidin-3-ol,
N-[2-(isopropylsulfonyl)phenyl]-N'-[2-methoxy-4-(4-methylpiperazin-1-yl)phenyl]-1,3,5-triazine-2,4-diamine, or
N$^4$-[2-(isopropylsulfonyl)phenyl]-N$^2$-{2-methoxy-4-[4-(1-methylpiperidin-4-yl)piperazin-1-yl]phenyl}quinazoline-2,4-diamine.

[10]
The compound according to [9] or a salt thereof, wherein said compound is:
N-ethyl-2-{[4-({2-methoxy-4-[4-(4-methylpiperazin-1-yl)piperidin-1-yl]phenyl}amino)-1,3,5-triazin-2-yl]amino}benzenesulfonamide,
2-{[4-({2-methoxy-4-[4-(4-methylpiperazin-1-yl)piperidin-1-yl]phenyl}amino)-1,3,5-triazin-2-yl]amino}-N,N-dimethylbenzenesulfonamide, N-isopropyl-2-{[4-({2-methoxy-4-[4-(4-methylpiperazin-1-yl)piperidin-1-yl]phenyl}amino)-1,3,5-triazin-2-yl]amino}benzenesulfonamide, N-isopropyl-2-{[4-({2-methoxy-4-[4-(4-methylpiperazin-1-yl)piperidin-1-yl]phenyl}amino)-1,3,5-triazin-2-yl]amino}-N-methylbenzenesulfonamide, 2-{[4-({2-methoxy-4-[4-(4-methylpiperazin-1-yl)piperidin-1-yl]phenyl}amino)-1,3,5-triazin-2-yl]amino}-N-methylbenzenesulfonamide, N-[2-(isopropylsulfonyl)phenyl]-N'-{2-methoxy-4-[3-(4-methylpiperazin-1-yl)azetidin-1-yl]phenyl}-1,3,5-triazine-2,4-diamine, $N^4$-[2-(isopropylsulfonyl)phenyl]-$N^2$-{2-methoxy-4-[4-(4-methylpiperazin-1-yl)piperidin-1-yl]phenyl}quinazoline-2,4-diamine, or N-[2-(isopropylsulfonyl)phenyl]-N'-{2-methoxy-4-[4-(4-methylpiperazin-1-yl)piperidin-1-yl]phenyl}-1,3,5-triazine-2,4-diamine.

[11]
The compound according to [10] or a salt thereof, wherein said compound is:

N-ethyl-2-{[4-({2-methoxy-4-[4-(4-methylpiperazin-1-yl)piperidin-1-yl]phenyl}amino)-1,3,5-triazin-2-yl]amino}benzenesulfonamide, 2-{[4-({2-methoxy-4-[4-(4-methylpiperazin-1-yl)piperidin-1-yl]phenyl}amino)-1,3,5-triazin-2-yl]amino}-N,N-dimethylbenzenesulfonamide, or N-[2-(isopropylsulfonyl)phenyl]-N'-{2-methoxy-4-[4-(4-methylpiperazin-1-yl)piperidin-1-yl]phenyl}-1,3,5-triazine-2,4-diamine.

[12]
The compound according to [11] or a salt thereof, wherein said compound is:

N-[2-(isopropylsulfonyl)phenyl]-N'-{2-methoxy-4-[4-(4-methylpiperazin-1-yl)piperidin-1-yl]phenyl}-1,3,5-triazine-2,4-diamine.

[13]
A pharmaceutical composition, which comprises the compound according to [1] or a salt thereof and a pharmaceutically acceptable excipient.

[14]
An inhibitor against the kinase activity of EML4-ALK fusion proteins and mutant EGFR proteins, which comprises the compound according to [1] or a salt thereof.

[15]
A pharmaceutical composition for preventing or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer, which comprises the compound according to [1] or a salt thereof.

[16]
Use of the compound according to [1] or a salt thereof for the manufacture of a pharmaceutical composition for preventing or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer.

[17]
The compound according to [1] or a salt thereof, which is used as an active ingredient in a pharmaceutical composition for preventing or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer.

[18]
A method for preventing or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer, which comprises administering an effective amount of the compound according to [1] or a salt thereof to a patient.

The present invention will now be described in more detail below.

As used herein, the term "halogen" means F, Cl, Br or I.

The term "lower alkyl" refers to linear or branched alkyl containing 1 to 6 carbon atoms (hereinafter abbreviated as "$C_{1-6}$"). Examples include methyl, ethyl, n-propyl, isopropyl, n-butyl, isobutyl, sec-butyl, tert-butyl, n-pentyl, n-hexyl, and the like. Another embodiment is $C_{1-4}$ alkyl, and yet another embodiment is methyl, ethyl or isopropyl.

The term "cyclic amino" refers to a monovalent group of a 3- to 8-membered monocyclic non-aromatic cyclic amine which has at least one nitrogen atom and may further have the same or different one or more heteroatoms selected from the group consisting of nitrogen, oxygen and sulfur, wherein its at least one nitrogen atom has a binding hand. Specific examples include aziridinyl, azetidinyl, pyrrolidinyl, piperidinyl, azepanyl, azocanyl, piperazinyl, homopiperazinyl, morpholinyl, oxazepanyl, thiomorpholinyl, thiazepanyl, and the like. Alternatively, another embodiment is a monovalent group of a 5- or 6-membered monocyclic non-aromatic cyclic amine. It should be noted that such a ring may be a bridged cyclic amino group, as exemplified by 2,5-diazabicyclo[2.2.1]heptane and the like, or may have an unsaturated bond in part of the ring, as exemplified by dihydropyrrolyl, tetrahydropyridyl, tetrahydropyrazyl, or the like.

The term "non-aromatic heterocyclic ring" refers to a 5- to 10-membered monocyclic non-aromatic heterocyclic ring which has 1 to 4 heteroatoms selected from the group consisting of nitrogen, oxygen and sulfur. Examples include aziridine, azetidine, pyrrolidine, piperidine, azepane, azocane, piperazine, homopiperazine, morpholine, oxazepane, thiomorpholine, thiazepane, tetrahydropyran, tetrahydrofuran, dioxane, dioxolane, and the like. Another embodiment is a 5- or 6-membered monocyclic non-aromatic cyclic amine, including pyrrolidine, piperidine, piperazine, morpholine, thiomorpholine, and the like. It should be noted that such a ring may have an unsaturated bond in part of the ring, as exemplified by dihydropyrrole, tetrahydropyridine, tetrahydropyrazine, or the like.

The term "aryl" refers to a $C_{6-14}$ monocyclic to tricyclic aromatic hydrocarbon group, including phenyl, naphthyl, and the like. Another embodiment is phenyl.

The term "cycloalkyl" refers to an optionally bridged $C_{3-10}$ saturated cyclic hydrocarbon group, including cyclopropyl, cyclobutyl, cyclopentyl, cyclohexyl, cycloheptyl, cyclooctyl, adamantyl, and the like. Other examples include those partially unsaturated, such as cyclohexenyl, cyclooctadienyl, and the like. Further examples include those in which one or two methylene groups on the ring are replaced with —O—, as exemplified by tetrahydropyranyl, tetrahydrofuranyl, dioxanyl, and the like. Still further examples include these rings which are each condensed with a benzene ring, as exemplified by indanyl, tetrahydronaphthyl, indenyl, dihydronaphthyl, dihydrochromenyl, and the like.

The term "aromatic heterocyclic ring" refers to a monovalent group of a 5- to 10-membered monocyclic or bicyclic aromatic heterocyclic ring which has 1 to 4 heteroatoms selected from the group consisting of nitrogen, oxygen and sulfur. Examples include pyridyl, pyrrolyl, pyrazinyl, pyrimidinyl, pyridazinyl, imidazolyl, thiazolyl, oxazolyl, thienyl, furyl, indolyl, benzimidazolyl, quinolyl, isoquinolyl, quinazolinyl, quinoxalinyl, phthalazinyl, benzothiazolyl, benzoxazolyl, and the like. Another embodiment is pyridyl, pyrazinyl, pyrimidinyl, quinolyl, isoquinolyl, quinazolinyl, quinoxalinyl or phthalazinyl, and yet another embodiment is pyridyl.

The phrase "which may be substituted" is intended to include both "substituted" and "unsubstituted" embodiments. When substituted with a plurality of groups, these groups may be the same or different from each other.

The phrase "lower alkyl which may be substituted with one or more halogens" refers to, for example, lower alkyl which may be substituted with the same or different 1 to 7 halogens. Another embodiment is lower alkyl which may be substituted with 1 to 5 halogens. Yet another embodiment is lower alkyl which may be substituted with 1 to 3 halogens.

In the phrase "amino which may be substituted with one or two $R^{ZA}$," when this amino is substituted with two $R^{ZA}$, these two $R^{ZA}$ substituents may be the same or different from each other.

Some embodiments of the present invention are given below.

(1) Compounds of formula (I), wherein —$R^{1a}$, —$R^{1b}$, —$R^{1c}$ and —$R^{1d}$ are each —H.
(2) Compounds of formula (I), wherein
  (2-1) —$R^2$ is —O-lower alkyl, or
  (2-2) —$R^2$ is —O-methyl.
(3) Compounds of formula (I), wherein
  (3-1) —$R^3$ is cyclic amino which may be substituted with lower alkyl (provided that the benzene ring to which —$R^3$ is attached is attached to the nitrogen atom in the cyclic amino),
  (3-2) —$R^3$ is piperazinyl which may be substituted with lower alkyl (provided that the benzene ring to which —$R^3$ is attached is attached to a nitrogen atom in the piperazine),
  (3-3) —$R^3$ is piperazinyl which may be substituted with methyl (provided that the benzene ring to which —$R^3$ is attached is attached to a nitrogen atom in the piperazine),
  (3-4) —$R^3$ is 4-methylpiperazin-1-yl,
  (3-5) —$R^3$ is a group represented by formula (IV), in which -$L^1$ and -$L^2$ taken together represent cyclic amino which may be substituted with lower alkyl,
  (3-6) —$R^3$ is a group represented by formula (IV), in which -$L^1$ and -$L^2$ taken together represent pyrrolidine or piperidine which may be substituted with lower alkyl,
  (3-7) —$R^3$ is a group represented by formula (IV), in which -$L^1$ and -$L^2$ taken together represent pyrrolidine or piperidine which may be substituted with methyl,
  (3-8) —$R^3$ is a group represented by —Y—Z, in which —Y— is piperidine-1,4-diyl, piperazine-1,4-diyl, azetidine-1,3-diyl or —N(-lower alkyl)-, and —Z is cyclic amino which may be substituted with one or more groups selected from the group consisting of lower alkyl and —OH,
  (3-9) —$R^3$ is a group represented by —Y—Z, in which —Y— is piperidine-1,4-diyl, piperazine-1,4-diyl, azetidine-1,3-diyl or —N(-methyl)-, and —Z is piperazinyl, piperidinyl or pyrrolidinyl which may be substituted with one or more groups selected from the group consisting of methyl and —OH, or
  (3-10) —$R^3$ is 4-(4-methylpiperazin-1-yl)piperidin-1-yl.
(4) Compounds of formula (I), wherein —$R^4$ is —H.
(5) Compounds of formula (I), wherein
  (5-1) —X— is a group represented by formula (II), and —$R^5$ is —H, or
  (5-2) —X— is a group represented by formula (III), and —$R^{6a}$, —$R^{6b}$, —$R^{6c}$ and —$R^{6d}$ are each —H.
(6) Compounds of formula (I), wherein
  (6-1) —W is a group represented by -A-B, in which -A- is —S(=O)$_2$—, and —B is lower alkyl,
  (6-2) —W is a group represented by -A-B, in which -A- is —S(=O)$_2$—, and —B is isopropyl, or
  (6-3) —W is a group represented by -A-B, in which -A- is —S(=O)$_2$—, and —B is amino which may be substituted with one or two $R^{ZA}$, and $R^{ZA}$ is methyl, ethyl, isopropyl or cyclopropyl.
(7) Compounds, in which any combination of two or more of (1) to (6) shown above is applied.
(8) Compounds of formula (VI), wherein —$R^{11a}$, —$R^{11b}$, —$R^{11c}$ and —$R^{11d}$ are each —H.
(9) Compounds of formula (VI), wherein
  (9-1) —$R^{12}$ is —O-lower alkyl, or
  (9-2) —$R^{12}$ is —O-methyl.
(10) Compounds of formula (VI), wherein
  (10-1) —$R^{13}$ is cyclic amino which may be substituted with lower alkyl (provided that the benzene ring to which —$R^{13}$ is attached is attached to the nitrogen atom in the cyclic amino),
  (10-2) —$R^{13}$ is piperazinyl which may be substituted with lower alkyl (provided that the benzene ring to which —$R^{13}$ is attached is attached to a nitrogen atom in the piperazine),
  (10-3) —$R^{13}$ is piperazinyl which may be substituted with methyl (provided that the benzene ring to which —$R^{13}$ is attached is attached to a nitrogen atom in the piperazine),
  (10-4) —$R^{13}$ is 4-methylpiperazin-1-yl,
  (10-5) —$R^{13}$ is a group represented by —$Y^1$—$Z^1$, in which —$Y^1$— is piperidine-1,4-diyl, piperazine-1,4-diyl or —N(-lower alkyl)-, and —$Z^1$ is cyclic amino which may be substituted with one or more groups selected from the group consisting of lower alkyl and —OH,
  (10-6) —$R^{13}$ is a group represented by —$Y^1$—$Z^1$, in which —$Y^1$— is piperidine-1,4-diyl, piperazine-1,4-diyl or —N(-methyl)-, and —$Z^1$ is piperazinyl, piperidinyl or pyrrolidinyl which may be substituted with one or more groups selected from the group consisting of methyl and —OH, or
  (10-7) —$R^{13}$ is 4-(4-methylpiperazin-1-yl)piperidin-1-yl.
(11) Compounds of formula (VI), wherein —$R^{14}$ is —H.
(12) Compounds of formula (VI), wherein
  (12-1) —$X^1$— is a group represented by formula (VII), and —$R^{15}$ is —H, or
  (12-2) —$X^1$— is a group represented by formula (VIII), and —$R^{16a}$, —$R^{16b}$, —$R^{16c}$ and —$R^{16d}$ are each —H.
(13) Compounds of formula (VI), wherein
  (13-1) —$W^1$ is a group represented by -$A^1$-$B^1$, in which -$A^1$- is —S(=O)$_2$—, and —$B^1$ is lower alkyl,
  (13-2) —$W^1$ is a group represented by -$A^1$-$B^1$, in which -$A^1$- is —S(=O)$_2$—, and —$B^1$ is isopropyl, or
  (13-3) —$W^1$ is a group represented by -$A^1$-$B^1$, in which -$A^1$- is —S(=O)$_2$—, and —$B^1$ is amino which may be substituted with one or two lower alkyls.
(14) Compounds, in which any combination of two or more of (8) to (13) shown above is applied.

Examples of specific compounds falling within the present invention include those selected from compound groups P, Q, R and S shown below.

Compound group P:
a group consisting of N-[2-(isopropylsulfonyl)phenyl]-N'-{2-methoxy-4-[4-(4-methylpiperazin-1-yl)piperidin-1-yl]phenyl}-1,3,5-triazine-2,4-diamine and salts of this compound.

Compound group Q:
a group consisting of N-ethyl-2-{[4-({2-methoxy-4-[4-(4-methylpiperazin-1-yl)piperidin-1-yl]phenyl}amino)-1,3,5-triazin-2-yl]amino}benzenesulfonamide, and
2-{[4-({2-methoxy-4-[4-(4-methylpiperazin-1-yl)piperidin-1-yl]phenyl}amino)-1,3,5-triazin-2-yl]amino}-N,N-dimethylbenzenesulfonamide, as well as salts of these compounds.

Compound group R:
a group consisting of N-isopropyl-2-{[4-({2-methoxy-4-[4-(4-methylpiperazin-1-yl)piperidin-1-yl]phenyl}amino)-1,3,5-triazin-2-yl]amino}benzenesulfonamide,
N-isopropyl-2-{[4-({2-methoxy-4-[4-(4-methylpiperazin-1-yl)piperidin-1-yl]phenyl}amino)-1,3,5-triazin-2-yl]amino}-N-methylbenzenesulfonamide,
2-{[4-({2-methoxy-4-[4-(4-methylpiperazin-1-yl)piperidin-1-yl]phenyl}amino)-1,3,5-triazin-2-yl]amino}-N-methylbenzenesulfonamide,
N-[2-(isopropylsulfonyl)phenyl]-N'-{2-methoxy-4-[3-(4-methylpiperazin-1-yl)azetidin-1-yl]phenyl}-1,3,5-triazine-2,4-diamine, and
$N^4$-[2-(isopropylsulfonyl)phenyl]-$N^2$-{2-methoxy-4-[4-(4-methylpiperazin-1-yl)piperidin-1-yl]phenyl}quinazoline-2,4-diamine, as well as salts of these compounds.

Compound group S:
a group consisting of N-[2-(isopropylsulfonyl)phenyl]-N'-(2-methoxy-4-piperazin-1-ylphenyl)-1,3,5-triazine-2,4-diamine,
N-[2-(isopropylsulfonyl)phenyl]-N'-[2-methoxy-4-(1-methyl-1,8-diazaspiro[4.5]decan-8-yl)phenyl]-1,3,5-triazine-2,4-diamine,
N-[2-(isopropylsulfonyl)phenyl]-N'-[2-methoxy-4-(1-methyl-1,9-diazaspiro[5.5]undecan-9-yl)phenyl]-1,3,5-triazine-2,4-diamine,
N-cyclopropyl-2-{[4-({2-methoxy-4-[4-(4-methylpiperazin-1-yl)piperidin-1-yl]phenyl}amino)-1,3,5-triazin-2-yl]amino}benzenesulfonamide,
N-[2-(isopropylsulfonyl)phenyl]-N'-{2-methoxy-4-[methyl(1-methylpiperidin-4-yl)amino]phenyl}-1,3,5-triazine-2,4-diamine,
N-[2-(isopropylsulfonyl)phenyl]-N'-[2-methoxy-4-(4-pyrrolidin-1-ylpiperidin-1-yl)phenyl]-1,3,5-triazine-2,4-diamine,
1-(1-{4-[(4-{[2-(isopropylsulfonyl)phenyl]amino}-1,3,5-triazin-2-yl)amino]-3-methoxyphenyl}piperidin-4-yl)pyrrolidin-3-ol,
N-[2-(isopropylsulfonyl)phenyl]-N'-[2-methoxy-4-(4-methylpiperazin-1-yl)phenyl]-1,3,5-triazine-2,4-diamine, and
$N^4$-[2-(isopropylsulfonyl)phenyl]-$N^2$-{2-methoxy-4-[4-(1-methylpiperidin-4-yl)piperazin-1-yl]phenyl}quinazoline-2,4-diamine, as well as salts of these compounds.

The compounds of formula (I) may have tautomers and/or geometrical isomers, depending on the type of their substituents. Even when the compounds of formula (I) appear herein only in one isomer form, the present invention encompasses the other isomers, and also encompasses separated isomers or mixtures thereof.

Further, since some compounds of formula (I) have an asymmetric carbon atom or axial asymmetry, optical isomers based on this asymmetry may also exist. The present invention also encompasses separated optical isomers of the compounds of formula (I) or mixtures thereof.

Furthermore, the present invention encompasses pharmaceutically acceptable prodrugs of the compounds represented by formula (I). The term "pharmaceutically acceptable prodrug" refers to a compound having a group which can be converted into an amino group, a hydroxyl group, a carboxyl group or the like by solvolysis or under physiological conditions. Examples of a prodrug-forming group include those described in Prog. Med., 5, 2157-2161 (1985) or those described in "Development of Pharmaceuticals" (Hirokawa Publishing, 1990) vol. 7, Molecular Design 163-198.

Likewise, salts of the compounds of formula (I) are pharmaceutically acceptable salts of the compounds of formula (I). The compounds of formula (I) may form acid or base addition salts, depending on the type of their substituents. Specific examples include acid addition salts with inorganic acids (e.g., hydrochloric acid, hydrobromic acid, hydroiodic acid, sulfuric acid, nitric acid, phosphoric acid, and the like) or with organic acids (e.g., formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like), salts with inorganic bases (e.g., sodium, potassium, magnesium, calcium, aluminum, and the like) or with organic bases (e.g., methylamine, ethylamine, ethanolamine, lysine, ornithine, and the like), salts with various amino acids and amino acid derivatives (e.g., acetylleucine, and the like), as well as ammonium salt, etc.

Moreover, the present invention also encompasses the compounds of formula (I) and salts thereof in the form of various hydrates, solvates, and crystalline polymorphic substances. The present invention also encompasses the compounds labeled with various radioactive or non-radioactive isotopes.

The compounds of formula (I) and pharmaceutically acceptable salts thereof can be prepared by applying various known synthesis methods on the basis of characteristics derived from their skeletal structure or the type of their substituents. In some cases, depending on the type of functional group, it is technically effective to replace such a functional group with an appropriate protecting group (a group which can be easily converted into the original functional group) at the starting material stage or at the intermediate stage. Examples of such a protecting group include those described in Greene and Wuts, "Protective Groups in Organic Synthesis (third edition, 1999)" and so on, which may be selected and used as appropriate, depending on reaction conditions. In such a method, after introduction of the protecting group and subsequent reaction, the protecting group may be removed if necessary to obtain a desired compound.

Likewise, a prodrug of the compound of formula (I) can be prepared by introducing a specific group at the starting material stage or at the intermediate stage, as in the case of the above protecting group, or by subjecting the obtained compound of formula (I) to further reaction. The reaction may be accomplished by applying conventional esterification, amidation, dehydration or other techniques known to those skilled in the art.

Explanation will be given below of typical processes for preparing the compounds of formula (I). Each process may also be accomplished by reference to the documents cited in this explanation. It should be noted that the processes of the present invention are not limited to the examples illustrated below.

(Preparation Process 1)

[Formula 14]

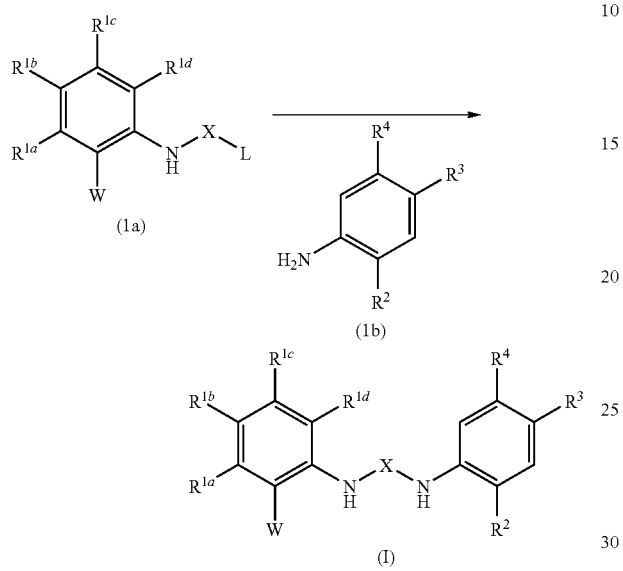

(wherein -L represents a leaving group (the same applying hereinafter))

This process is intended to prepare the compound (I) of the present invention by reacting compound (1a) having a leaving group with aniline derivative (1b). Examples of a leaving group used for this purpose include halogen (e.g., F, Cl, and the like), sulfonyloxy (e.g., methanesulfonyloxy, p-toluenesulfonyloxy, trifluoromethanesulfonyloxy, and the like), as well as lower alkylsulfanyl or lower alkanesulfonyl.

In this reaction, compound (1a) having a leaving group and aniline derivative (1b) are used in equal amounts or one of them is used in an excessive amount. A mixture of these compounds is stirred in a solvent inert to the reaction or in the absence of a solvent under cooling to reflux conditions, preferably at 0° C. to 80° C., generally for 0.1 hours to 5 days. Examples of a solvent used for this purpose include, but are not particularly limited to, aromatic hydrocarbons (e.g., benzene, toluene, xylene, and the like), ethers (e.g., diethyl ether, tetrahydrofuran, dioxane, dimethoxyethane, and the like), halogenated hydrocarbons (e.g., dichloromethane, 1,2-dichloroethane, chloroform, and the like), alcohols (e.g., methanol, ethanol, 2-propanol, and the like), N,N-dimethylformamide, dimethyl sulfoxide, ethyl acetate, acetonitrile, and mixtures thereof. The reaction may be performed in the presence of an organic base (e.g., triethylamine, N,N-diisopropylethylamine, N-methylmorpholine, or the like) or an inorganic base (e.g., potassium carbonate, sodium carbonate, potassium hydroxide, or the like), because it is advantageous for smooth reaction in some cases.

When the reaction is performed in the presence of such a base as shown above, depending on the properties or the like of starting compounds, the desired reaction is impossible or difficult to proceed, for example, due to decomposition or the like of the starting compounds. In this case, the reaction may be performed in the presence of a mineral acid (e.g., hydrochloric acid, hydrobromic acid, and the like), an organic acid (e.g., acetic acid, propionic acid, and the like) or a sulfonic acid (e.g., methanesulfonic acid, p-toluenesulfonic acid, and the like), because it is advantageous for smooth reaction in some cases.

[Documents]

S. R. Sandler and W. Karo, "Organic Functional Group Preparations," second edition, vol. 1, Academic Press Inc., 1991

The Chemical Society of Japan, "Fifth Series of Experimental Chemistry," vol. 14 (2005) (MARUZEN Co., Ltd., Japan)

(Preparation Process 2)

[Formula 15]

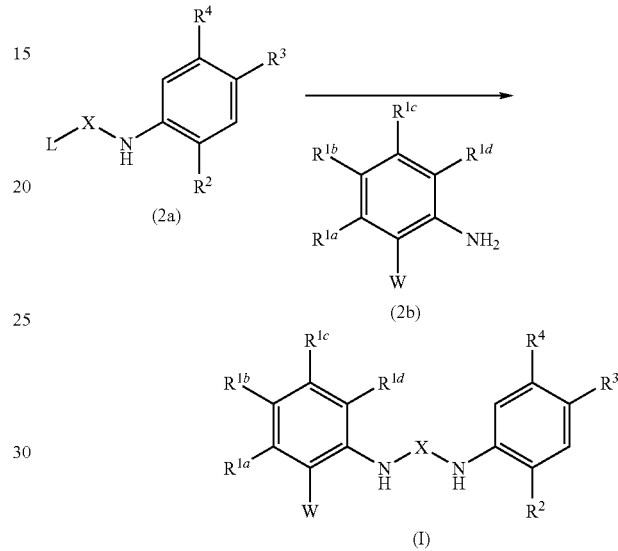

This process is intended to prepare the compound (I) of the present invention by reacting compound (2a) having a leaving group with aniline derivative (2b).

In this reaction, the procedure of Preparation Process 1 may be applied.

(Starting Material Synthesis)

[Formula 16]

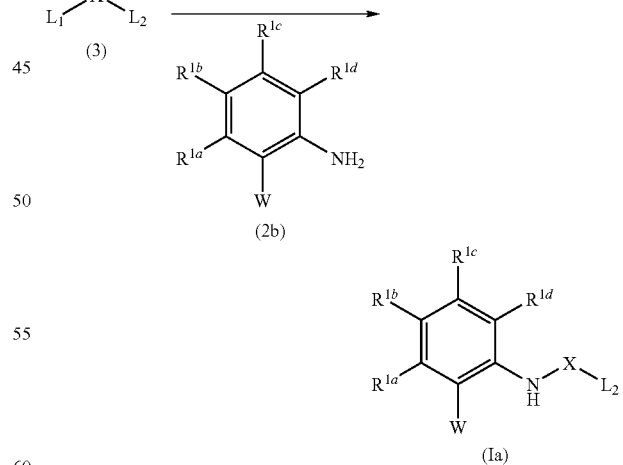

(wherein $L_1$ and $L_2$ each represent a leaving group selected from the members of L shown above (the same applying hereinafter))

This process is intended to prepare compound (1a) by reacting compound (3) having leaving groups with aniline derivative (2b).

In this reaction, the procedure of Preparation Process 1 may be applied.

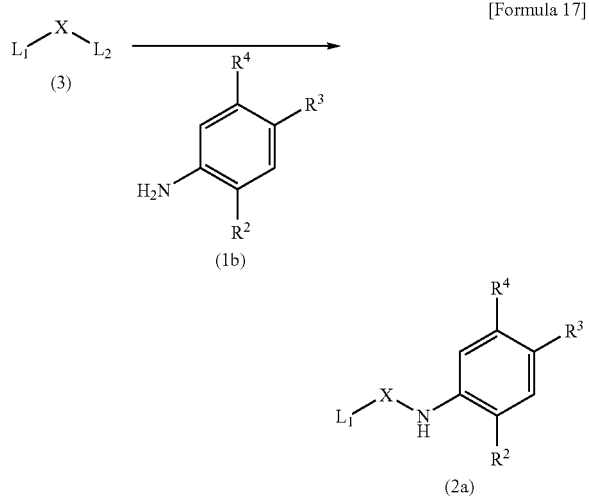

This process is intended to prepare compound (2a) by reacting compound (3) having leaving groups with aniline derivative (1b).

In this reaction, the procedure of Preparation Process 1 may be applied.

The compound of formula (I) is isolated and purified as a free compound or as a pharmaceutically acceptable salt, hydrate, solvate or crystalline polymorphic substance thereof. A pharmaceutically acceptable salt of the compound of formula (I) may also be prepared by being subjected to conventional salt-forming reaction.

Isolation and purification may be accomplished by applying conventional chemical operations such as extraction, fractional crystallization, various types of fractionation chromatography, etc.

Various isomers can be prepared by selecting appropriate starting compounds or can be separated on the basis of differences in the physical and chemical properties of isomers. For example, optical isomers can be derived into optically pure isomers by conventional optical resolution techniques (e.g., fractional crystallization resulting in a diastereomer salt with an optically active base or acid, chromatography on a chiral column or the like, and the like). They can also be prepared from appropriate optically active starting compounds.

The compounds of formula (I) were confirmed for their pharmacological activity in the following tests. Unless otherwise specified, the test examples shown below may be accomplished in a known manner and, when using commercially available reagents, kits, or the like, may be accomplished in accordance with the instructions attached to these commercially available products.

TEST EXAMPLE 1

Evaluation of Inhibitory Activity Against the Kinase Activity of EML4-ALK Fusion Protein v1

EML4-ALK fusion protein v1 (purified from BA/F3 cells expressing EML4-ALK fusion protein v1) was investigated for its phosphorylation activity toward a peptide substrate by using a kinase activity detection kit (HTRF KinEASE-TK; Cisbio Inc.). Test compounds were each added to a reaction solution containing the enzyme protein to give 8 final concentrations from 1000 nM to 0.3 nM (100 nM to 0.03 nM for TAE684), followed by addition of ATP and reaction for 1 hour. The ATP concentration used was 100 µM. Another reaction solution was prepared to contain the enzyme protein but no test compound (in which the solvent DMSO alone was added at 0.4% in place of the test compound), followed by reaction in the same manner with or without ATP addition. In the absence of the test compound, the phosphorylation count without ATP addition and with ATP addition was assumed to be 100% inhibition and 0% inhibition, respectively. The concentration causing 50% inhibition ($IC_{50}$) was calculated for each test compound by the logistic regression method.

As a result, the compounds of the present invention and TAE684 were found to have inhibitory activity against the kinase activity of EML4-ALK fusion protein v1. Table 1 shows the $IC_{50}$ values obtained for some compounds of the present invention and TAE684. Ex denotes Example No.

TABLE 1

| Ex | $IC_{50}$(nM) | Ex | $IC_{50}$(nM) |
| --- | --- | --- | --- |
| 1 | 42 | 128 | 2.3 |
| 23 | 17 | 12 | 61 |
| 24 | 29 | 149 | 40 |
| 45 | 66 | 166 | 49 |
| 52 | 72 | 7 | 50 |
| 58 | 25 | 171 | 33 |
| 63 | 26 | 176 | 150 |
| 72 | 51 | TAE684 | 0.63 |
| 120 | 74 | | |
| 123 | 33 | | |

TEST EXAMPLE 2

Evaluation of Inhibitory Activity Against the Kinase Activity of Mutant EGFR (L858R) Protein Mutant EGFR (L858R) protein (Carna Biosciences Inc., Japan) was investigated for its phosphorylation activity toward a peptide substrate by using a kinase activity detection kit (HTRF KinEASE-TK; Cisbio Inc.). Test compounds were each added to a reaction solution containing the enzyme protein to give 8 final concentrations from 10000 nM to 3 nM, followed by addition of ATP and reaction for 1 hour. The ATP concentration used was 5 µM. Another reaction solution was prepared to contain the enzyme protein but no test compound (in which the solvent DMSO alone was added at 0.4% in place of the test compound), followed by reaction in the same manner with or without ATP addition. In the absence of the test compound, the phosphorylation count without ATP addition and with ATP addition was assumed to be 100% inhibition and 0% inhibition, respectively. The concentration causing 50% inhibition ($IC_{50}$) was calculated for each test compound by the logistic regression method.

As a result, the compounds of the present invention and TAE684 were found to have inhibitory activity against the kinase activity of mutant EGFR (L858R) protein. Table 2 shows the $IC_{50}$ values obtained for some compounds of the present invention and TAE684. Ex denotes Example No.

TABLE 2

| Ex | $IC_{50}$(nM) |
| --- | --- |
| 23 | 120 |
| 123 | 100 |
| 128 | 98 |
| TAE684 | 92 |

TEST EXAMPLE 3

Evaluation of Inhibitory Effect Against Anchorage-Independent Cell Growth of Human Non-Small Cell Lung Cancer Cell Line NCI-H2228 Cells (EML4-ALK Fusion Protein-Expressing Cells)

Measurement for anchorage-independent cell growth (colony method, etc) has been known to be a system for investigating the anticancer action (pharmacological effect) of test compounds (Clinical Oncology, second edition, Cancer and Chemotherapy Publishers Inc.). In place of the colony method, there is a following method using spheroid plates for measuring the growth of non-attached cells.

In a 96-well spheroid plate (Sumilon Celltight Spheroid 96U; Sumitomo Bakelite Co., Ltd., Japan), human non-small cell lung cancer cell line NCI-H2228 cells were seeded at 2000 cells per well in RPMI1640 medium (Invitrogen) containing 10% fetal bovine serum. NCI-H2228 cells are those expressing another EML4-ALK fusion protein, which is different from the EML4-ALK fusion protein v1 because it is encoded by an EML4-ALK fusion polynucleotide whose fusion point on EML4 cDNA is different from that of the EML4-ALK fusion polynucleotide v1, but whose ALK region is the same as that of the EML4-ALK fusion polynucleotide v1. The above NCI-H2228 cells seeded in the plate were cultured overnight under 5% $CO_2$ at 37° C., followed by addition of a test compound (final concentration: 10 µM to 1 nM). As a negative control, DMSO used as a solvent was added at the same concentration as the test compound. Then, the cells were cultured under 5% $CO_2$ at 37° C. for 5 days. A cell counting reagent (CellTiter-Glo™ Luminescent Cell Viability Assay; Promega) was added and agitated for 20 minutes, followed by measurement with a luminometer (ML3000 microtiter plate luminometer; Dynatech Laboratories). Assuming that the value measured for the medium alone and the value measured for the negative control were 100% inhibition and 0% inhibition, respectively, the inhibition rate was calculated for each compound to thereby determine the concentration causing 50% inhibition ($IC_{50}$ value) by the logistic regression method.

As a result, the compounds of the present invention and TAE684 were found to have growth inhibitory activity against human non-small cell lung cancer cell line NCI-H2228 cells. Table 3 shows the $IC_{50}$ values obtained for some compounds of the present invention and TAE684. Ex denotes Example No.

TABLE 3

| Ex | $IC_{50}$(nM) | Ex | $IC_{50}$(nM) |
|---|---|---|---|
| 1 | 473 | 128 | 64 |
| 23 | 71 | 12 | 134 |
| 24 | 125 | 149 | 62 |
| 45 | 1039 | 166 | 125 |
| 52 | 159 | 7 | 87 |
| 58 | 156 | 171 | 61 |
| 63 | 96 | 176 | 119 |
| 72 | 93 | TAE684 | 8.5 |
| 120 | 168 | | |
| 123 | 30 | | |

TEST EXAMPLE 4

Evaluation of Inhibitory Effect Against Anchorage-Independent Cell Growth of Human Non-Small Cell Lung Cancer Cell Line HCC827 Cells (Mutant EGFR (with Partial Deletion of Exon 19 in EGFR) Protein-Expressing Cells, American Type Culture Collection)

Evaluation was performed in the same manner as shown in Test Example 3.

As a result, the compounds of the present invention and TAE684 were found to have growth inhibitory activity against human non-small cell lung cancer cell line HCC827 cells. Table 4 shows the $IC_{50}$ values obtained for some compounds of the present invention and TAE684. Ex denotes Example No.

TABLE 4

| Ex | $IC_{50}$(nM) | Ex | $IC_{50}$(nM) |
|---|---|---|---|
| 1 | 2513 | 128 | 175 |
| 23 | 272 | 12 | 509 |
| 24 | 1027 | 149 | 512 |
| 45 | 1899 | 166 | 419 |
| 52 | 820 | 7 | 214 |
| 58 | 648 | 171 | 252 |
| 63 | 791 | 176 | 496 |
| 72 | 670 | TAE684 | 301 |
| 120 | 660 | | |
| 123 | 238 | | |

From the results of Test Examples 1 to 4 shown above, it was confirmed that the compounds of the present invention and TAE684 had inhibitory activity against the kinase activity of EML4-ALK fusion protein v1 and growth inhibitory activity against human non-small cell lung cancer cell line NCI-H2228 cells, and that TAE684 had stronger activity than the compounds of the present invention. It was also confirmed that the compounds of the present invention and TAE684 had inhibitory activity against the kinase activity of mutant EGFR (L858R) protein and growth inhibitory activity against human non-small cell lung cancer cell line HCC827 cells, and that the compounds of the present invention and TAE684 had almost equal activity.

TEST EXAMPLE 5

Toxicity Test in Rats

Test compounds were each suspended in a 0.5% aqueous methylcellulose solution and repeatedly administered to SD rats (two females and four males in each group) by the oral route at each dose for 7 days. TAE684 was administered at 3, 10, 30 and 100 mg/kg, while the compound of Example 23 was administered at 10, 30, 100 and 300 mg/kg.

The results obtained are shown in Table 5.

TABLE 5

| | Dose | | | |
|---|---|---|---|---|
| | Compound of Example 23 | | TAE684 | |
| | Male (4 rats) | Female (2 rats) | Male (4 rats) | Female (2 rats) |
| Non-toxic dose | 10 | 10 | 3 | 3 |
| Bone marrow inhibition | 100 | 100 | 10 | 10 |

TABLE 5-continued

| | Dose | | | |
|---|---|---|---|---|
| | Compound of Example 23 | | TAE684 | |
| | Male (4 rats) | Female (2 rats) | Male (4 rats) | Female (2 rats) |
| Exacerbation of common symptoms | (>300) | (>300) | 100 | 30 |
| Moribund condition | (>300) | (>300) | (>100) | 100 |

At the doses used in this test, TAE684 produced the following clear toxic symptoms: exacerbation of common symptoms (e.g., decreased autonomic movement, eyelid closure, skinniness, blepharophimosis) in the females of the 30 mg/kg group; these findings as well as prone position, bradypnea and hypersalivation in the females and males of the 100 mg/kg group; and remarkable exacerbation of the post-administration state at Day 7 in the two females (all cases) of the 100 mg/kg group (for this reason, these two cases were examined by moribund autopsy). In contrast, although the compound of Example 23 was found to cause a decrease in the amount of feces in 2 of the 4 males in the 300 mg/kg group, there was no case in each dose group, which showed exacerbation of common symptoms during administration for 7 days. Also, no moribund case was observed in each dose group.

Namely, the compound of Example 23 has an effect equal to TAE684 on growth inhibition of mutant EGFR protein-expressing cells, but on the other hand causes no exacerbation of common symptoms or shows no moribund case even when administered at a dose of 300 mg/kg, which is higher than the dose of 30 mg/kg or 100 mg/kg at which exacerbation of common symptoms or moribund cases are observed for TAE684. Thus, the compound of Example 23 is regarded as a safer compound than TAE684.

Based on the above results, in cancer therapy for EML4-ALK fusion polynucleotide-positive cancer patients, TAE684 has fears about safety (e.g., exacerbation of common symptoms) at a lower dose than in the compound of Example 23 (Test Example 5), whereas TAE684 appears to produce a therapeutic effect at a lower dose than in the compound of Example 23 (Test Examples 1 and 3). It is therefore inferred that the compound of Example 23 and TAE684 are almost comparable to each other in terms of a balance between therapeutic effect and safety. On the other hand, in cancer therapy for mutant EGFR polynucleotide-positive cancer patients, the compound of Example 23 and TAE684 appear to produce a therapeutic effect at almost the same dose (Test Examples 2 and 4), whereas TAE684 has fears about safety (e.g., exacerbation of common symptoms) at a lower dose than in the compound of Example 23 (Test Example 5). It is therefore concluded that the compound of Example 23 is superior to TAE684 in terms of a balance between therapeutic effect and safety.

Thus, even if the compound of Example 23 and TAE684 can both produce a therapeutic effect on cancer with some degree of safety during cancer therapy for EML4-ALK fusion polynucleotide-positive cancer patients, the so-called margin of safety is narrower in TAE684 than in the compound of Example 23 in cancer therapy for mutant EGFR polynucleotide-positive cancer patients, and hence TAE684 has a possibility of failing to provide a sufficient therapeutic effect when the dose should be reduced to ensure safety. In contrast, the compound of Example 23 has a wider margin of safety than TAE684 and hence can be expected to be administered at a dose which ensures a sufficient therapeutic effect. Namely, the compound of Example 23 is expected as a therapeutic agent for cancer that is applicable to a wider spectrum of cancer patients than in TAE684.

TEST EXAMPLE 6

Kinase Inhibition Profiling

The inhibition rates against 88 types of kinases (ABL, ACK, AXL, BMX, BTK, CSK, DDR2, EGFR, EphA2, EphB4, FES, FGFR1, FGFR3, FLT1, FLT4, FMS, INSR, JAK2, JAK3, KDR, MER, MUSK, PDGFRa, RET, TEC, TIE2, TYK2, TYRO3, ABL[T315I], EGFR[L858R], EGFR [T790M], AKT2, AurC, BMPR1A, BRAF, BRAF[V600E], CaMK2a, CaMK4, CDK3, CHK2, CK1a, CK1d, COT, CRIK, DAPK1, DLK, Erk5, GSK3a, GSK3b, IKKa, IKKb, IKKe, IRAK4, JNK1, JNK3, MAP2K2, MAP2k3, MAP2K4, MAP2K5, MAP2K7, MAP3K1, MAP3K2, MAP3K3, MAP3K4, MAP3K5, MAPKAPK2, MAPKAPK3, MAPKAPK5, MLK1, MLK2, MLK3, MNK1, MNK2, MSK1, NEK2, p38d, p38g, PAK6, PHKG1, PIM1, PKACa, PKCh, PKD2, ROCK1, RSK2, SRPK1, TAK1, TTK) were calculated for each test compound at 100 nM. Activity measurement was made by Carna Biosciences Inc., Japan, and the data were analyzed as follows: assuming that the average signal of control wells containing all reaction components was 0% inhibition and the average signal in the absence of the enzyme was 100% inhibition, the inhibition rate was calculated for each test substance from the average signal of two test wells.

As a result, at a concentration of 100 nM, TAE684 showed 50% or more inhibitory activity against 29 types of kinases, whereas the compound of Example 23 showed inhibitory activity only against 4 types.

Namely, TAE684 has strong inhibitory activity against a wide range of kinases, whereas the compound of Example 23 at the same concentration has a different inhibition profile than that of TAE684 and appears to be highly selective for specific kinases, i.e., appears to have much fewer fears about safety than TAE684, which fears are induced by inhibition of non-target kinases responsible for side effects.

In addition, when a careful examination was actually made on various kinase inhibition profiles, kinases against which TAE684 has higher inhibitory activity than the compound of Example 23 were MUSK, MER and PHKG1. TAE684 showed 90% or more inhibitory activity against these kinases at concentration of 100 nM, whereas the compound of Example 23 showed little inhibitory activity at the same concentration (less than 20%).

MUSK is a kinase essential for acetylcholine receptor functions in the neuromuscular junction. If people have a mutation in this kinase or are positive for anti-MUSK antibody, they are known to develop a hereditary disease with myasthenia showing symptoms such as blepharoptosia, hypersalivation, and respiratory disturbance (Hum Mol Genet. 2004 13, 3229-3240 and Nat Med. 2001 7, 365-368). There are many symptoms in common between exacerbation of common symptoms observed for TAE684 in Test Example 5 and phenotypes caused by mutations in MUSK. Thus, exacerbation of common symptoms observed for TAE684 administered at 30 mg/kg or more may have some relationship with MUSK inhibition.

MER is a kinase required for retinal cells to maintain their survival. If people have a mutation in this kinase, they are known to develop a hereditary disease with retinitis pigmentosa responsible for gradual narrowing of the visual field, which may lead to blindness (Nature Genet. 2000 26, 270-271). Thus, the possibility of TAE684 to cause a defect in retinal cells due to its inhibitory activity against MER cannot be denied. In contrast, the compound of Example 23 appears to have almost no fear of causing a defect in retinal cells, because its inhibitory activity against MER is weaker than that of TAE684.

PHKG1 is an enzyme essential for glycogen metabolism in muscle, and is known to contribute to a hereditary disease caused by mutations in enzyme complex subunits, which is feared to show glycogenosis, muscle ache during exercise, easy fatigue, myotonia, liver swelling, abdominal swelling, glycogenosis (glycogen accumulation)-induced muscle tissue atrophy, and metabolic myopathy (Am. J. Med. Genet. 2005 133A, 82-84). Thus, the possibility of TAE684 to cause a defect in muscle tissue due to its inhibitory activity against PHKG1 cannot be denied. In contrast, the compound of Example 23 appears to have almost no fear of causing a defect in muscle tissue, because its inhibitory activity against PHKG1 is weaker than that of TAE684.

On the other hand, kinases against which the compound of Example 23 has higher inhibitory activity than TAE684 are MNK1 and MNK2. TAE684 showed 4.8% and 32% inhibitory activity against these kinases, respectively, at 100 nM, whereas the compound of Example 23 showed 60% and 80% inhibitory activity at the same concentration. However, it has been reported that mice whose MNK1 and MNK2 genes are both disrupted will grow normally (Molecular and Celluar Biology 2004 24, 6539-6549). It is therefore difficult to believe that serious diseases are caused by the inhibitory activity of the compound of Example 23 against MNK1 and MNK2.

TEST EXAMPLE 7

Evaluation of Inhibitory Activity Against the Kinase Activity of MUSK Protein

MUSK protein (Carna Biosciences Inc., Japan) was investigated for its phosphorylation activity toward a peptide substrate by using a kinase activity detection kit (HTRF KinEASE-TK; Cisbio Inc.). Test compounds were each added to a reaction solution containing the enzyme protein to give 8 final concentrations from 10000 nM to 3 nM, followed by addition of ATP and reaction for 1 hour. The ATP concentration used was 10 µM. Another reaction solution was prepared to contain the enzyme protein but no test compound (in which the solvent DMSO alone was added at 0.4% in place of the test compound), followed by reaction in the same manner with or without ATP addition. In the absence of the test compound, the phosphorylation count without ATP addition and with ATP addition was assumed to be 100% inhibition and 0% inhibition, respectively. The concentration causing 50% inhibition ($IC_{50}$) was calculated for each test compound by the logistic regression method.

As a result, the compounds of the present invention and TAE684 were found to have inhibitory activity against the kinase activity of MUSK protein. Table 6 shows the $IC_{50}$ values obtained for some compounds of the present invention and TAE684. Ex denotes Example No.

TABLE 6

| Ex | $IC_{50}$ (nM) |
| --- | --- |
| 23 | 1500 |
| 123 | 1100 |
| 128 | 1800 |
| TAE684 | 17 |

From the results of Test Example 7 shown above, it was confirmed that TAE684 had very strong inhibitory activity against the kinase activity of MUSK protein, when compared to the compounds of the present invention. There are many symptoms in common between exacerbation of common symptoms observed for TAE684 in Test Example 5 and phenotypes caused by mutations in MUSK. Thus, exacerbation of common symptoms observed for TAE684 administered at 30 mg/kg or more may have some relationship with MUSK inhibition.

TEST EXAMPLE 8

Antitumor Test (in vivo) on NCI-H2228 Cells $3 \times 10^6$ cells of NCI-H2228 cells suspended in PBS were inoculated subcutaneously by injection to the back of 5 weeks old male NOD/SCID mice (Charles River Japan, Inc.). After 3 weeks of the inoculation, the administration of test compounds was initiated. The test was conducted in the solvent group and test compound groups, 6 animals per group. The test compounds were each dissolved in a solvent composed of 10% 1-methyl-2-pyrrolidinone (SIGMA-ALDRICH Inc.)/90% polyethylene glycol 300 (Fluka Inc.) and administered orally at a dose of 3 mg/kg. Administrations were performed once a day for 14 days, and body weight and tumor size were measured every other day. Tumor volume was calculated using the following formula.

[Tumor volume (mm³)]=[Tumor major axis (mm)]×[tumor minor axis (mm)]²×0.5

Assuming that the tumor volume of the solvent group on the day of starting and the day of finishing administration was 100% inhibition and 0% inhibition, respectively, the inhibition rate was calculated for each compound.

As a result, the compound of the present invention were found to have an antitumor effect on NCI-H2228 cells (tumor). Among them, the compounds of Examples 23 and 123 inhibited the growth of NCI-H2228 cells (tumor) by 116% and 108%, respectively.

Thus, when orally administered, the compounds of the present invention inhibited tumor growth in mice inoculated with H2228 cells, thereby confirming that the compounds of the present invention had oral activity.

In view of the foregoing, in Test Examples 1 to 4, the compounds of the present invention were confirmed to have inhibitory activity against the kinase activity of both EML4-ALK fusion protein v 1 and mutant EGFR (L858R) protein, as well as growth inhibitory activity against human non-small cell lung cancer cell lines NCI-H2228 and HCC827. In Test Example 8, the compounds of the present invention were also confirmed to have an antitumor effect on NCI-H2228 cells (tumor) based on the above actions. Further, in Test Example 5, the compounds of the present invention were confirmed to be safer than TAE684, showing no toxicity even when administered at a dose of 300 mg/kg which is higher than the dose at which exacerbation of common symptoms was observed in TAE684. These indicate that the compounds of the present invention are useful as active ingredients in pharmaceutical compositions for preventing and/or treating cancer, such as lung cancer in one embodiment, non-small cell lung cancer or small cell lung cancer in another embodiment, EML4-ALK fusion polynucleotide-positive and/or mutant EGFR polynucleotide-positive cancer in yet another embodiment, EML4-ALK fusion polynucleotide-positive and/or mutant EGFR polynucleotide-positive lung cancer in yet another embodiment, or EML4-ALK fusion polynucleotide-positive and/or mutant EGFR polynucleotide-positive non-small cell lung cancer in yet another embodiment.

In Non-patent Document 7, it has been confirmed that among EML4-ALK fusion protein-expressing lung cancer cell lines, there are some lung cancer cell lines expressing a constitutively activated EGFR protein together with the EML4-ALK fusion protein. To inhibit the growth of these lung cancer cell lines, both proteins should be inhibited (Non-patent Document 7). The compounds of the present invention have equal inhibitory activity against both EML4-ALK fusion protein v1 and mutant EGFR (L858R) protein, and hence can be expected to have excellent growth inhibitory activity against such lung cancer cell lines at a certain dose. Thus, the compounds of the present invention would be useful as active ingredients in pharmaceutical compositions for preventing and/or treating EML4-ALK fusion polynucleotide-positive and mutant EGFR polynucleotide-positive cancer. Moreover, the compounds of the present invention can be used at a single dose for both EML4-ALK fusion polynucleotide-positive cancer and mutant EGFR polynucleotide-positive cancer.

In contrast, although TAE684 has inhibitory activity against the kinase activity of mutant EGFR (L858R) protein and growth inhibitory activity against HCC827 cells, each activity being equal to that of the compounds of the present invention, TAE684 started to develop serious toxicity at a lower dose than the compound of Example 23 in Test Example 5. Thus, when compared to the compound of Example 23, TAE684 has fears about safety in its effective dose required to produce a sufficient growth inhibitory effect on mutant EGFR polynucleotide-positive cancer.

The compounds of formula (I) were also confirmed for their pharmacological activity in the following series of tests. Unless otherwise specified, the test examples shown below may be accomplished in a known manner and, when using commercially available reagents and/or kits, may be accomplished in accordance with the instructions attached to these commercially available products.

The full-length ALK cDNA was kindly provided by Dr. Steve Morris, St. Jude Children's Research Hospital. This research project was approved by the ethical review committee for gene analysis research of Jichi Medical University.

The anti-phosphorylated ALK antibody used was a product of Cell Signaling Technology Inc., and the anti-ALK antibody used was a product of NEOMARKERS Inc.

TEST EXAMPLE 9

Isolation of EML4-ALK Fusion Polynucleotide v1

(1) Construction of cDNA Library

Using a RNA purification kit (RNeasy Mini Column; Qiagen Inc.), RNA was extracted from a resected specimen of lung adenocarcinoma of a 62 year old male who gave informed consent and cDNA was synthesized using reverse transcriptase (Power Script Reverse Transcriptase) and primers (an oligonucleotide of SEQ ID NO: 3 and CDS primer IIA) (all from Clontech Inc.). After selectively amplifying the full-length cDNA by polymerase chain reaction (PCR) (17 cycles of 98° C. for 10 seconds and 68° C. for 6 minutes) using a primer (5'-PCR primer IIA; Clontech Inc.) and a polymerase (primeSTAR HSDNA polymerase, Takara Bio Inc.), a BstX1 adapter (Invitrogen Inc.) was attached to the both ends of cDNA. The cDNA thus obtained was ligated to a retrovirus plasmid, and a retrovirus plasmid library was constructed by introducing this plasmid to *E. coli* DH10B (Invitrogen Inc.). As a result, the plasmid library containing clones more than 1,500,000 colony forming units in total has been successfully constructed.

(2) Focus Formation Assay

2 μg of the plasmid of the library described above and 0.5 μg of a plasmid for packaging (pGP and pE-eco, both of which were obtained from Takara Bio Inc.) were transfected into BOSC23 packaging cells using a transfection reagent. Two days after the transfection, the culture supernatant was recovered as a solution of recombinant retrovirus library, mixed with polybrene (Sigama Inc.) at a concentration of 4 μg/ml, and the mixture was added to mouse 3T3 cells at MOI (multiplicity of infection) of 0.1 concentration. Two days later, the culture supernatant of 3T3 cells was changed to DMEM-F12 medium (Invitrogen Inc.) supplemented with 5% bovine serum (Invitrogen Inc.) and 2 mM L-glutamine, and the cells were cultured 2 more weeks to obtain 10 or more kinds of transformed foci. After isolating each 3T3 cell clone, the culturing of the clones was continued separately, and the genomic DNA of each clone was extracted. The viral cDNA integrated in each 3T3 clone was amplified and recovered by carrying out PCR (30 cycles of 98° C. for 10 seconds and 68° C. for 6 minutes) using 10 ng of the genomic DNA as a template, 5'-PCR primer IIA primer and DNA polymerase (PrimeStar HS DNA polynerase; Takara Bio Inc.), and cloned into pT7Blue-2 vector.

One of the cDNA thus obtained was 3926 base pair long (SEQ ID NO: 1) and had a single long open reading frame (from the 271st to 3447th nucleotides of SEQ ID NO: 1) coding for a protein having 1059 amino acid residues (SEQ ID NO: 2). Interestingly, about half of the amino-terminus (1-496 amino acid residues of SEQ ID NO: 2) of a protein encoded by this cDNA having a novel full-length sequence was perfectly matched to 1-496 amino acid residues of echinoderm microtubule associated protein like-4 (EML4, GenBank accession No. NM_019063), and on the other hand, about half of the carboxyl terminus (497-1059 amino acid residues of SEQ ID NO: 2) was perfectly matched to the amino acid sequence of anaplastic lymphoma kinase (ALK, GenBank accession No. AB209477). From the above results, the present cDNA was believed to be a fused cDNA between EML4 cDNA and ALK cDNA. Further, the obtained cDNA (cDNA for EML4-ALK fusion polynucleotide v1) contained a domain of ALK tyrosine kinase.

TEST EXAMPLE 10

Detection of EML4-ALK Fusion Polynucleotide in Clinical Specimens cDNAs were synthesized from 33 cases of clinical specimens (resected specimens of non-small cell lung cancer) and from peripheral monocytes of one case of a normal healthy subject.

To detect the cDNA of EML4-ALK fusion polynucleotide v1, PCR (50 cycles of 94° C. for 15 seconds, 60° C. for 30 seconds and 72° C. for 1 minute) was carried out using a quantitative PCR kit (QuantiTect SYBR Green; Qiagen Inc.), the cDNAs as substrates prepared from the clinical specimens and the normal healthy subject described above and oligonucleotides of SEQ ID NOs: 4 and 5 as primers. Using the same specimens, PCR amplifications of the glyceraldehyde-3-phosphate dehydrogenase (hereinafter GAPDH) cDNA was tried as a control. To detect the GAPDH cDNA, oligonucleotides consisting of the nucleotide sequences represented by SEQ ID NOs: 6 and 7 were used as primers. Amplified respective samples were electrophoresed with a size marker DNA (Marker: 50 bp ladder, Invitrogen Inc.). As a result, as shown in the upper part of FIG. 1, in the 3 cases, the cDNA of EML4-ALK fusion polynucleotide v1 was detected. Further, in all the cases analyzed, an amplification of the GAPDH cDNA was confirmed clearly (Lower part of FIG. 1). In addition, the nucleotide sequences of the PCR products identified in these 3 cases were analyzed and the result confirmed that all had the same sequence (the 247 bp including the fusion point of the EML4 gene and the ALK gene; SEQ ID NO: 8). That is, the result of the analyses of the 33 cases of non-small cell lung cancer confirmed that the fusion of the EML4 gene and the ALK gene occurs in 9.1% of the cases (3/33 cases).

Mutation in the EGFR gene has been known to be one of the causes of lung cancer. In the 33 specimens of the cases analyzed as described above, the analysis of the presence of an abnormality in the nucleotide sequence of the EGFR gene according to the known method confirmed a partial deletion of exon 19 in 6 cases. The cases having the EGFR gene mutation and the cases positive for the EML4-ALK fusion polynucleotide belonged to different subgroups. That is, the existing therapeutic agents, which show a therapeutic effect on lung cancer patients having the EGFR gene mutation, are expected to be not effective for the lung cancer patients who are positive for the EML4-ALK fusion polynucleotide.

Also, the 33 cases analyzed as described above were subjected to the investigation whether the full-length ALK gene existed, and it was found that it existed in 8 cases. The specimens of the 7 cases among these 8 cases did not contain the EML4-ALK fusion polynucleotide. That is, the full-length ALK gene did not exist in the 2 cases among the 3 cases where the EML4-ALK fusion polynucleotide was positive.

TEST EXAMPLE 11

Investigation of Tumorgenicity of EML4-ALK Fusion Polypeptide v1

EML4-ALK (K589M)/pMXS, in which the 589th amino acid (ATP binding site), a lysine residue, of the EML4-ALK fusion polypeptide v1 was replaced with methionine, was produced using EML4-ALKv1/pMXS (prepared from a clone in which the EML4-ALK fusion polynucleotide v1 was cloned in the forward orientation into pT7Blue-2 vector, which clone was further digested with restriction enzymes EcoRI and SalI to release the insert, which was then subcloned into the EcoRI-SalI site of pMXS (J. Biol. Chem., vol. 275, p. 24945-24952, 2000)) as a substrate and using a mutation introducing kit (QuickChange Site-Directed Mutagenesis Kit; Stratagene Inc.). In the reaction, oligonucleotides of SEQ ID NO: 9 and SEQ ID NO: 10 were used. The ALK cDNA (Morris, S W et al, Science. 1994 Mar. 4; 263 (5151): 1281-4) was cloned into a retrovirus vector pMXS according to the standard method (designated as ALK/pMXS and ALK/pMX-iresCD8, respectively).

EML4-ALKv1/pMXS described above, full-length ALK/pMXS, a plasmid expressing EML4-ALK (K589M)/pMXS and a blank vector without inserted cDNA (pMXS) were transfected into 3T3 fibroblast cells by the phosphate calcium method and cultured for 21 days. As shown in the upper part of FIG. 2, many transformation foci were observed only when the EML4-ALK fusion protein v1-expressing virus was transfected. The scale bar indicates 100 µm. Further, the same transfected 3T3 cells were inoculated subcutaneously to nude mice at $5 \times 10^5$ cells/mouse and observed for 20 days. It turned out also that tumor was formed only when EML4-ALK fusion protein v1-expressing cells were inoculated. The tumor formation numbers (the number of inoculation sites of 3T3 cells and the number of tumor formation among them) are as follows. The tumor formation number of the full-length ALK expression was 0 among 8, while the tumor formation number in the EML4-ALK fusion protein v1-expressing cells was 8 among 8. In addition, the tumor formation number of EML4-ALK (K589M)-expressing cells was 0 among 8. These results demonstrate that since the full-length ALK protein expression does not induce tumor but the EML4-ALK fusion protein v1 is tumorgenic, the EML4-ALK fusion polynucleotide v1 is a causal gene of cancer. Also, since the tumorgenicity of EML4-ALK was not observed in EML4-ALK (K589M), it would appear that the tumorgenicity was dependent on the kinase activity. Hereinafter, the 3T3 cells modified to express EML4-ALK fusion protein v1 by transfection with the EML4-ALK fusion protein v1 expression plasmid are designated as the v1 expressing 3T3 cells.

TEST EXAMPLE 12

Screening for Inhibitors Against the Kinase Activity of EML4-ALK Fusion Protein (1) Preparation of EML4-ALK Fusion Protein v1

N-terminally FLAG-tagged EML4-ALK fusion protein v1 was inserted into a vector pMX-iresCD8 capable of co-expression of insert cDNA and cell surface antigen CD8 (J. Biol. Chem., 2001, vol. 276, p. 39012-39020) to create a vector FLAG-EML4-ALKv1/pMX-iresCD8 expressing both FLAG-EML4-ALKv1 and CD8. FLAG-EML4-ALKv1/pMX-iresCD8 was used to create a recombinant retrovirus in the same manner as described above and infected into mouse lymphoid cell line BA/F3 cells. Using a magnetic bead reagent for cell separation and a purification column (anti-CD8 monoclonal antibody immobilized on magnetic beads and a MiniMACS purification column; both are products of Miltenyi Biotec Inc.), cell surface CD8-expressing cells were purified conveniently. The BA/F3 cells expressing this N-terminally FLAG-tagged EML4-ALK fusion protein v1 were cultured in RPMI1640 medium containing 10% fetal bovine serum to obtain $2.7 \times 10^9$ cells. After washing 3 times with PBS, the cells were lysed in a lysis solution (50 mM Tris.HCl (pH 7.4), 150 mM NaCl, 1% Triton X100, 5 mM EDTA, 5 mM EGTA, 1 mM NaVO$_4$, 1 mM DTT and protease inhibitor cocktail complete). The EML4-ALK fusion protein v1 present in the supernatant obtained after centrifugation was purified using ANTI-FLAG M2 Affinity Gel (SIGMA-ALDRICH Inc.) according to the method described in the product information document.

(2) Detection of the in vitro Kinase Activity of EML4-ALK Fusion Protein v1

The EML4-ALK fusion protein v1 purified as above was investigated for its phosphorylation activity toward a peptide substrate using a kinase activity detection kit (HTRF KinEASE-TK; Cisbio Inc.). Using TK substrate 1, which was included in the kit, as the substrate, and after adding no ATP or 100 µM ATP, the mixtures were reacted at room temperature for 1 hour, and the count of HTRF was detected as recommended by the Kits manufacturer. As a result, it became clear that the count of HTRF (i.e., phosphorylation of the peptide substrate) was increased by about 12 times by the addition of ATP compare to no addition of ATP. As shown above, the in vitro kinase activity of EML4-ALK fusion protein v1 can be detected using anti-phosphorylated ALK antibody and the kinase activity detection kit.

(3) Inhibitory Effect of Compounds Against the in vitro Kinase Activity of EML4-ALK Fusion Protein v1

Compounds A, B, C and D, which are known as compounds having an inhibitory effect against ALK, were investigated for their inhibitory effect against the in vitro kinase activity of EML4-ALK fusion protein v1 using the kinase activity detection kit mentioned above. Respective compounds were added to a reaction solution containing the EML4-ALK fusion protein v1 to give a final concentration of 10 μM or 10 nM, followed by reaction with or without the addition of ATP. The rest of the operations were carried out as described in (2) above. In the absence of the compound, the phosphorylation count without ATP addition and with ATP addition was assumed to be 100% inhibition and 0% inhibition, respectively. The inhibition (%) of the kinase activity of EML4-ALK fusion protein v1 by each compound was calculated by the following formula.

[Kinase activity inhibition (%) by a compound]=(1−[phosphorylation count when the compound and ATP were added−phosphorylation count when the compound was not added and ATP was not added]/[phosphorylation count when the compound was not added and ATP was added−phosphorylation count when the compound was not added and ATP was not added])×100

The results obtained are shown in Table 7.

It should be noted that compounds A to D in the table below are those shown in Patent Document 1.

TABLE 7

| Test compound | Final concentration | Activity inhibition (%) |
|---|---|---|
| Compound A | 10 μM | 99 |
| Compound B | 10 μM | 56 |
| Compound C | 10 nM | 99 |
| Compound D | 10 nM | 99 |

It was found that all of the compounds inhibited the phosphorylation activity of the purified EML4-ALK fusion protein v1 on the peptide substrate.

The above results indicated that screening for a substance which inhibits the activity of the protein of the present invention could be performed by preparing the EML4-ALK fusion protein and using the in vitro kinase activity as an index.

TEST EXAMPLE 13

Cell Growth Inhibitory Effect of Inhibitors Against the Kinase Activity of EML4-ALK Fusion Protein on Cells Expressing EML4-ALK Fusion Polynucleotide v1

$3 \times 10^6$ cells of v1 expressing 3T3 cells suspended in PBS were inoculated subcutaneously by injection to the back of 5 weeks old male BALB/c nude mice (Charles River Japan, Inc.). After 7 days of the inoculation, the administration of compound C, an inhibitor against the kinase activity of EML4-ALK fusion protein, was initiated. The test was conducted in the solvent group and compound C group, 4 animals per group. Compound C was dissolved in a solvent composed of 10% 1-methyl-2-pyrrolidinone (SIGMA-ALDRICH Inc.)/ 90% polyethylene glycol 300 (Fluka Inc.) and administered orally at a dose of 10 mg/kg. Administrations were performed once a day for 14 days, and body weight and tumor size were measured every other day. Tumor volume was calculated using the following formula.

[Tumor volume $(mm^3)$]=[Tumor major axis (mm)]× [tumor minor axis $(mm)]^2 \times 0.5$ Assuming that the tumor volume of the solvent group on the day of starting and the day of finishing administration was 100% inhibition and 0% inhibition, respectively, the inhibition rate of compound C was calculated. The results indicated that compound C inhibited the growth of v1 expressing 3T3 cells (tumor) by 103%.

The antitumor effect of compound D was investigated by the similar procedure with the following exceptions. The administration of the compound was started after 6 days of the inoculation and carried out once a day for 10 days. As a result, compound D inhibited the growth of v1 expressing 3T3 cells (tumor) by 101%.

TEST EXAMPLE 14

Inhibitory Effect of Compounds Against the in vitro Kinase Activity of EML4-ALK Fusion Protein v1

In the same manner as shown in Test Example 12(3), compounds were investigated for their inhibitory effect against the in vitro kinase activity of EML4-ALK fusion protein v1 using the kinase activity detection kit mentioned above. Test compounds were each added to a reaction solution containing the EML4-ALK fusion protein v1 to give 8 final concentrations from 1000 nM to 0.3 nM, followed by addition of ATP. Another reaction solution was prepared to contain the EML4-ALK fusion protein v1 but no test compound (in which the solvent DMSO alone was added at 0.4% in place of the test compound), followed by reaction with or without ATP addition. The rest of the operations were carried out as described in Test Example 12 (2). In the absence of the test compound, the phosphorylation count without ATP addition and with ATP addition was assumed to be 100% inhibition and 0% inhibition, respectively. The concentration causing 50% inhibition ($IC_{50}$) was calculated for each test compound by the logistic regression method.

As a result, the compounds of formula (I) were found to inhibit the kinase activity of EML4-ALK fusion protein v1. In particular, some of the compounds of formula (I) showed $IC_{50}$ values not greater than 1000 nM or 100 nM in the above test. Among them, the compound of Example 1 showed an $IC_{50}$ value of 42 nM.

As a result of the above tests, the compounds of formula (I) were confirmed to have an inhibitory effect against the kinase activity of EML4-ALK fusion protein v1. This suggests that the compounds of formula (I) can be used as therapeutic agents, e.g., for EML4-ALK fusion gene-positive cancer in one embodiment or for EML4-ALK fusion gene-positive lung cancer in another embodiment.

A pharmaceutical composition which comprises one or more compounds of formula (I) or pharmaceutically acceptable salts thereof as an active ingredient can be prepared in a conventional manner by using a pharmaceutical excipient, a pharmaceutical carrier or other additives commonly used in the art.

Any mode of administration may be used, either oral administration in the dosage form of tablets, pills, capsules, granules, powders, solutions or the like, or parenteral administration in the dosage form of injections (e.g., intraarticular, intravenous, intramuscular, and the like), suppositories, eye drops, eye ointments, percutaneous solutions, ointments, percutaneous patches, transmucosal solutions, transmucosal patches, inhalants or the like.

Solid compositions used for oral administration include tablets, powders, granules, and the like. In these solid compositions, one or more active ingredients are mixed with at least one inert excipient, for example, lactose, mannitol, glucose, hydroxypropylcellulose, microcrystalline cellulose, starch, polyvinylpyrrolidone, and/or magnesium aluminometasilicate, or the like. The compositions may also comprise inert additives, for example, lubricants (e.g., magnesium stearate and the like), disintegrating agents (e.g., carboxymethyl starch sodium and the like), stabilizers, and/or solubilizers, as in the usual cases. Tablets or pills may be coated with sugar coating or a gastric or enteric film, if necessary.

Liquid compositions for oral administration include pharmaceutically acceptable emulsions, solutions, suspensions, syrups, elixirs, or the like, and comprise commonly-used inert diluents such as purified water or ethanol. These liquid compositions may comprise, in addition to inert diluents, auxiliaries (e.g., solubilizers, wetting agents, suspending agents, and the like), sweeteners, flavors, aromatics, and/or antiseptics.

Injections for parenteral administration include sterile aqueous or non-aqueous solutions, suspensions or emulsions. Examples of aqueous solvents include injectable distilled water or physiological saline. Examples of non-aqueous solvents include propylene glycol, polyethylene glycol or vegetable oils (e.g., olive oil and the like), as well as alcohols (e.g., ethanol and the like) or Polysorbate 80 (pharmacopoeia name), and the like. These compositions may further comprise isotonizing agents, antiseptics, wetting agents, emulsifiers, dispersants, stabilizers or solubilizers. They are sterilized, for example, by filtration through a bacteria-retaining filter, by incorporation with disinfectants or by irradiation. Alternatively, they may be formulated into a sterile solid composition and reconstituted for use by being dissolved or suspended in sterile water or a sterile injectable solvent before use.

Formulations for external use include ointments, plasters, creams, jellies, cataplasms, sprays, lotions, eye drops, eye ointments, and the like. They comprise commonly-used ointment bases, lotion bases, aqueous or non-aqueous solutions, suspensions, emulsions or the like. Examples of ointment or lotion bases include polyethylene glycol, propylene glycol, white petrolatum, white beeswax, polyoxyethylene hydrogenated castor oil, glycerine monostearate, stearyl alcohol, cetyl alcohol, Lauromacrogol, sorbitan sesquioleate, and the like.

Transmucosal formulations such as inhalants or transnasal formulations are used in solid, liquid or semi-solid form and can be prepared in a conventionally known manner. For example, such formulations may be supplemented as appropriate with known excipients and further with pH adjustors, antiseptics, surfactants, lubricants, stabilizers, thickeners and so on. For their administration, an appropriate device for inhalation or insufflation may be used. For example, using a known device (e.g., a metered-dose inhalation device and the like) or a nebulizer, the compound(s) may be administered alone or as a powder of a formulated mixture or as a solution or suspension in combination with a pharmaceutically acceptable carrier. Dry powder inhalers or the like may be for single or multiple administration use, and dry powders or powder-containing capsules may be used in such devices. Alternatively, they may be in the form of pressurized aerosol sprays or the like which use an appropriate propellant, for example, a preferred gas such as chlorofluoroalkane, hydrofluoroalkane, carbon dioxide, or the like.

In general, for oral administration, the daily dosage is desirably about 0.001 to 100 mg/kg, preferably 0.1 to 30 mg/kg, and more preferably 0.1 to 10 mg/kg body weight, given as a single dose or in 2 to 4 divided doses. For intravenous administration, the daily dosage is desirably about 0.0001 to 10 mg/kg body weight, given in one or several doses per day. Likewise, for transmucosal formulations, the daily dosage is about 0.001 to 100 mg/kg body weight, given in one or several doses per day. The dosage may be determined as appropriate for each case in consideration of symptom, age, sex and so on.

The compounds of formula (I) can be used in combination with various therapeutic or prophylactic agents for diseases against which the compounds of formula (I) would be effective. In general, when an antitumor agent is administered alone during chemotherapy for tumor, particularly malignant tumor, the antitumor agent has a limit in its effect in terms of side effects and the like, and thus often fails to produce a sufficient antitumor effect. For this reason, in clinical cases, multidrug therapy is used in which two or more drugs with different mechanisms of action are combined. By combining antitumor agents with different mechanisms of action, this combination therapy aims to reduce side effects and/or enhance the desired antitumor effect, for example, 1) to reduce the number of non-sensitive cell population, 2) to prevent or delay the development of drug resistance, 3) to disperse toxicity by combination of drugs with different toxicity levels, and the like. In such combination therapy, drugs may be administered simultaneously or separately in succession or at desired time intervals. Formulations for simultaneous administration may be in either mixed or separate form.

Drugs which can be combined include chemotherapeutics (e.g., alkylating agent, antimetabolite, and the like), immunotherapeutic agents, hormonal therapeutic agents, and cell growth factor inhibitors, more specifically drugs such as cisplatin, carboplatin, paclitaxel, docetaxel, gemcitabine, irinotecan, vinorelbine, bevacizumab, and the like.

EXAMPLES

How to prepare the compounds of formula (I) will be further explained in more detail by way of the following examples. It should be noted that the present invention is not limited to the compounds shown in the following examples. In addition, how to prepare the starting compounds is shown in preparation examples. Processes for preparing the compounds of formula (I) are not limited only to those actually shown in the following examples, and the compounds of formula (I) may also be prepared by any combination of these processes or by any process obvious to those skilled in the art.

In the examples, preparation examples and tables shown below, the following abbreviations are used as needed.

Rex: Preparation Example No., Ex: Example No., No: Compound No., Structure: chemical structural formula, Data: physical and chemical data (FAB+: FAB–MS[M+H]$^+$, FAB–: FAB–MS[M–H]$^-$, ESI+: ESI–MS[M+H]$^+$, CI+: CI[M+H]$^+$, EI: EI[M]$^+$, NMR-DMSOd6: δ (ppm) of $^1$H-NMR peaks in dimethyl sulfoxide-d$_6$, NMR-CDCl3: δ (ppm) of $^1$H-NMR peaks in chloroform-d, MP: melting point (° C.), Amrph: which means that the intended compound was in amorphous form, Cryst: which means that the intended compound was in crystal form, Salt: salt (if empty, the intended compound is in free form), CL1: monohydrochloride, CL2: dihydrochloride, CL3: trihydrochloride, FM: difumarate, Me: methyl, Et: ethyl, $^i$Pr: isopropyl, tBu: tert-butyl, nBu: n-butyl. Rsyn and Syn: preparation process (the number indicated means that the intended compound was prepared from corresponding starting materials in the same manner as used for a compound, in which the indicated number represents its Preparation Example No. or Example No.).

Preparation Example 1

To a mixture of propane-2-thiol (1.5 mL), potassium carbonate (3 g) and N,N-dimethylformamide (20 mL), 4-chloro-2-fluoronitrobenzene (2.5 g) was added and stirred at room temperature for 5 hours. After addition of water, the reaction mixture was extracted with ethyl acetate, and the extract was washed with water and saturated aqueous sodium chloride. After drying over anhydrous sodium sulfate, the solvent was distilled off under reduced pressure to give 4-chloro-2-isopropylsulfanyl-1-nitrobenzene (3.30 g) as a yellow oil.

Preparation Example 2

To a mixture of sodium isopropylsulfinate (3.3 g) and N-methyl-2-pyrrolidinone (20 mL), 2,3-dichloronitrobenzene (4 g) was added and stirred overnight at 70° C. The reaction mixture was diluted with water, and the precipitated solid was collected by filtration and washed with diethyl ether to give 3-chloro-2-isopropylsulfonyl-1-nitrobenzene (3.0 g) as a white solid.

Preparation Example 3

To a mixture of m-chloroperbenzoic acid (7.89 g) and chloroform (100 mL), a mixture of the compound of Preparation Example 1 (3.3 g) and chloroform (50 mL) was added and stirred at 50° C. for 7 hours. After cooling, the reaction mixture was diluted with saturated aqueous sodium hydrogen carbonate and extracted with chloroform. After the organic layer was dried over anhydrous sodium sulfate, the solvent was distilled off under reduced pressure, and the residue was purified by silica gel column chromatography (eluent; n-hexane:ethyl acetate=3:1-2:1) to give 4-chloro-2-isopropylsulfonyl-1-nitrobenzene (3.33 g) as a yellow solid.

Preparation Example 4

To a mixture of 2-nitrobenzenesulfonyl chloride (5.09 g), N-methylethylamine (1.35 g) and chloroform (100 mL), triethylamine (4.11 mL) was added under ice cooling and stirred at room temperature for 5 hours. The reaction mixture was diluted with water and extracted with chloroform. The organic layer was washed sequentially with 1 M hydrochloric acid, saturated aqueous sodium hydrogen carbonate and saturated aqueous sodium chloride, and then dried over anhydrous magnesium sulfate. The solvent was distilled off under reduced pressure to give N-ethyl-N-methyl-2-nitrobenzenesulfonamide (6.48 g) as a brown oil.

Preparation Example 5

To a mixture of N-cyclopropyl-2-nitrobenzenesulfonamide (5.63 g), potassium carbonate (4.82 g) and N,N-dimethylformamide (60 mL), methyl iodide (2.17 mL) was added and stirred at room temperature for 6 hours. The reaction mixture was evaporated under reduced pressure, and the residue was diluted with water and extracted with ethyl acetate. The organic layer was washed with saturated aqueous sodium chloride and dried over anhydrous magnesium sulfate, followed by distilling off the solvent under reduced pressure. The residue was purified by silica gel column chromatography (eluent; n-hexane:diethyl ether=1:0-1:1) to give N-cyclopropyl-N-methyl-2-nitrobenzenesulfonamide (5.35 g) as a brown solid.

Preparation Example 6

To a mixture of the compound of Preparation Example 3 (3.3 g) and acetic acid (30 mL), iron powder (2.23 g) was added and stirred at 80° C. for 3 hours. Insoluble materials in the reaction mixture were removed and the solvent was distilled off under reduced pressure. The residue was diluted with ethyl acetate (100 mL) and insoluble materials were removed, followed by washing with water and saturated aqueous sodium chloride. After drying over anhydrous sodium sulfate, the solvent was distilled off under reduced pressure. The residue was purified by silica gel column chromatography (eluent; n-hexane:ethyl acetate=3:1-2:1) to give 4-chloro-2-isopropylsulfonylaniline (2.79 g) as a light-orange solid.

Preparation Example 7

To a mixture of 2,4-dichloro-6-methoxy-1,3,5-triazine (370 mg) and tetrahydrofuran (10 mL), a mixture of 2-(isopropylsulfonyl)aniline (400 mg), N-ethyl-N-isopropylpropane-2-amine (0.72 mL) and tetrahydrofuran (5 mL) was added and stirred overnight at room temperature and further stirred at 70° C. for 7 hours. The reaction mixture was cooled on ice and diluted with water (60 mL). The precipitated solid was collected by filtration, purified by silica gel column chromatography (eluent; chloroform) and then washed with hexane to give 4-chloro-N-[2-(isopropylsulfonyl)phenyl]-6-methoxy-1,3,5-triazine-2-amine (200 mg) as a white solid.

Preparation Example 8

To a mixture of 2-(isopropylsulfonyl)aniline (450 mg) and N,N-dimethylformamide (10 mL), 55% sodium hydride in oil (200 mg) was added under ice cooling and stirred for 30 minutes, followed by addition of 2,4-dichloroquinazoline (500 mg). The reaction mixture was stirred for 30 minutes under ice cooling and further stirred overnight at room temperature. The reaction mixture was cooled on ice, diluted with water and then extracted with ethyl acetate. The organic layer was washed with water and saturated aqueous sodium chloride. After drying over anhydrous sodium sulfate, the solvent was distilled off under reduced pressure, and the residue was purified by silica gel column chromatography (eluent; n-hexane:ethyl acetate=5:1-3:1) to give 2-chloro-N-[2-(isopropylsulfonyl)phenyl]quinazoline-4-amine (0.67 g) as a light-yellow solid.

Preparation Example 9

To a mixture of 2-fluoroaniline (232 mg), 2,4-dichloroquinazoline (400 mg) and N,N-dimethylformamide (4 mL), potassium carbonate (430 mg) was added and stirred at room temperature for 8 hours. The reaction mixture was diluted with water (40 mL), and the precipitated solid was collected by filtration and purified by silica gel column chromatography (eluent; n-hexane:ethyl acetate=5:1-3:1) to give 2-chloro-N-(2-fluorophenyl)quinazoline-4-amine (0.22 g) as a light-yellow solid.

Preparation Example 10

To a mixture of the compound of Preparation Example 24 (309 mg) and acetonitrile (5 mL), azetidine hydrochloride (112 mg) and N-ethyl-N-isopropylpropane-2-amine (0.42 mL) were added and stirred at room temperature for 1 hour. The reaction mixture was diluted with water, and the precipitated solid was collected by filtration and dried to give 4-azetidin-1-yl-6-chloro-N-(2-fluorophenyl)-1,3,5-triazine-2-amine (253 mg) as a white solid.

Preparation Example 11

To a mixture of tert-butyl 4-hydroxypiperidine-1-carboxylate (1.49 g) and tetrahydrofuran (30 mL), potassium tert-butoxide (830 mg) was added under ice cooling and stirred for 30 minutes, followed by addition of a mixture of 4-fluoro-2-methoxy-1-nitrobenzene (1.00 g) and tetrahydrofuran (20 mL). After stirring at room temperature for 3 hours, the reaction mixture was extracted by addition of water and ethyl acetate, washed with saturated aqueous sodium chloride, and then dried over anhydrous magnesium sulfate. The solvent was distilled off under reduced pressure, and the residue was purified by silica gel column chromatography (eluent; n-hexane:diethyl ether=4:1) to give tert-butyl 4-(3-methoxy-4-nitrophenoxy)piperidine-1-carboxylate (898 mg).

Preparation Example 12

To a mixture of 4-fluoro-2-methoxy-1-nitrobenzene (5 g), potassium carbonate (10 g) and N,N-dimethylformamide (50 mL), 1,4-dioxa-8-azaspiro[4.5]decane (5 g) was added and stirred overnight at 70° C. The reaction mixture was diluted with water (150 mL), and the precipitated solid was collected by filtration and washed with diethyl ether to give 8-(3-methoxy-4-nitrophenyl)-1,4-dioxa-8-azaspiro[4.5]decane (7.86 g) as a light-yellow solid.

Preparation Example 13

To a mixture of tert-butyl 3-(4-methylpiperazin-1-yl)pyrrolidine-1-carboxylate (3.04 g) and chloroform (30 mL), trifluoroacetic acid (10 mL) was added and stirred at room temperature for 1 hour. The reaction mixture was evaporated under reduced pressure to remove the solvent, followed by addition of a mixture of 4-fluoro-2-methoxy-1-nitrobenzene (1.93 g), potassium carbonate (12.2 g) and N,N-dimethylformamide (60 mL). After stirring overnight at 80° C., the reaction mixture was evaporated under reduced pressure to remove the solvent, and the residue was diluted with water and extracted with ethyl acetate. The organic layer was washed with saturated aqueous sodium chloride, and then dried over anhydrous magnesium sulfate. The solvent was distilled off under reduced pressure to give 1-[1-(3-methoxy-4-nitrophenyl)pyrrolidin-3-yl]-4-methylpiperazine (2.16 g).

Preparation Example 14

To a mixture of the compound of Preparation Example 57 (6.68 g), 1-methylpiperazine (4.17 mL) and dichloromethane (100 mL), sodium triacetoxyborohydride (8.04 g) was added and stirred overnight at room temperature. The reaction mixture was diluted with water and saturated aqueous sodium hydrogen carbonate, extracted with chloroform, and then washed with saturated aqueous sodium chloride. The solvent was distilled off under reduced pressure, and the residue was purified by silica gel column chromatography (eluent; chloroform:methanol=1:0-20:1) to give 1-[1-(3-ethoxy-4-nitrophenyl)piperidin-4-yl]-4-methylpiperazine (6.68 g).

Preparation Example 15

To a mixture of 4-fluoro-2-methyl-1-nitrobenzene (3.08 g), potassium carbonate (6.80 g) and N,N-dimethylformamide (30 mL), piperidine-4,4-diol hydrochloride (3.83 g) was added and stirred at 70° C. for 2 days. The reaction mixture was evaporated under reduced pressure, and the residue was diluted with water and ethyl acetate. The precipitated solid was collected by filtration. After drying, dichloromethane (56 mL), 1-methylpiperazine (3.00 mL) and sodium triacetoxyborohydride (5.75 g) were added and stirred overnight at room temperature. The reaction mixture was diluted with water and saturated aqueous sodium hydrogen carbonate, extracted with chloroform, and then washed with saturated aqueous sodium chloride. After drying over anhydrous magnesium sulfate, the solvent was distilled off under reduced pressure, and the residue was purified by silica gel column chromatography (eluent; chloroform:methanol=1:0-20:1) to give 1-methyl-4-[1-(3-methyl-4-nitrophenyl)piperidin-4-yl] piperazine (1.29 g).

Preparation Example 16

To a mixture of concentrated sulfuric acid (40 mL) and acetic acid (60 mL), N-[2-(4-chlorophenyl)ethyl]-2,2,2-trifluoroacetamide (14.2 g) and paraformaldehyde (2.79 g) were added sequentially and stirred overnight under an argon atmosphere. The reaction mixture was added to ice-cold water, extracted with ethyl acetate, and then washed with saturated aqueous sodium hydrogen carbonate and saturated aqueous sodium chloride. After drying over anhydrous magnesium sulfate, the solvent was distilled off under reduced pressure to give 7-chloro-2-(trifluoroacetyl)-1,2,3,4-tetrahydroisoquinoline (13.7 g) as a light-yellow solid.

Preparation Example 17

The compound of Preparation Example 16 (13.7 g) was dissolved in concentrated sulfuric acid (60 mL) and then cooled to 0° C., followed by dropwise addition of a solution of potassium nitrate (3.3 g) in concentrated sulfuric acid (60 mL) over 1 hour. After stirring for 1 hour under ice cooling, the reaction mixture was added to ice-cold water. After extraction with ethyl acetate, the organic layer was washed with saturated aqueous sodium chloride and dried over anhydrous magnesium sulfate. The solvent was distilled off under reduced pressure, and the residue was recrystallized from ethyl acetate-hexane to give 7-chloro-6-nitro-2-(trifluoroacetyl)-1,2,3,4-tetrahydroisoquinoline (4.46 g) as a colorless solid.

Preparation Example 18

To a mixture of tert-butyl 1-oxa-4,9-diazaspiro[5.5]undecane-9-carboxylate (5.80 g) and dioxane (100 mL), 1 M aqueous sodium hydroxide (24.9 mL) and benzyl chloroformate (3.55 mL) were added sequentially under ice cooling and stirred at room temperature for 16 hours. The reaction mixture was concentrated under reduced pressure and then extracted with ethyl acetate. The organic layer was concentrated under reduced pressure, and the residue was purified by silica gel column chromatography (eluent; n-hexane:ethyl acetate=9:1-1:1) to give 4-benzyl 9-tert-butyl 1-oxa-4,9-diazaspiro[5.5]undecane-4,9-dicarboxylate (8.06 g) as a colorless syrup.

Preparation Example 19

To a mixture of the compound of Preparation Example 18 (8.06 g) and ethanol (200 mL), 4 M hydrochloric acid in dioxane (30 mL) was added and stirred at room temperature for 16 hours. The solvent was distilled off under reduced pressure, and the residue was recrystallized from diethyl ether-ethanol to give benzyl 1-oxa-4,9-diazaspiro[5.5]undecane-4-carboxylate hydrochloride (3.86 g) as a colorless solid.

Preparation Example 20

To a mixture of the compound of Preparation Example 12 (7.83 g) and ethanol (100 mL), 10% palladium on carbon (water content: 53%, 2.83 g) was added and stirred overnight at room temperature under a hydrogen atmosphere at normal pressure. After filtration through celite, the filtrate was evaporated under reduced pressure to give 4-(1,4-dioxa-8-azaspiro[4.5]decan-8-yl)-2-methoxyaniline (6.83 g) as a light-purple solid.

Preparation Example 21

To a mixture of the compound of Preparation Example 71 (1.32 g) and acetic acid (30 mL), iron powder (0.79 g) was added and stirred at 80° C. for 3 hours. Insoluble materials in the reaction mixture were removed and the solvent was distilled off under reduced pressure. The residue was diluted with ethyl acetate and insoluble materials were removed, followed by washing with saturated aqueous sodium chloride. After drying over anhydrous sodium sulfate, the solvent was distilled off under reduced pressure to give 2-chloro-4-[4-(4-methylpiperazin-1-yl)piperidin-1-yl]aniline (290 mg).

Tables 8 and 9 show the chemical structures of the compounds prepared in the above preparation examples. Further, in the same manner as shown in the above preparation examples, the additional compounds shown in Tables 10 to 16 were also prepared from their corresponding starting materials. Tables 17 to 19 show the instrumental analysis data of these compounds obtained in the preparation examples.

Example 1

To a mixture of 2-methoxy-4-[4-(4-methylpiperazin-1-yl)piperidin-1-yl]aniline (230 mg) and ethanol (3 mL), methanesulfonic acid (0.11 mL) was added and stirred at room temperature for 15 minutes, followed by addition of the compound of Preparation Example 8 (200 mg) and further stirring at 100° C. for 3 hours. After cooling, the reaction mixture was diluted with water (20 mL) and adjusted to pH 8 with saturated aqueous sodium hydrogen carbonate, followed by filtration to collect the precipitated solid. The resulting solid was purified by silica gel column chromatography (eluent; chloroform:methanol:saturated aqueous ammonia=50:1:0.1-30:1:0.1) to give $N^4$-[2-(isopropylsulfonyl)phenyl]-$N^2$-{2-methoxy-4-[4-(4-methylpiperazin-1-yl)piperidin-1-yl]phenyl}quinazoline-2,4-diamine (0.26 g) as a yellow amorphous substance.

Example 2

To a mixture of 2-methoxy-$N^4$-methyl-$N^4$-(1-methylpiperidin-4-yl)benzene-1,4-diamine (150 mg) and ethanol (3 mL), methanesulfonic acid (0.08 mL) was added and stirred at room temperature for 15 minutes, followed by addition of the compound of Preparation Example 8 (240 mg) and further stirring at 100° C. for 3 hours. After cooling, the reaction mixture was adjusted to pH 8 by addition of water and saturated aqueous sodium hydrogen carbonate, and then extracted with ethyl acetate. The extract was washed with water and saturated aqueous sodium chloride. After drying over anhydrous sodium sulfate, the solvent was distilled off under reduced pressure, and the residue was purified by silica gel column chromatography (eluent; chloroform:methanol:saturated aqueous ammonia=100:1:0.1-50:1:0.1) to give a brown amorphous substance. The resulting amorphous substance was dissolved in ethanol (5 mL) and ethyl acetate (5 mL), followed by addition of 4 M hydrogen chloride in ethyl acetate (0.3 mL). After stirring for 10 minutes, ethyl acetate (20 mL) was added, and the precipitated solid was collected by filtration to give $N^4$-[2-(isopropylsulfonyl)phenyl]-$N^2$-{2-methoxy-4-[methyl(1-methylpiperazin-4-yl)amino]phenyl}quinazoline-2,4-diamine trihydrochloride (0.15 g) as a light-yellow solid.

Example 3

To a mixture of the compound of Preparation Example 27 (200 mg), 2-methoxy-4-(morpholin-4-yl)aniline (158 mg) and acetonitrile (10 mL), N-ethyl-N-isopropylpropane-2-amine (0.13 mL) was added and heated under reflux for 12 hours. The reaction mixture was diluted with water, and the precipitated solid was collected by filtration, dried and then purified by silica gel column chromatography (eluent; chloroform:methanol=20:1) to give 2-({4-[(2-methoxy-4-morpholin-4-ylphenyl)amino]-1,3,5-triazin-2-yl}amino)-N-methylbenzamide (135 mg) as a white solid.

Example 4

A mixture of the compound of Preparation Example 22 (209 mg), 2-methoxy-4-(4-phenylpiperazin-1-yl)aniline (189 mg), N-ethyl-N-isopropylpropane-2-amine (0.12 mL) and N-methyl-2-pyrrolidinone (3 mL) was stirred at 120° C. for 20 minutes using a microwave reaction system. The reaction mixture was diluted with water, and the precipitated solid was collected by filtration, dried and then purified by silica gel column chromatography (eluent; chloroform:methanol=1:0-20:1). The resulting product was dissolved in ethyl acetate and 4 M hydrogen chloride in ethyl acetate was added thereto, followed by evaporation under reduced pressure to remove the solvent. The residue was crystallized from ethanol to give N-[2-(isopropylsulfonyl)phenyl]-N'-[2-methoxy-4-(4-phenylpiperazin-1-yl)phenyl]-1,3,5-triazine-2,4-diamine trihydrochloride (273 mg).

Example 5

To a mixture of the compound of Preparation Example 34 (850 mg) and acetonitrile (17 mL), the compound of Preparation Example 37 (806 mg) and N-ethyl-N-isopropylpropane-2-amine (0.44 mL) were added at room temperature and stirred for 1 hour. The reaction mixture was diluted with water, extracted with chloroform, and then washed with saturated aqueous sodium chloride. After drying over anhydrous magnesium sulfate, the solvent was distilled off under reduced pressure, and the residue was purified by silica gel column chromatography (eluent; n-hexane:ethyl acetate=1:1). The resulting product was dissolved in ethyl acetate and 4 M hydrogen chloride in ethyl acetate was added thereto, followed by evaporation under reduced pressure to remove the solvent. The residue was crystallized from a mixed solvent of ethanol and ethyl acetate to give 6-chloro-N-[2-(isopropylsulfonyl)phenyl]-N'-[2-methoxy-4-(piperidin-4-yloxy)phenyl]-1,3,5-triazine-2,4-diamine hydrochloride (323 mg).

Example 6

A mixture of the compound of Preparation Example 78 (320 mg), the compound of Preparation Example 20 (260 mg), N-ethyl-N-isopropylpropane-2-amine (0.17 mL) and N-methyl-2-pyrrolidinone (1 mL) was reacted at 120° C. for 20 minutes using a microwave reaction system. After cooling, the reaction mixture was poured into water (20 mL), and the precipitated solid was collected by filtration and then dried to give a light-purple solid. To the resulting solid, acetic acid (2 mL) and water (1 mL) were added and stirred overnight at 70° C. The reaction mixture was concentrated under reduced pressure, and the residue was partitioned by addition of ethyl acetate (50 mL) and saturated aqueous sodium hydrogen carbonate (25 mL). The organic layer was washed with water and saturated aqueous sodium chloride. After drying over anhydrous sodium sulfate, the solvent was distilled off under reduced pressure, and the residue was purified by silica gel column chromatography (eluent; n-hexane:ethyl acetate=1:1-1:3) to give N-isopropyl-2-[(4-{[2-methoxy-4-(4-oxopiperidin-1-yl)phenyl]amino}-1,3,5-triazin-2-yl)amino]benzenesulfonamide (0.32 g) as an amorphous substance.

Example 7

A mixture of the compound of Example 163 (174 mg), acetic acid (2 mL) and water (1 mL) was stirred overnight at 70° C. To the reaction mixture, ethyl acetate and saturated aqueous sodium hydrogen carbonate were added, and the organic layer was washed with saturated aqueous sodium chloride. After drying over anhydrous magnesium sulfate, the solvent was distilled off under reduced pressure, and the resulting residue was dissolved in dichloromethane (5 mL), followed by addition of 1-methylpiperazine (0.063 mL) and sodium triacetoxyborohydride (122 mg). After stirring at room temperature for two days, the reaction mixture was diluted with saturated aqueous sodium hydrogen carbonate, extracted with chloroform, and then dried over anhydrous magnesium sulfate. The solvent was distilled off under reduced pressure, and the residue was purified by silica gel column chromatography (eluent; chloroform:methanol=1:0-20:1) to give 2-{[4-({2-methoxy-4-[4-(4-methylpiperazin-1-yl)piperidin-1-yl]phenyl}amino)-1,3,5-triazin-2-yl]amino}-N-methylbenzenesulfonamide (42 mg) as a colorless solid.

Example 8

To a mixture of the compound of Example 31 (76 mg) and acetonitrile (5 mL), pyrrolidine (0.041 mL) was added and heated under reflux for 1 hour. The reaction mixture was diluted with water, and the precipitated solid was collected by filtration, dried and then purified by silica gel column chromatography (eluent; chloroform:methanol=20:1) to give 2-({4-[(2-methoxy-4-morpholin-4-ylphenyl)amino]-6-pyrrolidin-1-yl-1,3,5-triazin-2-yl}amino)-N-methylbenzamide (46 mg) as a white powder.

Example 9

To a mixture of the compound of Example 68 (3.15 g) and ethyl acetate (30 mL), 4 M hydrogen chloride in ethyl acetate (30 mL) was added and stirred at room temperature for 1 hour. The solvent was distilled off under reduced pressure, and the residue was diluted with saturated aqueous sodium hydrogen carbonate and then extracted with ethyl acetate. The organic layer was washed with saturated aqueous sodium chloride and then dried over anhydrous magnesium sulfate. The solvent was distilled off under reduced pressure, and the residue was purified by silica gel column chromatography (eluent; chloroform:methanol:saturated aqueous ammonia=100:10:1) to give N-[2-(isopropylsulfonyl)phenyl]-N'-[2-methoxy-4-(piperidin-4-yloxy)phenyl]-1,3,5-triazine-2,4-diamine (2.1 g) as a colorless amorphous substance.

Example 10

To a mixture of the compound of Example 62 (140 mg), morpholine (0.08 mL) and 1,2-dichloroethane (2 mL), sodium triacetoxyborohydride (80 mg) was added and stirred at room temperature for 5 hours. The reaction mixture was diluted with saturated aqueous sodium hydrogen carbonate and extracted with chloroform, and the organic layer was dried over anhydrous sodium sulfate. The solvent was distilled off under reduced pressure, and the residue was purified by silica gel column chromatography (eluent; chloroform:methanol=100:0-100:1) and then washed with diethyl ether to give $N^4$-[2-(isopropylsulfonyl)phenyl]-$N^2$-[2-methoxy-4-(4-morpholin-4-ylpiperidin-1-yl)phenyl]quinazoline-2,4-diamine (0.1 g) as a yellow powder.

Example 11

To a mixture of the compound of Example 66 (150 mg), triethylamine (0.05 mL) and tetrahydrofuran (2 mL), acetic anhydride (0.03 mL) was added and stirred at room temperature for 6 hours. The reaction mixture was diluted with saturated aqueous sodium hydrogen carbonate and extracted with ethyl acetate, and the organic layer was washed with water and saturated aqueous sodium chloride. After drying over anhydrous sodium sulfate, the solvent was distilled off under reduced pressure, and the residue was purified by silica gel column chromatography (eluent; chloroform:methanol=100:1-50:1) and then washed with hexane to give $N^2$-[4-(4-acetylpiperazin-1-yl)-2-methoxyphenyl]-$N^4$-[2-(isopropylsulfonyl)phenyl]quinazoline-2,4-diamine (0.11 g) as a yellow powder.

Example 12

To a mixture of the compound of Example 147 (240 mg), formalin (0.18 mL) and 1,2-dichloroethane (5 mL), sodium triacetoxyborohydride (280 mg) was added and stirred at room temperature for 3 days. The reaction mixture was diluted with saturated aqueous sodium hydrogen carbonate and extracted with chloroform, and the organic layer was dried over anhydrous sodium sulfate. After the solvent was distilled off under reduced pressure, the residue was purified by silica gel column chromatography (eluent; chloroform:methanol:saturated aqueous ammonia=50:1:0.1-30:10:1) and then washed with diethyl ether to give N-[2-(isopropylsulfonyl)phenyl]-N'-[2-methoxy-4-(1-methyl-diazaspiro[5.5]undecan-9-yl)phenyl]-1,3,5-triazine-2,4-diamine (135 mg) as a light-yellow powder.

Example 13

A mixture of the compound of Example 22 (169 mg) and 6 M hydrochloric acid (4 mL) was stirred at 50° C. for 2 hours. After cooling, the reaction mixture was basified by addition of water and 1 M aqueous sodium hydroxide, and then extracted with chloroform. The organic layer was washed with saturated aqueous sodium chloride and dried over anhydrous magnesium sulfate. The solvent was distilled off under reduced pressure, followed by recrystallization from ethanol-diethyl ether to give 6-{[2-(isopropylsulfonyl)phenyl]amino}-4-({2-methoxy-4-[4-(4-methylpiperazin-1-yl)piperidin-1-yl]phenyl}amino)-1,3,5-triazin-2(1H)-one (27 mg).

Example 14

A mixture of the compound of Example 23 (250 mg) and pyridine hydrochloride (1 g) was stirred at 200° C. for 10 minutes. After cooling to room temperature, the reaction mixture was diluted with water and washed with chloroform. The aqueous layer was evaporated under reduced pressure, and the residue was purified by silica gel column chromatography (eluent; chloroform:methanol=1:0-10:1) to give 2-[(4-{[2-(isopropylsulfonyl)phenyl]amino}-1,3,5-triazin-2-yl)amino]-5-[4-(4-methylpiperazin-1-yl)piperidin-1-yl]phenol (45 mg).

Example 15

To a mixture of the compound of Example 102 (630 mg), ethanol (10 mL) and tetrahydrofuran (10 mL), 10% palladium on carbon (water content: 53%, 500 mg) was added and stirred at room temperature for 2 hours under a hydrogen atmosphere at normal pressure. After filtration through celite, the filtrate was evaporated under reduced pressure, and the residue was purified by silica gel column chromatography (eluent; chloroform:methanol=1:0-20:1) to give N-[2-(isopropylsulfonyl)phenyl]-N'-[2-methoxy-4-(1-oxa-4,9-diazaspiro[5.5]undecan-9-yl)phenyl]-1,3,5-triazine-2,4-diamine (102 mg).

Example 16

To a mixture of the compound of Example 177 (1.09 g) and ethyl acetate (10 mL), 4 M hydrogen chloride in ethyl acetate (10 mL) was added and stirred at room temperature for 30 minutes. The reaction mixture was evaporated under reduced pressure, and the residue was washed with ethyl acetate, collected by filtration and then dried to give N-(7-fluoro-1,2,3,4-tetrahydroisoquinolin-6-yl)-N'-[2-(isopropylsulfonyl)phenyl]-1,3,5-triazine-2,4-diamine dihydrochloride (950 mg) as a colorless solid.

Example 17

To a mixture of the compound of Example 178 (1.2 g) and methanol (15 mL), 2 M hydrochloric acid (15 mL) was added and heated overnight under reflux. The reaction mixture was concentrated under reduced pressure, diluted with saturated aqueous sodium hydrogen carbonate, extracted with chloroform and then washed with saturated aqueous sodium chloride. The solvent was distilled off, and the residue was purified by silica gel column chromatography (eluent; chloroform:methanol=1:0-20:1) to give N-(7-chloro-1,2,3,4-tetrahydroisoquinolin-6-yl)-N'-[2-(isopropylsulfonyl)phenyl]-1,3,5-triazine-2,4-diamine (260 mg) as a colorless amorphous substance.

Example 18

To a mixture of the compound of Example 62 (13.6 mg), methylamine hydrochloride (2.0 mg), triethylamine (3.0 mg) and 1,2-dichloroethane (0.5 mL), sodium triacetoxyborohydride (10.5 mg) was added and stirred overnight at room temperature. The reaction mixture was partitioned by addition of chloroform and water, and the organic layer was evaporated under reduced pressure. The residue was separated and purified by HPLC (column: SunFire C18 5 μm 19 mm×100 mm (Waters Inc.), solvent: MeOH/0.1% HCOOH—H$_2$O=10/90 (0 min)-10/90 (1 min)-95/5 (9 min)-95/5 (12 min), flow rate: 25 mL/min) to give N$^4$-[2-(isopropylsulfonyl)phenyl]-N$^2$-{2-methoxy-4-[4-(methylamino)piperidin-1-yl]phenyl}quinazoline-2,4-diamine (12.5 mg).

In Examples 76, 77, 78, 85 and 110, the desired compounds were obtained by being reacted in the same manner, and then deprotected, separated and purified.

Example 19

To a mixture of the compound of Example 72 (9.6 mg), cyclohexanone (2.9 mg) and dichloromethane (0.5 mL), sodium triacetoxyborohydride (10.5 mg) was added and stirred overnight at room temperature. The reaction mixture was partitioned by addition of chloroform and water, and the organic layer was evaporated under reduced pressure. The residue was separated and purified by HPLC (column: SunFire C18 5 μm 19 mm×100 mm (Waters Inc.), solvent: MeOH/0.1% HCOOH—H$_2$O=10/90 (0 min)-10/90 (1 min)-95/5 (9 min)-95/5 (12 min), flow rate: 25 mL/min) to give N-[4-(4-cyclohexylpiperazin-1-yl)-2-methoxyphenyl]-N'-[2-(isopropylsulfonyl)phenyl]-1,3,5-triazine-2,4-diamine (5.1 mg).

In Examples 134 and 141, the desired compounds were obtained by being reacted in the same manner, and then deprotected, separated and purified.

Example 20

To a mixture of the compound of Example 72 (9.6 mg), acetic acid (1.8 mg), 1-hydroxybenzotriazole (3.4 mg) and N,N-dimethylformamide (0.5 mL), PS-Carbodiimide (100 mg, Argonaut Technologies Inc.) was added and stirred overnight at room temperature. After addition of MP-Carbonate (50 mg, Argonaut Technologies Inc) and PS-Isocyanate (50 mg, Argonaut Technologies Inc) at room temperature, the reaction mixture was stirred for 2 hours and filtered to remove insoluble materials. The filtrate was concentrated under reduced pressure, and the residue was separated and purified by HPLC (column: SunFire C18 5 μm 19 mm×100 mm (Waters Inc.), solvent: MeOH/0.1% HCOOH—H$_2$O=10/90 (0 min)-10/90 (1 min)-95/5 (9 min)-95/5 (12 min), flow rate: 25 ml/min) to give N-[4-(4-acetylpiperazin-1-yl)-2-methoxyphenyl]-N'-[2-(isopropylsulfonyl)phenyl]-1,3,5-triazine-2,4-diamine (6.8 mg).

In Examples 160, 161 and 162, the desired compounds were obtained by being reacted in the same manner, and then deprotected, separated and purified.

Tables 20 to 22 show the chemical structures of the compounds prepared in the above examples. Further, in the same manner as shown in the above examples, the additional compounds shown in Tables 23 to 42 were also prepared from their corresponding starting materials. Tables 43 to 50 show the instrumental analysis data of these compounds obtained in the examples.

TABLE 8

| Rex/Salt | Structure |
|---|---|
| 1 | (2-nitro-4-chlorophenyl isopropyl sulfide) |

TABLE 8-continued
| Rex/Salt | Structure |
|---|---|
| 2 | 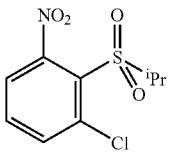 |
| 3 | 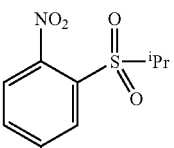 |
| 4 | 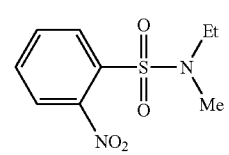 |
| 5 | 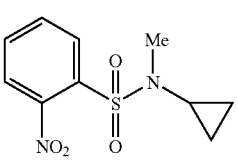 |
| 6 | 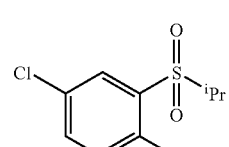 |
| 7 | 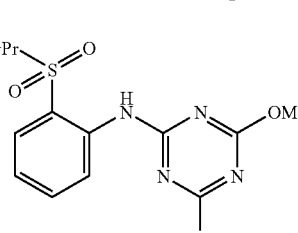 |
| 8 | 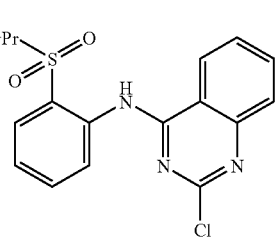 |
| 9 | 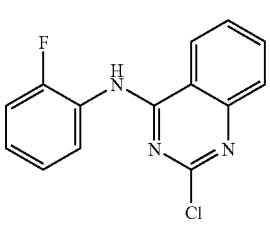 |
TABLE 8-continued
| Rex/Salt | Structure |
|---|---|
| 10 | 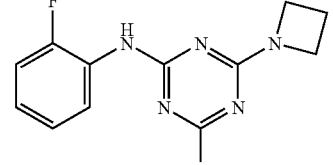 |
TABLE 9
| Rex/Salt | Structure |
|---|---|
| 11 | 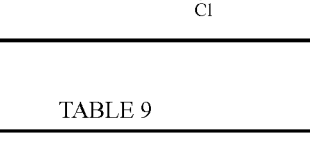 |
| 12 | 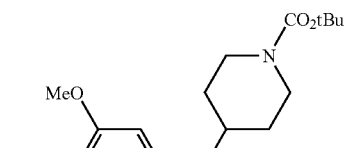 |
| 13 | 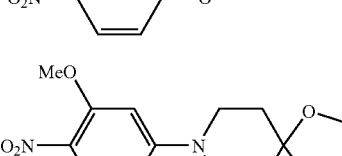 |
| 14 | 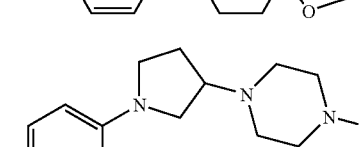 |
| 15 | 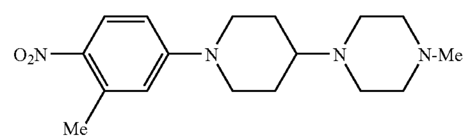 |
| 16 | 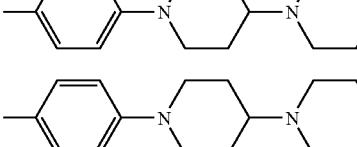 |
| 17 | 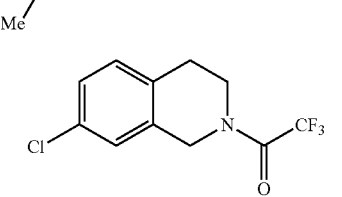 |

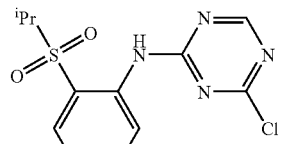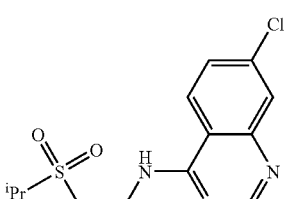

TABLE 10-continued

| Rex/Salt | Structure |
|---|---|
| 31 | 4-chloro-2-nitrophenyl isopropyl sulfide |

TABLE 11

| Rex/Salt | Structure |
|---|---|
| 32 | 4-chloro-2-nitrophenyl isopropyl sulfone |
| 33 | N-(2,5-dichloroquinazolin-4-yl)-2-(isopropylsulfonyl)aniline |
| 34 | N-(2,4-dichloro-1,3,5-triazin-6-yl)-2-(isopropylsulfonyl)aniline |
| 35 | 4-chloro-2-(isopropylsulfonyl)aniline |
| 36 | N-(2-chloroquinazolin-4-yl)-5-chloro-2-(isopropylsulfonyl)aniline |
| 37 | 4-(4-amino-3-methoxyphenoxy)piperidine-1-carboxylic acid tert-butyl ester |
| 38 | N-[4-chloro-6-morpholino-1,3,5-triazin-2-yl]-2-(isopropylsulfonyl)aniline |
| 39 | 4-methoxy-2-(isopropylthio)-1-nitrobenzene |
| 40 | 5-methoxy-2-nitrophenyl isopropyl sulfone |
| 41 | 4-methoxy-2-nitrophenyl isopropyl sulfide |

TABLE 12

| Rex/Salt | Structure |
|---|---|
| 42 | 4-methoxy-2-(isopropylsulfonyl)aniline |
| 43 | 4-methoxy-2-nitrophenyl isopropyl sulfone |
| 44 | N-(2-chloroquinazolin-4-yl)-5-methoxy-2-(isopropylsulfonyl)aniline |
| 45 | 5-methoxy-2-(isopropylsulfonyl)aniline |

TABLE 12-continued

| Rex/Salt | Structure |
|---|---|
| 46 | 2-(iPrSO2)-5-methoxyphenyl-NH-(2-chloroquinazolin-4-yl) |
| 47 | 2-methoxy-4-(tetrahydropyran-4-yloxy)-nitrobenzene |
| 48 | 2-methoxy-4-(tetrahydropyran-4-yloxy)-aniline |
| 49 | 2-amino-6-chlorophenyl iPr sulfone |
| 50 | 2-(iPrSO2)phenyl-NH-(4-chloro-6-methyl-1,3,5-triazin-2-yl) |
| 51 | 2-chloro-6-(iPrSO2)phenyl-NH-(2-chloroquinazolin-4-yl) |

TABLE 13

| Rex/Salt | Structure |
|---|---|
| 52 | 2-(N-methylcarbamoyl)phenyl-NH-(2-chloroquinazolin-4-yl) |
| 53 | 3-(methylsulfonyl)phenyl-NH-(2-chloroquinazolin-4-yl) |
| 54 | 4-(methylsulfonyl)phenyl-NH-(2-chloroquinazolin-4-yl) |
| 55 | 1-(4-nitro-3-methoxyphenyl)-4-phenylpiperazine |
| 56 | 1-(4-amino-3-methoxyphenyl)-4-phenylpiperazine |
| 57 | 1-(3-ethoxy-4-nitrophenyl)piperidin-4-one |
| 58 | 1-(3-isopropoxy-4-nitrophenyl)piperidin-4-one |
| 59 | 1-(3-isopropoxy-4-nitrophenyl)-4-(4-methylpiperazin-1-yl)piperidine |
| 60 | 1-(3-ethoxy-4-aminophenyl)-4-(4-methylpiperazin-1-yl)piperidine |

TABLE 13-continued
| Rex/Salt | Structure |
|---|---|
| 61 | 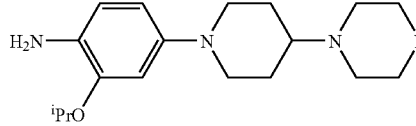 |
| 62 | 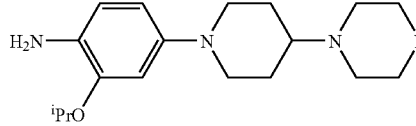 |
| 63 | 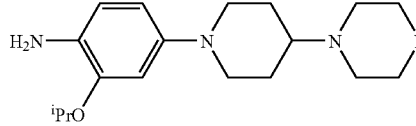 |
TABLE 14
| Rex/Salt | Structure |
|---|---|
| 64 | 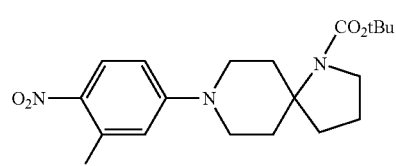 |
| 65 | 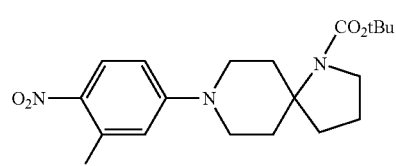 |
| 66 | 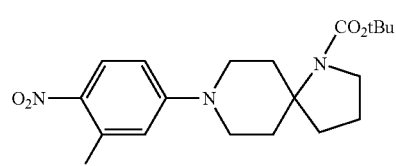 |
| 67 | 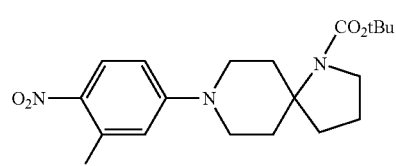 |
TABLE 14-continued
| Rex/Salt | Structure |
|---|---|
| 68 | 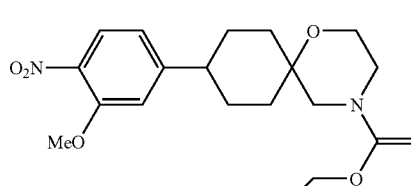 |
| 69 | 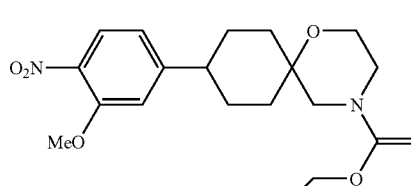 |
| 70 | 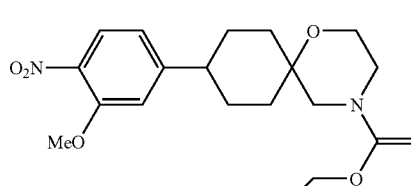 |
| 71 | 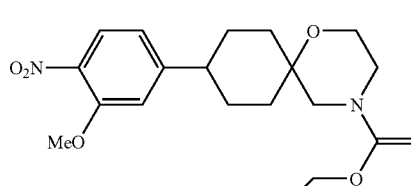 |
| 72 | 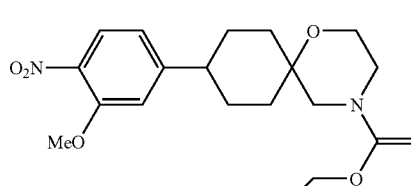 |
| 73 | 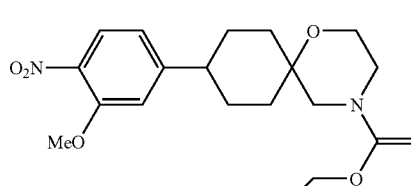 |
| 74 | 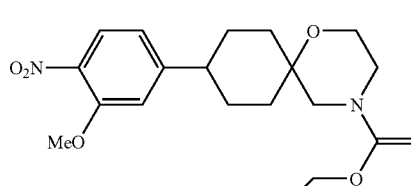 |
| 75 | 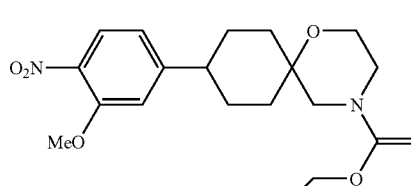 |

TABLE 15

| Rex/Salt | Structure |
|---|---|
| 76 | 3-methoxy-4-nitrophenyl-1,9-diazaspiro[5.5]undecane |
| 77 | 4-amino-3-methoxyphenyl-1,9-diazaspiro[5.5]undecane |
| 78 | N-isopropyl-2-((4-chloro-1,3,5-triazin-2-yl)amino)benzenesulfonamide |
| 79 | N-isopropyl-N-methyl-2-((4-chloro-1,3,5-triazin-2-yl)amino)benzenesulfonamide |
| 80 | N-methyl-2-((4-chloro-1,3,5-triazin-2-yl)amino)benzenesulfonamide |
| 81 | N,N-diethyl-2-((4-chloro-1,3,5-triazin-2-yl)amino)benzenesulfonamide |
| 82 | N-ethyl-N-methyl-2-aminobenzenesulfonamide |
| 83 | 1-((2-((4-chloro-1,3,5-triazin-2-yl)amino)phenyl)sulfonyl)pyrrolidine |
| 84 | N-cyclopropyl-2-((4-chloro-1,3,5-triazin-2-yl)amino)benzenesulfonamide |

TABLE 15-continued

| Rex/Salt | Structure |
|---|---|
| 85 | N-ethyl-N-methyl-2-((4-chloro-1,3,5-triazin-2-yl)amino)benzenesulfonamide |
| 86 | 4-((2-((4-chloro-1,3,5-triazin-2-yl)amino)phenyl)sulfonyl)morpholine |
| 87 | N-cyclopropyl-N-methyl-2-aminobenzenesulfonamide |

TABLE 16

| Rex/Salt | Structure |
|---|---|
| 88 | N-cyclopropyl-N-methyl-2-((4-chloro-1,3,5-triazin-2-yl)amino)benzenesulfonamide |
| 89 | 1-((2-((4-chloro-1,3,5-triazin-2-yl)amino)phenyl)sulfonyl)piperidine |
| 90 | 1-(3-methoxy-4-nitrophenyl)azetidin-3-ol |
| 91 | 1-(4-amino-3-methoxyphenyl)azetidin-3-ol |
| 92 | 6-amino-7-chloro-2-(trifluoroacetyl)-1,2,3,4-tetrahydroisoquinoline |

TABLE 16-continued

| Rex/Salt | Structure |
|---|---|
| 93 | iPr-SO2-C6H4-NH-[triazine-Cl] |
| 94 | Me2N-SO2-C6H4-NH-[triazine-Cl] |

TABLE 17

| Rex | Data |
|---|---|
| 1 | EI: 230.9 |
| 2 | CI+: 263.9 |
| 3 | FAB+: 264.0 |
| 4 | ESI+: 245.4 |
| 5 | ESI+: 257.3 |
| 6 | EI: 232.9 |
| 7 | ESI+: 343.0 |
| 8 | ESI+: 362.1 |
| 9 | ESI+: 274.2 |
| 10 | FAB+: 280.1 |
| 11 | FAB+: 353.2 |
| 12 | ESI+: 295.1 |
| 13 | FAB+: 321.1 |
| 14 | FAB+: 349.2 |
| 15 | ESI+: 319.15 |
| 16 | EI: 262.9, 265.0 |
| 17 | EI: 308.0 |
| 18 | ESI+: 391.1 |
| 19 | ESI+: 291.1 |
| 20 | EI: 264.0 |
| 21 | ESI+: 309.2 |

TABLE 18

| Rex | Rsyn | Data |
|---|---|---|
| 22 | 7 | ESI+: 313.1 |
| 23 | 8 | ESI+: 396.1 |
| 24 | 7 | EI: 259.8 |
| 25 | 7 | ESI+: 298.0, 300.0 |
| 26 | 7 | ESI+: 225.09 |
| 27 | 7 | EI: 264.11 |
| 28 | 8 | ESI+: 396.1 |
| 29 | 8 | FAB+: 396.0 |
| 30 | 8 | EI: 395.0 |
| 31 | 1 | EI: 230.9 |
| 32 | 3 | CI+: 264.0 |
| 33 | 8 | CI+: 396.1 |
| 34 | 7 | FAB+: 346.9 |
| 35 | 6 | EI: 232.9 |
| 36 | 8 | FAB+: 396.0 |
| 37 | 20 | EI: 322.1 |
| 38 | 10 | ESI+: 398.2 |
| 39 | 1 | EI: 226.9 |
| 40 | 3 | EI: 258.9 |
| 41 | 1 | EI: 226.9 |
| 42 | 6 | EI: 228.9 |
| 43 | 3 | EI: 258.9 |
| 44 | 8 | ESI+: 392.2 |
| 45 | 6 | EI: 228.9 |
| 46 | 8 | ESI+: 392.2 |
| 47 | 11 | FAB+: 254.1 |
| 48 | 20 | EI: 223.1 |
| 49 | 6 | EI: 232.9 |
| 50 | 7 | FAB+: 327.0 |
| 51 | 8 | ESI+: 396.1 |
| 52 | 8 | ESI+: 313.1 |
| 53 | 8 | ESI+: 334.2 |
| 54 | 8 | ESI+: 334.1 |
| 55 | 12 | ESI+: 314.2 |
| 56 | 20 | ESI+: 284.2 |
| 57 | 12 | EI: 264.0 |
| 58 | 12 | EI: 278.0 |
| 59 | 14 | ESI+: 363.2 |
| 60 | 20 | ESI+: 319.2 |
| 61 | 20 | ESI+: 333.2 |
| 62 | 12 | ESI+: 392.1 |
| 63 | 12 | ESI+: 442.2 |
| 64 | 20 | ESI+: 362.0 |
| 65 | 21 | ESI+: 412.2 |
| 66 | 7 | FAB+: 285.0 |
| 67 | 7 | ESI+: 314.1 |
| 68 | 20 | ESI+: 289.2 |

TABLE 19

| Rex | Rsyn | Data |
|---|---|---|
| 69 | 20 | ESI+: 291.3 |
| 70 | 7 | ESI+: 299.2 |
| 71 | 12 | ESI+: 338.9, 340.9 |
| 72 | 2 | EI: 227:9 |
| 73 | 6 | EI: 196.9 |
| 74 | 7 | ESI+: 314.1 |
| 75 | 7 | EI: 309.9 |
| 76 | 12 | EI: 305.1 |
| 77 | 20 | EI: 275.1 |
| 78 | 7 | ESI+: 328.2 |
| 79 | 7 | EI: 341.0 |
| 80 | 7 | ESI+: 300.06, 302.04 |
| 81 | 7 | ESI+: 342.3 |
| 82 | 6 | EI: 214.0 |
| 83 | 7 | ESI+: 340.2, 342.0 |
| 84 | 7 | ESI+: 326.0, 327.9 |
| 85 | 7 | ESI+: 327.9, 330.0 |
| 86 | 7 | ESI+: 356.0, 357.9 |
| 87 | 6 | EI: 226.0 |
| 88 | 7 | ESI+: 340.2 |
| 89 | 7 | ESI+: 354.3 |
| 90 | 12 | ESI+: 225.2 |
| 91 | 20 | ESI+: 195.0 |
| 92 | 20 | EI: 278.0 |
| 93 | 7 | ESI+: 312.9 |
| 94 | 7 | ESI+: 314 |

TABLE 20
| Ex/Salt | Structure |
|---|---|
| 1 | 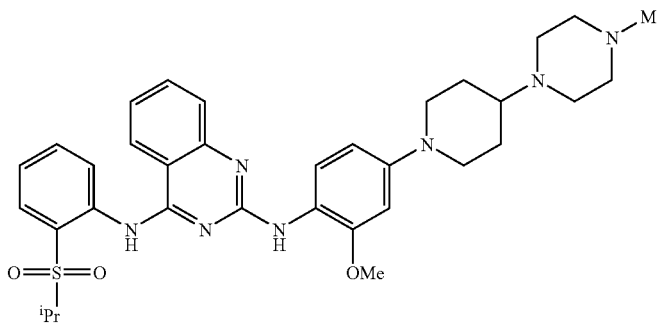 |
| 2/ CL3 | 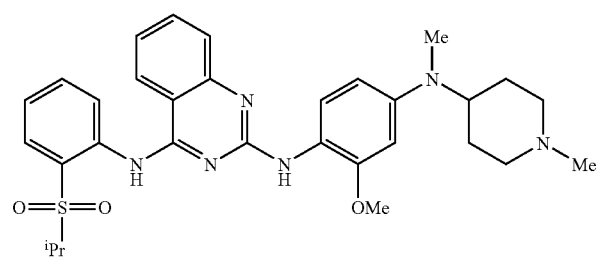 |
| 3 | 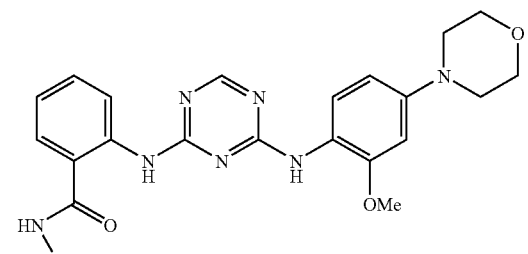 |
| 4/ CL3 | 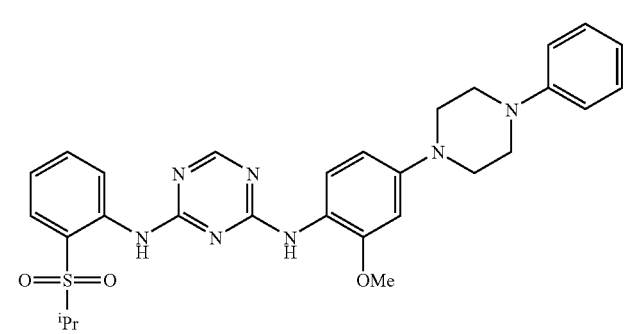 |
| 5/ CL1 | 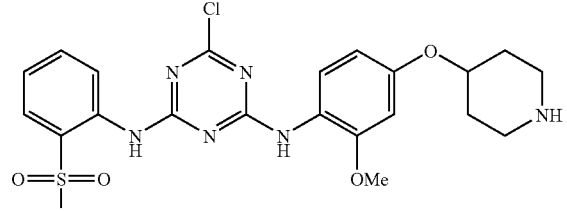 |

TABLE 20-continued
| Ex/Salt | Structure |
|---|---|
| 6 | 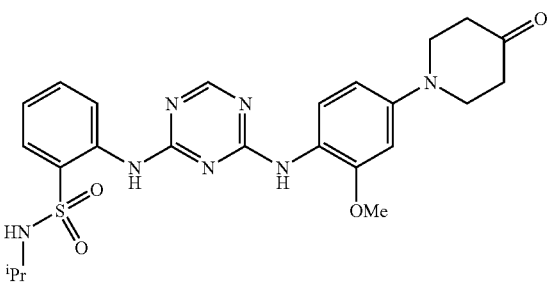 |
| 7 | 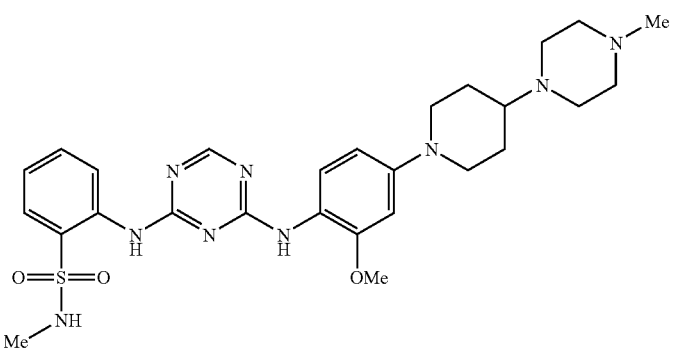 |
| 8 | 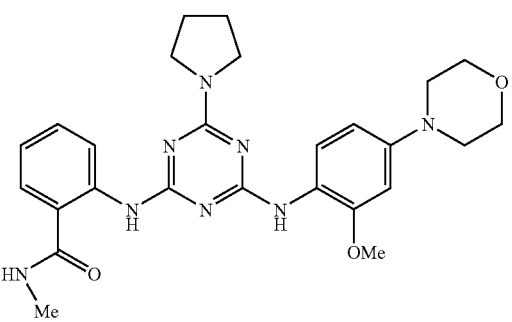 |
TABLE 21
| Ex/Salt | Structure |
|---|---|
| 9 | 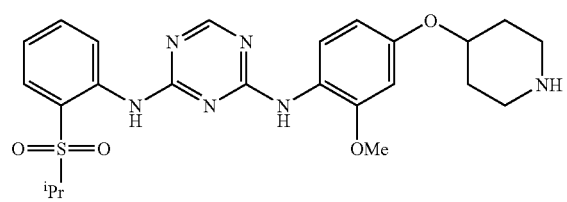 |

TABLE 21-continued
| Ex/Salt | Structure |
|---|---|
| 10 | 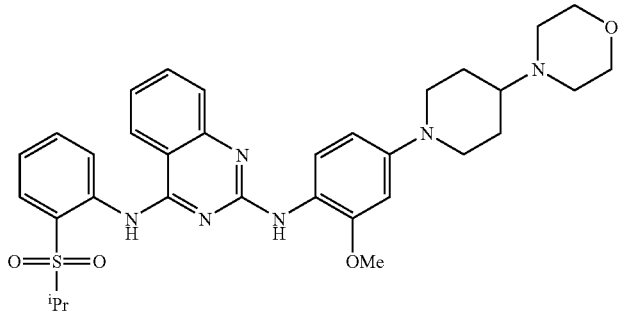 |
| 11 | 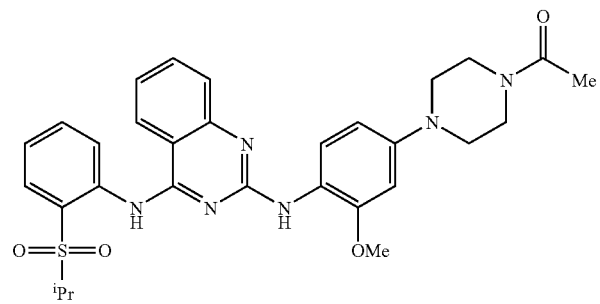 |
| 12 | 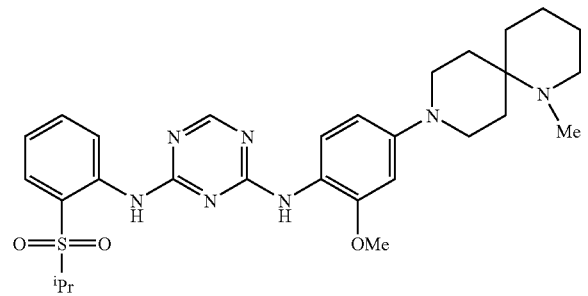 |
| 13 | 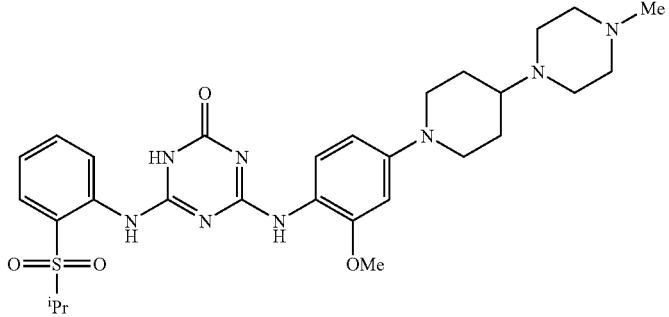 |

TABLE 21-continued
| Ex/Salt | Structure |
|---|---|
| 14 | 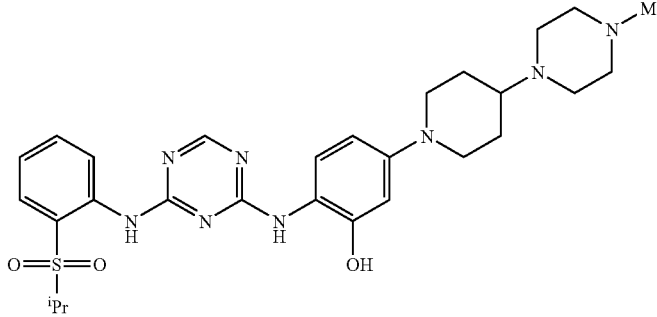 |
| 15 | 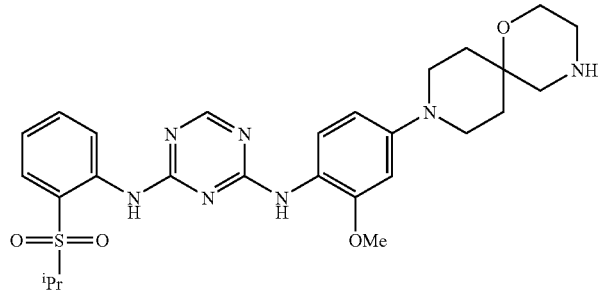 |
| 16/CL2 | 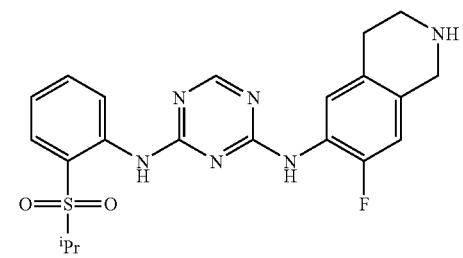 |
TABLE 22
| Ex/Salt | Structure |
|---|---|
| 17 | 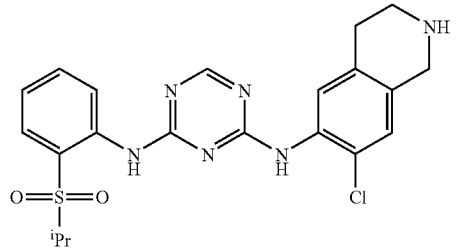 |
| 18 | 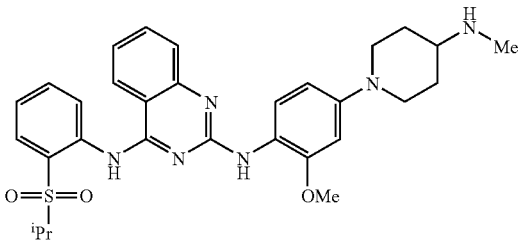 |
| 19 | 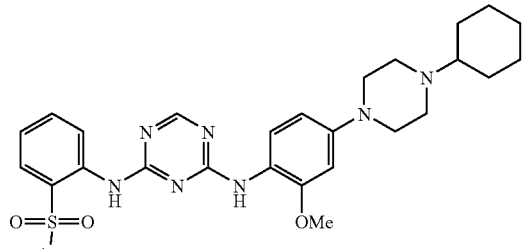 |
| 20 | 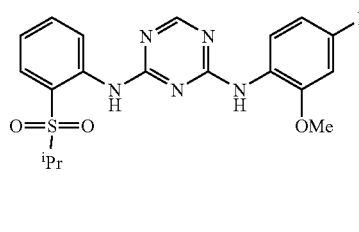 |

TABLE 23

| Ex/Salt | Structure |
| --- | --- |
| 21 | *(quinazoline with 2-iPrSO2-phenylamino at 4-position and 2-methoxy-4-(4-methylpiperazin-1-yl)phenylamino at 2-position)* |
| 22 | *(1,3,5-triazine with OMe, 2-iPrSO2-phenylamino, and 2-methoxy-4-[4-(4-methylpiperazin-1-yl)piperidin-1-yl]phenylamino substituents)* |
| 23 | *(1,3,5-triazine with 2-iPrSO2-phenylamino and 2-methoxy-4-[4-(4-methylpiperazin-1-yl)piperidin-1-yl]phenylamino substituents)* |
| 24 | *(1,3,5-triazine with 2-iPrSO2-phenylamino and 2-methoxy-4-(4-methylpiperazin-1-yl)phenylamino substituents)* |
| 25 | *(7-chloroquinazoline with 2-iPrSO2-phenylamino at 4-position and 2-methoxy-4-[4-(4-methylpiperazin-1-yl)piperidin-1-yl]phenylamino at 2-position)* |

TABLE 23-continued
| Ex/Salt | Structure |
|---|---|
| 26/FM | 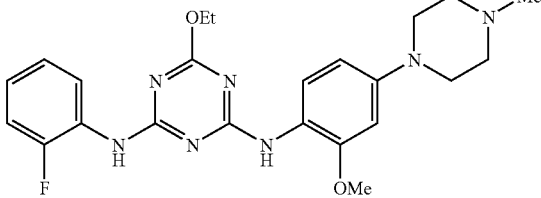 |
| 27 | 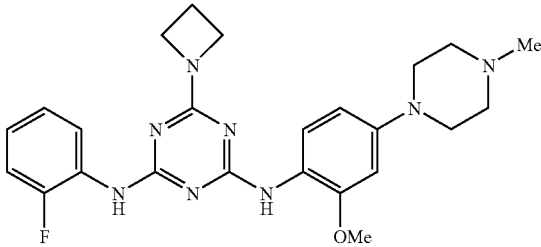 |
| 28 | 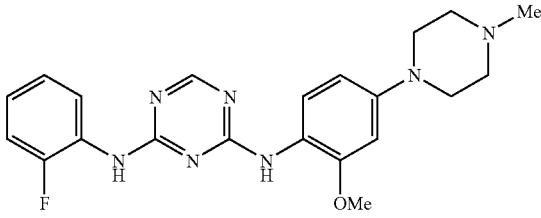 |
TABLE 24
| Ex/Salt | Structure |
|---|---|
| 29 | 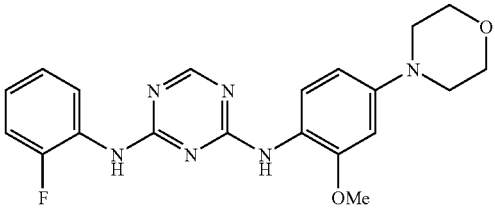 |
| 30 | 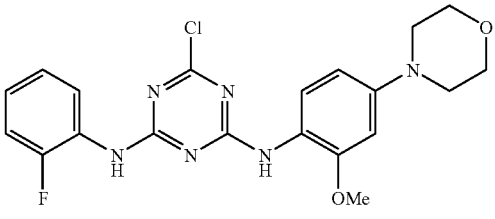 |
| 31 | 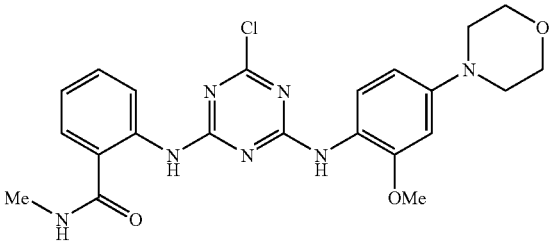 |

TABLE 24-continued

| Ex/Salt | Structure |
|---|---|
| 32 | 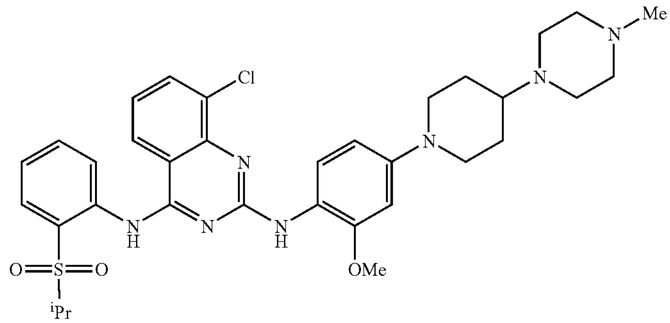 |
| 33 | 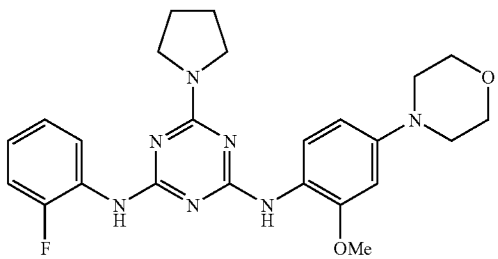 |
| 34/CL2 | 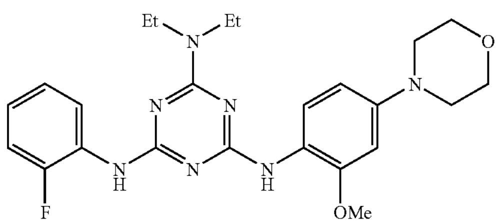 |
| 35 | 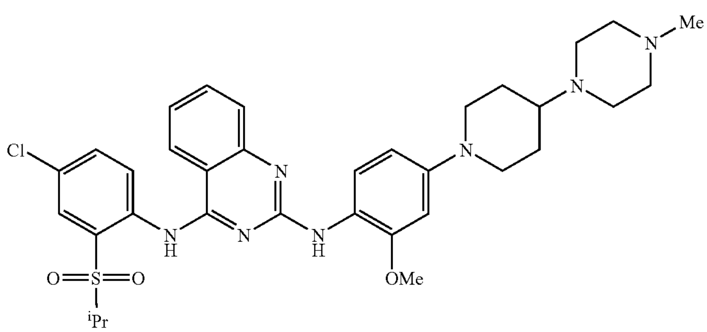 |
| 36 | 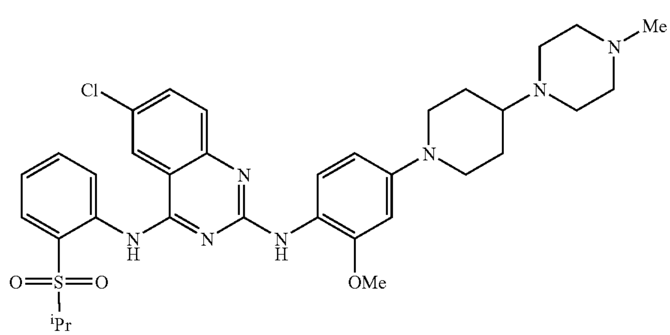 |

TABLE 25

| Ex/Salt | Structure |
|---|---|
| 37 | 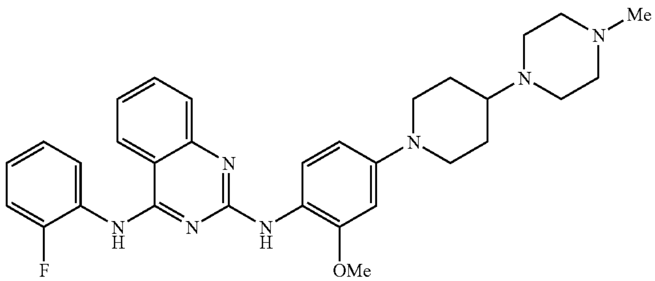 |
| 38 | 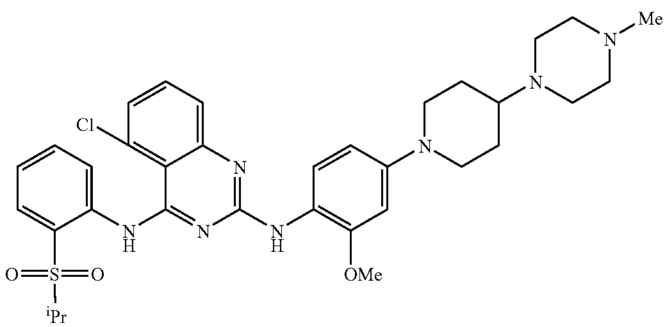 |
| 39 | 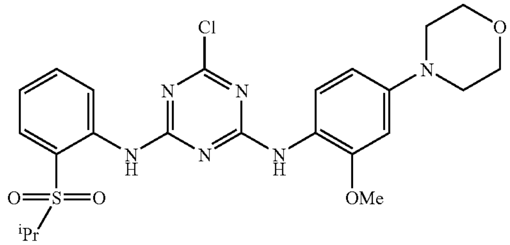 |
| 40 | 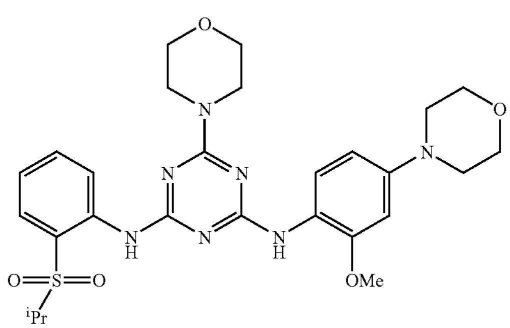 |
| 41 | 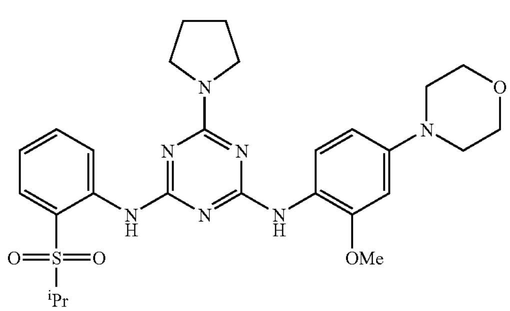 |

TABLE 25-continued
| Ex/Salt | Structure |
|---|---|
| 42 | 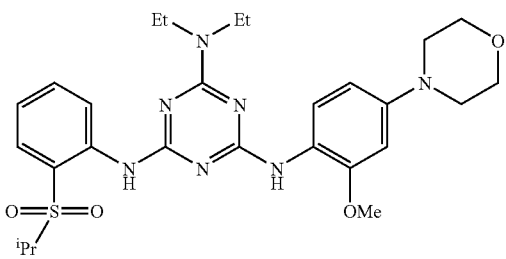 |
| 43 | 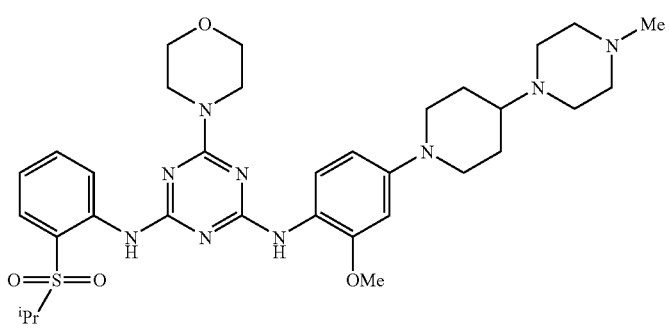 |
| 44 | 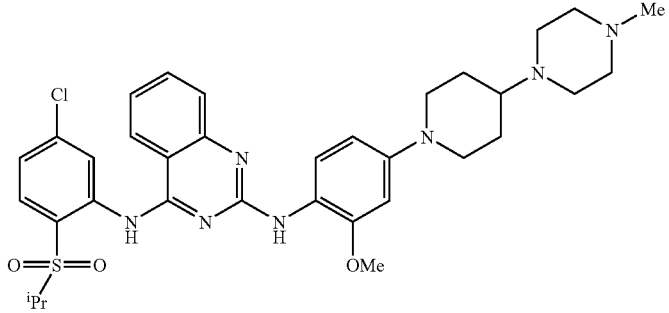 |
TABLE 26
| Ex/Salt | Structure |
|---|---|
| 45 | 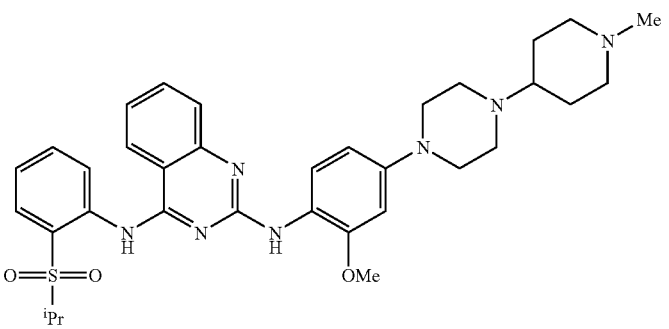 |

TABLE 26-continued

| Ex/Salt | Structure |
|---|---|
| 46 | 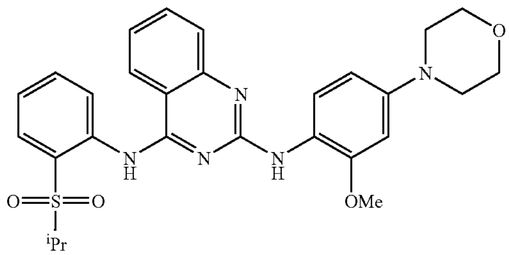 |
| 47 | 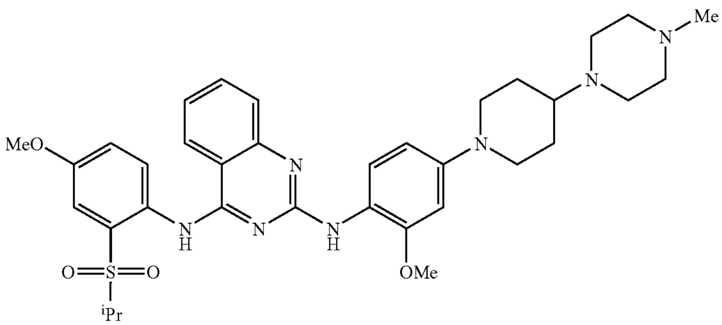 |
| 48 | 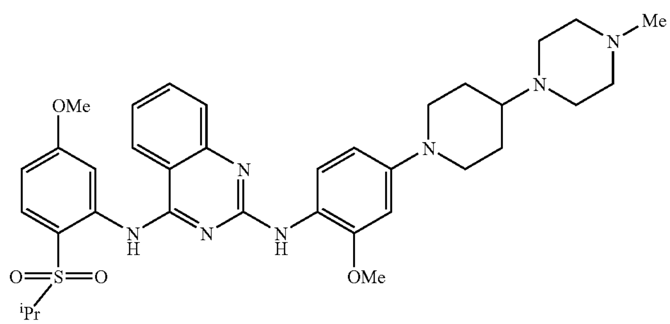 |
| 49 | 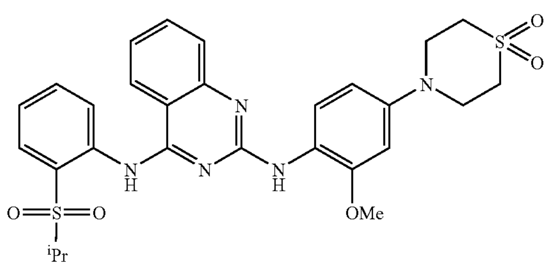 |
| 50 | 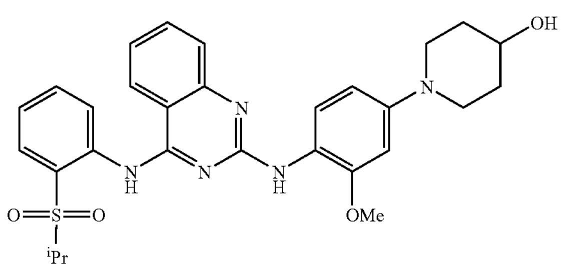 |

TABLE 26-continued

| Ex/Salt | Structure |
|---|---|
| 51 | (structure) |
| 52/CL3 | (structure) |

TABLE 27

| Ex/Salt | Structure |
|---|---|
| 53/CL1 | (structure) |
| 54 | (structure) |
| 55 | (structure) |

TABLE 27-continued

| Ex/Salt | Structure |
|---|---|
| 56 | 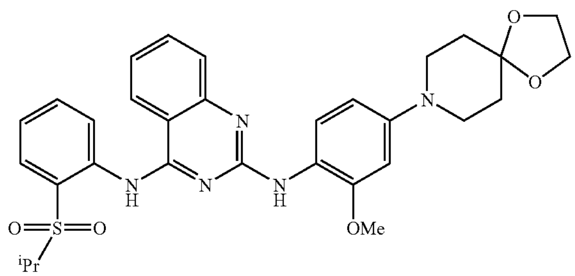 |
| 57 | 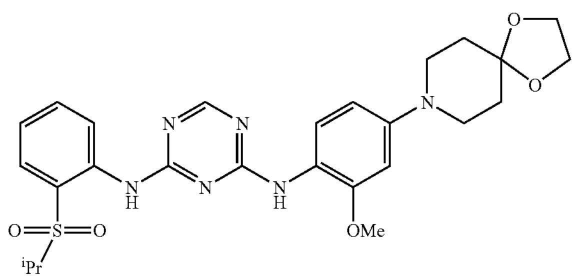 |
| 58 | 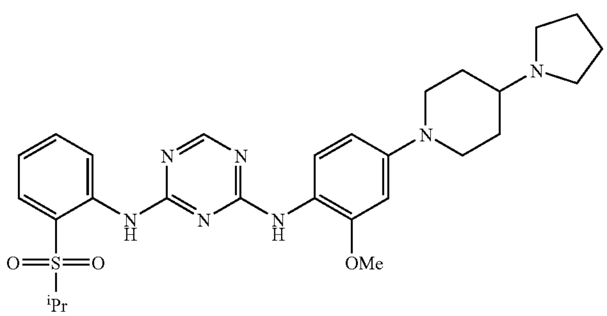 |
| 59 | 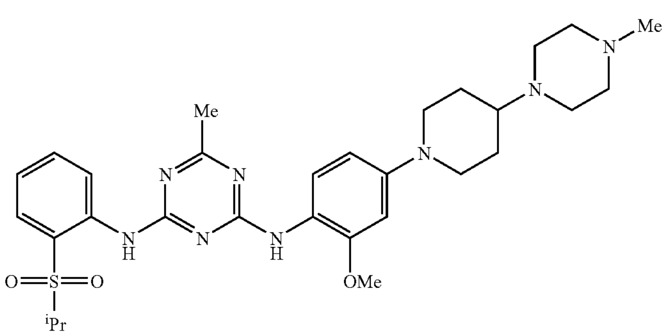 |
| 60 | 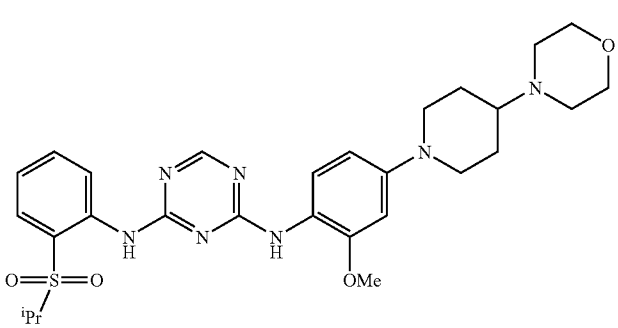 |

TABLE 28
| Ex/Salt | Structure |
|---|---|
| 61 | 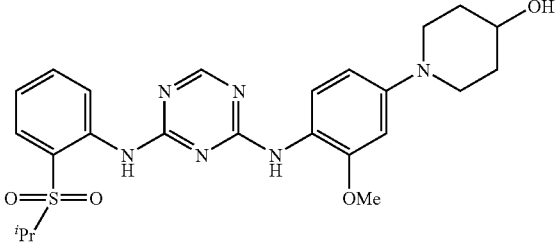 |
| 62 | 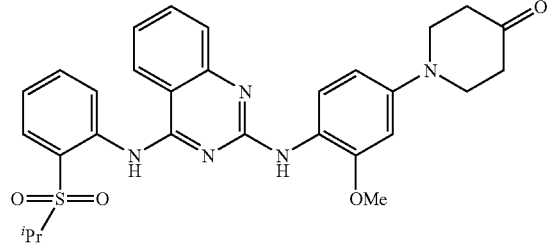 |
| 63/CL3 | 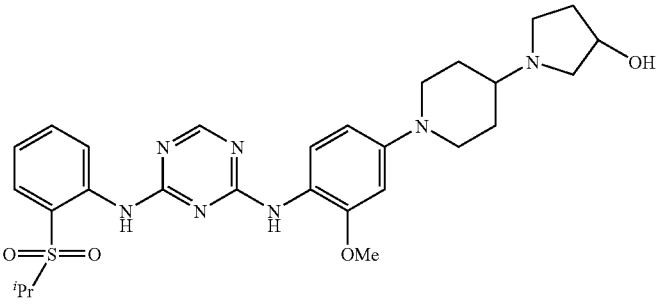 |
| 64 | 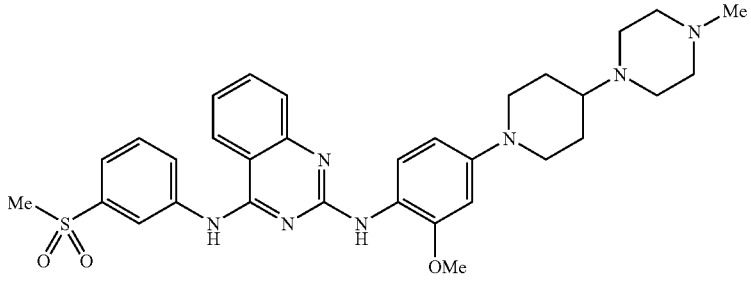 |
| 65 | 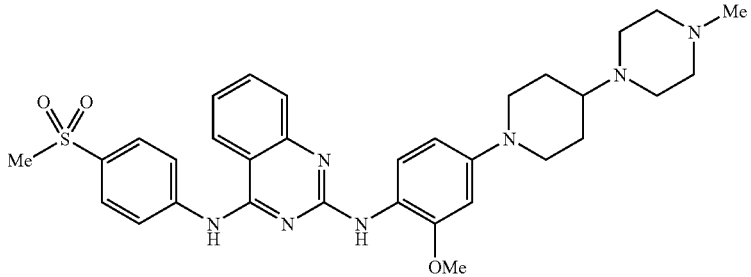 |

TABLE 28-continued

| Ex/Salt | Structure |
|---|---|
| 66 | *Structure: N-(2-(isopropylsulfonyl)phenyl)-N'-(2-methoxy-4-(piperazin-1-yl)phenyl)quinazoline-2,4-diamine* |
| 67 | *Structure: 1-(4-((4-((2-(isopropylsulfonyl)phenyl)amino)quinazolin-2-yl)amino)-3-methoxyphenyl)pyrrolidin-3-ol* |
| 68 | *Structure: tert-butyl 4-(4-((4-((2-(isopropylsulfonyl)phenyl)amino)-1,3,5-triazin-2-yl)amino)-3-methoxyphenoxy)piperidine-1-carboxylate* |

TABLE 29

| Ex/Salt | Structure |
|---|---|
| 69 | *Structure: N-(2-(isopropylsulfonyl)phenyl)-N'-(2-methoxy-4-((1-methylpiperidin-4-yl)oxy)phenyl)-1,3,5-triazine-2,4-diamine* |
| 70/CL2 | *Structure: N-(4-(4-cyclohexylpiperazin-1-yl)-2-methoxyphenyl)-N'-(2-(isopropylsulfonyl)phenyl)-1,3,5-triazine-2,4-diamine* |

TABLE 29-continued

| Ex/Salt | Structure |
|---|---|
| 71 | 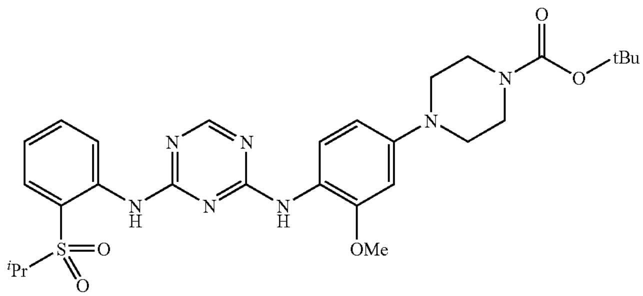 |
| 72 | 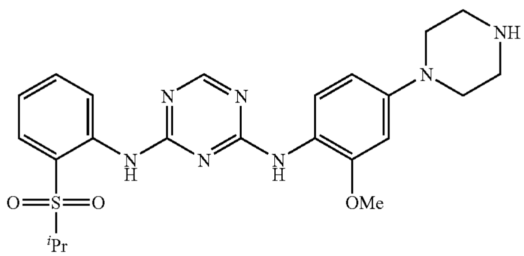 |
| 73 | 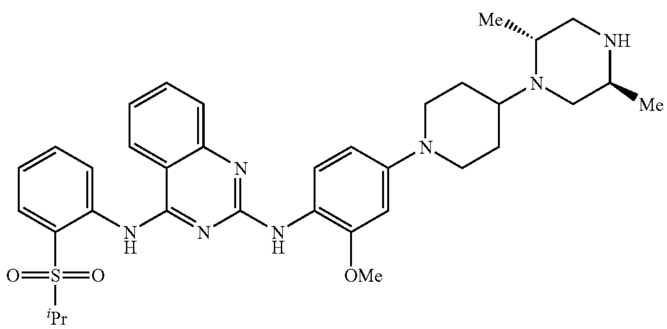 |
| 74 | 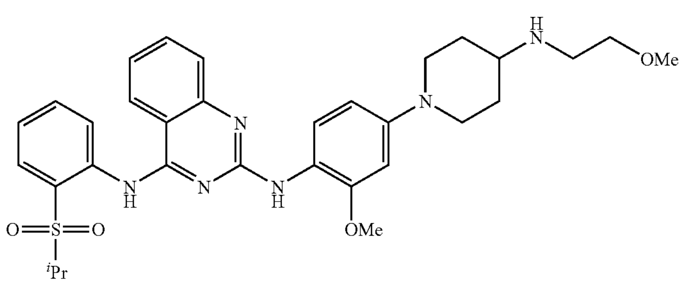 |
| 75 | 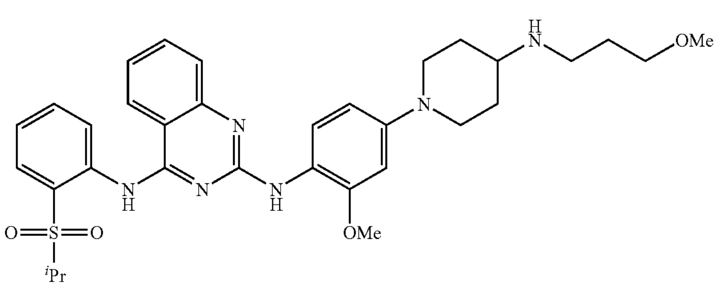 |

TABLE 29-continued
| Ex/Salt | Structure |
|---|---|
| 76 | 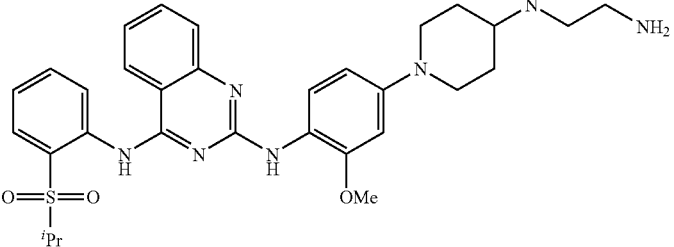 |
TABLE 30
| Ex/Salt | Structure |
|---|---|
| 77 | 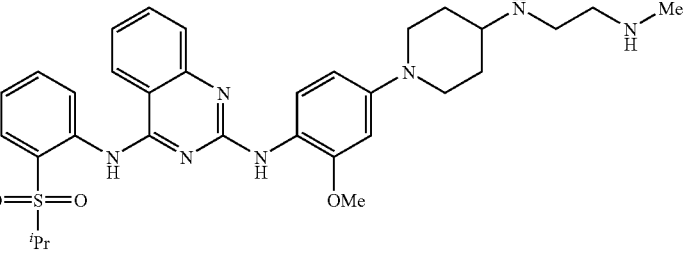 |
| 78 | 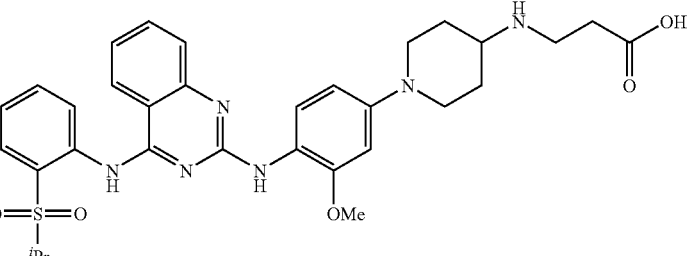 |
| 79 | 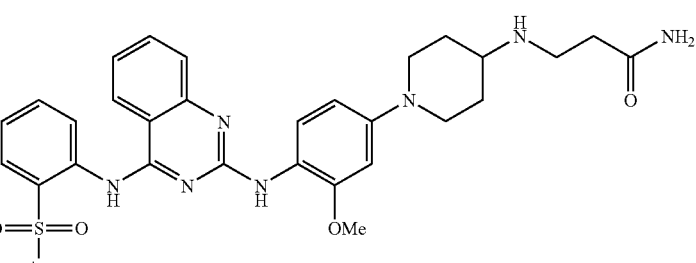 |
| 80 | 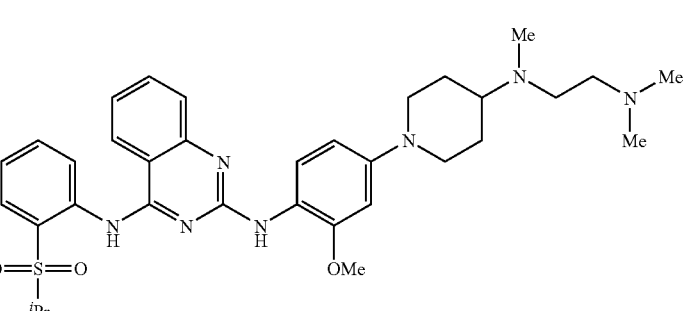 |

TABLE 30-continued
| Ex/Salt | Structure |
|---|---|
| 81 | 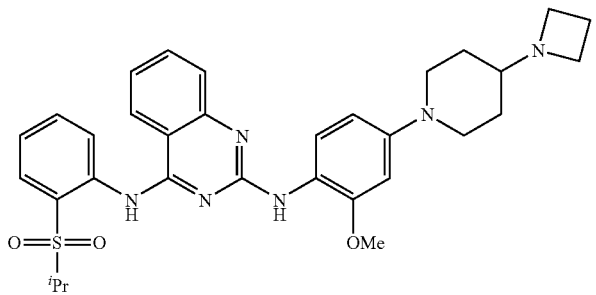 |
| 82 | 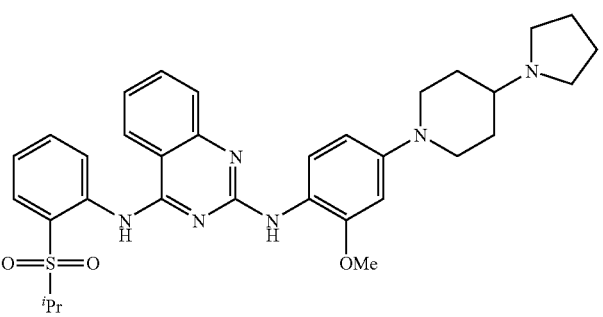 |
| 83 | 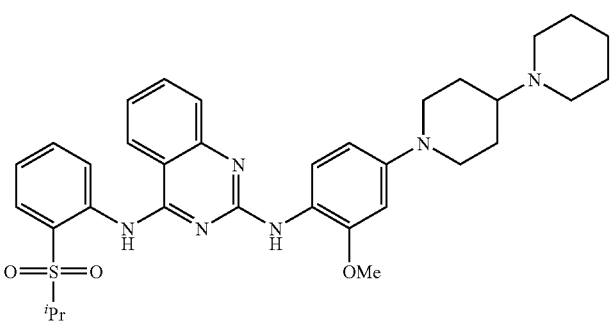 |
| 84 | 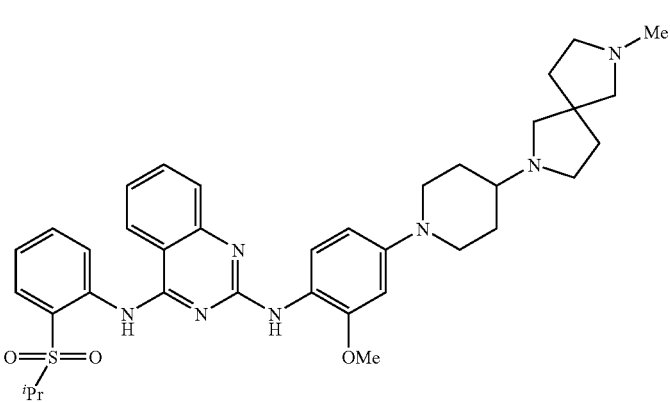 |

TABLE 31

| Ex/Salt | Structure |
|---|---|
| 85 | (structure) |
| 86 | (structure) |
| 87 | (structure) |
| 88 | (structure) |

TABLE 31-continued

| Ex/Salt | Structure |
|---|---|
| 89 | 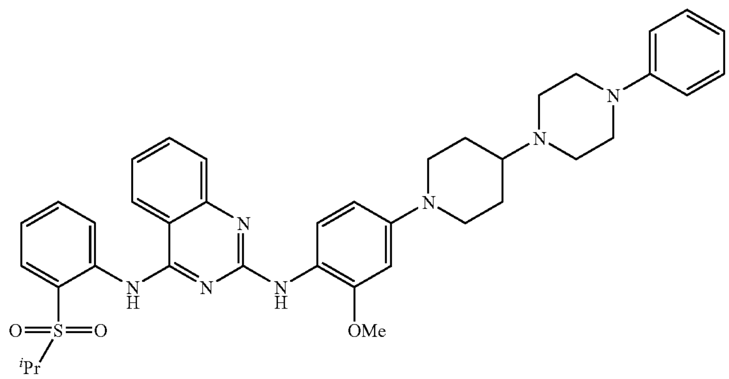 |
| 90 | 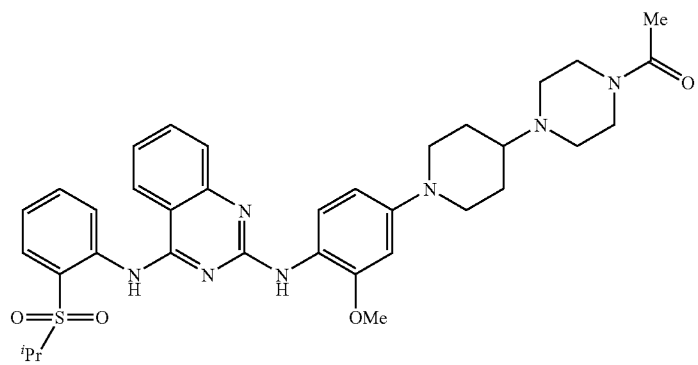 |
| 91 | 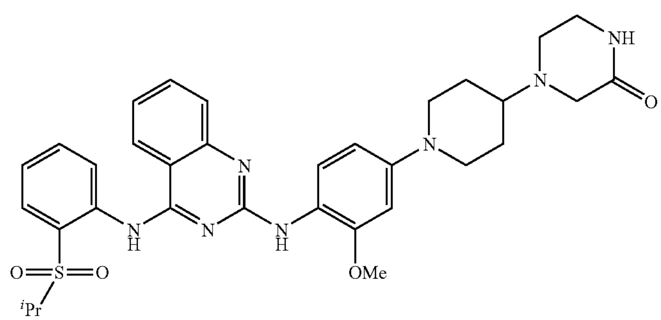 |
| 92 | 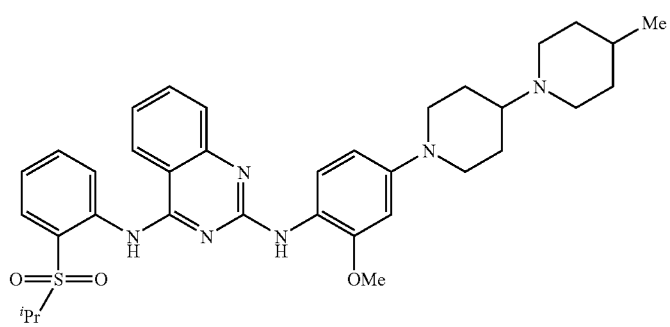 |

TABLE 32

| Ex/Salt | Structure |
|---|---|
| 93 | (structure) |
| 94 | (structure) |
| 95 | (structure) |
| 96 | (structure) |

TABLE 32-continued

| Ex/Salt | Structure |
|---|---|
| 97 | 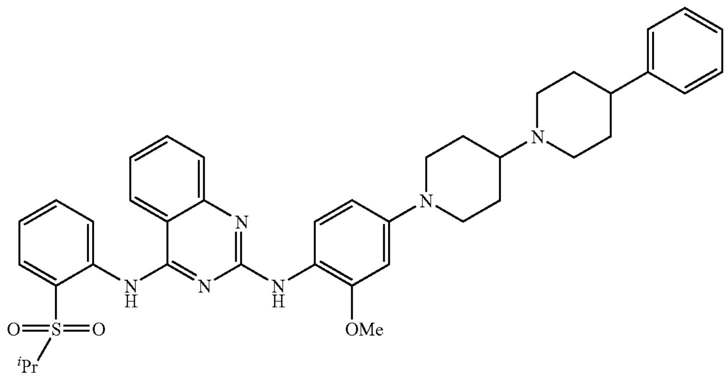 |
| 98 | 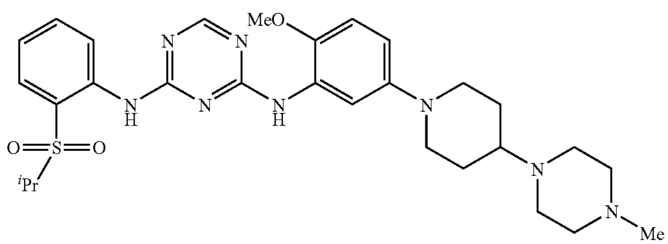 |
| 99 | 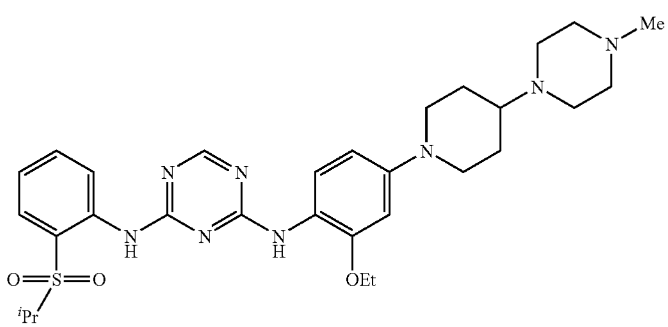 |
| 100 | 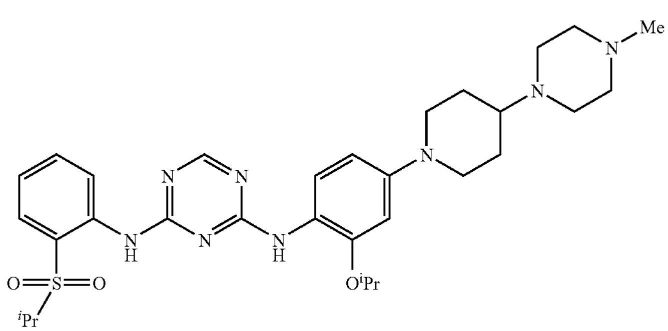 |

TABLE 33

| Ex/Salt | Structure |
|---|---|
| 101 | 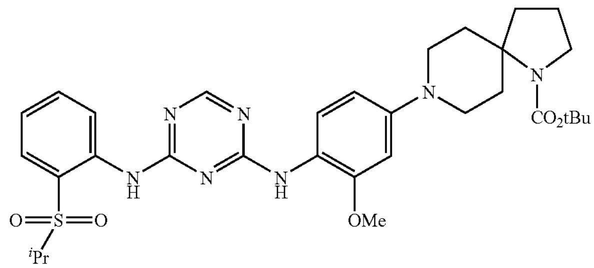 |
| 102 | 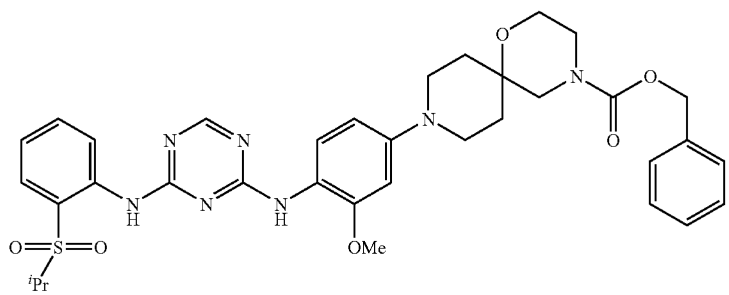 |
| 103 | 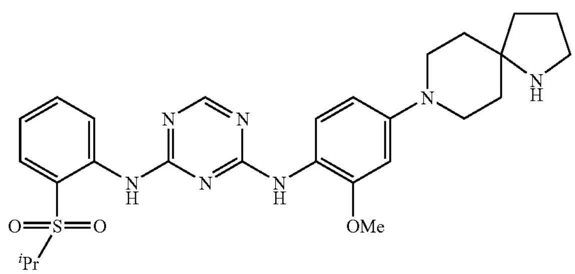 |
| 104 | 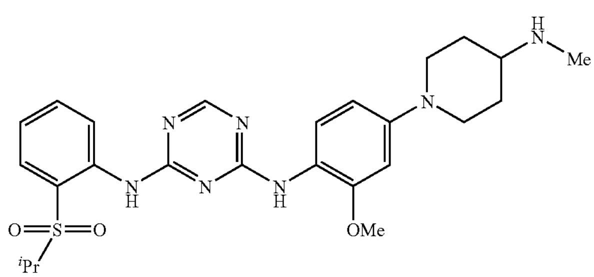 |
| 105 | 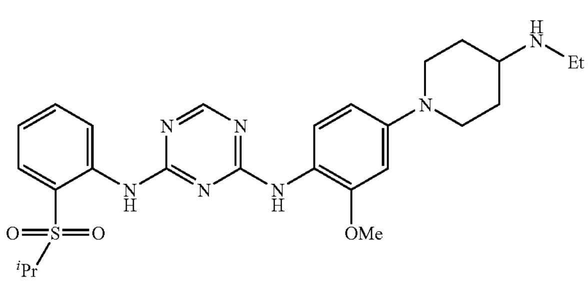 |

TABLE 33-continued

| Ex/Salt | Structure |
|---|---|
| 106 | (structure) |
| 107 | (structure) |
| 108 | (structure) |

TABLE 34

| Ex/Salt | Structure |
|---|---|
| 109 | (structure) |
| 110 | (structure) |

TABLE 34-continued
| Ex/Salt | Structure |
|---|---|
| 111 | 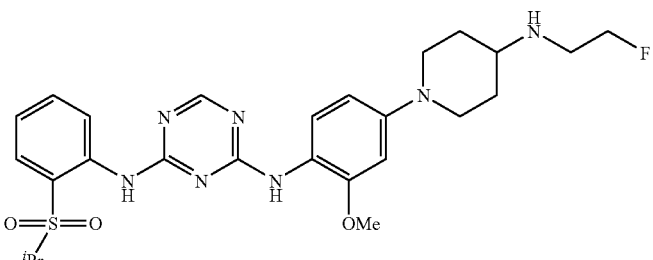 |
| 112 | 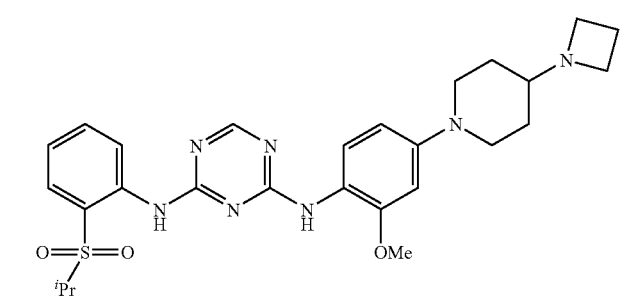 |
| 113 | 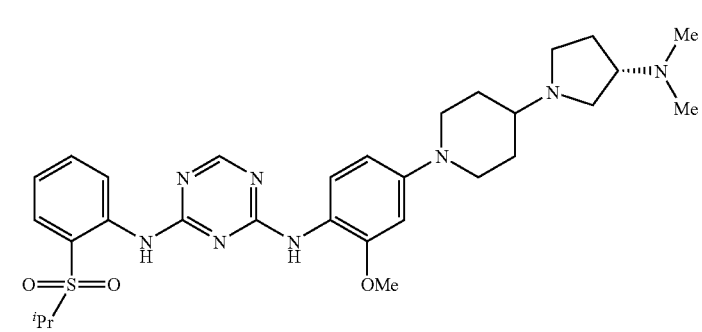 |
| 114 | 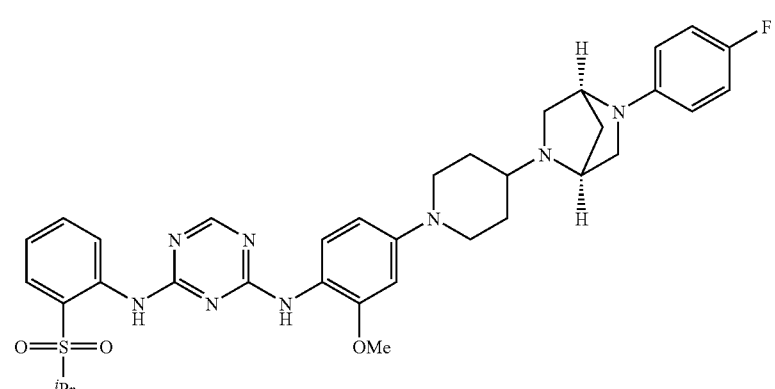 |

TABLE 34-continued
| Ex/Salt | Structure |
|---|---|
| 115 | 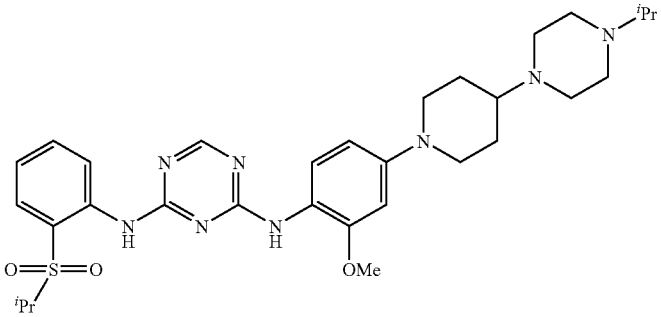 |
| 116 | 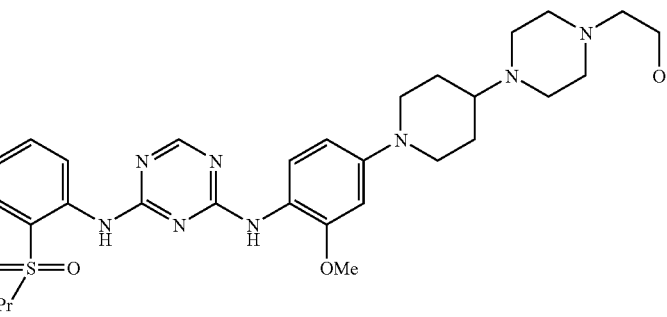 |
TABLE 35
| Ex/Salt | Structure |
|---|---|
| 117 | 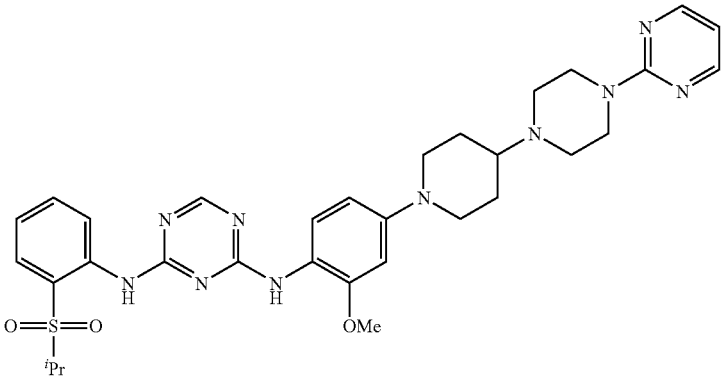 |
| 118 | 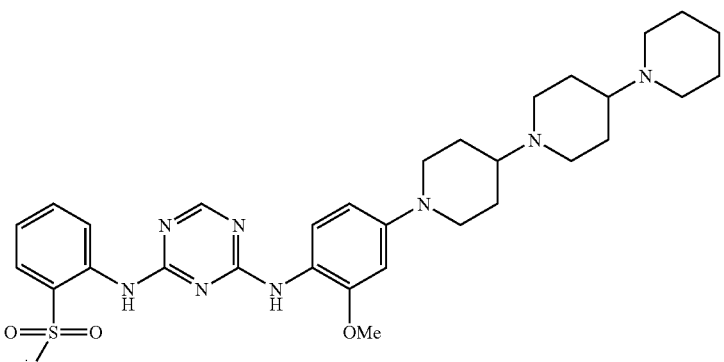 |

TABLE 35-continued
| Ex/Salt | Structure |
|---|---|
| 119 | 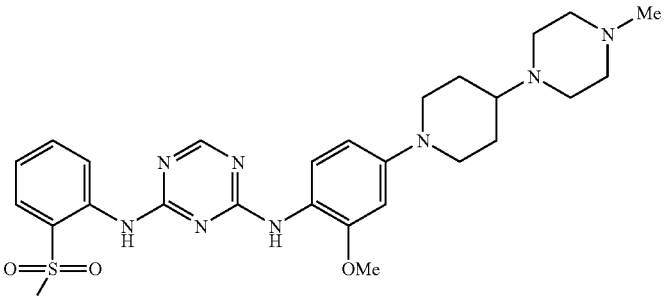 |
| 120 | 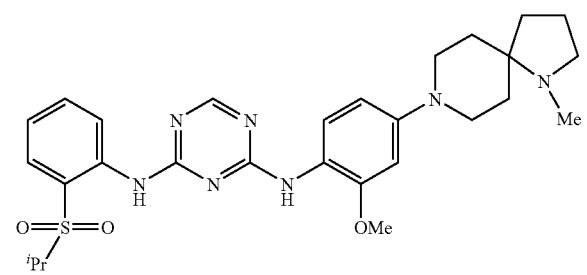 |
| 121 | 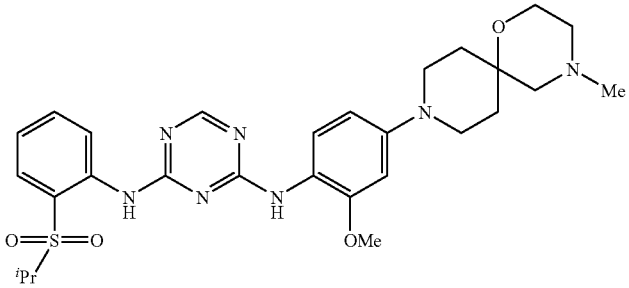 |
| 122 | 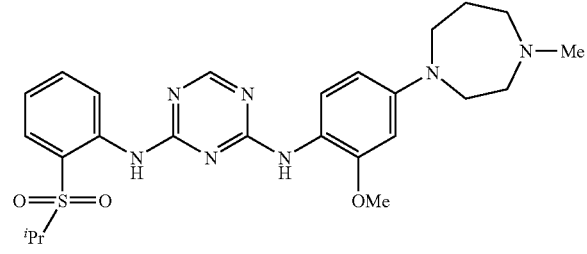 |
| 123 | 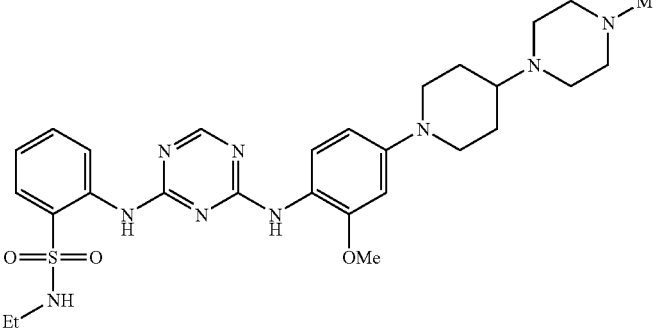 |

TABLE 35-continued
| Ex/Salt | Structure |
|---|---|
| 124 | 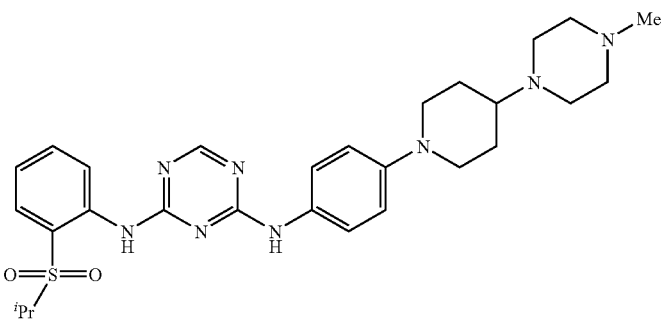 |
TABLE 36
| Ex/Salt | Structure |
|---|---|
| 125 | 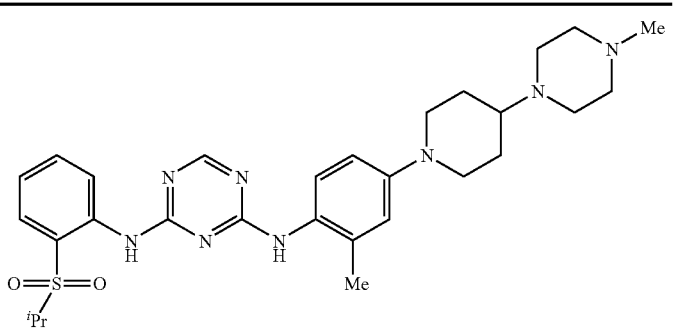 |
| 126 | 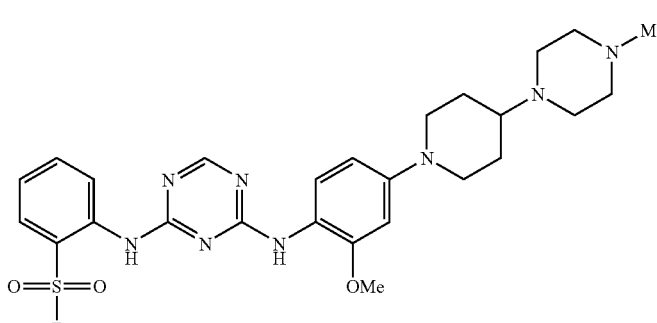 |
| 127 | 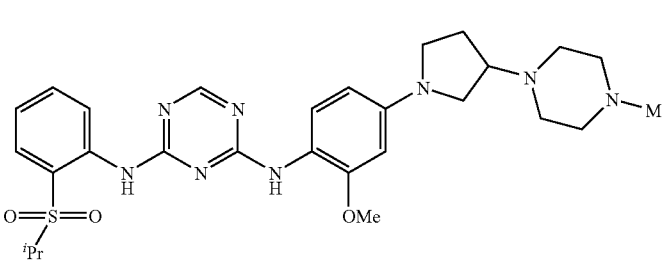 |

TABLE 36-continued
| Ex/Salt | Structure |
|---|---|
| 128 | 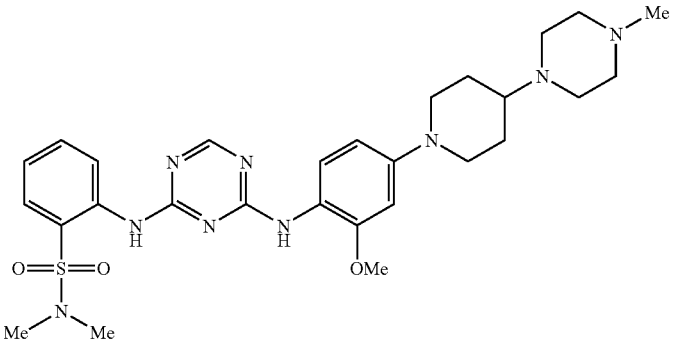 |
| 129 | 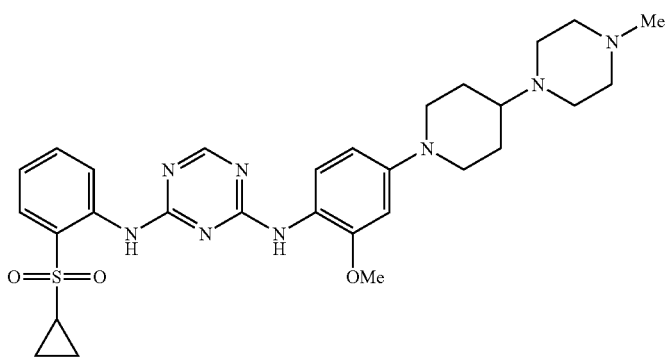 |
| 130 | 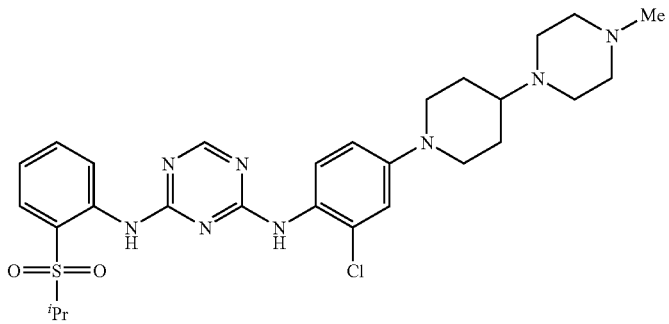 |
| 131 | 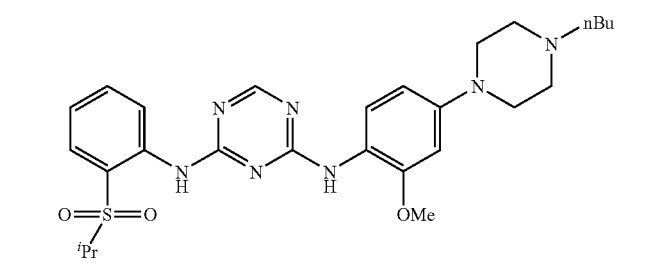 |
| 132 | 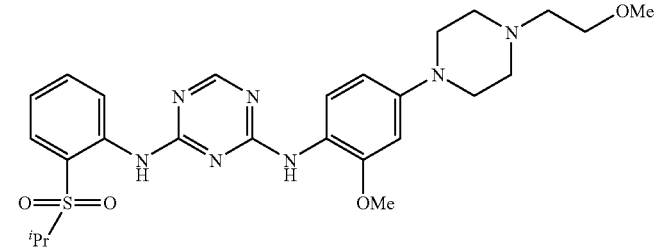 |

TABLE 37
| Ex/Salt | Structure |
|---|---|
| 133 | 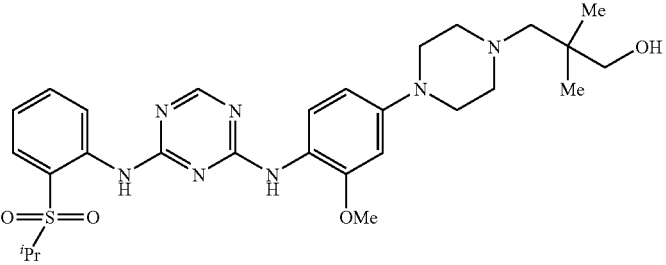 |
| 134 | 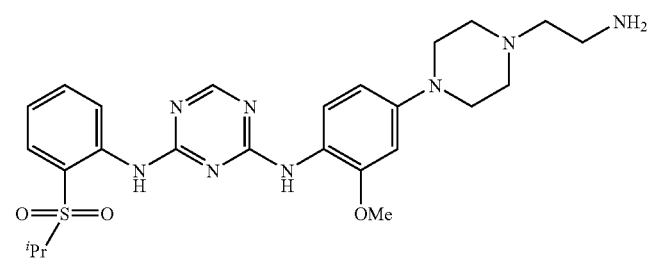 |
| 135 | 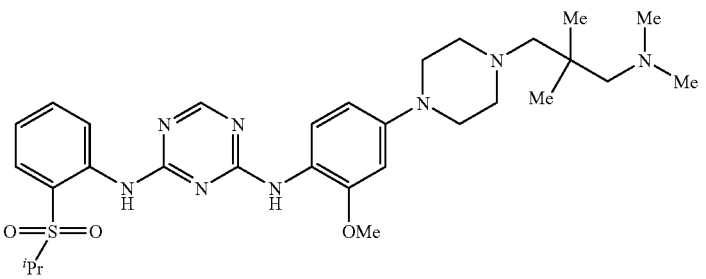 |
| 136 | 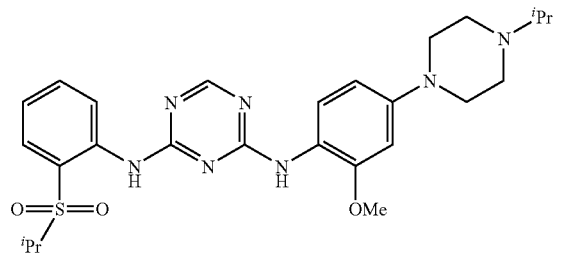 |
| 137 | 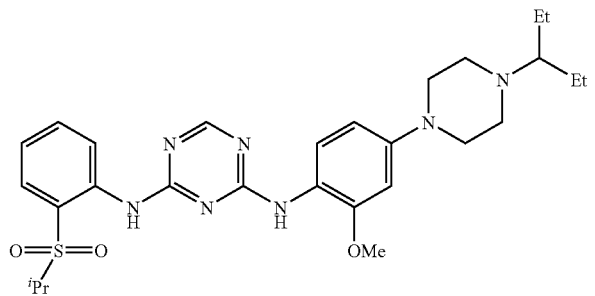 |

123
TABLE 37-continued
| Ex/Salt | Structure |
|---|---|
| 138 | 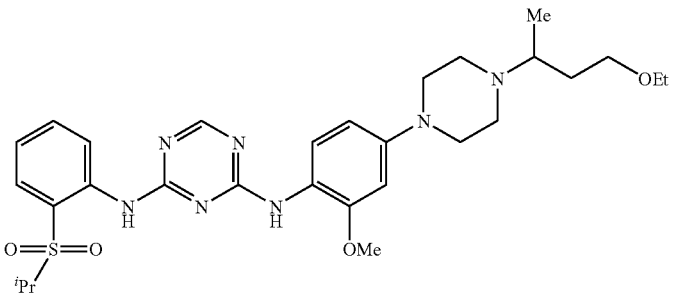 |
| 139 | 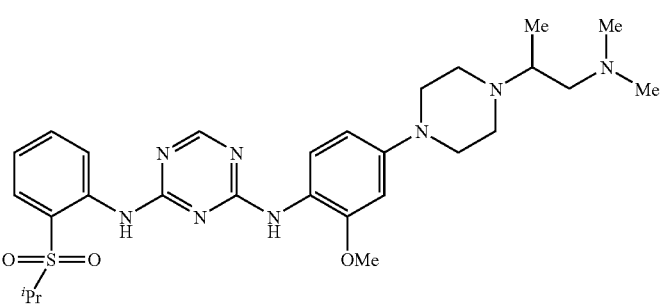 |
| 140 | 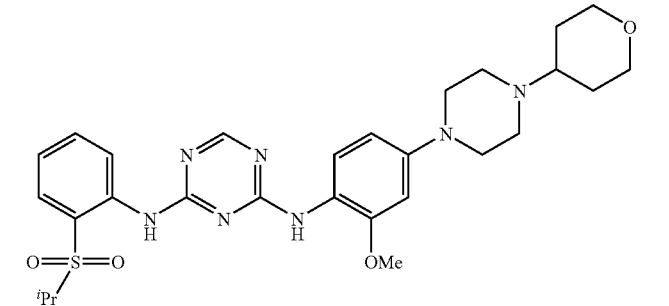 |
TABLE 38
| Ex/Salt | Structure |
|---|---|
| 141 | 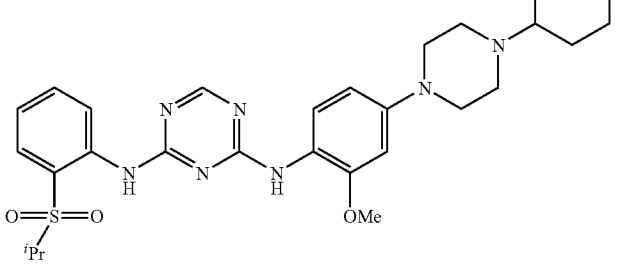 |

TABLE 38-continued

| Ex/Salt | Structure |
|---|---|
| 142 | (structure: 2-(isopropylsulfonyl)phenyl-NH-triazine-NH-(2-methoxy-4-(4-(1-methylpiperidin-4-yl)piperazin-1-yl)phenyl)) |
| 143 | (structure: 2-(isopropylsulfonyl)phenyl-NH-triazine-NH-(2-methoxy-4-(4-(1-ethylpiperidin-4-yl)piperazin-1-yl)phenyl)) |
| 144 | (structure: 2-(isopropylsulfonyl)phenyl-NH-triazine-NH-(2-methoxy-4-(4-(1-isopropylpiperidin-4-yl)piperazin-1-yl)phenyl)) |
| 145 | (structure: 2-(isopropylsulfonyl)phenyl-NH-triazine-NH-(2-methoxy-4-(4-(1-cyclopropylpiperidin-4-yl)piperazin-1-yl)phenyl)) |

TABLE 38-continued

| Ex/Salt | Structure |
|---|---|
| 146 | 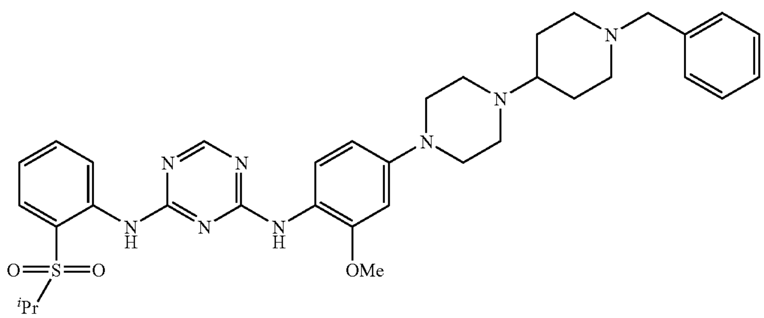 |
| 147 | 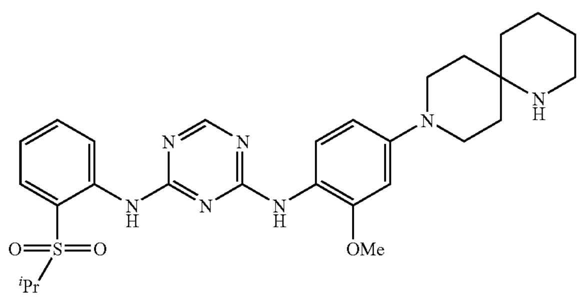 |
| 148 | 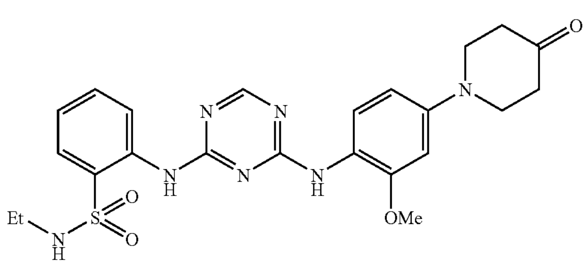 |

TABLE 39

| Ex/Salt | Structure |
|---|---|
| 149 | 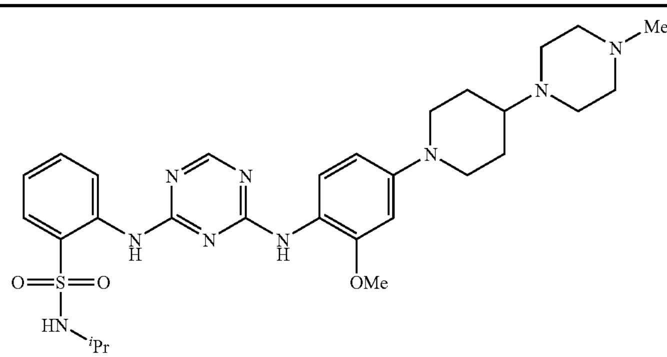 |

TABLE 39-continued
| Ex/Salt | Structure |
|---|---|
| 150 | 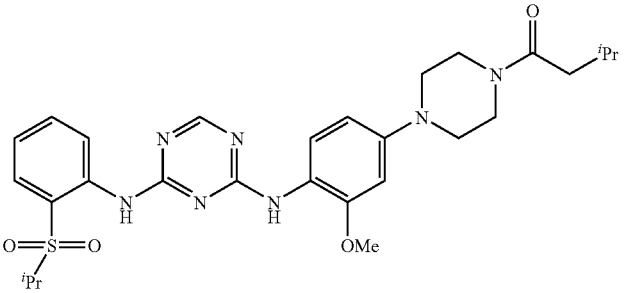 |
| 151 | 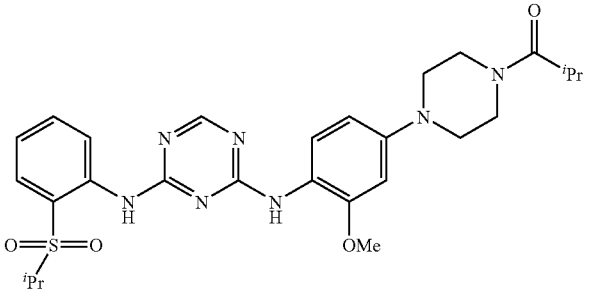 |
| 152 | 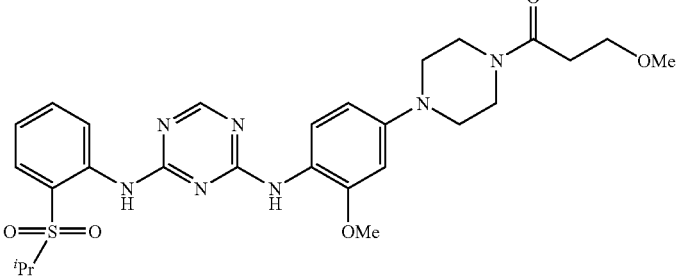 |
| 153 | 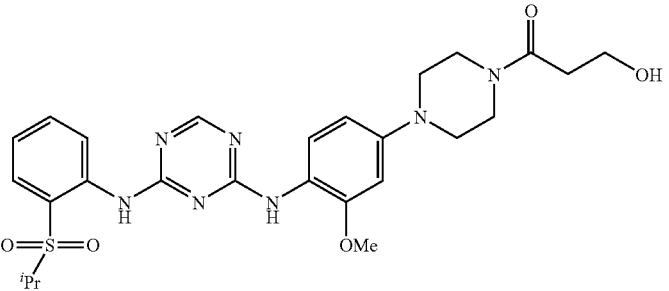 |
| 154 | 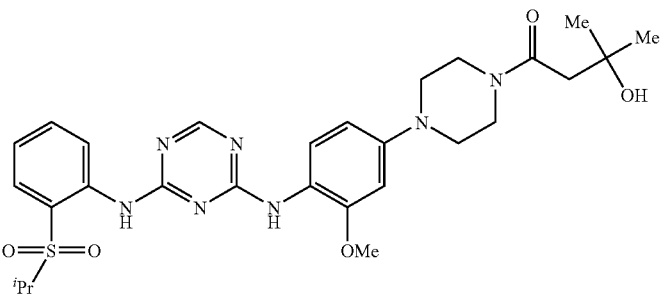 |

TABLE 39-continued
| Ex/Salt | Structure |
|---|---|
| 155 | 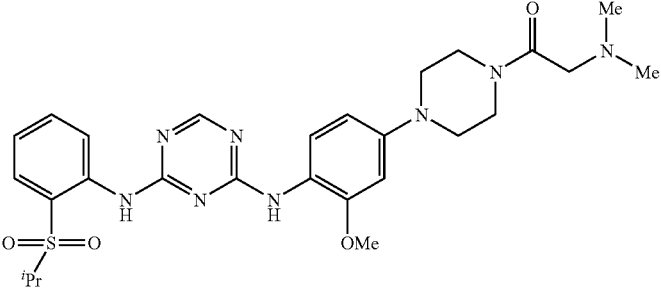 |
| 156 | 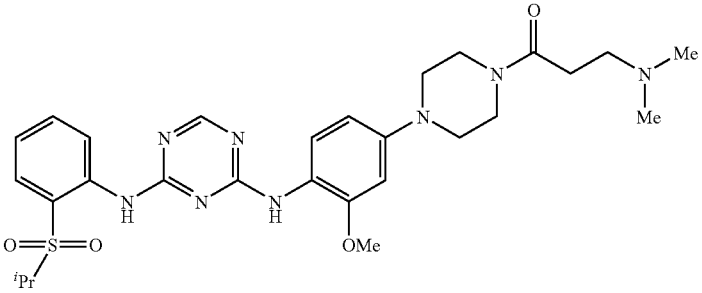 |
TABLE 40
| Ex/Salt | Structure |
|---|---|
| 157 | 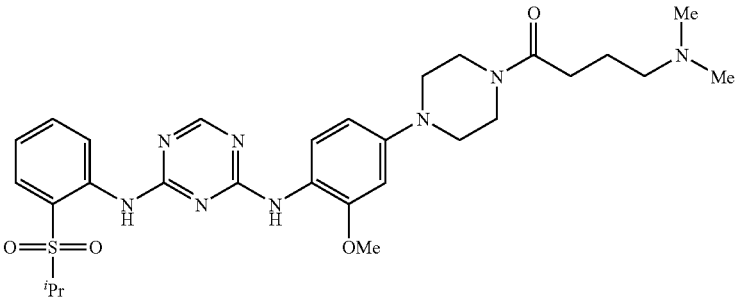 |
| 158 | 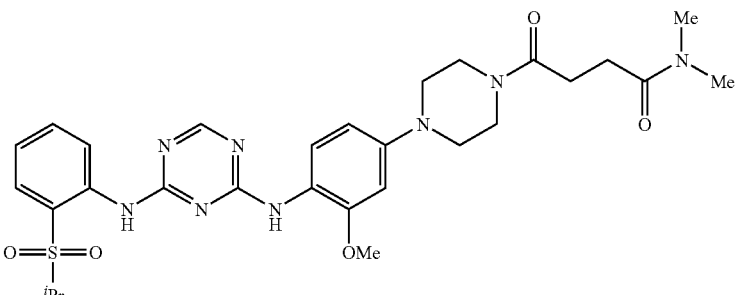 |

TABLE 40-continued
| Ex/Salt | Structure |
|---|---|
| 159 | 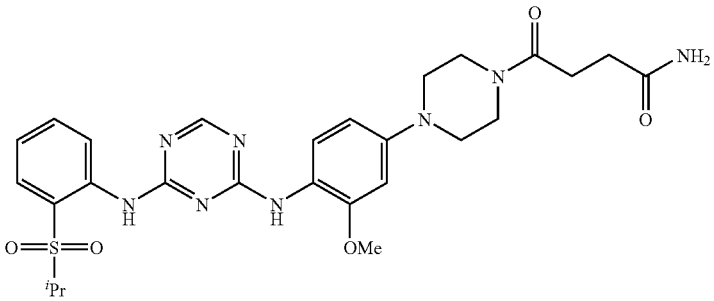 |
| 160 | 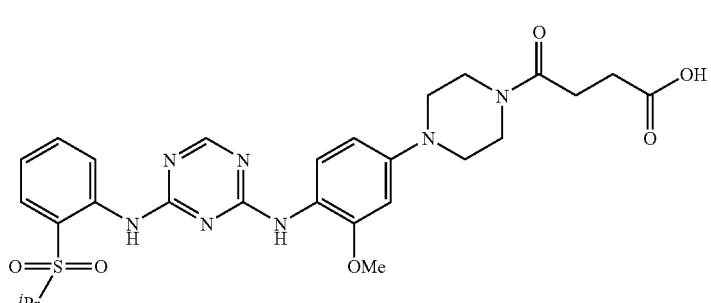 |
| 161 | 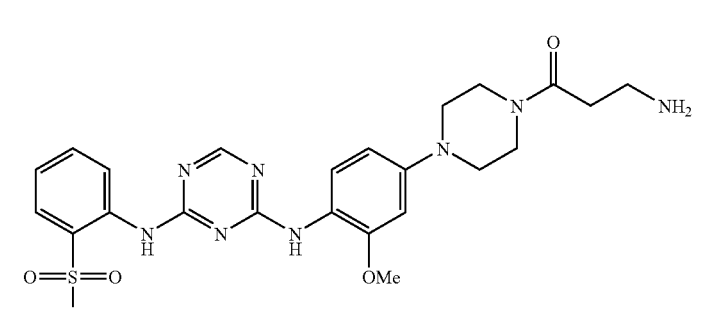 |
| 162 | 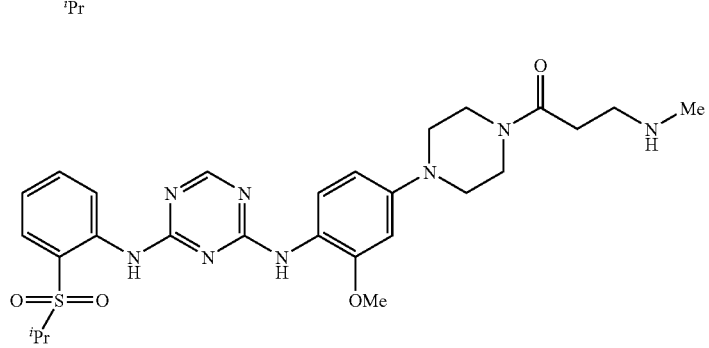 |
| 163 | 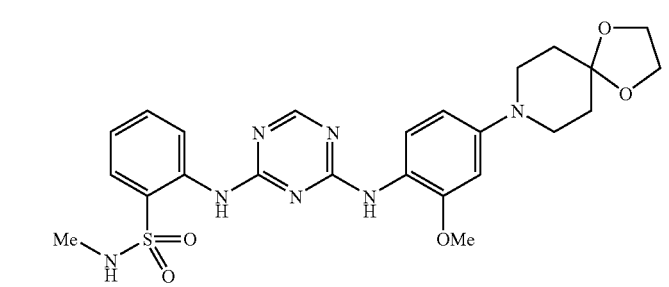 |

TABLE 40-continued
| Ex/Salt | Structure |
|---|---|
| 164 | 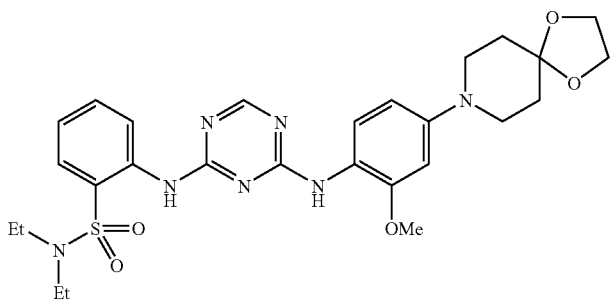 |
TABLE 41
| Ex/Salt | Structure |
|---|---|
| 165 | 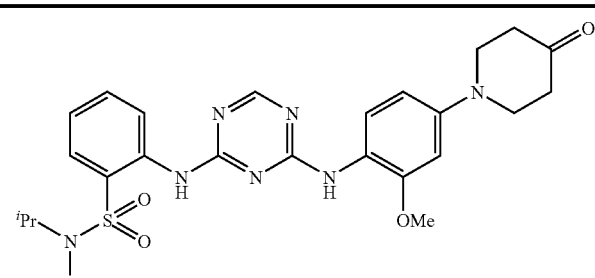 |
| 166 | 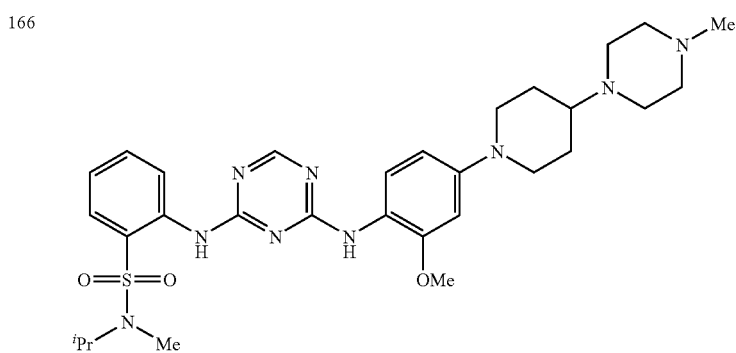 |
| 167 | 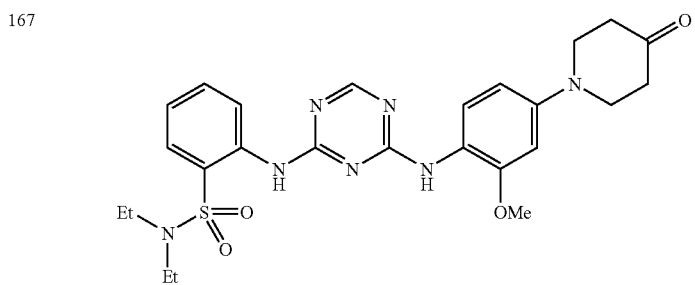 |

TABLE 41-continued

| Ex/Salt | Structure |
|---|---|
| 168 | Chemical structure |
| 169 | Chemical structure |
| 170 | Chemical structure |
| 171 | Chemical structure |

TABLE 41-continued
| Ex/Salt | Structure |
|---|---|
| 172 | 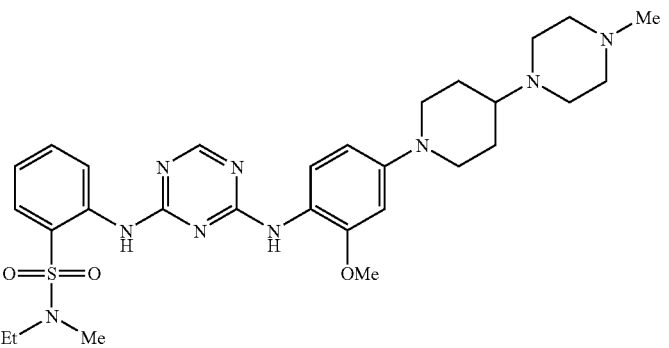 |
TABLE 42
| Ex/Salt | Structure |
|---|---|
| 173 | 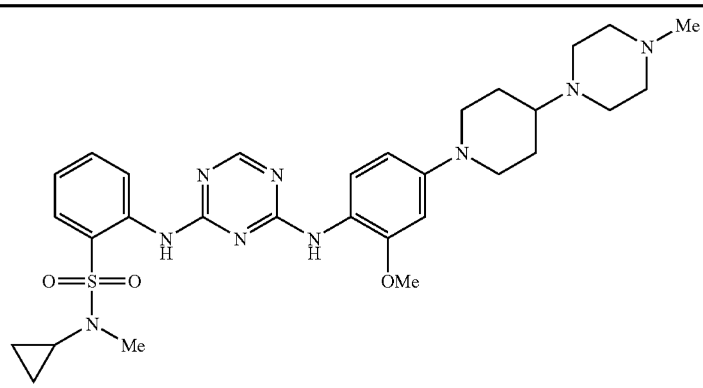 |
| 174 | 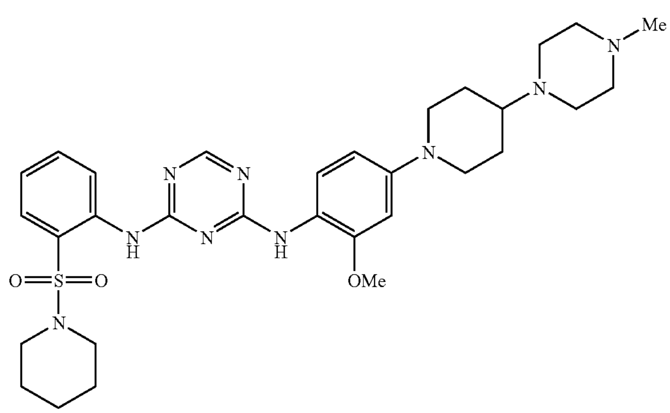 |
| 175 | 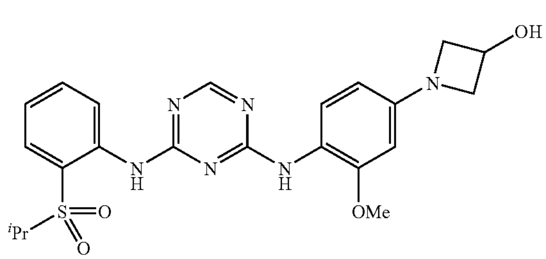 |

TABLE 42-continued
| Ex/Salt | Structure |
|---|---|
| 176 | 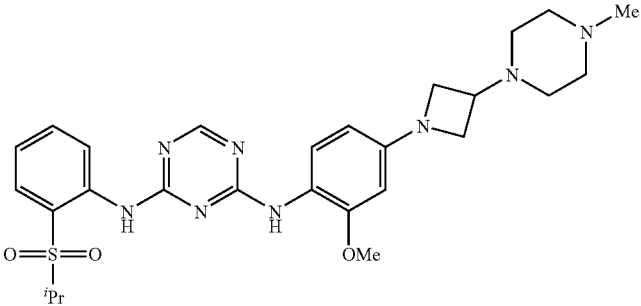 |
| 177 | 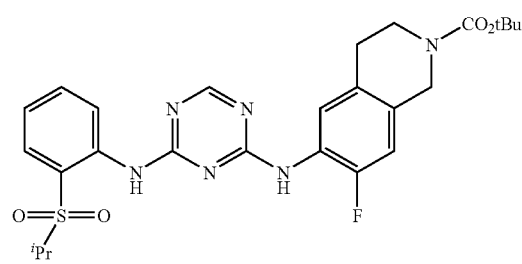 |
| 178 | 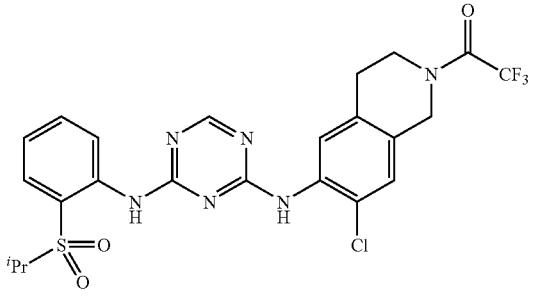 |
| 179 | 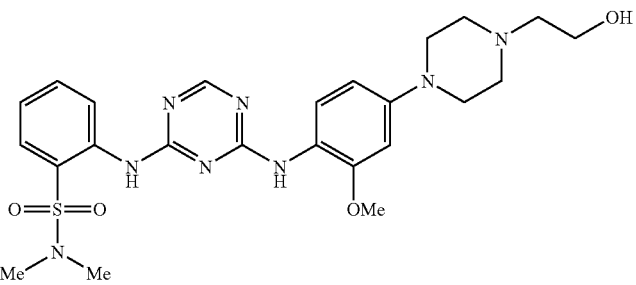 |
| 180 | 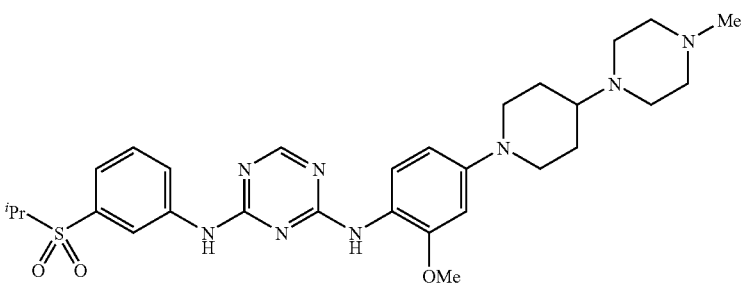 |

TABLE 42-continued

| Ex/Salt | Structure |
|---|---|
| 181 | (structure: 3-(N,N-dimethylsulfamoyl)phenyl-NH-triazine-NH-(2-methoxy-4-(4-(4-methylpiperazin-1-yl)piperidin-1-yl)phenyl)) |

TABLE 43

| Ex | Data |
|---|---|
| 1 | ESI+: 630.3<br>NMR-CDCl3: 1.30 (6H, d, J = 6.9 Hz),<br>1.65-1.8 (2H, m), 1.96 (2H, d, J = 11.8 Hz),<br>2.31 (3H, s), 2.35-2.8 (11H, m),<br>3.2-3.3 (1H, m), 3.68 (2H, d, J = 12.3 Hz),<br>3.90 (3H, s), 6.58 (2H, m), 7.2-7.3 (2H, m),<br>7.33 (1H, s), 7.6-7.7 (3H, m), 7.88 (1H,<br>d, J = 8.2 Hz), 7.91 (1H, d, J = 8.0 Hz),<br>8.45 (1H, d, J = 8.2 Hz), 8.90 (1H, d, J = 8.5 Hz),<br>10.18 (1H, s)<br>Amrph |
| 2 | ESI+: 575.3 |
| 3 | ESI+: 436.1 |
| 4 | ESI+: 560.4 |
| 5 | FAB+: 533.1 |
| 6 | FAB−: 510.3 |
| 7 | ESI+: 568.1<br>NMR-DMSOd6: 1.40-4.59 (2H,<br>m), 1.75-1.91 (2H, m),<br>2.08-2.19 (3H, m), 2.20-2.60 (12H, m),<br>2.60-2.78 (2H, m), 3.64-3.85 (5H,<br>m), 6.40-6.55 (1H, m),<br>6.55-6.69 (1H, br), 7.10-7.30 (2H, m),<br>7.30-7.90 (2H, m), 8.19-8.42 (2H,<br>m), 8.72-8.98 (1H, m),<br>8.98-9.16 (1H, m)<br>Amrph |
| 8 | ESI+: 505.3 |
| 9 | FAB+: 499.1 |
| 10 | ESI+: 617.4 |
| 11 | ESI+: 575.3 |
| 12 | ESI+: 566.4<br>NMR-CDCl3: 1.31 (6H, d, J = 6.8 Hz),<br>1.5-1.7 (8H, m), 2.0-2.15 (2H,<br>m), 2.37 (3H, s), 2.68 (2H, br),<br>2.99 (2H, t, J = 10.3 Hz), 3.2-3.3 (1H,<br>m), 3.4-3.5 (2H, m), 3.88 (3H, s),<br>6.55 (2H, br), 7.22 (1H, t, J = 7.8 Hz),<br>7.63 (2H, br), 7.88 (1H, dd, J = 1.5,<br>7.8 Hz), 8.10 (1H, br),<br>8.36 (1H, br), 8.54 (1H, br), 9.28 (1H, s)<br>Cryst (MP: 132-135) |
| 13 | ESI+: 597.3 |
| 14 | FAB+: 567.3 |
| 15 | ESI+: 554.4 |
| 16 | ESI+: 443.2 |
| 17 | ESI+: 459.2, 461.1 |
| 18 | ESI+: 561 |
| 19 | ESI+: 566 |
| 20 | ESI+: 526 |

TABLE 44

| Ex | Syn | Data |
|---|---|---|
| 21 | 1 | FAB+: 547.2 |
| 22 | 1 | ESI+: 611.2 |
| 23 | 1 | ESI+: 581.2<br>NMR-CDCl3: 1.31 (6H, d, J = 6.8 Hz),<br>1.65-1.8 (2H, m),<br>1.97 (2H, d, J = 11.7 Hz), 2.34 (3H, s),<br>2.3-2.8 (11H, m), 3.2-3.3 (1H, m),<br>3.70 (2H, d, J = 12.2 Hz), 3.88 (3H,<br>s), 6.54 (2H, m), 7.2 (1H, m),<br>7.62 (2H, br), 7.88 (1H, dd, J = 1.5, 7.8 Hz),<br>8.10 (1H, br), 8.37 (1H, br),<br>8.53 (1H, br), 9.29 (1H, s)<br>Cryst (MP: 164-165) |
| 24 | 1 | ESI+: 498.2<br>NMR-CDCl3: 1.31 (6H, d, J = 6.8 Hz),<br>2.42 (3H, s), 2.68 (4H, br),<br>3.15-3.35 (5H, m), 3.89 (3H, s),<br>6.54 (2H, br), 7.2 (1H, m),<br>7.63 (1H, d, J = 6.4 Hz),<br>7.89 (1H, d, J = 6.4 Hz),<br>8.12 (1H, br), 8.38 (1H, br), 8.53 (1H,<br>br), 9.30 (1H, s)<br>Amrph |
| 25 | 1 | FAB+: 664.2 |
| 26 | 2 | FAB+: 454 |
| 27 | 1 | ESI+: 465 |
| 28 | 1 | ESI+: 410.3 |
| 29 | 3 | ESI+: 397.2 |
| 30 | 3 | ESI+: 431.2 |
| 31 | 3 | ESI+: 470.1 |
| 32 | 1 | ESI+: 664.3 |
| 33 | 8 | FAB+: 465.2 |
| 34 | 8 | FAB+: 468.2 |
| 35 | 1 | FAB+: 664.2 |
| 36 | 1 | ESI+: 664.3 |
| 37 | 1 | FAB+: 542.3 |
| 38 | 1 | ESI+: 664.3 |
| 39 | 3 | ESI+: 519.2, 521.2 |
| 40 | 8 | ESI+: 570.4 |
| 41 | 8 | ESI+: 554.4 |
| 42 | 8 | ESI+: 556.3 |
| 43 | 1 | ESI+: 666.4 |
| 44 | 1 | ESI+: 664.3 |
| 45 | 1 | ESI+: 630.4<br>NMR-CDCl3: 1.30 (6H, d, J = 6.8 Hz),<br>1.6-1.7 (2H, m),<br>1.86 (2H, d, J = 12.7 Hz),<br>1.97 (2H, t, J = 11.7 Hz),<br>2.28 (3H, s), 2.3-2.4 (1H, m),<br>2.77 (4H, t, J = 4.8 Hz), 2.94 (2H,<br>d, J = 11.7 Hz), 3.19 (4H, t, J = 4.8 Hz),<br>3.2-3.3 (1H, m),<br>3.90 (3H, s), 6.57 (1H, d, J = 2.4 Hz),<br>6.58 (1H, d, J = 2.4 Hz),<br>7.2-7.4 (3H, m), |

TABLE 44-continued

| Ex | Syn | Data |
|---|---|---|
| | | 7.6-7.7 (3H, m), 7.85-7.95 (2H, m), 8.45 (1H, br), 8.90 (1H, d, J = 8.3 Hz), 10.19 (1H, s) Cryst (MP: 109-114) |

TABLE 45

| Ex | Syn | Data |
|---|---|---|
| 46 | 1 | ESI+: 534.3 |
| 47 | 1 | ESI+: 660.4 |
| 48 | 1 | ESI+: 660.4 |
| 49 | 1 | ESI+: 582.3 |
| 50 | 1 | ESI+: 548.3 |
| 51 | 6 | ESI+: 497.3 |
| 52 | 2 | ESI+: 526.3 NMR-DMSOd6: 1.03-1.21 (6H, m), 1.80-2.05 (2H, m), 2.09-2.22 (2H, m), 2.60-2.78 (3H, m), 2.85-3.15 (5H, m), 3.35-3.55 (3H, m), 3.83 (3H, s), 3.90-4.08 (1H, m), 4.10-4.70 (3H, br), 6.60-7.28 (1H, br), 7.30-7.90 (4H, m), 8.00-8.50 (2H, m), 9.28-9.52 (1H, br), 9.52-9.73 (1H, br), 10.51-10.85 (1H, br) Amrph |
| 53 | 2 | ESI+: 500.2 |
| 54 | 1 | ESI+: 664.3 |
| 55 | 1 | ESI+: 581.4 |
| 56 | 3 | ESI+: 590.3 |
| 57 | 3 | FAB+: 540.3 |
| 58 | 10 | ESI+: 552.3 NMR-DMSOd6: 1.01-1.29 (6H, br), 1.40-1.60 (2H, m), 1.60-1.78 (4H, m), 1.83-2.00 (2H, m), 2.06-2.20 (1H, m), 2.41-2.62 (4H, m), 2.69-2.82 (2H, m), 3.19-3.52 (1H, m), 3.58-3.71 (2H, m), 3.76 (3H, s), 5.90-6.56 (1H, m), 6.56-6.71 (1H, br), 7.15-7.35 (2H, m), 7.45-7.62 (1H, m), 7.62-7.89 (1H, m), 8.20-8.45 (2H, m), 8.60-9.03 (1H, m), 9.15-9.35 (1H, br) Amrph |
| 59 | 1 | ESI+: 595.3 |
| 60 | 10 | ESI+: 568.3 |
| 61 | 3 | ESI+: 499.3 |
| 62 | 6 | FAB+: 546.2 |
| 63 | 10 | ESI+: 568.3 NMR-DMSOd6: 1.05-1.25 (6H, m), 1.78-2.10 (4H, m), 2.10-2.35 (2H, m), 2.80-4.21 (17H, m), 4.35-4.51 (1H, m), 6.60-7.21 (1H, m), 7.30-7.55 (2H, m), 7.55-7.90 (2H, m), 8.10-8.50 (2H, m), 9.20-9.40 (1H, m), 9.40-9.65 (1H, m), 10.42-11.42 (1H, m) Amrph |

TABLE 46

| Ex | Syn | Data |
|---|---|---|
| 64 | 1 | ESI+: 602.3 |
| 65 | 1 | FAB+: 602.3 |
| 66 | 1 | ESI+: 533.3 |
| 67 | 1 | ESI+: 534.3 |
| 68 | 1 | FAB+: 599.2 |

TABLE 46-continued

| Ex | Syn | Data |
|---|---|---|
| 69 | 12 | ESI+: 513.3 |
| 70 | 2 | ESI+: 566.4 |
| 71 | 1 | FAB+: 583.3 |
| 72 | 9 | ESI+: 484.3 NHR-DMSOd6: 1.02-1.29 (6H, br), 2.73-2.98 (4H, m), 2.98-3.16 (4H, m), 3.17-3.50 (2H, m), 3.76 (3H, s), 6.40-6.55 (1H, m), 6.55-6.71 (1H, br), 7.18-7.39 (2H, m), 7.40-7.62 (1H, m), 7.62-7.90 (1H, m), 8.20-8.46 (2H, m), 8.58-9.53 (2H, m) Amrph |
| 73 | 10 | ESI+: 644.3 |
| 74 | 18 | ESI+: 605 |
| 75 | 18 | ESI+: 619 |
| 76 | 18 | ESI+: 590 |
| 77 | 18 | ESI+: 604 |
| 78 | 18 | ESI+: 619 |
| 79 | 18 | ESI+: 618 |
| 80 | 18 | ESI+: 632 |
| 81 | 18 | ESI+: 587 |
| 82 | 18 | ESI+: 601 |
| 83 | 18 | ESI+: 615 |
| 84 | 18 | ESI+: 670 |
| 85 | 18 | ESI+: 616 |
| 86 | 18 | ESI+: 658 |
| 87 | 18 | ESI+: 644 |
| 88 | 18 | ESI+: 660 |
| 89 | 18 | ESI+: 692 |
| 90 | 18 | ESI+: 658 |
| 91 | 18 | ESI+: 630 |
| 92 | 18 | ESI+: 629 |
| 93 | 18 | ESI+: 631 |
| 94 | 18 | ESI+: 659 |
| 95 | 18 | ESI+: 658 |
| 96 | 18 | ESI+: 672 |
| 97 | 18 | ESI+: 691 |
| 98 | 1 | FAB+: 581.3 |
| 99 | 1 | FAB+: 595.3 |
| 100 | 1 | FAB+: 609.3 |
| 101 | 3 | ESI+: 638.2 |
| 102 | 3 | ESI+: 688.4 |
| 103 | 9 | ESI+: 538.4 |
| 104 | 18 | ESI+: 512 |
| 105 | 18 | ESI+: 526 |
| 106 | 18 | ESI+: 540 |
| 107 | 18 | ESI+: 556 |

TABLE 47

| Ex | Syn | Data |
|---|---|---|
| 108 | 18 | ESI+: 570 |
| 109 | 18 | ESI+: 572 |
| 110 | 18 | ESI+: 541 |
| 111 | 18 | ESI+: 544 |
| 112 | 18 | ESI+: 538 |
| 113 | 18 | ESI+: 595 |
| 114 | 18 | ESI+: 673 |
| 115 | 19 | ESI+: 609 |
| 116 | 19 | ESI+: 611 |
| 117 | 19 | ESI+: 645 |
| 118 | 19 | ESI+: 649 |
| 119 | 1 | ESI+: 553.3 |
| 120 | 12 | ESI+: 552.4 NMR-DMSOd6: 1.03-1.22 (6H, m), 1.22-1.41 (2H, m), 1.59-1.87 (6H, m), 2.10-2.35 (2H, m), 2.60-2.85 (4H, m), 3.22-3.53 (4H, m), 3.76 (3H, s), 6.45-6.58 (1H, m), 6.58-6.70 (1H, m), 7.18-7.37 (2H, m), 7.42-7.61 (1H, m), |

TABLE 47-continued

| Ex | Syn | Data |
|---|---|---|
|  |  | 7.68-7.86 (1H, m), 8.21-8.42 (2H, m), 8.82-9.05 (1H, m), 9.20-9.31 (1H, m) Amrph |
| 121 | 12 | ESI+: 568.4 |
| 122 | 1 | FAB+: 512.3 |
| 123 | 10 | FAB+: 582.1 NMR-CDCl3: 1.03 (3H, t, J = 7.2 Hz), 1.6-1.7 (2H, m), 1.96 (2H, d, J = 12.2 Hz), 2.30 (3H, s), 2.3-2.8 (13H, m), 2.98 (2H, q, J = 7.2 Hz), 3.87 (3H, s), 4.86 (1H, br), 6.51 (1H, br), 6.53 (1H, d, J = 2.0 Hz), 7.22 (1H, d, J = 7.6 Hz), 7.5-7.7 (2H, m), 7.94 (1H, dd, J = 1.5, 7.8 Hz), 8.06 (1H, d, J = 8.3 Hz), 8.32 (1H, br), 8.40 (1H, br), 8.76 (1H, s) Cryst (MP: 155-160) |
| 124 | 1 | FAB+: 551.2 |
| 125 | 1 | FAB+: 565.2 |
| 126 | 1 | ESI+: 567.3 |
| 127 | 1 | ESI+: 567.4 |

TABLE 48

| Ex | Syn | Data |
|---|---|---|
| 128 | 1 | ESI+: 582.3 NMR-CDCl3: 1.6-1.8 (2H, m), 1.96 (2H, d, J = 12.2 Hz), 2.30 (3H, s), 2.3-2.8 (10H, m), 2.75 (6H, s), 3.70 (2H, d, J = 12.7 Hz), 3.88 (3H, s), 4.86 (1H, br), 6.5-6.6 (2H, m), 7.15-7.25 (1H, m), 7.5-7.7 (2H, m), 7.83 (1H, d, J = 7.8 Hz), 8.12 (1H, br), 8.35 (1H, br), 8.50 (1H, br), 9.11 (1H, s) Cryst (MP: 167-170) |
| 129 | 1 | ESI+: 579.3 |
| 130 | 1 | ESI+: 585.4, 587.2 |
| 131 | 19 | ESI+: 540 |
| 132 | 19 | ESI+: 542 |
| 133 | 19 | ESI+: 570 |
| 134 | 19 | ESI+: 527 |
| 135 | 19 | ESI+: 597 |
| 136 | 19 | ESI+: 526 |
| 137 | 19 | ESI+: 554 |
| 138 | 19 | ESI+: 584 |
| 139 | 19 | ESI+: 569 |
| 140 | 19 | ESI+: 568 |
| 141 | 19 | ESI+: 567 |
| 142 | 19 | ESI+: 581 |
| 143 | 19 | ESI+: 595 |
| 144 | 19 | ESI+: 609 |
| 145 | 19 | ESI+: 607 |
| 146 | 19 | ESI+: 657 |
| 147 | 1 | ESI+: 552.4 |
| 148 | 6 | FAB−: 496.1 |
| 149 | 10 | ESI+: 596.3 NMR-CDCl3: 1.00 (6H, d, J = 6.3 Hz), 1.6-1.8 (2H, m), 1.96 (2H, d, J = 11.7 Hz), 2.31 (3H, s), 2.3-2.8 (11H, m), 3.4-3.5 (1H, m), 3.69 (2H, d, J = 12.2 Hz), 3.88 (3H, s), 4.56 (1H, br), 6.48 (1H, br), 6.54 (1H, d, J = 2.4 Hz), 7.2-7.25 (1H, m), 7.5-7.7 (2H, m), 7.97 (1H, d, J = 6.8 Hz), 8.08 (1H, d, J = 8.8 Hz), 8.35 (2H, br), 8.61 (1H, s) Cryst (MP: 185-189) |
| 150 | 20 | ESI+: 568 |
| 151 | 20 | ESI+: 554 |
| 152 | 20 | ESI+: 570 |
| 153 | 20 | ESI+: 556 |
| 154 | 20 | ESI+: 584 |
| 155 | 20 | ESI+: 569 |
| 156 | 20 | ESI+: 583 |
| 157 | 20 | ESI+: 597 |

TABLE 49

| Ex | Syn | Data |
|---|---|---|
| 158 | 20 | ESI+: 611 |
| 159 | 20 | ESI+: 583 |
| 160 | 20 | ESI+: 584 |
| 161 | 20 | ESI+: 555 |
| 162 | 20 | ESI+: 569 |
| 163 | 3 | ESI+: 528.3 |
| 164 | 3 | ESI+: 570.3 |
| 165 | 6 | ESI+: 526.4 |
| 166 | 10 | ESI+: 610.3 NMR-CDCl3: 0.99 (6H, d, J = 6.3 Hz), 1.6-1.8 (2H, m), 1.96 (2H, d, J = 11.7 Hz), 2.31 (3H, s), 2.3-2.8 (11H, m), 2.7 (3H, m), 3.69 (2H, d, J = 12.2 Hz), 3.88 (3H, s), 4.15-4.2 (1H, m), 6.48 (1H, br), 6.54 (2H, br), 7.15-7.2 (1H, m), 7.5-7.6 (1H, m), 7.91 (1H, d, J = 7.8 Hz), 8.11 (1H, d, J = 8.8 Hz), 8.36 (1H, br), 8.42 (1H, br), 8.90 (1H, s) Cryst (MP: 162-164) |
| 167 | 6 | ESI+: 526.6 |
| 168 | 10 | ESI+: 610.4 |
| 169 | 1 | ESI+: 624.3 |
| 170 | 1 | ESI+: 608.3 |
| 171 | 1 | ESI+: 594.3 NMR-DMSOd6: 0.28-0.51 (4H, m), 1.41-1.59 (2H, m), 1.76-1.91 (2H, m), 2.01-2.20 (4H, m), 2.20-2.39 (5H, m), 2.40-2.60 (4H, m), 2.60-2.76 (2H, m), 3.62-3.85 (5H, m), 6.42-6.55 (1H, m), 6.55-6.70 (1H, m), 7.11-7.50 (2H, m), 7.72-7.89 (1H, m), 8.19-8.43 (1H, m), 8.75-8.95 (1H, m), 9.05-9.20 (1H, m) Amrph |
| 172 | 1 | ESI+: 596.3 |
| 173 | 1 | ESI+: 608.3 |
| 174 | 1 | ESI+: 622.4 |
| 175 | 1 | ESI+: 471.0 |

TABLE 50

| Ex | Syn | Data |
|---|---|---|
| 176 | 10 | ESI+: 553.3 NMR-DMSOd6: 1.04-1.29 (6H, br), 2.05-2.58 (11H, m), 3.18-3.50 (2H, m), 3.50-3.66 (2H, m), 3.73 (3H, s), 3.85-4.00 (2H, m), 5.90-6.22 (2H, m), 7.10-7.40 (2H, m), |

TABLE 50-continued

| Ex | Syn | Data |
|---|---|---|
| | | 7.40-7.88 (2H, m),<br>8.17-8.42 (2H, m), 8.60-9.01 (1H, m),<br>9.17-9.35 (1H, br)<br>Amrph |
| 177 | 3 | ESI+: 543.2 |
| 178 | 1 | ESI+: 555.2, 557.2 |
| 179 | 1 | ESI+: 529.2 |
| 180 | 1 | ESI+: 581.3 |
| 181 | 1 | ESI+: 582 |

Tables 51 to 95 show the structures of other compounds falling within the present invention. These compounds were synthesized or can be synthesized as described in the above preparation examples or examples, or by any process obvious to those skilled in the art with or without modifications.

It should be noted that the symbols in the tables are as defined below:

—$R^{1a'}$, —$R^{1b'}$, —$R^{1c'}$, —$R^{1d'}$, —$R^{2'}$, —$R^{3'}$, —$R^{4'}$, —$R^{5'}$, —$R^{6a'}$, —$R^{6b'}$, —$R^{6c'}$, —$R^{6d'}$ and —$R^A$ correspond to the substituents in the general formulae.

TABLE 51

[Core structure shown: 2-(iPr-sulfonyl)phenyl-NH-triazine-NH-(2-OMe-4-$R^{3'}$-phenyl)]

| No | —$R^{3'}$ |
|---|---|
| A1 | —N(piperidin-4-yl)-morpholine |
| A2 | —N(piperidin-4-yl)-piperidine |
| A3 | —N(piperidin-4-yl)-pyrrolidine |
| A4 | —N(piperidin-4-yl)-(2,6-diMe)-4-Me-piperazine |
| A5 | —N(piperidin-4-yl)-(2,6-diMe)-piperazine (NH) |
| A6 | —N(piperazin-4-yl)-N-Me-piperidine |

TABLE 51-continued

[Core structure shown: 2-(iPr-sulfonyl)phenyl-NH-triazine-NH-(2-OMe-4-$R^{3'}$-phenyl)]

| No | —$R^{3'}$ |
|---|---|
| A7 | —N(piperazin-4-yl)-cyclohexyl |
| A8 | —N(piperazin-4-yl)-phenyl |
| A9 | —N-(3,5-diMe-piperazin-4-yl)-cyclohexyl |
| A10 | —N(piperidin-4-yl)-(3-oxo)-4-Me-piperazine |
| A11 | —N(piperidin-4-yl)-(2-oxo)-4-Me-piperazine |
| A12 | —N(piperidin-4-yl)-(3-oxo)-piperazine (NH) |
| A13 | —N(piperazin-4-yl)-pyridin-2-yl |
| A14 | —N-(3,5-diMe-piperazin-4-yl)-phenyl |
| A15 | —N-(3,5-diMe-piperazin-4-yl)-pyridin-2-yl |
| A16 | —N-morpholine |

TABLE 51-continued

Structure: phenyl ring with iPr-SO₂ substituent, NH-triazine-NH linked to phenyl with OMe and R³′

| No | —R³′ |
|---|---|
| A17 | N-methylpiperidinyl |
| A18 | N-methylpyrrolidinyl |
| A19 | (2R,5S)-1,2,4,5-tetramethylpiperazinyl |
| A20 | (2R,5S)-2,5-dimethyl-1-methylpiperazinyl (NH) |
| A21 | 1,4-dimethyl-3-oxopiperazinyl |
| A22 | 4-methyl-3-oxopiperazinyl (NH) |
| A23 | 1-methyl-4-(azetidin-1-yl)piperidinyl |
| A24 | 1-methyl-4-(3-hydroxyazetidin-1-yl)piperidinyl |

TABLE 52

Structure: phenyl ring with iPr-SO₂ substituent, NH-triazine-NH linked to phenyl with OMe and R³′

| No | —R³′ |
|---|---|
| A25 | 1-methyl-4-(3-methoxyazetidin-1-yl)piperidinyl |
| A26 | 1-methyl-4-(3-hydroxypyrrolidin-1-yl)piperidinyl |
| A27 | 1-methyl-4-(3-methoxypyrrolidin-1-yl)piperidinyl |
| A28 | 1-methyl-4-(3-methoxypiperidin-1-yl)piperidinyl |
| A29 | 1-methyl-4-(2-oxopyrrolidin-1-yl)piperidinyl |
| A30 | 1-methyl-4-(2-oxopiperidin-1-yl)piperidinyl |
| A31 | 1-methylazetidinyl |
| A32 | 1-methyl-3-hydroxyazetidinyl |
| A33 | 1-methyl-4-hydroxypiperidinyl |
| A34 | 1-methyl-4-methoxypiperidinyl |
| A35 | 3-(methylamino)azetidinyl |
| A36 | 3-(methylamino)pyrrolidinyl |

TABLE 52-continued
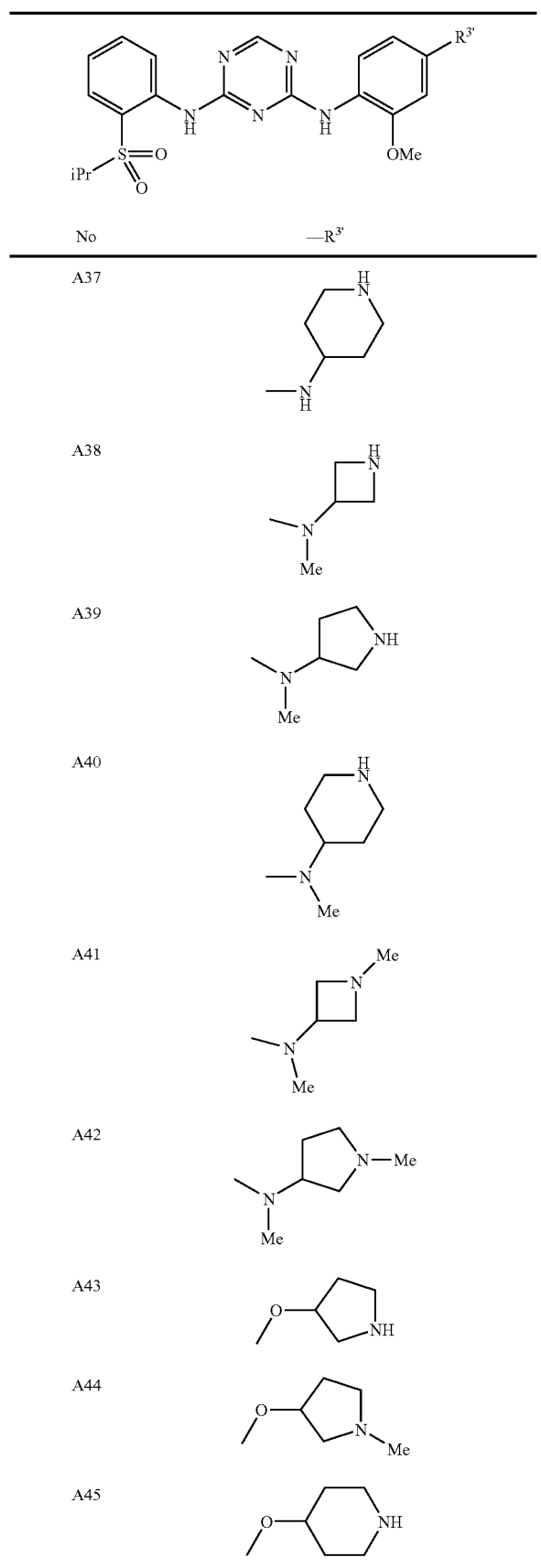
TABLE 53
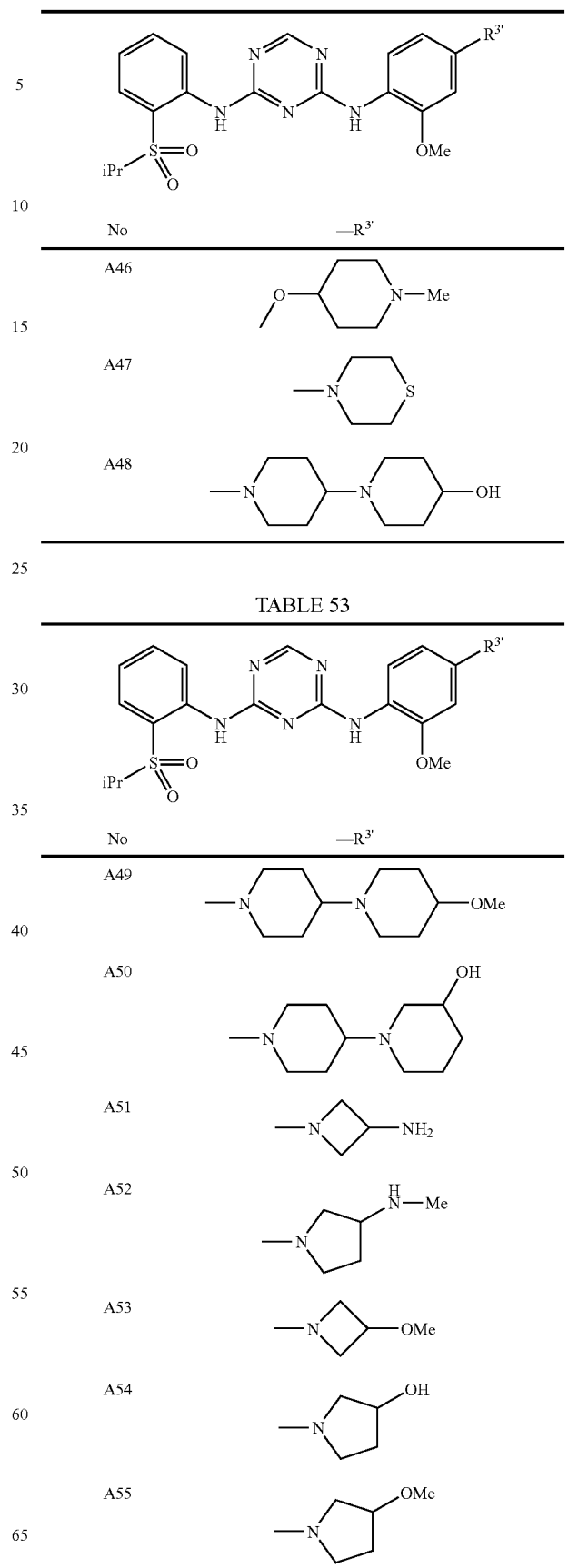

TABLE 53-continued
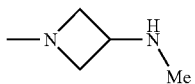
| No | —R3' |
|---|---|
| A56 | 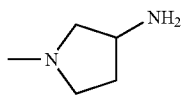 |
| A57 | 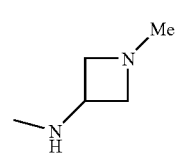 |
| A58 | 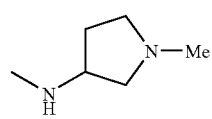 |
| A59 | 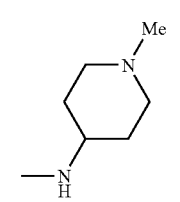 |
| A60 | 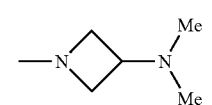 |
| A61 | 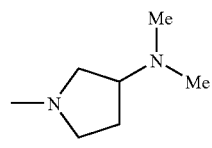 |
| A62 | 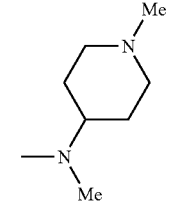 |
| A63 | 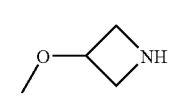 |
| A64 | 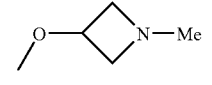 |
| A65 | 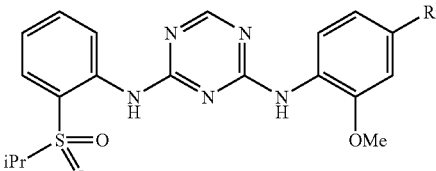 |
TABLE 53-continued
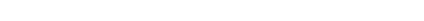
| No | —R3' |
|---|---|
| A66 | 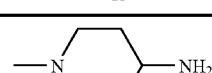 |
| A67 | 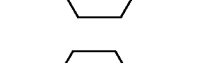 |
| A68 | 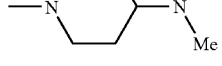 |
| A69 |  |
| A70 | 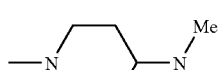 |
| A71 | 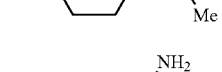 |
| A72 | 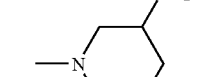 |
TABLE 54
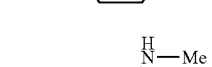
| No | —R4' |
|---|---|
| B1 | 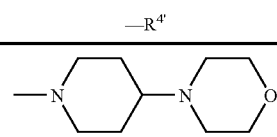 |

TABLE 54-continued

| No | —R⁴' |
|---|---|
| B2 | 4-(1-methylpiperidin-4-yl)piperidine |
| B3 | 1-(1-methylpiperidin-4-yl)pyrrolidine |
| B4 | (2S,5R)-1-(1-methylpiperidin-4-yl)-2,5-dimethyl-4-methylpiperazine |
| B5 | (2S,5R)-1-(1-methylpiperidin-4-yl)-2,5-dimethylpiperazine |
| B6 | 1-methyl-4-(1-methylpiperidin-4-yl)piperazine |
| B7 | 1-cyclohexyl-4-methylpiperazine |
| B8 | 1-methyl-4-phenylpiperazine |
| B9 | (2S,5R)-4-cyclohexyl-1-methyl-2,5-dimethylpiperazine |
| B10 | 1-methyl-4-(1-methylpiperidin-4-yl)piperazin-2-one |
| B11 | 4-methyl-1-(1-methylpiperidin-4-yl)piperazin-2-one |

TABLE 54-continued

| No | —R⁴' |
|---|---|
| B12 | 1-(1-methylpiperidin-4-yl)piperazin-2-one |
| B13 | 1-methyl-4-(pyridin-2-yl)piperazine |
| B14 | (2S,5R)-1-methyl-2,5-dimethyl-4-phenylpiperazine |
| B15 | (2S,5R)-1-methyl-2,5-dimethyl-4-(pyridin-2-yl)piperazine |
| B16 | morpholine (N-linked) |
| B17 | piperidine (N-linked) |
| B18 | pyrrolidine (N-linked) |
| B19 | (2S,5R)-1,4-dimethyl-2,5-dimethylpiperazine |
| B20 | (2S,5R)-1-methyl-2,5-dimethylpiperazine |

TABLE 54-continued
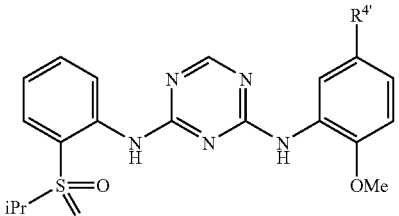
| No | —R⁴' |
|---|---|
| B21 | 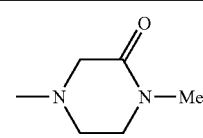 |
| B22 | 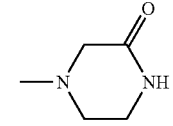 |
| B23 | 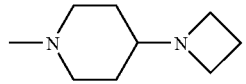 |
| B24 | 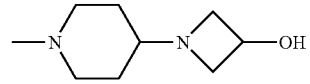 |
TABLE 55
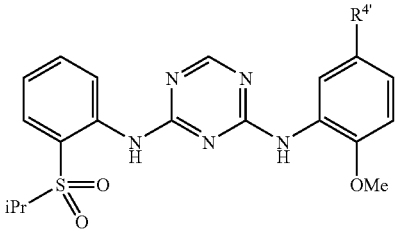
| No | —R⁴' |
|---|---|
| B25 | 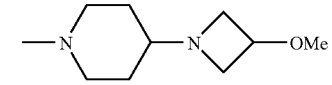 |
| B26 | 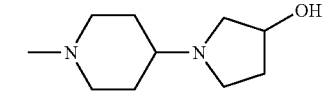 |
| B27 | 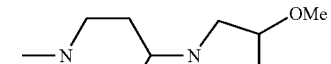 |
| B28 | 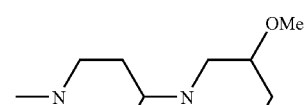 |
TABLE 55-continued
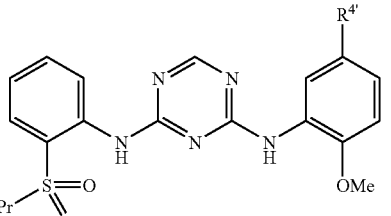
| No | —R⁴' |
|---|---|
| B29 | 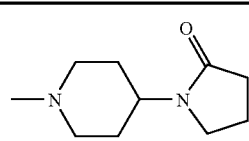 |
| B30 | 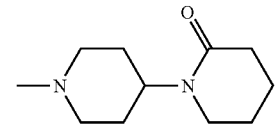 |
| B31 |  |
| B32 |  |
| B33 | 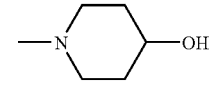 |
| B34 | 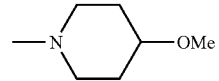 |
| B35 | 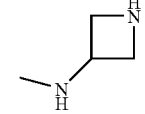 |
| B36 | 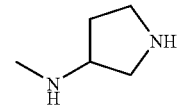 |
| B37 | 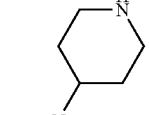 |
| B38 | 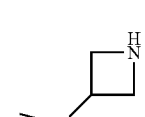 |

TABLE 55-continued

[Structure: phenyl-NH-triazine-NH-phenyl with iPr-SO2 on one ring and OMe, R4' on the other]

| No | —R4' |
|---|---|
| B39 | 3-(dimethylamino)pyrrolidin-NH |
| B40 | 4-(dimethylamino)piperidine-NH |
| B41 | 1-methyl-3-(dimethylamino)azetidine |
| B42 | 1-methyl-3-(dimethylamino)pyrrolidine |
| B43 | 3-methoxypyrrolidin-NH |
| B44 | 3-methoxy-1-methylpyrrolidine |
| B45 | 4-methoxypiperidin-NH |
| B46 | 4-methoxy-1-methylpiperidine |
| B47 | thiomorpholine |
| B48 | 1'-methyl-4-hydroxy-1,4'-bipiperidine |

TABLE 56

[Structure: phenyl-NH-triazine-NH-phenyl with iPr-SO2 on one ring and OMe, R4' on the other]

| No | —R4' |
|---|---|
| B49 | 1'-methyl-4-methoxy-1,4'-bipiperidine |
| B50 | 1'-methyl-3-hydroxy-1,4'-bipiperidine |
| B51 | 3-amino-1-methylazetidine |
| B52 | 3-(methylamino)-1-methylpyrrolidine |
| B53 | 3-methoxy-1-methylazetidine |
| B54 | 3-hydroxy-1-methylpyrrolidine |
| B55 | 3-methoxy-1-methylpyrrolidine |
| B56 | 3-(methylamino)-1-methylazetidine |
| B57 | 3-amino-1-methylpyrrolidine |
| B58 | 3-(methylamino)-1-methylazetidine |
| B59 | 3-(methylamino)-1-methylpyrrolidine |

TABLE 56-continued

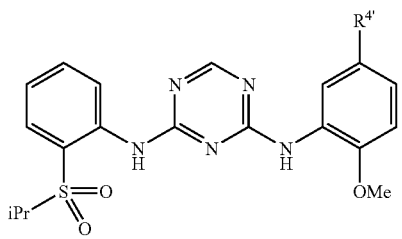

| No | —R⁴' |
|---|---|
| B60 | 1-methylpiperidin-4-yl(methyl)amino (—NH-(1-Me-piperidin-4-yl)) |
| B61 | 1-methylazetidin-3-yl dimethylamino |
| B62 | 1-methylpyrrolidin-3-yl dimethylamino |
| B63 | 1-methylpiperidin-4-yl N-methyl (—N(Me)-(1-Me-piperidin-4-yl)) |
| B64 | 3-methoxyazetidin-1-yl (NH) |
| B65 | 3-methoxy-1-methylazetidinyl |

TABLE 56-continued

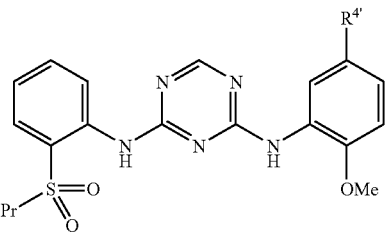

| No | —R⁴' |
|---|---|
| B66 | 1-methylpiperidin-4-yl amino (NH₂) |
| B67 | 1-methylpiperidin-4-yl N-methylamino |
| B68 | 1-methyl-1,1-dioxo-thiomorpholinyl |
| B69 | 1-methylpiperidin-4-yl dimethylamino |
| B70 | 1-methylpiperidin-3-yl amino (NH₂) |
| B71 | 1-methylpiperidin-3-yl N-methylamino |
| B72 | 1-methylpiperidin-3-yl dimethylamino |

TABLE 57

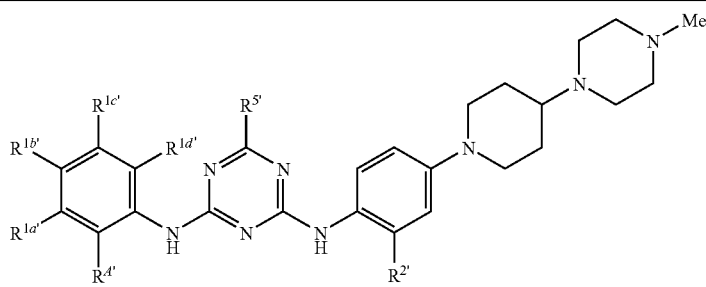

| No | —R¹ᵃ' | —R¹ᵇ' | —R¹ᶜ' | —R¹ᵈ' | —R²' | —R⁵' | —R⁴' |
|---|---|---|---|---|---|---|---|
| C1 | —H | —H | —H | —H | —F | —H | —S(=O)₂iPr |
| C2 | —H | —H | —H | —H | —Cl | —H | —S(=O)₂iPr |

TABLE 57-continued

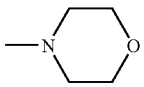

| No | —R$^{1a'}$ | —R$^{1b'}$ | —R$^{1c'}$ | —R$^{1d'}$ | —R$^{2'}$ | —R$^{5'}$ | —R$^{A'}$ |
|---|---|---|---|---|---|---|---|
| C3 | —H | —H | —H | —H | —Br | —H | —S(=O)$_2$iPr |
| C4 | —H | —H | —H | —H | —OEt | —H | —S(=O)$_2$iPr |
| C5 | —H | —H | —H | —H | —OiPr | —H | —S(=O)$_2$iPr |
| C6 | —H | —H | —H | —H | —CF$_3$ | —H | —S(=O)$_2$iPr |
| C7 | —H | —H | —H | —H | —CN | —H | —S(=O)$_2$iPr |
| C8 | —H | —H | —H | —H | Me | —H | —S(=O)$_2$iPr |
| C9 | —H | —H | —H | —H | Et | —H | —S(=O)$_2$iPr |
| C10 | —H | —H | —H | —H | —SMe | —H | —S(=O)$_2$iPr |
| C11 | —H | —H | —H | —H | —OCF$_3$ | —H | —S(=O)$_2$iPr |
| C12 | —H | —H | —H | —H | —OMe | —Cl | —S(=O)$_2$iPr |
| C13 | —H | —H | —H | —H | —OMe | —Br | —S(=O)$_2$iPr |
| C14 | —H | —H | —H | —H | —OMe | Me | —S(=O)$_2$iPr |
| C15 | —H | —H | —H | —H | —OMe | —SMe | —S(=O)$_2$iPr |
| C16 | —H | —H | —H | —H | —OMe | —NMe$_2$ | —S(=O)$_2$iPr |
| C17 | —H | —H | —H | —H | —OMe | —NEt$_2$ | —S(=O)$_2$iPr |
| C18 | —H | —H | —H | —H | —OMe | 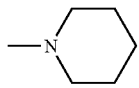 | —S(=O)$_2$iPr |
| C19 | —H | —H | —H | —H | —OMe | N-piperidinyl | —S(=O)$_2$iPr |
| C20 | —H | —H | —H | —H | —OMe | N-pyrrolidinyl | —S(=O)$_2$iPr |
| C21 | —H | —H | —H | —H | —OMe | N-azetidinyl | —S(=O)$_2$iPr |
| C22 | —H | —H | —H | —H | —OMe | —CN | —S(=O)$_2$iPr |
| C23 | —F | —H | —H | —H | —OMe | —H | —S(=O)$_2$iPr |
| C24 | —H | —F | —H | —H | —OMe | —H | —S(=O)$_2$iPr |
| C25 | —H | —H | —F | —H | —OMe | —H | —S(=O)$_2$iPr |
| C26 | —H | —H | —H | —F | —OMe | —H | —S(=O)$_2$iPr |

TABLE 58

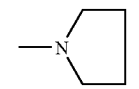

| No | —R$^{1a'}$ | —R$^{1b'}$ | —R$^{1c'}$ | —R$^{1d'}$ | —R$^{2'}$ | —R$^{5'}$ | —R$^{A'}$ |
|---|---|---|---|---|---|---|---|
| C27 | —Cl | —H | —H | —H | —OMe | —H | —S(=O)$_2$iPr |
| C28 | —H | —Cl | —H | —H | —OMe | —H | —S(=O)$_2$iPr |

TABLE 58-continued

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| C29 | —H | —H | —Cl | —H | —OMe | —H | —S(=O)$_2$iPr |
| C30 | —H | —H | —H | —Cl | —OMe | —H | —S(=O)$_2$iPr |
| C31 | —Br | —H | —H | —H | —OMe | —H | —S(=O)$_2$iPr |
| C32 | —H | —Br | —H | —H | —OMe | —H | —S(=O)$_2$iPr |
| C33 | —H | —H | —Br | —H | —OMe | —H | —S(=O)$_2$iPr |
| C34 | —H | —H | —H | —Br | —OMe | —H | —S(=O)$_2$iPr |
| C35 | Me | —H | —H | —H | —OMe | —H | —S(=O)$_2$iPr |
| C36 | —H | Me | —H | —H | —OMe | —H | —S(=O)$_2$iPr |
| C37 | —H | —H | Me | —H | —OMe | —H | —S(=O)$_2$iPr |
| C39 | —H | —H | —H | Me | —OMe | —H | —S(=O)$_2$iPr |
| C40 | —OMe | —H | —H | —H | —OMe | —H | —S(=O)$_2$iPr |
| C41 | —H | —OMe | —H | —H | —OMe | —H | —S(=O)$_2$iPr |
| C42 | —H | —H | —OMe | —H | —OMe | —H | —S(=O)$_2$iPr |
| C43 | —H | —H | —H | —OMe | —OMe | —H | —S(=O)$_2$iPr |
| C44 | —CN | —H | —H | —H | —OMe | —H | —S(=O)$_2$iPr |
| C45 | —H | —CN | —H | —H | —OMe | —H | —S(=O)$_2$iPr |
| C46 | —H | —H | —CN | —H | —OMe | —H | —S(=O)$_2$iPr |
| C47 | —H | —H | —H | —CN | —OMe | —H | —S(=O)$_2$iPr |
| C48 | —CF$_3$ | —H | —H | —H | —OMe | —H | —S(=O)$_2$iPr |
| C49 | —H | —CF$_3$ | —H | —H | —OMe | —H | —S(=O)$_2$iPr |
| C50 | —H | —H | —CF$_3$ | —H | —OMe | —H | —S(=O)$_2$iPr |
| C51 | —H | —H | —H | —CF$_3$ | —OMe | —H | —S(=O)$_2$iPr |
| C52 | —SMe | —H | —H | —H | —OMe | —H | —S(=O)$_2$iPr |
| C53 | —H | —SMe | —H | —H | —OMe | —H | —S(=O)$_2$iPr |
| C54 | —H | —H | —SMe | —H | —OMe | —H | —S(=O)$_2$iPr |
| C55 | —H | —H | —H | —SMe | —OMe | —H | —S(=O)$_2$iPr |
| C56 | —OCF$_3$ | —H | —H | —H | —OMe | —H | —S(=O)$_2$iPr |
| C57 | —H | —OCF$_3$ | —H | —H | —OMe | —H | —S(=O)$_2$iPr |
| C58 | —H | —H | —OCF$_3$ | —H | —OMe | —H | —S(=O)$_2$iPr |
| C59 | —H | —H | —H | —OCF$_3$ | —OMe | —H | —S(=O)$_2$iPr |

TABLE 59

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| C60 | —H | —H | —H | —H | —OMe | —H | —S(=O)$_2$Et |
| C61 | —H | —H | —H | —H | —OMe | —H | —S(=O)$_2$Me |
| C62 | —H | —H | —H | —H | —OMe | —H | —S(=O)$_2$NHMe |
| C63 | —H | —H | —H | —H | —OMe | —H | —S(=O)$_2$NMe$_2$ |
| C64 | —H | —H | —H | —H | —OMe | —H | —C(=O)NHMe |
| C65 | —H | —H | —H | —H | —OMe | —H | —C(=O)NMe$_2$ |
| C66 | —H | —H | —H | —H | —OMe | —H | —C(=O)iPr |
| C67 | —H | —H | —H | —H | —OMe | —H | —C(=O)Et |
| C68 | —H | —H | —H | —H | —OMe | —H | —F |
| C69 | —H | —H | —H | —H | —OMe | —H | —Cl |
| C70 | —H | —H | —H | —H | —OMe | —H | —Br |
| C71 | —H | —H | —H | —H | —OMe | —H | —OMe |

TABLE 59-continued

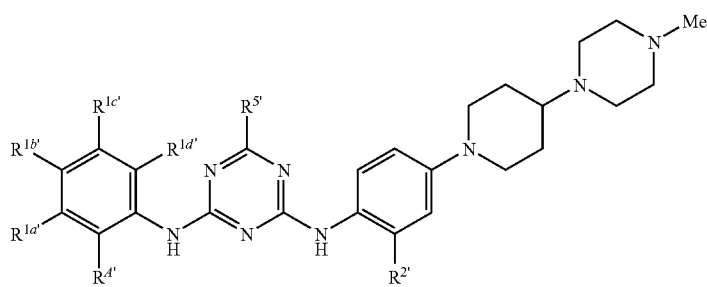

| No | —R$^{1a'}$ | —R$^{1b'}$ | —R$^{1c'}$ | —R$^{1d'}$ | —R$^{2'}$ | —R$^{5'}$ | —R$^{A'}$ |
|---|---|---|---|---|---|---|---|
| C72 | —H | —H | —H | —H | —OMe | —H | —OEt |
| C73 | —H | —H | —H | —H | —OMe | —H | —OiPr |
| C74 | —H | —H | —H | —H | —OMe | —H | —OCF$_3$ |
| C75 | —H | —H | —H | —H | —OMe | —H | —SMe |
| C76 | —H | —H | —H | —H | —OMe | —H | —SEt |
| C77 | —H | —H | —H | —H | —OMe | —H | —SiPr |
| C78 | —H | —H | —H | —H | —OMe | —H | Me |
| C79 | —H | —H | —H | —H | —OMe | —H | Et |
| C80 | —H | —H | —H | —H | —OMe | —H | iPr |
| C81 | —H | —H | —H | —H | —OMe | —H | —CF$_3$ |

TABLE 60

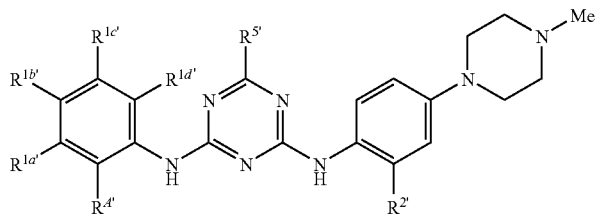

| No | —R$^{1a'}$ | —R$^{1b'}$ | —R$^{1c'}$ | —R$^{1d'}$ | —R$^{2'}$ | —R$^{5'}$ | —R$^{A'}$ |
|---|---|---|---|---|---|---|---|
| D1 | —H | —H | —H | —H | —F | —H | —S(=O)$_2$iPr |
| D2 | —H | —H | —H | —H | —Cl | —H | —S(=O)$_2$iPr |
| D3 | —H | —H | —H | —H | —Br | —H | —S(=O)$_2$iPr |
| D4 | —H | —H | —H | —H | —OEt | —H | —S(=O)$_2$iPr |
| D5 | —H | —H | —H | —H | —OiPr | —H | —S(=O)$_2$iPr |
| D6 | —H | —H | —H | —H | —CF$_3$ | —H | —S(=O)$_2$iPr |
| D7 | —H | —H | —H | —H | —CN | —H | —S(=O)$_2$iPr |
| D8 | —H | —H | —H | —H | Me | —H | —S(=O)$_2$iPr |
| D9 | —H | —H | —H | —H | Et | —H | —S(=O)$_2$iPr |
| D10 | —H | —H | —H | —H | —SMe | —H | —S(=O)$_2$iPr |
| D11 | —H | —H | —H | —H | —OCF$_3$ | —H | —S(=O)$_2$iPr |
| D12 | —H | —H | —H | —H | —OMe | —Cl | —S(=O)$_2$iPr |
| D13 | —H | —H | —H | —H | —OMe | —Br | —S(=O)$_2$iPr |
| D14 | —H | —H | —H | —H | —OMe | Me | —S(=O)$_2$iPr |
| D15 | —H | —H | —H | —H | —OMe | —SMe | —S(=O)$_2$iPr |
| D16 | —H | —H | —H | —H | —OMe | —NMe$_2$ | —S(=O)$_2$iPr |
| D17 | —H | —H | —H | —H | —OMe | —NEt$_2$ | —S(=O)$_2$iPr |
| D18 | —H | —H | —H | —H | —OMe | 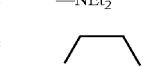 | —S(=O)$_2$iPr |
| D19 | —H | —H | —H | —H | —OMe | 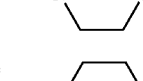 | —S(=O)$_2$iPr |
| D20 | —H | —H | —H | —H | —OMe | 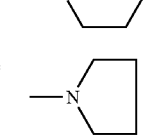 | —S(=O)$_2$iPr |

TABLE 60-continued

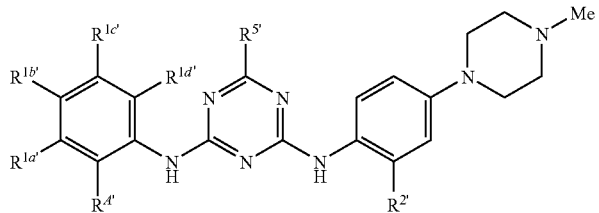

| No | —R$^{1a'}$ | —R$^{1b'}$ | —R$^{1c'}$ | —R$^{1d'}$ | —R$^{2'}$ | —R$^{5'}$ | —R$^{A'}$ |
|---|---|---|---|---|---|---|---|
| D21 | —H | —H | —H | —H | —OMe | 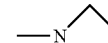 | —S(=O)$_2$iPr |
| D22 | —H | —H | —H | —H | —OMe | —CN | —S(=O)$_2$iPr |
| D23 | —F | —H | —H | —H | —OMe | —H | —S(=O)$_2$iPr |
| D24 | —H | —F | —H | —H | —OMe | —H | —S(=O)$_2$iPr |
| D25 | —H | —H | —F | —H | —OMe | —H | —S(=O)$_2$iPr |
| D26 | —H | —H | —H | —F | —OMe | —H | —S(=O)$_2$iPr |

TABLE 61

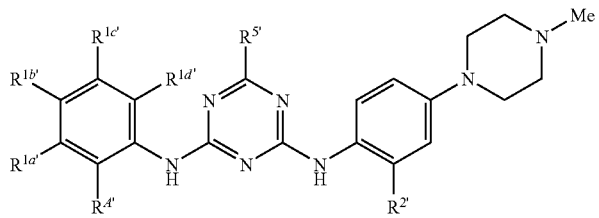

| No | —R$^{1a'}$ | —R$^{1b'}$ | —R$^{1c'}$ | —R$^{1d'}$ | —R$^{2'}$ | —R$^{5'}$ | —R$^{A'}$ |
|---|---|---|---|---|---|---|---|
| D27 | —Cl | —H | —H | —H | —OMe | —H | —S(=O)$_2$iPr |
| D28 | —H | —Cl | —H | —H | —OMe | —H | —S(=O)$_2$iPr |
| D29 | —H | —H | —Cl | —H | —OMe | —H | —S(=O)$_2$iPr |
| D30 | —H | —H | —H | —Cl | —OMe | —H | —S(=O)$_2$iPr |
| D31 | —Br | —H | —H | —H | —OMe | —H | —S(=O)$_2$iPr |
| D32 | —H | —Br | —H | —H | —OMe | —H | —S(=O)$_2$iPr |
| D33 | —H | —H | —Br | —H | —OMe | —H | —S(=O)$_2$iPr |
| D34 | —H | —H | —H | —Br | —OMe | —H | —S(=O)$_2$iPr |
| D35 | Me | —H | —H | —H | —OMe | —H | —S(=O)$_2$iPr |
| D36 | —H | Me | —H | —H | —OMe | —H | —S(=O)$_2$iPr |
| D37 | —H | —H | Me | —H | —OMe | —H | —S(=O)$_2$iPr |
| D39 | —H | —H | —H | Me | —OMe | —H | —S(=O)$_2$iPr |
| D40 | —OMe | —H | —H | —H | —OMe | —H | —S(=O)$_2$iPr |
| D41 | —H | —OMe | —H | —H | —OMe | —H | —S(=O)$_2$iPr |
| D42 | —H | —H | —OMe | —H | —OMe | —H | —S(=O)$_2$iPr |
| D43 | —H | —H | —H | —OMe | —OMe | —H | —S(=O)$_2$iPr |
| D44 | —CN | —H | —H | —H | —OMe | —H | —S(=O)$_2$iPr |
| D45 | —H | —CN | —H | —H | —OMe | —H | —S(=O)$_2$iPr |
| D46 | —H | —H | —CN | —H | —OMe | —H | —S(=O)$_2$iPr |
| D47 | —H | —H | —H | —CN | —OMe | —H | —S(=O)$_2$iPr |
| D48 | —CF$_3$ | —H | —H | —H | —OMe | —H | —S(=O)$_2$iPr |
| D49 | —H | —CF$_3$ | —H | —H | —OMe | —H | —S(=O)$_2$iPr |
| D50 | —H | —H | —CF$_3$ | —H | —OMe | —H | —S(=O)$_2$iPr |
| D51 | —H | —H | —H | —CF$_3$ | —OMe | —H | —S(=O)$_2$iPr |
| D52 | —SMe | —H | —H | —H | —OMe | —H | —S(=O)$_2$iPr |
| D53 | —H | —SMe | —H | —H | —OMe | —H | —S(=O)$_2$iPr |
| D54 | —H | —H | —SMe | —H | —OMe | —H | —S(=O)$_2$iPr |
| D55 | —H | —H | —H | —SMe | —OMe | —H | —S(=O)$_2$iPr |
| D56 | —OCF$_3$ | —H | —H | —H | —OMe | —H | —S(=O)$_2$iPr |
| D57 | —H | —OCF$_3$ | —H | —H | —OMe | —H | —S(=O)$_2$iPr |
| D58 | —H | —H | —OCF$_3$ | —H | —OMe | —H | —S(=O)$_2$iPr |
| D59 | —H | —H | —H | —OCF$_3$ | —OMe | —H | —S(=O)$_2$iPr |

TABLE 62

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| D60 | —H | —H | —H | —H | —OMe | —H | —S(=O)$_2$Et |
| D61 | —H | —H | —H | —H | —OMe | —H | —S(=O)$_2$Me |
| D62 | —H | —H | —H | —H | —OMe | —H | —S(=O)$_2$NHMe |
| D63 | —H | —H | —H | —H | —OMe | —H | —S(=O)$_2$NMe$_2$ |
| D64 | —H | —H | —H | —H | —OMe | —H | —C(=O)NHMe |
| D65 | —H | —H | —H | —H | —OMe | —H | —C(=O)NMe$_2$ |
| D66 | —H | —H | —H | —H | —OMe | —H | —C(=O)iPr |
| D67 | —H | —H | —H | —H | —OMe | —H | —C(=O)Et |
| D68 | —H | —H | —H | —H | —OMe | —H | —F |
| D69 | —H | —H | —H | —H | —OMe | —H | —Cl |
| D70 | —H | —H | —H | —H | —OMe | —H | —Br |
| D71 | —H | —H | —H | —H | —OMe | —H | —OMe |
| D72 | —H | —H | —H | —H | —OMe | —H | —OEt |
| D73 | —H | —H | —H | —H | —OMe | —H | —OiPr |
| D74 | —H | —H | —H | —H | —OMe | —H | —OCF$_3$ |
| D75 | —H | —H | —H | —H | —OMe | —H | —SMe |
| D76 | —H | —H | —H | —H | —OMe | —H | —SEt |
| D77 | —H | —H | —H | —H | —OMe | —H | —SiPr |
| D78 | —H | —H | —H | —H | —OMe | —H | Me |
| D79 | —H | —H | —H | —H | —OMe | —H | Et |
| D80 | —H | —H | —H | —H | —OMe | —H | iPr |
| D81 | —H | —H | —H | —H | —OMe | —H | —CF$_3$ |

TABLE 63

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| E1 | —H | —H | —H | —H | —F | —H | —S(=O)$_2$iPr |
| E2 | —H | —H | —H | —H | —Cl | —H | —S(=O)$_2$iPr |
| E3 | —H | —H | —H | —H | —Br | —H | —S(=O)$_2$iPr |
| E4 | —H | —H | —H | —H | —OEt | —H | —S(=O)$_2$iPr |
| E5 | —H | —H | —H | —H | —OiPr | —H | —S(=O)$_2$iPr |
| E6 | —H | —H | —H | —H | —CF$_3$ | —H | —S(=O)$_2$iPr |
| E7 | —H | —H | —H | —H | —CN | —H | —S(=O)$_2$iPr |
| E8 | —H | —H | —H | —H | Me | —H | —S(=O)$_2$iPr |
| E9 | —H | —H | —H | —H | Et | —H | —S(=O)$_2$iPr |
| E10 | —H | —H | —H | —H | —SMe | —H | —S(=O)$_2$iPr |
| E11 | —H | —H | —H | —H | —OCF$_3$ | —H | —S(=O)$_2$iPr |
| E12 | —H | —H | —H | —H | —OMe | —Cl | —S(=O)$_2$iPr |
| E13 | —H | —H | —H | —H | —OMe | —Br | —S(=O)$_2$iPr |
| E14 | —H | —H | —H | —H | —OMe | Me | —S(=O)$_2$iPr |
| E15 | —H | —H | —H | —H | —OMe | —SMe | —S(=O)$_2$iPr |
| E16 | —H | —H | —H | —H | —OMe | —NMe$_2$ | —S(=O)$_2$iPr |
| E17 | —H | —H | —H | —H | —OMe | —NEt$_2$ | —S(=O)$_2$iPr |
| E18 | —H | —H | —H | —H | —OMe | morpholino | —S(=O)$_2$iPr |
| E19 | —H | —H | —H | —H | —OMe | piperidino | —S(=O)$_2$iPr |

TABLE 63-continued

| No | —R$^{1a'}$ | —R$^{1b'}$ | —R$^{1c'}$ | —R$^{1d'}$ | —R$^{2'}$ | —R$^{5'}$ | —R$^{A'}$ |
|---|---|---|---|---|---|---|---|
| E20 | —H | —H | —H | —H | —OMe | pyrrolidinyl | —S(=O)$_2$iPr |
| E21 | —H | —H | —H | —H | —OMe | azetidinyl | —S(=O)$_2$iPr |
| E22 | —H | —H | —H | —H | —OMe | —CN | —S(=O)$_2$iPr |
| E23 | —F | —H | —H | —H | —OMe | —H | —S(=O)$_2$iPr |
| E24 | —H | —F | —H | —H | —OMe | —H | —S(=O)$_2$iPr |
| E25 | —H | —H | —F | —H | —OMe | —H | —S(=O)$_2$iPr |
| E26 | —H | —H | —H | —F | —OMe | —H | —S(=O)$_2$iPr |

TABLE 64

| No | —R$^{1a'}$ | —R$^{1b'}$ | —R$^{1c'}$ | —R$^{1d'}$ | —R$^{2'}$ | —R$^{5'}$ | —R$^{A'}$ |
|---|---|---|---|---|---|---|---|
| E27 | —Cl | —H | —H | —H | —OMe | —H | —S(=O)$_2$iPr |
| E28 | —H | —Cl | —H | —H | —OMe | —H | —S(=O)$_2$iPr |
| E29 | —H | —H | —Cl | —H | —OMe | —H | —S(=O)$_2$iPr |
| E30 | —H | —H | —H | —Cl | —OMe | —H | —S(=O)$_2$iPr |
| E31 | —Br | —H | —H | —H | —OMe | —H | —S(=O)$_2$iPr |
| E32 | —H | —Br | —H | —H | —OMe | —H | —S(=O)$_2$iPr |
| E33 | —H | —H | —Br | —H | —OMe | —H | —S(=O)$_2$iPr |
| E34 | —H | —H | —H | —Br | —OMe | —H | —S(=O)$_2$iPr |
| E35 | Me | —H | —H | —H | —OMe | —H | —S(=O)$_2$iPr |
| E36 | —H | Me | —H | —H | —OMe | —H | —S(=O)$_2$iPr |
| E37 | —H | —H | Me | —H | —OMe | —H | —S(=O)$_2$iPr |
| E39 | —H | —H | —H | Me | —OMe | —H | —S(=O)$_2$iPr |
| E40 | —OMe | —H | —H | —H | —OMe | —H | —S(=O)$_2$iPr |
| E41 | —H | —OMe | —H | —H | —OMe | —H | —S(=O)$_2$iPr |
| E42 | —H | —H | —OMe | —H | —OMe | —H | —S(=O)$_2$iPr |
| E43 | —H | —H | —H | —OMe | —OMe | —H | —S(=O)$_2$iPr |
| E44 | —CN | —H | —H | —H | —OMe | —H | —S(=O)$_2$iPr |
| E45 | —H | —CN | —H | —H | —OMe | —H | —S(=O)$_2$iPr |
| E46 | —H | —H | —CN | —H | —OMe | —H | —S(=O)$_2$iPr |
| E47 | —H | —H | —H | —CN | —OMe | —H | —S(=O)$_2$iPr |
| E48 | —CF$_3$ | —H | —H | —H | —OMe | —H | —S(=O)$_2$iPr |
| E49 | —H | —CF$_3$ | —H | —H | —OMe | —H | —S(=O)$_2$iPr |
| E50 | —H | —H | —CF$_3$ | —H | —OMe | —H | —S(=O)$_2$iPr |
| E51 | —H | —H | —H | —CF$_3$ | —OMe | —H | —S(=O)$_2$iPr |
| E52 | —SMe | —H | —H | —H | —OMe | —H | —S(=O)$_2$iPr |
| E53 | —H | —SMe | —H | —H | —OMe | —H | —S(=O)$_2$iPr |
| E54 | —H | —H | —SMe | —H | —OMe | —H | —S(=O)$_2$iPr |
| E55 | —H | —H | —H | —SMe | —OMe | —H | —S(=O)$_2$iPr |
| E56 | —OCF$_3$ | —H | —H | —H | —OMe | —H | —S(=O)$_2$iPr |
| E57 | —H | —OCF$_3$ | —H | —H | —OMe | —H | —S(=O)$_2$iPr |
| E58 | —H | —H | —OCF$_3$ | —H | —OMe | —H | —S(=O)$_2$iPr |
| E59 | —H | —H | —H | —OCF$_3$ | —OMe | —H | —S(=O)$_2$iPr |

TABLE 65

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| E60 | —H | —H | —H | —H | —OMe | —H | —S(=O)$_2$Et |
| E61 | —H | —H | —H | —H | —OMe | —H | —S(=O)$_2$Me |
| E62 | —H | —H | —H | —H | —OMe | —H | —S(=O)$_2$NHMe |
| E63 | —H | —H | —H | —H | —OMe | —H | —S(=O)$_2$NMe$_2$ |
| E64 | —H | —H | —H | —H | —OMe | —H | —C(=O)NHMe |
| E65 | —H | —H | —H | —H | —OMe | —H | —C(=O)NMe$_2$ |
| E66 | —H | —H | —H | —H | —OMe | —H | —C(=O)iPr |
| E67 | —H | —H | —H | —H | —OMe | —H | —C(=O)Et |
| E68 | —H | —H | —H | —H | —OMe | —H | —F |
| E69 | —H | —H | —H | —H | —OMe | —H | —Cl |
| E70 | —H | —H | —H | —H | —OMe | —H | —Br |
| E71 | —H | —H | —H | —H | —OMe | —H | —OMe |
| E72 | —H | —H | —H | —H | —OMe | —H | —OEt |
| E73 | —H | —H | —H | —H | —OMe | —H | —OiPr |
| E74 | —H | —H | —H | —H | —OMe | —H | —OCF$_3$ |
| E75 | —H | —H | —H | —H | —OMe | —H | —SMe |
| E76 | —H | —H | —H | —H | —OMe | —H | —SEt |
| E77 | —H | —H | —H | —H | —OMe | —H | —SiPr |
| E78 | —H | —H | —H | —H | —OMe | —H | Me |
| E79 | —H | —H | —H | —H | —OMe | —H | Et |
| E80 | —H | —H | —H | —H | —OMe | —H | iPr |
| E81 | —H | —H | —H | —H | —OMe | —H | —CF$_3$ |

TABLE 66

| No | —R$^{1a'}$ | —R$^{1b'}$ | —R$^{1c'}$ | —R$^{1d'}$ | —R$^{2'}$ | —R$^{5'}$ |
|---|---|---|---|---|---|---|
| F1 | —H | —H | —H | —H | —F | —H |
| F2 | —H | —H | —H | —H | —Cl | —H |
| F3 | —H | —H | —H | —H | —Br | —H |
| F4 | —H | —H | —H | —H | —OEt | —H |
| F5 | —H | —H | —H | —H | —OiPr | —H |
| F6 | —H | —H | —H | —H | —CF$_3$ | —H |
| F7 | —H | —H | —H | —H | —CN | —H |
| F8 | —H | —H | —H | —H | Me | —H |
| F9 | —H | —H | —H | —H | Et | —H |
| F10 | —H | —H | —H | —H | —SMe | —H |
| F11 | —H | —H | —H | —H | —OCF$_3$ | —H |
| F12 | —H | —H | —H | —H | —OMe | —Cl |
| F13 | —H | —H | —H | —H | —OMe | —Br |
| F14 | —H | —H | —H | —H | —OMe | Me |
| F15 | —H | —H | —H | —H | —OMe | —SMe |
| F16 | —H | —H | —H | —H | —OMe | —NMe$_2$ |
| F17 | —H | —H | —H | —H | —OMe | —NEt$_2$ |
| F18 | —H | —H | —H | —H | —OMe | morpholino |

TABLE 66-continued
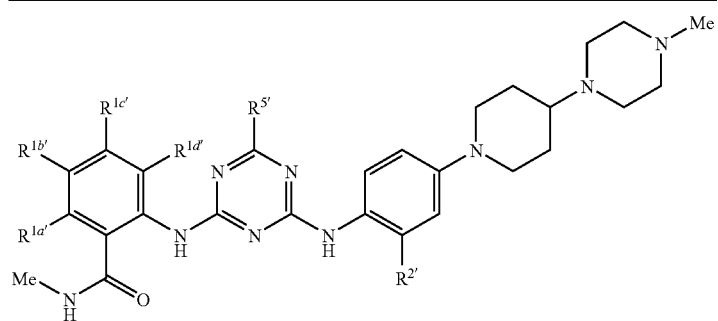
| No | —R$^{1a'}$ | —R$^{1b'}$ | —R$^{1c'}$ | —R$^{1d'}$ | —R$^{2'}$ | —R$^{5'}$ |
|---|---|---|---|---|---|---|
| F19 | —H | —H | —H | —H | —OMe | 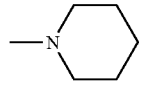 |
| F20 | —H | —H | —H | —H | —OMe | 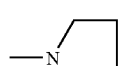 |
| F21 | —H | —H | —H | —H | —OMe | 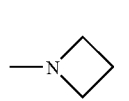 |
| F22 | —H | —H | —H | —H | —OMe | —CN |
| F23 | —F | —H | —H | —H | —OMe | —H |
| F24 | —H | —F | —H | —H | —OMe | —H |
| F25 | —H | —H | —F | —H | —OMe | —H |
| F26 | —H | —H | —H | —F | —OMe | —H |
| F27 | —Cl | —H | —H | —H | —OMe | —H |
| F28 | —H | —Cl | —H | —H | —OMe | —H |
TABLE 67
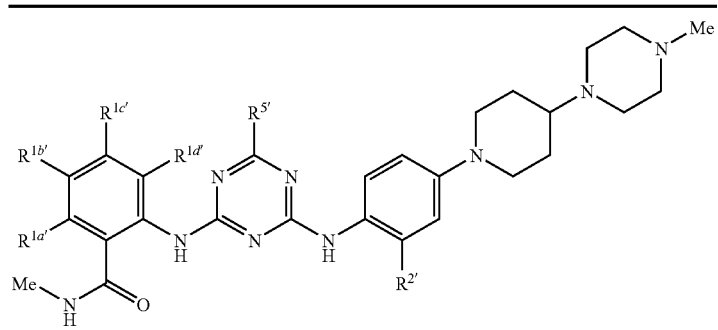
| No | —R$^{1a'}$ | —R$^{1b'}$ | —R$^{1c'}$ | —R$^{1d'}$ | —R$^{2'}$ | —R$^{5'}$ |
|---|---|---|---|---|---|---|
| F29 | —H | —H | —Cl | —H | —OMe | —H |
| F30 | —H | —H | —H | —Cl | —OMe | —H |
| F31 | —Br | —H | —H | —H | —OMe | —H |
| F32 | —H | —Br | —H | —H | —OMe | —H |
| F33 | —H | —H | —Br | —H | —OMe | —H |
| F34 | —H | —H | —H | —Br | —OMe | —H |
| F35 | Me | —H | —H | —H | —OMe | —H |
| F36 | —H | Me | —H | —H | —OMe | —H |
| F37 | —H | —H | Me | —H | —OMe | —H |
| F39 | —H | —H | —H | Me | —OMe | —H |
| F40 | —OMe | —H | —H | —H | —OMe | —H |

TABLE 67-continued

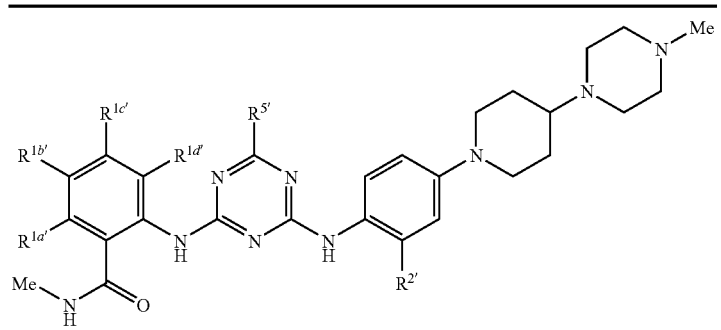

| No | —R1a' | —R1b' | —R1c' | —R1d' | —R2' | —R5' |
|---|---|---|---|---|---|---|
| F41 | —H | —OMe | —H | —H | —OMe | —H |
| F42 | —H | —H | —OMe | —H | —OMe | —H |
| F43 | —H | —H | —H | —OMe | —OMe | —H |
| F44 | —CN | —H | —H | —H | —OMe | —H |
| F45 | —H | —CN | —H | —H | —OMe | —H |
| F46 | —H | —H | —CN | —H | —OMe | —H |
| F47 | —H | —H | —H | —CN | —OMe | —H |
| F48 | —CF3 | —H | —H | —H | —OMe | —H |
| F49 | —H | —CF3 | —H | —H | —OMe | —H |
| F50 | —H | —H | —CF3 | —H | —OMe | —H |
| F51 | —H | —H | —H | —CF3 | —OMe | —H |
| F52 | —SMe | —H | —H | —H | —OMe | —H |
| F53 | —H | —SMe | —H | —H | —OMe | —H |
| F54 | —H | —H | —SMe | —H | —OMe | —H |
| F55 | —H | —H | —H | —SMe | —OMe | —H |
| F56 | —OCF3 | —H | —H | —H | —OMe | —H |
| F57 | —H | —OCF3 | —H | —H | —OMe | —H |
| F58 | —H | —H | —OCF3 | —H | —OMe | —H |
| F59 | —H | —H | —H | —OCF3 | —OMe | —H |

TABLE 68

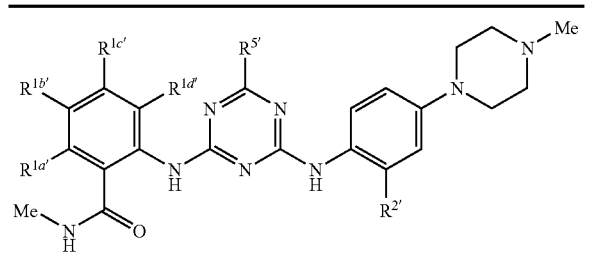

| No | —R1a' | —R1b' | —R1c' | —R1d' | —R2' | —R5' |
|---|---|---|---|---|---|---|
| G1 | —H | —H | —H | —H | —F | —H |
| G2 | —H | —H | —H | —H | —Cl | —H |
| G3 | —H | —H | —H | —H | —Br | —H |
| G4 | —H | —H | —H | —H | —OEt | —H |
| G5 | —H | —H | —H | —H | —OiPr | —H |
| G6 | —H | —H | —H | —H | —CF3 | —H |
| G7 | —H | —H | —H | —H | —CN | —H |
| G8 | —H | —H | —H | —H | Me | —H |
| G9 | —H | —H | —H | —H | Et | —H |
| G10 | —H | —H | —H | —H | —SMe | —H |
| G11 | —H | —H | —H | —H | —OCF3 | —H |
| G12 | —H | —H | —H | —H | —OMe | —Cl |
| G13 | —H | —H | —H | —H | —OMe | —Br |
| G14 | —H | —H | —H | —H | —OMe | Me |
| G15 | —H | —H | —H | —H | —OMe | —SMe |
| G16 | —H | —H | —H | —H | —OMe | —NMe2 |
| G17 | —H | —H | —H | —H | —OMe | —NEt2 |
| G18 | —H | —H | —H | —H | —OMe | 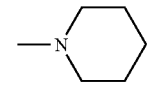 |

TABLE 68-continued

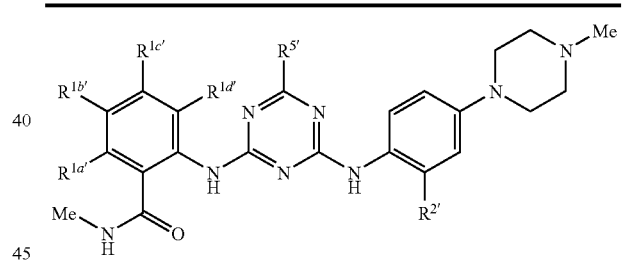

| No | —R1a' | —R1b' | —R1c' | —R1d' | —R2' | —R5' |
|---|---|---|---|---|---|---|
| G19 | —H | —H | —H | —H | —OMe | 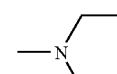 |
| G20 | —H | —H | —H | —H | —OMe | 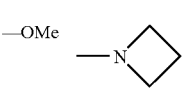 |
| G21 | —H | —H | —H | —H | —OMe | 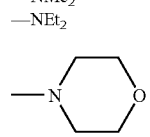 |
| G22 | —H | —H | —H | —H | —OMe | —CN |
| G23 | —F | —H | —H | —H | —OMe | —H |
| G24 | —H | —F | —H | —H | —OMe | —H |
| G25 | —H | —H | —F | —H | —OMe | —H |
| G26 | —H | —H | —H | —F | —OMe | —H |

TABLE 69

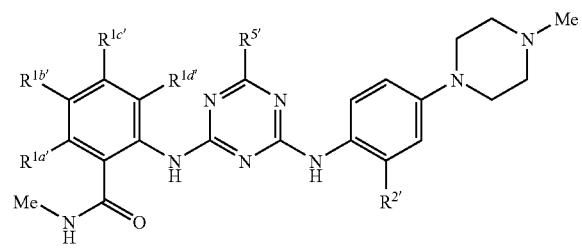

| No | —R1a' | —R1b' | —R1c' | —R1d' | —R2' | —R5' |
|---|---|---|---|---|---|---|
| G27 | —Cl | —H | —H | —H | —OMe | —H |
| G28 | —H | —Cl | —H | —H | —OMe | —H |
| G29 | —H | —H | —Cl | —H | —OMe | —H |
| G30 | —H | —H | —H | —Cl | —OMe | —H |
| G31 | —Br | —H | —H | —H | —OMe | —H |
| G32 | —H | —Br | —H | —H | —OMe | —H |
| G33 | —H | —H | —Br | —H | —OMe | —H |
| G34 | —H | —H | —H | —Br | —OMe | —H |
| G35 | Me | —H | —H | —H | —OMe | —H |
| G36 | —H | Me | —H | —H | —OMe | —H |
| G37 | —H | —H | Me | —H | —OMe | —H |
| G39 | —H | —H | —H | Me | —OMe | —H |
| G40 | —OMe | —H | —H | —H | —OMe | —H |
| G41 | —H | —OMe | —H | —H | —OMe | —H |
| G42 | —H | —H | —OMe | —H | —OMe | —H |
| G43 | —H | —H | —H | —OMe | —OMe | —H |
| G44 | —CN | —H | —H | —H | —OMe | —H |
| G45 | —H | —CN | —H | —H | —OMe | —H |
| G46 | —H | —H | —CN | —H | —OMe | —H |
| G47 | —H | —H | —H | —CN | —OMe | —H |
| G48 | —CF3 | —H | —H | —H | —OMe | —H |
| G49 | —H | —CF3 | —H | —H | —OMe | —H |
| G50 | —H | —H | —CF3 | —H | —OMe | —H |
| G51 | —H | —H | —H | —CF3 | —OMe | —H |
| G52 | —SMe | —H | —H | —H | —OMe | —H |
| G53 | —H | —SMe | —H | —H | —OMe | —H |
| G54 | —H | —H | —SMe | —H | —OMe | —H |
| G55 | —H | —H | —H | —SMe | —OMe | —H |
| G56 | —OCF3 | —H | —H | —H | —OMe | —H |
| G57 | —H | —OCF3 | —H | —H | —OMe | —H |
| G58 | —H | —H | —OCF3 | —H | —OMe | —H |
| G59 | —H | —H | —H | —OCF3 | —OMe | —H |

TABLE 70

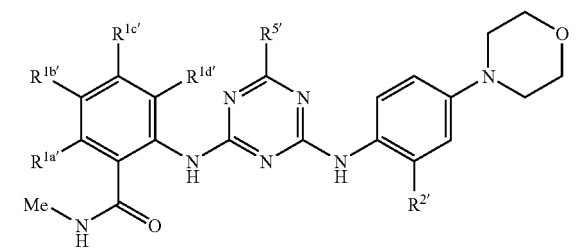

| No | —R1a' | —R1b' | —R1c' | —R1d' | —R2' | —R5' |
|---|---|---|---|---|---|---|
| H1 | —H | —H | —H | —H | —F | —H |
| H2 | —H | —H | —H | —H | —Cl | —H |
| H3 | —H | —H | —H | —H | —Br | —H |
| H4 | —H | —H | —H | —H | —OEt | —H |
| H5 | —H | —H | —H | —H | —OiPr | —H |
| H6 | —H | —H | —H | —H | —CF3 | —H |
| H7 | —H | —H | —H | —H | —CN | —H |
| H8 | —H | —H | —H | —H | Me | —H |
| H9 | —H | —H | —H | —H | Et | —H |
| H10 | —H | —H | —H | —H | —SMe | —H |
| H11 | —H | —H | —H | —H | —OCF3 | —H |
| H12 | —H | —H | —H | —H | —OMe | —Cl |
| H13 | —H | —H | —H | —H | —OMe | —Br |
| H14 | —H | —H | —H | —H | —OMe | Me |

TABLE 70-continued

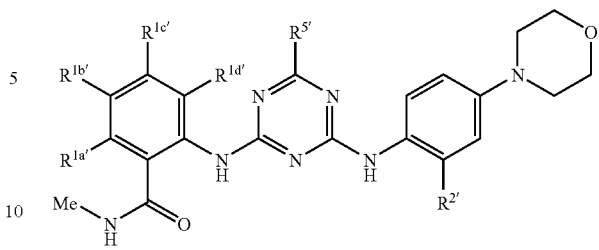

| No | —R1a' | —R1b' | —R1c' | —R1d' | —R2' | —R5' |
|---|---|---|---|---|---|---|
| H15 | —H | —H | —H | —H | —OMe | —SMe |
| H16 | —H | —H | —H | —H | —OMe | —NMe2 |
| H17 | —H | —H | —H | —H | —OMe | —NEt2 |
| H18 | —H | —H | —H | —H | —OMe | (morpholino) |
| H19 | —H | —H | —H | —H | —OMe | (piperidino) |
| H20 | —H | —H | —H | —H | —OMe | (pyrrolidino) |
| H21 | —H | —H | —H | —H | —OMe | (azetidino) |
| H22 | —H | —H | —H | —H | —OMe | —CN |
| H23 | —F | —H | —H | —H | —OMe | —H |
| H24 | —H | —F | —H | —H | —OMe | —H |
| H25 | —H | —H | —F | —H | —OMe | —H |
| H26 | —H | —H | —H | —F | —OMe | —H |

TABLE 71

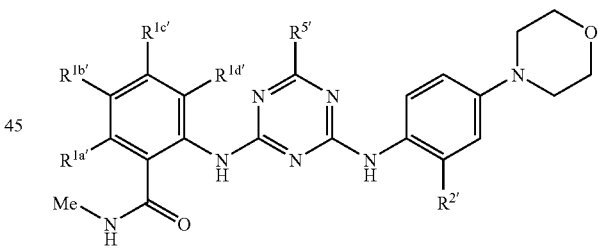

| No | —R1a' | —R1b' | —R1c' | —R1d' | —R2' | —R5' |
|---|---|---|---|---|---|---|
| H27 | —Cl | —H | —H | —H | —OMe | —H |
| H28 | —H | —Cl | —H | —H | —OMe | —H |
| H29 | —H | —H | —Cl | —H | —OMe | —H |
| H30 | —H | —H | —H | —Cl | —OMe | —H |
| H31 | —Br | —H | —H | —H | —OMe | —H |
| H32 | —H | —Br | —H | —H | —OMe | —H |
| H33 | —H | —H | —Br | —H | —OMe | —H |
| H34 | —H | —H | —H | —Br | —OMe | —H |
| H35 | Me | —H | —H | —H | —OMe | —H |
| H36 | —H | Me | —H | —H | —OMe | —H |
| H37 | —H | —H | Me | —H | —OMe | —H |
| H39 | —H | —H | —H | Me | —OMe | —H |
| H40 | —OMe | —H | —H | —H | —OMe | —H |
| H41 | —H | —OMe | —H | —H | —OMe | —H |
| H42 | —H | —H | —OMe | —H | —OMe | —H |
| H43 | —H | —H | —H | —OMe | —OMe | —H |
| H44 | —CN | —H | —H | —H | —OMe | —H |
| H45 | —H | —CN | —H | —H | —OMe | —H |

TABLE 71-continued
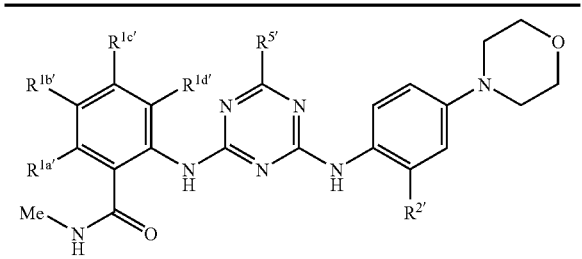
| No | —R¹ᵃ' | —R¹ᵇ' | —R¹ᶜ' | —R¹ᵈ' | —R²' | —R⁵' |
|---|---|---|---|---|---|---|
| H46 | —H | —H | —CN | —H | —OMe | —H |
| H47 | —H | —H | —H | —CN | —OMe | —H |
| H48 | —CF₃ | —H | —H | —H | —OMe | —H |
| H49 | —H | —CF₃ | —H | —H | —OMe | —H |
| H50 | —H | —H | —CF₃ | —H | —OMe | —H |
| H51 | —H | —H | —H | —CF₃ | —OMe | —H |
| H52 | —SMe | —H | —H | —H | —OMe | —H |
| H53 | —H | —SMe | —H | —H | —OMe | —H |
| H54 | —H | —H | —SMe | —H | —OMe | —H |
| H55 | —H | —H | —H | —SMe | —OMe | —H |
| H56 | —OCF₃ | —H | —H | —H | —OMe | —H |
| H57 | —H | —OCF₃ | —H | —H | —OMe | —H |
| H58 | —H | —H | —OCF₃ | —H | —OMe | —H |
| H59 | —H | —H | —H | —OCF₃ | —OMe | —H |
TABLE 72
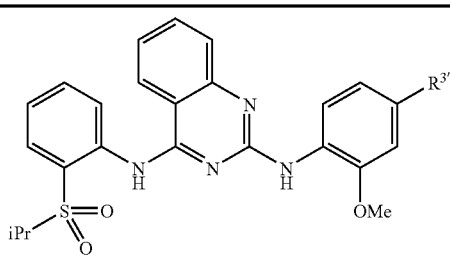
| No | —R³' |
|---|---|
| I1 |  |
| I2 |  |
| I3 |  |
| I4 | |
| I5 | |
TABLE 72-continued
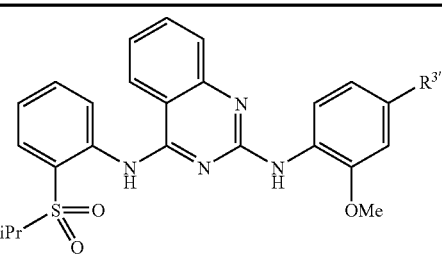
| No | —R³' |
|---|---|
| I6 | 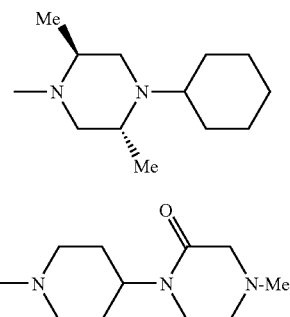 |
| I7 | |
| I8 | 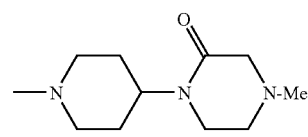 |
| I9 | |
| I10 | 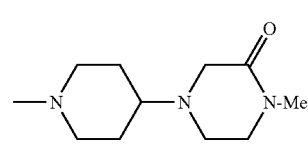 |
| I11 | |
| I12 | 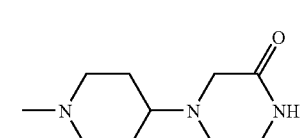 |
| I13 | 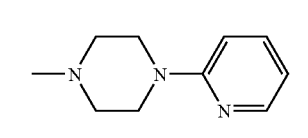 |
| I14 | 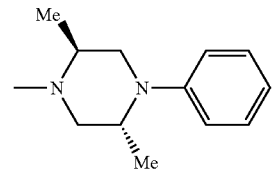 |

TABLE 72-continued

[Structure: quinazoline core with 2-(iPr-sulfonyl)phenylamino at 4-position and 2-methoxy-4-R3'-phenylamino at 2-position]

| No | —R3' |
|---|---|
| I15 | (2S,5R)-2,5-dimethyl-4-methyl-1-(pyridin-2-yl)piperazin-1-yl |
| I16 | morpholin-4-yl |
| I17 | piperidin-1-yl |
| I18 | pyrrolidin-1-yl |
| I19 | (2S,5R)-2,5-dimethyl-4-methylpiperazin-1-yl (N-Me on N4) |
| I20 | (2S,5R)-2,5-dimethylpiperazin-1-yl |
| I21 | 4-methyl-1-methyl-3-oxopiperazin-1-yl |
| I22 | 4-methyl-3-oxopiperazin-1-yl |
| I23 | 4-(azetidin-1-yl)-1-methylpiperidin-1-yl |
| I24 | 4-(3-hydroxyazetidin-1-yl)-1-methylpiperidin-1-yl |

TABLE 73

[Structure: quinazoline core with 2-(iPr-sulfonyl)phenylamino at 4-position and 2-methoxy-4-R3'-phenylamino at 2-position]

| No | —R3' |
|---|---|
| I25 | 4-(3-methoxyazetidin-1-yl)-1-methylpiperidin-1-yl |
| I26 | 4-(3-hydroxypyrrolidin-1-yl)-1-methylpiperidin-1-yl |
| I27 | 4-(3-methoxypyrrolidin-1-yl)-1-methylpiperidin-1-yl |
| I28 | 4-(3-methoxypiperidin-1-yl)-1-methylpiperidin-1-yl |
| I29 | 4-(2-oxopyrrolidin-1-yl)-1-methylpiperidin-1-yl |
| I30 | 4-(2-oxopiperidin-1-yl)-1-methylpiperidin-1-yl |
| I31 | azetidin-1-yl (N-Me) |
| I32 | 3-hydroxyazetidin-1-yl (N-Me) |
| I33 | 4-hydroxypiperidin-1-yl (N-Me) |
| I34 | 4-methoxypiperidin-1-yl (N-Me) |
| I35 | 3-(methylamino)azetidin-1-yl |

TABLE 73-continued
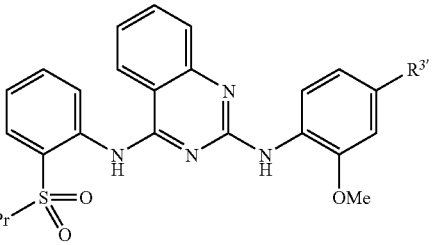
| No | —R³' |
|---|---|
| I36 | 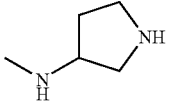 |
| I37 | 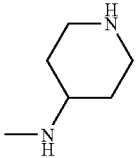 |
| I38 | 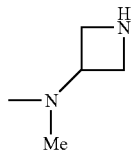 |
| I39 | 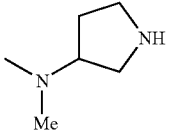 |
| I40 | 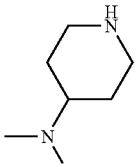 |
| I41 | 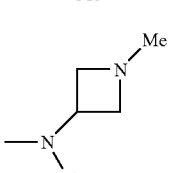 |
| I42 | 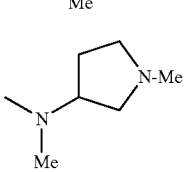 |
| I43 | 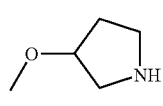 |
| I44 | 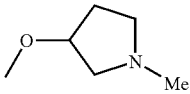 |
TABLE 73-continued
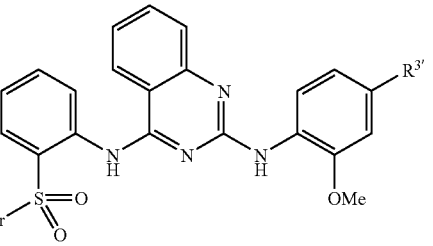
| No | —R³' |
|---|---|
| I45 | 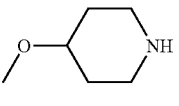 |
| I46 | 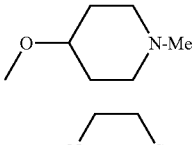 |
| I47 | 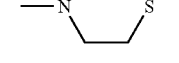 |
| I48 | 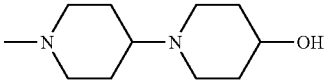 |
TABLE 74
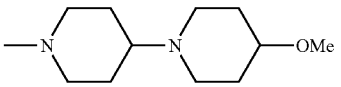
| No | —R³' |
|---|---|
| I49 |  |
| I50 |  |
| I51 | 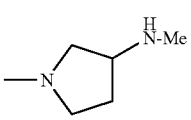 |
| I52 | 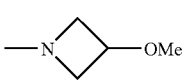 |
| I53 | |

TABLE 74-continued

[Structure: quinazoline with 2-(iPrSO2)phenyl-NH at 4-position and (4-R3'-2-methoxyphenyl)-NH at 2-position]

| No | —R3' |
|---|---|
| I54 | 1-methylpyrrolidin-3-ol (3-OH) |
| I55 | 1-methyl-3-methoxypyrrolidine |
| I56 | 1-methylazetidin-3-yl(methyl)amino |
| I57 | 1-methyl-3-aminopyrrolidine |
| I58 | (1-methylazetidin-3-yl)amino |
| I59 | (1-methylpyrrolidin-3-yl)(methyl)amino... N-H, N-Me |
| I60 | (1-methylpiperidin-4-yl)amino |
| I61 | 1-methyl-3-(dimethylamino)azetidine |
| I62 | 1-methyl-3-(dimethylamino)pyrrolidine |

TABLE 74-continued

[Same core structure]

| No | —R3' |
|---|---|
| I63 | 1-methyl-4-(dimethylamino)piperidine |
| I64 | 3-methoxyazetidine (NH) |
| I65 | 1-methyl-3-methoxyazetidine |
| I66 | 1-methyl-4-aminopiperidine |
| I67 | (1-methylpiperidin-4-yl)(methyl)amino |
| I68 | 1-methylthiomorpholine 1,1-dioxide |
| I69 | 1-methyl-4-(dimethylamino)piperidine |
| I70 | 1-methyl-3-aminopiperidine |
| I71 | (1-methylpiperidin-3-yl)(methyl)amino |
| I72 | 1-methyl-3-(dimethylamino)piperidine |

TABLE 75

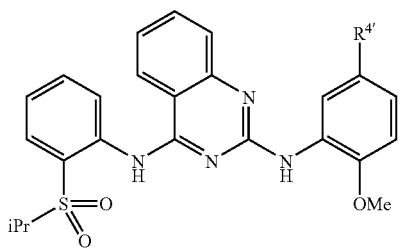

| No | —R4' |
|---|---|
| J1 | N-methylpiperidin-4-yl morpholine |
| J2 | N-methylpiperidin-4-yl piperidine |
| J3 | N-methylpiperidin-4-yl pyrrolidine |
| J4 | N-methylpiperidin-4-yl (2S,5R)-2,5-dimethyl-N'-methylpiperazine |
| J5 | N-methylpiperidin-4-yl (2S,5R)-2,5-dimethylpiperazine |
| J6 | N-methylpiperazin-4-yl N-methylpiperidine |
| J7 | N-methylpiperazin-4-yl cyclohexane |
| J8 | N-methylpiperazin-4-yl phenyl |
| J9 | (2S,5R)-2,5-dimethyl-N-methylpiperazin-4-yl cyclohexane |
| J10 | N-methylpiperidin-4-yl N'-methyl-2-oxopiperazine |

TABLE 75-continued

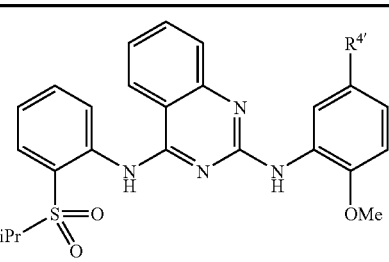

| No | —R4' |
|---|---|
| J11 | N-methylpiperidin-4-yl N'-methyl-3-oxopiperazine |
| J12 | N-methylpiperidin-4-yl 3-oxopiperazine |
| J13 | N-methylpiperazin-4-yl 2-pyridyl |
| J14 | (2S,5R)-2,5-dimethyl-N-methylpiperazin-4-yl phenyl |
| J15 | (2S,5R)-2,5-dimethyl-N-methylpiperazin-4-yl 2-pyridyl |
| J16 | morpholine |
| J17 | piperidine |
| J18 | pyrrolidine |
| J19 | (2S,5R)-2,5-dimethyl-N,N'-dimethylpiperazine |

TABLE 75-continued

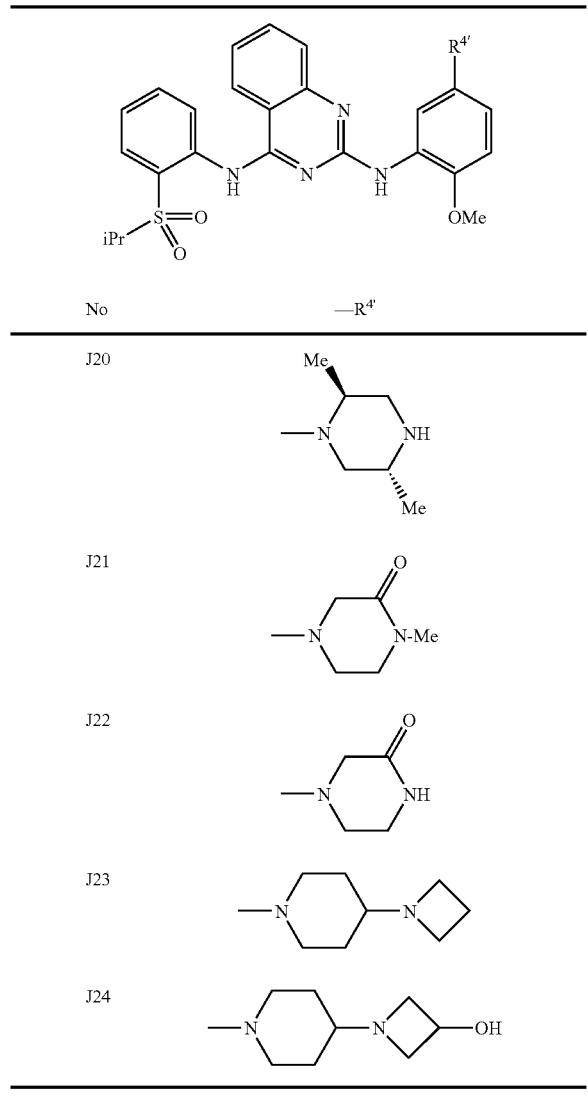

| No | —R4' |
|---|---|
| J20 | (2,5-dimethylpiperazin-1-yl, Me groups) |
| J21 | 4-methyl-1-methyl-piperazin-2-one |
| J22 | 4-methylpiperazin-2-one |
| J23 | 1-(1-methylpiperidin-4-yl)azetidine |
| J24 | 1-(1-methylpiperidin-4-yl)azetidin-3-ol |

TABLE 76

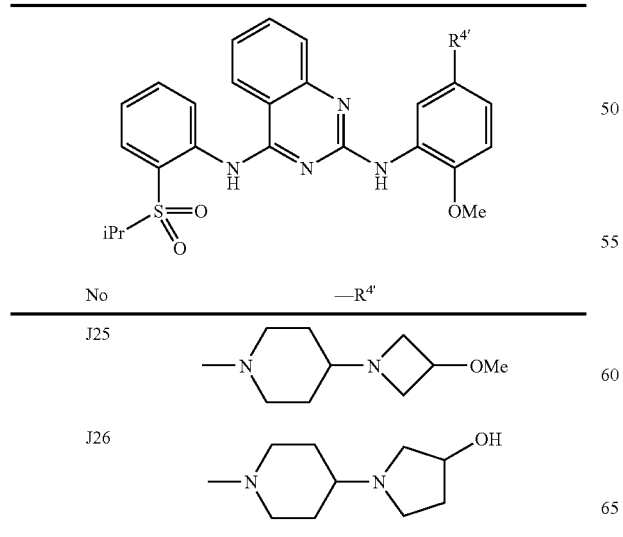

| No | —R4' |
|---|---|
| J25 | 1-(1-methylpiperidin-4-yl)-3-methoxyazetidine |
| J26 | 1-(1-methylpiperidin-4-yl)pyrrolidin-3-ol |
| J27 | 1-(1-methylpiperidin-4-yl)-3-methoxypyrrolidine |
| J28 | 1-(1-methylpiperidin-4-yl)-3-methoxypiperidine |
| J29 | 1-(1-methylpiperidin-4-yl)pyrrolidin-2-one |
| J30 | 1-(1-methylpiperidin-4-yl)piperidin-2-one |
| J31 | 1-methylazetidine |
| J32 | 1-methylazetidin-3-ol |
| J33 | 1-methylpiperidin-4-ol |
| J34 | 1-methyl-4-methoxypiperidine |
| J35 | N-methylazetidin-3-amine |
| J36 | N-methylpyrrolidin-3-amine |
| J37 | N-methylpiperidin-4-amine |

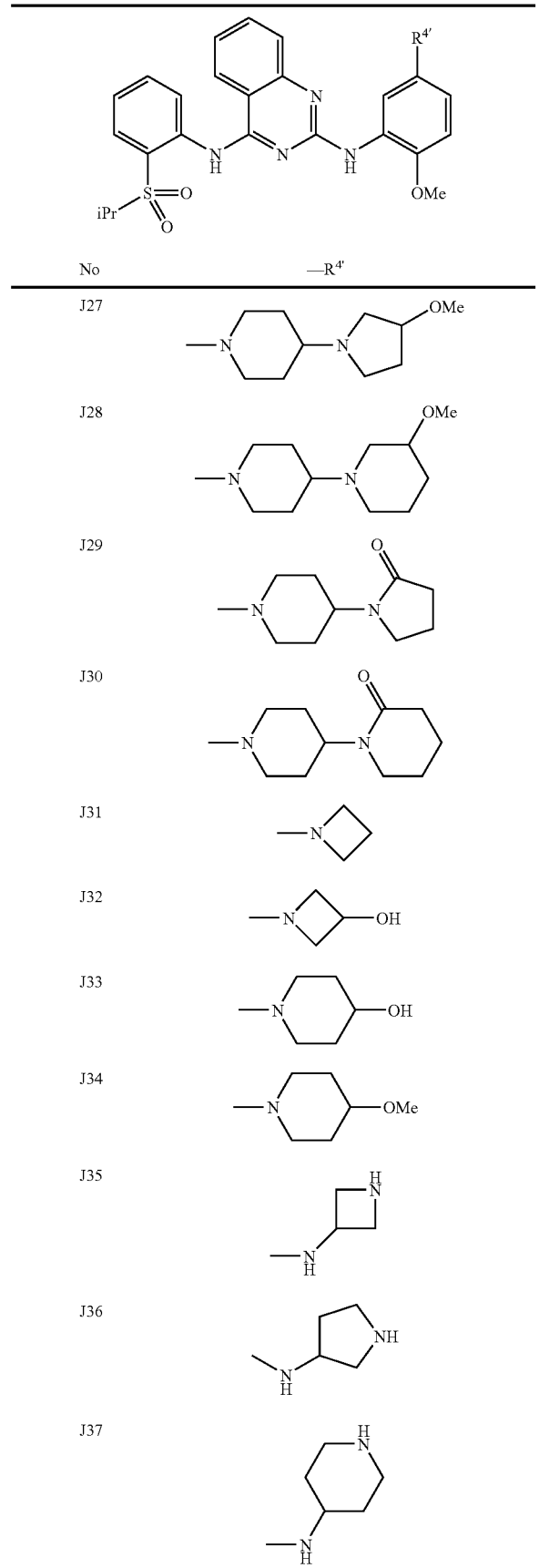

TABLE 76-continued
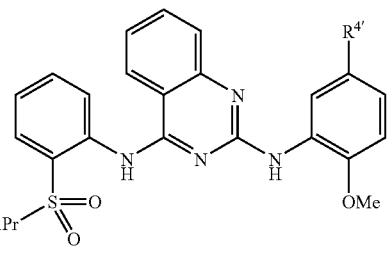
| No | —R⁴' |
|---|---|
| J38 | 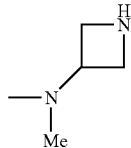 |
| J39 | 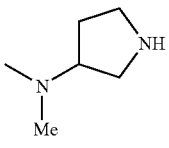 |
| J40 | 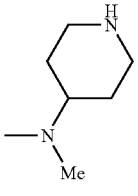 |
| J41 | 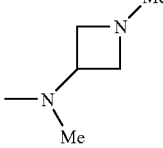 |
| J42 | 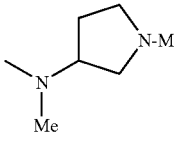 |
| J43 | 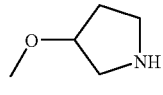 |
| J44 | 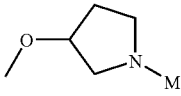 |
| J45 | 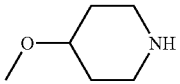 |
| J46 | 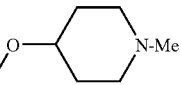 |
| J47 | 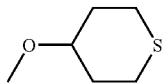 |
TABLE 76-continued
| No | —R⁴' |
|---|---|
| J48 | 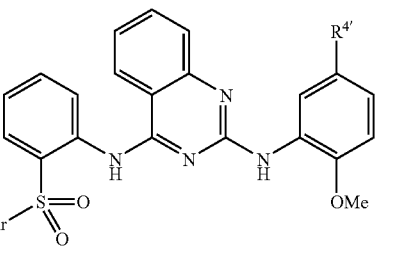 |
TABLE 77
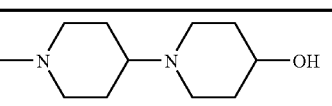
| No | —R⁴' |
|---|---|
| J49 | 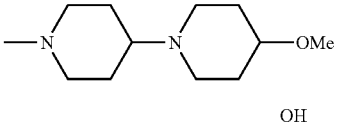 |
| J50 | 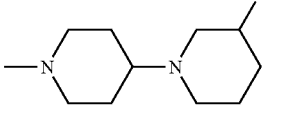 |
| J51 | 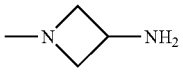 |
| J52 | 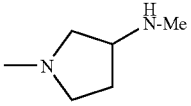 |
| J53 | 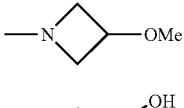 |
| J54 | 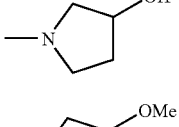 |
| J55 | 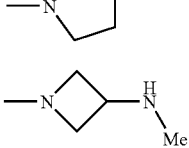 |
| J56 |  |

TABLE 77-continued
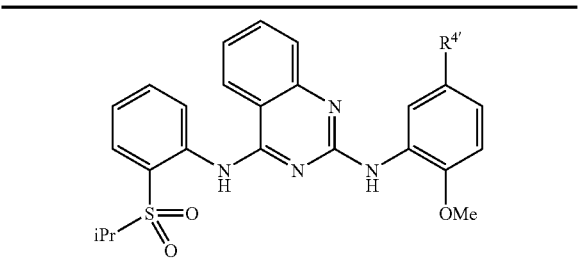
| No | —R⁴' |
|---|---|
| J57 | 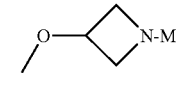 |
| J58 | 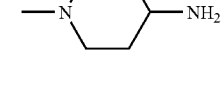 |
| J59 | 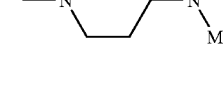 |
| J60 | 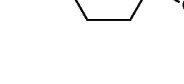 |
| J61 |  |
| J62 | 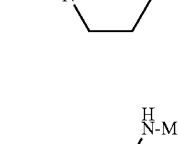 |
| J63 | 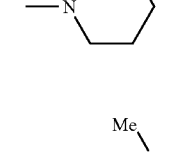 |
| J64 | 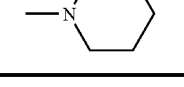 |
TABLE 77-continued
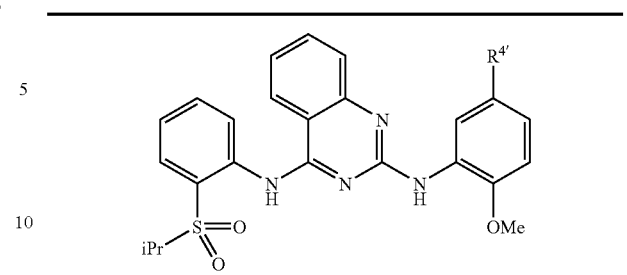
| No | —R⁴' |
|---|---|
| J65 | |
| J66 | |
| J67 | |
| J68 | |
| J69 | |
| J70 | |
| J71 | |
| J72 | |

TABLE 78

| No | —R$^{1a'}$ | —R$^{1b'}$ | —R$^{1c'}$ | —R$^{1d'}$ | —R$^{2'}$ | —R$^{A'}$ |
|---|---|---|---|---|---|---|
| K1 | —H | —H | —H | —H | —F | —S(=O)$_2$iPr |
| K2 | —H | —H | —H | —H | —Cl | —S(=O)$_2$iPr |
| K3 | —H | —H | —H | —H | —Br | —S(=O)$_2$iPr |
| K4 | —H | —H | —H | —H | —OEt | —S(=O)$_2$iPr |
| K5 | —H | —H | —H | —H | —OiPr | —S(=O)$_2$iPr |
| K6 | —H | —H | —H | —H | —CF$_3$ | —S(=O)$_2$iPr |
| K7 | —H | —H | —H | —H | —CN | —S(=O)$_2$iPr |
| K8 | —H | —H | —H | —H | Me | —S(=O)$_2$iPr |
| K9 | —H | —H | —H | —H | Et | —S(=O)$_2$iPr |
| K10 | —H | —H | —H | —H | —SMe | —S(=O)$_2$iPr |
| K11 | —H | —H | —H | —H | —OCF$_3$ | —S(=O)$_2$iPr |
| K12 | —F | —H | —H | —H | —OMe | —S(=O)$_2$iPr |
| K13 | —H | —F | —H | —H | —OMe | —S(=O)$_2$iPr |
| K14 | —H | —H | —F | —H | —OMe | —S(=O)$_2$iPr |
| K15 | —H | —H | —H | —F | —OMe | —S(=O)$_2$iPr |
| K16 | —Cl | —H | —H | —H | —OMe | —S(=O)$_2$iPr |
| K17 | —H | —Cl | —H | —H | —OMe | —S(=O)$_2$iPr |
| K18 | —H | —H | —Cl | —H | —OMe | —S(=O)$_2$iPr |
| K19 | —H | —H | —H | —Cl | —OMe | —S(=O)$_2$iPr |
| K20 | —Br | —H | —H | —H | —OMe | —S(=O)$_2$iPr |
| K21 | —H | —Br | —H | —H | —OMe | —S(=O)$_2$iPr |
| K22 | —H | —H | —Br | —H | —OMe | —S(=O)$_2$iPr |
| K23 | —H | —H | —H | —Br | —OMe | —S(=O)$_2$iPr |
| K24 | Me | —H | —H | —H | —OMe | —S(=O)$_2$iPr |
| K25 | —H | Me | —H | —H | —OMe | —S(=O)$_2$iPr |
| K26 | —H | —H | Me | —H | —OMe | —S(=O)$_2$iPr |
| K27 | —H | —H | —H | Me | —OMe | —S(=O)$_2$iPr |
| K28 | —OMe | —H | —H | —H | —OMe | —S(=O)$_2$iPr |
| K29 | —H | —OMe | —H | —H | —OMe | —S(=O)$_2$iPr |
| K30 | —H | —H | —OMe | —H | —OMe | —S(=O)$_2$iPr |
| K31 | —H | —H | —H | —OMe | —OMe | —S(=O)$_2$iPr |
| K32 | —CN | —H | —H | —H | —OMe | —S(=O)2iPr |
| K33 | —H | —CN | —H | —H | —OMe | —S(=O)2iPr |
| K34 | —H | —H | —CN | —H | —OMe | —S(=O)2iPr |
| K35 | —H | —H | —H | —CN | —OMe | —S(=O)2iPr |

TABLE 79

| No | —R$^{1a'}$ | —R$^{1b'}$ | —R$^{1c'}$ | —R$^{1d'}$ | —R$^{2'}$ | —R$^{A'}$ |
|---|---|---|---|---|---|---|
| K36 | —CF$_3$ | —H | —H | —H | —OMe | —S(=O)$_2$iPr |
| K37 | —H | —CF$_3$ | —H | —H | —OMe | —S(=O)$_2$iPr |
| K38 | —H | —H | —CF$_3$ | —H | —OMe | —S(=O)$_2$iPr |
| K39 | —H | —H | —H | —CF$_3$ | —OMe | —S(=O)$_2$iPr |
| K40 | —SMe | —H | —H | —H | —OMe | —S(=O)$_2$iPr |
| K41 | —H | —SMe | —H | —H | —OMe | —S(=O)$_2$iPr |
| K42 | —H | —H | —SMe | —H | —OMe | —S(=O)$_2$iPr |

TABLE 79-continued

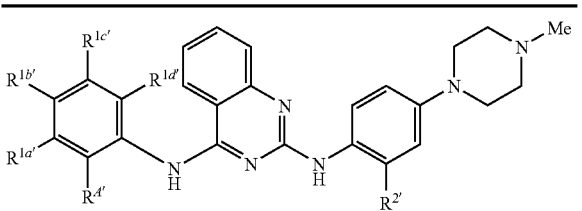

| No | —R$^{1a'}$ | —R$^{1b'}$ | —R$^{1c'}$ | —R$^{1d'}$ | —R$^{2'}$ | —R$^{A'}$ |
|---|---|---|---|---|---|---|
| K43 | —H | —H | —H | —SMe | —OMe | —S(=O)$_2$iPr |
| K44 | —OCF$_3$ | —H | —H | —H | —OMe | —S(=O)$_2$iPr |
| K45 | —H | —OCF$_3$ | —H | —H | —OMe | —S(=O)$_2$iPr |
| K46 | —H | —H | —OCF$_3$ | —H | —OMe | —S(=O)$_2$iPr |
| K47 | —H | —H | —H | —OCF$_3$ | —OMe | —S(=O)$_2$iPr |
| K48 | —H | —H | —H | —H | —OMe | —S(=O)$_2$Et |
| K49 | —H | —H | —H | —H | —OMe | —S(=O)$_2$Me |
| K50 | —H | —H | —H | —H | —OMe | —S(=O)$_2$NHMe |
| K51 | —H | —H | —H | —H | —OMe | —S(=O)$_2$NMe$_2$ |
| K52 | —H | —H | —H | —H | —OMe | —C(=O)NHMe |
| K53 | —H | —H | —H | —H | —OMe | —C(=O)NMe$_2$ |
| K54 | —H | —H | —H | —H | —OMe | —C(=O)iPr |
| K55 | —H | —H | —H | —H | —OMe | —C(=O)Et |
| K56 | —H | —H | —H | —H | —OMe | —F |
| K57 | —H | —H | —H | —H | —OMe | —Cl |
| K58 | —H | —H | —H | —H | —OMe | —Br |
| K59 | —H | —H | —H | —H | —OMe | —OMe |
| K60 | —H | —H | —H | —H | —OMe | —OEt |
| K61 | —H | —H | —H | —H | —OMe | —OiPr |
| K62 | —H | —H | —H | —H | —OMe | —OCF$_3$ |
| K63 | —H | —H | —H | —H | —OMe | —SMe |
| K64 | —H | —H | —H | —H | —OMe | —SEt |
| K65 | —H | —H | —H | —H | —OMe | —SiPr |
| K66 | —H | —H | —H | —H | —OMe | Me |
| K67 | —H | —H | —H | —H | —OMe | Et |
| K68 | —H | —H | —H | —H | —OMe | iPr |
| K69 | —H | —H | —H | —H | —OMe | —CF$_3$ |

TABLE 80

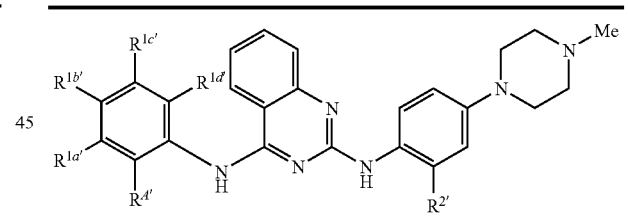

| No | —R$^{1a'}$ | —R$^{1b'}$ | —R$^{1c'}$ | —R$^{1d'}$ | —R$^{2'}$ | —R$^{A'}$ |
|---|---|---|---|---|---|---|
| L1 | —H | —H | —H | —H | —F | —S(=O)$_2$iPr |
| L2 | —H | —H | —H | —H | —Cl | —S(=O)$_2$iPr |
| L3 | —H | —H | —H | —H | —Br | —S(=O)$_2$iPr |
| L4 | —H | —H | —H | —H | —OEt | —S(=O)$_2$iPr |
| L5 | —H | —H | —H | —H | —OiPr | —S(=O)$_2$iPr |
| L6 | —H | —H | —H | —H | —CF$_3$ | —S(=O)$_2$iPr |
| L7 | —H | —H | —H | —H | —CN | —S(=O)$_2$iPr |
| L8 | —H | —H | —H | —H | Me | —S(=O)$_2$iPr |
| L9 | —H | —H | —H | —H | Et | —S(=O)$_2$iPr |
| L10 | —H | —H | —H | —H | —SMe | —S(=O)$_2$iPr |
| L11 | —H | —H | —H | —H | —OCF$_3$ | —S(=O)$_2$iPr |
| L12 | —F | —H | —H | —H | —OMe | —S(=O)$_2$iPr |
| L13 | —H | —F | —H | —H | —OMe | —S(=O)$_2$iPr |
| L14 | —H | —H | —F | —H | —OMe | —S(=O)$_2$iPr |
| L15 | —H | —H | —H | —F | —OMe | —S(=O)$_2$iPr |
| L16 | —Cl | —H | —H | —H | —OMe | —S(=O)$_2$iPr |
| L17 | —H | —Cl | —H | —H | —OMe | —S(=O)$_2$iPr |
| L18 | —H | —H | —Cl | —H | —OMe | —S(=O)$_2$iPr |
| L19 | —H | —H | —H | —Cl | —OMe | —S(=O)$_2$iPr |
| L20 | —Br | —H | —H | —H | —OMe | —S(=O)$_2$iPr |
| L21 | —H | —Br | —H | —H | —OMe | —S(=O)$_2$iPr |
| L22 | —H | —H | —Br | —H | —OMe | —S(=O)$_2$iPr |
| L23 | —H | —H | —H | —Br | —OMe | —S(=O)$_2$iPr |
| L24 | Me | —H | —H | —H | —OMe | —S(=O)$_2$iPr |
| L25 | —H | Me | —H | —H | —OMe | —S(=O)$_2$iPr |
| L26 | —H | —H | Me | —H | —OMe | —S(=O)$_2$iPr |
| L27 | —H | —H | —H | Me | —OMe | —S(=O)$_2$iPr |
| L28 | —OMe | —H | —H | —H | —OMe | —S(=O)$_2$iPr |
| L29 | —H | —OMe | —H | —H | —OMe | —S(=O)$_2$iPr |
| L30 | —H | —H | —OMe | —H | —OMe | —S(=O)$_2$iPr |
| L31 | —H | —H | —H | —OMe | —OMe | —S(=O)$_2$iPr |
| L32 | —CN | —H | —H | —H | —OMe | —S(=O)2iPr |
| L33 | —H | —CN | —H | —H | —OMe | —S(=O)2iPr |
| L34 | —H | —H | —CN | —H | —OMe | —S(=O)2iPr |
| L35 | —H | —H | —H | —CN | —OMe | —S(=O)2iPr |

TABLE 81

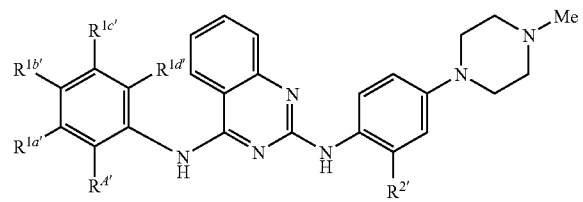

| No | —R1a' | —R1b' | —R1c' | —R1d' | —R2' | —RA' |
|---|---|---|---|---|---|---|
| L36 | —CF3 | —H | —H | —H | —OMe | —S(=O)2iPr |
| L37 | —H | —CF3 | —H | —H | —OMe | —S(=O)2iPr |
| L38 | —H | —H | —CF3 | —H | —OMe | —S(=O)2iPr |
| L39 | —H | —H | —H | —CF3 | —OMe | —S(=O)2iPr |
| L40 | —SMe | —H | —H | —H | —OMe | —S(=O)2iPr |
| L41 | —H | —SMe | —H | —H | —OMe | —S(=O)2iPr |
| L42 | —H | —H | —SMe | —H | —OMe | —S(=O)2iPr |
| L43 | —H | —H | —H | —SMe | —OMe | —S(=O)2iPr |
| L44 | —OCF3 | —H | —H | —H | —OMe | —S(=O)2iPr |
| L45 | —H | —OCF3 | —H | —H | —OMe | —S(=O)2iPr |
| L46 | —H | —H | —OCF3 | —H | —OMe | —S(=O)2iPr |
| L47 | —H | —H | —H | —OCF3 | —OMe | —S(=O)2iPr |
| L48 | —H | —H | —H | —H | —OMe | —S(=O)2Et |
| L49 | —H | —H | —H | —H | —OMe | —S(=O)2Me |
| L50 | —H | —H | —H | —H | —OMe | —S(=O)2NHMe |
| L51 | —H | —H | —H | —H | —OMe | —S(=O)2NMe2 |
| L52 | —H | —H | —H | —H | —OMe | —C(=O)NHMe |
| L53 | —H | —H | —H | —H | —OMe | —C(=O)NMe2 |
| L54 | —H | —H | —H | —H | —OMe | —C(=O)iPr |
| L55 | —H | —H | —H | —H | —OMe | —C(=O)Et |
| L56 | —H | —H | —H | —H | —OMe | —F |
| L57 | —H | —H | —H | —H | —OMe | —Cl |
| L58 | —H | —H | —H | —H | —OMe | —Br |
| L59 | —H | —H | —H | —H | —OMe | —OMe |
| L60 | —H | —H | —H | —H | —OMe | —OEt |
| L61 | —H | —H | —H | —H | —OMe | —OiPr |
| L62 | —H | —H | —H | —H | —OMe | —OCF3 |
| L63 | —H | —H | —H | —H | —OMe | —SMe |
| L64 | —H | —H | —H | —H | —OMe | —SEt |
| L65 | —H | —H | —H | —H | —OMe | —SiPr |
| L66 | —H | —H | —H | —H | —OMe | Me |
| L67 | —H | —H | —H | —H | —OMe | Et |
| L68 | —H | —H | —H | —H | —OMe | iPr |
| L69 | —H | —H | —H | —H | —OMe | —CF3 |

TABLE 82

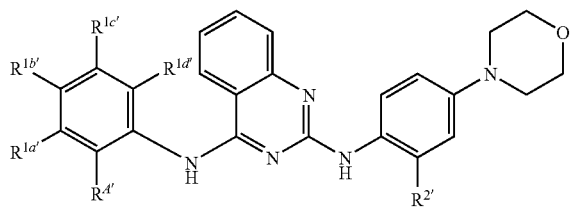

| No | —R1a' | —R1b' | —R1c' | —R1d' | —R2' | —RA' |
|---|---|---|---|---|---|---|
| M1 | —H | —H | —H | —H | —F | —S(=O)2iPr |
| M2 | —H | —H | —H | —H | —Cl | —S(=O)2iPr |
| M3 | —H | —H | —H | —H | —Br | —S(=O)2iPr |
| M4 | —H | —H | —H | —H | —OEt | —S(=O)2iPr |
| M5 | —H | —H | —H | —H | —OiPr | —S(=O)2iPr |
| M6 | —H | —H | —H | —H | —CF3 | —S(=O)2iPr |
| M7 | —H | —H | —H | —H | —CN | —S(=O)2iPr |
| M8 | —H | —H | —H | —H | Me | —S(=O)2iPr |
| M9 | —H | —H | —H | —H | Et | —S(=O)2iPr |
| M10 | —H | —H | —H | —H | —SMe | —S(=O)2iPr |
| M11 | —H | —H | —H | —H | —OCF3 | —S(=O)2iPr |
| M12 | —F | —H | —H | —H | —OMe | —S(=O)2iPr |
| M13 | —H | —F | —H | —H | —OMe | —S(=O)2iPr |
| M14 | —H | —H | —F | —H | —OMe | —S(=O)2iPr |
| M15 | —H | —H | —H | —F | —OMe | —S(=O)2iPr |

TABLE 82-continued

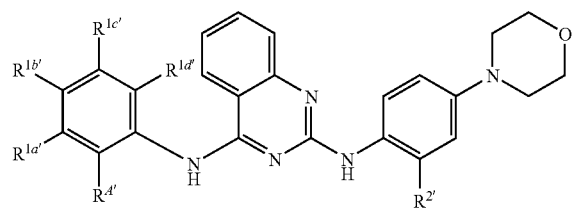

| No | —R1a' | —R1b' | —R1c' | —R1d' | —R2' | —RA' |
|---|---|---|---|---|---|---|
| M16 | —Cl | —H | —H | —H | —OMe | —S(=O)2iPr |
| M17 | —H | —Cl | —H | —H | —OMe | —S(=O)2iPr |
| M18 | —H | —H | —Cl | —H | —OMe | —S(=O)2iPr |
| M19 | —H | —H | —H | —Cl | —OMe | —S(=O)2iPr |
| M20 | —Br | —H | —H | —H | —OMe | —S(=O)2iPr |
| M21 | —H | —Br | —H | —H | —OMe | —S(=O)2iPr |
| M22 | —H | —H | —Br | —H | —OMe | —S(=O)2iPr |
| M23 | —H | —H | —H | —Br | —OMe | —S(=O)2iPr |
| M24 | Me | —H | —H | —H | —OMe | —S(=O)2iPr |
| M25 | —H | Me | —H | —H | —OMe | —S(=O)2iPr |
| M26 | —H | —H | Me | —H | —OMe | —S(=O)2iPr |
| M27 | —H | —H | —H | Me | —OMe | —S(=O)2iPr |
| M28 | —OMe | —H | —H | —H | —OMe | —S(=O)2iPr |
| M29 | —H | —OMe | —H | —H | —OMe | —S(=O)2iPr |
| M30 | —H | —H | —OMe | —H | —OMe | —S(=O)2iPr |
| M31 | —H | —H | —H | —OMe | —OMe | —S(=O)2iPr |
| M32 | —CN | —H | —H | —H | —OMe | —S(=O)2iPr |
| M33 | —H | —CN | —H | —H | —OMe | —S(=O)2iPr |
| M34 | —H | —H | —CN | —H | —OMe | —S(=O)2iPr |
| M35 | —H | —H | —H | —CN | —OMe | —S(=O)2iPr |

TABLE 83

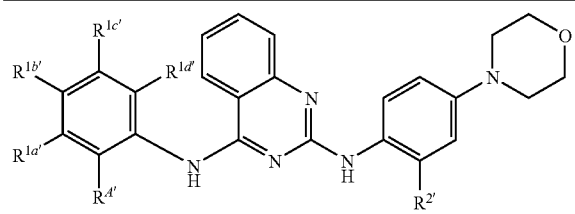

| No | —R1a' | —R1b' | —R1c' | —R1d' | —R2' | —RA' |
|---|---|---|---|---|---|---|
| M36 | —CF3 | —H | —H | —H | —OMe | —S(=O)2iPr |
| M37 | —H | —CF3 | —H | —H | —OMe | —S(=O)2iPr |
| M38 | —H | —H | —CF3 | —H | —OMe | —S(=O)2iPr |
| M39 | —H | —H | —H | —CF3 | —OMe | —S(=O)2iPr |
| M40 | —SMe | —H | —H | —H | —OMe | —S(=O)2iPr |
| M41 | —H | —SMe | —H | —H | —OMe | —S(=O)2iPr |
| M42 | —H | —H | —SMe | —H | —OMe | —S(=O)2iPr |
| M43 | —H | —H | —H | —SMe | —OMe | —S(=O)2iPr |
| M44 | —OCF3 | —H | —H | —H | —OMe | —S(=O)2iPr |
| M45 | —H | —OCF3 | —H | —H | —OMe | —S(=O)2iPr |
| M46 | —H | —H | —OCF3 | —H | —OMe | —S(=O)2iPr |
| M47 | —H | —H | —H | —OCF3 | —OMe | —S(=O)2iPr |
| M48 | —H | —H | —H | —H | —OMe | —S(=O)2Et |
| M49 | —H | —H | —H | —H | —OMe | —S(=O)2Me |
| M50 | —H | —H | —H | —H | —OMe | —S(=O)2NHMe |
| M51 | —H | —H | —H | —H | —OMe | —S(=O)2NMe2 |
| M52 | —H | —H | —H | —H | —OMe | —C(=O)NHMe |
| M53 | —H | —H | —H | —H | —OMe | —C(=O)NMe2 |
| M54 | —H | —H | —H | —H | —OMe | —C(=O)iPr |
| M55 | —H | —H | —H | —H | —OMe | —C(=O)Et |
| M56 | —H | —H | —H | —H | —OMe | —F |
| M57 | —H | —H | —H | —H | —OMe | —Cl |
| M58 | —H | —H | —H | —H | —OMe | —Br |
| M59 | —H | —H | —H | —H | —OMe | —OMe |
| M60 | —H | —H | —H | —H | —OMe | —OEt |
| M61 | —H | —H | —H | —H | —OMe | —OiPr |
| M62 | —H | —H | —H | —H | —OMe | —OCF3 |
| M63 | —H | —H | —H | —H | —OMe | —SMe |

TABLE 83-continued

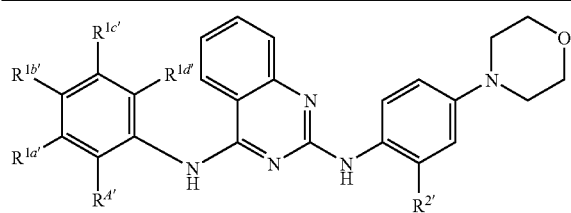

| No | —R1a' | —R1b' | —R1c' | —R1d' | —R2' | —RA' |
|---|---|---|---|---|---|---|
| M64 | —H | —H | —H | —H | —OMe | —SEt |
| M65 | —H | —H | —H | —H | —OMe | —SiPr |
| M66 | —H | —H | —H | —H | —OMe | Me |

TABLE 83-continued

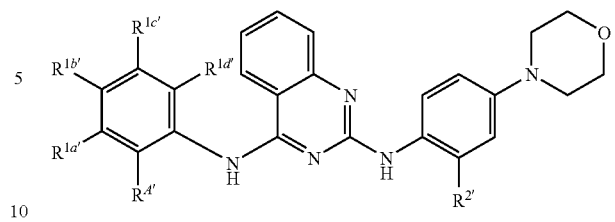

| No | —R1a' | —R1b' | —R1c' | —R1d' | —R2' | —RA' |
|---|---|---|---|---|---|---|
| M67 | —H | —H | —H | —H | —OMe | Et |
| M68 | —H | —H | —H | —H | —OMe | iPr |
| M69 | —H | —H | —H | —H | —OMe | —CF3 |

TABLE 84

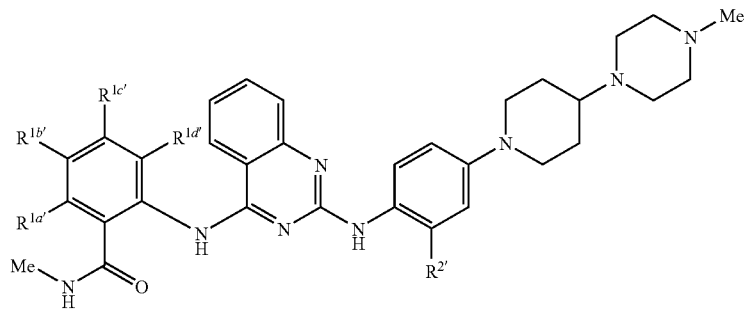

| No | —R1a' | —R1b' | —R1c' | —R1d' | —R2' |
|---|---|---|---|---|---|
| N1  | —H  | —H  | —H  | —H  | —F |
| N2  | —H  | —H  | —H  | —H  | —Cl |
| N3  | —H  | —H  | —H  | —H  | —Br |
| N4  | —H  | —H  | —H  | —H  | —OEt |
| N5  | —H  | —H  | —H  | —H  | —OiPr |
| N6  | —H  | —H  | —H  | —H  | —CF3 |
| N7  | —H  | —H  | —H  | —H  | —CN |
| N8  | —H  | —H  | —H  | —H  | Me |
| N9  | —H  | —H  | —H  | —H  | Et |
| N10 | —H  | —H  | —H  | —H  | —SMe |
| N11 | —H  | —H  | —H  | —H  | —OCF3 |
| N12 | —F  | —H  | —H  | —H  | —OMe |
| N13 | —H  | —F  | —H  | —H  | —OMe |
| N14 | —H  | —H  | —F  | —H  | —OMe |
| N15 | —H  | —H  | —H  | —F  | —OMe |
| N16 | —Cl | —H  | —H  | —H  | —OMe |
| N17 | —H  | —Cl | —H  | —H  | —OMe |
| N18 | —H  | —H  | —Cl | —H  | —OMe |
| N19 | —H  | —H  | —H  | —Cl | —OMe |
| N20 | —Br | —H  | —H  | —H  | —OMe |
| N21 | —H  | —Br | —H  | —H  | —OMe |
| N22 | —H  | —H  | —Br | —H  | —OMe |
| N23 | —H  | —H  | —H  | —Br | —OMe |
| N24 | Me  | —H  | —H  | —H  | —OMe |
| N25 | —H  | Me  | —H  | —H  | —OMe |
| N26 | —H  | —H  | Me  | —H  | —OMe |
| N27 | —H  | —H  | —H  | Me  | —OMe |

TABLE 85

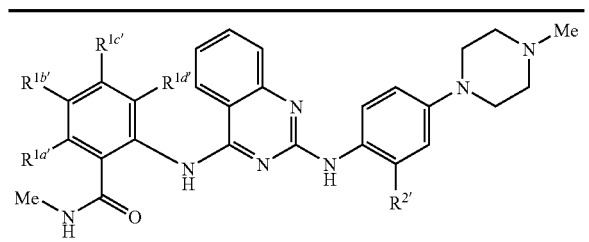

| No | —R1a' | —R1b' | —R1c' | —R1d' | —R2' |
|---|---|---|---|---|---|
| N28 | —OMe | —H | —H | —H | —OMe |
| N29 | —H | —OMe | —H | —H | —OMe |
| N30 | —H | —H | —OMe | —H | —OMe |
| N31 | —H | —H | —H | —OMe | —OMe |
| N32 | —CN | —H | —H | —H | —OMe |
| N33 | —H | —CN | —H | —H | —OMe |
| N34 | —H | —H | —CN | —H | —OMe |
| N35 | —H | —H | —H | —CN | —OMe |
| N36 | —CF3 | —H | —H | —H | —OMe |
| N37 | —H | —CF3 | —H | —H | —OMe |
| N38 | —H | —H | —CF3 | —H | —OMe |
| N39 | —H | —H | —H | —CF3 | —OMe |
| N40 | —SMe | —H | —H | —H | —OMe |
| N41 | —H | —SMe | —H | —H | —OMe |
| N42 | —H | —H | —SMe | —H | —OMe |
| N43 | —H | —H | —H | —SMe | —OMe |
| N44 | —OCF3 | —H | —H | —H | —OMe |
| N45 | —H | —OCF3 | —H | —H | —OMe |
| N46 | —H | —H | —OCF3 | —H | —OMe |
| N47 | —H | —H | —H | —OCF3 | —OMe |

TABLE 86

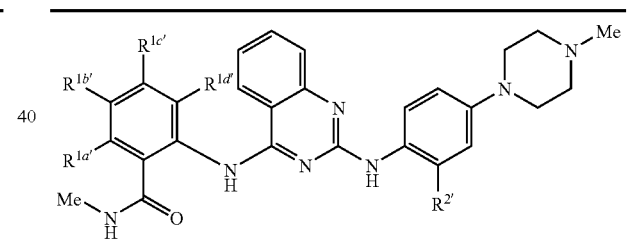

| No | —R1a' | —R1b' | —R1c' | —R1d' | —R2' |
|---|---|---|---|---|---|
| O1 | —H | —H | —H | —H | —F |
| O2 | —H | —H | —H | —H | —Cl |
| O3 | —H | —H | —H | —H | —Br |
| O4 | —H | —H | —H | —H | —OEt |
| O5 | —H | —H | —H | —H | —OiPr |
| O6 | —H | —H | —H | —H | —CF3 |
| O7 | —H | —H | —H | —H | —CN |
| O8 | —H | —H | —H | —H | Me |
| O9 | —H | —H | —H | —H | Et |
| O10 | —H | —H | —H | —H | —SMe |
| O11 | —H | —H | —H | —H | —OCF3 |
| O12 | —F | —H | —H | —H | —OMe |
| O13 | —H | —F | —H | —H | —OMe |
| O14 | —H | —H | —F | —H | —OMe |
| O15 | —H | —H | —H | —F | —OMe |
| O16 | —Cl | —H | —H | —H | —OMe |
| O17 | —H | —Cl | —H | —H | —OMe |
| O18 | —H | —H | —Cl | —H | —OMe |
| O19 | —H | —H | —H | —Cl | —OMe |
| O20 | —Br | —H | —H | —H | —OMe |
| O21 | —H | —Br | —H | —H | —OMe |
| O22 | —H | —H | —Br | —H | —OMe |
| O23 | —H | —H | —H | —Br | —OMe |
| O24 | Me | —H | —H | —H | —OMe |
| O25 | —H | Me | —H | —H | —OMe |
| O26 | —H | —H | Me | —H | —OMe |
| O27 | —H | —H | —H | Me | —OMe |

TABLE 87

| No | —R1a' | —R1b' | —R1c' | —R1d' | —R2' |
|---|---|---|---|---|---|
| O28 | —OMe | —H | —H | —H | —OMe |
| O29 | —H | —OMe | —H | —H | —OMe |

TABLE 87-continued

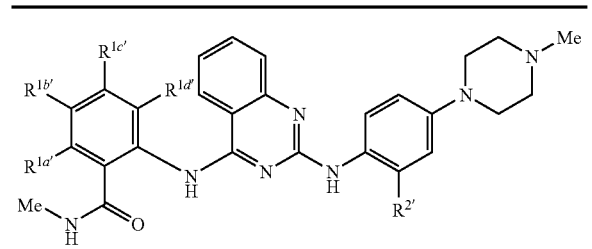

| No | —R1a' | —R1b' | —R1c' | —R1d' | —R2' |
|---|---|---|---|---|---|
| O30 | —H | —H | —OMe | —H | —OMe |
| O31 | —H | —H | —H | —OMe | —OMe |
| O32 | —CN | —H | —H | —H | —OMe |
| O33 | —H | —CN | —H | —H | —OMe |
| O34 | —H | —H | —CN | —H | —OMe |
| O35 | —H | —H | —H | —CN | —OMe |
| O36 | —CF3 | —H | —H | —H | —OMe |
| O37 | —H | —CF3 | —H | —H | —OMe |
| O38 | —H | —H | —CF3 | —H | —OMe |
| O39 | —H | —H | —H | —CF3 | —OMe |
| O40 | —SMe | —H | —H | —H | —OMe |
| O41 | —H | —SMe | —H | —H | —OMe |
| O42 | —H | —H | —SMe | —H | —OMe |
| O43 | —H | —H | —H | —SMe | —OMe |
| O44 | —OCF3 | —H | —H | —H | —OMe |
| O45 | —H | —OCF3 | —H | —H | —OMe |
| O46 | —H | —H | —OCF3 | —H | —OMe |
| O47 | —H | —H | —H | —OCF3 | —OMe |

TABLE 88

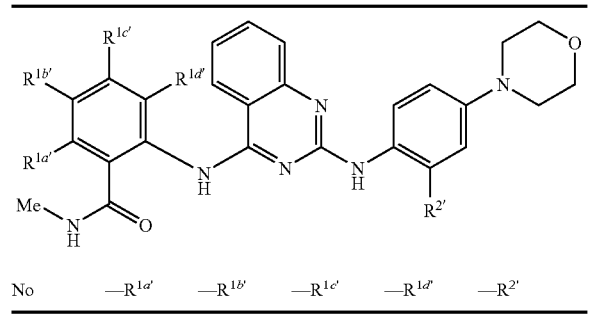

| No | —R1a' | —R1b' | —R1c' | —R1d' | —R2' |
|---|---|---|---|---|---|
| P1 | —H | —H | —H | —H | —F |
| P2 | —H | —H | —H | —H | —Cl |
| P3 | —H | —H | —H | —H | —Br |
| P4 | —H | —H | —H | —H | —OEt |
| P5 | —H | —H | —H | —H | —OiPr |
| P6 | —H | —H | —H | —H | —CF3 |
| P7 | —H | —H | —H | —H | —CN |
| P8 | —H | —H | —H | —H | Me |
| P9 | —H | —H | —H | —H | Et |
| P10 | —H | —H | —H | —H | —SMe |
| P11 | —H | —H | —H | —H | —OCF3 |
| P12 | —F | —H | —H | —H | —OMe |
| P13 | —H | —F | —H | —H | —OMe |
| P14 | —H | —H | —F | —H | —OMe |
| P15 | —H | —H | —H | —F | —OMe |

TABLE 88-continued

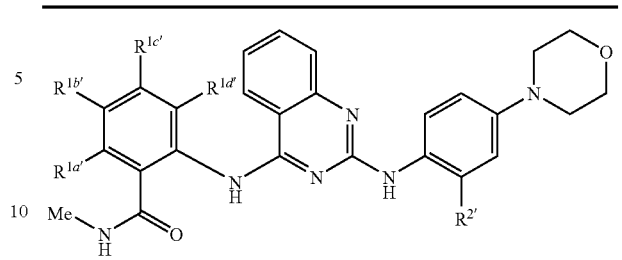

| No | —R1a' | —R1b' | —R1c' | —R1d' | —R2' |
|---|---|---|---|---|---|
| P16 | —Cl | —H | —H | —H | —OMe |
| P17 | —H | —Cl | —H | —H | —OMe |
| P18 | —H | —H | —Cl | —H | —OMe |
| P19 | —H | —H | —H | —Cl | —OMe |
| P20 | —Br | —H | —H | —H | —OMe |
| P21 | —H | —Br | —H | —H | —OMe |
| P22 | —H | —H | —Br | —H | —OMe |
| P23 | —H | —H | —H | —Br | —OMe |
| P24 | Me | —H | —H | —H | —OMe |
| P25 | —H | Me | —H | —H | —OMe |
| P26 | —H | —H | Me | —H | —OMe |
| P27 | —H | —H | —H | Me | —OMe |

TABLE 89

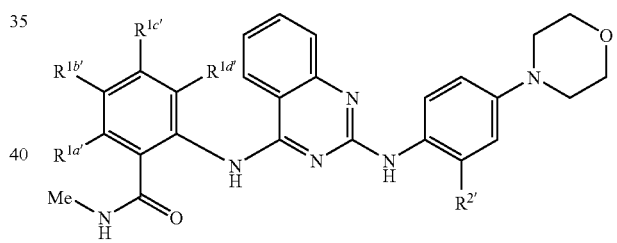

| No | —R1a' | —R1b' | —R1c' | —R1d' | —R2' |
|---|---|---|---|---|---|
| P28 | —OMe | —H | —H | —H | —OMe |
| P29 | —H | —OMe | —H | —H | —OMe |
| P30 | —H | —H | —OMe | —H | —OMe |
| P31 | —H | —H | —H | —OMe | —OMe |
| P32 | —CN | —H | —H | —H | —OMe |
| P33 | —H | —CN | —H | —H | —OMe |
| P34 | —H | —H | —CN | —H | —OMe |
| P35 | —H | —H | —H | —CN | —OMe |
| P36 | —CF3 | —H | —H | —H | —OMe |
| P37 | —H | —CF3 | —H | —H | —OMe |
| P38 | —H | —H | —CF3 | —H | —OMe |
| P39 | —H | —H | —H | —CF3 | —OMe |
| P40 | —SMe | —H | —H | —H | —OMe |
| P41 | —H | —SMe | —H | —H | —OMe |
| P42 | —H | —H | —SMe | —H | —OMe |
| P43 | —H | —H | —H | —SMe | —OMe |
| P44 | —OCF3 | —H | —H | —H | —OMe |
| P45 | —H | —OCF3 | —H | —H | —OMe |
| P46 | —H | —H | —OCF3 | —H | —OMe |
| P47 | —H | —H | —H | —OCF3 | —OMe |

TABLE 90

| No | —R$^{6a'}$ | —R$^{6b'}$ | —R$^{6c'}$ | —R$^{6d'}$ | —R$^{A'}$ |
|---|---|---|---|---|---|
| Q1 | —F | —H | —H | —H | —S(=O)$_2$iPr |
| Q2 | —H | —F | —H | —H | —S(=O)$_2$iPr |
| Q3 | —H | —H | —F | —H | —S(=O)$_2$iPr |
| Q4 | —H | —H | —H | —F | —S(=O)$_2$iPr |
| Q5 | —Cl | —H | —H | —H | —S(=O)$_2$iPr |
| Q6 | —H | —Cl | —H | —H | —S(=O)$_2$iPr |
| Q7 | —H | —H | —Cl | —H | —S(=O)$_2$iPr |
| Q8 | —H | —H | —H | —Cl | —S(=O)$_2$iPr |
| Q9 | —Br | —H | —H | —H | —S(=O)$_2$iPr |
| Q10 | —H | —Br | —H | —H | —S(=O)$_2$iPr |
| Q11 | —H | —H | —Br | —H | —S(=O)$_2$iPr |
| Q12 | —H | —H | —H | —Br | —S(=O)$_2$iPr |
| Q13 | Me | —H | —H | —H | —S(=O)$_2$iPr |
| Q14 | —H | Me | —H | —H | —S(=O)$_2$iPr |
| Q15 | —H | —H | Me | —H | —S(=O)$_2$iPr |
| Q16 | —H | —H | —H | Me | —S(=O)$_2$iPr |
| Q17 | —OMe | —H | —H | —H | —S(=O)$_2$iPr |
| Q18 | —H | —OMe | —H | —H | —S(=O)$_2$iPr |
| Q19 | —H | —H | —OMe | —H | —S(=O)$_2$iPr |
| Q20 | —H | —H | —H | —OMe | —S(=O)$_2$iPr |
| Q21 | —CN | —H | —H | —H | —S(=O)$_2$iPr |
| Q22 | —H | —CN | —H | —H | —S(=O)$_2$iPr |
| Q23 | —H | —H | —CN | —H | —S(=O)$_2$iPr |
| Q24 | —H | —H | —H | —CN | —S(=O)$_2$iPr |
| Q25 | —CF$_3$ | —H | —H | —H | —S(=O)$_2$iPr |
| Q26 | —H | —CF$_3$ | —H | —H | —S(=O)$_2$iPr |
| Q27 | —H | —H | —CF$_3$ | —H | —S(=O)$_2$iPr |
| Q28 | —H | —H | —H | —CF$_3$ | —S(=O)$_2$iPr |
| Q29 | —SMe | —H | —H | —H | —S(=O)$_2$iPr |
| Q30 | —H | —SMe | —H | —H | —S(=O)$_2$iPr |
| Q31 | —H | —H | —SMe | —H | —S(=O)$_2$iPr |
| Q32 | —H | —H | —H | —SMe | —S(=O)$_2$iPr |
| Q33 | —OCF$_3$ | —H | —H | —H | —S(=O)$_2$iPr |
| Q34 | —H | —OCF$_3$ | —H | —H | —S(=O)$_2$iPr |
| Q35 | —H | —H | —OCF$_3$ | —H | —S(=O)$_2$iPr |
| Q36 | —H | —H | —H | —OCF$_3$ | —S(=O)$_2$iPr |

TABLE 91

| No | —R$^{6a'}$ | —R$^{6b'}$ | —R$^{6c'}$ | —R$^{6d'}$ | —R$^{A'}$ |
|---|---|---|---|---|---|
| Q37 | —F | —H | —H | —H | —C(=O)NHMe |
| Q38 | —H | —F | —H | —H | —C(=O)NHMe |
| Q39 | —H | —H | —F | —H | —C(=O)NHMe |
| Q40 | —H | —H | —H | —F | —C(=O)NHMe |
| Q41 | —Cl | —H | —H | —H | —C(=O)NHMe |
| Q42 | —H | —Cl | —H | —H | —C(=O)NHMe |

TABLE 91-continued

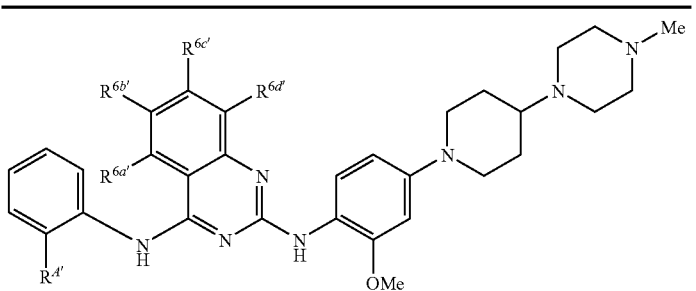

| No | —R6a' | —R6b' | —R6c' | —R6d' | —RA' |
|---|---|---|---|---|---|
| Q43 | —H | —H | —Cl | —H | —C(=O)NHMe |
| Q44 | —H | —H | —H | —Cl | —C(=O)NHMe |
| Q45 | —Br | —H | —H | —H | —C(=O)NHMe |
| Q46 | —H | —Br | —H | —H | —C(=O)NHMe |
| Q47 | —H | —H | —Br | —H | —C(=O)NHMe |
| Q48 | —H | —H | —H | —Br | —C(=O)NHMe |
| Q49 | Me | —H | —H | —H | —C(=O)NHMe |
| Q50 | —H | Me | —H | —H | —C(=O)NHMe |
| Q51 | —H | —H | Me | —H | —C(=O)NHMe |
| Q52 | —H | —H | —H | Me | —C(=O)NHMe |
| Q53 | —OMe | —H | —H | —H | —C(=O)NHMe |
| Q54 | —H | —OMe | —H | —H | —C(=O)NHMe |
| Q55 | —H | —H | —OMe | —H | —C(=O)NHMe |
| Q56 | —H | —H | —H | —OMe | —C(=O)NHMe |
| Q57 | —CN | —H | —H | —H | —C(=O)NHMe |
| Q58 | —H | —CN | —H | —H | —C(=O)NHMe |
| Q59 | —H | —H | —CN | —H | —C(=O)NHMe |
| Q60 | —H | —H | —H | —CN | —C(=O)NHMe |
| Q61 | —CF3 | —H | —H | —H | —C(=O)NHMe |
| Q62 | —H | —CF3 | —H | —H | —C(=O)NHMe |
| Q63 | —H | —H | —CF3 | —H | —C(=O)NHMe |
| Q64 | —H | —H | —H | —CF3 | —C(=O)NHMe |
| Q65 | —SMe | —H | —H | —H | —C(=O)NHMe |
| Q66 | —H | —SMe | —H | —H | —C(=O)NHMe |
| Q67 | —H | —H | —SMe | —H | —C(=O)NHMe |
| Q68 | —H | —H | —H | —SMe | —C(=O)NHMe |
| Q69 | —OCF3 | —H | —H | —H | —C(=O)NHMe |
| Q70 | —H | —OCF3 | —H | —H | —C(=O)NHMe |
| Q71 | —H | —H | —OCF3 | —H | —C(=O)NHMe |
| Q72 | —H | —H | —H | —OCF3 | —C(=O)NHMe |

TABLE 92

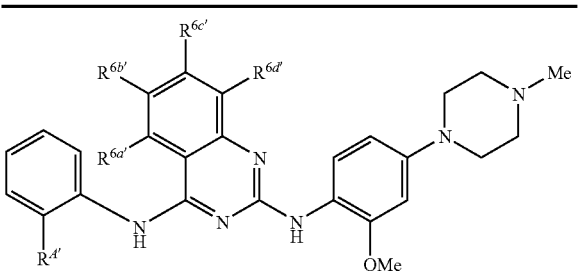

| No | —R6a' | —R6b' | —R6c' | —R6d' | —RA' | No | —R6a' | —R6b' | —R6c' | —R6d' | —RA' |
|---|---|---|---|---|---|---|---|---|---|---|---|
| R1 | —F | —H | —H | —H | —S(=O)2iPr | R14 | —H | Me | —H | —H | —S(=O)2iPr |
| R2 | —H | —F | —H | —H | —S(=O)2iPr | R15 | —H | —H | Me | —H | —S(=O)2iPr |
| R3 | —H | —H | —F | —H | —S(=O)2iPr | R16 | —H | —H | —H | Me | —S(=O)2iPr |
| R4 | —H | —H | —H | —F | —S(=O)2iPr | R17 | —OMe | —H | —H | —H | —S(=O)2iPr |
| R5 | —Cl | —H | —H | —H | —S(=O)2iPr | R18 | —H | —OMe | —H | —H | —S(=O)2iPr |
| R6 | —H | —Cl | —H | —H | —S(=O)2iPr | R19 | —H | —H | —OMe | —H | —S(=O)2iPr |
| R7 | —H | —H | —Cl | —H | —S(=O)2iPr | R20 | —H | —H | —H | —OMe | —S(=O)2iPr |
| R8 | —H | —H | —H | —Cl | —S(=O)2iPr | R21 | —CN | —H | —H | —H | —S(=O)2iPr |
| R9 | —Br | —H | —H | —H | —S(=O)2iPr | R22 | —H | —CN | —H | —H | —S(=O)2iPr |
| R10 | —H | —Br | —H | —H | —S(=O)2iPr | R23 | —H | —H | —CN | —H | —S(=O)2iPr |
| R11 | —H | —H | —Br | —H | —S(=O)2iPr | R24 | —H | —H | —H | —CN | —S(=O)2iPr |
| R12 | —H | —H | —H | —Br | —S(=O)2iPr | R25 | —CF3 | —H | —H | —H | —S(=O)2iPr |
| R13 | Me | —H | —H | —H | —S(=O)2iPr | R26 | —H | —CF3 | —H | —H | —S(=O)2iPr |

TABLE 92-continued

| No | —R^{6a'} | —R^{6b'} | —R^{6c'} | —R^{6d'} | —R^{A'} |
|---|---|---|---|---|---|
| R27 | —H | —H | —CF₃ | —H | —S(=O)₂iPr |
| R28 | —H | —H | —H | —CF₃ | —S(=O)₂iPr |
| R29 | —SMe | —H | —H | —H | —S(=O)₂iPr |
| R30 | —H | —SMe | —H | —H | —S(=O)₂iPr |
| R31 | —H | —H | —SMe | —H | —S(=O)₂iPr |
| R32 | —H | —H | —H | —SMe | —S(=O)₂iPr |
| R33 | —OCF₃ | —H | —H | —H | —S(=O)2iPr |
| R34 | —H | —OCF₃ | —H | —H | —S(=O)2iPr |
| R35 | —H | —H | —OCF3 | —H | —S(=O)2iPr |
| R36 | —H | —H | —H | —OCF3 | —S(=O)2iPr |

TABLE 93

| No | —R^{6a'} | —R^{6b'} | —R^{6c'} | —R^{6d'} | —R^{A'} |
|---|---|---|---|---|---|
| R37 | —F | —H | —H | —H | —C(=O)NHMe |
| R38 | —H | —F | —H | —H | —C(=O)NHMe |
| R39 | —H | —H | —F | —H | —C(=O)NHMe |
| R40 | —H | —H | —H | —F | —C(=O)NHMe |
| R41 | —Cl | —H | —H | —H | —C(=O)NHMe |
| R42 | —H | —Cl | —H | —H | —C(=O)NHMe |
| R43 | —H | —H | —Cl | —H | —C(=O)NHMe |
| R44 | —H | —H | —H | —Cl | —C(=O)NHMe |
| R45 | —Br | —H | —H | —H | —C(=O)NHMe |
| R46 | —H | —Br | —H | —H | —C(=O)NHMe |
| R47 | —H | —H | —Br | —H | —C(=O)NHMe |
| R48 | —H | —H | —H | —Br | —C(=O)NHMe |
| R49 | Me | —H | —H | —H | —C(=O)NHMe |
| R50 | —H | Me | —H | —H | —C(=O)NHMe |
| R51 | —H | —H | Me | —H | —C(=O)NHMe |
| R52 | —H | —H | —H | Me | —C(=O)NHMe |
| R53 | —OMe | —H | —H | —H | —C(=O)NHMe |
| R54 | —H | —OMe | —H | —H | —C(=O)NHMe |
| R55 | —H | —H | —OMe | —H | —C(=O)NHMe |
| R56 | —H | —H | —H | —OMe | —C(=O)NHMe |
| R57 | —CN | —H | —H | —H | —C(=O)NHMe |
| R58 | —H | —CN | —H | —H | —C(=O)NHMe |
| R59 | —H | —H | —CN | —H | —C(=O)NHMe |
| R60 | —H | —H | —H | —CN | —C(=O)NHMe |
| R61 | —CF₃ | —H | —H | —H | —C(=O)NHMe |
| R62 | —H | —CF₃ | —H | —H | —C(=O)NHMe |
| R63 | —H | —H | —CF₃ | —H | —C(=O)NHMe |
| R64 | —H | —H | —H | —CF₃ | —C(=O)NHMe |
| R65 | —SMe | —H | —H | —H | —C(=O)NHMe |
| R66 | —H | —SMe | —H | —H | —C(=O)NHMe |
| R67 | —H | —H | —SMe | —H | —C(=O)NHMe |
| R68 | —H | —H | —H | —SMe | —C(=O)NHMe |
| R69 | —OCF₃ | —H | —H | —H | —C(=O)NHMe |
| R70 | —H | —OCF₃ | —H | —H | —C(=O)NHMe |

TABLE 93-continued

| No | —R^{6a'} | —R^{6b'} | —R^{6c'} | —R^{6d'} | —R^{A'} |
|---|---|---|---|---|---|
| R71 | —H | —H | —OCF₃ | —H | —C(=O)NHMe |
| R72 | —H | —H | —H | —OCF₃ | —C(=O)NHMe |

TABLE 94

| No | —R^{6a'} | —R^{6b'} | —R^{6c'} | —R^{6d'} | —R^{A'} |
|---|---|---|---|---|---|
| S1 | —F | —H | —H | —H | —S(=O)₂iPr |
| S2 | —H | —F | —H | —H | —S(=O)₂iPr |
| S3 | —H | —H | —F | —H | —S(=O)₂iPr |
| S4 | —H | —H | —H | —F | —S(=O)₂iPr |
| S5 | —Cl | —H | —H | —H | —S(=O)₂iPr |
| S6 | —H | —Cl | —H | —H | —S(=O)₂iPr |
| S7 | —H | —H | —Cl | —H | —S(=O)₂iPr |
| S8 | —H | —H | —H | —Cl | —S(=O)₂iPr |
| S9 | —Br | —H | —H | —H | —S(=O)₂iPr |
| S10 | —H | —Br | —H | —H | —S(=O)₂iPr |
| S11 | —H | —H | —Br | —H | —S(=O)₂iPr |
| S12 | —H | —H | —H | —Br | —S(=O)₂iPr |
| S13 | Me | —H | —H | —H | —S(=O)₂iPr |
| S14 | —H | Me | —H | —H | —S(=O)₂iPr |
| S15 | —H | —H | Me | —H | —S(=O)₂iPr |
| S16 | —H | —H | —H | Me | —S(=O)₂iPr |
| S17 | —OMe | —H | —H | —H | —S(=O)₂iPr |
| S18 | —H | —OMe | —H | —H | —S(=O)₂iPr |
| S19 | —H | —H | —OMe | —H | —S(=O)₂iPr |
| S20 | —H | —H | —H | —OMe | —S(=O)₂iPr |
| S21 | —CN | —H | —H | —H | —S(=O)₂iPr |
| S22 | —H | —CN | —H | —H | —S(=O)₂iPr |
| S23 | —H | —H | —CN | —H | —S(=O)₂iPr |
| S24 | —H | —H | —H | —CN | —S(=O)₂iPr |
| S25 | —CF₃ | —H | —H | —H | —S(=O)₂iPr |
| S26 | —H | —CF₃ | —H | —H | —S(=O)₂iPr |
| S27 | —H | —H | —CF₃ | —H | —S(=O)₂iPr |
| S28 | —H | —H | —H | —CF₃ | —S(=O)₂iPr |
| S29 | —SMe | —H | —H | —H | —S(=O)₂iPr |
| S30 | —H | —SMe | —H | —H | —S(=O)₂iPr |
| S31 | —H | —H | —SMe | —H | —S(=O)₂iPr |
| S32 | —H | —H | —H | —SMe | —S(=O)₂iPr |
| S33 | —OCF₃ | —H | —H | —H | —S(=O)2iPr |
| S34 | —H | —OCF₃ | —H | —H | —S(=O)2iPr |
| S35 | —H | —H | —OCF3 | —H | —S(=O)2iPr |
| S36 | —H | —H | —H | —OCF3 | —S(=O)2iPr |

TABLE 95

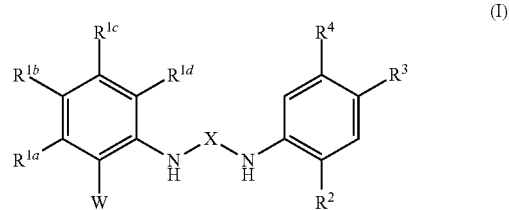

| No | —R6a' | —R6b' | —R6c' | —R6d' | —R4' |
|---|---|---|---|---|---|
| S37 | —F | —H | —H | —H | —C(=O)NHMe |
| S38 | —H | —F | —H | —H | —C(=O)NHMe |
| S39 | —H | —H | —F | —H | —C(=O)NHMe |
| S40 | —H | —H | —H | —F | —C(=O)NHMe |
| S41 | —Cl | —H | —H | —H | —C(=O)NHMe |
| S42 | —H | —Cl | —H | —H | —C(=O)NHMe |
| S43 | —H | —H | —Cl | —H | —C(=O)NHMe |
| S44 | —H | —H | —H | —Cl | —C(=O)NHMe |
| S45 | —Br | —H | —H | —H | —C(=O)NHMe |
| S46 | —H | —Br | —H | —H | —C(=O)NHMe |
| S47 | —H | —H | —Br | —H | —C(=O)NHMe |
| S48 | —H | —H | —H | —Br | —C(=O)NHMe |
| S49 | Me | —H | —H | —H | —C(=O)NHMe |
| S50 | —H | Me | —H | —H | —C(=O)NHMe |
| S51 | —H | —H | Me | —H | —C(=O)NHMe |
| S52 | —H | —H | —H | Me | —C(=O)NHMe |
| S53 | —OMe | —H | —H | —H | —C(=O)NHMe |
| S54 | —H | —OMe | —H | —H | —C(=O)NHMe |
| S55 | —H | —H | —OMe | —H | —C(=O)NHMe |
| S56 | —H | —H | —H | —OMe | —C(=O)NHMe |
| S57 | —CN | —H | —H | —H | —C(=O)NHMe |
| S58 | —H | —CN | —H | —H | —C(=O)NHMe |
| S59 | —H | —H | —CN | —H | —C(=O)NHMe |
| S60 | —H | —H | —H | —CN | —C(=O)NHMe |
| S61 | —CF3 | —H | —H | —H | —C(=O)NHMe |
| S62 | —H | —CF3 | —H | —H | —C(=O)NHMe |
| S63 | —H | —H | —CF3 | —H | —C(=O)NHMe |
| S64 | —H | —H | —H | —CF3 | —C(=O)NHMe |
| S65 | —SMe | —H | —H | —H | —C(=O)NHMe |
| S66 | —H | —SMe | —H | —H | —C(=O)NHMe |
| S67 | —H | —H | —SMe | —H | —C(=O)NHMe |
| S68 | —H | —H | —H | —SMe | —C(=O)NHMe |
| S69 | —OCF3 | —H | —H | —H | —C(=O)NHMe |
| S70 | —H | —OCF3 | —H | —H | —C(=O)NHMe |
| S71 | —H | —H | —OCF3 | —H | —C(=O)NHMe |
| S72 | —H | —H | —H | —OCF3 | —C(=O)NHMe |

INDUSTRIAL APPLICABILITY

The compounds of formula (I) or salts thereof have inhibitory activity against the kinase activity of EML4-ALK fusion proteins and mutant EGFR proteins, as well as growth inhibitory activity against human non-small cell lung cancer cell lines NCI-H2228 and HCC827, and can be used as active ingredients in pharmaceutical compositions for preventing and/or treating cancer, such as lung cancer in one embodiment, non-small cell lung cancer or small cell lung cancer in another embodiment, EML4-ALK fusion polynucleotide-positive and/or mutant EGFR polynucleotide-positive cancer in yet another embodiment, EML4-ALK fusion polynucleotide-positive and/or mutant EGFR polynucleotide-positive lung cancer in yet another embodiment, or EML4-ALK fusion polynucleotide-positive and/or mutant EGFR polynucleotide-positive non-small cell lung cancer in yet another embodiment.

SEQUENCE LISTING FREE TEXT

The numerical heading <223> in the Sequence Listing shown below contains an explanation of "Artificial Sequence." More specifically, each nucleotide sequence represented by the sequence of SEQ ID NO: 9 or 10 in the Sequence Listing is an artificially synthesized primer sequence.

The invention claimed is:
1. A compound of formula (I) or a salt thereof:

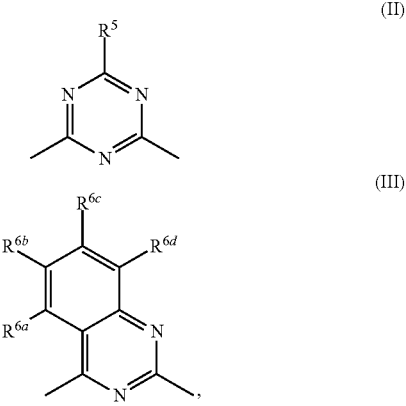

(wherein the symbols are as defined below:
—X— represents
(1) a group of formula (II), or
(2) a group of formula (III)

—R5 represents
(1) —H,
(2) —OH,
(3) halogen,
(4) lower alkyl which may be substituted with one or more halogens,
(5) O-lower alkyl which may be substituted with one or more halogens,
(6) —S-lower alkyl,
(7) cyano,
(8) amino which may be substituted with one or two lower alkyls, or
(9) cyclic amino which may be substituted with one or more groups selected from the group consisting of lower alkyl, oxo, —OH, —O-lower alkyl, and amino which may be substituted with one or two lower alkyls (provided that the triazine ring to which —R5 is attached is attached to the nitrogen atom in the cyclic amino),
—R6a, —R6b, —R6c and —R6d, which may be the same or different, each represent
(1) —H,
(2) halogen,
(3) lower alkyl which may be substituted with one or more halogens,
(4) O-lower alkyl which may be substituted with one or more halogens, (5) —S-lower alkyl, or
(6) cyano,
—W represents
a group represented by -A-B,
-A- is
—S(=O)$_2$—
—B is isopropyl,
—R$^{1a}$, —R$^{1b}$, R$^{1c}$ and —R$^{1d}$ are each —H, —R$^2$ is —O-methyl, —R$^4$ is —H and —R$^3$ is 4-(4-methylpiperazin-1-yl)piperidin-1-yl.

2. The compound according to claim 1 or a salt thereof, wherein —X— is a group represented by formula (II), and —R$^5$ is —H.

3. The compound according to claim 1 or a salt thereof, wherein said compound is:
N$^4$-[2-(isopropylsulfonyl)phenyl]-N$^2$-{2-methoxy-4-[4-(4-methylpiperazin-1-yl)piperidin-1-yl]phenyl}quinazoline-2,4-diamine.

4. The compound according to claim 1 or a salt thereof, wherein said compound is:
N-[2-(isopropylsulfonyl)phenyl]-N'-{2-methoxy-4-[4-(4-methylpiperazin-1-yl)piperidin-1-yl]phenyl}-1,3,5-triazine-2,4-diamine.

5. A pharmaceutical composition, which comprises the compound according to claim 1 or a salt thereof and a pharmaceutically acceptable excipient.

6. A pharmaceutical composition for treating non-small cell lung cancer, or EML4-ALK fusion polynucleotide-positive and/or mutant EGFR polynucleotide-positive non-small cell lung cancer, which comprises the compound according to claim 1 or a salt thereof.

7. The compound according to claim 1 or a salt thereof, which is used as an active ingredient in a pharmaceutical composition for treating non-small cell lung cancer, or EML4-ALK fusion polynucleotide-positive and/or mutant EGFR polynucleotide-positive non-small cell lung cancer.

* * * * *

UNITED STATES PATENT AND TRADEMARK OFFICE
CERTIFICATE OF CORRECTION

| | |
|---|---|
| PATENT NO. | : 8,318,702 B2 |
| APPLICATION NO. | : 12/448759 |
| DATED | : November 27, 2012 |
| INVENTOR(S) | : Yutaka Kondoh et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 229 days.

Signed and Sealed this
Twelfth Day of March, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,318,702 B2 | |
| APPLICATION NO. | : 12/448759 | |
| DATED | : November 27, 2012 | |
| INVENTOR(S) | : Yutaka Kondoh et al. | |

It is certified that error appears in the above-identified patent and that said Letters Patent is hereby corrected as shown below:

Please delete Patent No. 8,318,702 B2 in its entirety and insert Patent No. 8,318,702 B2 in its entirety as attached.

Signed and Sealed this
Twenty-fourth Day of September, 2013

Teresa Stanek Rea
*Deputy Director of the United States Patent and Trademark Office*

(12) United States Patent
Kondoh et al.

(10) Patent No.: US 8,318,702 B2
(45) Date of Patent: Nov. 27, 2012

(54) DI(ARYLAMINO)ARYL COMPOUNDS

(75) Inventors: Yutaka Kondoh, Tokyo (JP); Kazuhiko Iikubo, Tokyo (JP); Sadao Kuromitsu, Tokyo (JP); Nobuaki Shindo, Tokyo (JP); Takatoshi Soga, Tokyo (JP); Takashi Furutani, Tokyo (JP); Itsuro Shimada, Tokyo (JP); Takahiro Matsuya, Tokyo (JP); Kazuo Kurosawa, Tokyo (JP); Akio Kamikawa, Tokyo (JP); Hiroyuki Mano, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 235 days.

(21) Appl. No.: 12/448,759

(22) PCT Filed: Jul. 4, 2008

(86) PCT No.: PCT/JP2008/062188
§ 371 (c)(1),
(2), (4) Date: Aug. 6, 2009

(87) PCT Pub. No.: WO2009/008371
PCT Pub. Date: Jan. 15, 2009

(65) Prior Publication Data
US 2010/0099658 A1 Apr. 22, 2010

(30) Foreign Application Priority Data

Jul. 6, 2007 (JP) ................................. 2007-178795

(51) Int. Cl.
| | |
|---|---|
| *A01N 57/00* | (2006.01) |
| *A01N 43/00* | (2006.01) |
| *A01N 43/66* | (2006.01) |
| *A61K 31/675* | (2006.01) |
| *A61K 31/00* | (2006.01) |
| *A61K 31/53* | (2006.01) |
| *C07D 251/00* | (2006.01) |
| *C07D 253/00* | (2006.01) |
| *C07D 251/40* | (2006.01) |
| *C07D 251/18* | (2006.01) |
| *C07D 251/48* | (2006.01) |

(52) U.S. Cl. ................... 514/84; 514/210.21; 514/241; 544/180; 544/194; 544/204; 544/205

(58) Field of Classification Search ................ 514/84, 514/210.21, 241; 544/180, 194, 204, 205
See application file for complete search history.

(56) References Cited

U.S. PATENT DOCUMENTS

| | | |
|---|---|---|
| 2004/0116388 A1 | 6/2004 | Armistead et al. |
| 2005/0085637 A1 | 4/2005 | Cheung et al. |
| 2006/0100227 A1 | 5/2006 | Baenteli et al. |
| 2006/0247241 A1 | 11/2006 | Garcia-Echeverria et al. |
| 2006/0247262 A1 | 11/2006 | Baenteli et al. |
| 2007/0105839 A1 | 5/2007 | Imbach et al. |
| 2008/0090776 A1 | 4/2008 | Mano et al. |
| 2008/0132504 A1 | 6/2008 | Garcia-Echeverria et al. |
| 2008/0279870 A1 | 11/2008 | Inghirami et al. |
| 2008/0293708 A1 | 11/2008 | Kawahara et al. |
| 2009/0099193 A1 | 4/2009 | Mano et al. |
| 2009/0131436 A1 | 5/2009 | Imbach et al. |
| 2009/0156475 A1 | 6/2009 | Rikova et al. |
| 2010/0240673 A1 | 9/2010 | Mano et al. |

FOREIGN PATENT DOCUMENTS

| | | |
|---|---|---|
| EP | 1 479 397 | 11/2004 |
| EP | 1 914 240 A1 | 4/2008 |
| JP | 2005-522438 | 7/2005 |
| JP | 2006-520354 | 9/2006 |
| WO | WO 97/20822 | 6/1997 |
| WO | WO 01/25220 A1 | 4/2001 |
| WO | WO 03/055866 | 7/2003 |
| WO | WO 03/055866 | 7/2003 |
| WO | WO 03/066601 A1 | 8/2003 |
| WO | WO 03/078404 A1 | 9/2003 |
| WO | WO 2004/080980 | 9/2004 |
| WO | WO 2005/016894 A1 | 2/2005 |
| WO | WO 2005/026130 A1 | 3/2005 |
| WO | WO 2005/026158 A1 | 3/2005 |
| WO | WO 2006/021454 A2 | 3/2006 |
| WO | WO 2006/021457 A2 | 3/2006 |
| WO | WO 2007/059300 A2 | 5/2007 |
| WO | WO 2007/095812 | 8/2007 |
| WO | WO 2007/095812 A1 | 8/2007 |
| WO | WO 2008/051547 A1 | 5/2008 |
| WO | WO 2008/073687 A2 | 6/2008 |
| WO | WO 2008/127248 A1 | 10/2008 |

(Continued)

OTHER PUBLICATIONS

Supplementary European Search Report dated May 6, 2011 for European Application No. 0877903.9.

(Continued)

*Primary Examiner* — Samira Jean-Louis
(74) *Attorney, Agent, or Firm* — Oblon, Spivak, McClelland, Maier & Neustadt, L.L.P.

(57) ABSTRACT

The present invention provides a compound which is useful as an inhibitor against the kinase activity of EML4-ALK fusion proteins and mutant EGFR proteins.
As a result of extensive and intensive studies on compounds having an inhibitory effect against the kinase activity of EML4-ALK fusion proteins and mutant EGFR proteins, the inventors of the present invention have found that the di(arylamino)aryl compound of the present invention has inhibitory activity against the kinase activity of EML4-ALK fusion proteins and mutant EGFR proteins. This finding led to the completion of the present invention. The compound of the present invention can be used as a pharmaceutical composition for preventing and/or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer, etc.

7 Claims, 2 Drawing Sheets

FOREIGN PATENT DOCUMENTS

| | | |
|---|---|---|
| WO | WO 2009/020990 A1 | 2/2009 |
| WO | WO 2009/032694 | 3/2009 |
| WO | WO 2009/032703 A1 | 3/2009 |
| WO | WO 2009/054939 A1 | 4/2009 |
| WO | WO 2009/143389 | 9/2009 |
| WO | WO 2009/126514 | 10/2009 |
| WO | WO 2009/126515 | 10/2009 |

OTHER PUBLICATIONS

International Search Report for PCT/JP2008/062188, mailed Jul. 29, 2008.
Whitten, J.P. et al., "Rapid Microscale Synthesis, a New Method for Lead Optimization Using Robotics and Solution Phase Chemistry: Application to the Synthesis and Optimization of Corticotropin-Releasing Factor Receptor Antagonists", Journal of Medicinal Chemistry, vol. 39, No. 22, (1996), pp. 4354-4357.
Office Action dated Jul. 12, 2011 issued in connection with corresponding Chinese Appln. No. 200880023605.5 (2011070700484100) with English Translation.
Dirks et al, "Expression and Functional Analysis of the Anaplastic Lymphoma Kinase (ALK) Gene in Tumor Cell Lines", Int. J. Cancer 100:49-56 (2002).
Soda et al, "Identification of the transforming EML4-ALK fusion gene in non0small-cell lung cancer", Nature 448:561-566 (2007).
Marzec et al, "Inhibition of ALK enzymatic activity in T-cell lymphoma cells induces apoptosis and suppresses proliferation and STAT3 phosphorylation independently of Jak3", Laboratory Investigation 85:1544-1554 (2005).
Galkin et al, "Identification of NVP-TAE684, a potent, selective, and efficacious inhibitor of NPM-ALK", PNAS 104(1):270-275 (2007).
Rikova et al, "Global Survey of Phsophotyrosine Signaling Identifies Oncogenic Kinases in Lung Cancer", Cell 131:1190-1203 (2007).
McDermott et al, "Identification of genotype-correlated sensitivity to selective kinase inhibitors by using high-throughput tumor cell line profiling", PNAS 104(50):19936-19941 (2007).
Koivunen et al, "EML4-ALK fusion gene and sensitivity to an ALK kinase inhibitor in lung cancer", Proceedings of the American Associateion for Cancer Research 49:560, No. 2373 (2008).
Whitten et al, "Rapid Microscale Synthesis, a New Method for Lead Optimization Using Robotics and Solution Phase Chemistry: Application to the Synthesis and Optimization of Corticotropin-Releasing Factor, Receptor Antagonists", J. Med. Chem. 39:4354-4357 (1996).
Piva et al, "Ablation of oncogenic ALK is a viable therapeutic approach for anaplastic large-cell lymphomas", Blood 107:689-697 (2006).
Turturro et al, "Model of Inhibition of the NPM-ALK Kinase Activity by Herbimycin A", Clinical Cancer Research 8:240-245 (2002).
Elenitoba-Johnson et al, "Proteomic identification of oncogenic chromosomal translocation partners encoding chimeric anaplastic lymphoma kinase fusion proteins", PNAS 103(19):7402-7407 (2006).
Takeuchi et al, "KIF5B-ALK, a Novel Fusion Oncokinase Identified by an Immunohistochemistry-based Diagnostic System for ALK-positive Lung Cancer", Clin. Cancer Res. 15(9):3143-3149 (2009).
Wan et al, "Anaplastic lymphoma kinase activity is essential for the proliferation and survival of anaplastic large-cell lymphoma cells", Blood 107:1617-1623 (2006).
Du et al, "Proteomic profiling of proteins dysregulted in Chinese esophageal squamous cell carcinoma", J. Mol. Med. 85:863-875 (2007).
Chiarle et al, "The anaplastic lymphoma kinase in the pathogenesis of cancer", Nature Reviews Cancer 8:11-23 (2008).
Corrections, PNAS 104(6):2024-2025 (2007).
Official Action dated Dec. 2, 2011 issued in connection with Russian Appln. No. 2010103969/4.
Official Action dated Dec. 2, 2011 issued in connection with Russian Appln. No. 2010103969/4—English Translation.
Office Action issued May 30, 2012, in European Application No. 08 777 903.9.
Office Action issued Jun. 28, 2012, in Australian Patent Application No. 2008273426, filed Jul. 4, 2008 (with English-language Translation).
Office Action issued Jul. 20, 2012, in Indonesian Patent Application No. W-00 2010 00004, (with English-language Translation).

DI(ARYLAMINO)ARYL COMPOUNDS

This application is the U.S. national phase of International Application No. PCT/JP2008/062188 filed 4 Jul. 2008, which designated the U.S. and claims priority to Japan Application No. 2007-178795 filed 6 Jul. 2007, the entire contents of each of which are hereby incorporated by reference.

TECHNICAL FIELD

The present invention relates to di(arylamino)aryl compounds useful as active ingredients in pharmaceutical compositions, particularly pharmaceutical compositions for cancer therapy.

BACKGROUND ART

Lung cancer is caused by disordered growth of tracheal, bronchial and/or alveolar cells as a result of losing their normal functions. The number of people who die of lung cancer is the largest of the total of cancer deaths (17%), and worldwide about 1.3 million people die of lung cancer each year.

Treatment for lung cancer is divided into three major categories: surgical operation (surgical therapy), anticancer agent (chemotherapy) and radioactive irradiation (radiation therapy), but the effectiveness of treatment will vary depending on the tissue type of lung cancer. For example, although a definite diagnosis of lung cancer is made by a pathologist based on his cytohistopathological diagnosis on a microscope specimen, small cell lung cancer, which constitutes about 20% of lung cancer cases, has often reached an advanced stage at the time of discovery because it generally has a high grade of malignancy and will rapidly grow and spread and will often metastasize to other organs. For this reason, chemotherapy and/or radiation therapy is often used for treatment of this cancer, but the prognosis is poor because small cell lung cancer will often recur although it is relatively sensitive to these therapies. On the other hand, in the case of non-small cell lung cancer, which constitutes the remainder of about 80%, surgical therapy is considered for use until a certain stage, but there is little opportunity to use surgical operation in the subsequent stages where chemotherapy and/or radiation therapy is mainly used for treatment.

Thus, in either type of lung cancer, chemotherapy is an important option for treatment.

EGFR is a receptor tyrosine kinase and, when activated upon ligand binding, causes phosphorylation of tyrosine residues in the receptor's intracellular region and subsequently induces successive activation of cytoplasmic proteins, thereby facilitating cell differentiation and growth (Clinical Cancer Research, 12(18), 2006, p. 5268-5272). EGFR is found to be overexpressed in various malignant tumors (Journal of Cellular Physiology, 194(1), 2003, p. 13-19), and EGFR overexpression is shown to be a factor responsible for bad prognosis in cancer (Annals of Oncology, 15(1), 2004, p. 28-32, Journal of Clinical Oncology, 21(20), 2003, p. 3798-3807). In recent years, EGFR inhibitors have been observed to produce a high clinical effect on a limited population of non-small cell lung cancer patients, and it has been reported that active mutation of EGFR existed in such a patient segment (N. Engl. J. Med. 350, 2004, p. 2129-2139, Science 304, 2004, p. 1497-1500, Proc. Natl. Acad. Sci. 101, 2004, p. 13306-13311). As a result of a conformational change in the ATP-binding site of EGFR, this mutant EGFR is constitutively activated even in the absence of ligand stimulation, and thereby causes canceration of cells. In cancer cells having this mutant EGFR, it is known that they develop apoptosis by the action of gefitinib or erlotinib known as an EGFR inhibitor, resulting in a reduction of the tumor size (Nat. Rev. Cancer 7, 2007, p. 169-181).

ALK (Anaplastic Lymphoma Kinase) is a receptor tyrosine kinase and is a protein having a transmembrane region in the middle part, flanked by a tyrosine kinase region on the carboxyl-terminal side and an extracellular region on the amino-terminal side. It has previously been reported that full-length ALK is expressed in several types of cancer cells of ectodermal origin (e.g., neuroblastoma, glioblastoma, breast cancer, melanoma) (Non-patent Document 1). In some cases of human malignant lymphoma, it has also been reported that the ALK gene is fused with another gene (e.g., NPM gene, CLTCL gene, TFG gene) as a result of chromosomal translocation, and thereby produces an oncogenic fusion tyrosine kinase (Science, vol. 263, p. 1281, 1994; Blood, vol. 86, p. 1954, 1995; Blood, vol. 95, p. 3204, 2000; Blood, vol. 94, p. 3265, 1999). Also in the case of inflammatory myofibroblastic tumor, it is known that the ALK gene is fused with another gene (e.g., CARS gene, SEC31L1 gene) as a result of chromosomal translocation, and thereby produces a fusion tyrosine kinase (Laboratory Investigation, a journal of technical methods and pathology, vol. 83, p. 1255, 2003; International Journal of Cancer, vol. 118, p. 1181, 2006). Most of partner molecules (including EML4 (echinoderm microtubule associated protein like-4)) to be fused with ALK have a complex-forming domain, and the generated fusion products per se also appear to form complexes. This complex formation would induce uncontrol of ALK tyrosine kinase activity and abnormal activation of intracellular signals, thereby causing canceration (Cellular and Molecular Life Science, vol. 61, p. 2939, 2004; Nature Reviews Cancer, vol. 8, p. 11, 2008).

Moreover, recent reports have indicated the presence of a TPM4-ALK fusion protein in esophageal cancer by proteomics analysis procedures (World Journal of Gastroenterology, vol. 12, p. 7104, 2006; Journal Molecular Medicine, vol. 85, p. 863, 2007). Further, after the priority date of the present application, a fusion gene between EML4 and ALK was confirmed in specimens from lung cancer patients, and it was also reported that this EML4-ALK fusion gene has tumorgenicity and is a causal gene of cancer, and that inhibitors against its kinase activity suppress the growth of various cells where the EML4-ALK fusion protein is expressed (Patent Document 1 and Non-patent Document 2). These documents further show that inhibitors of the EML4-ALK fusion protein are useful as therapeutic agents for lung cancer in EML4-ALK polynucleotide-positive lung cancer patients.

Gefitinib and erlotinib mentioned above, which are EGFR inhibitors and are known as useful therapeutic agents for non-small cell lung cancer, have the following chemical structures.

[Formula 1]

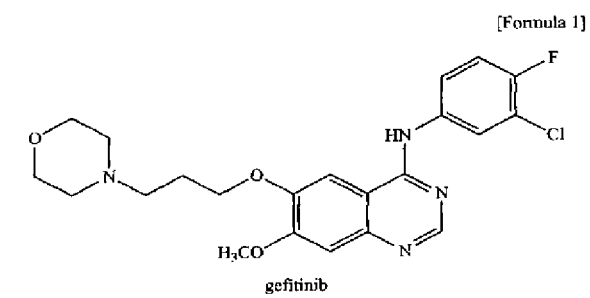

gefitinib

3

-continued

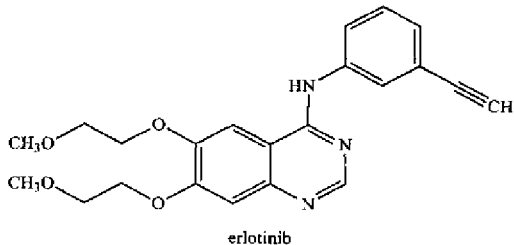
erlotinib

Moreover, Patent Document 1 published after the priority date of the present application shows the following compounds (each being known as an ALK inhibitor) as examples of compounds having inhibitory activity against the EML4-ALK fusion protein, and it also discloses the actual values of their inhibitory activity against the EML4-ALK fusion protein (Patent Document 1). It should be noted that abbreviations for the following compounds are those used in Patent Document 1.

[Formula 2]

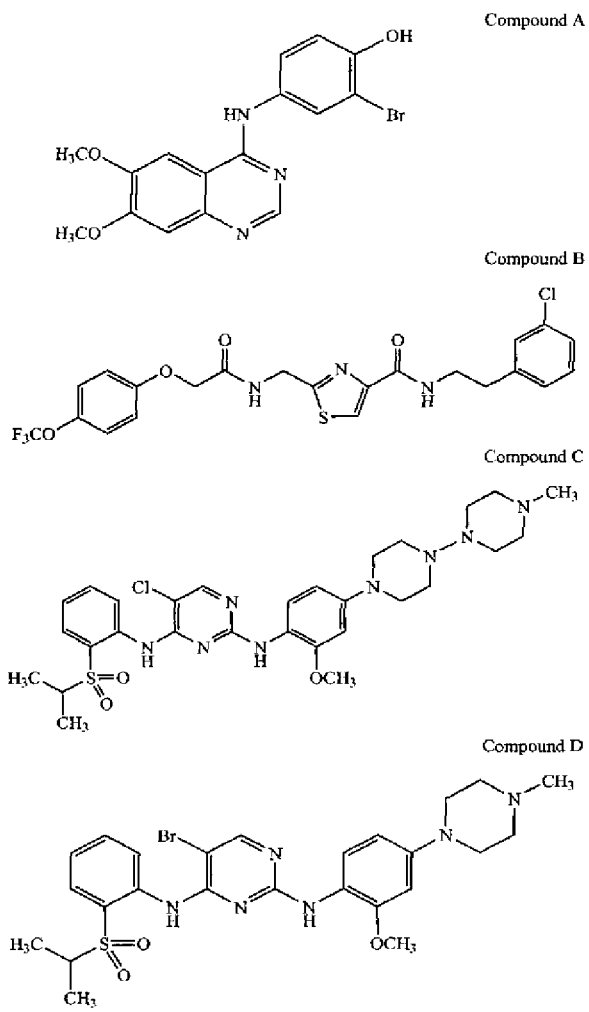

Compound A

Compound B

Compound C

Compound D

Their respective chemical names are: 4-[(3'-bromo-4'-hydroxyphenyl)amino]-6,7-dimethoxyquinazoline (also called

4

WHI-P154) for compound A; N-[2-(3-chlorophenyl)ethyl]-2-[({[4-(trifluoromethoxy)phenoxy]acetyl}amino)methyl]-1,3-thiazole-4-carboxamide for compound B; 5-chloro-$N^4$-[2-(isopropylsulfonyl)phenyl]-$N^2$-{2-methoxy-4-[4-(4-methylpiperazin-1-yl)piperidin-1-yl]phenyl}pyrimidine-2,4-diamine for compound C; and 2-[(5-bromo-2-{[2-methoxy-4-(4-methylpiperazin-1-yl)phenyl]amino}pyrimidin-4-yl)amino]-N-methylbenzenesulfonamide for compound D.

Moreover, in ALK fusion protein-expressing lymphoma cells, a compound having ALK inhibitory activity, WHI-P154, has been reported to inhibit cell growth and induce apoptosis (Non-patent Document 3). It should be noted that WHI-P154 is the same as compound A shown above.

Likewise, TAE684 represented by the following formula is known as an inhibitor of a fusion protein from a fusion gene between NPM gene and ALK gene. It should be noted that this compound is the same as compound C shown above.

[Formula 3]

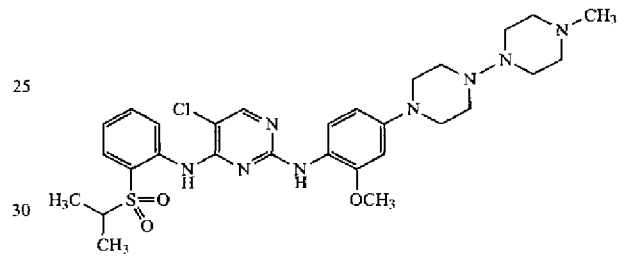

TAE684 structurally differs from the compounds of the present invention in that the center ring sandwiched between two —NH groups is a chloro-substituted pyrimidine ring.

Moreover, TAE684 has been reported to inhibit the spread of anaplastic large cell lymphoma (ALCL) by its inhibitory activity against the NPM-ALK fusion protein (Non-patent Document 4). On the other hand, although it is described that compounds including TAE684 have inhibitory activity against focal adhesion kinase (FAK) and are thereby useful for preventing and/or treating non-small cell lung cancer and small cell lung cancer, there is no information about actual therapeutic effects on these lung cancers (Patent Document 2).

After the priority date of the present application, further reports were issued showing that EML4-ALK is expressed in non-small cell lung cancer cells (NCI-H2228), that TFG-ALK is expressed in non-small cell lung cancer patients, and that TAE684 inhibits the growth of non-small cell lung cancer cells (NCI-H2228) (Patent Document 1 and Non-patent Documents 5 and 6).

The supplemental data of Non-patent Document 6 shows that TAE684 has little growth inhibitory activity (inhibition rate: 7.5%) on HCC-827 cells (mutant EGFR protein-expressing cells) under the conditions shown in the document.

Further, after the priority date of the present application, a more recent report has indicated that TAE684 shows growth inhibitory activity on EGFR (L858R mutation)/BaF cells (Non-patent Document 7).

Patent Document 1: European Patent Publication No. EP 1914240

Patent Document 2: International Publication No. WO 2004/080980

Non-patent Document 1: International Journal of Cancer, vol. 100, p. 49, 2002

Non-patent Document 2: Nature, vol. 448, no. 2, p. 561, 2007

Non-patent Document 3: Laboratory Investigation, vol. 85, p. 1544, 2005

Non-patent Document 4: Proceedings of the National Academy of Science, vol. 104, no. 1, p. 270, 2007

Non-patent Document 5: Cell, vol. 131, p. 1190, 2007

Non-patent Document 6: Proceedings of the National Academy of Science, vol. 104, no. 50, p. 19936, 2007

Non-patent Document 7: American Association for Cancer Research Annual Meeting 2008 Proceedings, vol. 49, April 2008, p. 560, #2373

DISCLOSURE OF THE INVENTION

Problems to be Solved by the Invention

The present invention provides a compound which is useful as an active ingredient in pharmaceutical compositions, particularly pharmaceutical compositions for cancer therapy, and which can be used more safely as an active ingredient in pharmaceutical compositions.

Means for Solving the Problem

As a result of extensive and intensive studies on compounds useful as active ingredients in pharmaceutical compositions for cancer therapy, the inventors of the present invention have found that the di(arylamino)aryl compound of the present invention has excellent inhibitory activity against the kinase activity of EML4-ALK fusion proteins and mutant EGFR proteins, and is useful as an active ingredient in pharmaceutical compositions for cancer therapy. This finding led to the completion of the present invention.

Namely, the present invention relates to a compound of formula (I) or a salt thereof, as well as a pharmaceutical composition comprising a compound of formula (I) or a salt thereof and an excipient.

[Formula 4]

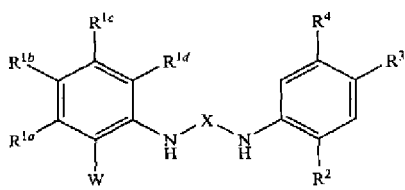

(I)

(wherein the symbols are as defined below:
—X— represents
(1) a group of formula (II), or
(2) a group of formula (III)

[Formula 5]

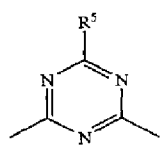

(II)

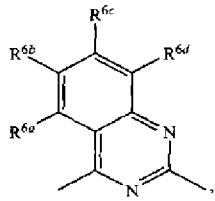

(III)

—$R^5$ represents
(1) —H,
(2) —OH,
(3) halogen,
(4) lower alkyl which may be substituted with one or more halogens,
(5) O-lower alkyl which may be substituted with one or more halogens,
(6) —S-lower alkyl,
(7) cyano,
(8) amino which may be substituted with one or two lower alkyls, or
(9) cyclic amino which may be substituted with one or more groups selected from the group consisting of lower alkyl, oxo, —OH, —O-lower alkyl, and amino which may be substituted with one or two lower alkyls (provided that the triazine ring to which —$R^5$ is attached is attached to the nitrogen atom in the cyclic amino), —$R^{6a}$, —$R^{6b}$, —$R^{6c}$ and —$R^{6d}$, which may be the same or different, each represent
(1) —H,
(2) halogen,
(3) lower alkyl which may be substituted with one or more halogens,
(4) O-lower alkyl which may be substituted with one or more halogens,
(5) —S-lower alkyl, or
(6) cyano, —W represents
(1) —H,
(2) halogen,
(3) lower alkyl which may be substituted with one or more halogens,
(4) O-lower alkyl which may be substituted with one or more halogens,
(5) —S-lower alkyl,
(6) cyano, or
(7) a group represented by -A-B,
-A- represents
(1) —S(=O)$_2$—, or
(2) —C(=O)—,
—B represents
(1) lower alkyl,
(2) amino which may be substituted with one or two $R^{ZA}$,
(3) cyclic amino (provided that -A- is attached to the nitrogen atom in the cyclic amino), or
(4) cycloalkyl,
$R^{ZA}$ represents
(1) lower alkyl, or
(2) cycloalkyl,
—$R^{1a}$, —$R^{1b}$, —$R^{1c}$ and —$R^{1d}$, which may be the same or different, each represent
(1) —H,
(2) halogen,
(3) lower alkyl which may be substituted with one or more halogens, (4) O-lower alkyl which may be substituted with one or more halogens,
(5) —S-lower alkyl, or
(6) cyano,
or alternatively
if —W is —H, one of —$R^{1a}$ or —$R^{1b}$ is a group represented by -A-B, and the other of —$R^{1a}$ or —$R^{1b}$, and —$R^{1c}$ and —$R^{1d}$, which may be the same or different, each represent any of (1) to (6) shown above,
—$R^2$ represents
(1) —H,
(2) —OH,
(3) halogen,
(4) lower alkyl which may be substituted with one or more halogens,
(5) O-lower alkyl which may be substituted with one or more halogens,
(6) —S-lower alkyl, or
(7) cyano,
—$R^3$ and —$R^4$ are as follows:
(1) one of them represents —H, and the other represents cyclic amino which may be substituted with one or more groups selected from the group consisting of $R^{ZB}$, oxo, —OH, —O-lower alkyl, and amino which may be substituted with one or two $R^{ZB}$ (provided that the benzene ring to which —$R^3$ or —$R^4$ is attached is attached to the nitrogen atom in the cyclic amino),
(2) one of them represents —H, and the other represents a group represented by formula (IV) (provided that -$L^1$ and -$L^2$ taken together with their adjacent carbon atom represent a non-aromatic heterocyclic ring, wherein if the non-aromatic heterocyclic ring has a nitrogen atom, this nitrogen atom may be substituted with $R^{ZC}$)

[Formula 6]

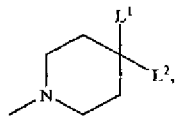

(IV)

(3) one of them represents —H, and the other represents a group represented by —Y—Z, or
(4) —$R^3$ and —$R^4$ taken together with their adjacent carbon atom represent a non-aromatic heterocyclic ring (provided that if the non-aromatic heterocyclic ring has a nitrogen atom, this nitrogen atom may be substituted with —$CO_2$-(lower alkyl which may be substituted with one or more halogens)),
$R^{ZB}$ represents
(1) lower alkyl which may be substituted with one or more groups selected from the group consisting of oxo, —OH, —O-lower alkyl, —S-lower alkyl, halogen and amino which may be substituted with one or two lower alkyls,
$R^{ZC}$ represents
(1) lower alkyl, or
(2) —$CO_2$-(lower alkyl which may be substituted with phenyl),
—Y— represents
(1) piperidine-1,4-diyl which may be substituted with one or more groups selected from the group consisting of lower alkyl and oxo (provided that the benzene ring to which —$R^3$ or —$R^4$ is attached is attached to the nitrogen atom at the 1-position of the piperidine, and —Z is attached to the carbon atom at the 4-position of the piperidine),
(2) piperazine-1,4-diyl which may be substituted with one or more groups selected from the group consisting of lower alkyl and oxo, (3) pyrrolidine-1,3-diyl which may be substituted with one or more groups selected from the group consisting of lower alkyl and oxo (provided that the benzene ring to which —$R^3$ or —$R^4$ is attached is attached to the nitrogen atom at the 1-position of the pyrrolidine, and —Z is attached to the carbon atom at the 3-position of the pyrrolidine),
(4) azetidine-1,3-diyl which may be substituted with one or more groups selected from the group consisting of lower alkyl and oxo (provided that the benzene ring to which —$R^3$ or —$R^4$ is attached is attached to the nitrogen atom at the 1-position of the azetidine, and —Z is attached to the carbon atom at the 3-position of the azetidine),
(5) —O—, or
(6) —N($R^{ZD}$)—,
—$R^{ZD}$ represents
(1) —H, or
(2) lower alkyl,
—Z represents
(1) cyclic amino which may be substituted with one or more groups selected from the group consisting of —$R^{ZE}$, oxo, —OH, —O-lower alkyl, phenyl which may be substituted with halogen, piperidin-1-yl, pyrimidin-2-yl, and amino which may be substituted with one or two lower alkyls,
(2) aryl which may be substituted with one or more groups selected from the group consisting of halogen, lower alkyl which may be substituted with one or more halogens, —O-lower alkyl, and cyano,
(3) cycloalkyl which may be substituted with one or more groups selected from the group consisting of halogen, lower alkyl which may be substituted with one or more halogens, —O-lower alkyl, cyano, and oxo,
(4) an aromatic heterocyclic ring which may be substituted with one or more groups selected from the group consisting of halogen, lower alkyl which may be substituted with one or more halogens, —OH, —O-lower alkyl, and cyano, or
(5) a group of formula (V)

[Formula 7]

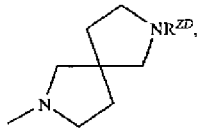

(V)

and
—$R^{ZE}$ represents
(1) lower alkyl which may be substituted with one or more groups selected from the group consisting of oxo, —OH, phenyl which may be substituted with halogen, and amino which may be substituted with one or two lower alkyls).

Unless otherwise specified, when symbols used in one chemical formula are also used in another chemical formula, the same symbols have the same meanings.

The present invention also relates to an inhibitor against the kinase activity of mutant EGFR proteins, which comprises a compound of formula (I) or a salt thereof. In a certain embodiment, the present invention relates to an inhibitor against the kinase activity of EML4-ALK fusion proteins and mutant EGFR proteins.

Moreover, the present invention also relates to a pharmaceutical composition for cancer therapy, which comprises a compound of formula (I) or a salt thereof, i.e., a therapeutic agent for cancer, which comprises a compound of formula (I) or a salt thereof.

Moreover, the present invention also relates to the use of a compound of formula (I) or a salt thereof for the manufacture of a pharmaceutical composition for cancer therapy, the use of a compound of formula (I) or a salt thereof for cancer therapy, as well as a method for cancer therapy, which comprises administering an effective amount of a compound of formula (I) or a salt thereof to a patient.

Advantages of the Invention

The compound of formula (I) or a salt thereof has inhibitory activity against the kinase activity of EML4-ALK fusion proteins and mutant EGFR proteins, as well as growth inhibitory activity against human non-small cell lung cancer cell lines NCI-H2228 and HCC827, and can be used as an active ingredient in pharmaceutical compositions for preventing and/or treating cancer, such as lung cancer in one embodiment, non-small cell lung cancer or small cell lung cancer in another embodiment, EML4-ALK fusion polynucleotide-positive and/or mutant EGFR polynucleotide-positive cancer in yet another embodiment, EML4-ALK fusion polynucleotide-positive and/or mutant EGFR polynucleotide-positive lung cancer in yet another embodiment, or EML4-ALK fusion polynucleotide-positive and/or mutant EGFR polynucleotide-positive non-small cell lung cancer in yet another embodiment.

BRIEF DESCRIPTION OF THE DRAWINGS

FIG. 1 shows the results of the screening for EML4-ALK fusion polynucleotide in specimens of lung cancer patients. Lane "46, XX" shows the result of using peripheral monocytes of a normal healthy female subject, and "ID #2" to "ID #42" show the result of using samples obtained from excised specimens from lung cancer patients. In addition, lane "NTC" shows the result without added substrate cDNA. Lane "marker" is the lane where the size marker DNA was electrophoresed (upper section). The results of amplification of GAPDH cDNA are shown in the lower section. Sex (M, male; F, female), pathology (S, squamous cell carcinoma; A, adenocarcinoma; AS, adenosquamous carcinoma; B, bronchiolo-aleveolar carcinoma) and the presence or absence of EGFR mutation and the presence or absence of smoking history are shown in the upper part of the figure.

Figure 2:
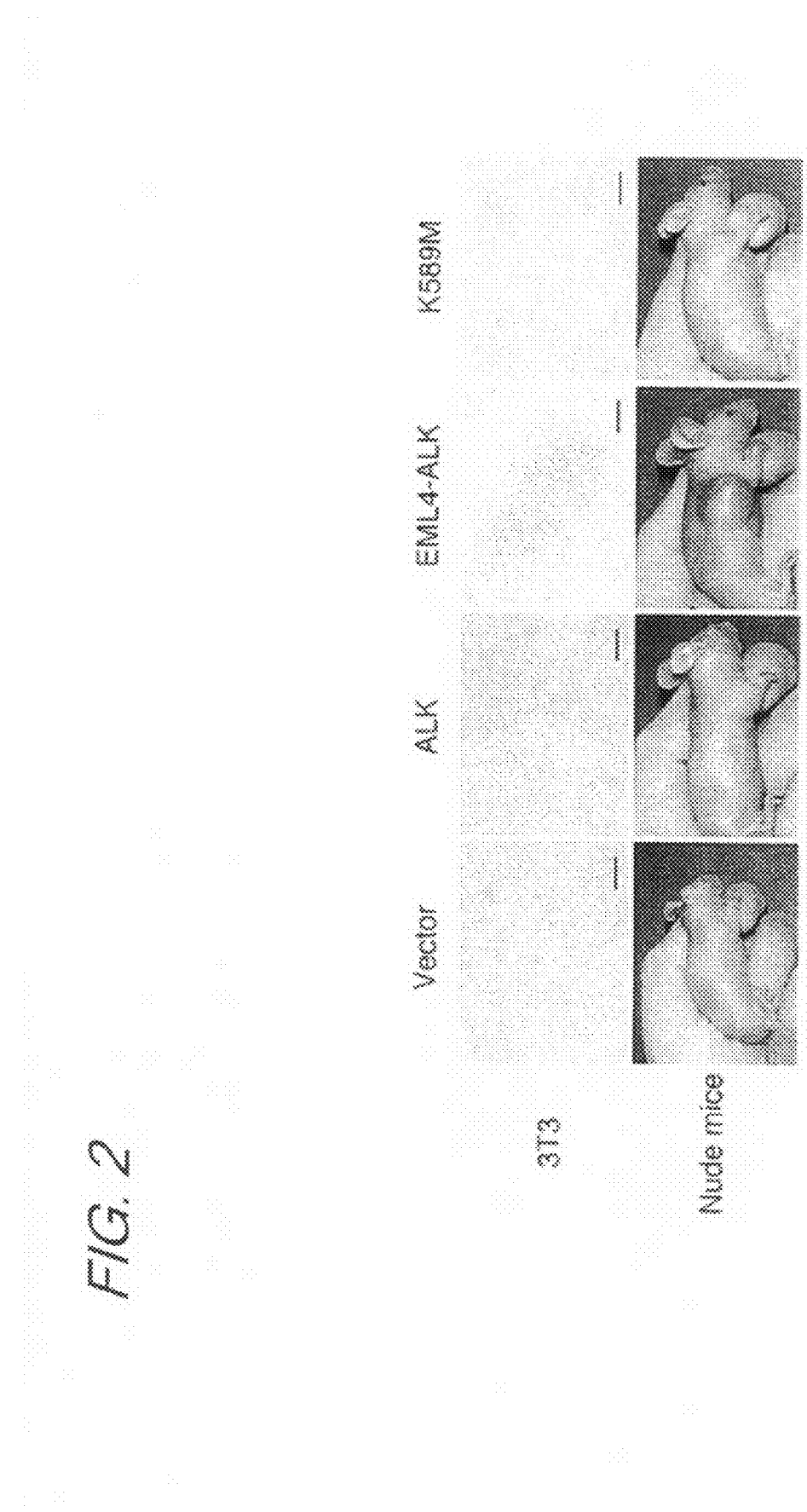
FIG. 2 shows tumorgenicity of the genes. The upper section of the figure (3T3) shows 3T3 fibroblast cells when a blank vector (Vector), and expression plasmid such as full-length ALK/pMXS (ALK), EML4-ALKv1/pMXS (EML4-ALK) or EML4-ALK (K589M)/pMXS were introduced. The scale bar represents 100 μm. The lower section of the figure (Nude mice) shows the result of the inoculation of each 3T3 fibroblast cell line to nude mice.
Figure 1:
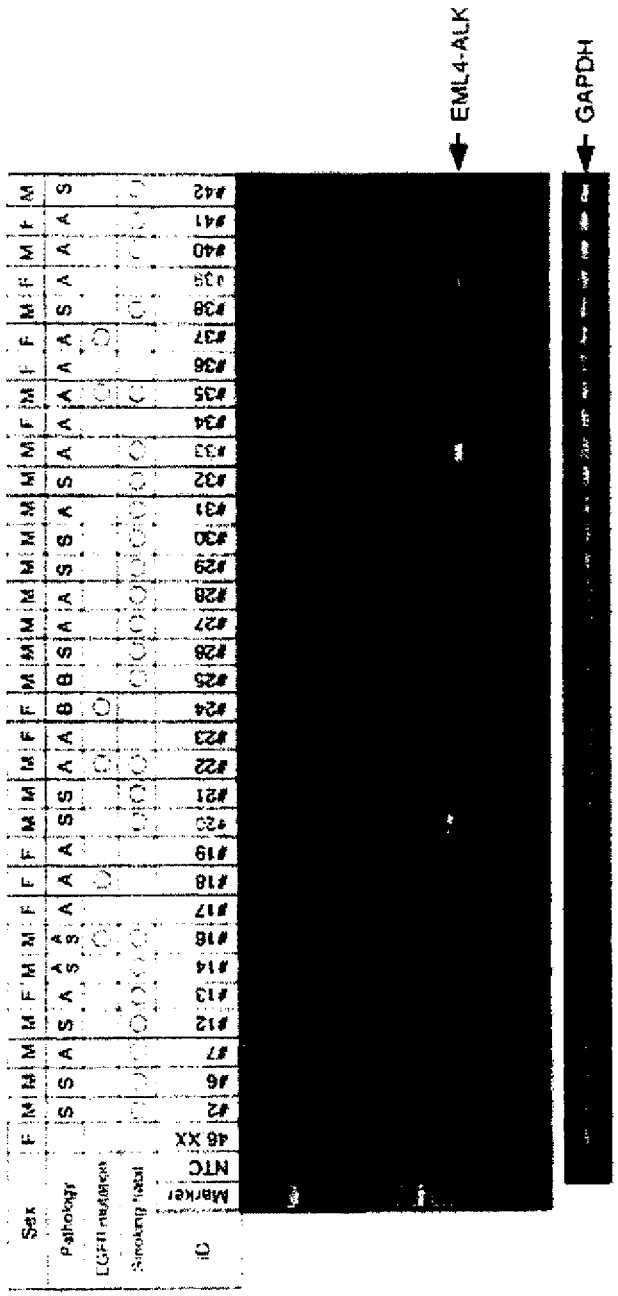
Figure 2:
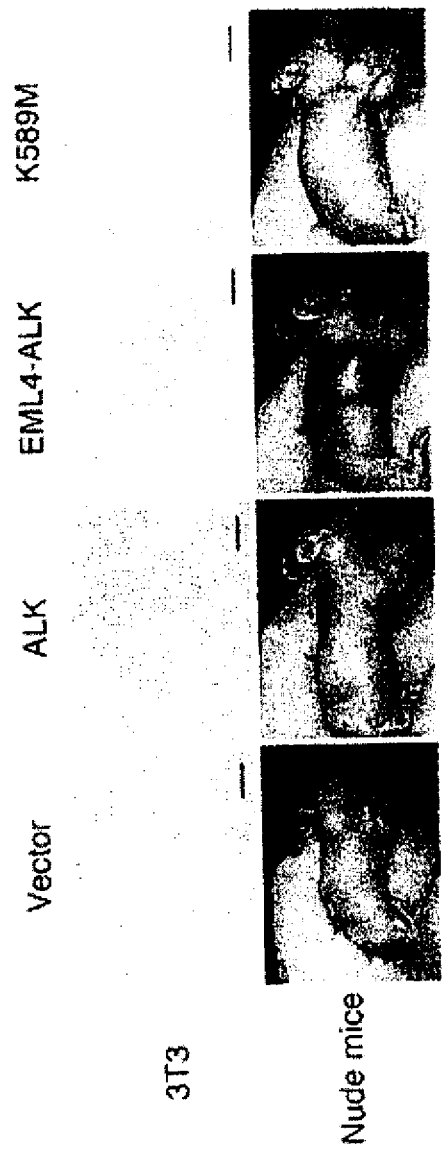

FIG. 2 shows tumorgenicity of the genes. The upper section of the figure (3T3) shows 3T3 fibroblast cells when a blank vector (Vector), and expression plasmid such as full-length ALK/pMXS (ALK), EML4-ALKv1/pMXS (EML4-ALK) or EML4-ALK (K589M)/pMXS were introduced. The scale bar represents 100 μm. The lower section of the figure (Nude mice) shows the result of the inoculation of each 3T3 fibroblast cell line to nude mice.

BEST MODE FOR CARRYING OUT THE INVENTION

The present invention provides the following.
[1] A compound of formula (I) or a salt thereof:

[Formula 8]

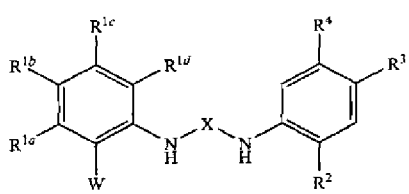

(I)

(wherein the symbols are as defined below:
—X— represents
(1) a group of formula (II), or
(2) a group of formula (III)

[Formula 9]

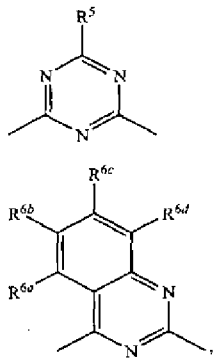

—$R^5$ represents
(1) —H,
(2) —OH,
(3) halogen,
(4) lower alkyl which may be substituted with one or more halogens,
(5) O-lower alkyl which may be substituted with one or more halogens,
(6) —S-lower alkyl,
(7) cyano,
(8) amino which may be substituted with one or two lower alkyls, or
(9) cyclic amino which may be substituted with one or more groups selected from the group consisting of lower alkyl, oxo, —OH, —O-lower alkyl, and amino which may be substituted with one or two lower alkyls (provided that the triazine ring to which —$R^5$ is attached is attached to the nitrogen atom in the cyclic amino),
—$R^{6a}$, —$R^{6b}$, —$R^{6c}$ and —$R^{6d}$, which may be the same or different, each represent
(1) —H,
(2) halogen,
(3) lower alkyl which may be substituted with one or more halogens,
(4) O-lower alkyl which may be substituted with one or more halogens,
(5) —S-lower alkyl, or
(6) cyano,
—W represents
(1) —H,
(2) halogen,
(3) lower alkyl which may be substituted with one or more halogens,
(4) O-lower alkyl which may be substituted with one or more halogens,
(5) —S-lower alkyl,
(6) cyano, or
(7) a group represented by -A-B,
-A- represents
(1) —S(=O)$_2$—, or
(2) —C(=O)—,
—B represents
(1) lower alkyl,
(2) amino which may be substituted with one or two $R^{Z4}$,
(3) cyclic amino (provided that -A- is attached to the nitrogen atom in the cyclic amino), or
(4) cycloalkyl, $R^{ZA}$ represents
(1) lower alkyl, or
(2) cycloalkyl,
—$R^{1a}$, —$R^{1b}$, —$R^{1c}$ and —$R^{1d}$, which may be the same or different, each represent
(1) —H,
(2) halogen,
(3) lower alkyl which may be substituted with one or more halogens,
(4) O-lower alkyl which may be substituted with one or more halogens,
(5) —S-lower alkyl, or
(6) cyano,
or alternatively
if —W is —H, one of —$R^{1a}$ or —$R^{1b}$ is a group represented by -A-B, and the other of —$R^{1a}$ or —$R^{1b}$, and —$R^{1c}$ and —$R^{1d}$, which may be the same or different, each represent any of (1) to (6) shown above,
—$R^2$ represents
(1) —H,
(2) —OH,
(3) halogen,
(4) lower alkyl which may be substituted with one or more halogens,
(5) O-lower alkyl which may be substituted with one or more halogens,
(6) —S-lower alkyl, or
(7) cyano,
—$R^3$ and —$R^4$ are as follows:
(1) one of them represents —H, and the other represents cyclic amino which may be substituted with one or more groups selected from the group consisting of $R^{ZB}$, oxo, —OH, —O-lower alkyl, and amino which may be substituted with one or two $R^{ZB}$ (provided that the benzene ring to which —$R^3$ or —$R^4$ is attached is attached to the nitrogen atom in the cyclic amino),
(2) one of them represents —H, and the other represents a group represented by formula (IV) (provided that -$L^1$ and -$L^2$ taken together with their adjacent carbon atom represent a non-aromatic heterocyclic ring, wherein if the non-aromatic heterocyclic ring has a nitrogen atom, this nitrogen atom may be substituted with $R^{ZC}$)

[Formula 10]

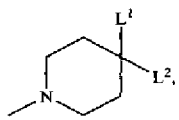

(IV)

(3) one of them represents —H, and the other represents a group represented by —Y—Z, or
(4) —$R^3$ and —$R^4$ taken together with their adjacent carbon atom represent a non-aromatic heterocyclic ring (provided that if the non-aromatic heterocyclic ring has a nitrogen atom, this nitrogen atom may be substituted with —$CO_2$-(lower alkyl which may be substituted with one or more halogens)),
$R^{ZB}$ represents
(1) lower alkyl which may be substituted with one or more groups selected from the group consisting of oxo, —OH, —O-lower alkyl, —S-lower alkyl, halogen and amino which may be substituted with one or two lower alkyls, $R^{ZC}$ represents
(1) lower alkyl, or
(2) —$CO_2$-(lower alkyl which may be substituted with phenyl),
—Y— represents
(1) piperidine-1,4-diyl which may be substituted with one or more groups selected from the group consisting of lower alkyl and oxo (provided that the benzene ring to which —$R^3$ or —$R^4$ is attached is attached to the nitrogen atom at the 1-position of the piperidine, and —Z is attached to the carbon atom at the 4-position of the piperidine),
(2) piperazine-1,4-diyl which may be substituted with one or more groups selected from the group consisting of lower alkyl and oxo,
(3) pyrrolidine-1,3-diyl which may be substituted with one or more groups selected from the group consisting of lower alkyl and oxo (provided that the benzene ring to which —$R^3$ or —$R^4$ is attached is attached to the nitrogen atom at the 1-position of the pyrrolidine, and —Z is attached to the carbon atom at the 3-position of the pyrrolidine),
(4) azetidine-1,3-diyl which may be substituted with one or more groups selected from the group consisting of lower alkyl and oxo (provided that the benzene ring to which —$R^3$ or —$R^4$ is attached is attached to the nitrogen atom at the 1-position of the azetidine, and —Z is attached to the carbon atom at the 3-position of the azetidine),
(5) —O—, or
(6) —N(—$R^{ZD}$)—,
—$R^{ZD}$ represents
(1) —H, or
(2) lower alkyl,
—Z represents
(1) cyclic amino which may be substituted with one or more groups selected from the group consisting of —$R^{ZE}$, oxo, —OH, —O-lower alkyl, phenyl which may be substituted with halogen, piperidin-1-yl, pyrimidin-2-yl, and amino which may be substituted with one or two lower alkyls,
(2) aryl which may be substituted with one or more groups selected from the group consisting of halogen, lower alkyl which may be substituted with one or more halogens, —O-lower alkyl, and cyano,
(3) cycloalkyl which may be substituted with one or more groups selected from the group consisting of halogen, lower alkyl which may be substituted with one or more halogens, —O-lower alkyl, cyano, and oxo,
(4) an aromatic heterocyclic ring which may be substituted with one or more groups selected from the group consisting of halogen, lower alkyl which may be substituted with one or more halogens, —OH, —O-lower alkyl, and cyano, or
(5) a group of formula (V)

[Formula 11]

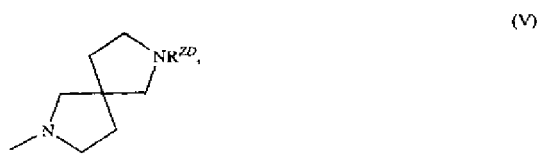

(V)

and
—$R^{ZE}$ represents
(1) lower alkyl which may be substituted with one or more groups selected from the group consisting of oxo, —OH, phenyl which may be substituted with halogen, and amino which may be substituted with one or two lower alkyls).

[2] The compound according to [1] or a salt thereof, wherein

—$R^5$ represents
(1) —H,
(2) —OH,
(3) halogen,
(4) lower alkyl,
(5) amino which may be substituted with one or two lower alkyls, or
(6) cyclic amino (provided that the triazine ring to which —$R^5$ is attached is attached to the nitrogen atom in the cyclic amino), —$R^{6a}$, —$R^{6b}$, —$R^{6c}$ and —$R^{6d}$, which may be the same or different, each represent
(1) —H, or
(2) halogen, —W represents
(1) —H,
(2) halogen, or
(3) a group represented by -A-B, —$R^{1a}$, —$R^{1b}$, —$R^{1c}$ and —$R^{1d}$, which may be the same or different, each represent
(1) —H,
(2) halogen, or
(3) —O-lower alkyl,
or alternatively
if —W is —H, one of —$R^{1a}$ or —$R^{1b}$ is a group represented by -A-B, and the other of —$R^{1a}$ or —$R^{1b}$, and —$R^{1c}$ and —$R^{1d}$, which may be the same or different, each represent any of (1) to (3) shown above, —$R^2$ represents
(1) —H,
(2) —OH,
(3) halogen,
(4) lower alkyl, or
(5) —O-lower alkyl, —$R^3$ and —$R^4$ are as follows:
(1) one of them represents —H, and the other represents cyclic amino which may be substituted with one or more groups selected from the group consisting of $R^{ZB}$, oxo, —OH, and amino which may be substituted with one or two $R^{ZB}$ (provided that the benzene ring to which —$R^3$ or —$R^4$ is attached is attached to the nitrogen atom in the cyclic amino),
(2) one of them represents —H, and the other represents a group represented by formula (IV) (provided that -$L^1$ and -$L^2$ taken together with their adjacent carbon atom represent a non-aromatic heterocyclic ring, wherein if the non-aromatic heterocyclic ring has a nitrogen atom, this nitrogen atom may be substituted with $R^{ZC}$),
(3) one of them represents —H, and the other represents a group represented by —Y—Z, or
(4) —$R^3$ and —$R^4$ taken together with their adjacent carbon atom represent a non-aromatic heterocyclic ring (provided that if the non-aromatic heterocyclic ring has a nitrogen atom, this nitrogen atom may be substituted with —$CO_2$-(lower alkyl which may be substituted with one or more halogens)), —Y— represents
(1) piperidine-1,4-diyl (provided that the benzene ring to which —$R^3$ or —$R^4$ is attached is attached to the nitrogen atom at the 1-position of the piperidine, and —Z is attached to the carbon atom at the 4-position of the piperidine),
(2) piperazine-1,4-diyl,
(3) pyrrolidine-1,3-diyl (provided that the benzene ring to which —$R^3$ or —$R^4$ is attached is attached to the nitrogen atom at the 1-position of the pyrrolidine, and —Z is attached to the carbon atom at the 3-position of the pyrrolidine),
(4) azetidine-1,3-diyl (provided that the benzene ring to which —$R^3$ or —$R^4$ is attached is attached to the nitrogen atom at the 1-position of the azetidine, and —Z is attached to the carbon atom at the 3-position of the azetidine),
(5) —O—, or
(6) —N($R^{ZD}$)—, —Z represents
(1) cyclic amino which may be substituted with one or more groups selected from the group consisting of —$R^{ZE}$, oxo, —OH, phenyl which may be substituted with halogen, piperidin-1-yl, pyrimidin-2-yl, and amino which may be substituted with one or two lower alkyls,
(2) aryl,
(3) cycloalkyl,
(4) an aromatic heterocyclic ring, or
(5) a group of formula (V), and —$R^{ZE}$ represents
(1) lower alkyl which may be substituted with one or more groups selected from the group consisting of oxo, —OH, phenyl, and amino which may be substituted with one or two lower alkyls.

[3] A compound of formula (VI) or a salt thereof:

[Formula 12]

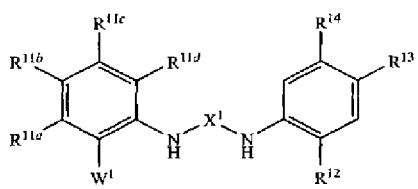

(VI)

(wherein the symbols are as defined below:
—$X^1$—: a group of formula (VII) or (VIII)

[Formula 13]

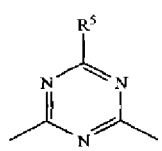

(VII)

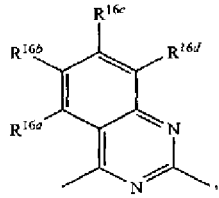

(VIII)

—$R^{15}$: —H, halogen, lower alkyl which may be substituted with one or more halogens, O-lower alkyl which may be substituted with one or more halogens, —S-lower alkyl, cyano, amino which may be substituted with one or two lower alkyls, or cyclic amino which may be substituted with one or more groups selected from the group consisting of lower alkyl, oxo, —OH, —O-lower alkyl, and amino which may be substituted with one or two lower alkyls,

15

—$R^{16a}$, —$R^{16b}$, —$R^{16c}$ and —$R^{16d}$, which may be the same or different: —H, halogen, lower alkyl which may be substituted with one or more halogens, O-lower alkyl which may be substituted with one or more halogens, —S-lower alkyl, or cyano, —$W^1$: halogen, lower alkyl which may be substituted with one or more halogens, O-lower alkyl which may be substituted with one or more halogens, —S-lower alkyl, cyano, or a group represented by -$A^1$-$B^1$, -$A^1$-: —S(=O)$_2$—, or —C(=O)—, —$B^1$: lower alkyl, or amino which may be substituted with one or two lower alkyls, —$R^{11a}$, —$R^{11b}$, —$R^{11c}$ and —$R^{11d}$, which may be the same or different: —H, halogen, lower alkyl which may be substituted with one or more halogens, O-lower alkyl which may be substituted with one or more halogens, —S-lower alkyl, or cyano, —$R^{12}$: halogen, lower alkyl which may be substituted with one or more halogens, O-lower alkyl which may be substituted with one or more halogens, —S-lower alkyl, or cyano, —$R^{13}$ and —$R^{14}$: one of them represents —H, and the other represents cyclic amino which may be substituted with one or more groups selected from the group consisting of lower alkyl, oxo, —OH, —O-lower alkyl, and amino which may be substituted with one or two lower alkyls, or a group represented by —$Y^1$—$Z^1$, —$Y^1$—: piperidine-1,4-diyl or piperazine-1,4-diyl, each of which may be substituted with one or more groups selected from the group consisting of lower alkyl and oxo, or —O— or —N(—$R^Y$)—, provided that if —$R^{13}$ or and —$R^{14}$ is —$Y^1$—$Z^1$ is piperidine-1,4-diyl, the benzene ring to which —$R^{13}$ or —$R^{14}$ is attached is attached to the nitrogen atom at the 1-position of the piperidine, and —$Z^1$ is attached to the carbon atom at the 4-position of the piperidine, and wherein —$R^Y$ represents —H or lower alkyl, and —$Z^1$: cyclic amino which may be substituted with one or more groups selected from the group consisting of lower alkyl, oxo, —OH, —O-lower alkyl, and amino which may be substituted with one or two lower alkyls; aryl which may be substituted with one or more groups selected from the group consisting of halogen, lower alkyl which may be substituted with one or more halogens, —O-lower alkyl, and cyano; cycloalkyl which may be substituted with one or more groups selected from the group consisting of halogen, lower alkyl which may be substituted with one or more halogens, —O-lower alkyl, cyano, and oxo; or an aromatic heterocyclic ring which may be substituted with one or more groups selected from the group consisting of halogen, lower alkyl which may be substituted with one or more halogens, —OH, —O-lower alkyl, and cyano).

[4]
The compound according to [1] or a salt thereof, wherein —$R^{1a}$, —$R^{1b}$, —$R^{1c}$ and —$R^{1d}$ are each —H, —$R^2$ is —O-methyl, and —$R^4$ is —H.

[5]
The compound according to [4] or a salt thereof, wherein —$R^3$ is 4-(4-methylpiperazin-1-yl)piperidin-1-yl.

[6]
The compound according to [5] or a salt thereof, wherein —X— is a group represented by formula (II), and —$R^5$ is —H.

[7]
The compound according to [6] or a salt thereof, wherein —W is a group represented by -A-B, -A- is —S(=O)$_2$—, and —B is isopropyl.

16

[8]
The compound according to [6] or a salt thereof, wherein —W is a group represented by -A-B, -A- is —S(=O)$_2$—, —B is amino which may be substituted with one or two $R^{Z4}$, and $R^{Z4}$ is methyl, ethyl, isopropyl or cyclopropyl.

[9]
The compound according to [1] or a salt thereof, wherein said compound is:
N-ethyl-2-{[4-({2-methoxy-4-[4-(4-methylpiperazin-1-yl)piperidin-1-yl]phenyl}amino)-1,3,5-triazin-2-yl]amino}benzenesulfonamide,
2-{[4-({2-methoxy-4-[4-(4-methylpiperazin-1-yl)piperidin-1-yl]phenyl}amino)-1,3,5-triazin-2-yl]amino}-N,N-dimethylbenzenesulfonamide,
N-isopropyl-2-{[4-({2-methoxy-4-[4-(4-methylpiperazin-1-yl)piperidin-1-yl]phenyl}amino)-1,3,5-triazin-2-yl]amino}benzenesulfonamide,
N-isopropyl-2-{[4-({2-methoxy-4-[4-(4-methylpiperazin-1-yl)piperidin-1-yl]phenyl}amino)-1,3,5-triazin-2-yl]amino}-N-methylbenzenesulfonamide,
2-{[4-({2-methoxy-4-[4-(4-methylpiperazin-1-yl)piperidin-1-yl]phenyl}amino)-1,3,5-triazin-2-yl]amino}-N-methylbenzenesulfonamide,
N-[2-(isopropylsulfonyl)phenyl]-N'-{2-methoxy-4-[3-(4-methylpiperazin-1-yl)azetidin-1-yl]phenyl}-1,3,5-triazine-2,4-diamine,
$N^4$-[2-(isopropylsulfonyl)phenyl]-$N^2$-{2-methoxy-4-[4-(4-methylpiperazin-1-yl)piperidin-1-yl]phenyl}quinazoline-2,4-diamine,
N-[2-(isopropylsulfonyl)phenyl]-N'-{2-methoxy-4-[4-(4-methylpiperazin-1-yl)piperidin-1-yl]phenyl}-1,3,5-triazine-2,4-diamine,
N-[2-(isopropylsulfonyl)phenyl]-N'-(2-methoxy-4-piperazin-1-ylphenyl)-1,3,5-triazine-2,4-diamine,
N-[2-(isopropylsulfonyl)phenyl]-N'-[2-methoxy-4-(1-methyl-1,8-diazaspiro[4.5]decan-8-yl)phenyl]-1,3,5-triazine-2,4-diamine,
N-[2-(isopropylsulfonyl)phenyl]-N'-[2-methoxy-4-(1-methyl-1,9-diazaspiro[5.5]undecan-9-yl)phenyl]-1,3,5-triazine-2,4-diamine,
N-cyclopropyl-2-{[4-({2-methoxy-4-[4-(4-methylpiperazin-1-yl)piperidin-1-yl]phenyl}amino)-1,3,5-triazin-2-yl]amino}benzenesulfonamide,
N-[2-(isopropylsulfonyl)phenyl]-N'-{2-methoxy-4-[methyl(1-methylpiperidin-4-yl)amino]phenyl}-1,3,5-triazine-2,4-diamine,
N-[2-(isopropylsulfonyl)phenyl]-N'-[2-methoxy-4-(4-pyrrolidin-1-ylpiperidin-1-yl)phenyl]-1,3,5-triazine-2,4-diamine,
1-(1-{4-[(4-{[2-(isopropylsulfonyl)phenyl]amino}-1,3,5-triazin-2-yl)amino]-3-methoxyphenyl}piperidin-4-yl)pyrrolidin-3-ol,
N-[2-(isopropylsulfonyl)phenyl]-N'-[2-methoxy-4-(4-methylpiperazin-1-yl)phenyl]-1,3,5-triazine-2,4-diamine, or
$N^4$-[2-(isopropylsulfonyl)phenyl]-$N^2$-{2-methoxy-4-[4-(1-methylpiperidin-4-yl)piperazin-1-yl]phenyl}quinazoline-2,4-diamine.

[10]
The compound according to [9] or a salt thereof, wherein said compound is:
N-ethyl-2-{[4-({2-methoxy-4-[4-(4-methylpiperazin-1-yl)piperidin-1-yl]phenyl}amino)-1,3,5-triazin-2-yl]amino}benzenesulfonamide,
2-{[4-({2-methoxy-4-[4-(4-methylpiperazin-1-yl)piperidin-1-yl]phenyl}amino)-1,3,5-triazin-2-yl]amino}-N,N-dimethylbenzenesulfonamide, N-isopropyl-2-{[4-({2-methoxy-4-[4-(4-methylpiperazin-1-yl)piperidin-1-yl]phenyl}amino)-1,3,5-triazin-2-yl]amino}benzenesulfonamide, N-isopropyl-2-{[4-({2-methoxy-4-[4-(4-methylpiperazin-1-yl)piperidin-1-yl]phenyl}amino)-1,3,5-triazin-2-yl]amino}-N-methylbenzenesulfonamide, 2-{[4-({2-methoxy-4-[4-(4-methylpiperazin-1-yl)piperidin-1-yl]phenyl}amino)-1,3,5-triazin-2-yl]amino}-N-methylbenzenesulfonamide, N-[2-(isopropylsulfonyl)phenyl]-N'-{2-methoxy-4-[3-(4-methylpiperazin-1-yl)azetidin-1-yl]phenyl}-1,3,5-triazine-2,4-diamine, $N^4$-[2-(isopropylsulfonyl)phenyl]-$N^2$-{2-methoxy-4-[4-(4-methylpiperazin-1-yl)piperidin-1-yl]phenyl}quinazoline-2,4-diamine, or N-[2-(isopropylsulfonyl)phenyl]-N'-{2-methoxy-4-[4-(4-methylpiperazin-1-yl)piperidin-1-yl]phenyl}-1,3,5-triazine-2,4-diamine.

[11]

The compound according to [10] or a salt thereof, wherein said compound is:

N-ethyl-2-{[4-({2-methoxy-4-[4-(4-methylpiperazin-1-yl)piperidin-1-yl]phenyl}amino)-1,3,5-triazin-2-yl]amino}benzenesulfonamide, 2-{[4-({2-methoxy-4-[4-(4-methylpiperazin-1-yl)piperidin-1-yl]phenyl}amino)-1,3,5-triazin-2-yl]amino}-N,N-dimethylbenzenesulfonamide, or N-[2-(isopropylsulfonyl)phenyl]-N'-{2-methoxy-4-[4-(4-methylpiperazin-1-yl)piperidin-1-yl]phenyl}-1,3,5-triazine-2,4-diamine.

[12]

The compound according to [11] or a salt thereof, wherein said compound is:

N-[2-(isopropylsulfonyl)phenyl]-N'-{2-methoxy-4-[4-(4-methylpiperazin-1-yl)piperidin-1-yl]phenyl}-1,3,5-triazine-2,4-diamine.

[13]

A pharmaceutical composition, which comprises the compound according to [1] or a salt thereof and a pharmaceutically acceptable excipient.

[14]

An inhibitor against the kinase activity of EML4-ALK fusion proteins and mutant EGFR proteins, which comprises the compound according to [1] or a salt thereof.

[15]

A pharmaceutical composition for preventing or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer, which comprises the compound according to [1] or a salt thereof.

[16]

Use of the compound according to [1] or a salt thereof for the manufacture of a pharmaceutical composition for preventing or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer.

[17]

The compound according to [1] or a salt thereof, which is used as an active ingredient in a pharmaceutical composition for preventing or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer.

[18]

A method for preventing or treating cancer, lung cancer, non-small cell lung cancer, small cell lung cancer, EML4-ALK fusion polynucleotide-positive and/or mutant EGFR polynucleotide-positive cancer, EML4-ALK fusion polynucleotide-positive and/or mutant EGFR polynucleotide-positive lung cancer, or EML4-ALK fusion polynucleotide-positive and/or mutant EGFR polynucleotide-positive non-small cell lung cancer, which comprises administering an effective amount of the compound according to [1] or a salt thereof to a patient.

The present invention will now be described in more detail below.

As used herein, the term "halogen" means F, Cl, Br or I.

The term "lower alkyl" refers to linear or branched alkyl containing 1 to 6 carbon atoms (hereinafter abbreviated as "$C_{1-6}$"). Examples include methyl, ethyl, n-propyl, isopropyl, n-butyl, isobutyl, sec-butyl, tert-butyl, n-pentyl, n-hexyl, and the like. Another embodiment is $C_{1-4}$ alkyl, and yet another embodiment is methyl, ethyl or isopropyl.

The term "cyclic amino" refers to a monovalent group of a 3- to 8-membered monocyclic non-aromatic cyclic amine which has at least one nitrogen atom and may further have the same or different one or more heteroatoms selected from the group consisting of nitrogen, oxygen and sulfur, wherein its at least one nitrogen atom has a binding hand. Specific examples include aziridinyl, azetidinyl, pyrrolidinyl, piperidinyl, azepanyl, azocanyl, piperazinyl, homopiperazinyl, morpholinyl, oxazepanyl, thiomorpholinyl, thiazepanyl, and the like. Alternatively, another embodiment is a monovalent group of a 5- or 6-membered monocyclic non-aromatic cyclic amine. It should be noted that such a ring may be a bridged cyclic amino group, as exemplified by 2,5-diazabicyclo[2.2.1]heptane and the like, or may have an unsaturated bond in part of the ring, as exemplified by dihydropyrrolyl, tetrahydropyridyl, tetrahydropyrazyl, or the like.

The term "non-aromatic heterocyclic ring" refers to a 5- to 10-membered monocyclic non-aromatic heterocyclic ring which has 1 to 4 heteroatoms selected from the group consisting of nitrogen, oxygen and sulfur. Examples include aziridine, azetidine, pyrrolidine, piperidine, azepane, azocane, piperazine, homopiperazine, morpholine, oxazepane, thiomorpholine, thiazepane, tetrahydropyran, tetrahydrofuran, dioxane, dioxolane, and the like. Another embodiment is a 5- or 6-membered monocyclic non-aromatic cyclic amine, including pyrrolidine, piperidine, piperazine, morpholine, thiomorpholine, and the like. It should be noted that such a ring may have an unsaturated bond in part of the ring, as exemplified by dihydropyrrole, tetrahydropyridine, tetrahydropyrazine, or the like.

The term "aryl" refers to a $C_{6-14}$ monocyclic to tricyclic aromatic hydrocarbon group, including phenyl, naphthyl, and the like. Another embodiment is phenyl.

The term "cycloalkyl" refers to an optionally bridged $C_{3-10}$ saturated cyclic hydrocarbon group, including cyclopropyl, cyclobutyl, cyclopentyl, cyclohexyl, cycloheptyl, cyclooctyl, adamantyl, and the like. Other examples include those partially unsaturated, such as cyclohexenyl, cyclooctadienyl, and the like. Further examples include those in which one or two methylene groups on the ring are replaced with —O—, as exemplified by tetrahydropyranyl, tetrahydrofuranyl, dioxanyl, and the like. Still further examples include these rings which are each condensed with a benzene ring, as exemplified by indanyl, tetrahydronaphthyl, indenyl, dihydronaphthyl, dihydrochromenyl, and the like.

The term "aromatic heterocyclic ring" refers to a monovalent group of a 5- to 10-membered monocyclic or bicyclic aromatic heterocyclic ring which has 1 to 4 heteroatoms selected from the group consisting of nitrogen, oxygen and sulfur. Examples include pyridyl, pyrrolyl, pyrazinyl, pyrimidinyl, pyridazinyl, imidazolyl, thiazolyl, oxazolyl, thienyl, furyl, indolyl, benzimidazolyl, quinolyl, isoquinolyl, quinazolinyl, quinoxalinyl, phthalazinyl, benzothiazolyl, benzoxazolyl, and the like. Another embodiment is pyridyl, pyrazinyl, pyrimidinyl, quinolyl, isoquinolyl, quinazolinyl, quinoxalinyl or phthalazinyl, and yet another embodiment is pyridyl.

The phrase "which may be substituted" is intended to include both "substituted" and "unsubstituted" embodiments. When substituted with a plurality of groups, these groups may be the same or different from each other.

The phrase "lower alkyl which may be substituted with one or more halogens" refers to, for example, lower alkyl which may be substituted with the same or different 1 to 7 halogens. Another embodiment is lower alkyl which may be substituted with 1 to 5 halogens. Yet another embodiment is lower alkyl which may be substituted with 1 to 3 halogens.

In the phrase "amino which may be substituted with one or two $R^{Z4}$," when this amino is substituted with two $R^{Z4}$, these two $R^{Z4}$ substituents may be the same or different from each other.

Some embodiments of the present invention are given below.

(1) Compounds of formula (I), wherein —$R^{1a}$, —$R^{1b}$, —$R^{1c}$ and —$R^{1d}$ are each —H.

(2) Compounds of formula (I), wherein
(2-1) —$R^2$ is —O-lower alkyl, or
(2-2) —$R^2$ is —O-methyl.

(3) Compounds of formula (I), wherein
(3-1) —$R^3$ is cyclic amino which may be substituted with lower alkyl (provided that the benzene ring to which —$R^3$ is attached is attached to the nitrogen atom in the cyclic amino),
(3-2) —$R^3$ is piperazinyl which may be substituted with lower alkyl (provided that the benzene ring to which —$R^3$ is attached is attached to a nitrogen atom in the piperazine),
(3-3) —$R^3$ is piperazinyl which may be substituted with methyl (provided that the benzene ring to which —$R^3$ is attached is attached to a nitrogen atom in the piperazine),
(3-4) —$R^3$ is 4-methylpiperazin-1-yl,
(3-5) —$R^3$ is a group represented by formula (IV), in which -$L^1$ and -$L^2$ taken together represent cyclic amino which may be substituted with lower alkyl,
(3-6) —$R^3$ is a group represented by formula (IV), in which -$L^1$ and -$L^2$ taken together represent pyrrolidine or piperidine which may be substituted with lower alkyl,
(3-7) —$R^3$ is a group represented by formula (IV), in which -$L^1$ and -$L^2$ taken together represent pyrrolidine or piperidine which may be substituted with methyl,
(3-8) —$R^3$ is a group represented by —Y—Z, in which —Y— is piperidine-1,4-diyl, piperazine-1,4-diyl, azetidine-1,3-diyl or —N(-lower alkyl)-, and —Z is cyclic amino which may be substituted with one or more groups selected from the group consisting of lower alkyl and —OH,
(3-9) —$R^3$ is a group represented by —Y—Z, in which —Y— is piperidine-1,4-diyl, piperazine-1,4-diyl, azetidine-1,3-diyl or —N(-methyl)-, and —Z is piperazinyl, piperidinyl or pyrrolidinyl which may be substituted with one or more groups selected from the group consisting of methyl and —OH, or
(3-10) —$R^3$ is 4-(4-methylpiperazin-1-yl)piperidin-1-yl.

(4) Compounds of formula (I), wherein —$R^4$ is —H.

(5) Compounds of formula (I), wherein
(5-1) —X— is a group represented by formula (II), and —$R^5$ is —H, or
(5-2) —X— is a group represented by formula (III), and —$R^{6a}$, —$R^{6b}$, —$R^{6c}$ and —$R^{6d}$ are each —H.

(6) Compounds of formula (I), wherein
(6-1) —W is a group represented by -A-B, in which -A- is —S(=O)$_2$—, and —B is lower alkyl,
(6-2) —W is a group represented by -A-B, in which -A- is —S(=O)$_2$—, and —B is isopropyl, or
(6-3) —W is a group represented by -A-B, in which -A- is —S(=O)$_2$—, and —B is amino which may be substituted with one or two $R^{Z4}$, and $R^{Z4}$ is methyl, ethyl, isopropyl or cyclopropyl.

(7) Compounds, in which any combination of two or more of (1) to (6) shown above is applied.

(8) Compounds of formula (VI), wherein —$R^{11a}$, —$R^{11b}$, —$R^{11c}$ and —$R^{11d}$ are each —H.

(9) Compounds of formula (VI), wherein
(9-1) —$R^{12}$ is —O-lower alkyl, or
(9-2) —$R^{12}$ is —O-methyl.

(10) Compounds of formula (VI), wherein
(10-1) —$R^{13}$ is cyclic amino which may be substituted with lower alkyl (provided that the benzene ring to which —$R^{13}$ is attached is attached to the nitrogen atom in the cyclic amino),
(10-2) —$R^{13}$ is piperazinyl which may be substituted with lower alkyl (provided that the benzene ring to which —$R^{13}$ is attached is attached to a nitrogen atom in the piperazine),
(10-3) —$R^{13}$ is piperazinyl which may be substituted with methyl (provided that the benzene ring to which —$R^{13}$ is attached is attached to a nitrogen atom in the piperazine),
(10-4) —$R^{13}$ is 4-methylpiperazin-1-yl,
(10-5) —$R^{13}$ is a group represented by —$Y^1$—$Z^1$, in which —$Y^1$— is piperidine-1,4-diyl, piperazine-1,4-diyl or —N(-lower alkyl)-, and —$Z^1$ is cyclic amino which may be substituted with one or more groups selected from the group consisting of lower alkyl and —OH,
(10-6) —$R^{13}$ is a group represented by —$Y^1$—$Z^1$, in which —$Y^1$— is piperidine-1,4-diyl, piperazine-1,4-diyl or —N(-methyl)-, and —$Z^1$ is piperazinyl, piperidinyl or pyrrolidinyl which may be substituted with one or more groups selected from the group consisting of methyl and —OH, or
(10-7) —$R^{13}$ is 4-(4-methylpiperazin-1-yl)piperidin-1-yl.

(11) Compounds of formula (VI), wherein —$R^{14}$ is —H.

(12) Compounds of formula (VI), wherein
(12-1) —$X^1$— is a group represented by formula (VII), and —$R^{15}$ is —H, or
(12-2) —$X^1$— is a group represented by formula (VIII), and —$R^{16a}$, —$R^{16b}$, —$R^{16c}$ and —$R^{16d}$ are each —H.

(13) Compounds of formula (VI), wherein
(13-1) —$W^1$ is a group represented by -$A^1$-$B^1$, in which -$A^1$- is —S(=O)$_2$—, and —$B^1$ is lower alkyl,
(13-2) —$W^1$ is a group represented by -$A^1$-$B^1$, in which -$A^1$- is —S(=O)$_2$—, and —$B^1$ is isopropyl, or
(13-3) —$W^1$ is a group represented by -$A^1$-$B^1$, in which -$A^1$- is —S(=O)$_2$—, and —$B^1$ is amino which may be substituted with one or two lower alkyls.

(14) Compounds, in which any combination of two or more of (8) to (13) shown above is applied.

Examples of specific compounds falling within the present invention include those selected from compound groups P, Q, R and S shown below.

Compound group P:

a group consisting of N-[2-(isopropylsulfonyl)phenyl]-N'-{2-methoxy-4-[4-(4-methylpiperazin-1-yl)piperidin-1-yl]phenyl}-1,3,5-triazine-2,4-diamine and salts of this compound.

Compound group Q:

a group consisting of N-ethyl-2-{[4-({2-methoxy-4-[4-(4-methylpiperazin-1-yl)piperidin-1-yl]phenyl}amino)-1,3,5-triazin-2-yl]amino}benzenesulfonamide, and 2-{[4-({2-methoxy-4-[4-(4-methylpiperazin-1-yl)piperidin-1-yl]phenyl}amino)-1,3,5-triazin-2-yl]amino}-N,N-dimethylbenzenesulfonamide, as well as salts of these compounds.

Compound group R:

a group consisting of N-isopropyl-2-{[4-({2-methoxy-4-[4-(4-methylpiperazin-1-yl)piperidin-1-yl]phenyl}amino)-1,3,5-triazin-2-yl]amino}benzenesulfonamide, N-isopropyl-2-{[4-({2-methoxy-4-[4-(4-methylpiperazin-1-yl)piperidin-1-yl]phenyl}amino)-1,3,5-triazin-2-yl]amino}-N-methylbenzenesulfonamide, 2-{[4-({2-methoxy-4-[4-(4-methylpiperazin-1-yl)piperidin-1-yl]phenyl}amino)-1,3,5-triazin-2-yl]amino}-N-methylbenzenesulfonamide, N-[2-(isopropylsulfonyl)phenyl]-N'-{2-methoxy-4-[3-(4-methylpiperazin-1-yl)azetidin-1-yl]phenyl}-1,3,5-triazine-2,4-diamine, and $N^4$-[2-(isopropylsulfonyl)phenyl]-$N^2$-{2-methoxy-4-[4-(4-methylpiperazin-1-yl)piperidin-1-yl]phenyl}quinazoline-2,4-diamine, as well as salts of these compounds.

Compound group S:

a group consisting of N-[2-(isopropylsulfonyl)phenyl]-N'-(2-methoxy-4-piperazin-1-ylphenyl)-1,3,5-triazine-2,4-diamine, N-[2-(isopropylsulfonyl)phenyl]-N'-[2-methoxy-4-(1-methyl-1,8-diazaspiro[4.5]decan-8-yl)phenyl]-1,3,5-triazine-2,4-diamine, N-[2-(isopropylsulfonyl)phenyl]-N'-[2-methoxy-4-(1-methyl-1,9-diazaspiro[5.5]undecan-9-yl)phenyl]-1,3,5-triazine-2,4-diamine, N-cyclopropyl-2-{[4-({2-methoxy-4-[4-(4-methylpiperazin-1-yl)piperidin-1-yl]phenyl}amino)-1,3,5-triazin-2-yl]amino}benzenesulfonamide, N-[2-(isopropylsulfonyl)phenyl]-N'-{2-methoxy-4-[methyl(1-methylpiperidin-4-yl)amino]phenyl}-1,3,5-triazine-2,4-diamine, N-[2-(isopropylsulfonyl)phenyl]-N'-[2-methoxy-4-(4-pyrrolidin-1-ylpiperidin-1-yl)phenyl]-1,3,5-triazine-2,4-diamine, 1-(1-{4-[(4-{[2-(isopropylsulfonyl)phenyl]amino}-1,3,5-triazin-2-yl)amino]-3-methoxyphenyl}piperidin-4-yl)pyrrolidin-3-ol, N-[2-(isopropylsulfonyl)phenyl]-N'-[2-methoxy-4-(4-methylpiperazin-1-yl)phenyl]-1,3,5-triazine-2,4-diamine, and $N^4$-[2-(isopropylsulfonyl)phenyl]-$N^2$-{2-methoxy-4-[4-(1-methylpiperidin-4-yl)piperazin-1-yl]phenyl}quinazoline-2,4-diamine, as well as salts of these compounds.

The compounds of formula (I) may have tautomers and/or geometrical isomers, depending on the type of their substituents. Even when the compounds of formula (I) appear herein only in one isomer form, the present invention encompasses the other isomers, and also encompasses separated isomers or mixtures thereof.

Further, since some compounds of formula (I) have an asymmetric carbon atom or axial asymmetry, optical isomers based on this asymmetry may also exist. The present invention also encompasses separated optical isomers of the compounds of formula (I) or mixtures thereof.

Furthermore, the present invention encompasses pharmaceutically acceptable prodrugs of the compounds represented by formula (I). The term "pharmaceutically acceptable prodrug" refers to a compound having a group which can be converted into an amino group, a hydroxyl group, a carboxyl group or the like by solvolysis or under physiological conditions. Examples of a prodrug-forming group include those described in Prog. Med., 5, 2157-2161 (1985) or those described in "Development of Pharmaceuticals" (Hirokawa Publishing, 1990) vol. 7, Molecular Design 163-198.

Likewise, salts of the compounds of formula (I) are pharmaceutically acceptable salts of the compounds of formula (I). The compounds of formula (I) may form acid or base addition salts, depending on the type of their substituents. Specific examples include acid addition salts with inorganic acids (e.g., hydrochloric acid, hydrobromic acid, hydroiodic acid, sulfuric acid, nitric acid, phosphoric acid, and the like) or with organic acids (e.g., formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like), salts with inorganic bases (e.g., sodium, potassium, magnesium, calcium, aluminum, and the like) or with organic bases (e.g., methylamine, ethylamine, ethanolamine, lysine, ornithine, and the like), salts with various amino acids and amino acid derivatives (e.g., acetylleucine, and the like), as well as ammonium salt, etc.

Moreover, the present invention also encompasses the compounds of formula (I) and salts thereof in the form of various hydrates, solvates, and crystalline polymorphic substances. The present invention also encompasses the compounds labeled with various radioactive or non-radioactive isotopes.

The compounds of formula (I) and pharmaceutically acceptable salts thereof can be prepared by applying various known synthesis methods on the basis of characteristics derived from their skeletal structure or the type of their substituents. In some cases, depending on the type of functional group, it is technically effective to replace such a functional group with an appropriate protecting group (a group which can be easily converted into the original functional group) at the starting material stage or at the intermediate stage. Examples of such a protecting group include those described in Greene and Wuts, "Protective Groups in Organic Synthesis (third edition, 1999)" and so on, which may be selected and used as appropriate, depending on reaction conditions. In such a method, after introduction of the protecting group and subsequent reaction, the protecting group may be removed if necessary to obtain a desired compound.

Likewise, a prodrug of the compound of formula (I) can be prepared by introducing a specific group at the starting material stage or at the intermediate stage, as in the case of the above protecting group, or by subjecting the obtained compound of formula (I) to further reaction. The reaction may be accomplished by applying conventional esterification, amidation, dehydration or other techniques known to those skilled in the art.

Explanation will be given below of typical processes for preparing the compounds of formula (I). Each process may also be accomplished by reference to the documents cited in this explanation. It should be noted that the processes of the present invention are not limited to the examples illustrated below.

(Preparation Process 1)

[Formula 14]

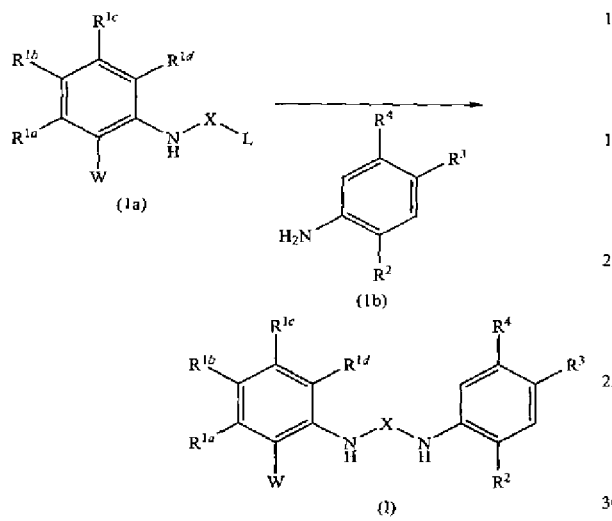

(wherein -L represents a leaving group (the same applying hereinafter))

This process is intended to prepare the compound (I) of the present invention by reacting compound (1a) having a leaving group with aniline derivative (1b). Examples of a leaving group used for this purpose include halogen (e.g., F, Cl, and the like), sulfonyloxy (e.g., methanesulfonyloxy, p-toluenesulfonyloxy, trifluoromethanesulfonyloxy, and the like), as well as lower alkylsulfanyl or lower alkanesulfonyl.

In this reaction, compound (1a) having a leaving group and aniline derivative (1b) are used in equal amounts or one of them is used in an excessive amount. A mixture of these compounds is stirred in a solvent inert to the reaction or in the absence of a solvent under cooling to reflux conditions, preferably at 0° C. to 80° C., generally for 0.1 hours to 5 days. Examples of a solvent used for this purpose include, but are not particularly limited to, aromatic hydrocarbons (e.g., benzene, toluene, xylene, and the like), ethers (e.g., diethyl ether, tetrahydrofuran, dioxane, dimethoxyethane, and the like), halogenated hydrocarbons (e.g., dichloromethane, 1,2-dichloroethane, chloroform, and the like), alcohols (e.g., methanol, ethanol, 2-propanol, and the like), N,N-dimethylformamide, dimethyl sulfoxide, ethyl acetate, acetonitrile, and mixtures thereof. The reaction may be performed in the presence of an organic base (e.g., triethylamine, N,N-diisopropylethylamine, N-methylmorpholine, or the like) or an inorganic base (e.g., potassium carbonate, sodium carbonate, potassium hydroxide, or the like), because it is advantageous for smooth reaction in some cases.

When the reaction is performed in the presence of such a base as shown above, depending on the properties or the like of starting compounds, the desired reaction is impossible or difficult to proceed, for example, due to decomposition or the like of the starting compounds. In this case, the reaction may be performed in the presence of a mineral acid (e.g., hydrochloric acid, hydrobromic acid, and the like), an organic acid (e.g., acetic acid, propionic acid, and the like) or a sulfonic acid (e.g., methanesulfonic acid, p-toluenesulfonic acid, and the like), because it is advantageous for smooth reaction in some cases.

[Documents]
S. R. Sandler and W. Karo, "Organic Functional Group Preparations," second edition, vol. 1, Academic Press Inc., 1991

The Chemical Society of Japan, "Fifth Series of Experimental Chemistry," vol. 14 (2005) (MARUZEN Co., Ltd., Japan)

(Preparation Process 2)

[Formula 15]

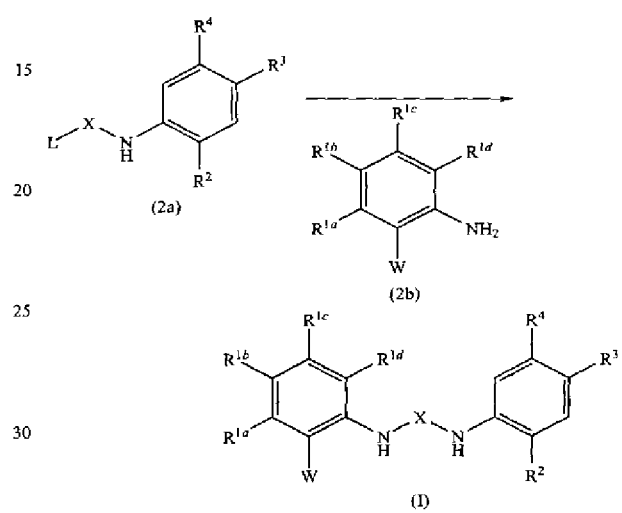

This process is intended to prepare the compound (I) of the present invention by reacting compound (2a) having a leaving group with aniline derivative (2b).

In this reaction, the procedure of Preparation Process 1 may be applied.

(Starting Material Synthesis)

[Formula 16]

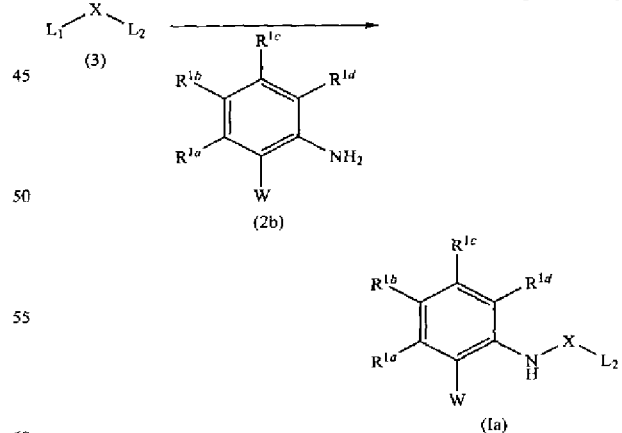

(wherein $L_1$ and $L_2$ each represent a leaving group selected from the members of L shown above (the same applying hereinafter))

This process is intended to prepare compound (1a) by reacting compound (3) having leaving groups with aniline derivative (2b).

In this reaction, the procedure of Preparation Process 1 may be applied.

[Formula 17]

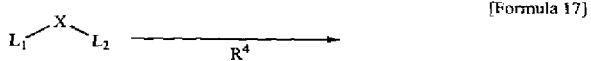

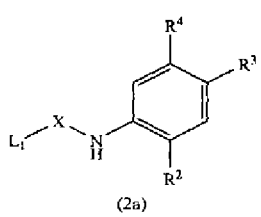

This process is intended to prepare compound (2a) by reacting compound (3) having leaving groups with aniline derivative (1b).

In this reaction, the procedure of Preparation Process 1 may be applied.

The compound of formula (I) is isolated and purified as a free compound or as a pharmaceutically acceptable salt, hydrate, solvate or crystalline polymorphic substance thereof. A pharmaceutically acceptable salt of the compound of formula (I) may also be prepared by being subjected to conventional salt-forming reaction.

Isolation and purification may be accomplished by applying conventional chemical operations such as extraction, fractional crystallization, various types of fractionation chromatography, etc.

Various isomers can be prepared by selecting appropriate starting compounds or can be separated on the basis of differences in the physical and chemical properties of isomers. For example, optical isomers can be derived into optically pure isomers by conventional optical resolution techniques (e.g., fractional crystallization resulting in a diastereomer salt with an optically active base or acid, chromatography on a chiral column or the like, and the like). They can also be prepared from appropriate optically active starting compounds.

The compounds of formula (I) were confirmed for their pharmacological activity in the following tests. Unless otherwise specified, the test examples shown below may be accomplished in a known manner and, when using commercially available reagents, kits, or the like, may be accomplished in accordance with the instructions attached to these commercially available products.

TEST EXAMPLE 1

Evaluation of Inhibitory Activity Against the Kinase Activity of EML4-ALK Fusion Protein v1

EML4-ALK fusion protein v1 (purified from BA/F3 cells expressing EML4-ALK fusion protein v1) was investigated for its phosphorylation activity toward a peptide substrate by using a kinase activity detection kit (HTRF KinEASE-TK; Cisbio Inc.). Test compounds were each added to a reaction solution containing the enzyme protein to give 8 final concentrations from 1000 nM to 0.3 nM (100 nM to 0.03 nM for TAE684), followed by addition of ATP and reaction for 1 hour. The ATP concentration used was 100 μM. Another reaction solution was prepared to contain the enzyme protein but no test compound (in which the solvent DMSO alone was added at 0.4% in place of the test compound), followed by reaction in the same manner with or without ATP addition. In the absence of the test compound, the phosphorylation count without ATP addition and with ATP addition was assumed to be 100% inhibition and 0% inhibition, respectively. The concentration causing 50% inhibition ($IC_{50}$) was calculated for each test compound by the logistic regression method.

As a result, the compounds of the present invention and TAE684 were found to have inhibitory activity against the kinase activity of EML4-ALK fusion protein v1. Table 1 shows the $IC_{50}$ values obtained for some compounds of the present invention and TAE684. Ex denotes Example No.

TABLE 1

| Ex | $IC_{50}$(nM) | Ex | $IC_{50}$(nM) |
|---|---|---|---|
| 1 | 42 | 128 | 2.3 |
| 23 | 17 | 12 | 61 |
| 24 | 29 | 149 | 40 |
| 45 | 66 | 166 | 49 |
| 52 | 72 | 7 | 50 |
| 58 | 25 | 171 | 33 |
| 63 | 26 | 176 | 150 |
| 72 | 51 | TAE684 | 0.63 |
| 120 | 74 | | |
| 123 | 33 | | |

TEST EXAMPLE 2

Evaluation of Inhibitory Activity Against the Kinase Activity of Mutant EGFR (L858R) Protein Mutant EGFR (L858R) protein (Carna Biosciences Inc., Japan) was investigated for its phosphorylation activity toward a peptide substrate by using a kinase activity detection kit (HTRF KinEASE-TK; Cisbio Inc.). Test compounds were each added to a reaction solution containing the enzyme protein to give 8 final concentrations from 10000 nM to 3 nM, followed by addition of ATP and reaction for 1 hour. The ATP concentration used was 5 μM. Another reaction solution was prepared to contain the enzyme protein but no test compound (in which the solvent DMSO alone was added at 0.4% in place of the test compound), followed by reaction in the same manner with or without ATP addition. In the absence of the test compound, the phosphorylation count without ATP addition and with ATP addition was assumed to be 100% inhibition and 0% inhibition, respectively. The concentration causing 50% inhibition ($IC_{50}$) was calculated for each test compound by the logistic regression method.

As a result, the compounds of the present invention and TAE684 were found to have inhibitory activity against the kinase activity of mutant EGFR (L858R) protein. Table 2 shows the $IC_{50}$ values obtained for some compounds of the present invention and TAE684. Ex denotes Example No.

TABLE 2

| Ex | $IC_{50}$(nM) |
|---|---|
| 23 | 120 |
| 123 | 100 |
| 128 | 98 |
| TAE684 | 92 |

27
TEST EXAMPLE 3

Evaluation of Inhibitory Effect Against Anchorage-Independent Cell Growth of Human Non-Small Cell Lung Cancer Cell Line NCI-H2228 Cells (EML4-ALK Fusion Protein-Expressing Cells)

Measurement for anchorage-independent cell growth (colony method, etc) has been known to be a system for investigating the anticancer action (pharmacological effect) of test compounds (Clinical Oncology, second edition, Cancer and Chemotherapy Publishers Inc.). In place of the colony method, there is a following method using spheroid plates for measuring the growth of non-attached cells.

In a 96-well spheroid plate (Sumilon Celltight Spheroid 96U; Sumitomo Bakelite Co., Ltd., Japan), human non-small cell lung cancer cell line NCI-H2228 cells were seeded at 2000 cells per well in RPMI1640 medium (Invitrogen) containing 10% fetal bovine serum. NCI-H2228 cells are those expressing another EML4-ALK fusion protein, which is different from the EML4-ALK fusion protein v1 because it is encoded by an EML4-ALK fusion polynucleotide whose fusion point on EML4 cDNA is different from that of the EML4-ALK fusion polynucleotide v1, but whose ALK region is the same as that of the EML4-ALK fusion polynucleotide v1. The above NCI-H2228 cells seeded in the plate were cultured overnight under 5% $CO_2$ at 37° C., followed by addition of a test compound (final concentration: 10 μM to 1 nM). As a negative control, DMSO used as a solvent was added at the same concentration as the test compound. Then, the cells were cultured under 5% $CO_2$ at 37° C. for 5 days. A cell counting reagent (CellTiter-Glo™ Luminescent Cell Viability Assay; Promega) was added and agitated for 20 minutes, followed by measurement with a luminometer (ML3000 microtiter plate luminometer; Dynatech Laboratories). Assuming that the value measured for the medium alone and the value measured for the negative control were 100% inhibition and 0% inhibition, respectively, the inhibition rate was calculated for each compound to thereby determine the concentration causing 50% inhibition ($IC_{50}$ value) by the logistic regression method.

As a result, the compounds of the present invention and TAE684 were found to have growth inhibitory activity against human non-small cell lung cancer cell line NCI-H2228 cells. Table 3 shows the $IC_{50}$ values obtained for some compounds of the present invention and TAE684. Ex denotes Example No.

TABLE 3

| Ex | $IC_{50}$(nM) | Ex | $IC_{50}$(nM) |
|---|---|---|---|
| 1 | 473 | 128 | 64 |
| 23 | 71 | 12 | 134 |
| 24 | 125 | 149 | 62 |
| 45 | 1039 | 166 | 125 |
| 52 | 159 | 7 | 87 |
| 58 | 156 | 171 | 61 |
| 63 | 96 | 176 | 119 |
| 72 | 93 | TAE684 | 8.5 |
| 120 | 168 | | |
| 123 | 30 | | |

28
TEST EXAMPLE 4

Evaluation of Inhibitory Effect Against Anchorage-Independent Cell Growth of Human Non-Small Cell Lung Cancer Cell Line HCC827 Cells (Mutant EGFR (with Partial Deletion of Exon 19 in EGFR) Protein-Expressing Cells, American Type Culture Collection)

Evaluation was performed in the same manner as shown in Test Example 3.

As a result, the compounds of the present invention and TAE684 were found to have growth inhibitory activity against human non-small cell lung cancer cell line HCC827 cells. Table 4 shows the $IC_{50}$ values obtained for some compounds of the present invention and TAE684. Ex denotes Example No.

TABLE 4

| Ex | $IC_{50}$(nM) | Ex | $IC_{50}$(nM) |
|---|---|---|---|
| 1 | 2513 | 128 | 175 |
| 23 | 272 | 12 | 509 |
| 24 | 1027 | 149 | 512 |
| 45 | 1899 | 166 | 419 |
| 52 | 820 | 7 | 214 |
| 58 | 648 | 171 | 252 |
| 63 | 791 | 176 | 496 |
| 72 | 670 | TAE684 | 301 |
| 120 | 660 | | |
| 123 | 238 | | |

From the results of Test Examples 1 to 4 shown above, it was confirmed that the compounds of the present invention and TAE684 had inhibitory activity against the kinase activity of EML4-ALK fusion protein v1 and growth inhibitory activity against human non-small cell lung cancer cell line NCI-H2228 cells, and that TAE684 had stronger activity than the compounds of the present invention. It was also confirmed that the compounds of the present invention and TAE684 had inhibitory activity against the kinase activity of mutant EGFR (L858R) protein and growth inhibitory activity against human non-small cell lung cancer cell line HCC827 cells, and that the compounds of the present invention and TAE684 had almost equal activity.

TEST EXAMPLE 5

Toxicity Test in Rats

Test compounds were each suspended in a 0.5% aqueous methylcellulose solution and repeatedly administered to SD rats (two females and four males in each group) by the oral route at each dose for 7 days. TAE684 was administered at 3, 10, 30 and 100 mg/kg, while the compound of Example 23 was administered at 10, 30, 100 and 300 mg/kg.

The results obtained are shown in Table 5.

TABLE 5

| | Dose | | | |
|---|---|---|---|---|
| | Compound of Example 23 | | TAE684 | |
| | Male (4 rats) | Female (2 rats) | Male (4 rats) | Female (2 rats) |
| Non-toxic dose | 10 | 10 | 3 | 3 |
| Bone marrow inhibition | 100 | 100 | 10 | 10 |

TABLE 5-continued

| | Dose | | | |
|---|---|---|---|---|
| | Compound of Example 23 | | TAE684 | |
| | Male (4 rats) | Female (2 rats) | Male (4 rats) | Female (2 rats) |
| Exacerbation of common symptoms | (>300) | (>300) | 100 | 30 |
| Moribund condition | (>300) | (>300) | (>100) | 100 |

At the doses used in this test, TAE684 produced the following clear toxic symptoms: exacerbation of common symptoms (e.g., decreased autonomic movement, eyelid closure, skinniness, blepharophimosis) in the females of the 30 mg/kg group; these findings as well as prone position, bradypnea and hypersalivation in the females and males of the 100 mg/kg group; and remarkable exacerbation of the post-administration state at Day 7 in the two females (all cases) of the 100 mg/kg group (for this reason, these two cases were examined by moribund autopsy). In contrast, although the compound of Example 23 was found to cause a decrease in the amount of feces in 2 of the 4 males in the 300 mg/kg group, there was no case in each dose group, which showed exacerbation of common symptoms during administration for 7 days. Also, no moribund case was observed in each dose group.

Namely, the compound of Example 23 has an effect equal to TAE684 on growth inhibition of mutant EGFR protein-expressing cells, but on the other hand causes no exacerbation of common symptoms or shows no moribund case even when administered at a dose of 300 mg/kg, which is higher than the dose of 30 mg/kg or 100 mg/kg at which exacerbation of common symptoms or moribund cases are observed for TAE684. Thus, the compound of Example 23 is regarded as a safer compound than TAE684.

Based on the above results, in cancer therapy for EML4-ALK fusion polynucleotide-positive cancer patients, TAE684 has fears about safety (e.g., exacerbation of common symptoms) at a lower dose than in the compound of Example 23 (Test Example 5), whereas TAE684 appears to produce a therapeutic effect at a lower dose than in the compound of Example 23 (Test Examples 1 and 3). It is therefore inferred that the compound of Example 23 and TAE684 are almost comparable to each other in terms of a balance between therapeutic effect and safety. On the other hand, in cancer therapy for mutant EGFR polynucleotide-positive cancer patients, the compound of Example 23 and TAE684 appear to produce a therapeutic effect at almost the same dose (Test Examples 2 and 4), whereas TAE684 has fears about safety (e.g., exacerbation of common symptoms) at a lower dose than in the compound of Example 23 (Test Example 5). It is therefore concluded that the compound of Example 23 is superior to TAE684 in terms of a balance between therapeutic effect and safety.

Thus, even if the compound of Example 23 and TAE684 can both produce a therapeutic effect on cancer with some degree of safety during cancer therapy for EML4-ALK fusion polynucleotide-positive cancer patients, the so-called margin of safety is narrower in TAE684 than in the compound of Example 23 in cancer therapy for mutant EGFR polynucleotide-positive cancer patients, and hence TAE684 has a possibility of failing to provide a sufficient therapeutic effect when the dose should be reduced to ensure safety. In contrast, the compound of Example 23 has a wider margin of safety than TAE684 and hence can be expected to be administered at a dose which ensures a sufficient therapeutic effect. Namely, the compound of Example 23 is expected as a therapeutic agent for cancer that is applicable to a wider spectrum of cancer patients than in TAE684.

TEST EXAMPLE 6

Kinase Inhibition Profiling

The inhibition rates against 88 types of kinases (ABL, ACK, AXL, BMX, BTK, CSK, DDR2, EGFR, EphA2, EphB4, FES, FGFR1, FGFR3, FLT1, FLT4, FMS, INSR, JAK2, JAK3, KDR, MER, MUSK, PDGFRa, RET, TEC, TIE2, TYK2, TYRO3, ABL[T315I], EGFR[L858R], EGFR [T790M], AKT2, AurC, BMPR1A, BRAF, BRAF[V600E], CaMK2a, CaMK4, CDK3, CHK2, CK1a, CK1d, COT, CRIK, DAPK1, DLK, Erk5, GSK3a, GSK3b, IKKa, IKKb, IKKe, IRAK4, JNK1, JNK3, MAP2K2, MAP2k3, MAP2K4, MAP2K5, MAP2K7, MAP3K1, MAP3K2, MAP3K3, MAP3K4, MAP3K5, MAPKAPK2, MAPKAPK3, MAPKAPK5, MLK1, MLK2, MLK3, MNK1, MNK2, MSK1, NEK2, p38d, p38g, PAK6, PHKG1, PIM1, PKACa, PKCh, PKD2, ROCK1, RSK2, SRPK1, TAK1, TTK) were calculated for each test compound at 100 nM. Activity measurement was made by Carna Biosciences Inc., Japan, and the data were analyzed as follows: assuming that the average signal of control wells containing all reaction components was 0% inhibition and the average signal in the absence of the enzyme was 100% inhibition, the inhibition rate was calculated for each test substance from the average signal of two test wells.

As a result, at a concentration of 100 nM, TAE684 showed 50% or more inhibitory activity against 29 types of kinases, whereas the compound of Example 23 showed inhibitory activity only against 4 types.

Namely, TAE684 has strong inhibitory activity against a wide range of kinases, whereas the compound of Example 23 at the same concentration has a different inhibition profile than that of TAE684 and appears to be highly selective for specific kinases, i.e., appears to have much fewer fears about safety than TAE684, which fears are induced by inhibition of non-target kinases responsible for side effects.

In addition, when a careful examination was actually made on various kinase inhibition profiles, kinases against which TAE684 has higher inhibitory activity than the compound of Example 23 were MUSK, MER and PHKG1. TAE684 showed 90% or more inhibitory activity against these kinases at concentration of 100 nM, whereas the compound of Example 23 showed little inhibitory activity at the same concentration (less than 20%).

MUSK is a kinase essential for acetylcholine receptor functions in the neuromuscular junction. If people have a mutation in this kinase or are positive for anti-MUSK antibody, they are known to develop a hereditary disease with myasthenia showing symptoms such as blepharoptosia, hypersalivation, and respiratory disturbance (Hum Mol Genet. 2004 13, 3229-3240 and Nat Med. 2001 7, 365-368). There are many symptoms in common between exacerbation of common symptoms observed for TAE684 in Test Example 5 and phenotypes caused by mutations in MUSK. Thus, exacerbation of common symptoms observed for TAE684 administered at 30 mg/kg or more may have some relationship with MUSK inhibition.

MER is a kinase required for retinal cells to maintain their survival. If people have a mutation in this kinase, they are known to develop a hereditary disease with retinitis pigmentosa responsible for gradual narrowing of the visual field, which may lead to blindness (Nature Genet. 2000 26, 270-271). Thus, the possibility of TAE684 to cause a defect in retinal cells due to its inhibitory activity against MER cannot be denied. In contrast, the compound of Example 23 appears to have almost no fear of causing a defect in retinal cells, because its inhibitory activity against MER is weaker than that of TAE684.

PHKG1 is an enzyme essential for glycogen metabolism in muscle, and is known to contribute to a hereditary disease caused by mutations in enzyme complex subunits, which is feared to show glycogenosis, muscle ache during exercise, easy fatigue, myotonia, liver swelling, abdominal swelling, glycogenosis (glycogen accumulation)-induced muscle tissue atrophy, and metabolic myopathy (Am. J. Med. Genet. 2005 133A, 82-84). Thus, the possibility of TAE684 to cause a defect in muscle tissue due to its inhibitory activity against PHKG1 cannot be denied. In contrast, the compound of Example 23 appears to have almost no fear of causing a defect in muscle tissue, because its inhibitory activity against PHKG1 is weaker than that of TAE684.

On the other hand, kinases against which the compound of Example 23 has higher inhibitory activity than TAE684 are MNK1 and MNK2. TAE684 showed 4.8% and 32% inhibitory activity against these kinases, respectively, at 100 nM, whereas the compound of Example 23 showed 60% and 80% inhibitory activity at the same concentration. However, it has been reported that mice whose MNK1 and MNK2 genes are both disrupted will grow normally (Molecular and Celluar Biology 2004 24, 6539-6549). It is therefore difficult to believe that serious diseases are caused by the inhibitory activity of the compound of Example 23 against MNK1 and MNK2.

TEST EXAMPLE 7

Evaluation of Inhibitory Activity Against the Kinase Activity of MUSK Protein

MUSK protein (Carna Biosciences Inc., Japan) was investigated for its phosphorylation activity toward a peptide substrate by using a kinase activity detection kit (HTRF Kin-EASE-TK; Cisbio Inc.). Test compounds were each added to a reaction solution containing the enzyme protein to give 8 final concentrations from 10000 nM to 3 nM, followed by addition of ATP and reaction for 1 hour. The ATP concentration used was 10 µM. Another reaction solution was prepared to contain the enzyme protein but no test compound (in which the solvent DMSO alone was added at 0.4% in place of the test compound), followed by reaction in the same manner with or without ATP addition. In the absence of the test compound, the phosphorylation count without ATP addition and with ATP addition was assumed to be 100% inhibition and 0% inhibition, respectively. The concentration causing 50% inhibition ($IC_{50}$) was calculated for each test compound by the logistic regression method.

As a result, the compounds of the present invention and TAE684 were found to have inhibitory activity against the kinase activity of MUSK protein. Table 6 shows the $IC_{50}$ values obtained for some compounds of the present invention and TAE684. Ex denotes Example No.

TABLE 6

| Ex | $IC_{50}$(nM) |
|---|---|
| 23 | 1500 |
| 123 | 1100 |
| 128 | 1800 |
| TAE684 | 17 |

From the results of Test Example 7 shown above, it was confirmed that TAE684 had very strong inhibitory activity against the kinase activity of MUSK protein, when compared to the compounds of the present invention. There are many symptoms in common between exacerbation of common symptoms observed for TAE684 in Test Example 5 and phenotypes caused by mutations in MUSK. Thus, exacerbation of common symptoms observed for TAE684 administered at 30 mg/kg or more may have some relationship with MUSK inhibition.

TEST EXAMPLE 8

Antitumor Test (in vivo) on NCI-H2228 Cells $3 \times 10^6$ cells of NCI-H2228 cells suspended in PBS were inoculated subcutaneously by injection to the back of 5 weeks old male NOD/SCID mice (Charles River Japan, Inc.). After 3 weeks of the inoculation, the administration of test compounds was initiated. The test was conducted in the solvent group and test compound groups, 6 animals per group. The test compounds were each dissolved in a solvent composed of 10% 1-methyl-2-pyrrolidinone (SIGMA-ALDRICH Inc.)/90% polyethylene glycol 300 (Fluka Inc.) and administered orally at a dose of 3 mg/kg. Administrations were performed once a day for 14 days, and body weight and tumor size were measured every other day. Tumor volume was calculated using the following formula.

$$[\text{Tumor volume (mm}^3)] = [\text{Tumor major axis (mm)}] \times [\text{tumor minor axis (mm)}]^2 \times 0.5$$

Assuming that the tumor volume of the solvent group on the day of starting and the day of finishing administration was 100% inhibition and 0% inhibition, respectively, the inhibition rate was calculated for each compound.

As a result, the compound of the present invention were found to have an antitumor effect on NCI-H2228 cells (tumor). Among them, the compounds of Examples 23 and 123 inhibited the growth of NCI-H2228 cells (tumor) by 116% and 108%, respectively.

Thus, when orally administered, the compounds of the present invention inhibited tumor growth in mice inoculated with H2228 cells, thereby confirming that the compounds of the present invention had oral activity.

In view of the foregoing, in Test Examples 1 to 4, the compounds of the present invention were confirmed to have inhibitory activity against the kinase activity of both EML4-ALK fusion protein v 1 and mutant EGFR (L858R) protein, as well as growth inhibitory activity against human non-small cell lung cancer cell lines NCI-H2228 and HCC827. In Test Example 8, the compounds of the present invention were also confirmed to have an antitumor effect on NCI-H2228 cells (tumor) based on the above actions. Further, in Test Example 5, the compounds of the present invention were confirmed to be safer than TAE684, showing no toxicity even when administered at a dose of 300 mg/kg which is higher than the dose at which exacerbation of common symptoms was observed in TAE684. These indicate that the compounds of the present invention are useful as active ingredients in pharmaceutical compositions for preventing and/or treating cancer, such as lung cancer in one embodiment, non-small cell lung cancer or small cell lung cancer in another embodiment, EML4-ALK fusion polynucleotide-positive and/or mutant EGFR polynucleotide-positive cancer in yet another embodiment, EML4-ALK fusion polynucleotide-positive and/or mutant EGFR polynucleotide-positive lung cancer in yet another embodiment, or EML4-ALK fusion polynucleotide-positive and/or mutant EGFR polynucleotide-positive non-small cell lung cancer in yet another embodiment.

In Non-patent Document 7, it has been confirmed that among EML4-ALK fusion protein-expressing lung cancer cell lines, there are some lung cancer cell lines expressing a constitutively activated EGFR protein together with the EML4-ALK fusion protein. To inhibit the growth of these lung cancer cell lines, both proteins should be inhibited (Non-patent Document 7). The compounds of the present invention have equal inhibitory activity against both EML4-ALK fusion protein v1 and mutant EGFR (L858R) protein, and hence can be expected to have excellent growth inhibitory activity against such lung cancer cell lines at a certain dose. Thus, the compounds of the present invention would be useful as active ingredients in pharmaceutical compositions for preventing and/or treating EML4-ALK fusion polynucleotide-positive and mutant EGFR polynucleotide-positive cancer. Moreover, the compounds of the present invention can be used at a single dose for both EML4-ALK fusion polynucleotide-positive cancer and mutant EGFR polynucleotide-positive cancer.

In contrast, although TAE684 has inhibitory activity against the kinase activity of mutant EGFR (L858R) protein and growth inhibitory activity against HCC827 cells, each activity being equal to that of the compounds of the present invention, TAE684 started to develop serious toxicity at a lower dose than the compound of Example 23 in Test Example 5. Thus, when compared to the compound of Example 23, TAE684 has fears about safety in its effective dose required to produce a sufficient growth inhibitory effect on mutant EGFR polynucleotide-positive cancer.

The compounds of formula (I) were also confirmed for their pharmacological activity in the following series of tests. Unless otherwise specified, the test examples shown below may be accomplished in a known manner and, when using commercially available reagents and/or kits, may be accomplished in accordance with the instructions attached to these commercially available products.

The full-length ALK cDNA was kindly provided by Dr. Steve Morris, St. Jude Children's Research Hospital. This research project was approved by the ethical review committee for gene analysis research of Jichi Medical University.

The anti-phosphorylated ALK antibody used was a product of Cell Signaling Technology Inc., and the anti-ALK antibody used was a product of NEOMARKERS Inc.

TEST EXAMPLE 9

Isolation of EML4-ALK Fusion Polynucleotide v1

(1) Construction of cDNA Library

Using a RNA purification kit (RNeasy Mini Column; Qiagen Inc.), RNA was extracted from a resected specimen of lung adenocarcinoma of a 62 year old male who gave informed consent and cDNA was synthesized using reverse transcriptase (Power Script Reverse Transcriptase) and primers (an oligonucleotide of SEQ ID NO: 3 and CDS primer IIA) (all from Clontech Inc.). After selectively amplifying the full-length cDNA by polymerase chain reaction (PCR) (17 cycles of 98° C. for 10 seconds and 68° C. for 6 minutes) using a primer (5'-PCR primer IIA; Clontech Inc.) and a polymerase (primeSTAR HSDNA polymerase, Takara Bio Inc.), a BstX1 adapter (Invitrogen Inc.) was attached to the both ends of cDNA. The cDNA thus obtained was ligated to a retrovirus plasmid, and a retrovirus plasmid library was constructed by introducing this plasmid to *E. coli* DH10B (Invitrogen Inc.). As a result, the plasmid library containing clones more than 1,500,000 colony forming units in total has been successfully constructed.

(2) Focus Formation Assay

2 μg of the plasmid of the library described above and 0.5 μg of a plasmid for packaging (pGP and pE-eco, both of which were obtained from Takara Bio Inc.) were transfected into BOSC23 packaging cells using a transfection reagent. Two days after the transfection, the culture supernatant was recovered as a solution of recombinant retrovirus library, mixed with polybrene (Sigama Inc.) at a concentration of 4 μg/ml, and the mixture was added to mouse 3T3 cells at MOI (multiplicity of infection) of 0.1 concentration. Two days later, the culture supernatant of 3T3 cells was changed to DMEM-F12 medium (Invitrogen Inc.) supplemented with 5% bovine serum (Invitrogen Inc.) and 2 mM L-glutamine, and the cells were cultured 2 more weeks to obtain 10 or more kinds of transformed foci. After isolating each 3T3 cell clone, the culturing of the clones was continued separately, and the genomic DNA of each clone was extracted. The viral cDNA integrated in each 3T3 clone was amplified and recovered by carrying out PCR (30 cycles of 98° C. for 10 seconds and 68° C. for 6 minutes) using 10 ng of the genomic DNA as a template, 5'-PCR primer IIA primer and DNA polymerase (PrimeStar HS DNA polymerase; Takara Bio Inc.), and cloned into pT7Blue-2 vector.

One of the cDNA thus obtained was 3926 base pair long (SEQ ID NO: 1) and had a single long open reading frame (from the 271st to 3447th nucleotides of SEQ ID NO: 1) coding for a protein having 1059 amino acid residues (SEQ ID NO: 2). Interestingly, about half of the amino-terminus (1-496 amino acid residues of SEQ ID NO: 2) of a protein encoded by this cDNA having a novel full-length sequence was perfectly matched to 1-496 amino acid residues of echinoderm microtubule associated protein like-4 (EML4, GenBank accession No. NM_019063), and on the other hand, about half of the carboxyl terminus (497-1059 amino acid residues of SEQ ID NO: 2) was perfectly matched to the amino acid sequence of anaplastic lymphoma kinase (ALK, GenBank accession No. AB209477). From the above results, the present cDNA was believed to be a fused cDNA between EML4 cDNA and ALK cDNA. Further, the obtained cDNA (cDNA for EML4-ALK fusion polynucleotide v1) contained a domain of ALK tyrosine kinase.

TEST EXAMPLE 10

Detection of EML4-ALK Fusion Polynucleotide in Clinical Specimens cDNAs were synthesized from 33 cases of clinical specimens (resected specimens of non-small cell lung cancer) and from peripheral monocytes of one case of a normal healthy subject.

To detect the cDNA of EML4-ALK fusion polynucleotide v1, PCR (50 cycles of 94° C. for 15 seconds, 60° C. for 30 seconds and 72° C. for 1 minute) was carried out using a quantitative PCR kit (QuantiTect SYBR Green; Qiagen Inc.), the cDNAs as substrates prepared from the clinical specimens and the normal healthy subject described above and oligonucleotides of SEQ ID NOs: 4 and 5 as primers. Using the same specimens, PCR amplifications of the glyceraldehyde-3-phosphate dehydrogenase (hereinafter GAPDH) cDNA was tried as a control. To detect the GAPDH cDNA, oligonucleotides consisting of the nucleotide sequences represented by SEQ ID NOs: 6 and 7 were used as primers. Amplified respective samples were electrophoresed with a size marker DNA (Marker: 50 bp ladder, Invitrogen Inc.). As a result, as shown in the upper part of FIG. 1, in the 3 cases, the cDNA of EML4-ALK fusion polynucleotide v1 was detected. Further, in all the cases analyzed, an amplification of the GAPDH cDNA was confirmed clearly (Lower part of FIG. 1). In addition, the nucleotide sequences of the PCR products identified in these 3 cases were analyzed and the result confirmed that all had the same sequence (the 247 bp including the fusion point of the EML4 gene and the ALK gene; SEQ ID NO: 8). That is, the result of the analyses of the 33 cases of non-small cell lung cancer confirmed that the fusion of the EML4 gene and the ALK gene occurs in 9.1% of the cases (3/33 cases).

Mutation in the EGFR gene has been known to be one of the causes of lung cancer. In the 33 specimens of the cases analyzed as described above, the analysis of the presence of an abnormality in the nucleotide sequence of the EGFR gene according to the known method confirmed a partial deletion of exon 19 in 6 cases. The cases having the EGFR gene mutation and the cases positive for the EML4-ALK fusion polynucleotide belonged to different subgroups. That is, the existing therapeutic agents, which show a therapeutic effect on lung cancer patients having the EGFR gene mutation, are expected to be not effective for the lung cancer patients who are positive for the EML4-ALK fusion polynucleotide.

Also, the 33 cases analyzed as described above were subjected to the investigation whether the full-length ALK gene existed, and it was found that it existed in 8 cases. The specimens of the 7 cases among these 8 cases did not contain the EML4-ALK fusion polynucleotide. That is, the full-length ALK gene did not exist in the 2 cases among the 3 cases where the EML4-ALK fusion polynucleotide was positive.

TEST EXAMPLE 11

Investigation of Tumorgenicity of EML4-ALK Fusion Polypeptide v1

EML4-ALK (K589M)/pMXS, in which the 589th amino acid (ATP binding site), a lysine residue, of the EML4-ALK fusion polypeptide v1 was replaced with methionine, was produced using EML4-ALKv1/pMXS (prepared from a clone in which the EML4-ALK fusion polynucleotide v1 was cloned in the forward orientation into pT7Blue-2 vector, which clone was further digested with restriction enzymes EcoRI and SalI to release the insert, which was then subcloned into the EcoRI-SalI site of pMXS (J. Biol. Chem., vol. 275, p. 24945-24952, 2000)) as a substrate and using a mutation introducing kit (QuickChange Site-Directed Mutagenesis Kit; Stratagene Inc.). In the reaction, oligonucleotides of SEQ ID NO: 9 and SEQ ID NO: 10 were used. The ALK cDNA (Morris, S W et al, Science. 1994 Mar. 4; 263 (5151): 1281-4) was cloned into a retrovirus vector pMXS according to the standard method (designated as ALK/pMXS and ALK/pMX-iresCD8, respectively).

EML4-ALKv1/pMXS described above, full-length ALK/pMXS, a plasmid expressing EML4-ALK (K589M)/pMXS and a blank vector without inserted cDNA (pMXS) were transfected into 3T3 fibroblast cells by the phosphate calcium method and cultured for 21 days. As shown in the upper part of FIG. 2, many transformation foci were observed only when the EML4-ALK fusion protein v1-expressing virus was transfected. The scale bar indicates 100 µm. Further, the same transfected 3T3 cells were inoculated subcutaneously to nude mice at $5 \times 10^5$ cells/mouse and observed for 20 days. It turned out also that tumor was formed only when EML4-ALK fusion protein v1-expressing cells were inoculated. The tumor formation numbers (the number of inoculation sites of 3T3 cells and the number of tumor formation among them) are as follows. The tumor formation number of the full-length ALK expression was 0 among 8, while the tumor formation number in the EML4-ALK fusion protein v1-expressing cells was 8 among 8. In addition, the tumor formation number of EML4-ALK (K589M)-expressing cells was 0 among 8. These results demonstrate that since the full-length ALK protein expression does not induce tumor but the EML4-ALK fusion protein v1 is tumorgenic, the EML4-ALK fusion polynucleotide v1 is a causal gene of cancer. Also, since the tumorgenicity of EML4-ALK was not observed in EML4-ALK (K589M), it would appear that the tumorgenicity was dependent on the kinase activity. Hereinafter, the 3T3 cells modified to express EML4-ALK fusion protein v1 by transfection with the EML4-ALK fusion protein v1 expression plasmid are designated as the v1 expressing 3T3 cells.

TEST EXAMPLE 12

Screening for Inhibitors Against the Kinase Activity of EML4-ALK Fusion Protein (1) Preparation of EML4-ALK Fusion Protein v1

N-terminally FLAG-tagged EML4-ALK fusion protein v1 was inserted into a vector pMX-iresCD8 capable of co-expression of insert cDNA and cell surface antigen CD8 (J. Biol. Chem., 2001, vol. 276, p. 39012-39020) to create a vector FLAG-EML4-ALKv1/pMX-iresCD8 expressing both FLAG-EML4-ALKv1 and CD8. FLAG-EML4-ALKv1/pMX-iresCD8 was used to create a recombinant retrovirus in the same manner as described above and infected into mouse lymphoid cell line BA/F3 cells. Using a magnetic bead reagent for cell separation and a purification column (anti-CD8 monoclonal antibody immobilized on magnetic beads and a MiniMACS purification column; both are products of Miltenyi Biotec Inc.), cell surface CD8-expressing cells were purified conveniently. The BA/F3 cells expressing this N-terminally FLAG-tagged EML4-ALK fusion protein v1 were cultured in RPMI1640 medium containing 10% fetal bovine serum to obtain $2.7 \times 10^9$ cells. After washing 3 times with PBS, the cells were lysed in a lysis solution (50 mM Tris.HCl (pH 7.4), 150 mM NaCl, 1% Triton X100, 5 mM EDTA, 5 mM EGTA, 1 mM NaVO$_4$, 1 mM DTT and protease inhibitor cocktail complete). The EML4-ALK fusion protein v1 present in the supernatant obtained after centrifugation was purified using ANTI-FLAG M2 Affinity Gel (SIGMA-ALDRICH Inc.) according to the method described in the product information document.

(2) Detection of the in vitro Kinase Activity of EML4-ALK Fusion Protein v1

The EML4-ALK fusion protein v1 purified as above was investigated for its phosphorylation activity toward a peptide substrate using a kinase activity detection kit (HTRF KinEASE-TK; Cisbio Inc.). Using TK substrate 1, which was included in the kit, as the substrate, and after adding no ATP or 100 µM ATP, the mixtures were reacted at room temperature for 1 hour, and the count of HTRF was detected as recommended by the Kits manufacturer. As a result, it became clear that the count of HTRF (i.e., phosphorylation of the peptide substrate) was increased by about 12 times by the addition of ATP compare to no addition of ATP. As shown above, the in vitro kinase activity of EML4-ALK fusion protein v1 can be detected using anti-phosphorylated ALK antibody and the kinase activity detection kit.

(3) Inhibitory Effect of Compounds Against the in vitro Kinase Activity of EML4-ALK Fusion Protein v1

Compounds A, B, C and D, which are known as compounds having an inhibitory effect against ALK, were investigated for their inhibitory effect against the in vitro kinase activity of EML4-ALK fusion protein v1 using the kinase activity detection kit mentioned above. Respective compounds were added to a reaction solution containing the EML4-ALK fusion protein v1 to give a final concentration of 10 µM or 10 nM, followed by reaction with or without the addition of ATP. The rest of the operations were carried out as described in (2) above. In the absence of the compound, the phosphorylation count without ATP addition and with ATP addition was assumed to be 100% inhibition and 0% inhibition, respectively. The inhibition (%) of the kinase activity of EML4-ALK fusion protein v1 by each compound was calculated by the following formula.

[Kinase activity inhibition (%) by a compound]=(1−
[phosphorylation count when the compound and
ATP were added−phosphorylation count when
the compound was not added and ATP was not
added]/[phosphorylation count when the compound was not added and ATP was added−phosphorylation count when the compound was not
added and ATP was not added])×100

The results obtained are shown in Table 7.

It should be noted that compounds A to D in the table below are those shown in Patent Document 1.

TABLE 7

| Test compound | Final concentration | Activity inhibition (%) |
|---|---|---|
| Compound A | 10 µM | 99 |
| Compound B | 10 µM | 56 |
| Compound C | 10 nM | 99 |
| Compound D | 10 nM | 99 |

It was found that all of the compounds inhibited the phosphorylation activity of the purified EML4-ALK fusion protein v1 on the peptide substrate.

The above results indicated that screening for a substance which inhibits the activity of the protein of the present invention could be performed by preparing the EML4-ALK fusion protein and using the in vitro kinase activity as an index.

TEST EXAMPLE 13

Cell Growth Inhibitory Effect of Inhibitors Against the Kinase Activity of EML4-ALK Fusion Protein on Cells Expressing EML4-ALK Fusion Polynucleotide v1

$3 \times 10^6$ cells of v1 expressing 3T3 cells suspended in PBS were inoculated subcutaneously by injection to the back of 5 weeks old male BALB/c nude mice (Charles River Japan, Inc.). After 7 days of the inoculation, the administration of compound C, an inhibitor against the kinase activity of EML4-ALK fusion protein, was initiated. The test was conducted in the solvent group and compound C group, 4 animals per group. Compound C was dissolved in a solvent composed of 10% 1-methyl-2-pyrrolidinone (SIGMA-ALDRICH Inc.)/90% polyethylene glycol 300 (Fluka Inc.) and administered orally at a dose of 10 mg/kg. Administrations were performed once a day for 14 days, and body weight and tumor size were measured every other day. Tumor volume was calculated using the following formula.

[Tumor volume (mm$^3$)]=[Tumor major axis (mm)]×
[tumor minor axis (mm)]$^2$×0.5

Assuming that the tumor volume of the solvent group on the day of starting and the day of finishing administration was 100% inhibition and 0% inhibition, respectively, the inhibition rate of compound C was calculated. The results indicated that compound C inhibited the growth of v1 expressing 3T3 cells (tumor) by 103%.

The antitumor effect of compound D was investigated by the similar procedure with the following exceptions. The administration of the compound was started after 6 days of the inoculation and carried out once a day for 10 days. As a result, compound D inhibited the growth of v1 expressing 3T3 cells (tumor) by 101%.

TEST EXAMPLE 14

Inhibitory Effect of Compounds Against the in vitro Kinase Activity of EML4-ALK Fusion Protein v1

In the same manner as shown in Test Example 12(3), compounds were investigated for their inhibitory effect against the in vitro kinase activity of EML4-ALK fusion protein v1 using the kinase activity detection kit mentioned above. Test compounds were each added to a reaction solution containing the EML4-ALK fusion protein v1 to give 8 final concentrations from 1000 nM to 0.3 nM, followed by addition of ATP. Another reaction solution was prepared to contain the EML4-ALK fusion protein v1 but no test compound (in which the solvent DMSO alone was added at 0.4% in place of the test compound), followed by reaction with or without ATP addition. The rest of the operations were carried out as described in Test Example 12 (2). In the absence of the test compound, the phosphorylation count without ATP addition and with ATP addition was assumed to be 100% inhibition and 0% inhibition, respectively. The concentration causing 50% inhibition ($IC_{50}$) was calculated for each test compound by the logistic regression method.

As a result, the compounds of formula (I) were found to inhibit the kinase activity of EML4-ALK fusion protein v1. In particular, some of the compounds of formula (I) showed $IC_{50}$ values not greater than 1000 nM or 100 nM in the above test. Among them, the compound of Example 1 showed an $IC_{50}$ value of 42 nM.

As a result of the above tests, the compounds of formula (I) were confirmed to have an inhibitory effect against the kinase activity of EML4-ALK fusion protein v1. This suggests that the compounds of formula (I) can be used as therapeutic agents, e.g., for EML4-ALK fusion gene-positive cancer in one embodiment or for EML4-ALK fusion gene-positive lung cancer in another embodiment.

A pharmaceutical composition which comprises one or more compounds of formula (I) or pharmaceutically acceptable salts thereof as an active ingredient can be prepared in a conventional manner by using a pharmaceutical excipient, a pharmaceutical carrier or other additives commonly used in the art.

Any mode of administration may be used, either oral administration in the dosage form of tablets, pills, capsules, granules, powders, solutions or the like, or parenteral administration in the dosage form of injections (e.g., intraarticular, intravenous, intramuscular, and the like), suppositories, eye drops, eye ointments, percutaneous solutions, ointments, percutaneous patches, transmucosal solutions, transmucosal patches, inhalants or the like.

Solid compositions used for oral administration include tablets, powders, granules, and the like. In these solid compositions, one or more active ingredients are mixed with at least one inert excipient, for example, lactose, mannitol, glucose, hydroxypropylcellulose, microcrystalline cellulose, starch, polyvinylpyrrolidone, and/or magnesium aluminometasilicate, or the like. The compositions may also comprise inert additives, for example, lubricants (e.g., magnesium stearate and the like), disintegrating agents (e.g., carboxymethyl starch sodium and the like), stabilizers, and/or solubilizers, as in the usual cases. Tablets or pills may be coated with sugar coating or a gastric or enteric film, if necessary.

Liquid compositions for oral administration include pharmaceutically acceptable emulsions, solutions, suspensions, syrups, elixirs, or the like, and comprise commonly-used inert diluents such as purified water or ethanol. These liquid compositions may comprise, in addition to inert diluents, auxiliaries (e.g., solubilizers, wetting agents, suspending agents, and the like), sweeteners, flavors, aromatics, and/or antiseptics.

Injections for parenteral administration include sterile aqueous or non-aqueous solutions, suspensions or emulsions. Examples of aqueous solvents include injectable distilled water or physiological saline. Examples of non-aqueous solvents include propylene glycol, polyethylene glycol or vegetable oils (e.g., olive oil and the like), as well as alcohols (e.g., ethanol and the like) or Polysorbate 80 (pharmacopoeia name), and the like. These compositions may further comprise isotonizing agents, antiseptics, wetting agents, emulsifiers, dispersants, stabilizers or solubilizers. They are sterilized, for example, by filtration through a bacteria-retaining filter, by incorporation with disinfectants or by irradiation. Alternatively, they may be formulated into a sterile solid composition and reconstituted for use by being dissolved or suspended in sterile water or a sterile injectable solvent before use.

Formulations for external use include ointments, plasters, creams, jellies, cataplasms, sprays, lotions, eye drops, eye ointments, and the like. They comprise commonly-used ointment bases, lotion bases, aqueous or non-aqueous solutions, suspensions, emulsions or the like. Examples of ointment or lotion bases include polyethylene glycol, propylene glycol, white petrolatum, white beeswax, polyoxyethylene hydrogenated castor oil, glycerine monostearate, stearyl alcohol, cetyl alcohol, Lauromacrogol, sorbitan sesquioleate, and the like.

Transmucosal formulations such as inhalants or transnasal formulations are used in solid, liquid or semi-solid form and can be prepared in a conventionally known manner. For example, such formulations may be supplemented as appropriate with known excipients and further with pH adjustors, antiseptics, surfactants, lubricants, stabilizers, thickeners and so on. For their administration, an appropriate device for inhalation or insufflation may be used. For example, using a known device (e.g., a metered-dose inhalation device and the like) or a nebulizer, the compound(s) may be administered alone or as a powder of a formulated mixture or as a solution or suspension in combination with a pharmaceutically acceptable carrier. Dry powder inhalators or the like may be for single or multiple administration use, and dry powders or powder-containing capsules may be used in such devices. Alternatively, they may be in the form of pressurized aerosol sprays or the like which use an appropriate propellant, for example, a preferred gas such as chlorofluoroalkane, hydrofluoroalkane, carbon dioxide, or the like.

In general, for oral administration, the daily dosage is desirably about 0.001 to 100 mg/kg, preferably 0.1 to 30 mg/kg, and more preferably 0.1 to 10 mg/kg body weight, given as a single dose or in 2 to 4 divided doses. For intravenous administration, the daily dosage is desirably about 0.0001 to 10 mg/kg body weight, given in one or several doses per day. Likewise, for transmucosal formulations, the daily dosage is about 0.001 to 100 mg/kg body weight, given in one or several doses per day. The dosage may be determined as appropriate for each case in consideration of symptom, age, sex and so on.

The compounds of formula (I) can be used in combination with various therapeutic or prophylactic agents for diseases against which the compounds of formula (I) would be effective. In general, when an antitumor agent is administered alone during chemotherapy for tumor, particularly malignant tumor, the antitumor agent has a limit in its effect in terms of side effects and the like, and thus often fails to produce a sufficient antitumor effect. For this reason, in clinical cases, multidrug therapy is used in which two or more drugs with different mechanisms of action are combined. By combining antitumor agents with different mechanisms of action, this combination therapy aims to reduce side effects and/or enhance the desired antitumor effect, for example, 1) to reduce the number of non-sensitive cell population, 2) to prevent or delay the development of drug resistance, 3) to disperse toxicity by combination of drugs with different toxicity levels, and the like. In such combination therapy, drugs may be administered simultaneously or separately in succession or at desired time intervals. Formulations for simultaneous administration may be in either mixed or separate form.

Drugs which can be combined include chemotherapeutics (e.g., alkylating agent, antimetabolite, and the like), immunotherapeutic agents, hormonal therapeutic agents, and cell growth factor inhibitors, more specifically drugs such as cisplatin, carboplatin, paclitaxel, docetaxel, gemcitabine, irinotecan, vinorelbine, bevacizumab, and the like.

EXAMPLES

How to prepare the compounds of formula (I) will be further explained in more detail by way of the following examples. It should be noted that the present invention is not limited to the compounds shown in the following examples. In addition, how to prepare the starting compounds is shown in preparation examples. Processes for preparing the compounds of formula (I) are not limited only to those actually shown in the following examples, and the compounds of formula (I) may also be prepared by any combination of these processes or by any process obvious to those skilled in the art.

In the examples, preparation examples and tables shown below, the following abbreviations are used as needed.

Rex: Preparation Example No., Ex: Example No., No: Compound No., Structure: chemical structural formula, Data: physical and chemical data (FAB+: FAB–MS[M+H]$^+$, FAB–: FAB–MS[M–H]$^−$, ESI+: ESI–MS[M+H]$^+$, CI+: CI[M+H]$^+$, EI: EI[M]$^+$, NMR-DMSOd6: δ (ppm) of $^1$H-NMR peaks in dimethyl sulfoxide-$d_6$, NMR-CDCl3: δ (ppm) of $^1$H-NMR peaks in chloroform-d, MP: melting point (° C.), Amrph: which means that the intended compound was in amorphous form, Cryst: which means that the intended compound was in crystal form, Salt: salt (if empty, the intended compound is in free form), CL1: monohydrochloride, CL2: dihydrochloride, CL3: trihydrochloride, FM: difumarate, Me: methyl, Et: ethyl, $^i$Pr: isopropyl, tBu: tert-butyl,

41 nBu: n-butyl. Rsyn and Syn: preparation process (the number indicated means that the intended compound was prepared from corresponding starting materials in the same manner as used for a compound, in which the indicated number represents its Preparation Example No. or Example No.).

Preparation Example 1

To a mixture of propane-2-thiol (1.5 mL), potassium carbonate (3 g) and N,N-dimethylformamide (20 mL), 4-chloro-2-fluoronitrobenzene (2.5 g) was added and stirred at room temperature for 5 hours. After addition of water, the reaction mixture was extracted with ethyl acetate, and the extract was washed with water and saturated aqueous sodium chloride. After drying over anhydrous sodium sulfate, the solvent was distilled off under reduced pressure to give 4-chloro-2-isopropylsulfanyl-1-nitrobenzene (3.30 g) as a yellow oil.

Preparation Example 2

To a mixture of sodium isopropylsulfinate (3.3 g) and N-methyl-2-pyrrolidinone (20 mL), 2,3-dichloronitrobenzene (4 g) was added and stirred overnight at 70° C. The reaction mixture was diluted with water, and the precipitated solid was collected by filtration and washed with diethyl ether to give 3-chloro-2-isopropylsulfonyl-1-nitrobenzene (3.0 g) as a white solid.

Preparation Example 3

To a mixture of m-chloroperbenzoic acid (7.89 g) and chloroform (100 mL), a mixture of the compound of Preparation Example 1 (3.3 g) and chloroform (50 mL) was added and stirred at 50° C. for 7 hours. After cooling, the reaction mixture was diluted with saturated aqueous sodium hydrogen carbonate and extracted with chloroform. After the organic layer was dried over anhydrous sodium sulfate, the solvent was distilled off under reduced pressure, and the residue was purified by silica gel column chromatography (eluent; n-hexane:ethyl acetate=3:1-2:1) to give 4-chloro-2-isopropylsulfonyl-1-nitrobenzene (3.33 g) as a yellow solid.

Preparation Example 4

To a mixture of 2-nitrobenzenesulfonyl chloride (5.09 g), N-methylethylamine (1.35 g) and chloroform (100 mL), triethylamine (4.11 mL) was added under ice cooling and stirred at room temperature for 5 hours. The reaction mixture was diluted with water and extracted with chloroform. The organic layer was washed sequentially with 1 M hydrochloric acid, saturated aqueous sodium hydrogen carbonate and saturated aqueous sodium chloride, and then dried over anhydrous magnesium sulfate. The solvent was distilled off under reduced pressure to give N-ethyl-N-methyl-2-nitrobenzenesulfonamide (6.48 g) as a brown oil.

Preparation Example 5

To a mixture of N-cyclopropyl-2-nitrobenzenesulfonamide (5.63 g), potassium carbonate (4.82 g) and N,N-dimethylformamide (60 mL), methyl iodide (2.17 mL) was added and stirred at room temperature for 6 hours. The reaction mixture was evaporated under reduced pressure, and the residue was diluted with water and extracted with ethyl acetate. The organic layer was washed with saturated aqueous sodium chloride and dried over anhydrous magnesium sulfate, followed by distilling off the solvent under reduced pressure.

42

The residue was purified by silica gel column chromatography (eluent; n-hexane:diethyl ether=1:0-1:1) to give N-cyclopropyl-N-methyl-2-nitrobenzenesulfonamide (5.35 g) as a brown solid.

Preparation Example 6

To a mixture of the compound of Preparation Example 3 (3.3 g) and acetic acid (30 mL), iron powder (2.23 g) was added and stirred at 80° C. for 3 hours. Insoluble materials in the reaction mixture were removed and the solvent was distilled off under reduced pressure. The residue was diluted with ethyl acetate (100 mL) and insoluble materials were removed, followed by washing with water and saturated aqueous sodium chloride. After drying over anhydrous sodium sulfate, the solvent was distilled off under reduced pressure. The residue was purified by silica gel column chromatography (eluent; n-hexane:ethyl acetate=3:1-2:1) to give 4-chloro-2-isopropylsulfonylaniline (2.79 g) as a light-orange solid.

Preparation Example 7

To a mixture of 2,4-dichloro-6-methoxy-1,3,5-triazine (370 mg) and tetrahydrofuran (10 mL), a mixture of 2-(isopropylsulfonyl)aniline (400 mg), N-ethyl-N-isopropylpropane-2-amine (0.72 mL) and tetrahydrofuran (5 mL) was added and stirred overnight at room temperature and further stirred at 70° C. for 7 hours. The reaction mixture was cooled on ice and diluted with water (60 mL). The precipitated solid was collected by filtration, purified by silica gel column chromatography (eluent; chloroform) and then washed with hexane to give 4-chloro-N-[2-(isopropylsulfonyl)phenyl]-6-methoxy-1,3,5-triazine-2-amine (200 mg) as a white solid.

Preparation Example 8

To a mixture of 2-(isopropylsulfonyl)aniline (450 mg) and N,N-dimethylformamide (10 mL), 55% sodium hydride in oil (200 mg) was added under ice cooling and stirred for 30 minutes, followed by addition of 2,4-dichloroquinazoline (500 mg). The reaction mixture was stirred for 30 minutes under ice cooling and further stirred overnight at room temperature. The reaction mixture was cooled on ice, diluted with water and then extracted with ethyl acetate. The organic layer was washed with water and saturated aqueous sodium chloride. After drying over anhydrous sodium sulfate, the solvent was distilled off under reduced pressure, and the residue was purified by silica gel column chromatography (eluent; n-hexane:ethyl acetate=5:1-3:1) to give 2-chloro-N-[2-(isopropylsulfonyl)phenyl]quinazoline-4-amine (0.67 g) as a light-yellow solid.

Preparation Example 9

To a mixture of 2-fluoroaniline (232 mg), 2,4-dichloroquinazoline (400 mg) and N,N-dimethylformamide (4 mL), potassium carbonate (430 mg) was added and stirred at room temperature for 8 hours. The reaction mixture was diluted with water (40 mL), and the precipitated solid was collected by filtration and purified by silica gel column chromatography (eluent; n-hexane:ethyl acetate=5:1-3:1) to give 2-chloro-N-(2-fluorophenyl)quinazoline-4-amine (0.22 g) as a light-yellow solid.

Preparation Example 10

To a mixture of the compound of Preparation Example 24 (309 mg) and acetonitrile (5 mL), azetidine hydrochloride (112 mg) and N-ethyl-N-isopropylpropane-2-amine (0.42 mL) were added and stirred at room temperature for 1 hour. The reaction mixture was diluted with water, and the precipitated solid was collected by filtration and dried to give 4-azetidin-1-yl-6-chloro-N-(2-fluorophenyl)-1,3,5-triazine-2-amine (253 mg) as a white solid.

Preparation Example 11

To a mixture of tert-butyl 4-hydroxypiperidine-1-carboxylate (1.49 g) and tetrahydrofuran (30 mL), potassium tert-butoxide (830 mg) was added under ice cooling and stirred for 30 minutes, followed by addition of a mixture of 4-fluoro-2-methoxy-1-nitrobenzene (1.00 g) and tetrahydrofuran (20 mL). After stirring at room temperature for 3 hours, the reaction mixture was extracted by addition of water and ethyl acetate, washed with saturated aqueous sodium chloride, and then dried over anhydrous magnesium sulfate. The solvent was distilled off under reduced pressure, and the residue was purified by silica gel column chromatography (eluent; n-hexane:diethyl ether=4:1) to give tert-butyl 4-(3-methoxy-4-nitrophenoxy)piperidine-1-carboxylate (898 mg).

Preparation Example 12

To a mixture of 4-fluoro-2-methoxy-1-nitrobenzene (5 g), potassium carbonate (10 g) and N,N-dimethylformamide (50 mL), 1,4-dioxa-8-azaspiro[4.5]decane (5 g) was added and stirred overnight at 70° C. The reaction mixture was diluted with water (150 mL), and the precipitated solid was collected by filtration and washed with diethyl ether to give 8-(3-methoxy-4-nitrophenyl)-1,4-dioxa-8-azaspiro[4.5]decane (7.86 g) as a light-yellow solid.

Preparation Example 13

To a mixture of tert-butyl 3-(4-methylpiperazin-1-yl)pyrrolidine-1-carboxylate (3.04 g) and chloroform (30 mL), trifluoroacetic acid (10 mL) was added and stirred at room temperature for 1 hour. The reaction mixture was evaporated under reduced pressure to remove the solvent, followed by addition of a mixture of 4-fluoro-2-methoxy-1-nitrobenzene (1.93 g), potassium carbonate (12.2 g) and N,N-dimethylformamide (60 mL). After stirring overnight at 80° C., the reaction mixture was evaporated under reduced pressure to remove the solvent, and the residue was diluted with water and extracted with ethyl acetate. The organic layer was washed with saturated aqueous sodium chloride, and then dried over anhydrous magnesium sulfate. The solvent was distilled off under reduced pressure to give 1-[1-(3-methoxy-4-nitrophenyl)pyrrolidin-3-yl]-4-methylpiperazine (2.16 g).

Preparation Example 14

To a mixture of the compound of Preparation Example 57 (6.68 g), 1-methylpiperazine (4.17 mL) and dichloromethane (100 mL), sodium triacetoxyborohydride (8.04 g) was added and stirred overnight at room temperature. The reaction mixture was diluted with water and saturated aqueous sodium hydrogen carbonate, extracted with chloroform, and then washed with saturated aqueous sodium chloride. The solvent was distilled off under reduced pressure, and the residue was purified by silica gel column chromatography (eluent; chloroform:methanol=1:0-20:1) to give 1-[1-(3-ethoxy-4-nitrophenyl)piperidin-4-yl]-4-methylpiperazine (6.68 g).

Preparation Example 15

To a mixture of 4-fluoro-2-methyl-1-nitrobenzene (3.08 g), potassium carbonate (6.80 g) and N,N-dimethylformamide (30 mL), piperidine-4,4-diol hydrochloride (3.83 g) was added and stirred at 70° C. for 2 days. The reaction mixture was evaporated under reduced pressure, and the residue was diluted with water and ethyl acetate. The precipitated solid was collected by filtration. After drying, dichloromethane (56 mL), 1-methylpiperazine (3.00 mL) and sodium triacetoxyborohydride (5.75 g) were added and stirred overnight at room temperature. The reaction mixture was diluted with water and saturated aqueous sodium hydrogen carbonate, extracted with chloroform, and then washed with saturated aqueous sodium chloride. After drying over anhydrous magnesium sulfate, the solvent was distilled off under reduced pressure, and the residue was purified by silica gel column chromatography (eluent; chloroform:methanol=1:0-20:1) to give 1-methyl-4-[1-(3-methyl-4-nitrophenyl)piperidin-4-yl]piperazine (1.29 g).

Preparation Example 16

To a mixture of concentrated sulfuric acid (40 mL) and acetic acid (60 mL), N-[2-(4-chlorophenyl)ethyl]-2,2,2-trifluoroacetamide (14.2 g) and paraformaldehyde (2.79 g) were added sequentially and stirred overnight under an argon atmosphere. The reaction mixture was added to ice-cold water, extracted with ethyl acetate, and then washed with saturated aqueous sodium hydrogen carbonate and saturated aqueous sodium chloride. After drying over anhydrous magnesium sulfate, the solvent was distilled off under reduced pressure to give 7-chloro-2-(trifluoroacetyl)-1,2,3,4-tetrahydroisoquinoline (13.7 g) as a light-yellow solid.

Preparation Example 17

The compound of Preparation Example 16 (13.7 g) was dissolved in concentrated sulfuric acid (60 mL) and then cooled to 0° C., followed by dropwise addition of a solution of potassium nitrate (3.3 g) in concentrated sulfuric acid (60 mL) over 1 hour. After stirring for 1 hour under ice cooling, the reaction mixture was added to ice-cold water. After extraction with ethyl acetate, the organic layer was washed with saturated aqueous sodium chloride and dried over anhydrous magnesium sulfate. The solvent was distilled off under reduced pressure, and the residue was recrystallized from ethyl acetate-hexane to give 7-chloro-6-nitro-2-(trifluoroacetyl)-1,2,3,4-tetrahydroisoquinoline (4.46 g) as a colorless solid.

Preparation Example 18

To a mixture of tert-butyl 1-oxa-4,9-diazaspiro[5.5]undecane-9-carboxylate (5.80 g) and dioxane (100 mL), 1 M aqueous sodium hydroxide (24.9 mL) and benzyl chloroformate (3.55 mL) were added sequentially under ice cooling and stirred at room temperature for 16 hours. The reaction mixture was concentrated under reduced pressure and then extracted with ethyl acetate. The organic layer was concentrated under reduced pressure, and the residue was purified by silica gel column chromatography (eluent; n-hexane:ethyl acetate=9:1-1:1) to give 4-benzyl 9-tert-butyl 1-oxa-4,9-diazaspiro[5.5]undecane-4,9-dicarboxylate (8.06 g) as a colorless syrup.

Preparation Example 19

To a mixture of the compound of Preparation Example 18 (8.06 g) and ethanol (200 mL), 4 M hydrochloric acid in dioxane (30 mL) was added and stirred at room temperature for 16 hours. The solvent was distilled off under reduced pressure, and the residue was recrystallized from diethyl ether-ethanol to give benzyl 1-oxa-4,9-diazaspiro[5.5]undecane-4-carboxylate hydrochloride (3.86 g) as a colorless solid.

Preparation Example 20

To a mixture of the compound of Preparation Example 12 (7.83 g) and ethanol (100 mL), 10% palladium on carbon (water content: 53%, 2.83 g) was added and stirred overnight at room temperature under a hydrogen atmosphere at normal pressure. After filtration through celite, the filtrate was evaporated under reduced pressure to give 4-(1,4-dioxa-8-azaspiro[4.5]decan-8-yl)-2-methoxyaniline (6.83 g) as a light-purple solid.

Preparation Example 21

To a mixture of the compound of Preparation Example 71 (1.32 g) and acetic acid (30 mL), iron powder (0.79 g) was added and stirred at 80° C. for 3 hours. Insoluble materials in the reaction mixture were removed and the solvent was distilled off under reduced pressure. The residue was diluted with ethyl acetate and insoluble materials were removed, followed by washing with saturated aqueous sodium chloride. After drying over anhydrous sodium sulfate, the solvent was distilled off under reduced pressure to give 2-chloro-4-[4-(4-methylpiperazin-1-yl)piperidin-1-yl]aniline (290 mg).

Tables 8 and 9 show the chemical structures of the compounds prepared in the above preparation examples. Further, in the same manner as shown in the above preparation examples, the additional compounds shown in Tables 10 to 16 were also prepared from their corresponding starting materials. Tables 17 to 19 show the instrumental analysis data of these compounds obtained in the preparation examples.

Example 1

To a mixture of 2-methoxy-4-[4-(4-methylpiperazin-1-yl)piperidin-1-yl]aniline (230 mg) and ethanol (3 mL), methanesulfonic acid (0.11 mL) was added and stirred at room temperature for 15 minutes, followed by addition of the compound of Preparation Example 8 (200 mg) and further stirring at 100° C. for 3 hours. After cooling, the reaction mixture was diluted with water (20 mL) and adjusted to pH 8 with saturated aqueous sodium hydrogen carbonate, followed by filtration to collect the precipitated solid. The resulting solid was purified by silica gel column chromatography (eluent; chloroform:methanol:saturated aqueous ammonia=50:1:0.1-30:1:0.1) to give $N^4$-[2-(isopropylsulfonyl)phenyl]-$N^2$-{2-methoxy-4-[4-(4-methylpiperazin-1-yl)piperidin-1-yl]phenyl}quinazoline-2,4-diamine (0.26 g) as a yellow amorphous substance.

Example 2

To a mixture of 2-methoxy-$N^4$-methyl-$N^4$-(1-methylpiperidin-4-yl)benzene-1,4-diamine (150 mg) and ethanol (3 mL), methanesulfonic acid (0.08 mL) was added and stirred at room temperature for 15 minutes, followed by addition of the compound of Preparation Example 8 (240 mg) and further stirring at 100° C. for 3 hours. After cooling, the reaction mixture was adjusted to pH 8 by addition of water and saturated aqueous sodium hydrogen carbonate, and then extracted with ethyl acetate. The extract was washed with water and saturated aqueous sodium chloride. After drying over anhydrous sodium sulfate, the solvent was distilled off under reduced pressure, and the residue was purified by silica gel column chromatography (eluent; chloroform:methanol:saturated aqueous ammonia=100:1:0.1-50:1:0.1) to give a brown amorphous substance. The resulting amorphous substance was dissolved in ethanol (5 mL) and ethyl acetate (5 mL), followed by addition of 4 M hydrogen chloride in ethyl acetate (0.3 mL). After stirring for 10 minutes, ethyl acetate (20 mL) was added, and the precipitated solid was collected by filtration to give $N^4$-[2-(isopropylsulfonyl)phenyl]-$N^2$-{2-methoxy-4-[methyl(1-methylpiperazin-4-yl)amino]phenyl}quinazoline-2,4-diamine trihydrochloride (0.15 g) as a light-yellow solid.

Example 3

To a mixture of the compound of Preparation Example 27 (200 mg), 2-methoxy-4-(morpholin-4-yl)aniline (158 mg) and acetonitrile (10 mL), N-ethyl-N-isopropylpropane-2-amine (0.13 mL) was added and heated under reflux for 12 hours. The reaction mixture was diluted with water, and the precipitated solid was collected by filtration, dried and then purified by silica gel column chromatography (eluent; chloroform:methanol=20:1) to give 2-({4-[(2-methoxy-4-morpholin-4-ylphenyl)amino]-1,3,5-triazin-2-yl}amino)-N-methylbenzamide (135 mg) as a white solid.

Example 4

A mixture of the compound of Preparation Example 22 (209 mg), 2-methoxy-4-(4-phenylpiperazin-1-yl)aniline (189 mg), N-ethyl-N-isopropylpropane-2-amine (0.12 mL) and N-methyl-2-pyrrolidinone (3 mL) was stirred at 120° C. for 20 minutes using a microwave reaction system. The reaction mixture was diluted with water, and the precipitated solid was collected by filtration, dried and then purified by silica gel column chromatography (eluent; chloroform:methanol=1:0-20:1). The resulting product was dissolved in ethyl acetate and 4 M hydrogen chloride in ethyl acetate was added thereto, followed by evaporation under reduced pressure to remove the solvent. The residue was crystallized from ethanol to give N-[2-(isopropylsulfonyl)phenyl]-N'-[2-methoxy-4-(4-phenylpiperazin-1-yl)phenyl]-1,3,5-triazine-2,4-diamine trihydrochloride (273 mg).

Example 5

To a mixture of the compound of Preparation Example 34 (850 mg) and acetonitrile (17 mL), the compound of Preparation Example 37 (806 mg) and N-ethyl-N-isopropylpropane-2-amine (0.44 mL) were added at room temperature and stirred for 1 hour. The reaction mixture was diluted with water, extracted with chloroform, and then washed with saturated aqueous sodium chloride. After drying over anhydrous magnesium sulfate, the solvent was distilled off under reduced pressure, and the residue was purified by silica gel column chromatography (eluent; n-hexane:ethyl acetate=1:1). The resulting product was dissolved in ethyl acetate and 4 M hydrogen chloride in ethyl acetate was added thereto, followed by evaporation under reduced pressure to remove the solvent. The residue was crystallized from a mixed solvent of ethanol and ethyl acetate to give 6-chloro-N-[2-(isopropylsulfonyl)phenyl]-N'-[2-methoxy-4-(piperidin-4-yloxy)phenyl]-1,3,5-triazine-2,4-diamine hydrochloride (323 mg).

Example 6

A mixture of the compound of Preparation Example 78 (320 mg), the compound of Preparation Example 20 (260 mg), N-ethyl-N-isopropylpropane-2-amine (0.17 mL) and N-methyl-2-pyrrolidinone (1 mL) was reacted at 120° C. for 20 minutes using a microwave reaction system. After cooling, the reaction mixture was poured into water (20 mL), and the precipitated solid was collected by filtration and then dried to give a light-purple solid. To the resulting solid, acetic acid (2 mL) and water (1 mL) were added and stirred overnight at 70° C. The reaction mixture was concentrated under reduced pressure, and the residue was partitioned by addition of ethyl acetate (50 mL) and saturated aqueous sodium hydrogen carbonate (25 mL). The organic layer was washed with water and saturated aqueous sodium chloride. After drying over anhydrous sodium sulfate, the solvent was distilled off under reduced pressure, and the residue was purified by silica gel column chromatography (eluent; n-hexane:ethyl acetate=1: 1-1:3) to give N-isopropyl-2-[(4-{[2-methoxy-4-(4-oxopiperidin-1-yl)phenyl]amino}-1,3,5-triazin-2-yl)amino]benzenesulfonamide (0.32 g) as an amorphous substance.

Example 7

A mixture of the compound of Example 163 (174 mg), acetic acid (2 mL) and water (1 mL) was stirred overnight at 70° C. To the reaction mixture, ethyl acetate and saturated aqueous sodium hydrogen carbonate were added, and the organic layer was washed with saturated aqueous sodium chloride. After drying over anhydrous magnesium sulfate, the solvent was distilled off under reduced pressure, and the resulting residue was dissolved in dichloromethane (5 mL), followed by addition of 1-methylpiperazine (0.063 mL) and sodium triacetoxyborohydride (122 mg). After stirring at room temperature for two days, the reaction mixture was diluted with saturated aqueous sodium hydrogen carbonate, extracted with chloroform, and then dried over anhydrous magnesium sulfate. The solvent was distilled off under reduced pressure, and the residue was purified by silica gel column chromatography (eluent; chloroform:methanol=1:0-20:1) to give 2-{[4-({2-methoxy-4-[4-(4-methylpiperazin-1-yl)piperidin-1-yl]phenyl}amino)-1,3,5-triazin-2-yl]amino}-N-methylbenzenesulfonamide (42 mg) as a colorless solid.

Example 8

To a mixture of the compound of Example 31 (76 mg) and acetonitrile (5 mL), pyrrolidine (0.041 mL) was added and heated under reflux for 1 hour. The reaction mixture was diluted with water, and the precipitated solid was collected by filtration, dried and then purified by silica gel column chromatography (eluent; chloroform:methanol=20:1) to give 2-({4-[(2-methoxy-4-morpholin-4-ylphenyl)amino]-6-pyrrolidin-1-yl-1,3,5-triazin-2-yl}amino)-N-methylbenzamide (46 mg) as a white powder.

Example 9

To a mixture of the compound of Example 68 (3.15 g) and ethyl acetate (30 mL), 4 M hydrogen chloride in ethyl acetate (30 mL) was added and stirred at room temperature for 1 hour. The solvent was distilled off under reduced pressure, and the residue was diluted with saturated aqueous sodium hydrogen carbonate and then extracted with ethyl acetate. The organic layer was washed with saturated aqueous sodium chloride and then dried over anhydrous magnesium sulfate. The solvent was distilled off under reduced pressure, and the residue was purified by silica gel column chromatography (eluent; chloroform:methanol:saturated aqueous ammonia=100:10:1) to give N-[2-(isopropylsulfonyl)phenyl]-N'-[2-methoxy-4-(piperidin-4-yloxy)phenyl]-1,3,5-triazine-2,4-diamine (2.1 g) as a colorless amorphous substance.

Example 10

To a mixture of the compound of Example 62 (140 mg), morpholine (0.08 mL) and 1,2-dichloroethane (2 mL), sodium triacetoxyborohydride (80 mg) was added and stirred at room temperature for 5 hours. The reaction mixture was diluted with saturated aqueous sodium hydrogen carbonate and extracted with chloroform, and the organic layer was dried over anhydrous sodium sulfate. The solvent was distilled off under reduced pressure, and the residue was purified by silica gel column chromatography (eluent; chloroform:methanol=100:0-100:1) and then washed with diethyl ether to give $N^4$-[2-(isopropylsulfonyl)phenyl]-$N^2$-[2-methoxy-4-(4-morpholin-4-ylpiperidin-1-yl)phenyl]quinazoline-2,4-diamine (0.1 g) as a yellow powder.

Example 11

To a mixture of the compound of Example 66 (150 mg), triethylamine (0.05 mL) and tetrahydrofuran (2 mL), acetic anhydride (0.03 mL) was added and stirred at room temperature for 6 hours. The reaction mixture was diluted with saturated aqueous sodium hydrogen carbonate and extracted with ethyl acetate, and the organic layer was washed with water and saturated aqueous sodium chloride. After drying over anhydrous sodium sulfate, the solvent was distilled off under reduced pressure, and the residue was purified by silica gel column chromatography (eluent; chloroform:methanol=100:1-50:1) and then washed with hexane to give $N^2$-[4-(4-acetylpiperazin-1-yl)-2-methoxyphenyl]-$N^4$-[2-(isopropylsulfonyl)phenyl]quinazoline-2,4-diamine (0.11 g) as a yellow powder.

Example 12

To a mixture of the compound of Example 147 (240 mg), formalin (0.18 mL) and 1,2-dichloroethane (5 mL), sodium triacetoxyborohydride (280 mg) was added and stirred at room temperature for 3 days. The reaction mixture was diluted with saturated aqueous sodium hydrogen carbonate and extracted with chloroform, and the organic layer was dried over anhydrous sodium sulfate. After the solvent was distilled off under reduced pressure, the residue was purified by silica gel column chromatography (eluent; chloroform:methanol:saturated aqueous ammonia=50:1:0.1-30:10:1) and then washed with diethyl ether to give N-[2-(isopropylsulfonyl)phenyl]-N'-[2-methoxy-4-(1-methyl-diazaspiro[5.5]undecan-9-yl)phenyl]-1,3,5-triazine-2,4-diamine (135 mg) as a light-yellow powder.

Example 13

A mixture of the compound of Example 22 (169 mg) and 6 M hydrochloric acid (4 mL) was stirred at 50° C. for 2 hours. After cooling, the reaction mixture was basified by addition of water and 1 M aqueous sodium hydroxide, and then extracted with chloroform. The organic layer was washed with saturated aqueous sodium chloride and dried over anhydrous magnesium sulfate. The solvent was distilled off under reduced pressure, followed by recrystallization from ethanol-diethyl ether to give 6-{[2-(isopropylsulfonyl)phenyl]amino}-4-({2-methoxy-4-[4-(4-methylpiperazin-1-yl)piperidin-1-yl]phenyl}amino)-1,3,5-triazin-2(1H)-one (27 mg).

Example 14

A mixture of the compound of Example 23 (250 mg) and pyridine hydrochloride (1 g) was stirred at 200° C. for 10 minutes. After cooling to room temperature, the reaction mixture was diluted with water and washed with chloroform. The aqueous layer was evaporated under reduced pressure, and the residue was purified by silica gel column chromatography (eluent; chloroform:methanol=1:0-10:1) to give 2-[(4-{[2-(isopropylsulfonyl)phenyl]amino}-1,3,5-triazin-2-yl)amino]-5-[4-(4-methylpiperazin-1-yl)piperidin-1-yl]phenol (45 mg).

Example 15

To a mixture of the compound of Example 102 (630 mg), ethanol (10 mL) and tetrahydrofuran (10 mL), 10% palladium on carbon (water content: 53%, 500 mg) was added and stirred at room temperature for 2 hours under a hydrogen atmosphere at normal pressure. After filtration through celite, the filtrate was evaporated under reduced pressure, and the residue was purified by silica gel column chromatography (eluent; chloroform:methanol=1:0-20:1) to give N-[2-(isopropylsulfonyl)phenyl]-N'-[2-methoxy-4-(1-oxa-4,9-diazaspiro[5.5]undecan-9-yl)phenyl]-1,3,5-triazine-2,4-diamine (102 mg).

Example 16

To a mixture of the compound of Example 177 (1.09 g) and ethyl acetate (10 mL), 4 M hydrogen chloride in ethyl acetate (10 mL) was added and stirred at room temperature for 30 minutes. The reaction mixture was evaporated under reduced pressure, and the residue was washed with ethyl acetate, collected by filtration and then dried to give N-(7-fluoro-1,2,3,4-tetrahydroisoquinolin-6-yl)-N'-[2-(isopropylsulfonyl)phenyl]-1,3,5-triazine-2,4-diamine dihydrochloride (950 mg) as a colorless solid.

Example 17

To a mixture of the compound of Example 178 (1.2 g) and methanol (15 mL), 2 M hydrochloric acid (15 mL) was added and heated overnight under reflux. The reaction mixture was concentrated under reduced pressure, diluted with saturated aqueous sodium hydrogen carbonate, extracted with chloroform and then washed with saturated aqueous sodium chloride. The solvent was distilled off, and the residue was purified by silica gel column chromatography (eluent; chloroform:methanol=1:0-20:1) to give N-(7-chloro-1,2,3,4-tetrahydroisoquinolin-6-yl)-N'-[2-(isopropylsulfonyl)phenyl]-1,3,5-triazine-2,4-diamine (260 mg) as a colorless amorphous substance.

Example 18

To a mixture of the compound of Example 62 (13.6 mg), methylamine hydrochloride (2.0 mg), triethylamine (3.0 mg) and 1,2-dichloroethane (0.5 mL), sodium triacetoxyborohydride (10.5 mg) was added and stirred overnight at room temperature. The reaction mixture was partitioned by addition of chloroform and water, and the organic layer was evaporated under reduced pressure. The residue was separated and purified by HPLC (column: SunFire C18 5 μm 19 mm×100 mm (Waters Inc.), solvent: MeOH/0.1% HCOOH—H₂O=10/90 (0 min)-10/90 (1 min)-95/5 (9 min)-95/5 (12 min), flow rate: 25 mL/min) to give N⁴-[2-(isopropylsulfonyl)phenyl]-N²-{2-methoxy-4-[4-(methylamino)piperidin-1-yl]phenyl}quinazoline-2,4-diamine (12.5 mg).

In Examples 76, 77, 78, 85 and 110, the desired compounds were obtained by being reacted in the same manner, and then deprotected, separated and purified.

Example 19

To a mixture of the compound of Example 72 (9.6 mg), cyclohexanone (2.9 mg) and dichloromethane (0.5 mL), sodium triacetoxyborohydride (10.5 mg) was added and stirred overnight at room temperature. The reaction mixture was partitioned by addition of chloroform and water, and the organic layer was evaporated under reduced pressure. The residue was separated and purified by HPLC (column: SunFire C18 5 μm 19 mm×100 mm (Waters Inc.), solvent: MeOH/0.1% HCOOH—H₂O=10/90 (0 min)-10/90 (1 min)-95/5 (9 min)-95/5 (12 min), flow rate: 25 mL/min) to give N-[4-(4-cyclohexylpiperazin-1-yl)-2-methoxyphenyl]-N'-[2-(isopropylsulfonyl)phenyl]-1,3,5-triazine-2,4-diamine (5.1 mg).

In Examples 134 and 141, the desired compounds were obtained by being reacted in the same manner, and then deprotected, separated and purified.

Example 20

To a mixture of the compound of Example 72 (9.6 mg), acetic acid (1.8 mg), 1-hydroxybenzotriazole (3.4 mg) and N,N-dimethylformamide (0.5 mL), PS-Carbodiimide (100 mg, Argonaut Technologies Inc.) was added and stirred overnight at room temperature. After addition of MP-Carbonate (50 mg, Argonaut Technologies Inc) and PS-Isocyanate (50 mg, Argonaut Technologies Inc) at room temperature, the reaction mixture was stirred for 2 hours and filtered to remove insoluble materials. The filtrate was concentrated under reduced pressure, and the residue was separated and purified by HPLC (column: SunFire C18 5 μm 19 mm×100 mm (Waters Inc.), solvent: MeOH/0.1% HCOOH—H₂O=10/90 (0 min)-10/90 (1 min)-95/5 (9 min)-95/5 (12 min), flow rate: 25 mL/min) to give N-[4-(4-acetylpiperazin-1-yl)-2-methoxyphenyl]-N'-[2-(isopropylsulfonyl)phenyl]-1,3,5-triazine-2,4-diamine (6.8 mg).

In Examples 160, 161 and 162, the desired compounds were obtained by being reacted in the same manner, and then deprotected, separated and purified.

Tables 20 to 22 show the chemical structures of the compounds prepared in the above examples. Further, in the same manner as shown in the above examples, the additional compounds shown in Tables 23 to 42 were also prepared from their corresponding starting materials. Tables 43 to 50 show the instrumental analysis data of these compounds obtained in the examples.

TABLE 8

| Rex/Salt | Structure |
|---|---|
| 1 | 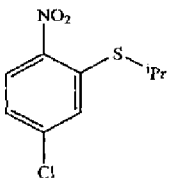 |

TABLE 8-continued

| Rex/Salt | Structure |
|---|---|
| 2 | 2-nitro-6-chlorophenyl isopropyl sulfone |
| 3 | 2-nitro-5-chlorophenyl isopropyl sulfone |
| 4 | 2-nitro-N-ethyl-N-methylbenzenesulfonamide |
| 5 | N-cyclopropyl-N-methyl-2-nitrobenzenesulfonamide |
| 6 | 2-amino-5-chlorophenyl isopropyl sulfone |
| 7 | N-(4-chloro-6-methoxy-1,3,5-triazin-2-yl)-2-(isopropylsulfonyl)aniline |
| 8 | N-(2-chloroquinazolin-4-yl)-2-(isopropylsulfonyl)aniline |
| 9 | N-(2-chloroquinazolin-4-yl)-2-fluoroaniline |

TABLE 8-continued

| Rex/Salt | Structure |
|---|---|
| 10 | 4-(azetidin-1-yl)-6-chloro-N-(2-fluorophenyl)-1,3,5-triazin-2-amine |

TABLE 9

| Rex/Salt | Structure |
|---|---|
| 11 | tert-butyl 4-(3-methoxy-4-nitrophenoxy)piperidine-1-carboxylate |
| 12 | 8-(3-methoxy-4-nitrophenyl)-1,4-dioxa-8-azaspiro[4.5]decane |
| 13 | 1-(3-methoxy-4-nitrophenyl)-3-(4-methylpiperazin-1-yl)pyrrolidine |
| 14 | 1-(3-ethoxy-4-nitrophenyl)-4-(4-methylpiperazin-1-yl)piperidine |
| 15 | 1-(3-methyl-4-nitrophenyl)-4-(4-methylpiperazin-1-yl)piperidine |
| 16 | 1-(7-chloro-3,4-dihydroisoquinolin-2(1H)-yl)-2,2,2-trifluoroethanone |
| 17 | 1-(7-chloro-6-nitro-3,4-dihydroisoquinolin-2(1H)-yl)-2,2,2-trifluoroethanone |

TABLE 9-continued

| Rex/Salt | Structure |
|---|---|
| 18 | piperidine-N-CO2tBu with spiro oxa-piperidine-N-C(O)O-benzyl |
| 19/CL1 | piperidine-NH with spiro oxa-piperidine-N-C(O)O-benzyl |
| 20 | 4-amino-3-methoxyphenyl attached to 1,4-dioxa-8-azaspiro[4.5]decane |
| 21 | 4-amino-3-chlorophenyl-piperidin-4-yl-(4-methylpiperazine) |

TABLE 10

| Rex/Salt | Structure |
|---|---|
| 22 | 2-(isopropylsulfonyl)phenyl-NH-(4-chloro-1,3,5-triazin-2-yl) |
| 23 | 2-(isopropylsulfonyl)phenyl-NH-(2,7-dichloroquinazolin-4-yl) |

TABLE 10-continued

| Rex/Salt | Structure |
|---|---|
| 24 | 2-fluorophenyl-NH-(4,6-dichloro-1,3,5-triazin-2-yl) |
| 25 | 2-(N-methylcarbamoyl)phenyl-NH-(4,6-dichloro-1,3,5-triazin-2-yl) |
| 26 | 2-fluorophenyl-NH-(4-chloro-1,3,5-triazin-2-yl) |
| 27 | 2-(N-methylcarbamoyl)phenyl-NH-(4-chloro-1,3,5-triazin-2-yl) |
| 28 | 2-(isopropylsulfonyl)phenyl-NH-(2,8-dichloroquinazolin-4-yl) |
| 29 | 2-(isopropylsulfonyl)-4-chlorophenyl-NH-(2-chloroquinazolin-4-yl) |
| 30 | 2-(isopropylsulfonyl)phenyl-NH-(2,6-dichloroquinazolin-4-yl) |

TABLE 10-continued

| Rex/Salt | Structure |
|---|---|
| 31 | 4-chloro-2-nitrophenyl isopropyl sulfide |

TABLE 11

| Rex/Salt | Structure |
|---|---|
| 32 | 4-chloro-2-nitrophenyl isopropyl sulfone |
| 33 | N-(2-(isopropylsulfonyl)phenyl)-2,5-dichloroquinazolin-4-amine |
| 34 | N-(2-(isopropylsulfonyl)phenyl)-4,6-dichloro-1,3,5-triazin-2-amine |
| 35 | 2-amino-4-chlorophenyl isopropyl sulfone |
| 36 | N-(4-chloro-2-(isopropylsulfonyl)phenyl)-2-chloroquinazolin-4-amine |
| 37 | tert-butyl 4-(4-amino-3-methoxyphenoxy)piperidine-1-carboxylate |

TABLE 11-continued

| Rex/Salt | Structure |
|---|---|
| 38 | N-(2-(isopropylsulfonyl)phenyl)-4-chloro-6-morpholino-1,3,5-triazin-2-amine |
| 39 | 4-methoxy-2-nitrophenyl isopropyl sulfide (with iPr on S) |
| 40 | 4-methoxy-2-nitrophenyl isopropyl sulfone |
| 41 | 4-methoxy-2-nitrophenyl isopropyl sulfide |

TABLE 12

| Rex/Salt | Structure |
|---|---|
| 42 | 2-amino-5-methoxyphenyl isopropyl sulfone |
| 43 | 4-methoxy-2-nitrophenyl isopropyl sulfone |
| 44 | N-(4-methoxy-2-(isopropylsulfonyl)phenyl)-2-chloroquinazolin-4-amine |
| 45 | 2-amino-5-methoxyphenyl isopropyl sulfone |

TABLE 12-continued

| Rex/Salt | Structure |
|---|---|
| 46 | 2-(iPr-sulfonyl)-4-methoxyphenyl-NH-(2-chloroquinazolin-4-yl) |
| 47 | 2-methoxy-4-(tetrahydropyran-4-yloxy)-1-nitrobenzene |
| 48 | 2-methoxy-4-(tetrahydropyran-4-yloxy)-aniline |
| 49 | 2-amino-6-chlorophenyl iPr-sulfone |
| 50 | 2-(iPr-sulfonyl)phenyl-NH-(4-chloro-6-methyl-1,3,5-triazin-2-yl) |
| 51 | 2-(iPr-sulfonyl)-3-chlorophenyl-NH-(2-chloroquinazolin-4-yl) |

TABLE 13

| Rex/Salt | Structure |
|---|---|
| 52 | 2-(N-methylcarbamoyl)phenyl-NH-(2-chloroquinazolin-4-yl) |
| 53 | 3-(methylsulfonyl)phenyl-NH-(2-chloroquinazolin-4-yl) |
| 54 | 4-(methylsulfonyl)phenyl-NH-(2-chloroquinazolin-4-yl) |
| 55 | 1-(4-nitro-3-methoxyphenyl)-4-phenylpiperazine |
| 56 | 1-(4-amino-3-methoxyphenyl)-4-phenylpiperazine |
| 57 | 1-(3-ethoxy-4-nitrophenyl)piperidin-4-one |
| 58 | 1-(3-iPrO-4-nitrophenyl)piperidin-4-one |
| 59 | 1-(3-iPrO-4-nitrophenyl)-4-(4-methylpiperazin-1-yl)piperidine |
| 60 | 1-(3-ethoxy-4-aminophenyl)-4-(4-methylpiperazin-1-yl)piperidine |

TABLE 13-continued
| Rex/Salt | Structure |
|---|---|
| 61 | 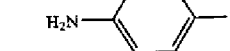 |
| 62 | 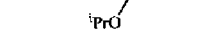 |
| 63 | 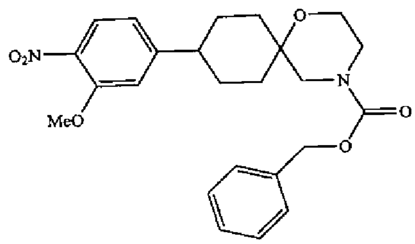 |
TABLE 14
| Rex/Salt | Structure |
|---|---|
| 64 | 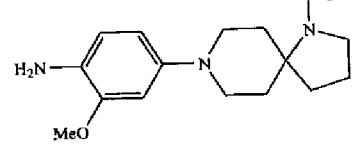 |
| 65 | 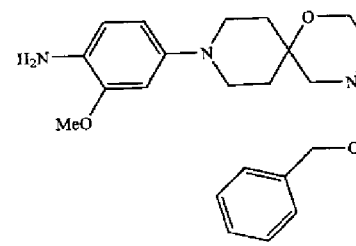 |
| 66 | 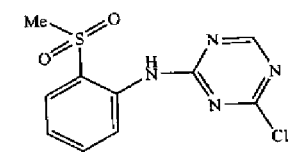 |
| 67 | 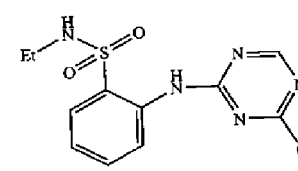 |
TABLE 14-continued
| Rex/Salt | Structure |
|---|---|
| 68 | 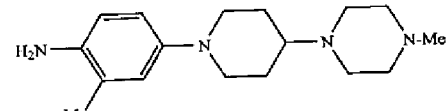 |
| 69 | 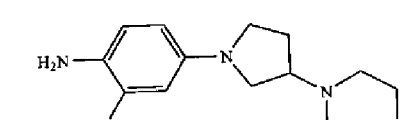 |
| 70 | 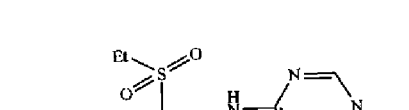 |
| 71 | 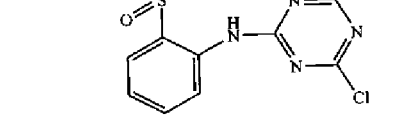 |
| 72 | 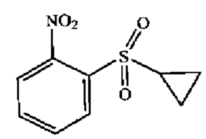 |
| 73 | 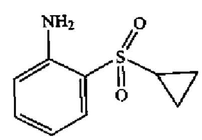 |
| 74 | 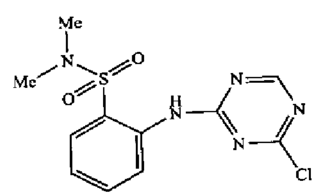 |
| 75 | 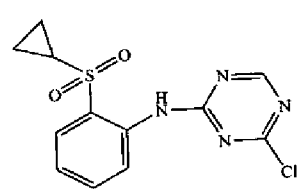 |

TABLE 15

| Rex/Salt | Structure |
|---|---|
| 76 | 3-methoxy-4-nitrophenyl substituted 1,9-diazaspiro[5.5]undecane |
| 77 | 4-amino-3-methoxyphenyl substituted 1,9-diazaspiro[5.5]undecane |
| 78 | N-isopropyl 2-[(4-chloro-1,3,5-triazin-2-yl)amino]benzenesulfonamide |
| 79 | N-isopropyl-N-methyl 2-[(4-chloro-1,3,5-triazin-2-yl)amino]benzenesulfonamide |
| 80 | N-methyl 2-[(4-chloro-1,3,5-triazin-2-yl)amino]benzenesulfonamide |
| 81 | N,N-diethyl 2-[(4-chloro-1,3,5-triazin-2-yl)amino]benzenesulfonamide |
| 82 | N-ethyl-N-methyl 2-aminobenzenesulfonamide |
| 83 | pyrrolidin-1-yl 2-[(4-chloro-1,3,5-triazin-2-yl)amino]phenyl sulfone |
| 84 | N-cyclopropyl 2-[(4-chloro-1,3,5-triazin-2-yl)amino]benzenesulfonamide |

TABLE 15-continued

| Rex/Salt | Structure |
|---|---|
| 85 | N-ethyl-N-methyl 2-[(4-chloro-1,3,5-triazin-2-yl)amino]benzenesulfonamide |
| 86 | morpholin-4-yl 2-[(4-chloro-1,3,5-triazin-2-yl)amino]phenyl sulfone |
| 87 | N-cyclopropyl-N-methyl 2-aminobenzenesulfonamide |

TABLE 16

| Rex/Salt | Structure |
|---|---|
| 88 | N-cyclopropyl-N-methyl 2-[(4-chloro-1,3,5-triazin-2-yl)amino]benzenesulfonamide |
| 89 | piperidin-1-yl 2-[(4-chloro-1,3,5-triazin-2-yl)amino]phenyl sulfone |
| 90 | 1-(3-methoxy-4-nitrophenyl)azetidin-3-ol |
| 91 | 1-(4-amino-3-methoxyphenyl)azetidin-3-ol |
| 92 | 6-amino-7-chloro-2-(trifluoroacetyl)-1,2,3,4-tetrahydroisoquinoline |

TABLE 16-continued

| Rex/Salt | Structure |
|---|---|
| 93 | iPr-SO2-C6H4-NH-triazine-Cl |
| 94 | Me2N-SO2-C6H4-NH-triazine-Cl |

TABLE 17

| Rex | Data |
|---|---|
| 1 | EI: 230.9 |
| 2 | CI+: 263.9 |
| 3 | FAB+: 264.0 |
| 4 | ESI+: 245.4 |
| 5 | ESI+: 257.3 |
| 6 | EI: 232.9 |
| 7 | ESI+: 343.0 |
| 8 | ESI+: 362.1 |
| 9 | ESI+: 274.2 |
| 10 | FAB+: 280.1 |
| 11 | FAB+: 353.2 |
| 12 | ESI+: 295.1 |
| 13 | FAB+: 321.1 |
| 14 | FAB+: 349.2 |
| 15 | ESI+: 319.15 |
| 16 | EI: 262.9, 265.0 |
| 17 | EI: 308.0 |
| 18 | ESI+: 391.1 |
| 19 | ESI+: 291.1 |
| 20 | EI: 264.0 |
| 21 | ESI+: 309.2 |

TABLE 18

| Rex | Rsyn | Data |
|---|---|---|
| 22 | 7 | ESI+: 313.1 |
| 23 | 8 | ESI+: 396.1 |
| 24 | 7 | EI: 259.8 |
| 25 | 7 | ESI+: 298.0, 300.0 |
| 26 | 7 | ESI+: 225.09 |
| 27 | 7 | EI: 264.11 |
| 28 | 8 | ESI+: 396.1 |
| 29 | 8 | FAB+: 396.0 |
| 30 | 8 | EI: 395.0 |
| 31 | 1 | EI: 230.9 |
| 32 | 3 | CI+: 264.0 |
| 33 | 8 | CI+: 396.1 |
| 34 | 7 | FAB+: 346.9 |
| 35 | 6 | EI: 232.9 |
| 36 | 8 | FAB+: 396.0 |
| 37 | 20 | EI: 322.1 |
| 38 | 10 | ESI+: 398.2 |
| 39 | 1 | EI: 226.9 |
| 40 | 3 | EI: 258.9 |
| 41 | 1 | EI: 226.9 |
| 42 | 6 | EI: 228.9 |
| 43 | 3 | EI: 258.9 |

TABLE 18-continued

| Rex | Rsyn | Data |
|---|---|---|
| 44 | 8 | ESI+: 392.2 |
| 45 | 6 | EI: 228.9 |
| 46 | 8 | ESI+: 392.2 |
| 47 | 11 | FAB+: 254.1 |
| 48 | 20 | EI: 223.1 |
| 49 | 6 | EI: 232.9 |
| 50 | 7 | FAB+: 327.0 |
| 51 | 8 | ESI+: 396.1 |
| 52 | 8 | ESI+: 313.1 |
| 53 | 8 | ESI+: 334.2 |
| 54 | 8 | ESI+: 334.1 |
| 55 | 12 | ESI+: 314.2 |
| 56 | 20 | ESI+: 284.2 |
| 57 | 12 | EI: 264.0 |
| 58 | 12 | EI: 278.0 |
| 59 | 14 | ESI+: 363.2 |
| 60 | 20 | ESI+: 319.2 |
| 61 | 20 | ESI+: 333.2 |
| 62 | 12 | ESI+: 392.1 |
| 63 | 12 | ESI+: 442.2 |
| 64 | 20 | ESI+: 362.0 |
| 65 | 21 | ESI+: 412.2 |
| 66 | 7 | FAB+: 285.0 |
| 67 | 7 | ESI+: 314.1 |
| 68 | 20 | ESI+: 289.2 |

TABLE 19

| Rex | Rsyn | Data |
|---|---|---|
| 69 | 20 | ESI+: 291.3 |
| 70 | 7 | ESI+: 299.2 |
| 71 | 12 | ESI+: 338.9, 340.9 |
| 72 | 2 | EI: 227.9 |
| 73 | 6 | EI: 196.9 |
| 74 | 7 | ESI+: 314.1 |
| 75 | 7 | EI: 309.9 |
| 76 | 12 | EI: 305.1 |
| 77 | 20 | EI: 275.1 |
| 78 | 7 | ESI+: 328.2 |
| 79 | 7 | EI: 341.0 |
| 80 | 7 | ESI+: 300.06, 302.04 |
| 81 | 7 | ESI+: 342.3 |
| 82 | 6 | EI: 214.0 |
| 83 | 7 | ESI+: 340.2, 342.0 |
| 84 | 7 | ESI+: 326.0, 327.9 |
| 85 | 7 | ESI+: 327.9, 330.0 |
| 86 | 7 | ESI+: 356.0, 357.9 |
| 87 | 6 | EI: 226.0 |
| 88 | 7 | ESI+: 340.2 |
| 89 | 7 | ESI+: 354.3 |
| 90 | 12 | ESI+: 225.2 |
| 91 | 20 | ESI+: 195.0 |
| 92 | 20 | EI: 278.0 |
| 93 | 7 | ESI+: 312.9 |
| 94 | 7 | ESI+: 314 |

TABLE 20

| Ex/Salt | Structure |
|---|---|
| 1 | (structure) |
| 2/ Cl3 | (structure) |
| 3 | (structure) |
| 4/ Cl3 | (structure) |
| 5/ Cl1 | (structure) |

TABLE 20-continued
| Ex/Salt | Structure |
|---|---|
| 6 | 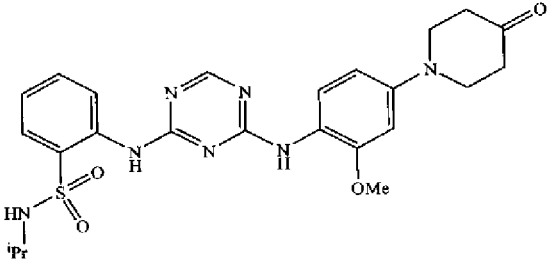 |
| 7 | 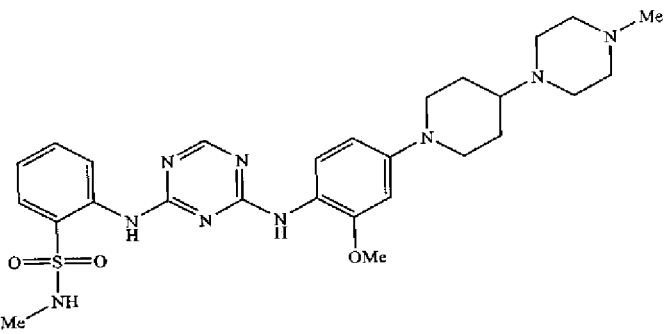 |
| 8 | 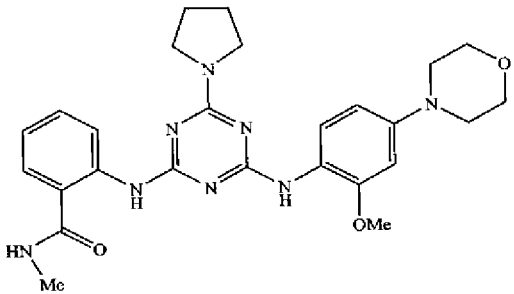 |
TABLE 21
| Ex/Salt | Structure |
|---|---|
| 9 | 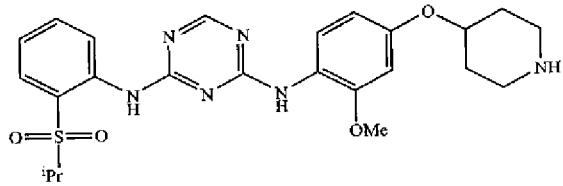 |

TABLE 21-continued

| Ex/Salt | Structure |
|---|---|
| 10 | 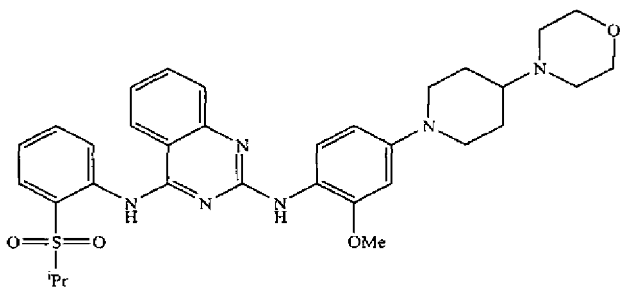 |
| 11 | 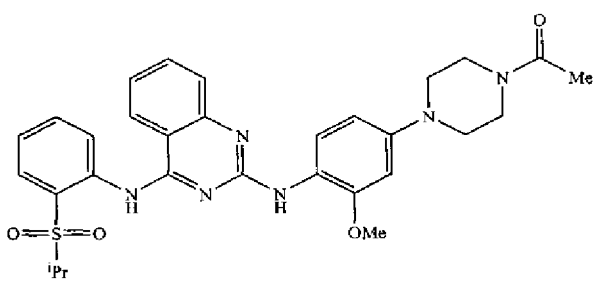 |
| 12 | 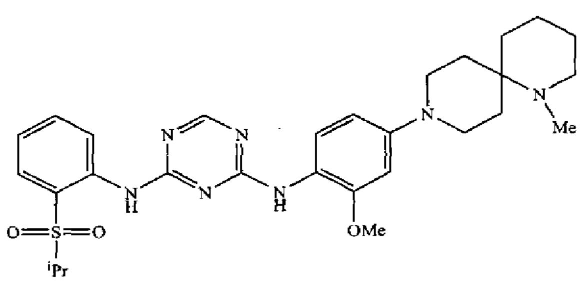 |
| 13 | 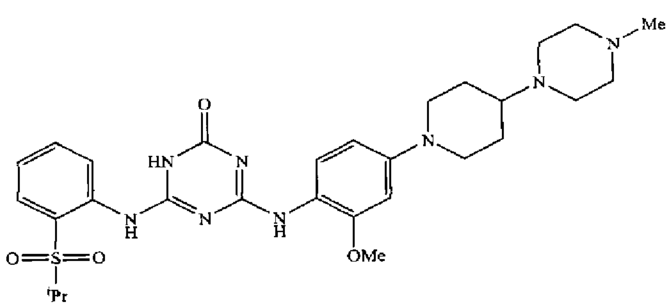 |

TABLE 21-continued

| Ex/Salt | Structure |
|---|---|
| 14 | [Structure: 2-(isopropylsulfonyl)phenyl-NH-triazine-NH-(2-hydroxy-4-(4-(4-methylpiperazin-1-yl)piperidin-1-yl)phenyl)] |
| 15 | [Structure: 2-(isopropylsulfonyl)phenyl-NH-triazine-NH-(2-methoxy-4-(1-oxa-4,9-diazaspiro[5.5]undecan-9-yl)phenyl)] |
| 16/CL2 | [Structure: 2-(isopropylsulfonyl)phenyl-NH-triazine-NH-(7-fluoro-1,2,3,4-tetrahydroisoquinolin-6-yl)] |

TABLE 22

| Ex/Salt | Structure |
|---|---|
| 17 | [Structure: 2-(isopropylsulfonyl)phenyl-NH-triazine-NH-(7-chloro-1,2,3,4-tetrahydroisoquinolin-6-yl)] |
| 18 | [Structure: 2-(isopropylsulfonyl)phenyl-NH-quinazoline-NH-(2-methoxy-4-(4-(methylamino)piperidin-1-yl)phenyl)] |
| 19 | [Structure: 2-(isopropylsulfonyl)phenyl-NH-triazine-NH-(4-(4-cyclohexylpiperazin-1-yl)-2-methoxyphenyl)] |
| 20 | [Structure: 2-(isopropylsulfonyl)phenyl-NH-triazine-NH-(4-(4-acetylpiperazin-1-yl)-2-methoxyphenyl)] |

TABLE 23

| Ex/Salt | Structure |
|---|---|
| 21 | (structure) |
| 22 | (structure) |
| 23 | (structure) |
| 24 | (structure) |
| 25 | (structure) |

TABLE 23-continued
| Ex/Salt | Structure |
|---|---|
| 26/FM | 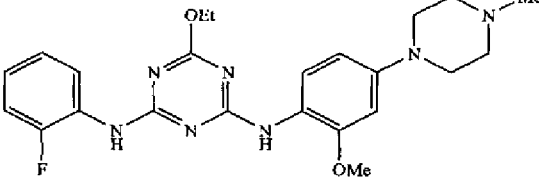 |
| 27 | 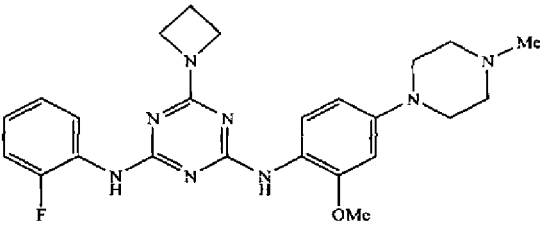 |
| 28 | 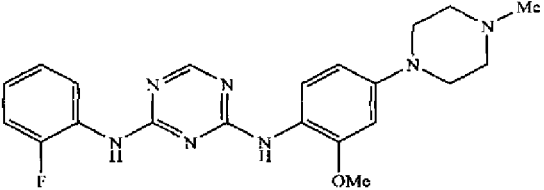 |
TABLE 24
| Ex/Salt | Structure |
|---|---|
| 29 | 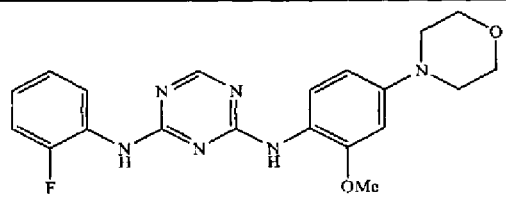 |
| 30 | 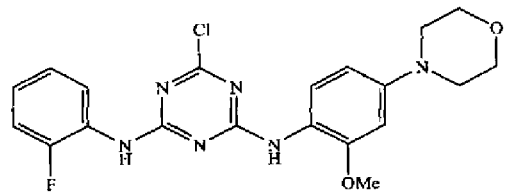 |
| 31 | 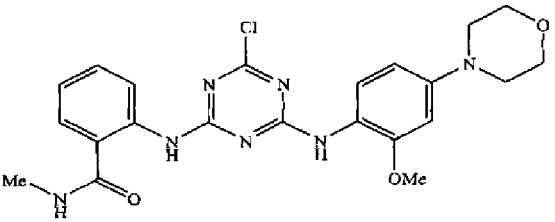 |

TABLE 24-continued
| Ex/Salt | Structure |
|---|---|
| 32 | 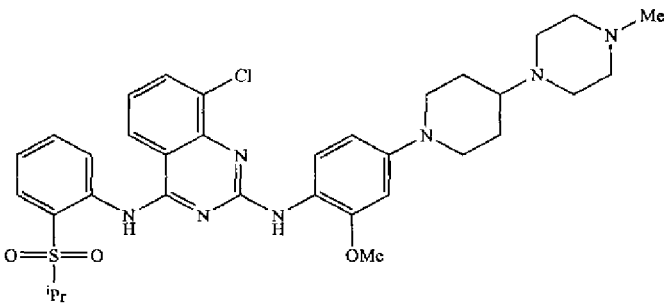 |
| 33 | 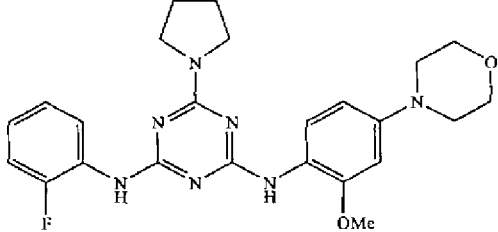 |
| 34/CL2 | 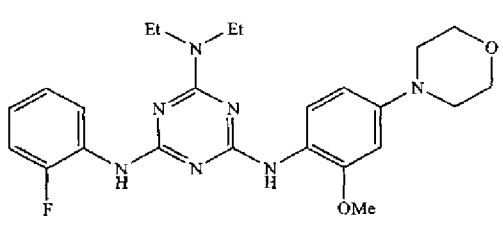 |
| 35 | 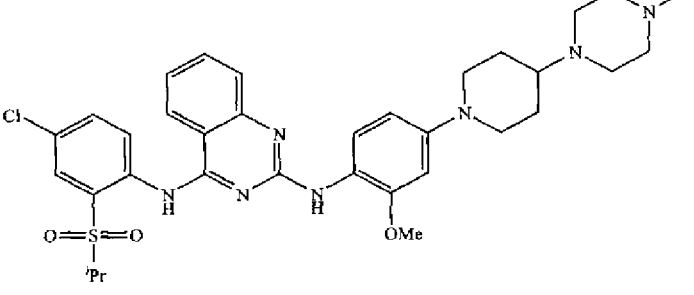 |
| 36 | 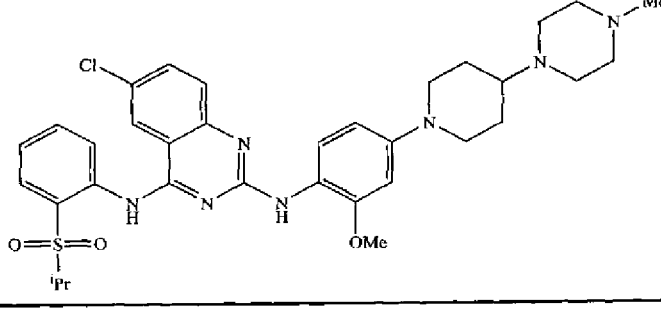 |

TABLE 25

| Ex/Salt | Structure |
|---|---|
| 37 | (structure) |
| 38 | (structure) |
| 39 | (structure) |
| 40 | (structure) |
| 41 | (structure) |

TABLE 25-continued
| Ex/Salt | Structure |
|---|---|
| 42 | 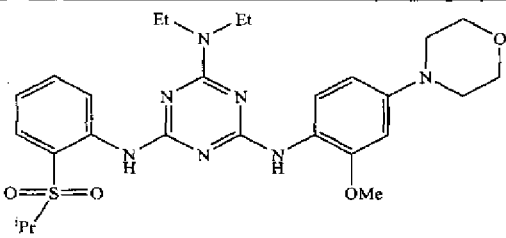 |
| 43 | 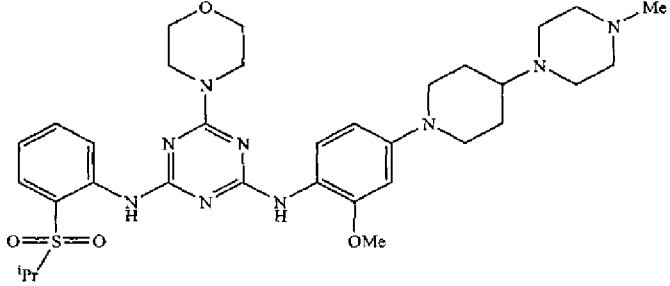 |
| 44 | 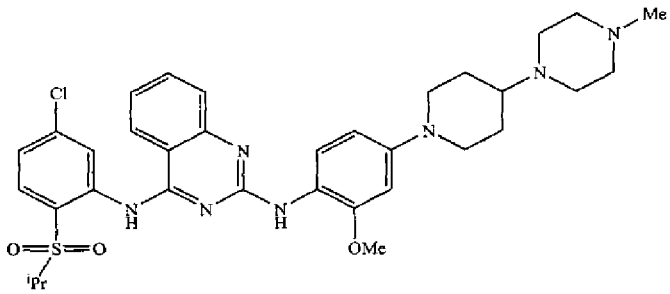 |
TABLE 26
| Ex/Salt | Structure |
|---|---|
| 45 | 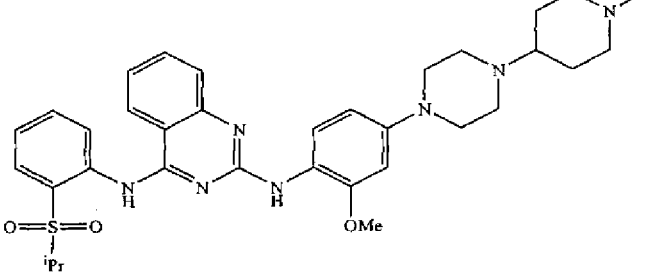 |

TABLE 26-continued
| Ex/Salt | Structure |
|---|---|
| 46 | 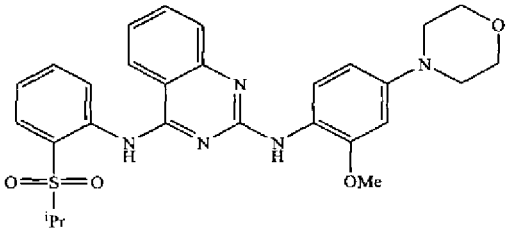 |
| 47 | 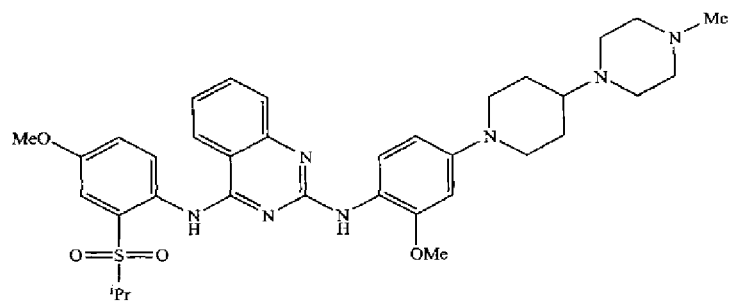 |
| 48 | 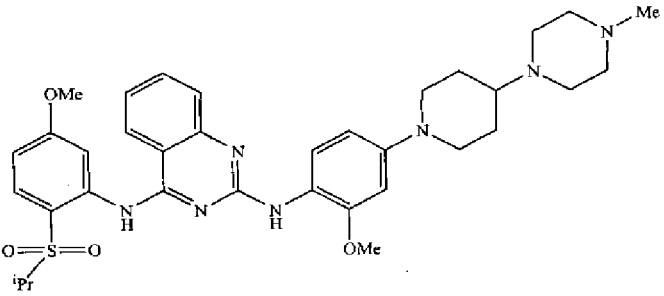 |
| 49 | 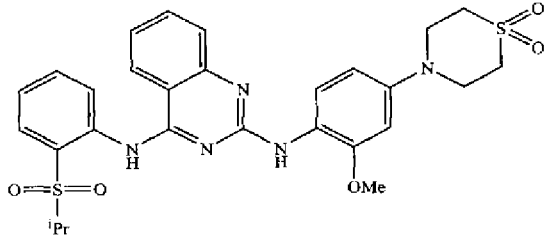 |
| 50 | 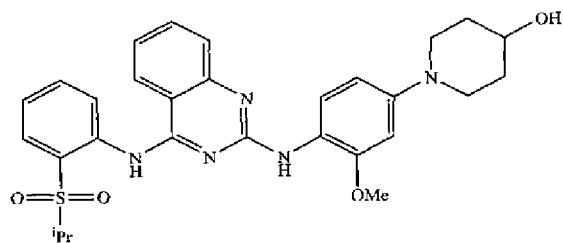 |

TABLE 26-continued

| Ex/Salt | Structure |
|---|---|
| 51 | (structure) |
| 52/ CL3 | (structure) |

TABLE 27

| Ex/Salt | Structure |
|---|---|
| 53/ CL1 | (structure) |
| 54 | (structure) |
| 55 | (structure) |

TABLE 27-continued
| Ex/Salt | Structure |
|---|---|
| 56 | 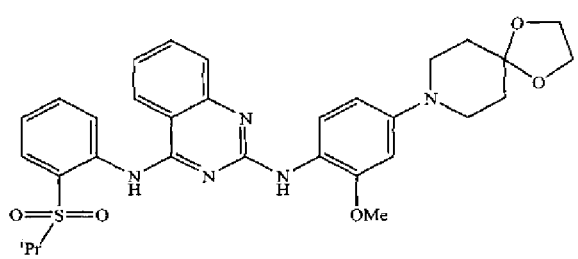 |
| 57 | 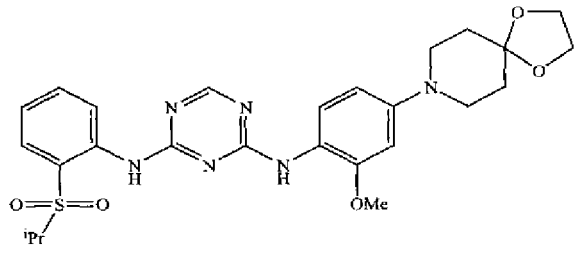 |
| 58 | 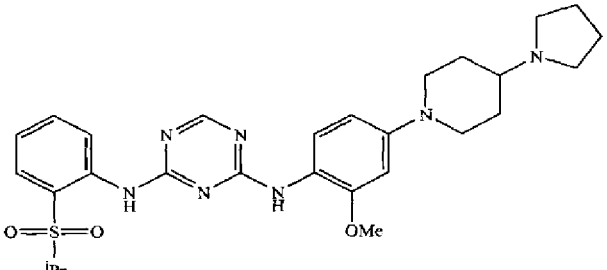 |
| 59 | 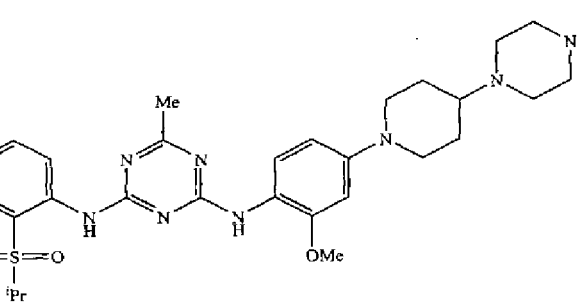 |
| 60 | 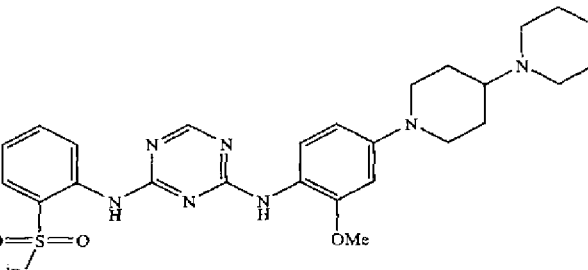 |

TABLE 28

| Ex/Salt | Structure |
|---|---|
| 61 | 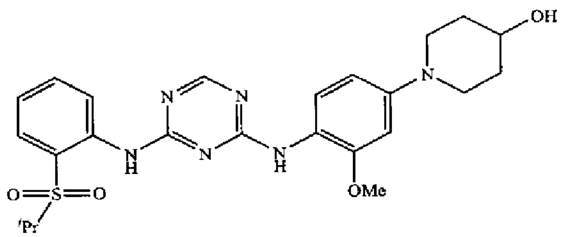 |
| 62 | 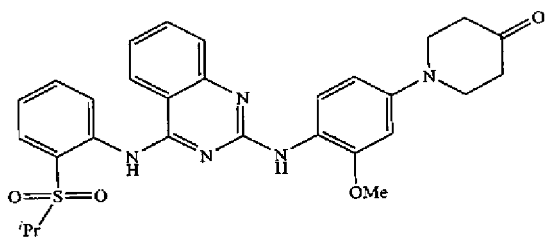 |
| 63/CL3 | 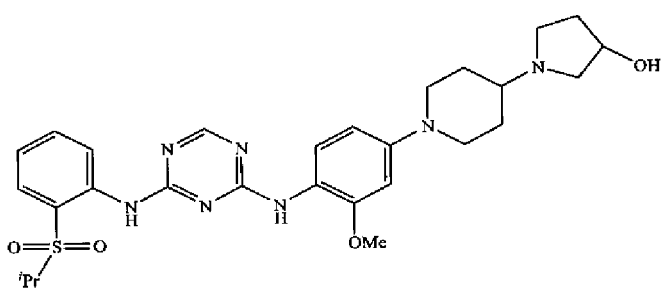 |
| 64 | 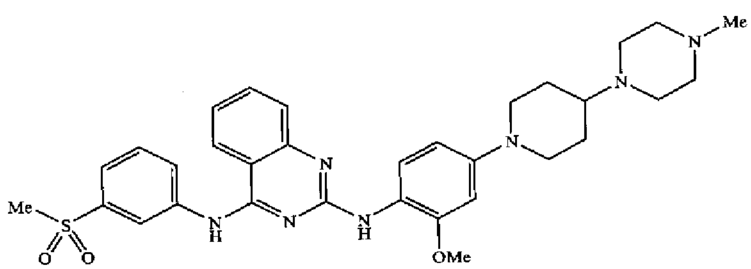 |
| 65 | 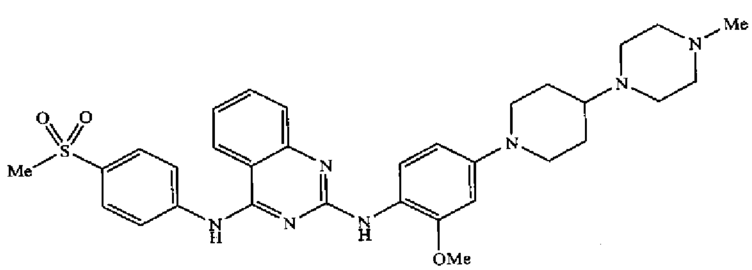 |

TABLE 28-continued

| Ex/Salt | Structure |
|---|---|
| 66 | (structure: 2-(isopropylsulfonyl)phenylamino-quinazoline-2-amino-4-piperazinyl-2-methoxyphenyl) |
| 67 | (structure: 2-(isopropylsulfonyl)phenylamino-quinazoline-2-amino-4-(3-hydroxypyrrolidin-1-yl)-2-methoxyphenyl) |
| 68 | (structure: 2-(isopropylsulfonyl)phenylamino-triazine-amino-(2-methoxy-4-(1-Boc-piperidin-4-yloxy)phenyl)) |

TABLE 29

| Ex/Salt | Structure |
|---|---|
| 69 | (structure: 2-(isopropylsulfonyl)phenylamino-triazine-amino-(2-methoxy-4-(1-methylpiperidin-4-yloxy)phenyl)) |
| 70/CL2 | (structure: 2-(isopropylsulfonyl)phenylamino-triazine-amino-(2-methoxy-4-(4-cyclohexylpiperazin-1-yl)phenyl)) |

TABLE 29-continued

| Ex/Salt | Structure |
|---|---|
| 71 | 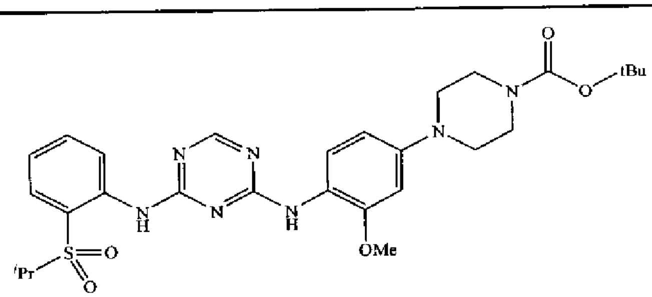 |
| 72 | 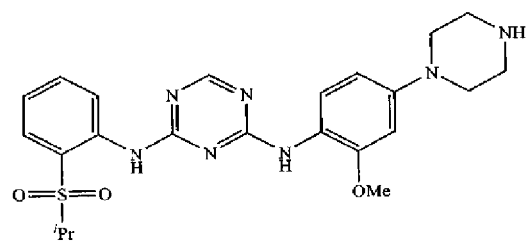 |
| 73 | 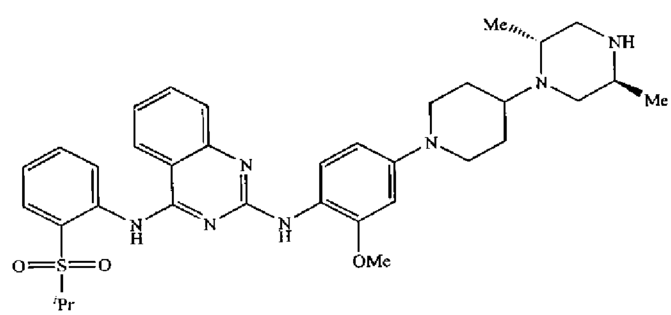 |
| 74 | 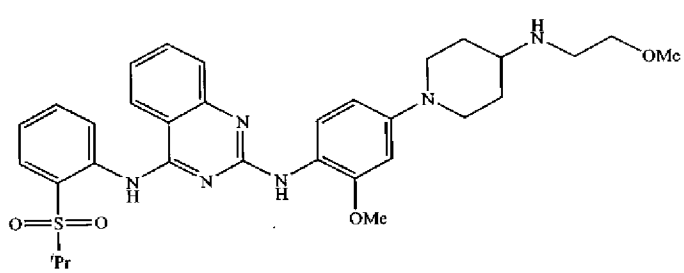 |
| 75 | 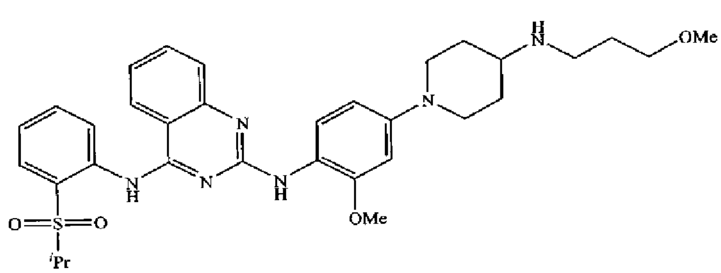 |

TABLE 29-continued
| Ex/Salt | Structure |
|---|---|
| 76 | 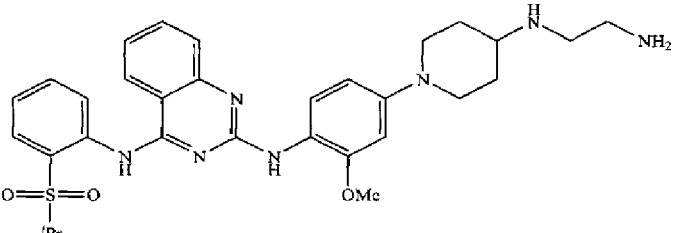 |
TABLE 30
| Ex/Salt | Structure |
|---|---|
| 77 | 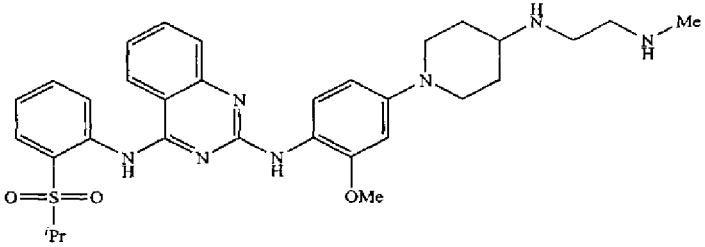 |
| 78 | 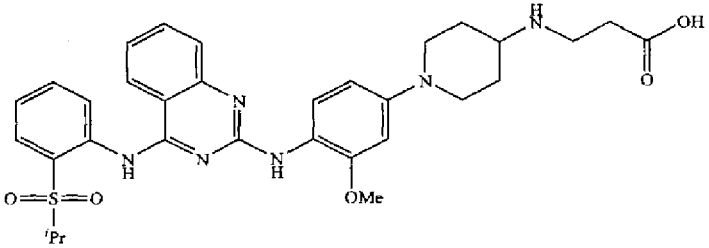 |
| 79 | 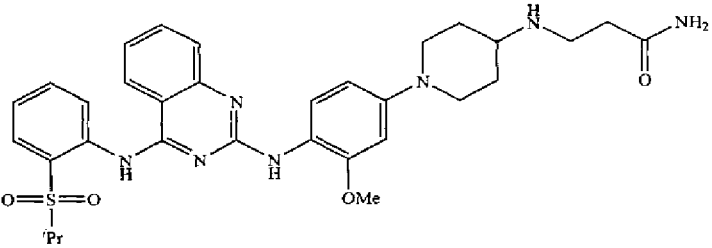 |
| 80 | 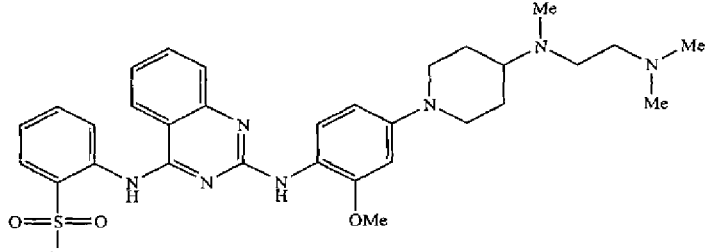 |

TABLE 30-continued
| Ex/Salt | Structure |
|---|---|
| 81 | 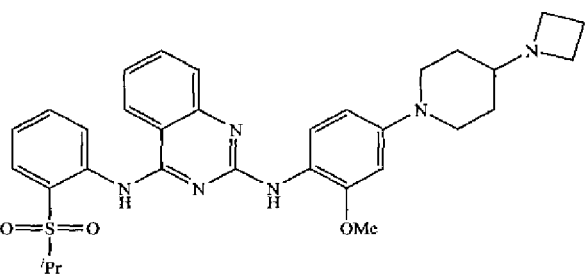 |
| 82 | 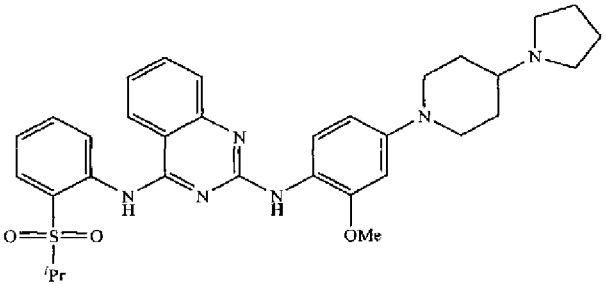 |
| 83 | 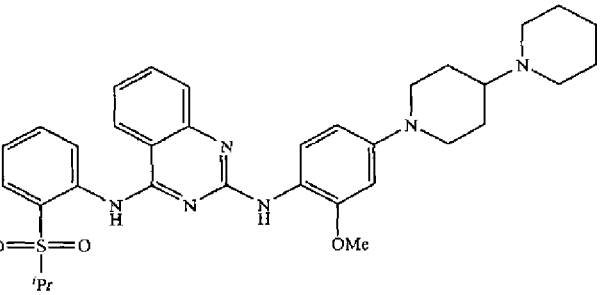 |
| 84 | 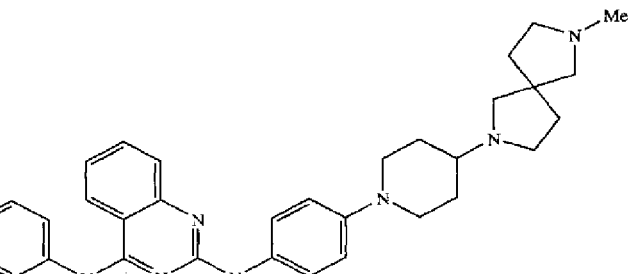 |

TABLE 31

| Ex/Salt | Structure |
|---|---|
| 85 | 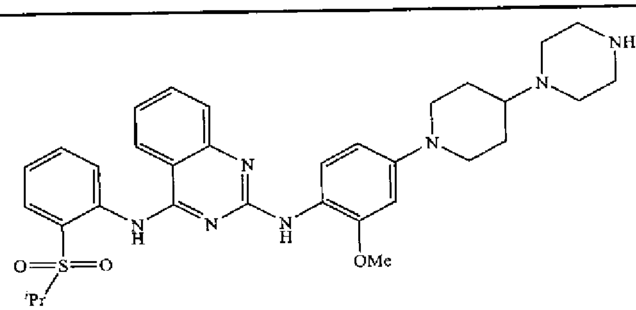 |
| 86 | 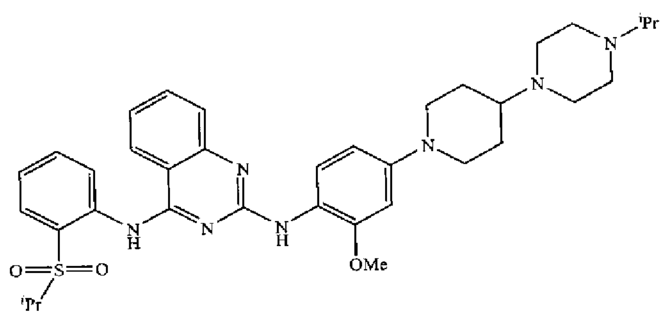 |
| 87 | 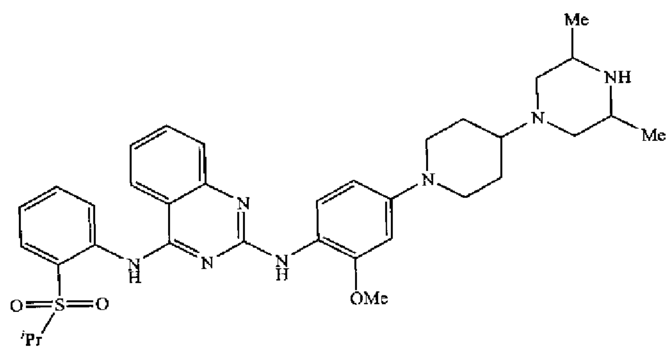 |
| 88 | 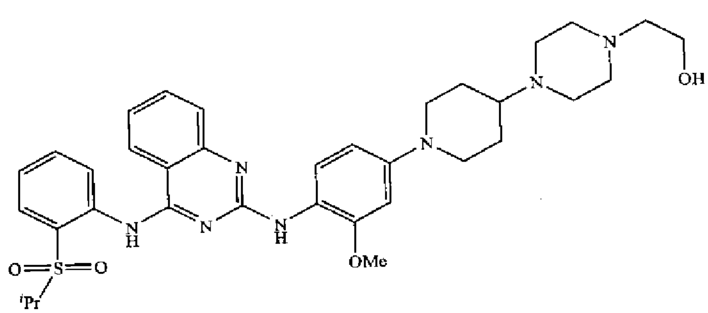 |

TABLE 31-continued

| Ex/Salt | Structure |
|---|---|
| 89 | 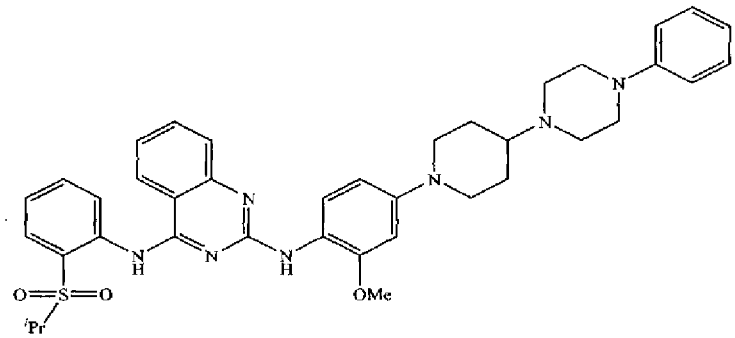 |
| 90 | 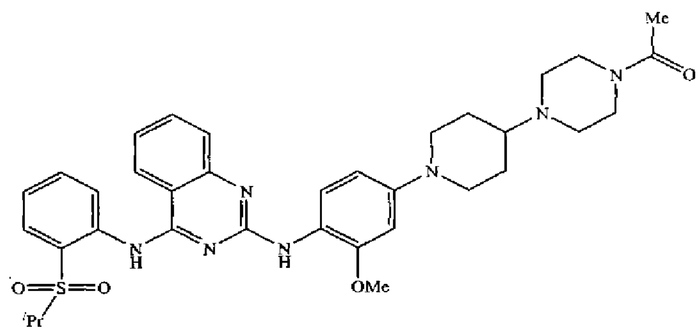 |
| 91 | 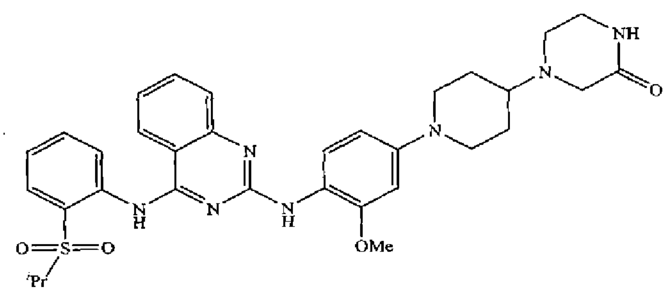 |
| 92 | 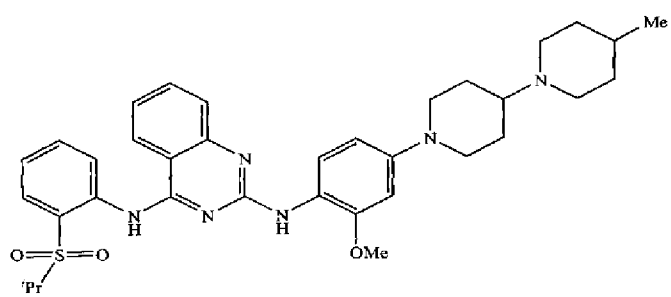 |

TABLE 32
| Ex/Salt | Structure |
|---|---|
| 93 | 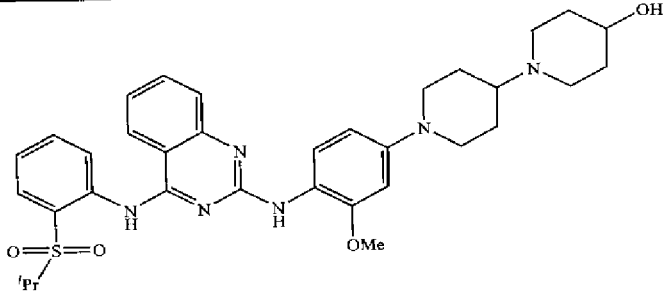 |
| 94 | 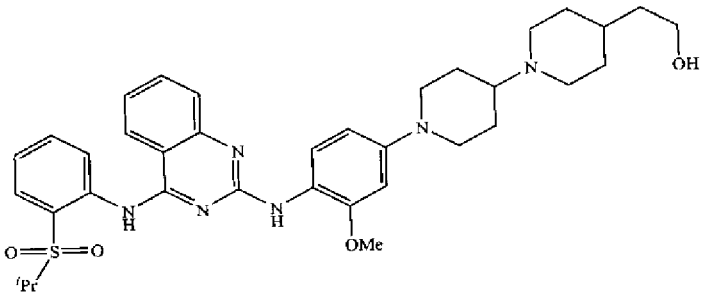 |
| 95 | 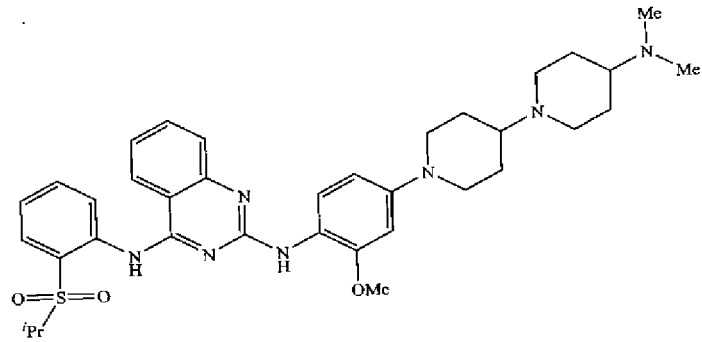 |
| 96 | 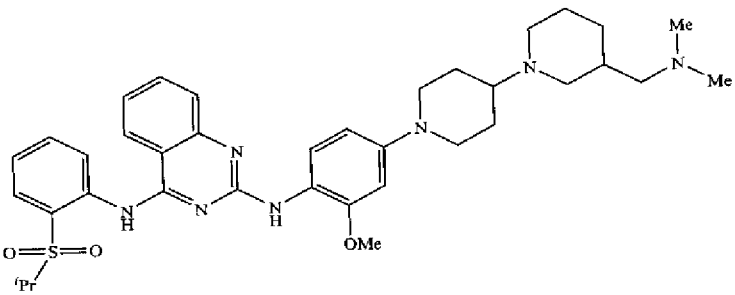 |

TABLE 32-continued

| Ex/Salt | Structure |
|---|---|
| 97 | 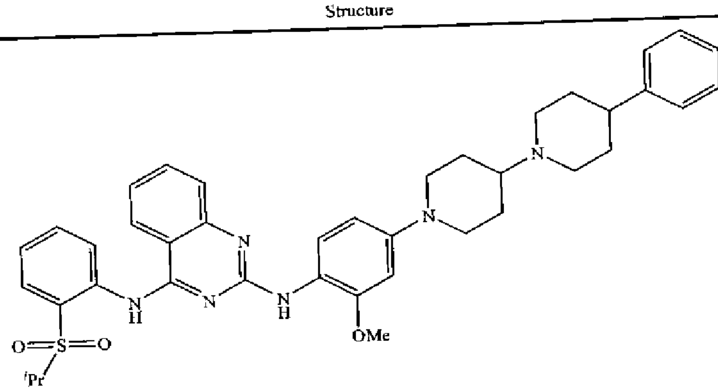 |
| 98 | 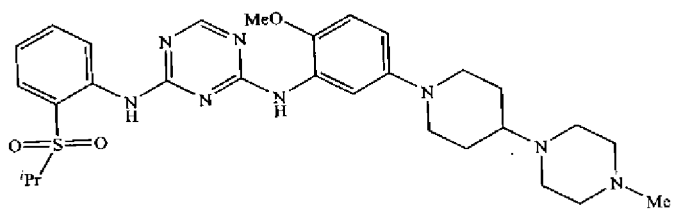 |
| 99 | 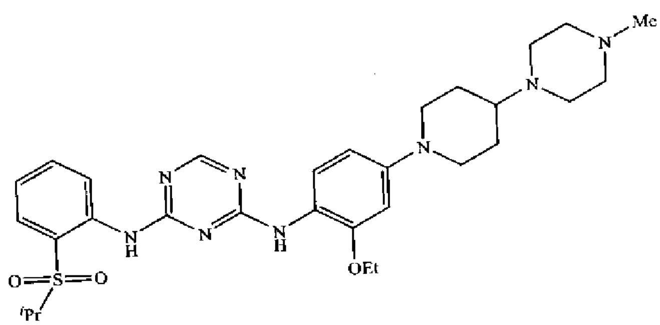 |
| 100 | 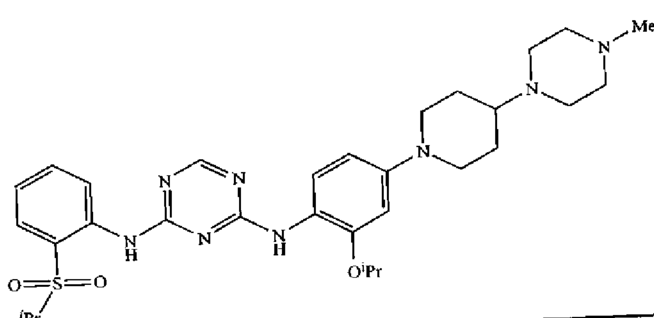 |

TABLE 33

| Ex/Salt | Structure |
|---|---|
| 101 | 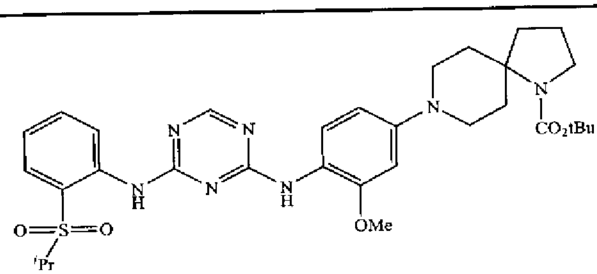 |
| 102 | 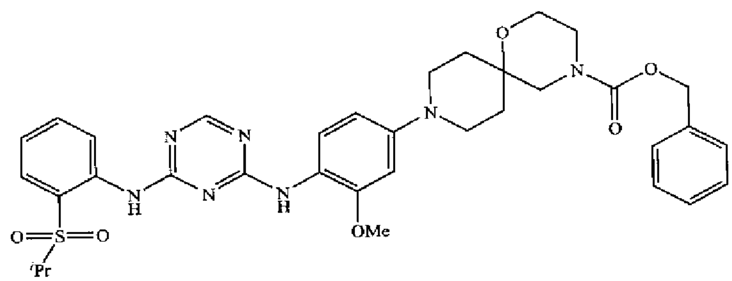 |
| 103 | 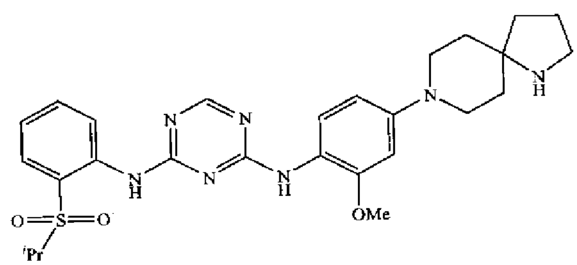 |
| 104 | 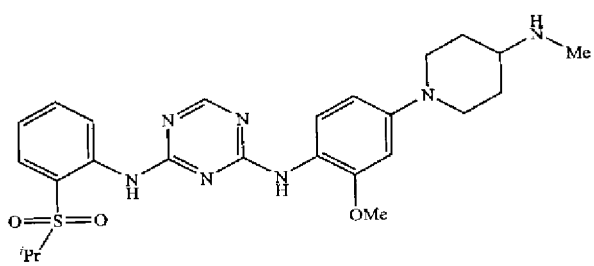 |
| 105 | 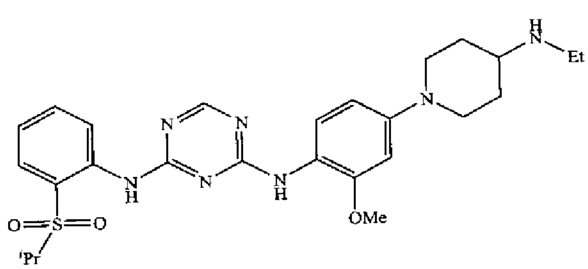 |

TABLE 33-continued
| Ex/Salt | Structure |
|---|---|
| 106 | 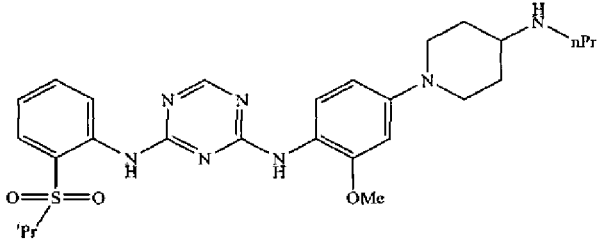 |
| 107 | 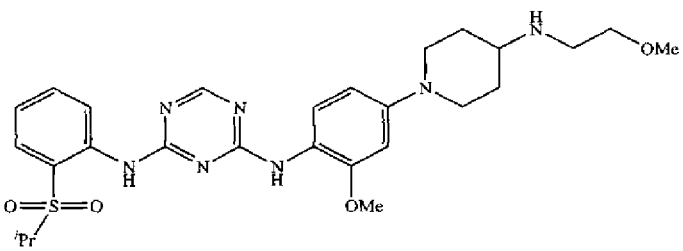 |
| 108 | 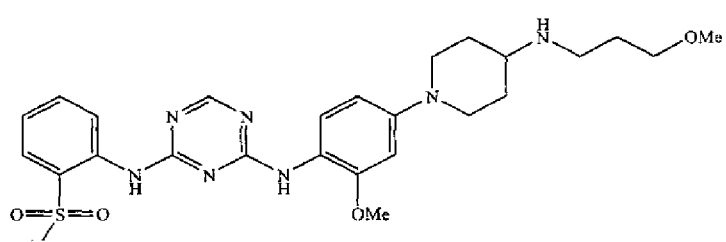 |
TABLE 34
| Ex/Salt | Structure |
|---|---|
| 109 | 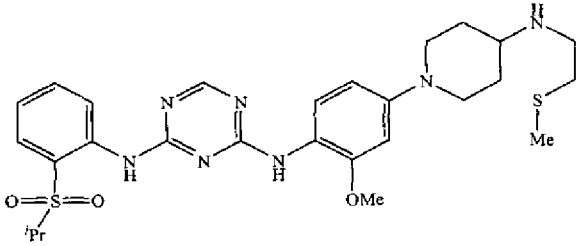 |
| 110 | 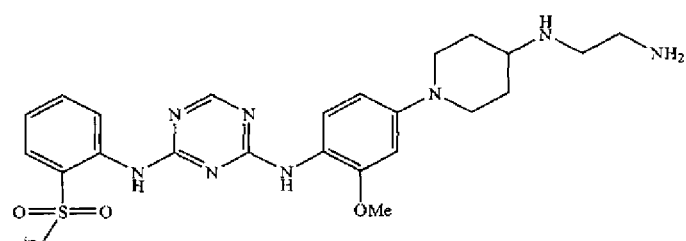 |

TABLE 34-continued
| Ex/Salt | Structure |
|---|---|
| 111 | 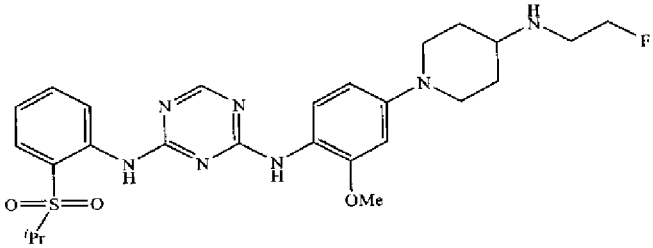 |
| 112 | 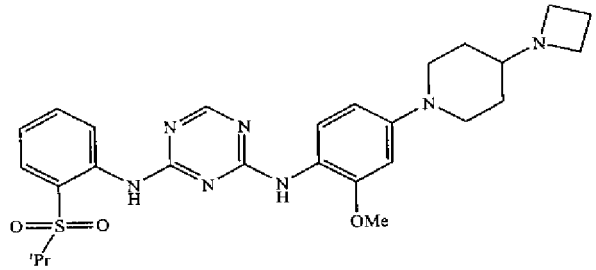 |
| 113 | 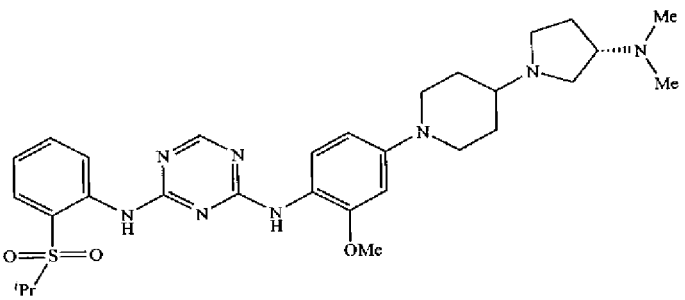 |
| 114 | 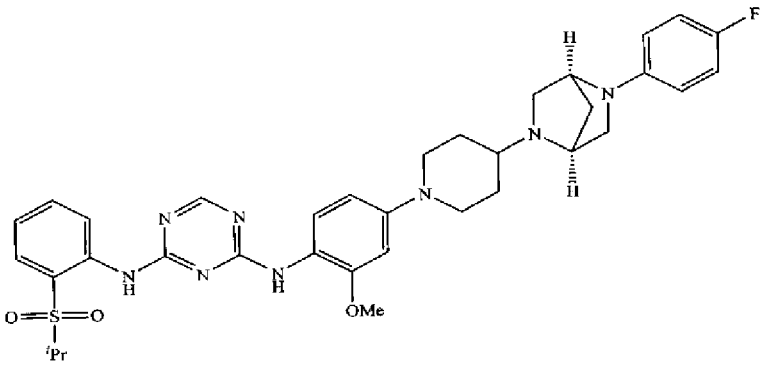 |

TABLE 34-continued
| Ex/Salt | Structure |
|---|---|
| 115 | 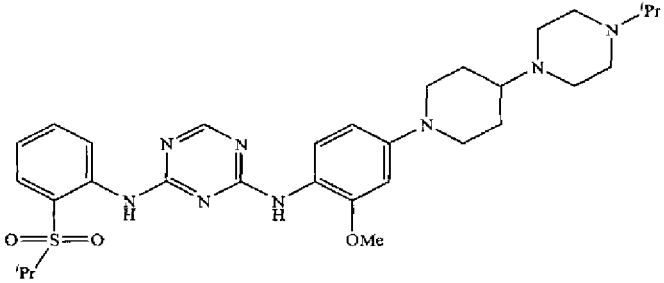 |
| 116 | 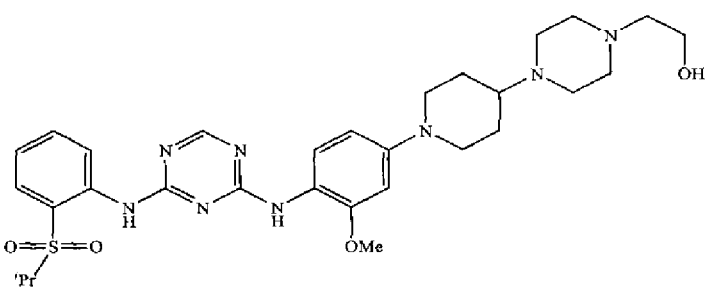 |
TABLE 35
| Ex/Salt | Structure |
|---|---|
| 117 | 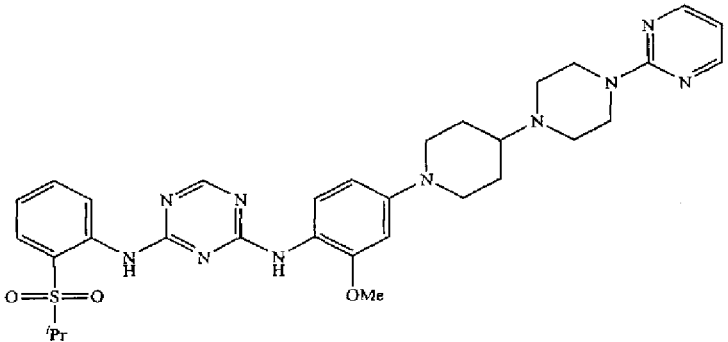 |
| 118 | 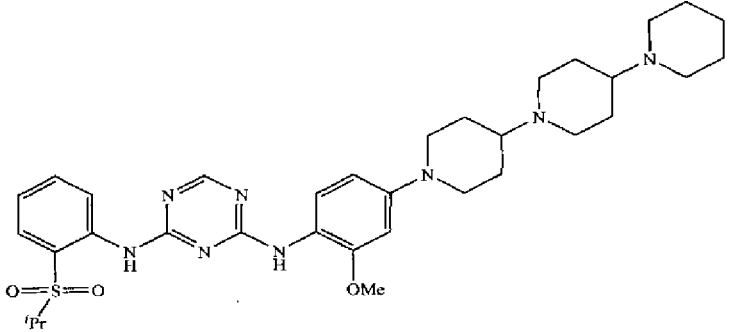 |

TABLE 35-continued
| Ex/Salt | Structure |
|---|---|
| 119 | 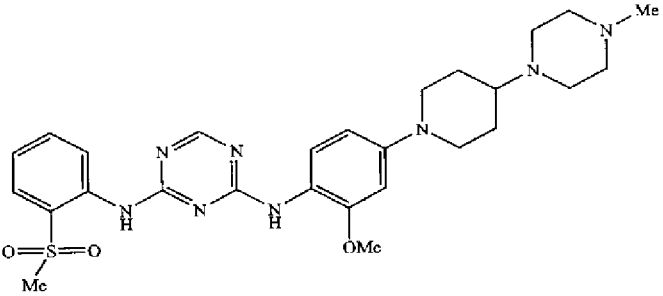 |
| 120 | 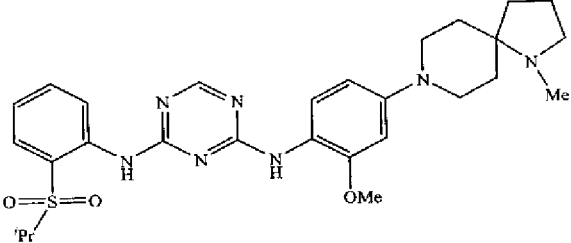 |
| 121 | 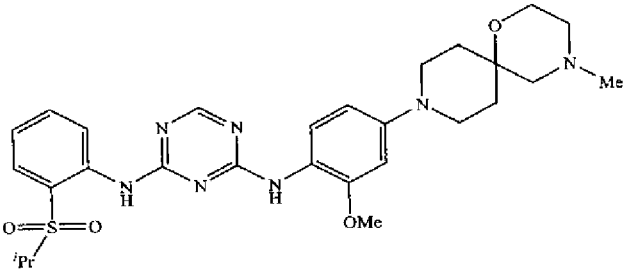 |
| 122 | 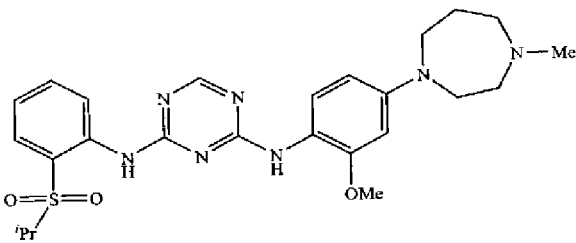 |
| 123 | 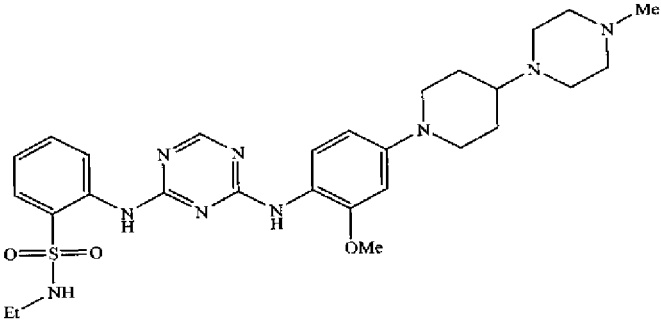 |

TABLE 35-continued
| Ex/Salt | Structure |
|---|---|
| 124 | 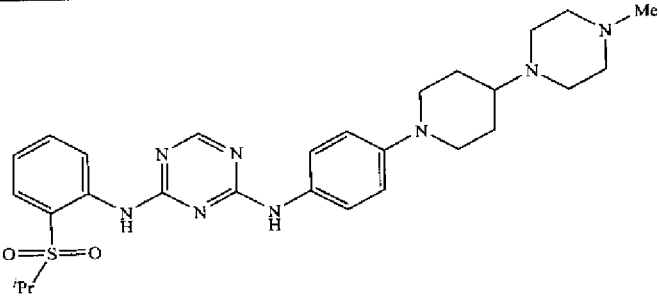 |
TABLE 36
| Ex/Salt | Structure |
|---|---|
| 125 | 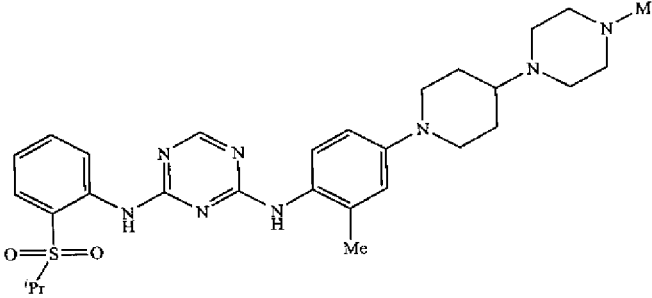 |
| 126 | 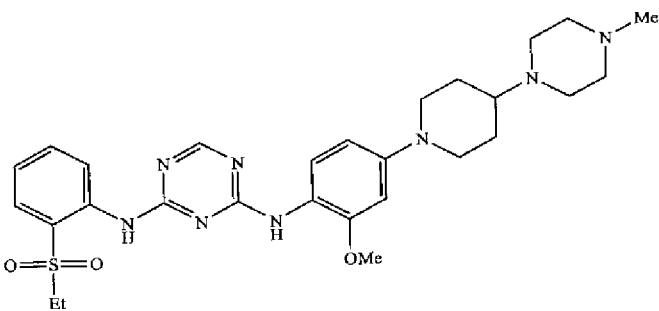 |
| 127 | 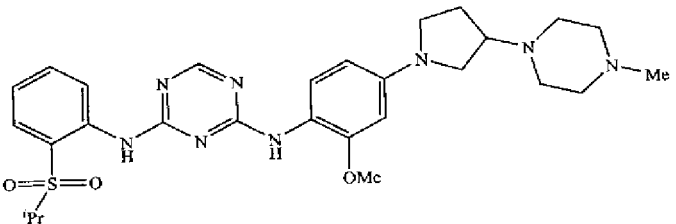 |

TABLE 36-continued

| Ex/Salt | Structure |
|---|---|
| 128 | 2-(dimethylsulfamoyl)phenyl-NH-triazine-NH-(2-methoxy-4-(4-(4-methylpiperazin-1-yl)piperidin-1-yl)phenyl) |
| 129 | 2-(cyclopropylsulfonyl)phenyl-NH-triazine-NH-(2-methoxy-4-(4-(4-methylpiperazin-1-yl)piperidin-1-yl)phenyl) |
| 130 | 2-(isopropylsulfonyl)phenyl-NH-triazine-NH-(2-chloro-4-(4-(4-methylpiperazin-1-yl)piperidin-1-yl)phenyl) |
| 131 | 2-(isopropylsulfonyl)phenyl-NH-triazine-NH-(2-methoxy-4-(4-n-butylpiperazin-1-yl)phenyl) |
| 132 | 2-(isopropylsulfonyl)phenyl-NH-triazine-NH-(2-methoxy-4-(4-(2-methoxyethyl)piperazin-1-yl)phenyl) |

TABLE 37
| Ex/Salt | Structure |
|---|---|
| 133 | 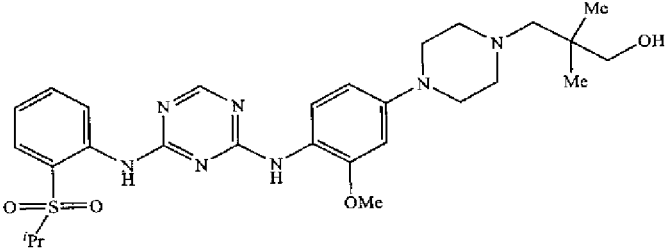 |
| 134 | 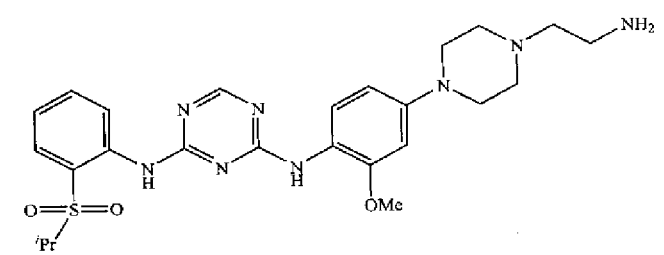 |
| 135 | 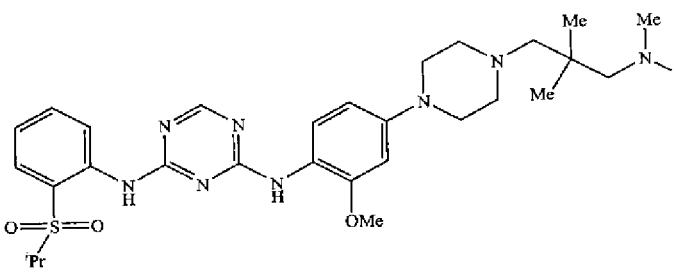 |
| 136 | 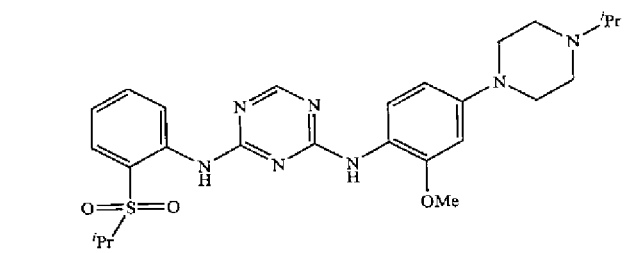 |
| 137 | 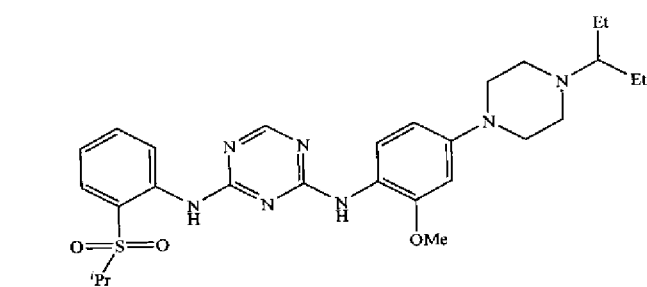 |

TABLE 37-continued
| Ex/Salt | Structure |
|---|---|
| 138 | 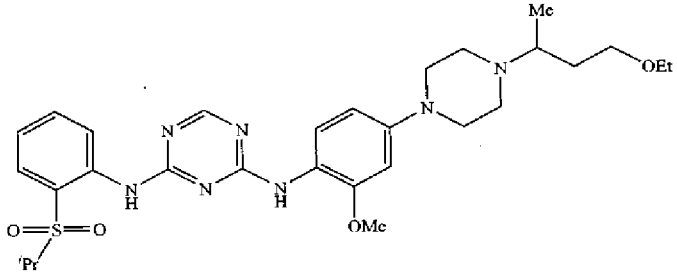 |
| 139 | 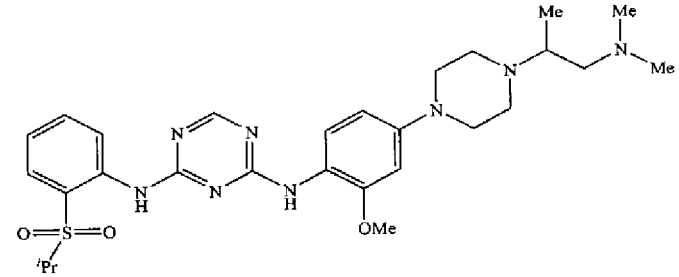 |
| 140 | 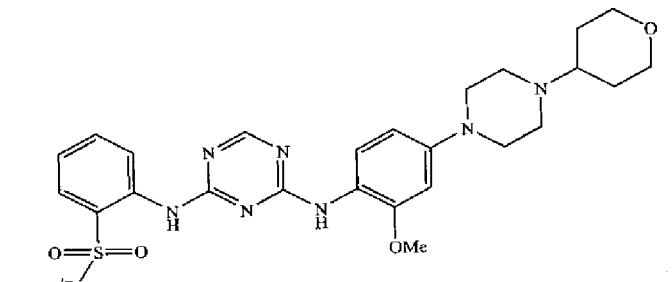 |
TABLE 38
| Ex/Salt | Structure |
|---|---|
| 141 | 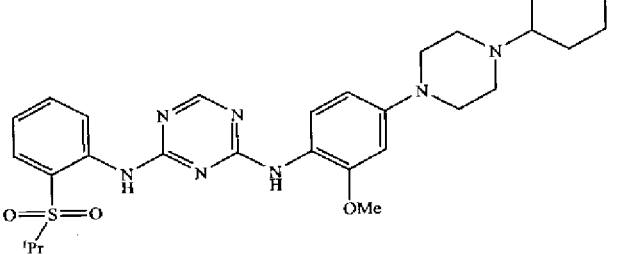 |

TABLE 38-continued

| Ex/Salt | Structure |
|---|---|
| 142 | 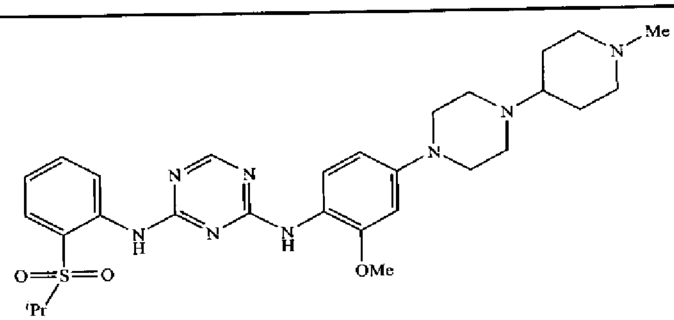 |
| 143 | 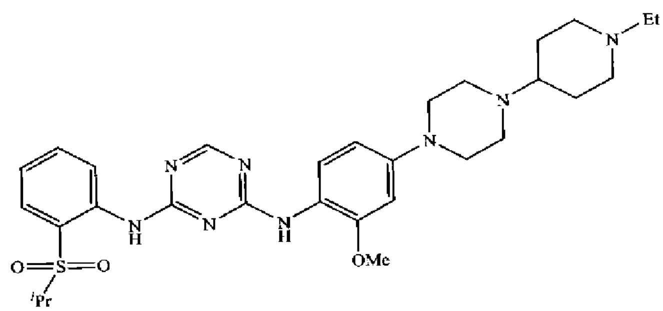 |
| 144 | 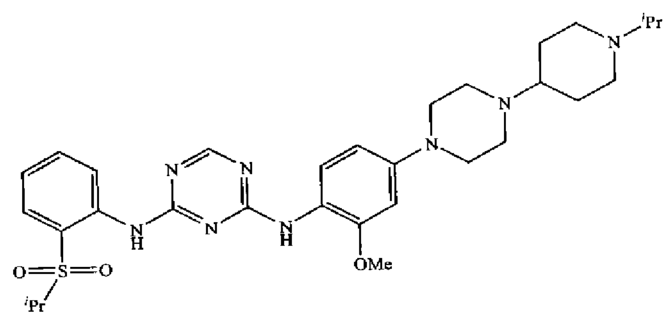 |
| 145 | 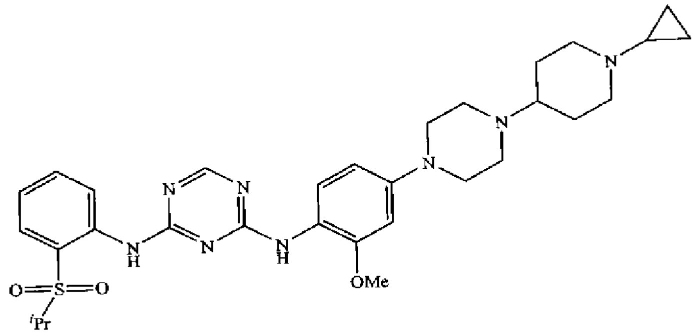 |

TABLE 38-continued
| Ex/Salt | Structure |
|---|---|
| 146 | 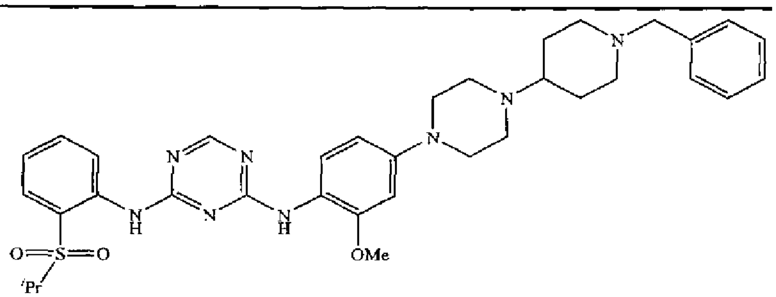 |
| 147 | 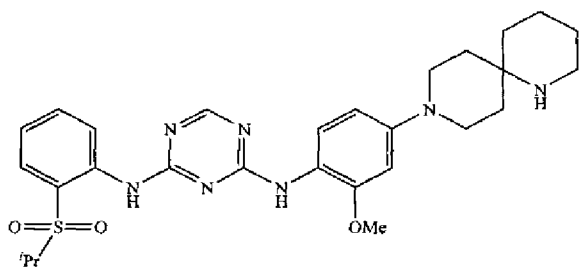 |
| 148 | 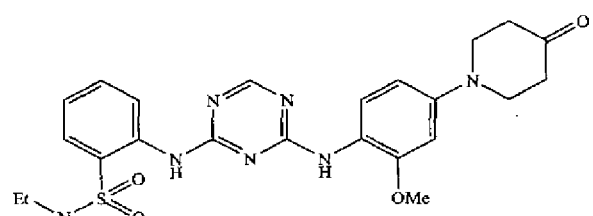 |
TABLE 39
| Ex/Salt | Structure |
|---|---|
| 149 | 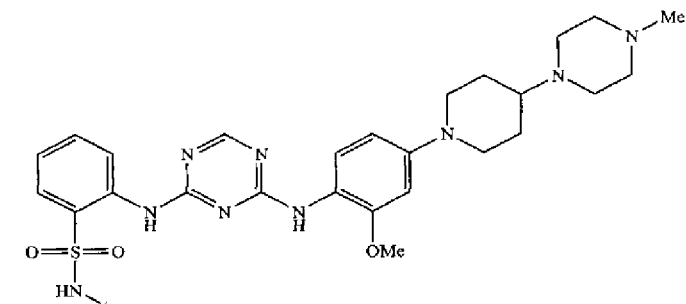 |

TABLE 39-continued

| Ex/Salt | Structure |
|---|---|
| 150 | *(chemical structure)* |
| 151 | *(chemical structure)* |
| 152 | *(chemical structure)* |
| 153 | *(chemical structure)* |
| 154 | *(chemical structure)* |

TABLE 39-continued

| Ex/Salt | Structure |
|---|---|
| 155 | (structure) |
| 156 | (structure) |

TABLE 40

| Ex/Salt | Structure |
|---|---|
| 157 | (structure) |
| 158 | (structure) |

TABLE 40-continued

| Ex/Salt | Structure |
|---|---|
| 159 | (chemical structure) |
| 160 | (chemical structure) |
| 161 | (chemical structure) |
| 162 | (chemical structure) |
| 163 | (chemical structure) |

TABLE 40-continued
| Ex/Salt | Structure |
|---|---|
| 164 | 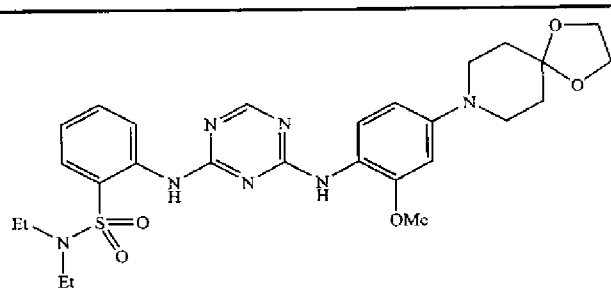 |
TABLE 41
| Ex/Salt | Structure |
|---|---|
| 165 | 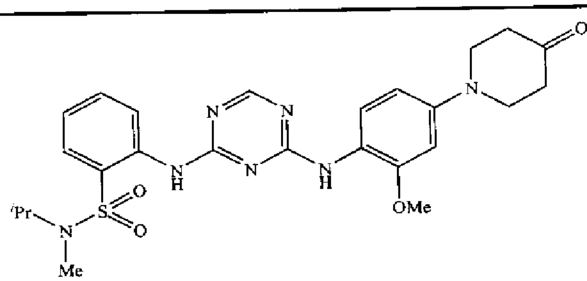 |
| 166 | 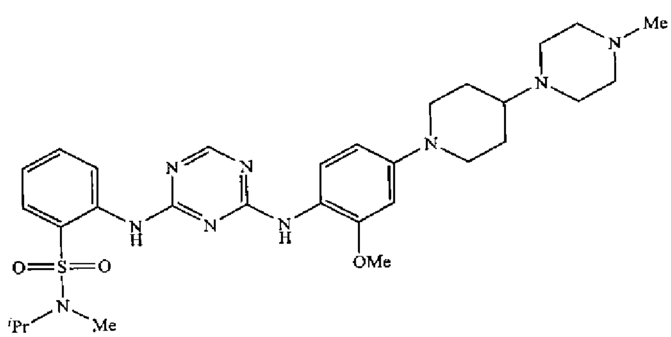 |
| 167 | 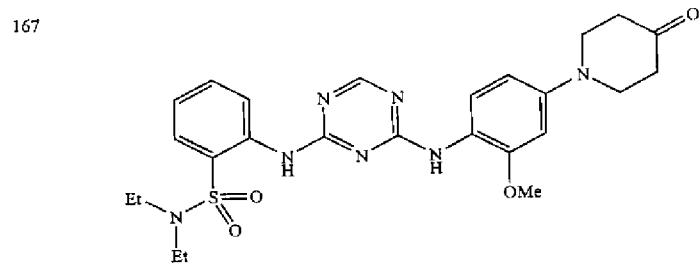 |

TABLE 41-continued

| Ex/Salt | Structure |
|---|---|
| 168 | 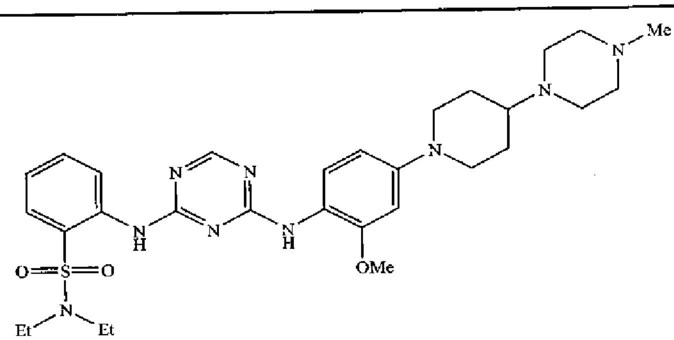 |
| 169 | 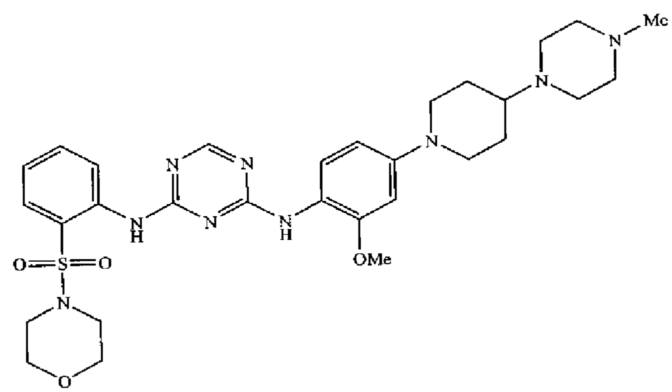 |
| 170 | 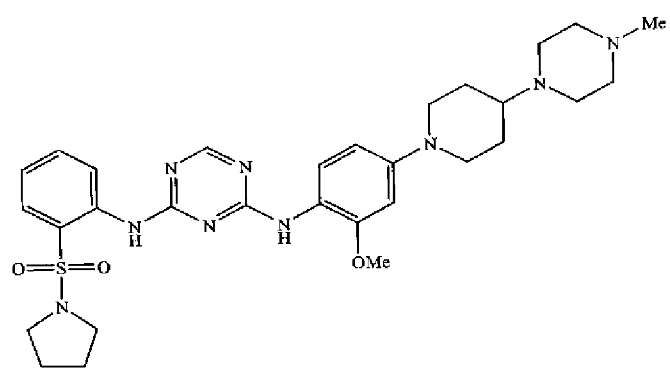 |
| 171 | 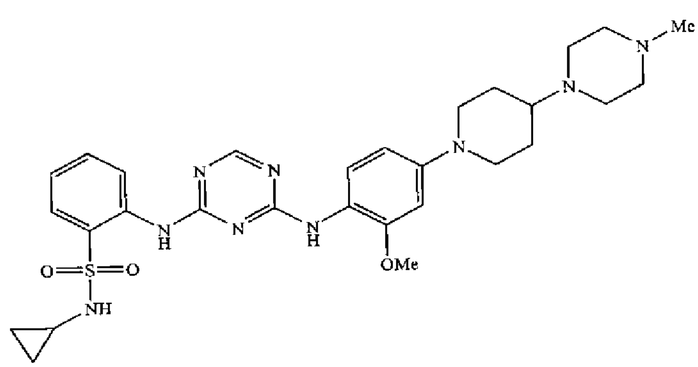 |

TABLE 41-continued
| Ex/Salt | Structure |
|---|---|
| 172 | 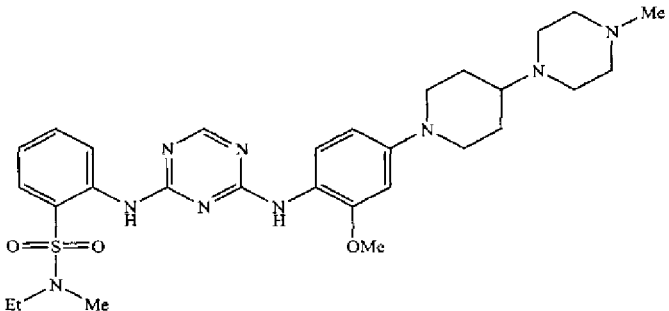 |
TABLE 42
| Ex/Salt | Structure |
|---|---|
| 173 | 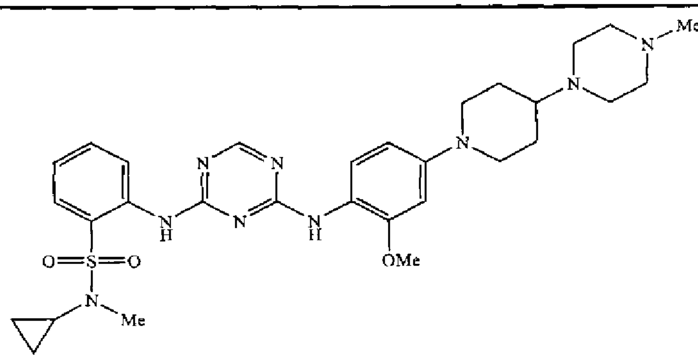 |
| 174 | 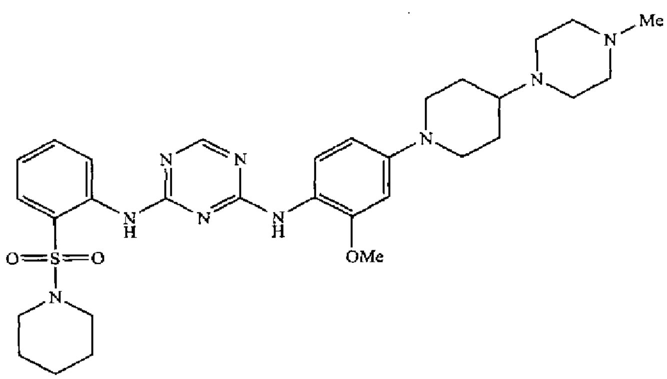 |
| 175 | 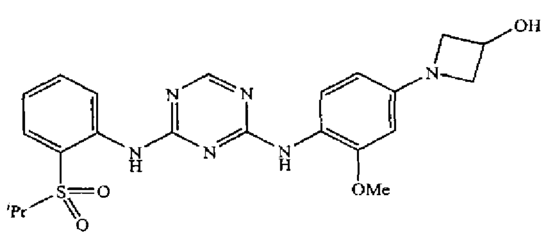 |

TABLE 42-continued

| Ex/Salt | Structure |
|---|---|
| 176 | 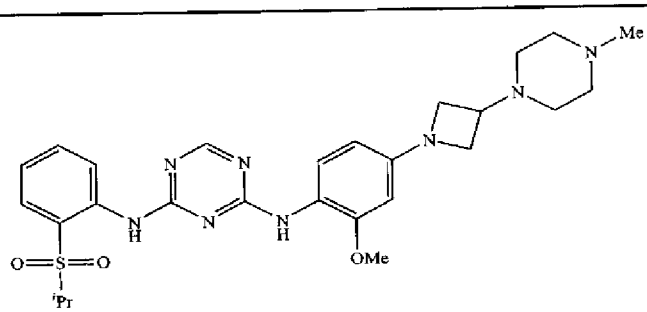 |
| 177 | 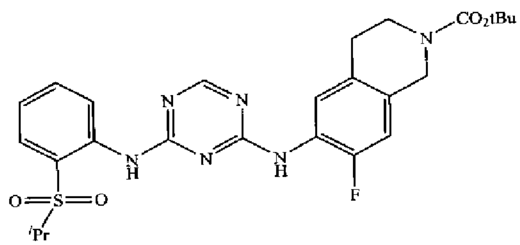 |
| 178 | 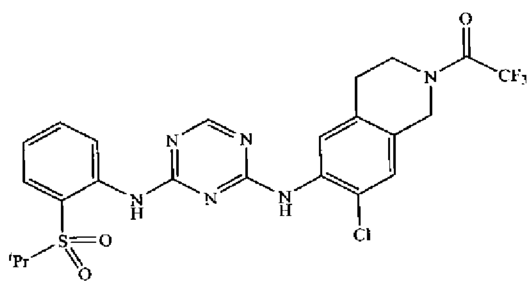 |
| 179 | 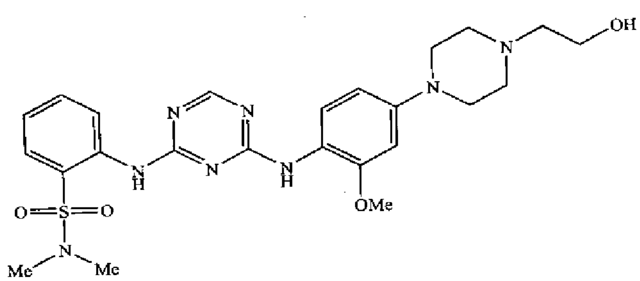 |
| 180 | 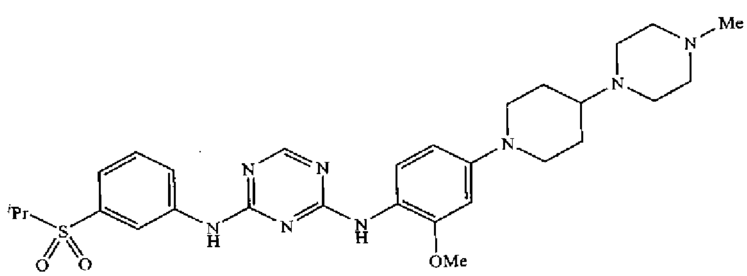 |

TABLE 42-continued

| Ex/Salt | Structure |
|---|---|
| 181 | (structure shown) |

TABLE 43

| Ex | Data |
|---|---|
| 1 | ESI+: 630.3 |
| | NMR-CDCl3: 1.30 (6H, d, J = 6.9 Hz), |
| | 1.65-1.8 (2H, m), 1.96 (2H, d, J = 11.8 Hz), |
| | 2.31 (3H, s), 2.35-2.8 (11H, m), |
| | 3.2-3.3 (1H, m), 3.68 (2H, d, J = 12.3 Hz), |
| | 3.90 (3H, s), 6.58 (2H, m), 7.2-7.3 (2H, m), |
| | 7.33 (1H, s), 7.6-7.7 (3H, m), 7.88 (1H, |
| | d, J = 8.2 Hz), 7.91 (1H, d, J = 8.0 Hz), |
| | 8.45 (1H, d, J = 8.2 Hz), 8.90 (1H, d, J = 8.5 Hz), |
| | 10.18 (1H, s) |
| | Amrph |
| 2 | ESI+: 575.3 |
| 3 | ESI+: 436.1 |
| 4 | ESI+: 560.4 |
| 5 | FAB+: 533.1 |
| 6 | FAB−: 510.3 |
| 7 | ESI+: 568.1 |
| | NMR-DMSOd6: 1.40-4.59 (2H, |
| | m), 1.75-1.91 (2H, m), |
| | 2.08-2.19 (3H, m), 2.20-2.60 (12H, m), |
| | 2.60-2.78 (2H, m), 3.64-3.85 (5H, |
| | m), 6.40-6.55 (1H, m), |
| | 6.55-6.69 (1H, br), 7.10-7.30 (2H, m), |
| | 7.30-7.90 (2H, m), 8.19-8.42 (2H, |
| | m), 8.72-8.98 (1H, m), |
| | 8.98-9.16 (1H, m) |
| | Amrph |
| 8 | ESI+: 505.3 |
| 9 | FAB+: 499.1 |
| 10 | ESI+: 617.4 |
| 11 | ESI+: 575.3 |
| 12 | ESI+: 566.4 |
| | NMR-CDCl3: 1.31 (6H, d, J = 6.8 Hz), |
| | 1.5-1.7 (8H, m), 2.0-2.15 (2H, |
| | m), 2.37 (3H, s), 2.68 (2H, br), |
| | 2.99 (2H, t, J = 10.3 Hz), 3.2-3.3 (1H, |
| | m), 3.4-3.5 (2H, m), 3.88 (3H, s), |
| | 6.55 (2H, br), 7.22 (1H, t, J = 7.8 Hz), |
| | 7.63 (2H, br), 7.88 (1H, dd, J = 1.5, |
| | 7.8 Hz), 8.10 (1H, br), |
| | 8.36 (1H, br), 8.54 (1H, br), 9.28 (1H, s) |
| | Cryst (MP: 132-135) |
| 13 | ESI+: 597.3 |
| 14 | FAB+: 567.3 |
| 15 | ESI+: 554.4 |
| 16 | ESI+: 443.2 |
| 17 | ESI+: 459.2, 461.1 |
| 18 | ESI+: 561 |
| 19 | ESI+: 566 |
| 20 | ESI+: 526 |

TABLE 44

| Ex | Syn | Data |
|---|---|---|
| 21 | 1 | FAB+: 547.2 |
| 22 | 1 | ESI+: 611.2 |
| 23 | 1 | ESI+: 581.2 |
| | | NMR-CDCl3: 1.31 (6H, d, J = 6.8 Hz), |
| | | 1.65-1.8 (2H, m), |
| | | 1.97 (2H, d, J = 11.7 Hz), 2.34 (3H, s), |
| | | 2.3-2.8 (11H, m), 3.2-3.3 (1H, m), |
| | | 3.70 (2H, d, J = 12.2 Hz), 3.88 (3H, |
| | | s), 6.54 (2H, m), 7.2 (1H, m), |
| | | 7.62 (2H, br), 7.88 (1H, dd, J = 1.5, 7.8 Hz), |
| | | 8.10 (1H, br), 8.37 (1H, br), |
| | | 8.53 (1H, br), 9.29 (1H, s) |
| | | Cryst (MP: 164-165) |
| 24 | 1 | ESI+: 498.2 |
| | | NMR-CDCl3: 1.31 (6H, d, J = 6.8 Hz), |
| | | 2.42 (3H, s), 2.68 (4H, br), |
| | | 3.15-3.35 (5H, m), 3.89 (3H, s), |
| | | 6.54 (2H, br), 7.2 (1H, m), |
| | | 7.63 (2H, br), 7.89 (1H, d, J = 6.4 Hz), |
| | | 8.12 (1H, br), 8.38 (1H, br), 8.53 (1H, |
| | | br), 9.30 (1H, s) |
| | | Amrph |
| 25 | 1 | FAB+: 664.2 |
| 26 | 2 | FAB+: 454 |
| 27 | 1 | ESI+: 465 |
| 28 | 1 | ESI+: 410.3 |
| 29 | 3 | ESI+: 397.2 |
| 30 | 3 | ESI+: 431.2 |
| 31 | 3 | ESI+: 470.1 |
| 32 | 1 | ESI+: 664.3 |
| 33 | 8 | FAB+: 465.2 |
| 34 | 8 | FAB+: 468.2 |
| 35 | 1 | FAB+: 664.2 |
| 36 | 1 | ESI+: 664.3 |
| 37 | 1 | FAB+: 542.3 |
| 38 | 1 | ESI+: 664.3 |
| 39 | 3 | ESI+: 519.2, 521.2 |
| 40 | 8 | ESI+: 570.4 |
| 41 | 8 | ESI+: 554.4 |
| 42 | 8 | ESI+: 556.3 |
| 43 | 1 | ESI+: 666.4 |
| 44 | 1 | ESI+: 664.3 |
| 45 | 1 | ESI+: 630.4 |
| | | NMR-CDCl3: 1.30 (6H, d, J = 6.8 Hz), |
| | | 1.6-1.7 (2H, m), |
| | | 1.86 (2H, d, J = 12.7 Hz), |
| | | 1.97 (2H, t, J = 11.7 Hz), |
| | | 2.28 (3H, s), 2.3-2.4 (1H, m), |
| | | 2.77 (4H, t, J = 4.8 Hz), 2.94 (2H, |
| | | d, J = 11.7 Hz), 3.19 (4H, t, J = 4.8 Hz), |
| | | 3.2-3.3 (1H, m), |
| | | 3.90 (3H, s), 6.57 (1H, d, J = 2.4 Hz), |
| | | 6.58 (1H, d, J = 2.4 Hz), |
| | | 7.2-7.4 (3H, m), |

TABLE 44-continued

| Ex | Syn | Data |
|----|-----|------|
|  |  | 7.6-7.7 (3H, m), 7.85-7.95 (2H, m), 8.45 (1H, br), 8.90 (1H, d, J = 8.3 Hz), 10.19 (1H, s)<br>Cryst (MP: 109-114) |

TABLE 45

| Ex | Syn | Data |
|----|-----|------|
| 46 | 1 | ESI+: 534.3 |
| 47 | 1 | ESI+: 660.4 |
| 48 | 1 | ESI+: 660.4 |
| 49 | 1 | ESI+: 582.3 |
| 50 | 1 | ESI+: 548.3 |
| 51 | 6 | ESI+: 497.3 |
| 52 | 2 | ESI+: 526.3<br>NMR-DMSOd6:<br>1.03-1.21 (6H, m), 1.80-2.05 (2H, m), 2.09-2.22 (2H, m),<br>2.60-2.78 (3H, m), 2.85-3.15 (5H, m), 3.35-3.55 (3H, m), 3.83 (3H, s), 3.90-4.08 (1H, m),<br>4.10-4.70 (3H, br),<br>6.60-7.28 (1H, br), 7.30-7.90 (4H, m), 8.00-8.50 (2H, m),<br>9.28-9.52 (1H, br), 9.52-9.73 (1H, br), 10.51-10.85 (1H, br)<br>Amrph |
| 53 | 2 | ESI+: 500.2 |
| 54 | 1 | ESI+: 664.3 |
| 55 | 1 | ESI+: 581.4 |
| 56 | 3 | ESI+: 590.3 |
| 57 | 3 | FAB+: 540.3 |
| 58 | 10 | ESI+: 552.3<br>NMR-DMSOd6:<br>1.01-1.29 (6H, br), 1.40-1.60 (2H, m), 1.60-1.78 (4H, m),<br>1.83-2.00 (2H, m), 2.06-2.20 (1H, m), 2.41-2.62 (4H, m),<br>2.69-2.82 (2H, m), 3.19-3.52 (1H, m), 3.58-3.71 (2H, m), 3.76 (3H, s), 5.90-6.56 (1H, m),<br>6.56-6.71 (1H, br),<br>7.15-7.35 (2H, m), 7.45-7.62 (1H, m), 7.62-7.89 (1H, m),<br>8.20-8.45 (2H, m), 8.60-9.03 (1H, m), 9.15-9.35 (1H, br)<br>Amrph |
| 59 | 1 | ESI+: 595.3 |
| 60 | 10 | ESI+: 568.3 |
| 61 | 3 | ESI+: 499.3 |
| 62 | 6 | FAB+: 546.2 |
| 63 | 10 | ESI+: 568.3<br>NMR-DMSOd6:<br>1.05-1.25 (6H, m), 1.78-2.10 (4H, m), 2.10-2.35 (2H, m),<br>2.80-4.21 (17H, m), 4.35-4.51 (1H, m), 6.60-7.21 (1H, m),<br>7.30-7.55 (2H, m), 7.55-7.90 (2H, m), 8.10-8.50 (2H, m),<br>9.20-9.40 (1H, m), 9.40-9.65 (1H, m), 10.42-11.42 (1H, m)<br>Amrph |

TABLE 46

| Ex | Syn | Data |
|----|-----|------|
| 64 | 1 | ESI+: 602.3 |
| 65 | 1 | FAB+: 602.3 |
| 66 | 1 | ESI+: 533.3 |
| 67 | 1 | ESI+: 534.3 |
| 68 | 1 | FAB+: 599.2 |

TABLE 46-continued

| Ex | Syn | Data |
|----|-----|------|
| 69 | 12 | ESI+: 513.3 |
| 70 | 2 | ESI+: 566.4 |
| 71 | 1 | FAB+: 583.3 |
| 72 | 9 | ESI+: 484.3<br>NMR-DMSOd6:<br>1.02-1.29 (6H, br), 2.73-2.98 (4H, m), 2.98-3.16 (4H, m),<br>3.17-3.50 (2H, m), 3.76 (3H, s),<br>6.40-6.55 (1H, m),<br>6.55-6.71 (1H, br), 7.18-7.39 (2H, m), 7.40-7.62 (1H, m),<br>7.62-7.90 (1H, m), 8.20-8.46 (2H, m), 8.58-9.53 (2H, m)<br>Amrph |
| 73 | 10 | ESI+: 644.3 |
| 74 | 18 | ESI+: 605 |
| 75 | 18 | ESI+: 619 |
| 76 | 18 | ESI+: 590 |
| 77 | 18 | ESI+: 604 |
| 78 | 18 | ESI+: 619 |
| 79 | 18 | ESI+: 618 |
| 80 | 18 | ESI+: 632 |
| 81 | 18 | ESI+: 587 |
| 82 | 18 | ESI+: 601 |
| 83 | 18 | ESI+: 615 |
| 84 | 18 | ESI+: 670 |
| 85 | 18 | ESI+: 616 |
| 86 | 18 | ESI+: 658 |
| 87 | 18 | ESI+: 644 |
| 88 | 18 | ESI+: 660 |
| 89 | 18 | ESI+: 692 |
| 90 | 18 | ESI+: 658 |
| 91 | 18 | ESI+: 630 |
| 92 | 18 | ESI+: 629 |
| 93 | 18 | ESI+: 631 |
| 94 | 18 | ESI+: 659 |
| 95 | 18 | ESI+: 658 |
| 96 | 18 | ESI+: 672 |
| 97 | 18 | ESI+: 691 |
| 98 | 1 | FAB+: 581.3 |
| 99 | 1 | FAB+: 595.3 |
| 100 | 1 | FAB+: 609.3 |
| 101 | 3 | ESI+: 638.2 |
| 102 | 3 | ESI+: 688.4 |
| 103 | 9 | ESI+: 538.4 |
| 104 | 18 | ESI+: 512 |
| 105 | 18 | ESI+: 526 |
| 106 | 18 | ESI+: 540 |
| 107 | 18 | ESI+: 556 |

TABLE 47

| Ex | Syn | Data |
|----|-----|------|
| 108 | 18 | ESI+: 570 |
| 109 | 18 | ESI+: 572 |
| 110 | 18 | ESI+: 541 |
| 111 | 18 | ESI+: 544 |
| 112 | 18 | ESI+: 538 |
| 113 | 18 | ESI+: 595 |
| 114 | 18 | ESI+: 673 |
| 115 | 19 | ESI+: 609 |
| 116 | 19 | ESI+: 611 |
| 117 | 19 | ESI+: 645 |
| 118 | 19 | ESI+: 649 |
| 119 | 1 | ESI+: 553.3 |
| 120 | 12 | ESI+: 552.4<br>NMR-DMSOd6:<br>1.03-1.22 (6H, m), 1.22-1.41 (2H, m), 1.59-1.87 (6H, m),<br>2.10-2.35 (2H, m), 2.60-2.85 (4H, m), 3.22-3.53 (4H, m), 3.76 (3H, s), 6.45-6.58 (1H, m),<br>6.58-6.70 (1H, m),<br>7.18-7.37 (2H, m), 7.42-7.61 (1H, m), |

TABLE 47-continued

| Ex | Syn | Data |
|---|---|---|
|  |  | 7.68-7.86 (1H, m), 8.21-8.42 (2H, m), 8.82-9.05 (1H, m), 9.20-9.31 (1H, m) Amrph |
| 121 | 12 | ESI+: 568.4 |
| 122 | 1 | FAB+: 512.3 |
| 123 | 10 | FAB+: 582.1 NMR-CDCl3: 1.03 (3H, t, J = 7.2 Hz), 1.6-1.7 (2H, m), 1.96 (2H, d, J = 12.2 Hz), 2.30 (3H, s), 2.3-2.8 (13H, m), 2.98 (2H, q, J = 7.2 Hz), 3.87 (3H, s), 4.86 (1H, br), 6.51 (1H, br), 6.53 (1H, d, J = 2.0 Hz), 7.22 (1H, d, J = 7.6 Hz), 7.5-7.7 (2H, m), 7.94 (1H, dd, J = 1.5, 7.8 Hz), 8.06 (1H, d, J = 8.3 Hz), 8.32 (1H, br), 8.40 (1H, br), 8.76 (1H, s) Cryst (MP: 155-160) |
| 124 | 1 | FAB+: 551.2 |
| 125 | 1 | FAB+: 565.2 |
| 126 | 1 | ESI+: 567.3 |
| 127 | 1 | ESI+: 567.4 |

TABLE 48

| Ex | Syn | Data |
|---|---|---|
| 128 | 1 | ESI+: 582.3 NMR-CDCl3: 1.6-1.8 (2H, m), 1.96 (2H, d, J = 12.2 Hz), 2.30 (3H, s), 2.3-2.8 (10H, m), 2.75 (6H, s), 3.70 (2H, d, J = 12.7 Hz), 3.88 (3H, s), 4.86 (1H, br), 6.5-6.6 (2H, m), 7.15-7.25 (1H, m), 7.5-7.7 (2H, m), 7.83 (2H, d, J = 7.8 Hz), 8.12 (1H, br), 8.35 (1H, br), 8.50 (1H, br), 9.11 (1H, s) Cryst (MP: 167-170) |
| 129 | 1 | ESI+: 579.3 |
| 130 | 1 | ESI+: 585.4, 587.2 |
| 131 | 19 | ESI+: 540 |
| 132 | 19 | ESI+: 542 |
| 133 | 19 | ESI+: 570 |
| 134 | 19 | ESI+: 527 |
| 135 | 19 | ESI+: 597 |
| 136 | 19 | ESI+: 526 |
| 137 | 19 | ESI+: 554 |
| 138 | 19 | ESI+: 584 |
| 139 | 19 | ESI+: 569 |
| 140 | 19 | ESI+: 568 |
| 141 | 19 | ESI+: 567 |
| 142 | 19 | ESI+: 581 |
| 143 | 19 | ESI+: 595 |
| 144 | 19 | ESI+: 609 |
| 145 | 19 | ESI+: 607 |
| 146 | 19 | ESI+: 657 |
| 147 | 1 | ESI+: 552.4 |
| 148 | 6 | FAB−: 496.1 |
| 149 | 10 | ESI+: 596.3 NMR-CDCl3: 1.00 (6H, d, J = 6.3 Hz), 1.6-1.8 (2H, m), 1.96 (2H, d, J = 11.7 Hz), 2.31 (3H, s), 2.3-2.8 (11H, m), 3.4-3.5 (1H, m), 3.69 (2H, d, J = 12.2 Hz), 3.88 (3H, s), 4.56 (1H, br), 6.48 (1H, br), 6.54 (1H, d, J = 2.4 Hz), 7.2-7.25 (1H, m), 7.5-7.7 (2H, m), 7.97 (1H, d, J = 6.8 Hz), 8.08 (1H, d, J = 8.8 Hz), |

TABLE 48-continued

| Ex | Syn | Data |
|---|---|---|
|  |  | 8.35 (2H, br), 8.61 (1H, s) Cryst (MP: 185-189) |
| 150 | 20 | ESI+: 568 |
| 151 | 20 | ESI+: 554 |
| 152 | 20 | ESI+: 570 |
| 153 | 20 | ESI+: 556 |
| 154 | 20 | ESI+: 584 |
| 155 | 20 | ESI+: 569 |
| 156 | 20 | ESI+: 583 |
| 157 | 20 | ESI+: 597 |

TABLE 49

| Ex | Syn | Data |
|---|---|---|
| 158 | 20 | ESI+: 611 |
| 159 | 20 | ESI+: 583 |
| 160 | 20 | ESI+: 584 |
| 161 | 20 | ESI+: 555 |
| 162 | 20 | ESI+: 569 |
| 163 | 3 | ESI+: 528.3 |
| 164 | 3 | ESI+: 570.3 |
| 165 | 6 | ESI+: 526.4 |
| 166 | 10 | ESI+: 610.3 NMR-CDCl3: 0.99 (6H, d, J = 6.3 Hz), 1.6-1.8 (2H, m), 1.96 (2H, d, J = 11.7 Hz), 2.31 (3H, s), 2.3-2.8 (11H, m), 2.7 (3H, m), 3.69 (2H, d, J = 12.2 Hz), 3.88 (3H, s), 4.15-4.2 (1H, m), 6.48 (1H, br), 6.54 (2H, br), 7.15-7.2 (1H, m), 7.5-7.6 (1H, m), 7.91 (1H, d, J = 7.8 Hz), 8.11 (1H, d, J = 8.8 Hz), 8.36 (1H, br), 8.42 (1H, br), 8.90 (1H, s) Cryst (MP: 162-164) |
| 167 | 6 | ESI+: 526.6 |
| 168 | 10 | ESI+: 610.4 |
| 169 | 1 | ESI+: 624.3 |
| 170 | 1 | ESI+: 608.3 |
| 171 | 1 | ESI+: 594.3 NMR-DMSOd6: 0.28-0.51 (4H, m), 1.41-1.59 (2H, m), 1.76-1.91 (2H, m), 2.01-2.20 (4H, m), 2.20-2.39 (5H, m), 2.40-2.60 (4H, m), 2.60-2.76 (2H, m), 3.62-3.85 (5H, m), 6.42-6.55 (1H, m), 6.55-6.70 (1H, m), 7.11-7.50 (2H, m), 7.72-7.89 (1H, m), 8.19-8.43 (1H, m), 8.75-8.95 (1H, m), 9.05-9.20 (1H, m) Amrph |
| 172 | 1 | ESI+: 596.3 |
| 173 | 1 | ESI+: 608.3 |
| 174 | 1 | ESI+: 622.4 |
| 175 | 1 | ESI+: 471.0 |

TABLE 50

| Ex | Syn | Data |
|---|---|---|
| 176 | 10 | ESI+: 553.3 NMR-DMSOd6: 1.04-1.29 (6H, br), 2.05-2.58 (11H, m), 3.18-3.50 (2H, m), 3.50-3.66 (2H, m), 3.73 (3H, s), 3.85-4.00 (2H, m), 5.90-6.22 (2H, m), 7.10-7.40 (2H, m), |

TABLE 50-continued

| Ex | Syn | Data |
|----|-----|------|
|    |     | 7.40-7.88 (2H, m), 8.17-8.42 (2H, m), 8.60-9.01 (1H, m), 9.17-9.35 (1H, br) Amrph |
| 177 | 3 | ESI+: 543.2 |
| 178 | 1 | ESI+: 555.2, 557.2 |
| 179 | 1 | ESI+: 529.2 |
| 180 | 1 | ESI+: 581.3 |
| 181 | 1 | ESI+: 582 |

Tables 51 to 95 show the structures of other compounds falling within the present invention. These compounds were synthesized or can be synthesized as described in the above preparation examples or examples, or by any process obvious to those skilled in the art with or without modifications.

It should be noted that the symbols in the tables are as defined below:
—$R^{1a'}$, —$R^{1b'}$, —$R^{1c'}$, —$R^{1d'}$, —$R^{2'}$, —$R^{3'}$, —$R^{4'}$, —$R^{5'}$, —$R^{6a'}$, —$R^{6b'}$, —$R^{6c'}$, —$R^{6d'}$ and —$R^{4}$ correspond to the substituents in the general formulae.

TABLE 51

| No | —$R^{3'}$ |
|----|-----------|
| A1 | (piperidine-morpholine) |
| A2 | (piperidine-piperidine) |
| A3 | (piperidine-pyrrolidine) |
| A4 | (piperidine-(2,6-diMe)piperazine-Me) |
| A5 | (piperidine-(2,6-diMe)piperazine-NH) |
| A6 | (piperazine-piperidine-N-Me) |
| A7 | (piperazine-piperidine) |
| A8 | (piperazine-N-phenyl) |
| A9 | ((2,6-diMe)piperazine-cyclohexyl) |
| A10 | (piperidine-piperazinone-N-Me) |
| A11 | (piperidine-piperazinone-N-Me) |
| A12 | (piperidine-piperazinone-NH) |
| A13 | (piperazine-pyridyl) |
| A14 | ((2,6-diMe)piperazine-phenyl) |
| A15 | ((2,6-diMe)piperazine-pyridyl) |
| A16 | (morpholine) |

151
TABLE 51-continued
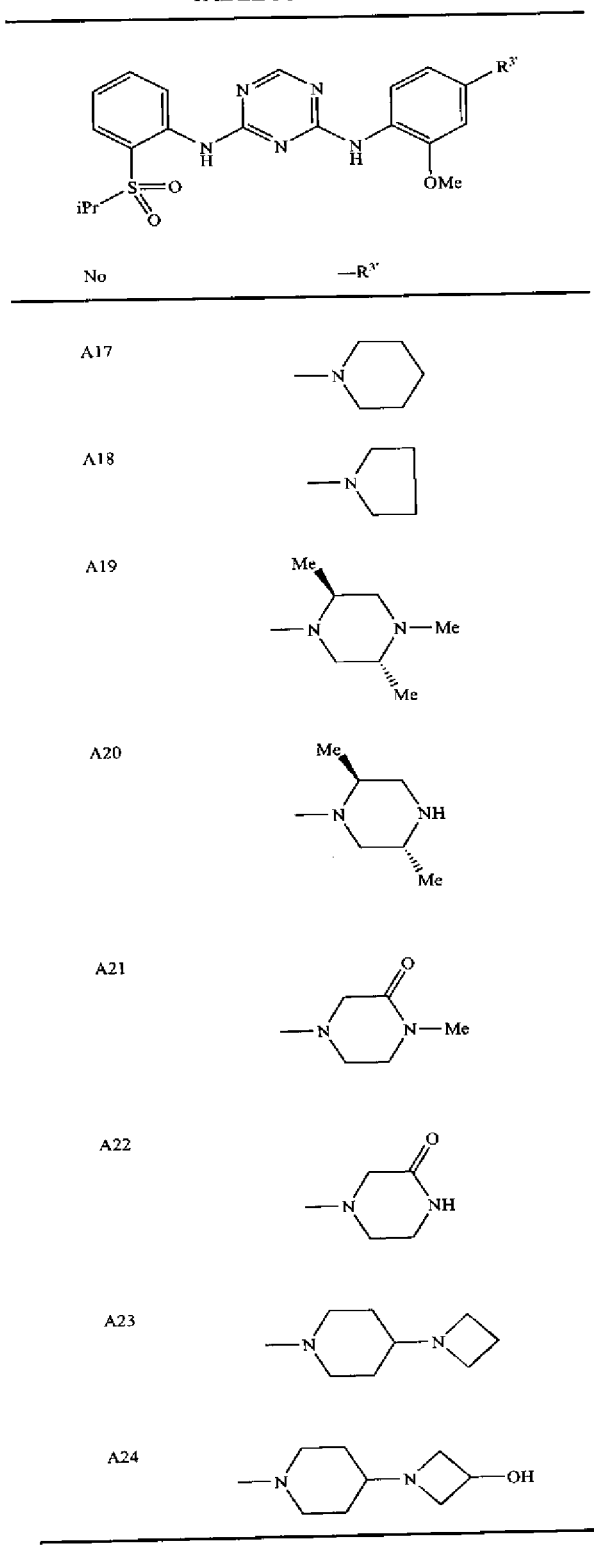
152
TABLE 52
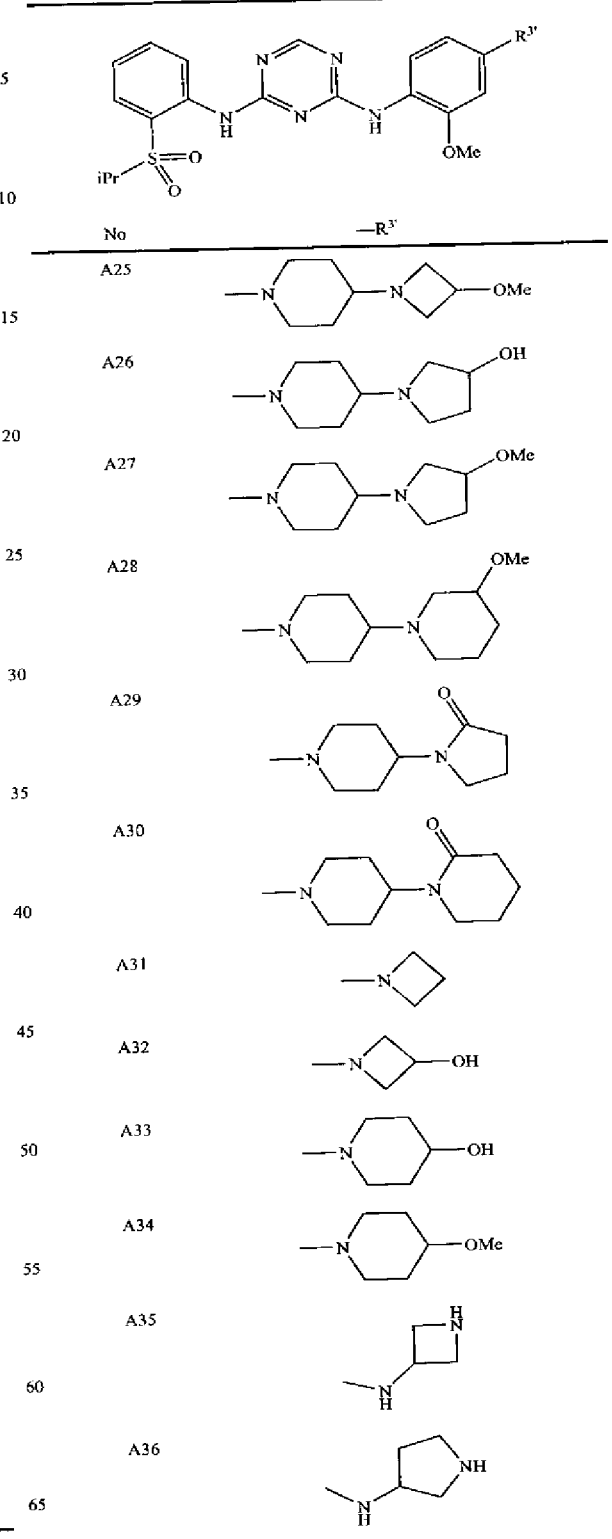

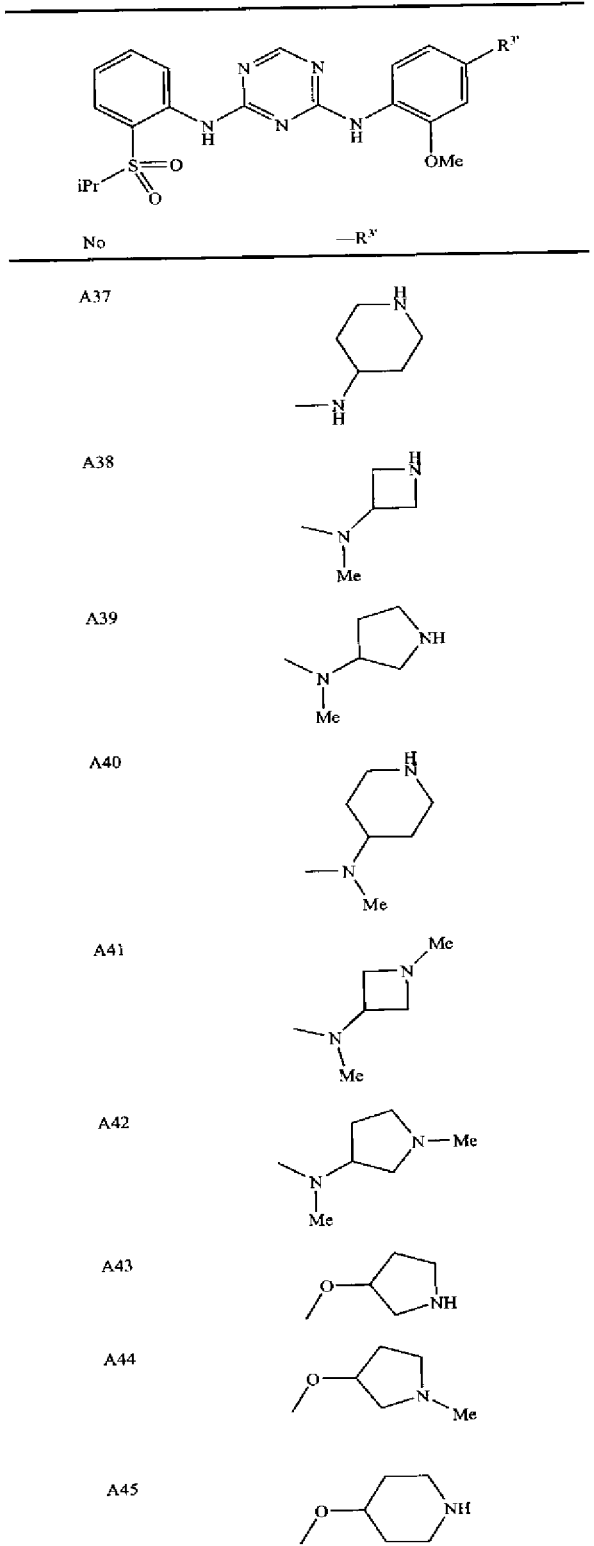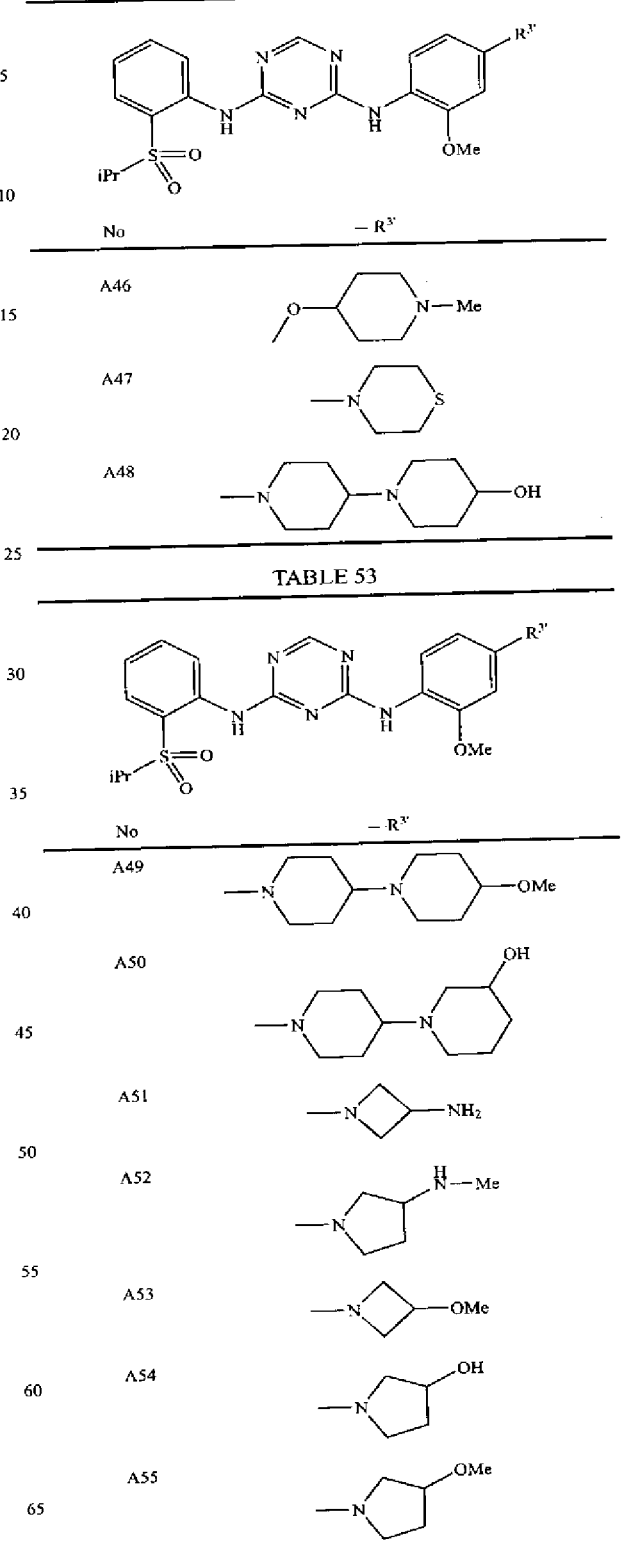

TABLE 53-continued

| No | -R³' |
|---|---|
| A56 | azetidine-N-Me, 3-NHMe |
| A57 | pyrrolidine-N-Me, 3-NH₂ |
| A58 | azetidine-N-Me, 3-NHMe |
| A59 | pyrrolidine-N-Me, 3-NHMe |
| A60 | piperidine-N-Me, 4-NHMe |
| A61 | azetidine-N-Me, 3-NMe₂ |
| A62 | pyrrolidine-N-Me, 3-NMe₂ |
| A63 | piperidine-N-Me, 4-N(Me)Me |
| A64 | 3-methoxyazetidine-NH |
| A65 | 3-methoxyazetidine-N-Me |

TABLE 53-continued

| No | -R³' |
|---|---|
| A66 | piperidine-N-Me, 4-NH₂ |
| A67 | piperidine-N-Me, 4-NHMe |
| A68 | thiomorpholine-1,1-dioxide-N- |
| A69 | piperidine-N-Me, 4-NMe₂ |
| A70 | piperidine-N-Me, 3-NH₂ |
| A71 | piperidine-N-Me, 3-NHMe |
| A72 | piperidine-N-Me, 3-NMe₂ |

TABLE 54

| No | -R⁴' |
|---|---|
| B1 | piperidine-N-Me, 4-morpholino |

TABLE 54-continued

Structure with R4' substituent on phenyl ring attached via NH to triazine, with iPr-sulfonyl aniline and OMe groups.

| No | —R4' |
|---|---|
| B2 | —N(piperidine)-piperidine |
| B3 | —N(piperidine)-pyrrolidine |
| B4 | —N(piperidine)-(2,5-dimethyl-4-methylpiperazine) |
| B5 | —N(piperidine)-(2,5-dimethylpiperazine-NH) |
| B6 | —N(piperazine)-(N-Me piperidine) |
| B7 | —N(piperazine)-cyclohexyl |
| B8 | —N(piperazine)-phenyl |
| B9 | —N(2,5-dimethylpiperazine)-cyclohexyl |
| B10 | —N(piperidine)-(3-oxo-4-methylpiperazine) |
| B11 | —N(piperidine)-(3-oxo-4-methylpiperazine) |
| B12 | —N(piperidine)-(3-oxopiperazine-NH) |
| B13 | —N(piperazine)-(2-pyridyl) |
| B14 | —N(2,5-dimethylpiperazine)-phenyl |
| B15 | —N(2,5-dimethylpiperazine)-(2-pyridyl) |
| B16 | —N-morpholine |
| B17 | —N-piperidine |
| B18 | —N-pyrrolidine |
| B19 | —N(2,5-dimethyl-4-methylpiperazine) |
| B20 | —N(2,5-dimethylpiperazine-NH) |

TABLE 54-continued

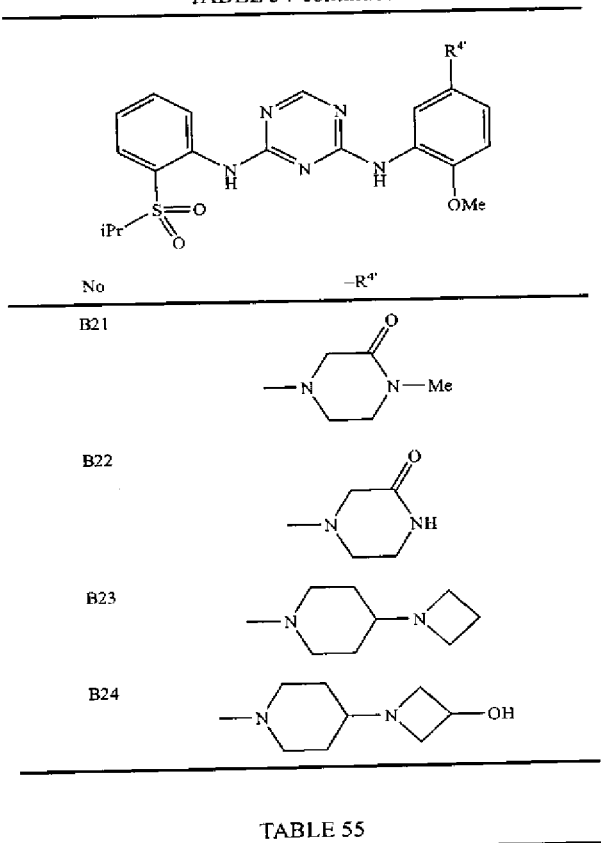

| No | -R4' |
|---|---|
| B21 | (N-methylpiperazinone, N-Me) |
| B22 | (N-methylpiperazinone, NH) |
| B23 | (N-methylpiperidine-azetidine) |
| B24 | (N-methylpiperidine-azetidine-OH) |

TABLE 55

| No | -R4' |
|---|---|
| B25 | (N-methylpiperidine-azetidine-OMe) |
| B26 | (N-methylpiperidine-pyrrolidine-OH) |
| B27 | (N-methylpiperidine-pyrrolidine-OMe) |
| B28 | (N-methylpiperidine-piperidine-OMe) |

TABLE 55-continued

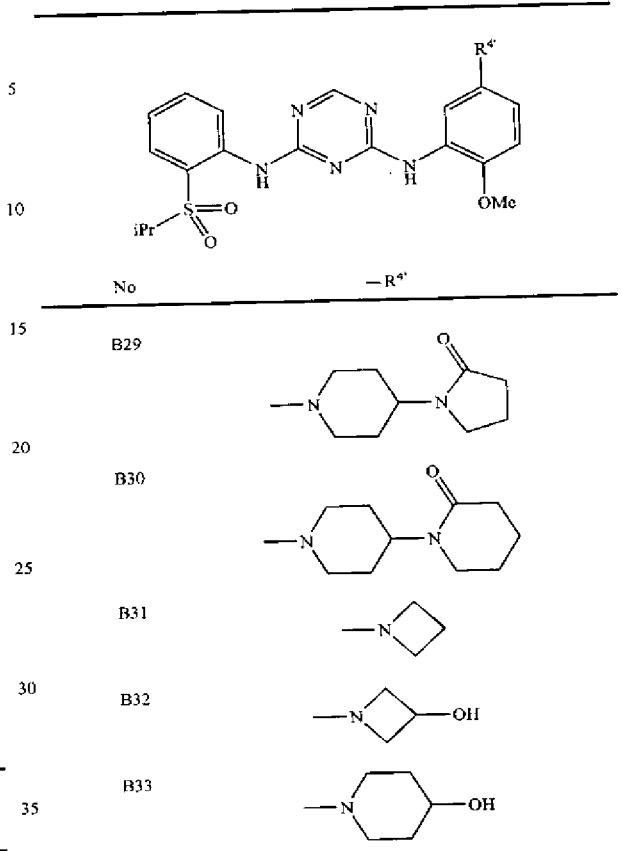

| No | -R4' |
|---|---|
| B29 | (N-methylpiperidine-pyrrolidinone) |
| B30 | (N-methylpiperidine-piperidinone) |
| B31 | (azetidine) |
| B32 | (azetidine-OH) |
| B33 | (piperidine-OH) |
| B34 | (piperidine-OMe) |
| B35 | (azetidine-NH) |
| B36 | (pyrrolidine-NH) |
| B37 | (piperidine-NH) |
| B38 | (azetidine-N-Me) |

TABLE 55-continued
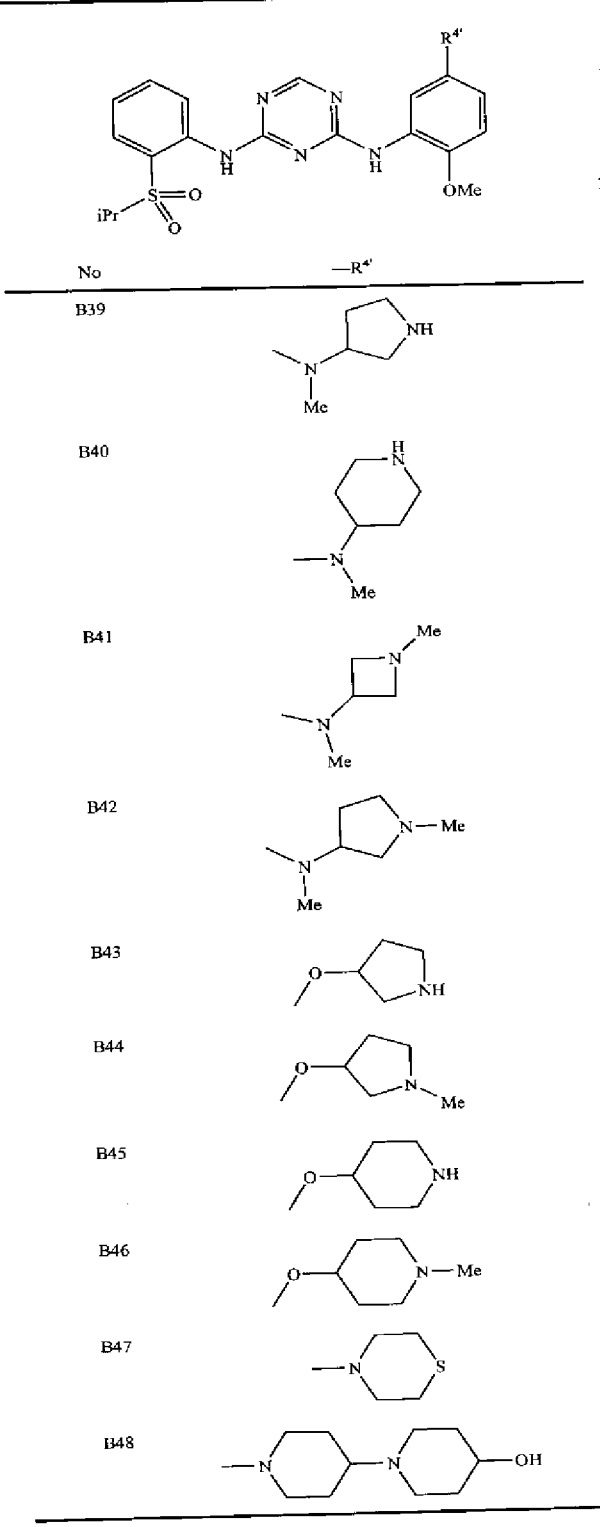
TABLE 56
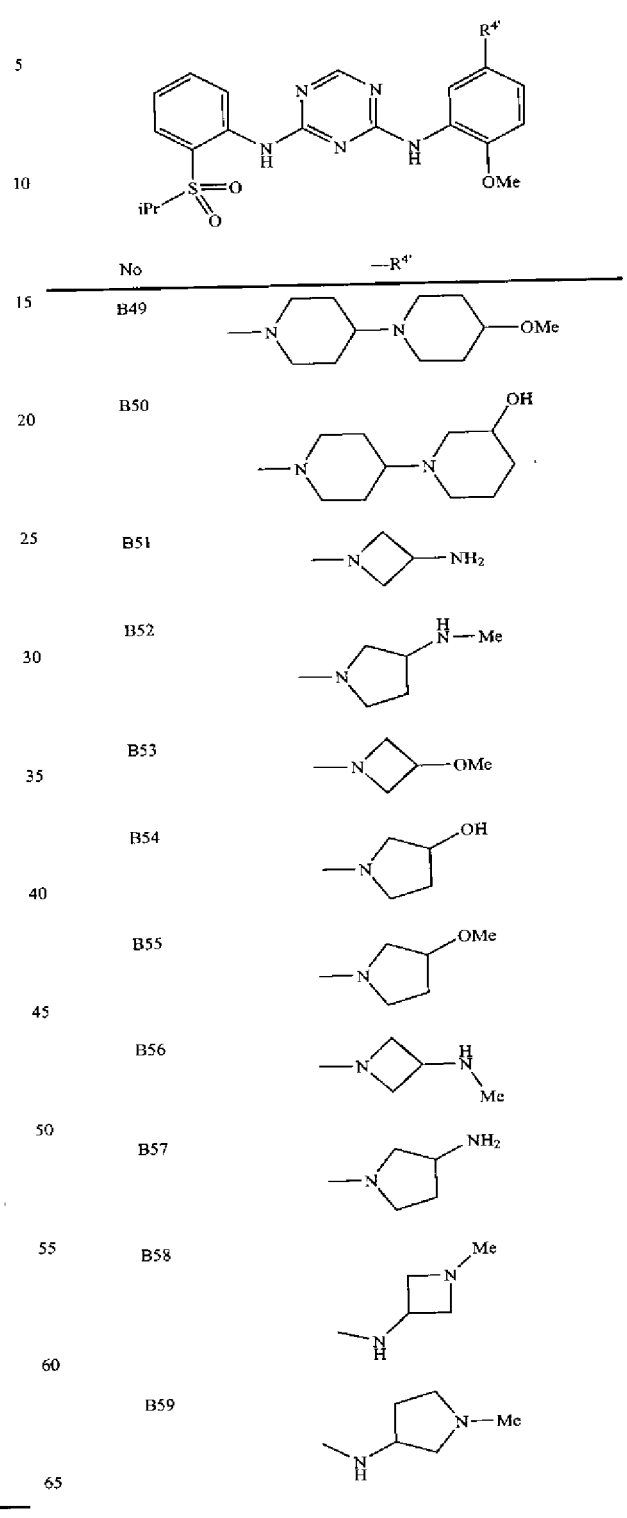

TABLE 56-continued
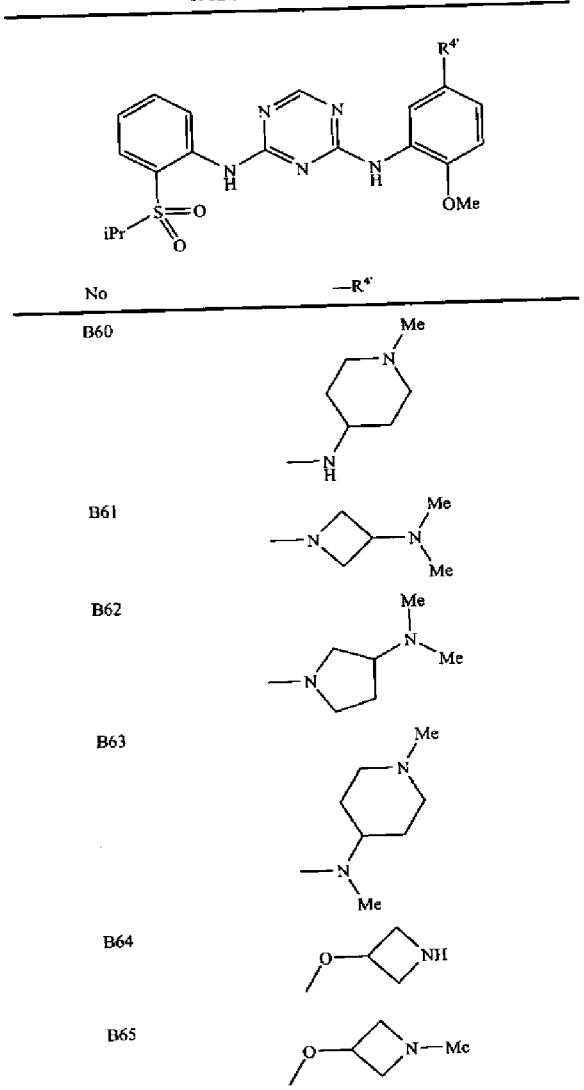
TABLE 56-continued
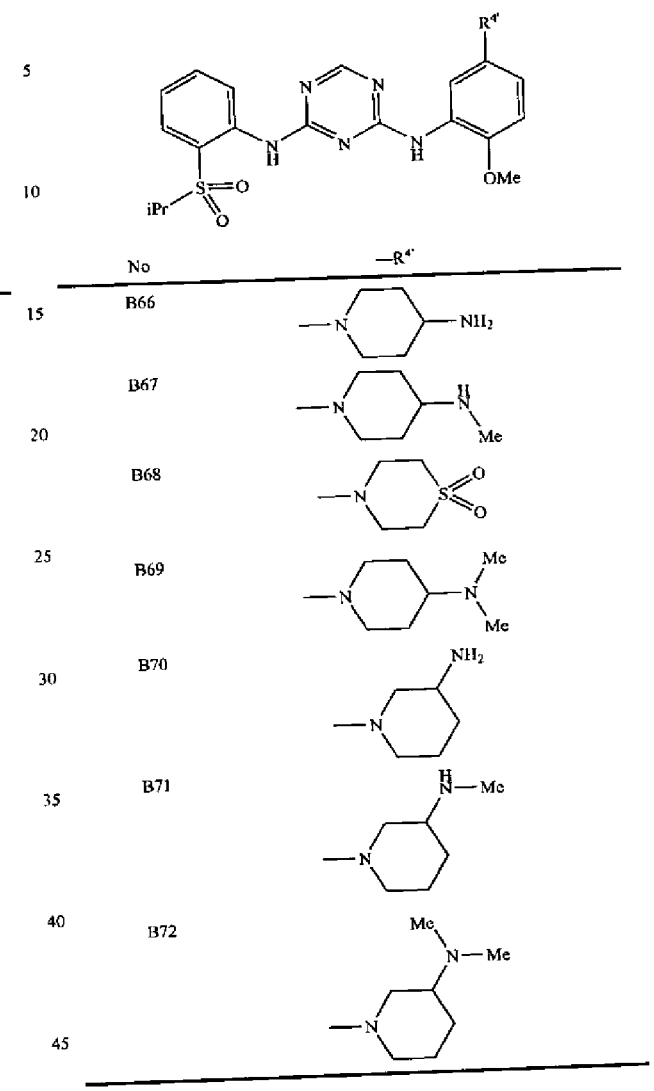
TABLE 57
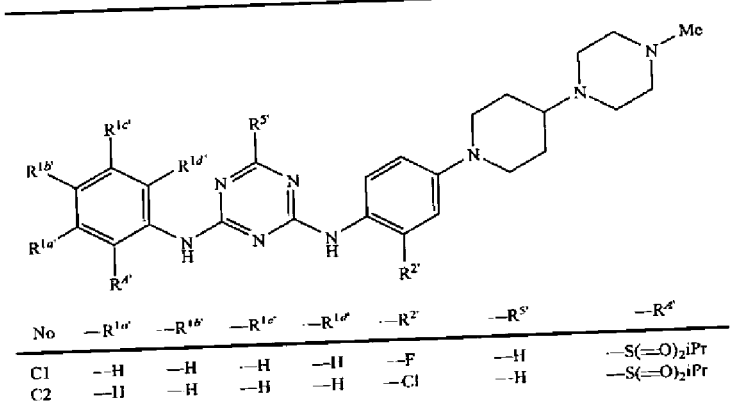

TABLE 57-continued

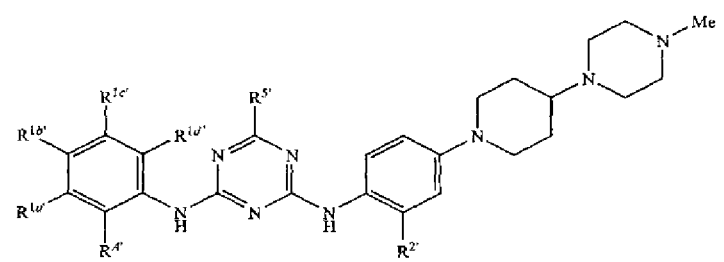

| No | —R1a' | —R1b' | —R1c' | —R1d' | —R2' | —R5' | —R4' |
|---|---|---|---|---|---|---|---|
| C3 | —H | —H | —H | —H | —Br | —H | —S(=O)₂iPr |
| C4 | —H | —H | —H | —H | —OEt | —H | —S(=O)₂iPr |
| C5 | —H | —H | —H | —H | —OiPr | —H | —S(=O)₂iPr |
| C6 | —H | —H | —H | —H | —CF₃ | —H | —S(=O)₂iPr |
| C7 | —H | —H | —H | —H | —CN | —H | —S(=O)₂iPr |
| C8 | —H | —H | —H | —H | Me | —H | —S(=O)₂iPr |
| C9 | —H | —H | —H | —H | Et | —H | —S(=O)₂iPr |
| C10 | —H | —H | —H | —H | —SMe | —H | —S(=O)₂iPr |
| C11 | —H | —H | —H | —H | —OCF₃ | —H | —S(=O)₂iPr |
| C12 | —H | —H | —H | —H | —OMe | —Cl | —S(=O)₂iPr |
| C13 | —H | —H | —H | —H | —OMe | —Br | —S(=O)₂iPr |
| C14 | —H | —H | —H | —H | —OMe | Me | —S(=O)₂iPr |
| C15 | —H | —H | —H | —H | —OMe | —SMe | —S(=O)₂iPr |
| C16 | —H | —H | —H | —H | —OMe | —NMe₂ | —S(=O)₂iPr |
| C17 | —H | —H | —H | —H | —OMe | —NEt₂ | —S(=O)₂iPr |
| C18 | —H | —H | —H | —H | —OMe | morpholino | —S(=O)₂iPr |
| C19 | —H | —H | —H | —H | —OMe | piperidino | —S(=O)₂iPr |
| C20 | —H | —H | —H | —H | —OMe | pyrrolidino | —S(=O)₂iPr |
| C21 | —H | —H | —H | —H | —OMe | azetidino | —S(=O)₂iPr |
| C22 | —H | —H | —H | —H | —OMe | —CN | —S(=O)₂iPr |
| C23 | —F | —H | —H | —H | —OMe | —H | —S(=O)₂iPr |
| C24 | —H | —F | —H | —H | —OMe | —H | —S(=O)₂iPr |
| C25 | —H | —H | —F | —H | —OMe | —H | —S(=O)₂iPr |
| C26 | —H | —H | —H | —F | —OMe | —H | —S(=O)₂iPr |

TABLE 58

| No | —R1a' | —R1b' | —R1c' | —R1d' | —R2' | —R5' | —R4' |
|---|---|---|---|---|---|---|---|
| C27 | —Cl | —H | —H | —H | —OMe | —H | —S(=O)₂iPr |
| C28 | —H | —Cl | —H | —H | —OMe | —H | —S(=O)₂iPr |

TABLE 58-continued

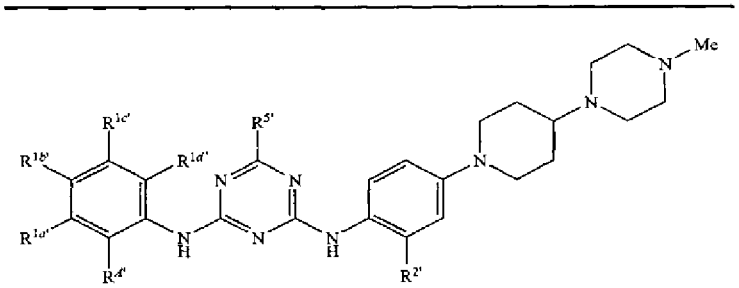

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| C29 | —H | —H | —Cl | —H | —OMe | —H | —S(=O)$_2$iPr |
| C30 | —H | —H | —H | —Cl | —OMe | —H | —S(=O)$_2$iPr |
| C31 | —Br | —H | —H | —H | —OMe | —H | —S(=O)$_2$iPr |
| C32 | —H | —Br | —H | —H | —OMe | —H | —S(=O)$_2$iPr |
| C33 | —H | —H | —Br | —H | —OMe | —H | —S(=O)$_2$iPr |
| C34 | —H | —H | —H | —Br | —OMe | —H | —S(=O)$_2$iPr |
| C35 | Me | —H | —H | —H | —OMe | —H | —S(=O)$_2$iPr |
| C36 | —H | Me | —H | —H | —OMe | —H | —S(=O)$_2$iPr |
| C37 | —H | —H | Me | —H | —OMe | —H | —S(=O)$_2$iPr |
| C39 | —H | —H | —H | Me | —OMe | —H | —S(=O)$_2$iPr |
| C40 | —OMe | —H | —H | —H | —OMe | —H | —S(=O)$_2$iPr |
| C41 | —H | —OMe | —H | —H | —OMe | —H | —S(=O)$_2$iPr |
| C42 | —H | —H | —OMe | —H | —OMe | —H | —S(=O)$_2$iPr |
| C43 | —H | —H | —H | —OMe | —OMe | —H | —S(=O)$_2$iPr |
| C44 | —CN | —H | —H | —H | —OMe | —H | —S(=O)$_2$iPr |
| C45 | —H | —CN | —H | —H | —OMe | —H | —S(=O)$_2$iPr |
| C46 | —H | —H | —CN | —H | —OMe | —H | —S(=O)$_2$iPr |
| C47 | —H | —H | —H | —CN | —OMe | —H | —S(=O)$_2$iPr |
| C48 | —CF$_3$ | —H | —H | —H | —OMe | —H | —S(=O)$_2$iPr |
| C49 | —H | —CF$_3$ | —H | —H | —OMe | —H | —S(=O)$_2$iPr |
| C50 | —H | —H | —CF$_3$ | —H | —OMe | —H | —S(=O)$_2$iPr |
| C51 | —H | —H | —H | —CF$_3$ | —OMe | —H | —S(=O)$_2$iPr |
| C52 | —SMe | —H | —H | —H | —OMe | —H | —S(=O)$_2$iPr |
| C53 | —H | —SMe | —H | —H | —OMe | —H | —S(=O)$_2$iPr |
| C54 | —H | —H | —SMe | —H | —OMe | —H | —S(=O)$_2$iPr |
| C55 | —H | —H | —H | —SMe | —OMe | —H | —S(=O)$_2$iPr |
| C56 | —OCF$_3$ | —H | —H | —H | —OMe | —H | —S(=O)$_2$iPr |
| C57 | —H | —OCF$_3$ | —H | —H | —OMe | —H | —S(=O)$_2$iPr |
| C58 | —H | —H | —OCF$_3$ | —H | —OMe | —H | —S(=O)$_2$iPr |
| C59 | —H | —H | —H | —OCF$_3$ | —OMe | —H | —S(=O)$_2$iPr |

TABLE 59

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| C60 | —H | —H | —H | —H | —OMe | —H | —S(=O)$_2$Et |
| C61 | —H | —H | —H | —H | —OMe | —H | —S(=O)$_2$Me |
| C62 | —H | —H | —H | —H | —OMe | —H | —S(=O)$_2$NHMe |
| C63 | —H | —H | —H | —H | —OMe | —H | —S(=O)$_2$NMe$_2$ |
| C64 | —H | —H | —H | —H | —OMe | —H | —C(=O)NHMe |
| C65 | —H | —H | —H | —H | —OMe | —H | —C(=O)NMe$_2$ |
| C66 | —H | —H | —H | —H | —OMe | —H | —C(=O)iPr |
| C67 | —H | —H | —H | —H | —OMe | —H | —C(=O)Et |
| C68 | —H | —H | —H | —H | —OMe | —H | —F |
| C69 | —H | —H | —H | —H | —OMe | —H | —Cl |
| C70 | —H | —H | —H | —H | —OMe | —H | —Br |
| C71 | —H | —H | —H | —H | —OMe | —H | —OMe |

TABLE 59-continued

| No | —R1a' | —R1b' | —R1c' | —R1d' | —R2' | —R5' | —R4' |
|---|---|---|---|---|---|---|---|
| C72 | —H | —H | —H | —H | —OMe | —H | —OEt |
| C73 | —H | —H | —H | —H | —OMe | —H | —OiPr |
| C74 | —H | —H | —H | —H | —OMe | —H | —OCF3 |
| C75 | —H | —H | —H | —H | —OMe | —H | —SMe |
| C76 | —H | —H | —H | —H | —OMe | —H | —SEt |
| C77 | —H | —H | —H | —H | —OMe | —H | —SiPr |
| C78 | —H | —H | —H | —H | —OMe | —H | Me |
| C79 | —H | —H | —H | —H | —OMe | —H | Et |
| C80 | —H | —H | —H | —H | —OMe | —H | iPr |
| C81 | —H | —H | —H | —H | —OMe | —H | —CF3 |

TABLE 60

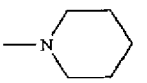

| No | —R1a' | —R1b' | —R1c' | —R1d' | —R2' | —R5' | —R4' |
|---|---|---|---|---|---|---|---|
| D1 | —H | —H | —H | —H | —F | —H | —S(=O)2iPr |
| D2 | —H | —H | —H | —H | —Cl | —H | —S(=O)2iPr |
| D3 | —H | —H | —H | —H | —Br | —H | —S(=O)2iPr |
| D4 | —H | —H | —H | —H | —OEt | —H | —S(=O)2iPr |
| D5 | —H | —H | —H | —H | —OiPr | —H | —S(=O)2iPr |
| D6 | —H | —H | —H | —H | —CF3 | —H | —S(=O)2iPr |
| D7 | —H | —H | —H | —H | —CN | —H | —S(=O)2iPr |
| D8 | —H | —H | —H | —H | Me | —H | —S(=O)2iPr |
| D9 | —H | —H | —H | —H | Et | —H | —S(=O)2iPr |
| D10 | —H | —H | —H | —H | —SMe | —H | —S(=O)2iPr |
| D11 | —H | —H | —H | —H | —OCF3 | —H | —S(=O)2iPr |
| D12 | —H | —H | —H | —H | —OMe | —Cl | —S(=O)2iPr |
| D13 | —H | —H | —H | —H | —OMe | —Br | —S(=O)2iPr |
| D14 | —H | —H | —H | —H | —OMe | Me | —S(=O)2iPr |
| D15 | —H | —H | —H | —H | —OMe | —SMe | —S(=O)2iPr |
| D16 | —H | —H | —H | —H | —OMe | —NMe2 | —S(=O)2iPr |
| D17 | —H | —H | —H | —H | —OMe | —NEt2 | —S(=O)2iPr |
| D18 | —H | —H | —H | —H | —OMe | 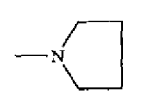 morpholinyl | —S(=O)2iPr |
| D19 | —H | —H | —H | —H | —OMe | piperidinyl | —S(=O)2iPr |
| D20 | —H | —H | —H | —H | —OMe | pyrrolidinyl | —S(=O)2iPr |

TABLE 60-continued

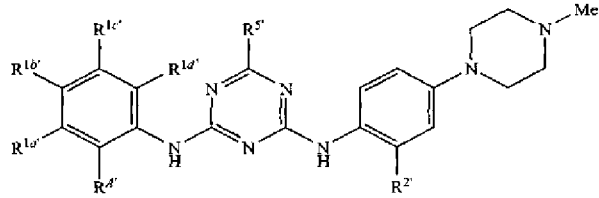

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| D21 | —H | —H | —H | —H | —OMe | 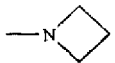 | —S(=O)$_2$iPr |
| D22 | —H | —H | —H | —H | —OMe | —CN | —S(=O)$_2$iPr |
| D23 | —F | —H | —H | —H | —OMe | —H | —S(=O)$_2$iPr |
| D24 | —H | —F | —H | —H | —OMe | —H | —S(=O)$_2$iPr |
| D25 | —H | —H | —F | —H | —OMe | —H | —S(=O)$_2$iPr |
| D26 | —H | —H | —H | —F | —OMe | —H | —S(=O)$_2$iPr |

TABLE 61

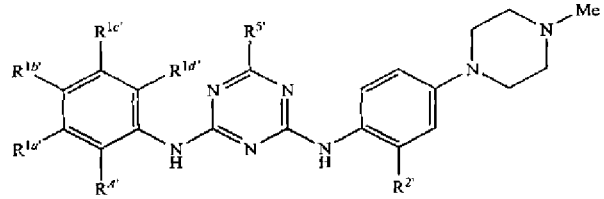

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| D27 | —Cl | —H | —H | —H | —OMe | —H | —S(=O)$_2$iPr |
| D28 | —H | —Cl | —H | —H | —OMe | —H | —S(=O)$_2$iPr |
| D29 | —H | —H | —Cl | —H | —OMe | —H | —S(=O)$_2$iPr |
| D30 | —H | —H | —H | —Cl | —OMe | —H | —S(=O)$_2$iPr |
| D31 | —Br | —H | —H | —H | —OMe | —H | —S(=O)$_2$iPr |
| D32 | —H | —Br | —H | —H | —OMe | —H | —S(=O)$_2$iPr |
| D33 | —H | —H | —Br | —H | —OMe | —H | —S(=O)$_2$iPr |
| D34 | —H | —H | —H | —Br | —OMe | —H | —S(=O)$_2$iPr |
| D35 | Me | —H | —H | —H | —OMe | —H | —S(=O)$_2$iPr |
| D36 | —H | Me | —H | —H | —OMe | —H | —S(=O)$_2$iPr |
| D37 | —H | —H | Me | —H | —OMe | —H | —S(=O)$_2$iPr |
| D39 | —H | —H | —H | Me | —OMe | —H | —S(=O)$_2$iPr |
| D40 | —OMe | —H | —H | —H | —OMe | —H | —S(=O)$_2$iPr |
| D41 | —H | —OMe | —H | —H | —OMe | —H | —S(=O)$_2$iPr |
| D42 | —H | —H | —OMe | —H | —OMe | —H | —S(=O)$_2$iPr |
| D43 | —H | —H | —H | —OMe | —OMe | —H | —S(=O)$_2$iPr |
| D44 | —CN | —H | —H | —H | —OMe | —H | —S(=O)$_2$iPr |
| D45 | —H | —CN | —H | —H | —OMe | —H | —S(=O)$_2$iPr |
| D46 | —H | —H | —CN | —H | —OMe | —H | —S(=O)$_2$iPr |
| D47 | —H | —H | —H | —CN | —OMe | —H | —S(=O)$_2$iPr |
| D48 | —CF$_3$ | —H | —H | —H | —OMe | —H | —S(=O)$_2$iPr |
| D49 | —H | —CF$_3$ | —H | —H | —OMe | —H | —S(=O)$_2$iPr |
| D50 | —H | —H | —CF$_3$ | —H | —OMe | —H | —S(=O)$_2$iPr |
| D51 | —H | —H | —H | —CF$_3$ | —OMe | —H | —S(=O)$_2$iPr |
| D52 | —SMe | —H | —H | —H | —OMe | —H | —S(=O)$_2$iPr |
| D53 | —H | —SMe | —H | —H | —OMe | —H | —S(=O)$_2$iPr |
| D54 | —H | —H | —SMe | —H | —OMe | —H | —S(=O)$_2$iPr |
| D55 | —H | —H | —H | —SMe | —OMe | —H | —S(=O)$_2$iPr |
| D56 | —OCF$_3$ | —H | —H | —H | —OMe | —H | —S(=O)$_2$iPr |
| D57 | —H | —OCF$_3$ | —H | —H | —OMe | —H | —S(=O)$_2$iPr |
| D58 | —H | —H | —OCF$_3$ | —H | —OMe | —H | —S(=O)$_2$iPr |
| D59 | —H | —H | —H | —OCF$_3$ | —OMe | —H | —S(=O)$_2$iPr |

TABLE 62

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| D60 | —H | —H | —H | —H | —OMe | —H | —S(=O)$_2$Et |
| D61 | —H | —H | —H | —H | —OMe | —H | —S(=O)$_2$Me |
| D62 | —H | —H | —H | —H | —OMe | —H | —S(=O)$_2$NHMe |
| D63 | —H | —H | —H | —H | —OMe | —H | —S(=O)$_2$NMe$_2$ |
| D64 | —H | —H | —H | —H | —OMe | —H | —C(=O)NHMe |
| D65 | —H | —H | —H | —H | —OMe | —H | —C(=O)NMe$_2$ |
| D66 | —H | —H | —H | —H | —OMe | —H | —C(=O)iPr |
| D67 | —H | —H | —H | —H | —OMe | —H | —C(=O)Et |
| D68 | —H | —H | —H | —H | —OMe | —H | —F |
| D69 | —H | —H | —H | —H | —OMe | —H | —Cl |
| D70 | —H | —H | —H | —H | —OMe | —H | —Br |
| D71 | —H | —H | —H | —H | —OMe | —H | —OMe |
| D72 | —H | —H | —H | —H | —OMe | —H | —OEt |
| D73 | —H | —H | —H | —H | —OMe | —H | —OiPr |
| D74 | —H | —H | —H | —H | —OMe | —H | —OCF$_3$ |
| D75 | —H | —H | —H | —H | —OMe | —H | —SMe |
| D76 | —H | —H | —H | —H | —OMe | —H | —SEt |
| D77 | —H | —H | —H | —H | —OMe | —H | —SiPr |
| D78 | —H | —H | —H | —H | —OMe | —H | Me |
| D79 | —H | —H | —H | —H | —OMe | —H | Et |
| D80 | —H | —H | —H | —H | —OMe | —H | iPr |
| D81 | —H | —H | —H | —H | —OMe | —H | —CF$_3$ |

TABLE 63

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| E1 | —H | —H | —H | —H | —F | —H | —S(=O)$_2$iPr |
| E2 | —H | —H | —H | —H | —Cl | —H | —S(=O)$_2$iPr |
| E3 | —H | —H | —H | —H | —Br | —H | —S(=O)$_2$iPr |
| E4 | —H | —H | —H | —H | —OEt | —H | —S(=O)$_2$iPr |
| E5 | —H | —H | —H | —H | —OiPr | —H | —S(=O)$_2$iPr |
| E6 | —H | —H | —H | —H | —CF$_3$ | —H | —S(=O)$_2$iPr |
| E7 | —H | —H | —H | —H | —CN | —H | —S(=O)$_2$iPr |
| E8 | —H | —H | —H | —H | Me | —H | —S(=O)$_2$iPr |
| E9 | —H | —H | —H | —H | Et | —H | —S(=O)$_2$iPr |
| E10 | —H | —H | —H | —H | —SMe | —H | —S(=O)$_2$iPr |
| E11 | —H | —H | —H | —H | —OCF$_3$ | —H | —S(=O)$_2$iPr |
| E12 | —H | —H | —H | —H | —OMe | —Cl | —S(=O)$_2$iPr |
| E13 | —H | —H | —H | —H | —OMe | —Br | —S(=O)$_2$iPr |
| E14 | —H | —H | —H | —H | —OMe | Me | —S(=O)$_2$iPr |
| E15 | —H | —H | —H | —H | —OMe | —SMe | —S(=O)$_2$iPr |
| E16 | —H | —H | —H | —H | —OMe | —NMe$_2$ | —S(=O)$_2$iPr |
| E17 | —H | —H | —H | —H | —OMe | —NEt$_2$ | —S(=O)$_2$iPr |
| E18 | —H | —H | —H | —H | —OMe | —N-morpholinyl | —S(=O)$_2$iPr |
| E19 | —H | —H | —H | —H | —OMe | —N-piperidinyl | —S(=O)$_2$iPr |

TABLE 63-continued

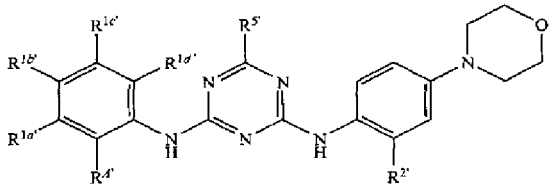

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| E20 | —H | —H | —H | —H | —OMe | 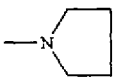 | —S(=O)$_2$iPr |
| E21 | —H | —H | —H | —H | —OMe | 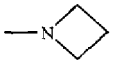 | —S(=O)$_2$iPr |
| E22 | —H | —H | —H | —H | —OMe | —CN | —S(=O)$_2$iPr |
| E23 | —F | —H | —H | —H | —OMe | —H | —S(=O)$_2$iPr |
| E24 | —H | —F | —H | —H | —OMe | —H | —S(=O)$_2$iPr |
| E25 | —H | —H | —F | —H | —OMe | —H | —S(=O)$_2$iPr |
| E26 | —H | —H | —H | —F | —OMe | —H | —S(=O)$_2$iPr |

TABLE 64

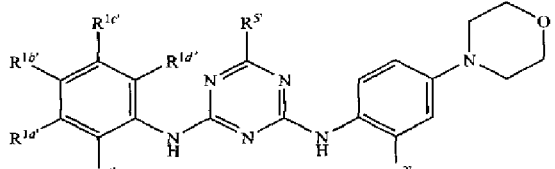

| No | —R$^{1a'}$ | —R$^{1b'}$ | —R$^{1c'}$ | —R$^{1d'}$ | —R$^{2'}$ | —R$^{5'}$ | —R$^{4'}$ |
|---|---|---|---|---|---|---|---|
| E27 | —Cl | —H | —H | —H | —OMe | —H | —S(=O)$_2$iPr |
| E28 | —H | —Cl | —H | —H | —OMe | —H | —S(=O)$_2$iPr |
| E29 | —H | —H | —Cl | —H | —OMe | —H | —S(=O)$_2$iPr |
| E30 | —H | —H | —H | —Cl | —OMe | —H | —S(=O)$_2$iPr |
| E31 | —Br | —H | —H | —H | —OMe | —H | —S(=O)$_2$iPr |
| E32 | —H | —Br | —H | —H | —OMe | —H | —S(=O)$_2$iPr |
| E33 | —H | —H | —Br | —H | —OMe | —H | —S(=O)$_2$iPr |
| E34 | —H | —H | —H | —Br | —OMe | —H | —S(=O)$_2$iPr |
| E35 | Me | —H | —H | —H | —OMe | —H | —S(=O)$_2$iPr |
| E36 | —H | Me | —H | —H | —OMe | —H | —S(=O)$_2$iPr |
| E37 | —H | —H | Me | —H | —OMe | —H | —S(=O)$_2$iPr |
| E39 | —H | —H | —H | Me | —OMe | —H | —S(=O)$_2$iPr |
| E40 | —OMe | —H | —H | —H | —OMe | —H | —S(=O)$_2$iPr |
| E41 | —H | —OMe | —H | —H | —OMe | —H | —S(=O)$_2$iPr |
| E42 | —H | —H | —OMe | —H | —OMe | —H | —S(=O)$_2$iPr |
| E43 | —H | —H | —H | —OMe | —OMe | —H | —S(=O)$_2$iPr |
| E44 | —CN | —H | —H | —H | —OMe | —H | —S(=O)$_2$iPr |
| E45 | —H | —CN | —H | —H | —OMe | —H | —S(=O)$_2$iPr |
| E46 | —H | —H | —CN | —H | —OMe | —H | —S(=O)$_2$iPr |
| E47 | —H | —H | —H | —CN | —OMe | —H | —S(=O)$_2$iPr |
| E48 | —CF$_3$ | —H | —H | —H | —OMe | —H | —S(=O)$_2$iPr |
| E49 | —H | —CF$_3$ | —H | —H | —OMe | —H | —S(=O)$_2$iPr |
| E50 | —H | —H | —CF$_3$ | —H | —OMe | —H | —S(=O)$_2$iPr |
| E51 | —H | —H | —H | —CF$_3$ | —OMe | —H | —S(=O)$_2$iPr |
| E52 | —SMe | —H | —H | —H | —OMe | —H | —S(=O)$_2$iPr |
| E53 | —H | —SMe | —H | —H | —OMe | —H | —S(=O)$_2$iPr |
| E54 | —H | —H | —SMe | —H | —OMe | —H | —S(=O)$_2$iPr |
| E55 | —H | —H | —H | —SMe | —OMe | —H | —S(=O)$_2$iPr |
| E56 | —OCF$_3$ | —H | —H | —H | —OMe | —H | —S(=O)$_2$iPr |
| E57 | —H | —OCF$_3$ | —H | —H | —OMe | —H | —S(=O)$_2$iPr |
| E58 | —H | —H | —OCF$_3$ | —H | —OMe | —H | —S(=O)$_2$iPr |
| E59 | —H | —H | —H | —OCF$_3$ | —OMe | —H | —S(=O)$_2$iPr |

TABLE 65

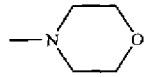

| No | —R1a' | —R1b' | —R1c' | —R1d' | —R2' | —R5' | —R4' |
|---|---|---|---|---|---|---|---|
| E60 | —H | —H | —H | —H | —OMe | —H | —S(=O)2Et |
| E61 | —H | —H | —H | —H | —OMe | —H | —S(=O)2Me |
| E62 | —H | —H | —H | —H | —OMe | —H | —S(=O)2NHMe |
| E63 | —H | —H | —H | —H | —OMe | —H | —S(=O)2NMe2 |
| E64 | —H | —H | —H | —H | —OMe | —H | —C(=O)NHMe |
| E65 | —H | —H | —H | —H | —OMe | —H | —C(=O)NMe2 |
| E66 | —H | —H | —H | —H | —OMe | —H | —C(=O)iPr |
| E67 | —H | —H | —H | —H | —OMe | —H | —C(=O)Et |
| E68 | —H | —H | —H | —H | —OMe | —H | —F |
| E69 | —H | —H | —H | —H | —OMe | —H | —Cl |
| E70 | —H | —H | —H | —H | —OMe | —H | —Br |
| E71 | —H | —H | —H | —H | —OMe | —H | —OMe |
| E72 | —H | —H | —H | —H | —OMe | —H | —OEt |
| E73 | —H | —H | —H | —H | —OMe | —H | —OiPr |
| E74 | —H | —H | —H | —H | —OMe | —H | —OCF3 |
| E75 | —H | —H | —H | —H | —OMe | —H | —SMe |
| E76 | —H | —H | —H | —H | —OMe | —H | —SEt |
| E77 | —H | —H | —H | —H | —OMe | —H | —SiPr |
| E78 | —H | —H | —H | —H | —OMe | —H | Me |
| E79 | —H | —H | —H | —H | —OMe | —H | Et |
| E80 | —H | —H | —H | —H | —OMe | —H | iPr |
| E81 | —H | —H | —H | —H | —OMe | —H | —CF3 |

TABLE 66

| No | —R1a' | —R1b' | —R1c' | —R1d' | —R2' | —R5' |
|---|---|---|---|---|---|---|
| F1 | —H | —H | —H | —H | —F | —H |
| F2 | —H | —H | —H | —H | —Cl | —H |
| F3 | —H | —H | —H | —H | —Br | —H |
| F4 | —H | —H | —H | —H | —OEt | —H |
| F5 | —H | —H | —H | —H | —OiPr | —H |
| F6 | —H | —H | —H | —H | —CF3 | —H |
| F7 | —H | —H | —H | —H | —CN | —H |
| F8 | —H | —H | —H | —H | Me | —H |
| F9 | —H | —H | —H | —H | Et | —H |
| F10 | —H | —H | —H | —H | —SMe | —H |
| F11 | —H | —H | —H | —H | —OCF3 | —H |
| F12 | —H | —H | —H | —H | —OMe | —Cl |
| F13 | —H | —H | —H | —H | —OMe | —Br |
| F14 | —H | —H | —H | —H | —OMe | Me |
| F15 | —H | —H | —H | —H | —OMe | —SMe |
| F16 | —H | —H | —H | —H | —OMe | —NMe2 |
| F17 | —H | —H | —H | —H | —OMe | —NEt2 |
| F18 | —H | —H | —H | —H | —OMe | —N(morpholine) |

TABLE 66-continued
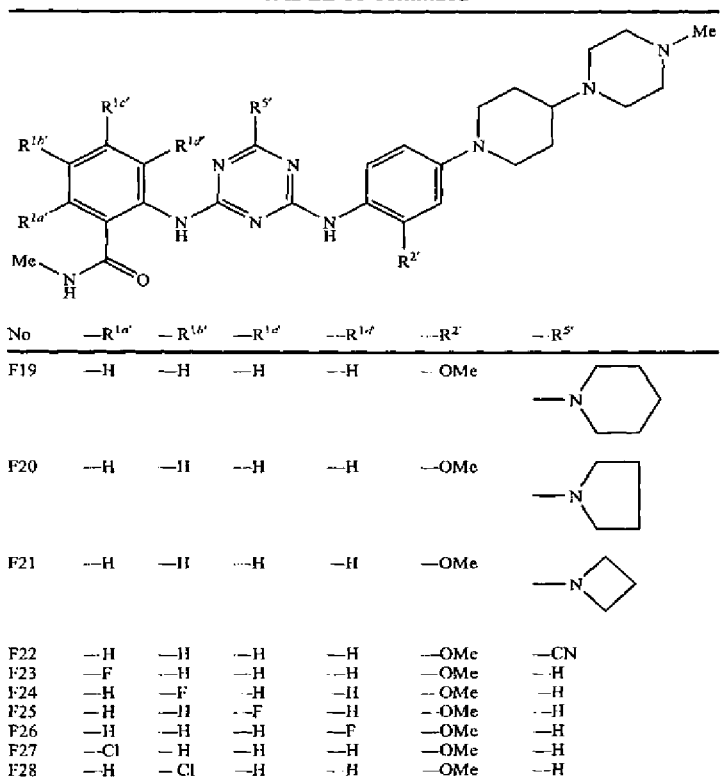
| No | —R1a' | —R1b' | —R1c' | —R1d' | —R2' | —R5' |
|---|---|---|---|---|---|---|
| F19 | —H | —H | —H | —H | —OMe | —N(piperidine) |
| F20 | —H | —H | —H | —H | —OMe | —N(pyrrolidine) |
| F21 | —H | —H | —H | —H | —OMe | —N(azetidine) |
| F22 | —H | —H | —H | —H | —OMe | —CN |
| F23 | —F | —H | —H | —H | —OMe | —H |
| F24 | —H | —F | —H | —H | —OMe | —H |
| F25 | —H | —H | —F | —H | —OMe | —H |
| F26 | —H | —H | —H | —F | —OMe | —H |
| F27 | —Cl | —H | —H | —H | —OMe | —H |
| F28 | —H | —Cl | —H | —H | —OMe | —H |
TABLE 67
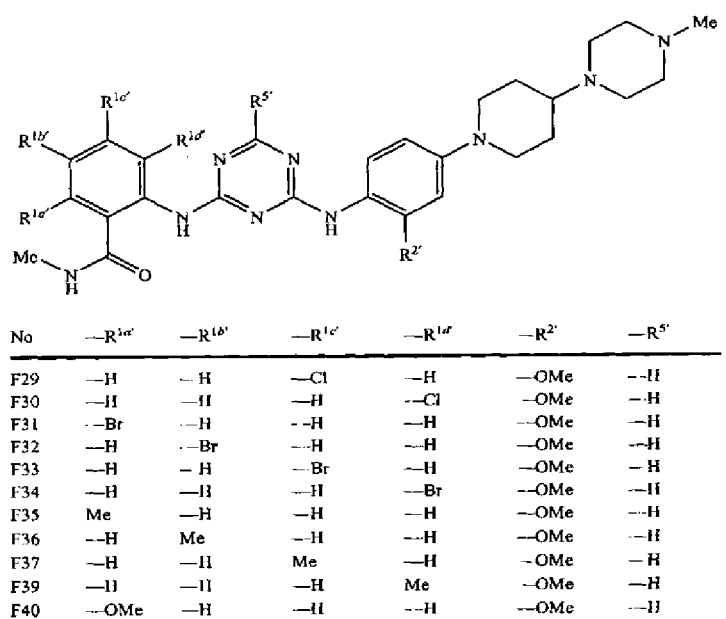
| No | —R1a' | —R1b' | —R1c' | —R1d' | —R2' | —R5' |
|---|---|---|---|---|---|---|
| F29 | —H | —H | —Cl | —H | —OMe | —H |
| F30 | —H | —H | —H | —Cl | —OMe | —H |
| F31 | —Br | —H | —H | —H | —OMe | —H |
| F32 | —H | —Br | —H | —H | —OMe | —H |
| F33 | —H | —H | —Br | —H | —OMe | —H |
| F34 | —H | —H | —H | —Br | —OMe | —H |
| F35 | Me | —H | —H | —H | —OMe | —H |
| F36 | —H | Me | —H | —H | —OMe | —H |
| F37 | —H | —H | Me | —H | —OMe | —H |
| F39 | —H | —H | —H | Me | —OMe | —H |
| F40 | —OMe | —H | —H | —H | —OMe | —H |

TABLE 67-continued

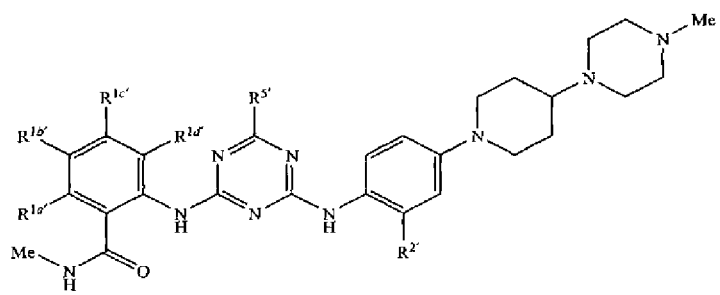

| No | —R1a' | —R1b' | —R1c' | —R1d' | —R2' | —R5' |
|---|---|---|---|---|---|---|
| F41 | —H | —OMe | —H | —H | —OMe | —H |
| F42 | —H | —H | —OMe | —H | —OMe | —H |
| F43 | —H | —H | —H | —OMe | —OMe | —H |
| F44 | —CN | —H | —H | —H | —OMe | —H |
| F45 | —H | —CN | —H | —H | —OMe | —H |
| F46 | —H | —H | —CN | —H | —OMe | —H |
| F47 | —H | —H | —H | —CN | —OMe | —H |
| F48 | —CF3 | —H | —H | —H | —OMe | —H |
| F49 | —H | —CF3 | —H | —H | —OMe | —H |
| F50 | —H | —H | —CF3 | —H | —OMe | —H |
| F51 | —H | —H | —H | —CF3 | —OMe | —H |
| F52 | —SMe | —H | —H | —H | —OMe | —H |
| F53 | —H | —SMe | —H | —H | —OMe | —H |
| F54 | —H | —H | —SMe | —H | —OMe | —H |
| F55 | —H | —H | —H | —SMe | —OMe | —H |
| F56 | —OCF3 | —H | —H | —H | —OMe | —H |
| F57 | —H | —OCF3 | —H | —H | —OMe | —H |
| F58 | —H | —H | —OCF3 | —H | —OMe | —H |
| F59 | —H | —H | —H | —OCF3 | —OMe | —H |

TABLE 68

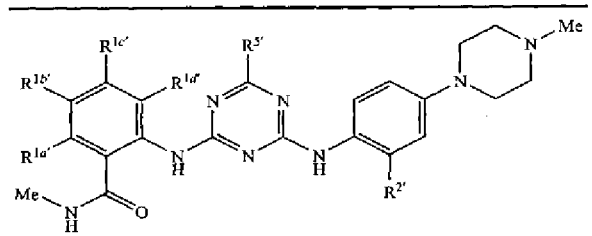

| No | —R1a' | —R1b' | —R1c' | —R1d' | —R2' | —R5' |
|---|---|---|---|---|---|---|
| G1 | —H | —H | —H | —H | —F | —H |
| G2 | —H | —H | —H | —H | —Cl | —H |
| G3 | —H | —H | —H | —H | —Br | —H |
| G4 | —H | —H | —H | —H | —OEt | —H |
| G5 | —H | —H | —H | —H | —OiPr | —H |
| G6 | —H | —H | —H | —H | —CF3 | —H |
| G7 | —H | —H | —H | —H | —CN | —H |
| G8 | —H | —H | —H | —H | Me | —H |
| G9 | —H | —H | —H | —H | Et | —H |
| G10 | —H | —H | —H | —H | —SMe | —H |
| G11 | —H | —H | —H | —H | —OCF3 | —H |
| G12 | —H | —H | —H | —H | —OMe | —Cl |
| G13 | —H | —H | —H | —H | —OMe | —Br |
| G14 | —H | —H | —H | —H | —OMe | Me |
| G15 | —H | —H | —H | —H | —OMe | —SMe |
| G16 | —H | —H | —H | —H | —OMe | —NMe2 |
| G17 | —H | —H | —H | —H | —OMe | —NEt2 |
| G18 | —H | —H | —H | —H | —OMe | —N(morpholine) |

TABLE 68-continued

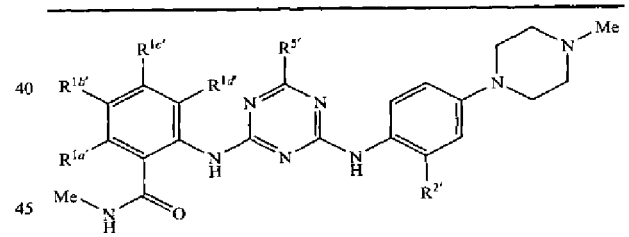

| No | —R1a' | —R1b' | —R1c' | —R1d' | —R2' | —R5' |
|---|---|---|---|---|---|---|
| G19 | —H | —H | —H | —H | —OMe | —N(piperidine) |
| G20 | —H | —H | —H | —H | —OMe | —N(pyrrolidine) |
| G21 | —H | —H | —H | —H | —OMe | —N(azetidine) |
| G22 | —H | —H | —H | —H | —OMe | —CN |
| G23 | —F | —H | —H | —H | —OMe | —H |
| G24 | —H | —F | —H | —H | —OMe | —H |
| G25 | —H | —H | —F | —H | —OMe | —H |
| G26 | —H | —H | —H | —F | —OMe | —H |

TABLE 69

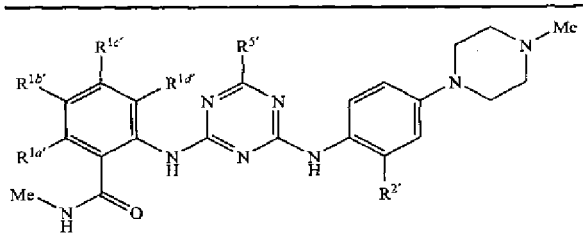

| No | —R¹ᵃ' | —R¹ᵇ' | —R¹ᶜ' | —R¹ᵈ' | —R²' | —R⁵' |
|---|---|---|---|---|---|---|
| G27 | —Cl | —H | —H | —H | —OMe | —H |
| G28 | —H | —Cl | —H | —H | —OMe | —H |
| G29 | —H | —H | —Cl | —H | —OMe | —H |
| G30 | —H | —H | —H | —Cl | —OMe | —H |
| G31 | —Br | —H | —H | —H | —OMe | —H |
| G32 | —H | —Br | —H | —H | —OMe | —H |
| G33 | —H | —H | —Br | —H | —OMe | —H |
| G34 | —H | —H | —H | —Br | —OMe | —H |
| G35 | Me | —H | —H | —H | —OMe | —H |
| G36 | —H | Me | —H | —H | —OMe | —H |
| G37 | —H | —H | Me | —H | —OMe | —H |
| G39 | —H | —H | —H | Me | —OMe | —H |
| G40 | —OMe | —H | —H | —H | —OMe | —H |
| G41 | —H | —OMe | —H | —H | —OMe | —H |
| G42 | —H | —H | —OMe | —H | —OMe | —H |
| G43 | —H | —H | —H | —OMe | —OMe | —H |
| G44 | —CN | —H | —H | —H | —OMe | —H |
| G45 | —H | —CN | —H | —H | —OMe | —H |
| G46 | —H | —H | —CN | —H | —OMe | —H |
| G47 | —H | —H | —H | —CN | —OMe | —H |
| G48 | —CF₃ | —H | —H | —H | —OMe | —H |
| G49 | —H | —CF₃ | —H | —H | —OMe | —H |
| G50 | —H | —H | —CF₃ | —H | —OMe | —H |
| G51 | —H | —H | —H | —CF₃ | —OMe | —H |
| G52 | —SMe | —H | —H | —H | —OMe | —H |
| G53 | —H | —SMe | —H | —H | —OMe | —H |
| G54 | —H | —H | —SMe | —H | —OMe | —H |
| G55 | —H | —H | —H | —SMe | —OMe | —H |
| G56 | —OCF₃ | —H | —H | —H | —OMe | —H |
| G57 | —H | —OCF₃ | —H | —H | —OMe | —H |
| G58 | —H | —H | —OCF₃ | —H | —OMe | —H |
| G59 | —H | —H | —H | —OCF₃ | —OMe | —H |

TABLE 70

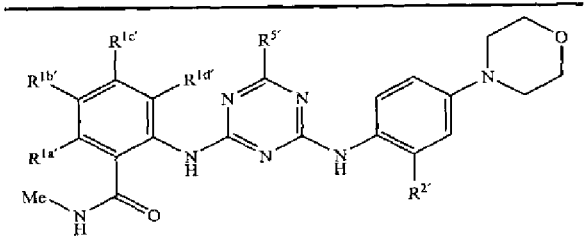

| No | —R¹ᵃ' | —R¹ᵇ' | —R¹ᶜ' | —R¹ᵈ' | —R²' | —R⁵' |
|---|---|---|---|---|---|---|
| H1 | —H | —H | —H | —H | —F | —H |
| H2 | —H | —H | —H | —H | —Cl | —H |
| H3 | —H | —H | —H | —H | —Br | —H |
| H4 | —H | —H | —H | —H | —OEt | —H |
| H5 | —H | —H | —H | —H | —OiPr | —H |
| H6 | —H | —H | —H | —H | —CF₃ | —H |
| H7 | —H | —H | —H | —H | —CN | —H |
| H8 | —H | —H | —H | —H | Me | —H |
| H9 | —H | —H | —H | —H | Et | —H |
| H10 | —H | —H | —H | —H | —SMe | —H |
| H11 | —H | —H | —H | —H | —OCF₃ | —H |
| H12 | —H | —H | —H | —H | —OMe | —Cl |
| H13 | —H | —H | —H | —H | —OMe | —Br |
| H14 | —H | —H | —H | —H | —OMe | Me |

TABLE 70-continued

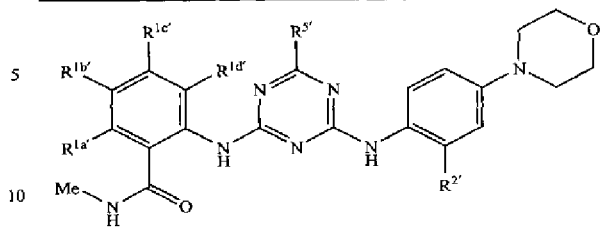

| No | —R¹ᵃ' | —R¹ᵇ' | —R¹ᶜ' | —R¹ᵈ' | —R²' | —R⁵' |
|---|---|---|---|---|---|---|
| H15 | —H | —H | —H | —H | —OMe | —SMe |
| H16 | —H | —H | —H | —H | —OMe | —NMe₂ |
| H17 | —H | —H | —H | —H | —OMe | —NEt₂ |
| H18 | —H | —H | —H | —H | —OMe | 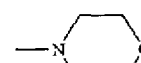 |
| H19 | —H | —H | —H | —H | —OMe | 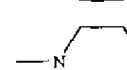 |
| H20 | —H | —H | —H | —H | —OMe | 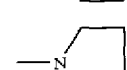 |
| H21 | —H | —H | —H | —H | —OMe | 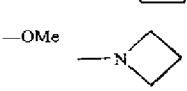 |
| H22 | —H | —H | —H | —H | —OMe | —CN |
| H23 | —F | —H | —H | —H | —OMe | —H |
| H24 | —H | —F | —H | —H | —OMe | —H |
| H25 | —H | —H | —F | —H | —OMe | —H |
| H26 | —H | —H | —H | —F | —OMe | —H |

TABLE 71

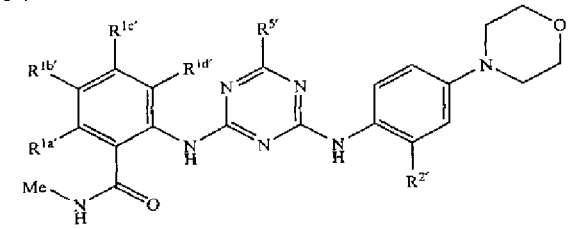

| No | —R¹ᵃ' | —R¹ᵇ' | —R¹ᶜ' | —R¹ᵈ' | —R²' | —R⁵' |
|---|---|---|---|---|---|---|
| H27 | —Cl | —H | —H | —H | —OMe | —H |
| H28 | —H | —Cl | —H | —H | —OMe | —H |
| H29 | —H | —H | —Cl | —H | —OMe | —H |
| H30 | —H | —H | —H | —Cl | —OMe | —H |
| H31 | —Br | —H | —H | —H | —OMe | —H |
| H32 | —H | —Br | —H | —H | —OMe | —H |
| H33 | —H | —H | —Br | —H | —OMe | —H |
| H34 | —H | —H | —H | —Br | —OMe | —H |
| H35 | Me | —H | —H | —H | —OMe | —H |
| H36 | —H | Me | —H | —H | —OMe | —H |
| H37 | —H | —H | Me | —H | —OMe | —H |
| H39 | —H | —H | —H | Me | —OMe | —H |
| H40 | —OMe | —H | —H | —H | —OMe | —H |
| H41 | —H | —OMe | —H | —H | —OMe | —H |
| H42 | —H | —H | —OMe | —H | —OMe | —H |
| H43 | —H | —H | —H | —OMe | —OMe | —H |
| H44 | —CN | —H | —H | —H | —OMe | —H |
| H45 | —H | —CN | —H | —H | —OMe | —H |

TABLE 71-continued
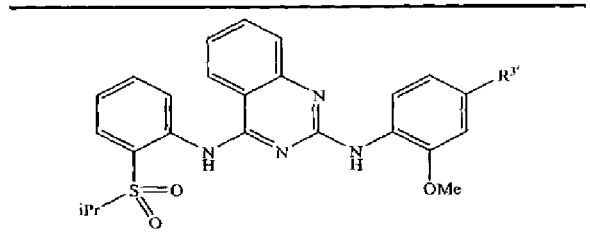
| No | —R¹ᵃ' | —R¹ᵇ' | —R¹ᶜ' | —R¹ᵈ' | —R²' | —R⁵' |
|---|---|---|---|---|---|---|
| H46 | —H | —H | —CN | —H | —OMe | —H |
| H47 | —H | —H | —H | —CN | —OMe | —H |
| H48 | —CF₃ | —H | —H | —H | —OMe | —H |
| H49 | —H | —CF₃ | —H | —H | —OMe | —H |
| H50 | —H | —H | —CF₃ | —H | —OMe | —H |
| H51 | —H | —H | —H | —CF₃ | —OMe | —H |
| H52 | —SMe | —H | —H | —H | —OMe | —H |
| H53 | —H | —SMe | —H | —H | —OMe | —H |
| H54 | —H | —H | —SMe | —H | —OMe | —H |
| H55 | —H | —H | —H | —SMe | —OMe | —H |
| H56 | —OCF₃ | —H | —H | —H | —OMe | —H |
| H57 | —H | —OCF₃ | —H | —H | —OMe | —H |
| H58 | —H | —H | —OCF₃ | —H | —OMe | —H |
| H59 | —H | —H | —H | —OCF₃ | —OMe | —H |
TABLE 72
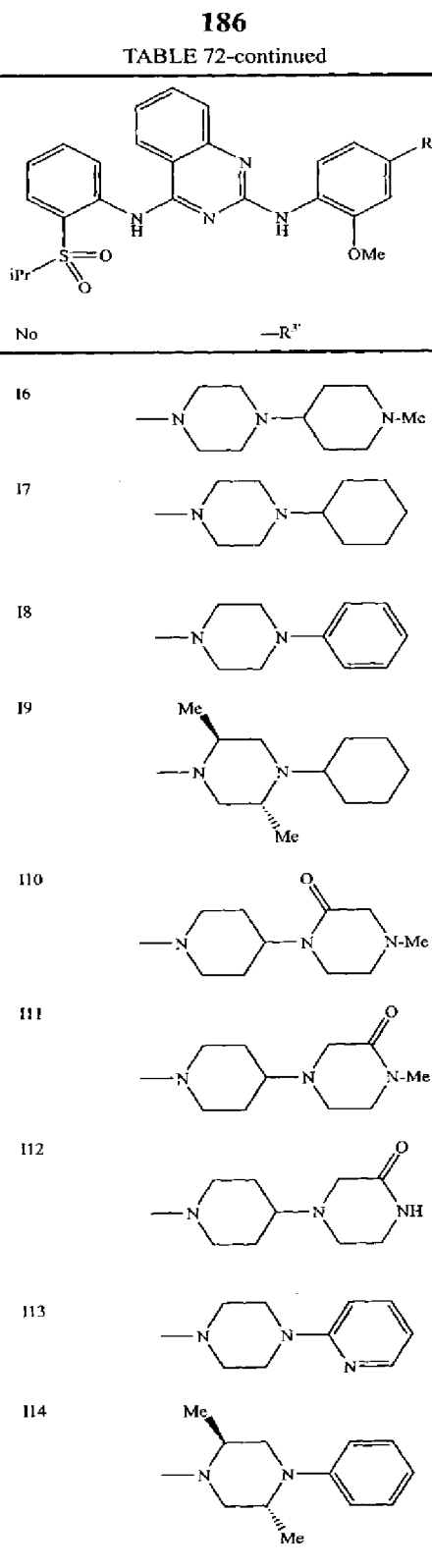

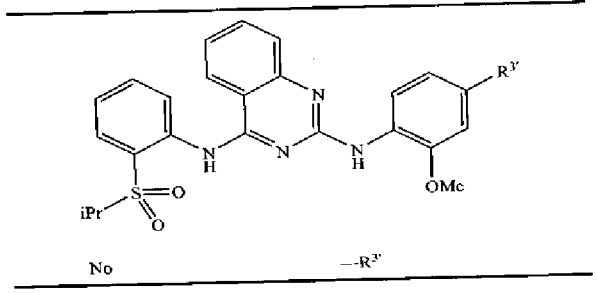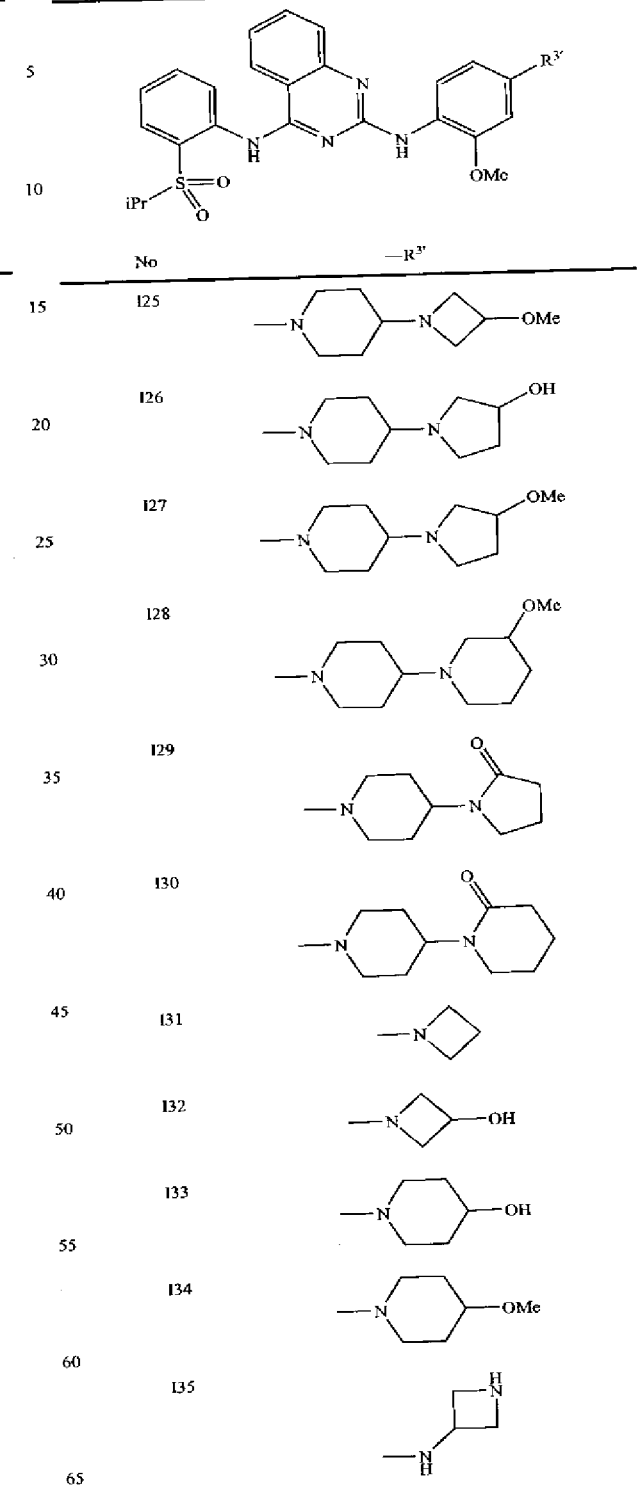

TABLE 73-continued
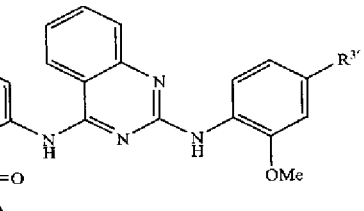
| No | —R³' |
|---|---|
| 136 | 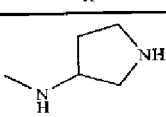 |
| 137 | 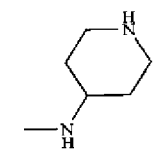 |
| 138 | 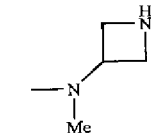 |
| 139 | 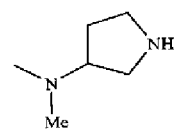 |
| 140 | 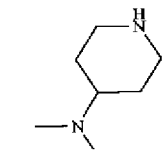 |
| 141 | 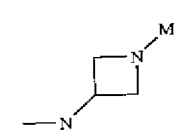 |
| 142 | 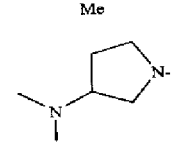 |
| 143 | 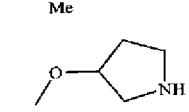 |
| 144 | 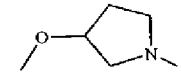 |
TABLE 73-continued
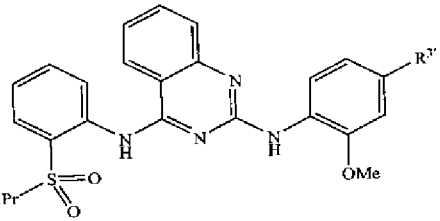
| No | —R³' |
|---|---|
| 145 | 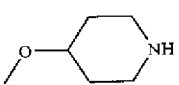 |
| 146 | 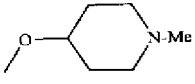 |
| 147 | 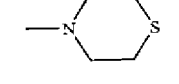 |
| 148 | 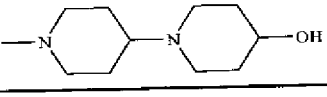 |
TABLE 74
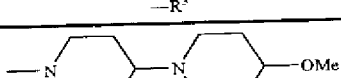
| No | —R³' |
|---|---|
| 149 |  |
| 150 | 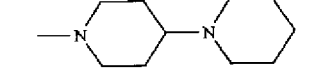 |
| 151 | 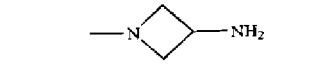 |
| 152 |  |
| 153 | 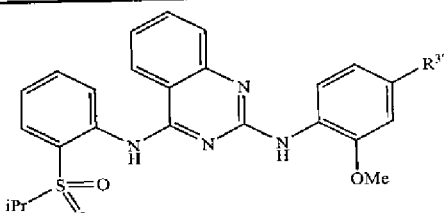 |

TABLE 74-continued
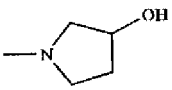
| No | —R³' |
|---|---|
| 154 | 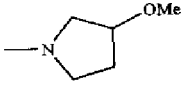 |
| 155 |  |
| 156 | 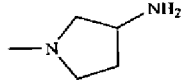 |
| 157 |  |
| 158 | 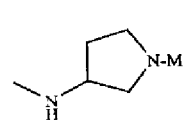 |
| 159 | 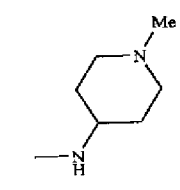 |
| 160 | 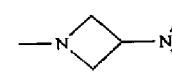 |
| 161 | 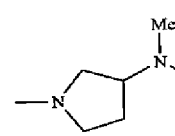 |
| 162 | 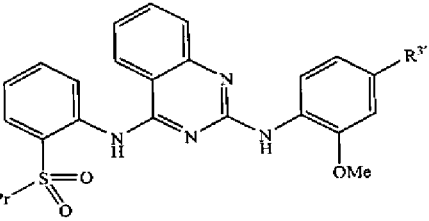 |
TABLE 74-continued
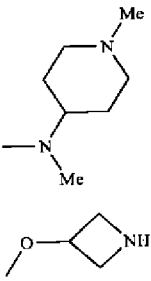
| No | —R³' |
|---|---|
| 163 | 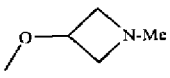 |
| 164 | 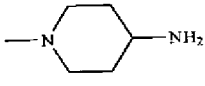 |
| 165 | 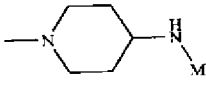 |
| 166 | 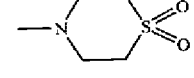 |
| 167 |  |
| 168 | 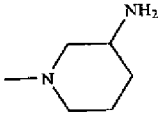 |
| 169 |  |
| 170 | 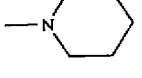 |
| 171 | |
| 172 | |

TABLE 75
| No | —R⁴' |
|---|---|
| J1 | 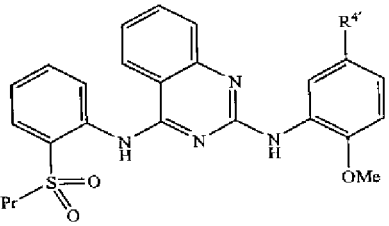 |
| J2 | 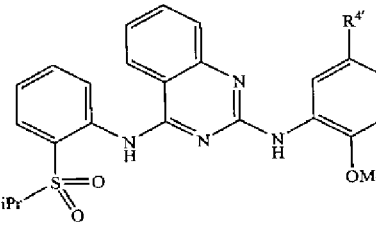 |
| J3 | 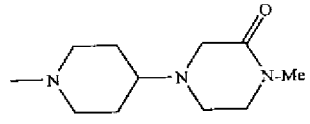 |
| J4 | 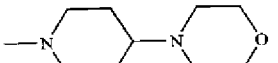 |
| J5 | 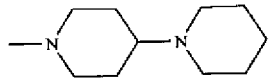 |
| J6 |  |
| J7 | 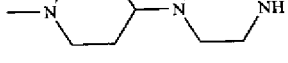 |
| J8 | 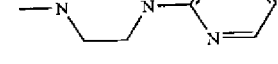 |
| J9 | 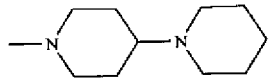 |
| J10 | 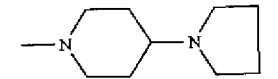 |
TABLE 75-continued
| No | —R⁴' |
|---|---|
| J11 | 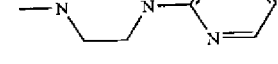 |
| J12 | 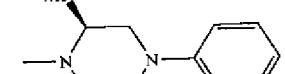 |
| J13 | 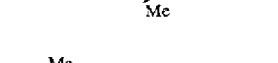 |
| J14 | 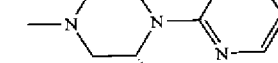 |
| J15 | 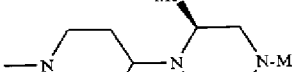 |
| J16 |  |
| J17 |  |
| J18 | 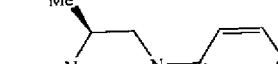 |
| J19 | 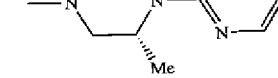 |

TABLE 75-continued
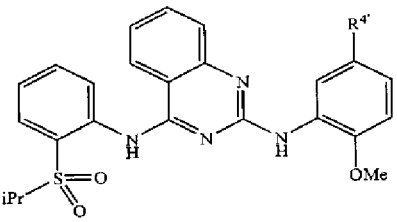
| No | —R4' |
|---|---|
| J20 | 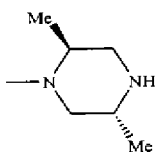 |
| J21 | 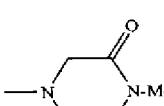 |
| J22 | 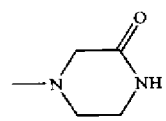 |
| J23 | 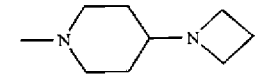 |
| J24 | 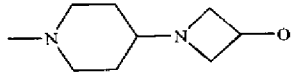 |
TABLE 76
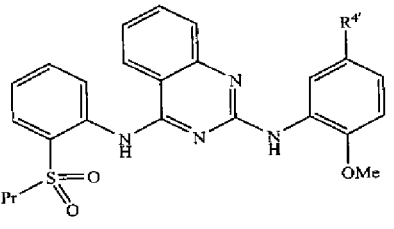
| No | —R4' |
|---|---|
| J25 | 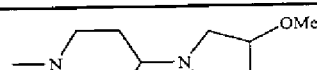 |
| J26 | 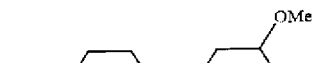 |
TABLE 76-continued
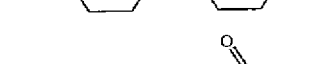
| No | —R4' |
|---|---|
| J27 | 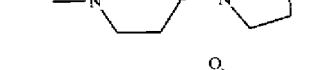 |
| J28 |  |
| J29 |  |
| J30 | 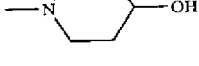 |
| J31 | —N⬜ |
| J32 | 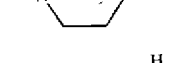 |
| J33 | 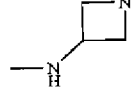 |
| J34 | 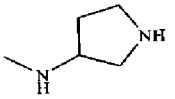 |
| J35 | 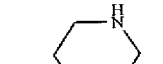 |
| J36 | |
| J37 | |

TABLE 76-continued

| No | —R4' |
|---|---|
| J38 | azetidine-N(Me)- with NH |
| J39 | pyrrolidine-N(Me)- with NH |
| J40 | piperidine-N(Me)- with NH |
| J41 | azetidine(N-Me)-N(Me)- |
| J42 | pyrrolidine(N-Me)-N(Me)- |
| J43 | 3-methoxypyrrolidine-NH |
| J44 | 3-methoxy-N-Me-pyrrolidine |
| J45 | 4-methoxypiperidine-NH |
| J46 | 4-methoxy-N-Me-piperidine |
| J47 | 4-methoxytetrahydrothiopyran |

TABLE 76-continued

| No | —R4' |
|---|---|
| J48 | N-Me-piperidinyl-piperidin-4-ol |

TABLE 77

| No | —R4' |
|---|---|
| J49 | N-Me-piperidinyl-piperidine-OMe |
| J50 | N-Me-piperidinyl-piperidin-3-ol |
| J51 | N-azetidinyl-NH2 |
| J52 | N-pyrrolidinyl-NHMe |
| J53 | N-azetidinyl-OMe |
| J54 | N-pyrrolidinyl-OH |
| J55 | N-pyrrolidinyl-OMe |
| J56 | N-azetidinyl-NHMe |

TABLE 77-continued
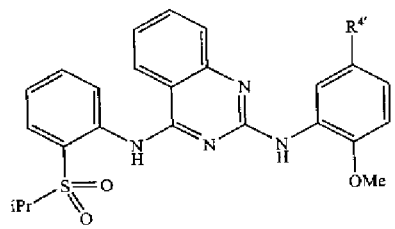
| No | —R⁴' |
|---|---|
| J57 | 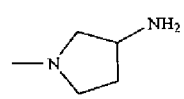 |
| J58 | 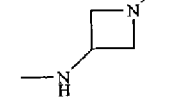 |
| J59 | 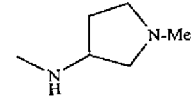 |
| J60 | 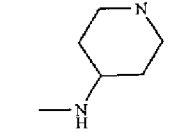 |
| J61 | 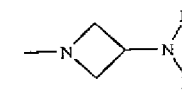 |
| J62 | 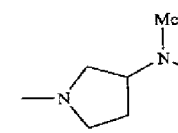 |
| J63 | 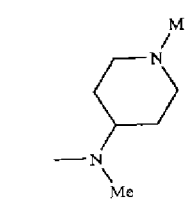 |
TABLE 77-continued
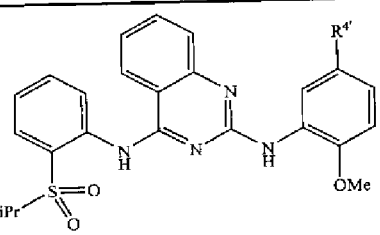
| No | —R⁴' |
|---|---|
| J64 |  |
| J65 | 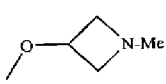 |
| J66 | 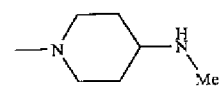 |
| J67 |  |
| J68 | 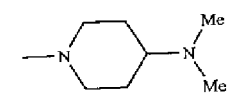 |
| J69 | |
| J70 | 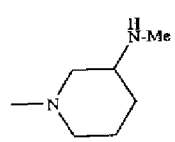 |
| J71 | |
| J72 |  |

TABLE 78

| No | —R$^{1a'}$ | —R$^{1b'}$ | —R$^{1c'}$ | —R$^{1d'}$ | —R$^{2'}$ | —R$^{4'}$ |
|---|---|---|---|---|---|---|
| K1 | —H | —H | —H | —H | —F | —S(=O)$_2$iPr |
| K2 | —H | —H | —H | —H | —Cl | —S(=O)$_2$iPr |
| K3 | —H | —H | —H | —H | —Br | —S(=O)$_2$iPr |
| K4 | —H | —H | —H | —H | —OEt | —S(=O)$_2$iPr |
| K5 | —H | —H | —H | —H | —OiPr | —S(=O)$_2$iPr |
| K6 | —H | —H | —H | —H | —CF$_3$ | —S(=O)$_2$iPr |
| K7 | —H | —H | —H | —H | —CN | —S(=O)$_2$iPr |
| K8 | —H | —H | —H | —H | Me | —S(=O)$_2$iPr |
| K9 | —H | —H | —H | —H | Et | —S(=O)$_2$iPr |
| K10 | —H | —H | —H | —H | —SMe | —S(=O)$_2$iPr |
| K11 | —H | —H | —H | —H | —OCF$_3$ | —S(=O)$_2$iPr |
| K12 | —F | —H | —H | —H | —OMe | —S(=O)$_2$iPr |
| K13 | —H | —F | —H | —H | —OMe | —S(=O)$_2$iPr |
| K14 | —H | —H | —F | —H | —OMe | —S(=O)$_2$iPr |
| K15 | —H | —H | —H | —F | —OMe | —S(=O)$_2$iPr |
| K16 | —Cl | —H | —H | —H | —OMe | —S(=O)$_2$iPr |
| K17 | —H | —Cl | —H | —H | —OMe | —S(=O)$_2$iPr |
| K18 | —H | —H | —Cl | —H | —OMe | —S(=O)$_2$iPr |
| K19 | —H | —H | —H | —Cl | —OMe | —S(=O)$_2$iPr |
| K20 | —Br | —H | —H | —H | —OMe | —S(=O)$_2$iPr |
| K21 | —H | —Br | —H | —H | —OMe | —S(=O)$_2$iPr |
| K22 | —H | —H | —Br | —H | —OMe | —S(=O)$_2$iPr |
| K23 | —H | —H | —H | —Br | —OMe | —S(=O)$_2$iPr |
| K24 | Me | —H | —H | —H | —OMe | —S(=O)$_2$iPr |
| K25 | —H | Me | —H | —H | —OMe | —S(=O)$_2$iPr |
| K26 | —H | —H | Me | —H | —OMe | —S(=O)$_2$iPr |
| K27 | —H | —H | —H | Me | —OMe | —S(=O)$_2$iPr |
| K28 | —OMe | —H | —H | —H | —OMe | —S(=O)$_2$iPr |
| K29 | —H | —OMe | —H | —H | —OMe | —S(=O)$_2$iPr |
| K30 | —H | —H | —OMe | —H | —OMe | —S(=O)$_2$iPr |
| K31 | —H | —H | —H | —OMe | —OMe | —S(=O)$_2$iPr |
| K32 | —CN | —H | —H | —H | —OMe | —S(=O)2iPr |
| K33 | —H | —CN | —H | —H | —OMe | —S(=O)2iPr |
| K34 | —H | —H | —CN | —H | —OMe | —S(=O)2iPr |
| K35 | —H | —H | —H | —CN | —OMe | —S(=O)2iPr |

TABLE 79

| No | —R$^{1a'}$ | —R$^{1b'}$ | —R$^{1c'}$ | —R$^{1d'}$ | —R$^{2'}$ | —R$^{4'}$ |
|---|---|---|---|---|---|---|
| K36 | —CF$_3$ | —H | —H | —H | —OMe | —S(=O)$_2$iPr |
| K37 | —H | —CF$_3$ | —H | —H | —OMe | —S(=O)$_2$iPr |
| K38 | —H | —H | —CF$_3$ | —H | —OMe | —S(=O)$_2$iPr |
| K39 | —H | —H | —H | —CF$_3$ | —OMe | —S(=O)$_2$iPr |
| K40 | —SMe | —H | —H | —H | —OMe | —S(=O)$_2$iPr |
| K41 | —H | —SMe | —H | —H | —OMe | —S(=O)$_2$iPr |
| K42 | —H | —H | —SMe | —H | —OMe | —S(=O)$_2$iPr |

TABLE 79-continued

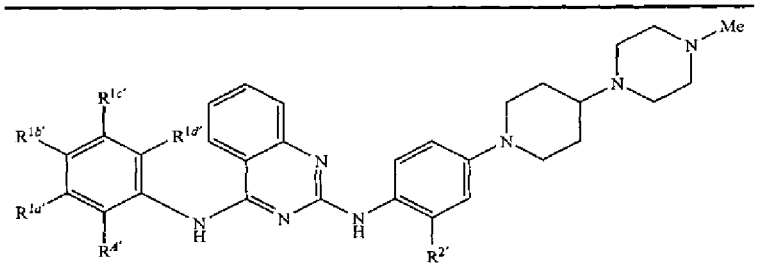

| No | —R^{1a'} | —R^{1b'} | —R^{1c'} | —R^{1d'} | —R^{2'} | —R^{4'} |
|---|---|---|---|---|---|---|
| K43 | —H | —H | —H | —SMe | —OMe | —S(=O)₂iPr |
| K44 | —OCF₃ | —H | —H | —H | —OMe | —S(=O)₂iPr |
| K45 | —H | —OCF₃ | —H | —H | —OMe | —S(=O)₂iPr |
| K46 | —H | —H | —OCF₃ | —H | —OMe | —S(=O)₂iPr |
| K47 | —H | —H | —H | —OCF₃ | —OMe | —S(=O)₂iPr |
| K48 | —H | —H | —H | —H | —OMe | —S(=O)₂Et |
| K49 | —H | —H | —H | —H | —OMe | —S(=O)₂Me |
| K50 | —H | —H | —H | —H | —OMe | —S(=O)₂NHMe |
| K51 | —H | —H | —H | —H | —OMe | —S(=O)₂NMe₂ |
| K52 | —H | —H | —H | —H | —OMe | —C(=O)NHMe |
| K53 | —H | —H | —H | —H | —OMe | —C(=O)NMe₂ |
| K54 | —H | —H | —H | —H | —OMe | —C(=O)iPr |
| K55 | —H | —H | —H | —H | —OMe | —C(=O)Et |
| K56 | —H | —H | —H | —H | —OMe | —F |
| K57 | —H | —H | —H | —H | —OMe | —Cl |
| K58 | —H | —H | —H | —H | —OMe | —Br |
| K59 | —H | —H | —H | —H | —OMe | —OMe |
| K60 | —H | —H | —H | —H | —OMe | —OEt |
| K61 | —H | —H | —H | —H | —OMe | —OiPr |
| K62 | —H | —H | —H | —H | —OMe | —OCF₃ |
| K63 | —H | —H | —H | —H | —OMe | —SMe |
| K64 | —H | —H | —H | —H | —OMe | —SEt |
| K65 | —H | —H | —H | —H | —OMe | —SiPr |
| K66 | —H | —H | —H | —H | —OMe | Me |
| K67 | —H | —H | —H | —H | —OMe | Et |
| K68 | —H | —H | —H | —H | —OMe | iPr |
| K69 | —H | —H | —H | —H | —OMe | —CF₃ |

TABLE 80

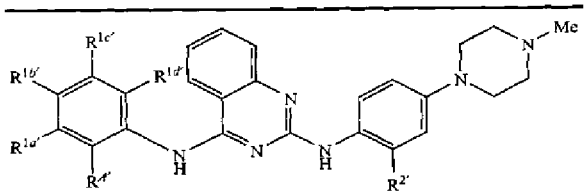
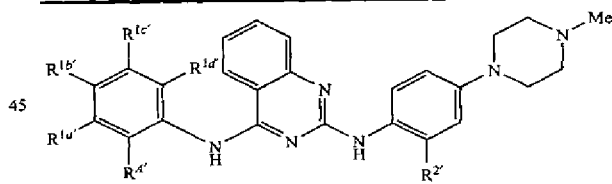

| No | —R^{1a'} | —R^{1b'} | —R^{1c'} | —R^{1d'} | —R^{2'} | —R^{4'} |
|---|---|---|---|---|---|---|
| L1 | —H | —H | —H | —H | —F | —S(=O)₂iPr |
| L2 | —H | —H | —H | —H | —Cl | —S(=O)₂iPr |
| L3 | —H | —H | —H | —H | —Br | —S(=O)₂iPr |
| L4 | —H | —H | —H | —H | —OEt | —S(=O)₂iPr |
| L5 | —H | —H | —H | —H | —OiPr | —S(=O)₂iPr |
| L6 | —H | —H | —H | —H | —CF₃ | —S(=O)₂iPr |
| L7 | —H | —H | —H | —H | —CN | —S(=O)₂iPr |
| L8 | —H | —H | —H | —H | Me | —S(=O)₂iPr |
| L9 | —H | —H | —H | —H | Et | —S(=O)₂iPr |
| L10 | —H | —H | —H | —H | —SMe | —S(=O)₂iPr |
| L11 | —H | —H | —H | —H | —OCF₃ | —S(=O)₂iPr |
| L12 | —F | —H | —H | —H | —OMe | —S(=O)₂iPr |
| L13 | —H | —F | —H | —H | —OMe | —S(=O)₂iPr |
| L14 | —H | —H | —F | —H | —OMe | —S(=O)₂iPr |
| L15 | —H | —H | —H | —F | —OMe | —S(=O)₂iPr |
| L16 | —Cl | —H | —H | —H | —OMe | —S(=O)₂iPr |
| L17 | —H | —Cl | —H | —H | —OMe | —S(=O)₂iPr |
| L18 | —H | —H | —Cl | —H | —OMe | —S(=O)₂iPr |
| L19 | —H | —H | —H | —Cl | —OMe | —S(=O)₂iPr |
| L20 | —Br | —H | —H | —H | —OMe | —S(=O)₂iPr |
| L21 | —H | —Br | —H | —H | —OMe | —S(=O)₂iPr |
| L22 | —H | —H | —Br | —H | —OMe | —S(=O)₂iPr |
| L23 | —H | —H | —H | —Br | —OMe | —S(=O)₂iPr |
| L24 | Me | —H | —H | —H | —OMe | —S(=O)₂iPr |
| L25 | —H | Me | —H | —H | —OMe | —S(=O)₂iPr |
| L26 | —H | —H | Me | —H | —OMe | —S(=O)₂iPr |
| L27 | —H | —H | —H | Me | —OMe | —S(=O)₂iPr |
| L28 | —OMe | —H | —H | —H | —OMe | —S(=O)₂iPr |
| L29 | —H | —OMe | —H | —H | —OMe | —S(=O)₂iPr |
| L30 | —H | —H | —OMe | —H | —OMe | —S(=O)₂iPr |
| L31 | —H | —H | —H | —OMe | —OMe | —S(=O)₂iPr |
| L32 | —CN | —H | —H | —H | —OMe | —S(=O)₂iPr |
| L33 | —H | —CN | —H | —H | —OMe | —S(=O)₂iPr |
| L34 | —H | —H | —CN | —H | —OMe | —S(=O)₂iPr |
| L35 | —H | —H | —H | —CN | —OMe | —S(=O)₂iPr |

TABLE 81

| No | −R1a′ | −R1b′ | −R1c′ | −R1d′ | −R2′ | −R4′ |
|---|---|---|---|---|---|---|
| L36 | −CF3 | −H | −H | −H | −OMe | −S(=O)2iPr |
| L37 | −H | −CF3 | −H | −H | −OMe | −S(=O)2iPr |
| L38 | −H | −H | −CF3 | −H | −OMe | −S(=O)2iPr |
| L39 | −H | −H | −H | −CF3 | −OMe | −S(=O)2iPr |
| L40 | −SMe | −H | −H | −H | −OMe | −S(=O)2iPr |
| L41 | −H | −SMe | −H | −H | −OMe | −S(=O)2iPr |
| L42 | −H | −H | −SMe | −H | −OMe | −S(=O)2iPr |
| L43 | −H | −H | −H | −SMe | −OMe | −S(=O)2iPr |
| L44 | −OCF3 | −H | −H | −H | −OMe | −S(=O)2iPr |
| L45 | −H | −OCF3 | −H | −H | −OMe | −S(=O)2iPr |
| L46 | −H | −H | −OCF3 | −H | −OMe | −S(=O)2iPr |
| L47 | −H | −H | −H | −OCF3 | −OMe | −S(=O)2iPr |
| L48 | −H | −H | −H | −H | −OMe | −S(=O)2Et |
| L49 | −H | −H | −H | −H | −OMe | −S(=O)2Me |
| L50 | −H | −H | −H | −H | −OMe | −S(=O)2NHMe |
| L51 | −H | −H | −H | −H | −OMe | −S(=O)2NMe2 |
| L52 | −H | −H | −H | −H | −OMe | −C(=O)NHMe |
| L53 | −H | −H | −H | −H | −OMe | −C(=O)NMe2 |
| L54 | −H | −H | −H | −H | −OMe | −C(=O)iPr |
| L55 | −H | −H | −H | −H | −OMe | −C(=O)Et |
| L56 | −H | −H | −H | −H | −OMe | −F |
| L57 | −H | −H | −H | −H | −OMe | −Cl |
| L58 | −H | −H | −H | −H | −OMe | −Br |
| L59 | −H | −H | −H | −H | −OMe | −OMe |
| L60 | −H | −H | −H | −H | −OMe | −OEt |
| L61 | −H | −H | −H | −H | −OMe | −OiPr |
| L62 | −H | −H | −H | −H | −OMe | −OCF3 |
| L63 | −H | −H | −H | −H | −OMe | −SMe |
| L64 | −H | −H | −H | −H | −OMe | −SEt |
| L65 | −H | −H | −H | −H | −OMe | −SiPr |
| L66 | −H | −H | −H | −H | −OMe | Me |
| L67 | −H | −H | −H | −H | −OMe | Et |
| L68 | −H | −H | −H | −H | −OMe | iPr |
| L69 | −H | −H | −H | −H | −OMe | −CF3 |

TABLE 82

| No | −R1a′ | −R1b′ | −R1c′ | −R1d′ | −R2′ | −R4′ |
|---|---|---|---|---|---|---|
| M1 | −H | −H | −H | −H | −F | −S(=O)2iPr |
| M2 | −H | −H | −H | −H | −Cl | −S(=O)2iPr |
| M3 | −H | −H | −H | −H | −Br | −S(=O)2iPr |
| M4 | −H | −H | −H | −H | −OEt | −S(=O)2iPr |
| M5 | −H | −H | −H | −H | −OiPr | −S(=O)2iPr |
| M6 | −H | −H | −H | −H | −CF3 | −S(=O)2iPr |
| M7 | −H | −H | −H | −H | −CN | −S(=O)2iPr |
| M8 | −H | −H | −H | −H | Me | −S(=O)2iPr |
| M9 | −H | −H | −H | −H | Et | −S(=O)2iPr |
| M10 | −H | −H | −H | −H | −SMe | −S(=O)2iPr |
| M11 | −H | −H | −H | −H | −OCF3 | −S(=O)2iPr |
| M12 | −F | −H | −H | −H | −OMe | −S(=O)2iPr |
| M13 | −H | −F | −H | −H | −OMe | −S(=O)2iPr |
| M14 | −H | −H | −F | −H | −OMe | −S(=O)2iPr |
| M15 | −H | −H | −H | −F | −OMe | −S(=O)2iPr |
| M16 | −Cl | −H | −H | −H | −OMe | −S(=O)2iPr |
| M17 | −H | −Cl | −H | −H | −OMe | −S(=O)2iPr |
| M18 | −H | −H | −Cl | −H | −OMe | −S(=O)2iPr |
| M19 | −H | −H | −H | −Cl | −OMe | −S(=O)2iPr |
| M20 | −Br | −H | −H | −H | −OMe | −S(=O)2iPr |
| M21 | −H | −Br | −H | −H | −OMe | −S(=O)2iPr |
| M22 | −H | −H | −Br | −H | −OMe | −S(=O)2iPr |
| M23 | −H | −H | −H | −Br | −OMe | −S(=O)2iPr |
| M24 | Me | −H | −H | −H | −OMe | −S(=O)2iPr |
| M25 | −H | Me | −H | −H | −OMe | −S(=O)2iPr |
| M26 | −H | −H | Me | −H | −OMe | −S(=O)2iPr |
| M27 | −H | −H | −H | Me | −OMe | −S(=O)2iPr |
| M28 | −OMe | −H | −H | −H | −OMe | −S(=O)2iPr |
| M29 | −H | −OMe | −H | −H | −OMe | −S(=O)2iPr |
| M30 | −H | −H | −OMe | −H | −OMe | −S(=O)2iPr |
| M31 | −H | −H | −H | −OMe | −OMe | −S(=O)2iPr |
| M32 | −CN | −H | −H | −H | −OMe | −S(=O)2iPr |
| M33 | −H | −CN | −H | −H | −OMe | −S(=O)2iPr |
| M34 | −H | −H | −CN | −H | −OMe | −S(=O)2iPr |
| M35 | −H | −H | −H | −CN | −OMe | −S(=O)2iPr |

TABLE 83

| No | −R1a′ | −R1b′ | −R1c′ | −R1d′ | −R2′ | −R4′ |
|---|---|---|---|---|---|---|
| M36 | −CF3 | −H | −H | −H | −OMe | −S(=O)2iPr |
| M37 | −H | −CF3 | −H | −H | −OMe | −S(=O)2iPr |
| M38 | −H | −H | −CF3 | −H | −OMe | −S(=O)2iPr |
| M39 | −H | −H | −H | −CF3 | −OMe | −S(=O)2iPr |
| M40 | −SMe | −H | −H | −H | −OMe | −S(=O)2iPr |
| M41 | −H | −SMe | −H | −H | −OMe | −S(=O)2iPr |
| M42 | −H | −H | −SMe | −H | −OMe | −S(=O)2iPr |
| M43 | −H | −H | −H | −SMe | −OMe | −S(=O)2iPr |
| M44 | −OCF3 | −H | −H | −H | −OMe | −S(=O)2iPr |
| M45 | −H | −OCF3 | −H | −H | −OMe | −S(=O)2iPr |
| M46 | −H | −H | −OCF3 | −H | −OMe | −S(=O)2iPr |
| M47 | −H | −H | −H | −OCF3 | −OMe | −S(=O)2iPr |
| M48 | −H | −H | −H | −H | −OMe | −S(=O)2Et |
| M49 | −H | −H | −H | −H | −OMe | −S(=O)2Me |
| M50 | −H | −H | −H | −H | −OMe | −S(=O)2NHMe |
| M51 | −H | −H | −H | −H | −OMe | −S(=O)2NMe2 |
| M52 | −H | −H | −H | −H | −OMe | −C(=O)NHMe |
| M53 | −H | −H | −H | −H | −OMe | −C(=O)NMe2 |
| M54 | −H | −H | −H | −H | −OMe | −C(=O)iPr |
| M55 | −H | −H | −H | −H | −OMe | −C(=O)Et |
| M56 | −H | −H | −H | −H | −OMe | −F |
| M57 | −H | −H | −H | −H | −OMe | −Cl |
| M58 | −H | −H | −H | −H | −OMe | −Br |
| M59 | −H | −H | −H | −H | −OMe | −OMe |
| M60 | −H | −H | −H | −H | −OMe | −OEt |
| M61 | −H | −H | −H | −H | −OMe | −OiPr |
| M62 | −H | −H | −H | −H | −OMe | −OCF3 |
| M63 | −H | −H | −H | −H | −OMe | −SMe |

TABLE 83-continued

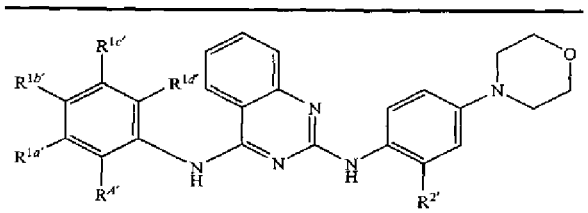

| No | —R¹ᵃ' | —R¹ᵇ' | —R¹ᶜ' | —R¹ᵈ' | —R²' | —Rᵈ' |
|---|---|---|---|---|---|---|
| M64 | —H | —H | —H | —H | —OMe | —SEt |
| M65 | —H | —H | —H | —H | —OMe | —SiPr |
| M66 | —H | —H | —H | —H | —OMe | Me |

TABLE 83-continued

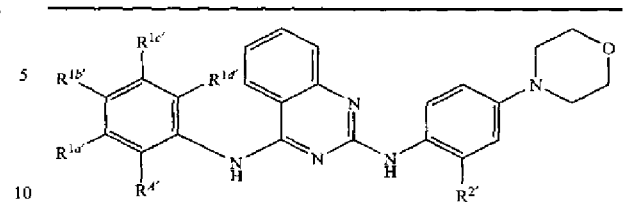

| No | —R¹ᵃ' | —R¹ᵇ' | —R¹ᶜ' | —R¹ᵈ' | —R²' | —Rᵈ' |
|---|---|---|---|---|---|---|
| M67 | —H | —H | —H | —H | —OMe | Et |
| M68 | —H | —H | —H | —H | —OMe | iPr |
| M69 | —H | —H | —H | —H | —OMe | —CF₃ |

TABLE 84

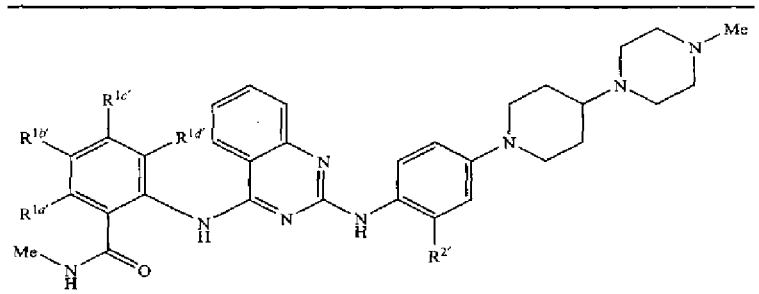

| No | —R¹ᵃ' | —R¹ᵇ' | —R¹ᶜ' | —R¹ᵈ' | —R²' |
|---|---|---|---|---|---|
| N1 | —H | —H | —H | —H | —F |
| N2 | —H | —H | —H | —H | —Cl |
| N3 | —H | —H | —H | —H | —Br |
| N4 | —H | —H | —H | —H | —OEt |
| N5 | —H | —H | —H | —H | —OiPr |
| N6 | —H | —H | —H | —H | —CF₃ |
| N7 | —H | —H | —H | —H | —CN |
| N8 | —H | —H | —H | —H | Me |
| N9 | —H | —H | —H | —H | Et |
| N10 | —H | —H | —H | —H | —SMe |
| N11 | —H | —H | —H | —H | —OCF₃ |
| N12 | —F | —H | —H | —H | —OMe |
| N13 | —H | —F | —H | —H | —OMe |
| N14 | —H | —H | —F | —H | —OMe |
| N15 | —H | —H | —H | —F | —OMe |
| N16 | —Cl | —H | —H | —H | —OMe |
| N17 | —H | —Cl | —H | —H | —OMe |
| N18 | —H | —H | —Cl | —H | —OMe |
| N19 | —H | —H | —H | —Cl | —OMe |
| N20 | —Br | —H | —H | —H | —OMe |
| N21 | —H | —Br | —H | —H | —OMe |
| N22 | —H | —H | —Br | —H | —OMe |
| N23 | —H | —H | —H | —Br | —OMe |
| N24 | Me | —H | —H | —H | —OMe |
| N25 | —H | Me | —H | —H | —OMe |
| N26 | —H | —H | Me | —H | —OMe |
| N27 | —H | —H | —H | Me | —OMe |

TABLE 85

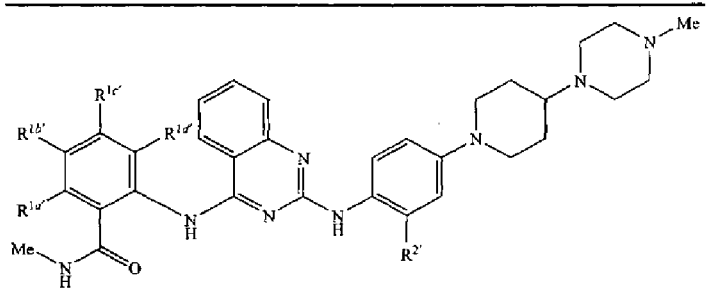

| No | —R$^{1a'}$ | —R$^{1b'}$ | —R$^{1c'}$ | —R$^{1d'}$ | —R$^{2'}$ |
|---|---|---|---|---|---|
| N28 | —OMe | —H | —H | —H | —OMe |
| N29 | —H | —OMe | —H | —H | —OMe |
| N30 | —H | —H | —OMe | —H | —OMe |
| N31 | —H | —H | —H | —OMe | —OMe |
| N32 | —CN | —H | —H | —H | —OMe |
| N33 | —H | —CN | —H | —H | —OMe |
| N34 | —H | —H | —CN | —H | —OMe |
| N35 | —H | —H | —H | —CN | —OMe |
| N36 | —CF$_3$ | —H | —H | —H | —OMe |
| N37 | —H | —CF$_3$ | —H | —H | —OMe |
| N38 | —H | —H | —CF$_3$ | —H | —OMe |
| N39 | —H | —H | —H | —CF$_3$ | —OMe |
| N40 | —SMe | —H | —H | —H | —OMe |
| N41 | —H | —SMe | —H | —H | —OMe |
| N42 | —H | —H | —SMe | —H | —OMe |
| N43 | —H | —H | —H | —SMe | —OMe |
| N44 | —OCF$_3$ | —H | —H | —H | —OMe |
| N45 | —H | —OCF$_3$ | —H | —H | —OMe |
| N46 | —H | —H | —OCF$_3$ | —H | —OMe |
| N47 | —H | —H | —H | —OCF$_3$ | —OMe |

TABLE 86

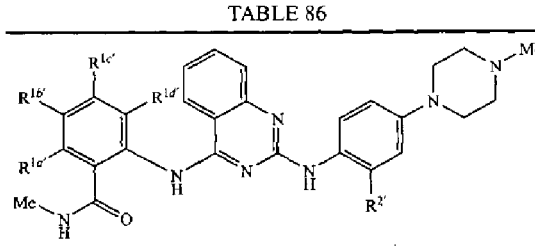

| No | —R$^{1a'}$ | —R$^{1b'}$ | —R$^{1c'}$ | —R$^{1d'}$ | —R$^{2'}$ |
|---|---|---|---|---|---|
| O1 | —H | —H | —H | —H | —F |
| O2 | —H | —H | —H | —H | —Cl |
| O3 | —H | —H | —H | —H | —Br |
| O4 | —H | —H | —H | —H | —OEt |
| O5 | —H | —H | —H | —H | —OiPr |
| O6 | —H | —H | —H | —H | —CF$_3$ |
| O7 | —H | —H | —H | —H | —CN |
| O8 | —H | —H | —H | —H | Me |
| O9 | —H | —H | —H | —H | Et |
| O10 | —H | —H | —H | —H | —SMe |
| O11 | —H | —H | —H | —H | —OCF$_3$ |
| O12 | —F | —H | —H | —H | —OMe |
| O13 | —H | —F | —H | —H | —OMe |
| O14 | —H | —H | —F | —H | —OMe |
| O15 | —H | —H | —H | —F | —OMe |
| O16 | —Cl | —H | —H | —H | —OMe |
| O17 | —H | —Cl | —H | —H | —OMe |
| O18 | —H | —H | —Cl | —H | —OMe |
| O19 | —H | —H | —H | —Cl | —OMe |
| O20 | —Br | —H | —H | —H | —OMe |
| O21 | —H | —Br | —H | —H | —OMe |
| O22 | —H | —H | —Br | —H | —OMe |
| O23 | —H | —H | —H | —Br | —OMe |
| O24 | Me | —H | —H | —H | —OMe |

TABLE 86-continued

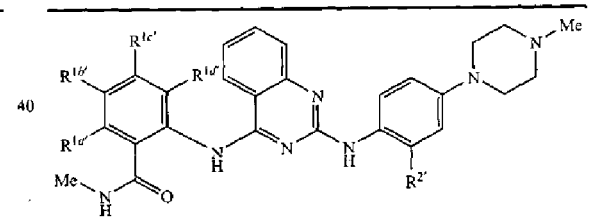

| No | —R$^{1a'}$ | —R$^{1b'}$ | —R$^{1c'}$ | —R$^{1d'}$ | —R$^{2'}$ |
|---|---|---|---|---|---|
| O25 | —H | Me | —H | —H | —OMe |
| O26 | —H | —H | Me | —H | —OMe |
| O27 | —H | —H | —H | Me | —OMe |

TABLE 87

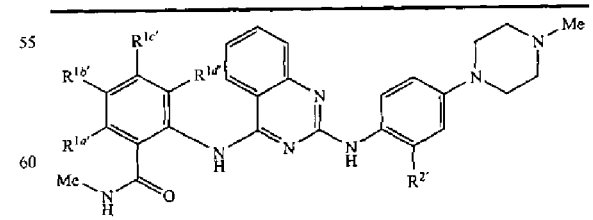

| No | —R$^{1a'}$ | —R$^{1b'}$ | —R$^{1c'}$ | —R$^{1d'}$ | —R$^{2'}$ |
|---|---|---|---|---|---|
| O28 | —OMe | —H | —H | —H | —OMe |
| O29 | —H | —OMe | —H | —H | —OMe |

TABLE 87-continued

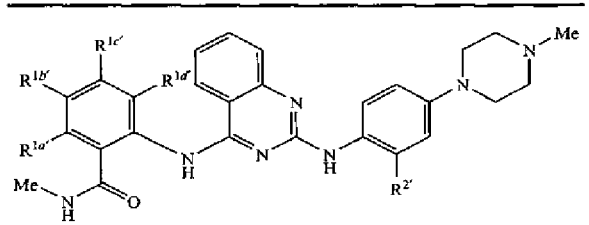

| No | —R[1a'] | —R[1b'] | —R[1c'] | —R[1d'] | —R[2'] |
|---|---|---|---|---|---|
| O30 | —H | —H | —OMe | —H | —OMe |
| O31 | —H | —H | —H | —OMe | —OMe |
| O32 | —CN | —H | —H | —H | —OMe |
| O33 | —H | —CN | —H | —H | —OMe |
| O34 | —H | —H | —CN | —H | —OMe |
| O35 | —H | —H | —H | —CN | —OMe |
| O36 | —CF₃ | —H | —H | —H | —OMe |
| O37 | —H | —CF₃ | —H | —H | —OMe |
| O38 | —H | —H | —CF₃ | —H | —OMe |
| O39 | —H | —H | —H | —CF₃ | —OMe |
| O40 | —SMe | —H | —H | —H | —OMe |
| O41 | —H | —SMe | —H | —H | —OMe |
| O42 | —H | —H | —SMe | —H | —OMe |
| O43 | —H | —H | —H | —SMe | —OMe |
| O44 | —OCF₃ | —H | —H | —H | —OMe |
| O45 | —H | —OCF₃ | —H | —H | —OMe |
| O46 | —H | —H | —OCF₃ | —H | —OMe |
| O47 | —H | —H | —H | —OCF₃ | —OMe |

TABLE 88

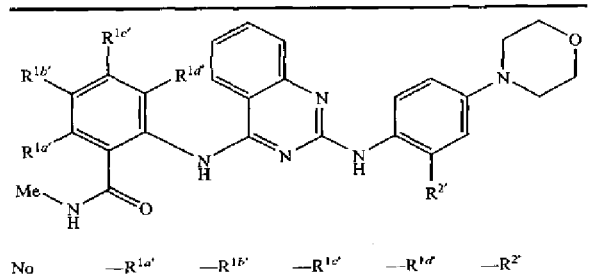

| No | —R[1a'] | —R[1b'] | —R[1c'] | —R[1d'] | —R[2'] |
|---|---|---|---|---|---|
| P1 | —H | —H | —H | —H | —F |
| P2 | —H | —H | —H | —H | —Cl |
| P3 | —H | —H | —H | —H | —Br |
| P4 | —H | —H | —H | —H | —OEt |
| P5 | —H | —H | —H | —H | —OiPr |
| P6 | —H | —H | —H | —H | —CF₃ |
| P7 | —H | —H | —H | —H | —CN |
| P8 | —H | —H | —H | —H | Me |
| P9 | —H | —H | —H | —H | Et |
| P10 | —H | —H | —H | —H | —SMe |
| P11 | —H | —H | —H | —H | —OCF₃ |
| P12 | —F | —H | —H | —H | —OMe |
| P13 | —H | —F | —H | —H | —OMe |
| P14 | —H | —H | —F | —H | —OMe |
| P15 | —H | —H | —H | —F | —OMe |

TABLE 88-continued

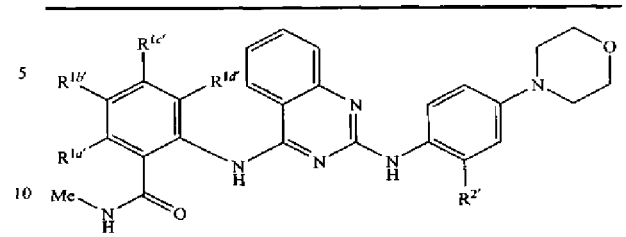

| No | —R[1a'] | —R[1b'] | —R[1c'] | —R[1d'] | —R[2'] |
|---|---|---|---|---|---|
| P16 | —Cl | —H | —H | —H | —OMe |
| P17 | —H | —Cl | —H | —H | —OMe |
| P18 | —H | —H | —Cl | —H | —OMe |
| P19 | —H | —H | —H | —Cl | —OMe |
| P20 | —Br | —H | —H | —H | —OMe |
| P21 | —H | —Br | —H | —H | —OMe |
| P22 | —H | —H | —Br | —H | —OMe |
| P23 | —H | —H | —H | —Br | —OMe |
| P24 | Me | —H | —H | —H | —OMe |
| P25 | —H | Me | —H | —H | —OMe |
| P26 | —H | —H | Me | —H | —OMe |
| P27 | —H | —H | —H | Me | —OMe |

TABLE 89

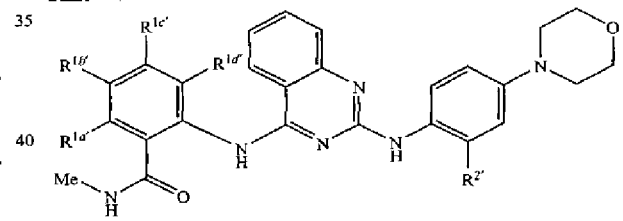

| No | —R[1a'] | —R[1b'] | —R[1c'] | —R[1d'] | —R[2'] |
|---|---|---|---|---|---|
| P28 | —OMe | —H | —H | —H | —OMe |
| P29 | —H | —OMe | —H | —H | —OMe |
| P30 | —H | —H | —OMe | —H | —OMe |
| P31 | —H | —H | —H | —OMe | —OMe |
| P32 | —CN | —H | —H | —H | —OMe |
| P33 | —H | —CN | —H | —H | —OMe |
| P34 | —H | —H | —CN | —H | —OMe |
| P35 | —H | —H | —H | —CN | —OMe |
| P36 | —CF₃ | —H | —H | —H | —OMe |
| P37 | —H | —CF₃ | —H | —H | —OMe |
| P38 | —H | —H | —CF₃ | —H | —OMe |
| P39 | —H | —H | —H | —CF₃ | —OMe |
| P40 | —SMe | —H | —H | —H | —OMe |
| P41 | —H | —SMe | —H | —H | —OMe |
| P42 | —H | —H | —SMe | —H | —OMe |
| P43 | —H | —H | —H | —SMe | —OMe |
| P44 | —OCF₃ | —H | —H | —H | —OMe |
| P45 | —H | —OCF₃ | —H | —H | —OMe |
| P46 | —H | —H | —OCF₃ | —H | —OMe |
| P47 | —H | —H | —H | —OCF₃ | —OMe |

TABLE 90

| No | $-R^{6a'}$ | $-R^{6b'}$ | $-R^{6c'}$ | $-R^{6d'}$ | $-R^{4'}$ |
|---|---|---|---|---|---|
| Q1 | —F | —H | —H | —H | —S(=O)$_2$iPr |
| Q2 | —H | —F | —H | —H | —S(=O)$_2$iPr |
| Q3 | —H | —H | —F | —H | —S(=O)$_2$iPr |
| Q4 | —H | —H | —H | —F | —S(=O)$_2$iPr |
| Q5 | —Cl | —H | —H | —H | —S(=O)$_2$iPr |
| Q6 | —H | —Cl | —H | —H | —S(=O)$_2$iPr |
| Q7 | —H | —H | —Cl | —H | —S(=O)$_2$iPr |
| Q8 | —H | —H | —H | —Cl | —S(=O)$_2$iPr |
| Q9 | —Br | —H | —H | —H | —S(=O)$_2$iPr |
| Q10 | —H | —Br | —H | —H | —S(=O)$_2$iPr |
| Q11 | —H | —H | —Br | —H | —S(=O)$_2$iPr |
| Q12 | —H | —H | —H | —Br | —S(=O)$_2$iPr |
| Q13 | Me | —H | —H | —H | —S(=O)$_2$iPr |
| Q14 | —H | Me | —H | —H | —S(=O)$_2$iPr |
| Q15 | —H | —H | Me | —H | —S(=O)$_2$iPr |
| Q16 | —H | —H | —H | Me | —S(=O)$_2$iPr |
| Q17 | —OMe | —H | —H | —H | —S(=O)$_2$iPr |
| Q18 | —H | —OMe | —H | —H | —S(=O)$_2$iPr |
| Q19 | —H | —H | —OMe | —H | —S(=O)$_2$iPr |
| Q20 | —H | —H | —H | —OMe | —S(=O)$_2$iPr |
| Q21 | —CN | —H | —H | —H | —S(=O)$_2$iPr |
| Q22 | —H | —CN | —H | —H | —S(=O)$_2$iPr |
| Q23 | —H | —H | —CN | —H | —S(=O)$_2$iPr |
| Q24 | —H | —H | —H | —CN | —S(=O)$_2$iPr |
| Q25 | —CF$_3$ | —H | —H | —H | —S(=O)$_2$iPr |
| Q26 | —H | —CF$_3$ | —H | —H | —S(=O)$_2$iPr |
| Q27 | —H | —H | —CF$_3$ | —H | —S(=O)$_2$iPr |
| Q28 | —H | —H | —H | —CF$_3$ | —S(=O)$_2$iPr |
| Q29 | —SMe | —H | —H | —H | —S(=O)$_2$iPr |
| Q30 | —H | —SMe | —H | —H | —S(=O)$_2$iPr |
| Q31 | —H | —H | —SMe | —H | —S(=O)$_2$iPr |
| Q32 | —H | —H | —H | —SMe | —S(=O)$_2$iPr |
| Q33 | —OCF$_3$ | —H | —H | —H | —S(=O)$_2$iPr |
| Q34 | —H | —OCF$_3$ | —H | —H | —S(=O)$_2$iPr |
| Q35 | —H | —H | —OCF$_3$ | —H | —S(=O)$_2$iPr |
| Q36 | —H | —H | —H | —OCF$_3$ | —S(=O)$_2$iPr |

TABLE 91

| No | $-R^{6a'}$ | $-R^{6b'}$ | $-R^{6c'}$ | $-R^{6d'}$ | $-R^{4'}$ |
|---|---|---|---|---|---|
| Q37 | —F | —H | —H | —H | —C(=O)NHMe |
| Q38 | —H | —F | —H | —H | —C(=O)NHMe |
| Q39 | —H | —H | —F | —H | —C(=O)NHMe |
| Q40 | —H | —H | —H | —F | —C(=O)NHMe |
| Q41 | —Cl | —H | —H | —H | —C(=O)NHMe |
| Q42 | —H | —Cl | —H | —H | —C(=O)NHMe |

TABLE 91-continued

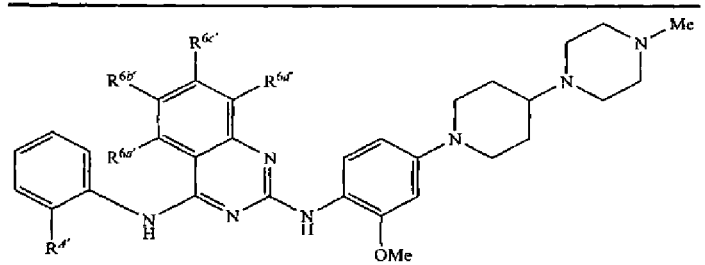

| No | —R6a' | —R6b' | —R6c' | —R6d' | —R4' |
|---|---|---|---|---|---|
| Q43 | —H | —H | —Cl | —H | —C(=O)NHMe |
| Q44 | —H | —H | —H | —Cl | —C(=O)NHMe |
| Q45 | —Br | —H | —H | —H | —C(=O)NHMe |
| Q46 | —H | —Br | —H | —H | —C(=O)NHMe |
| Q47 | —H | —H | —Br | —H | —C(=O)NHMe |
| Q48 | —H | —H | —H | —Br | —C(=O)NHMe |
| Q49 | Me | —H | —H | —H | —C(=O)NHMe |
| Q50 | —H | Me | —H | —H | —C(=O)NHMe |
| Q51 | —H | —H | Me | —H | —C(=O)NHMe |
| Q52 | —H | —H | —H | Me | —C(=O)NHMe |
| Q53 | —OMe | —H | —H | —H | —C(=O)NHMe |
| Q54 | —H | —OMe | —H | —H | —C(=O)NHMe |
| Q55 | —H | —H | —OMe | —H | —C(=O)NHMe |
| Q56 | —H | —H | —H | —OMe | —C(=O)NHMe |
| Q57 | —CN | —H | —H | —H | —C(=O)NHMe |
| Q58 | —H | —CN | —H | —H | —C(=O)NHMe |
| Q59 | —H | —H | —CN | —H | —C(=O)NHMe |
| Q60 | —H | —H | —H | —CN | —C(=O)NHMe |
| Q61 | —CF3 | —H | —H | —H | —C(=O)NHMe |
| Q62 | —H | —CF3 | —H | —H | —C(=O)NHMe |
| Q63 | —H | —H | —CF3 | —H | —C(=O)NHMe |
| Q64 | —H | —H | —H | —CF3 | —C(=O)NHMe |
| Q65 | —SMe | —H | —H | —H | —C(=O)NHMe |
| Q66 | —H | —SMe | —H | —H | —C(=O)NHMe |
| Q67 | —H | —H | —SMe | —H | —C(=O)NHMe |
| Q68 | —H | —H | —H | —SMe | —C(=O)NHMe |
| Q69 | —OCF3 | —H | —H | —H | —C(=O)NHMe |
| Q70 | —H | —OCF3 | —H | —H | —C(=O)NHMe |
| Q71 | —H | —H | —OCF3 | —H | —C(=O)NHMe |
| Q72 | —H | —H | —H | —OCF3 | —C(=O)NHMe |

TABLE 92

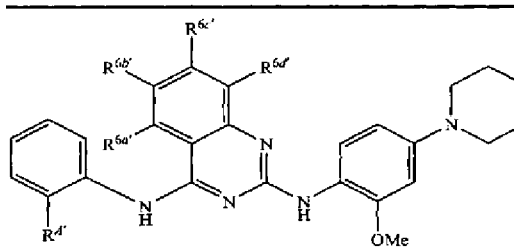
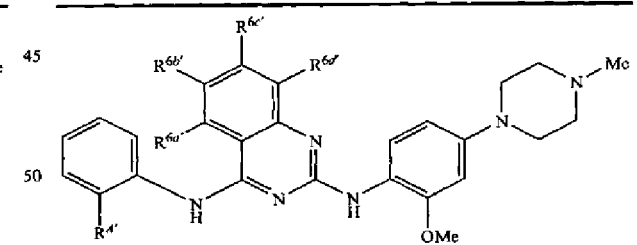

| No | —R6a' | —R6b' | —R6c' | —R6d' | —R4' |
|---|---|---|---|---|---|
| R1 | —F | —H | —H | —H | —S(=O)2iPr |
| R2 | —H | —F | —H | —H | —S(=O)2iPr |
| R3 | —H | —H | —F | —H | —S(=O)2iPr |
| R4 | —H | —H | —H | —F | —S(=O)2iPr |
| R5 | —Cl | —H | —H | —H | —S(=O)2iPr |
| R6 | —H | —Cl | —H | —H | —S(=O)2iPr |
| R7 | —H | —H | —Cl | —H | —S(=O)2iPr |
| R8 | —H | —H | —H | —Cl | —S(=O)2iPr |
| R9 | —Br | —H | —H | —H | —S(=O)2iPr |
| R10 | —H | —Br | —H | —H | —S(=O)2iPr |
| R11 | —H | —H | —Br | —H | —S(=O)2iPr |
| R12 | —H | —H | —H | —Br | —S(=O)2iPr |
| R13 | Me | —H | —H | —H | —S(=O)2iPr |
| R14 | —H | Me | —H | —H | —S(=O)2iPr |
| R15 | —H | —H | Me | —H | —S(=O)2iPr |
| R16 | —H | —H | —H | Me | —S(=O)2iPr |
| R17 | —OMe | —H | —H | —H | —S(=O)2iPr |
| R18 | —H | —OMe | —H | —H | —S(=O)2iPr |
| R19 | —H | —H | —OMe | —H | —S(=O)2iPr |
| R20 | —H | —H | —H | —OMe | —S(=O)2iPr |
| R21 | —CN | —H | —H | —H | —S(=O)2iPr |
| R22 | —H | —CN | —H | —H | —S(=O)2iPr |
| R23 | —H | —H | —CN | —H | —S(=O)2iPr |
| R24 | —H | —H | —H | —CN | —S(=O)2iPr |
| R25 | —CF3 | —H | —H | —H | —S(=O)2iPr |
| R26 | —H | —CF3 | —H | —H | —S(=O)2iPr |

TABLE 92-continued

| No | —R6a' | —R6b' | —R6c' | —R6d' | —R4' |
|---|---|---|---|---|---|
| R27 | —H | —H | —CF3 | —H | —S(=O)2iPr |
| R28 | —H | —H | —H | —CF3 | —S(=O)2iPr |
| R29 | —SMe | —H | —H | —H | —S(=O)2iPr |
| R30 | —H | —SMe | —H | —H | —S(=O)2iPr |
| R31 | —H | —H | —SMe | —H | —S(=O)2iPr |
| R32 | —H | —H | —H | —SMe | —S(=O)2iPr |
| R33 | —OCF3 | —H | —H | —H | —S(=O)2iPr |
| R34 | —H | —OCF3 | —H | —H | —S(=O)2iPr |
| R35 | —H | —H | —OCF3 | —H | —S(=O)2iPr |
| R36 | —H | —H | —H | —OCF3 | —S(=O)2iPr |

TABLE 93

| No | —R6a' | —R6b' | —R6c' | —R6d' | —R4' |
|---|---|---|---|---|---|
| R37 | —F | —H | —H | —H | —C(=O)NHMe |
| R38 | —H | —F | —H | —H | —C(=O)NHMe |
| R39 | —H | —H | —F | —H | —C(=O)NHMe |
| R40 | —H | —H | —H | —F | —C(=O)NHMe |
| R41 | —Cl | —H | —H | —H | —C(=O)NHMe |
| R42 | —H | —Cl | —H | —H | —C(=O)NHMe |
| R43 | —H | —H | —Cl | —H | —C(=O)NHMe |
| R44 | —H | —H | —H | —Cl | —C(=O)NHMe |
| R45 | —Br | —H | —H | —H | —C(=O)NHMe |
| R46 | —H | —Br | —H | —H | —C(=O)NHMe |
| R47 | —H | —H | —Br | —H | —C(=O)NHMe |
| R48 | —H | —H | —H | —Br | —C(=O)NHMe |
| R49 | Me | —H | —H | —H | —C(=O)NHMe |
| R50 | —H | Me | —H | —H | —C(=O)NHMe |
| R51 | —H | —H | Me | —H | —C(=O)NHMe |
| R52 | —H | —H | —H | Me | —C(=O)NHMe |
| R53 | —OMe | —H | —H | —H | —C(=O)NHMe |
| R54 | —H | —OMe | —H | —H | —C(=O)NHMe |
| R55 | —H | —H | —OMe | —H | —C(=O)NHMe |
| R56 | —H | —H | —H | —OMe | —C(=O)NHMe |
| R57 | —CN | —H | —H | —H | —C(=O)NHMe |
| R58 | —H | —CN | —H | —H | —C(=O)NHMe |
| R59 | —H | —H | —CN | —H | —C(=O)NHMe |
| R60 | —H | —H | —H | —CN | —C(=O)NHMe |
| R61 | —CF3 | —H | —H | —H | —C(=O)NHMe |
| R62 | —H | —CF3 | —H | —H | —C(=O)NHMe |
| R63 | —H | —H | —CF3 | —H | —C(=O)NHMe |
| R64 | —H | —H | —H | —CF3 | —C(=O)NHMe |
| R65 | —SMe | —H | —H | —H | —C(=O)NHMe |
| R66 | —H | —SMe | —H | —H | —C(=O)NHMe |
| R67 | —H | —H | —SMe | —H | —C(=O)NHMe |
| R68 | —H | —H | —H | —SMe | —C(=O)NHMe |
| R69 | —OCF3 | —H | —H | —H | —C(=O)NHMe |
| R70 | —H | —OCF3 | —H | —H | —C(=O)NHMe |

TABLE 93-continued

| No | —R6a' | —R6b' | —R6c' | —R6d' | —R4' |
|---|---|---|---|---|---|
| R71 | —H | —H | —OCF3 | —H | —C(=O)NHMe |
| R72 | —H | —H | —H | —OCF3 | —C(=O)NHMe |

TABLE 94

| No | —R6a' | —R6b' | —R6c' | —R6d' | —R4' |
|---|---|---|---|---|---|
| S1 | —F | —H | —H | —H | —S(=O)2iPr |
| S2 | —H | —F | —H | —H | —S(=O)2iPr |
| S3 | —H | —H | —F | —H | —S(=O)2iPr |
| S4 | —H | —H | —H | —F | —S(=O)2iPr |
| S5 | —Cl | —H | —H | —H | —S(=O)2iPr |
| S6 | —H | —Cl | —H | —H | —S(=O)2iPr |
| S7 | —H | —H | —Cl | —H | —S(=O)2iPr |
| S8 | —H | —H | —H | —Cl | —S(=O)2iPr |
| S9 | —Br | —H | —H | —H | —S(=O)2iPr |
| S10 | —H | —Br | —H | —H | —S(=O)2iPr |
| S11 | —H | —H | —Br | —H | —S(=O)2iPr |
| S12 | —H | —H | —H | —Br | —S(=O)2iPr |
| S13 | Me | —H | —H | —H | —S(=O)2iPr |
| S14 | —H | Me | —H | —H | —S(=O)2iPr |
| S15 | —H | —H | Me | —H | —S(=O)2iPr |
| S16 | —H | —H | —H | Me | —S(=O)2iPr |
| S17 | —OMe | —H | —H | —H | —S(=O)2iPr |
| S18 | —H | —OMe | —H | —H | —S(=O)2iPr |
| S19 | —H | —H | —OMe | —H | —S(=O)2iPr |
| S20 | —H | —H | —H | —OMe | —S(=O)2iPr |
| S21 | —CN | —H | —H | —H | —S(=O)2iPr |
| S22 | —H | —CN | —H | —H | —S(=O)2iPr |
| S23 | —H | —H | —CN | —H | —S(=O)2iPr |
| S24 | —H | —H | —H | —CN | —S(=O)2iPr |
| S25 | —CF3 | —H | —H | —H | —S(=O)2iPr |
| S26 | —H | —CF3 | —H | —H | —S(=O)2iPr |
| S27 | —H | —H | —CF3 | —H | —S(=O)2iPr |
| S28 | —H | —H | —H | —CF3 | —S(=O)2iPr |
| S29 | —SMe | —H | —H | —H | —S(=O)2iPr |
| S30 | —H | —SMe | —H | —H | —S(=O)2iPr |
| S31 | —H | —H | —SMe | —H | —S(=O)2iPr |
| S32 | —H | —H | —H | —SMe | —S(=O)2iPr |
| S33 | —OCF3 | —H | —H | —H | —S(=O)2iPr |
| S34 | —H | —OCF3 | —H | —H | —S(=O)2iPr |
| S35 | —H | —H | —OCF3 | —H | —S(=O)2iPr |
| S36 | —H | —H | —H | —OCF3 | —S(=O)2iPr |

TABLE 95

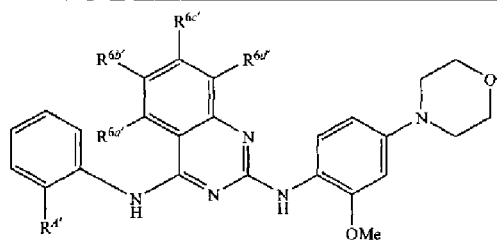

| No | —R6a' | —R6b' | —R6c' | —R6d' | —R4' |
|---|---|---|---|---|---|
| S37 | —F | —H | —H | —H | —C(=O)NHMe |
| S38 | —H | —F | —H | —H | —C(=O)NHMe |
| S39 | —H | —H | —F | —H | —C(=O)NHMe |
| S40 | —H | —H | —H | —F | —C(=O)NHMe |
| S41 | —Cl | —H | —H | —H | —C(=O)NHMe |
| S42 | —H | —Cl | —H | —H | —C(=O)NHMe |
| S43 | —H | —H | —Cl | —H | —C(=O)NHMe |
| S44 | —H | —H | —H | —Cl | —C(=O)NHMe |
| S45 | —Br | —H | —H | —H | —C(=O)NHMe |
| S46 | —H | —Br | —H | —H | —C(=O)NHMe |
| S47 | —H | —H | —Br | —H | —C(=O)NHMe |
| S48 | —H | —H | —H | —Br | —C(=O)NHMe |
| S49 | Me | —H | —H | —H | —C(=O)NHMe |
| S50 | —H | Me | —H | —H | —C(=O)NHMe |
| S51 | —H | —H | Me | —H | —C(=O)NHMe |
| S52 | —H | —H | —H | Me | —C(=O)NHMe |
| S53 | —OMe | —H | —H | —H | —C(=O)NHMe |
| S54 | —H | —OMe | —H | —H | —C(=O)NHMe |
| S55 | —H | —H | —OMe | —H | —C(=O)NHMe |
| S56 | —H | —H | —H | —OMe | —C(=O)NHMe |
| S57 | —CN | —H | —H | —H | —C(=O)NHMe |
| S58 | —H | —CN | —H | —H | —C(=O)NHMe |
| S59 | —H | —H | —CN | —H | —C(=O)NHMe |
| S60 | —H | —H | —H | —CN | —C(=O)NHMe |
| S61 | —CF3 | —H | —H | —H | —C(=O)NHMe |
| S62 | —H | —CF3 | —H | —H | —C(=O)NHMe |
| S63 | —H | —H | —CF3 | —H | —C(=O)NHMe |
| S64 | —H | —H | —H | —CF3 | —C(=O)NHMe |
| S65 | —SMe | —H | —H | —H | —C(=O)NHMe |
| S66 | —H | —SMe | —H | —H | —C(=O)NHMe |
| S67 | —H | —H | —SMe | —H | —C(=O)NHMe |
| S68 | —H | —H | —H | —SMe | —C(=O)NHMe |
| S69 | —OCF3 | —H | —H | —H | —C(=O)NHMe |
| S70 | —H | —OCF3 | —H | —H | —C(=O)NHMe |

TABLE 95-continued

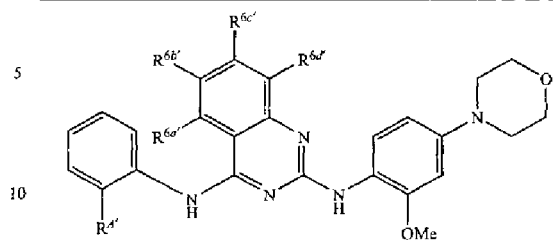

| No | —R6a' | —R6b' | —R6c' | —R6d' | —R4' |
|---|---|---|---|---|---|
| S71 | —H | —H | —OCF3 | —H | —C(=O)NHMe |
| S72 | —H | —H | —H | —OCF3 | —C(=O)NHMe |

INDUSTRIAL APPLICABILITY

The compounds of formula (I) or salts thereof have inhibitory activity against the kinase activity of EML4-ALK fusion proteins and mutant EGFR proteins, as well as growth inhibitory activity against human non-small cell lung cancer cell lines NCI-H2228 and HCC827, and can be used as active ingredients in pharmaceutical compositions for preventing and/or treating cancer, such as lung cancer in one embodiment, non-small cell lung cancer or small cell lung cancer in another embodiment, EML4-ALK fusion polynucleotide-positive and/or mutant EGFR polynucleotide-positive cancer in yet another embodiment, EML4-ALK fusion polynucleotide-positive and/or mutant EGFR polynucleotide-positive lung cancer in yet another embodiment, or EML4-ALK fusion polynucleotide-positive and/or mutant EGFR polynucleotide-positive non-small cell lung cancer in yet another embodiment.

SEQUENCE LISTING FREE TEXT

The numerical heading <223> in the Sequence Listing shown below contains an explanation of "Artificial Sequence." More specifically, each nucleotide sequence represented by the sequence of SEQ ID NO: 9 or 10 in the Sequence Listing is an artificially synthesized primer sequence.

The invention claimed is:

1. A compound of formula (I) or a salt thereof:

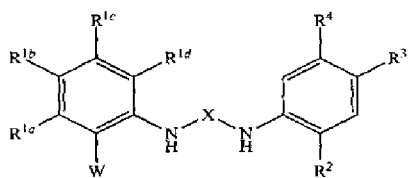

(I)

(wherein the symbols are defined below:
—X— represents
(1) a group of formula (II), or
(2) a group of formula (III)

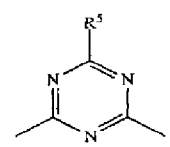

(II)

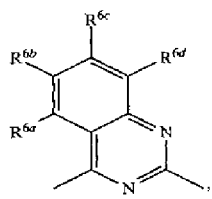

(III)

—$R^5$ represents
(1) —H,
(2) —OH,
(3) halogen,
(4) lower alkyl which may be substituted with one or more halogens,
(5) O-lower alkyl which may be substituted with one or more halogens,
(6) —S-lower alkyl,
(7) cyano,
(8) amino which may be substituted with one or two lower alkyls, or
(9) cyclic amino which may be substituted with one or more groups selected from the group consisting of lower alkyl, oxo, —OH, —O-lower alkyl, and amino which may be substituted with one or two lower alkyls (provided that the triazine ring to which —$R^5$ is attached is attached to the nitrogen atom in the cyclic amino),
—$R^{6a}$, —$R^{6b}$, —$R^{6c}$ and —$R^{6d}$, which may be the same or different, each represent
(1) —H,
(2) halogen,
(3) lower alkyl which may be substituted with one or more halogens,
(4) O-lower alkyl which may be substituted with one or more halogens,
(5) —S-lower alkyl, or
(6) cyano,
—W represents
a group represented by -A-B,
-A- is
—S(=O)$_2$—
—B is isopropyl,
—$R^{1a}$, —$R^{1b}$, $R^{1c}$ and —$R^{1d}$ are each —H, —$R^2$ is —O-methyl, —$R^4$ is —H and —$R^3$ is 4-(4-methylpiperazin-1-yl)piperidin-1-yl.

2. The compound according to claim 1 or a salt thereof, wherein —X— is a group represented by formula (II), and —$R^5$ is —H.

3. The compound according to claim 1 or a salt thereof, wherein said compound is:
$N^4$-[2-(isopropylsulfonyl)phenyl]-$N^2$-{2-methoxy-4-[4-(4-methylpiperazin-1-yl)piperidin-1-yl]phenyl}quinazoline-2,4-diamine.

4. The compound according to claim 1 or a salt thereof, wherein said compound is:
N-[2-(isopropylsulfonyl)phenyl]-N'-{2-methoxy-4-[4-(4-methylpiperazin-1-yl)piperidin-1-yl]phenyl}-1,3,5-triazine-2,4-diamine.

5. A pharmaceutical composition, which comprises the compound according to claim 1 or a salt thereof and a pharmaceutically acceptable excipient.

6. A pharmaceutical composition for treating non-small cell lung cancer, or EML4-ALK fusion polynucleotide-positive and/or mutant EGFR polynucleotide-positive non-small cell lung cancer, which comprises the compound according to claim 1 or a salt thereof.

7. The compound according to claim 1 or a salt thereof, which is used as an active ingredient in a pharmaceutical composition for treating non-small cell lung cancer, or EML4-ALK fusion polynucleotide-positive and/or mutant EGFR polynucleotide-positive non-small cell lung cancer.

* * * * *